US012698486B2

(12) United States Patent
Jungbauer et al.

(10) Patent No.: US 12,698,486 B2
(45) Date of Patent: Aug. 4, 2026

(54) CASPASE-2 VARIANTS

(71) Applicant: BOEHRINGER INGELHEIM RCV GMBH & CO KG, Vienna (AT)

(72) Inventors: Alois Jungbauer, Vienna (AT); Nico Lingg, Vienna (AT); Gerald Striedner, Vienna (AT); Monika Cserjan-Puschmann, Langenzersdorf (AT); Chris Oostenbrink, Vienna (AT); Christoph Oehlknecht, Vienna (AT); Christina Kroess, Innsbruck (AT); Petra Engele, Innsbruck (AT); Rainer Schneider, Woergl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1165 days.

(21) Appl. No.: 17/635,215

(22) PCT Filed: Aug. 14, 2020

(86) PCT No.: PCT/EP2020/072934
§ 371 (c)(1),
(2) Date: Feb. 14, 2022

(87) PCT Pub. No.: WO2021/028590
PCT Pub. Date: Feb. 18, 2021

(65) Prior Publication Data

US 2022/0380739 A1 Dec. 1, 2022

(30) Foreign Application Priority Data

Aug. 14, 2019 (EP) .................................... 19191767

(51) Int. Cl.

| | |
|---|---|
| ***C12N 9/14*** | (2006.01) |
| ***A61P 25/16*** | (2006.01) |
| ***A61P 25/28*** | (2006.01) |
| ***A61P 29/00*** | (2006.01) |
| ***A61P 35/00*** | (2006.01) |
| ***C12N 9/64*** | (2006.01) |
| ***C12N 15/70*** | (2006.01) |
| ***C12P 21/02*** | (2006.01) |
| ***C12P 21/06*** | (2006.01) |

(52) U.S. Cl.
CPC ............... *C12N 9/14* (2013.01); *C12N 15/70* (2013.01); *C12Y 304/22055* (2013.01)

(58) Field of Classification Search
None
See application file for complete search history.

(56) References Cited

U.S. PATENT DOCUMENTS

| | | | |
|---|---|---|---|
| 6,376,226 B1 * | 4/2002 | Alnemri ............... | C12N 9/6475 435/325 |
| 6,379,950 B1 | 4/2002 | Alnemri | |
| 7,604,980 B2 | 10/2009 | Galande et al. | |
| 8,535,908 B2 | 9/2013 | Freimuth et al. | |
| 2007/0141662 A1 | 6/2007 | Stennicke et al. | |

FOREIGN PATENT DOCUMENTS

| | | |
|---|---|---|
| EP | 0711174 A1 | 5/1996 |
| EP | 1827486 A2 | 9/2007 |
| EP | 1597369 B1 | 10/2007 |
| JP | 2007512008 A | 5/2007 |
| WO | 2005004984 A1 | 1/2005 |
| WO | 2005049847 A1 | 6/2005 |
| WO | 2006067198 A2 | 6/2006 |
| WO | 2009044988 A1 | 4/2009 |
| WO | 2013151672 A2 | 10/2013 |
| WO | 2014113089 A2 | 7/2014 |
| WO | 2019147844 A1 | 8/2019 |

OTHER PUBLICATIONS

Esposito (Current opinion in biotechnology 17.4 (2006): 353-358) (Year: 2006).*
Delgado (Biochimica et Biophysica Acta (BBA)-Molecular Cell Research 1833.10 (2013): 2279-2292) (Year: 2013).*
Garcia-Calvo et al., "Purification and Catalytic Properties of Human Caspase Family Members", Cell Death and Differentiation, Nature Publishing Group, vol. 6, Jan. 1, 1999, pp. 362-369.
International Search Report and Written Opinion for corresponding application, PCT/EP2020/072934, date of mailing Dec. 21, 2020.
Lok et al., "CASP2 from *Castor canadensis* (American beaver)", Nov. 22, 2017 (Nov. 22, 2017) Retrieved from the Internet: <URL:https://www.uniprot.org/uniprot'AOA250YIA5.txt>.
Mackenzie et al., "Death by Caspase Dimerization" In: "Retinal Degenerative Diseases: Advances in Experimental Medicine and Biology", Jan. 1, 2012, vol. 747, pp. 55-73.
Srinivasula et al., "Generation of constitutively active recombinant Caspases-3 and -6 by rearrangement of their subunits", Journal of Biological Chemistry, American Society for Biochemistry and Molecular Biology, vol. 273, No. 17, Apr. 24, 1998, pp. 10107-1011.
Yu et al., "Circular permutation: a different way to engineer enzyme structure and function", Trends in Biotechnology, Elsevier Publications, Cambridge, vol. 29, No. 1, Jan. 1, 2011, pp. 18-25.
Ho et al., "Caspase-2 is resistant to inhibition by inhibitor of apoptosis proteins (IAPs) and can activate caspase-7", The FEBS Journal, vol. 272, 2005, p. 1401-1414.

(Continued)

*Primary Examiner* — Manjunath N Rao
*Assistant Examiner* — Jae W Lee
(74) *Attorney, Agent, or Firm* — Mary Breen Smith

(57) ABSTRACT

The invention refers to a single-chain circular permuted caspase-2 comprising the following structure from N- to C-terminus: i) a small subunit of a caspase-2, or a functionally active variant thereof; and ii) a large subunit of a caspase-2, or a functionally active variant thereof, wherein the cp caspase-2 comprises one or more amino acid substitutions increasing P1' tolerance of the cp caspase-2 compared to a cp caspase-2 without the amino acid substitutions.

13 Claims, 86 Drawing Sheets

Specification includes a Sequence Listing.

(56) References Cited

OTHER PUBLICATIONS

Dahal et al., "Caspase-2 cleaves DNA fragmentation factor (DFF45)/ Inhibitor of caspase-activated DNase(ICAD)", Archives of Biochemistry and Biophysics, vol. 468, No. 1, 2007, p. 134-139.
Oehlknecht et al., "Enhancing the promiscuity of a member of the Caspase protease family by rational design", Proteins: Structure, Function, and Bioinformatics, vol. 88, No. 10, 2020, p. 1303-1318.
Allet B., et al., "Dissecting Processing and Apoptotic Activity of a Cysteine Protease by Mutant Analysis," Journal of Cell Biology, 1996, vol. 135, No. 2, pp. 479-486.
Alnemri E.S., et al., "Human ICE/CED-3 Protease Nomenclature," Cell, 1996, vol. 87, No. 2, p. 171.
Arama E., et al., "Caspase Activity and a Specific Cytochrome C Are Required for Sperm Differentiation in Drosophila," Developmental Cell, 2003, vol. 4, No. 5, pp. 687-697.
Beernink P. T., et al., "Random Circular Permutation Leading to Chain Disruption Within and Near Alpha Helices in the Catalytic Chains of Aspartate Transcarbamoylase: Effects on Assembly, Stability, and Function," Protein Science, 2001, vol. 10, No. 3, pp. 528-537, DOI: 10.1110/ps.39001, XP001011142.
Boucher D., et al., "General In Vitro Caspase Assay Procedures," Caspases, Paracaspases, and Metacaspases, Methods and Protocols, Springer Science+Business Media, 2014, pp. 3-30.
Cheung R.C.F., et al., "Immobilized Metal Ion Affinity Chromatography: A Review on Its Applications," Applied Microbiology and Biotechnology, 2012, vol. 96, No. 6, pp. 1411-1420, DOI: 10.1007/ s00253-012-4507-0, XP035139558.
Choilee, Applied Microbiology and Biotechnology, 2004, vol. 64, pp. 625-635.
Feeney B., et al., "Novel Protein Purification System Utilizing an N-Terminal Fusion Protein and a Caspase-3 Cleavable Linker," Protein Expression and Purification, 2006.
Geisbrecht E.R., et al., "A Role for Drosophila IAP1-Mediated Caspase Inhibition in Rac-Dependent Cell Migration," Cell, 2004, vol. 118, No. 1, pp. 111-125.
Goeddel D.V., et al., "Expression in Escherichia coli of Chemically Synthesized Genes for Human Insulin," Proceedings of the National Academy of Sciences USA, 1979, vol. 76, No. 1, pp. 106-110.
Grinshpon, et al., Biochemistry Journal—AC, 2019, vol. 476, No. 22, pp. 3475-3492.
Guan D., et al., "Challenges and Recent Advances in Affinity Purification of Tag-Free Proteins," Biotechnology Letters, 2014, vol. 36, pp. 1391-1406, DOI: 10.1007/s10529-014-1509-2, XP055699654.
Itakura K., et al., "Expression in Escherichia coli of a Chemically Synthesized Gene for the Hormone Somatostatin," Science, 1977, vol. 198, No. 4321, pp. 1056 LP-1063, XP000562701.
Karyolaimos, et al., Frontiers in Microbiology, 2019, vol. 10, pp. 101-128.
Khan F., et al., "Histidine Affinity Tags Affect MSP142 Structural Stability and Immunodominance in Mice," Biotechnology Journal, 2012, vol. 7, No. 1, pp. 133-147.
Kitevska T., et al., "Analysis of the Minimal Specificity of Caspase-2 and Identification of Ac-VDTTD-AFC as a Caspase-2-Selective Peptide Substrate," Bioscience Reports, 2014, vol. 34.
Kumar P., et al., "The Mycobacterium tuberculosis Protein Kinase K Modulates Activation of Transcription From the Promoter of Mycobacterial Monooxygenase Operon Through Phosphorylation of the Transcriptional Regulator VirS," Journal of Biological Chemistry, 2009, vol. 284, No. 17, pp. 11090-11099.
Purbey P. K., et al., "GST Fusion Vector With Caspase-6 Cleavage Site for Removal of Fusion Tag During col. Purification," BioTechniques, 2005, vol. 38, No. 3, pp. 360-366, XP055624091.
Salmena L., et al., "Essential Role for Caspase 8 in T-Cell Homeostasis and T-Cell Mediated Immunity," Genes and Development, 2003, vol. 17, pp. 883-895, DOI: 10.1101/gad.1063703, XP002320054.
Sauer, et al., "A Two-Step Process for Capture and Purification of Human Basic Fibroblast Growth Factor From E. coli Homogenate: Yield Versus Endotoxin Clearance," Protein Expression and Purification, 2019, vol. 153, pp. 70-82.
Schweizer A., et al., "Crystal Structure of Caspase-2, Apical Initiator of the Intrinsic Apoptotic Pathway," Journal of Biological Chemistry, 2003, vol. 278, No. 43, pp. 42441-42447, DOI: 10.1074/ jbc.M304895200, XP055068115.
Shalini S., et al., "Old, New and Emerging Functions of Caspases," Cell Death and Differentiation, 2015, vol. 22, No. 4.
Srivastava A., et al., "Role of a Disulphide Bond in Helicobacter Pylori Arginase," Biochemical and Biophysical Research Communications, 2010, vol. 395, No. 3, pp. 348-351.
Stennicke H.R., et al., "Caspases: Preparation and Characterization," Methods: A Companion to Methods in Enzymology, 1999, vol. 17, No. 4, pp. 313-319, DOI: 10. 1006/meth.1999.0745, XP004466981.
Talanian R.V., et al., "Substrate Specificities of Caspase Family Proteases," Journal of Biological Chemistry, 1997, vol. 272, No. 15, pp. 9677-9682, DOI: 10.1074/jbc.272.15.9677, XP000652322.
Thornberry N.A., et al., "A Combinatorial Approach Defines Specificities of Members of the Caspase Family and Granzyme B : Functional Relationships Established for Key Mediators of Apoptosis," The Journal of Biological Chemistry, 1997, vol. 272, No. 29, pp. 17907-17911, DOI: 10.1074/jbc.272.29.17907, XP002145059.
Timmer J., et al., "Caspase Substrates," Cell Death and Differentiation, 2007, vol. 14, pp. 66-72, DOI: 10.1038/SJ.CDD.4402059, XP002516738.
Walsh J.G., et al., "Executioner Caspase-3 and Caspase-7 Are Functionally Distinct Proteases," Proceedings of the National Academy of Sciences, 2008, vol. 105, No. 35, pp. 12815-12819.
Xue D., et al., "The Caenorhabditis elegans Cell-Death Protein CED-3 Is a Cysteine Protease With Substrate Specificities Similar to Those of the Human CPP32 Protease," Genes and Development, 1996, vol. 10, No. 9, pp. 1073-1083.

* cited by examiner

Fig. 1 (Caspase Sequences)

SEQ ID No. 1 (S9 D285E variant with N-terminal *His Tag*, CEESA, GS linker and E105V, D285E substitutions)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETERGVDQQD

SEQ ID No. 2 (human small cp caspase-2 subunit pro-peptide):

GKNHAGSPGCEESX

SEQ ID No. 3 (human small cp caspase-2 subunit):

AGKEKLPKMRLPTRSDMICGYACLKGTAAMRNTKRGSWYIEALAQVFSERAC
DMHVADMLVKVNALIKDREGYAPGTEFHRCKEMSEYCSTLCRHLYLFPGHPPT

SEQ ID No. 4 (human large cp caspase-2 subunit):

GPVCLQVKPCTPGFYQTHFQLAYRLQSRPRGLALVLSNVHFTGEKELEFRSG
GDVDHSTLVTLFKLLGYDVRVLCDQTAQEMQEKLQNFAQLPAHRVTDSCIVALLSHG
VEGAIYGVDGKLLQLQEVFQLFDNANCPSLQNKPKMFFIQACRGDETD

SEQ ID No. 5 (human large cp caspase-2 subunit pro-peptide):

RGVDQQD

SEQ ID No. 6 (amino acid sequence of cp caspase-2 with *N-terminal His Tag*, GS linker and CEESA)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

Fig. 1 continued

SEQ ID No. 7 (nucleotide sequence of cp caspase-2 with *N-terminal His Tag*, GS linker and CEESA)

ATGCACCATCATCACCATCATGGCAAAAATCATGCAGGTAGTCCGGGTTGT
GAAGAAAGCGCAGCAGGTAAAGAAAAACTGCCGAAAATGCGTCTGCCGACCCGT
AGCGATATGATTTGTGGTTATGCATGTCTGAAAGGCACCGCAGCAATGCGTAATA
CCAAACGTGGTAGCTGGTATATTGAAGCACTGGCACAGGTTTTTAGCGAACGTGC
ATGTGATATGCATGTTGCAGATATGCTGGTTAAAGTGAACGCCCTGATTAAAGATC
GTGAAGGTTATGCACCGGGTACAGAATTTCATCGTTGTAAAGAAATGAGCGAGTA
TTGTAGCACCCTGTGTCGTCATCTGTACCTGTTTCCGGGTCATCCTCCGACCGGA
TCCGGTCCGGTTTGTCTGCAGGTTAAACCGTGTACACCGGAATTTTATCAGACCC
ATTTTCAGCTGGCATATCGTCTGCAGAGCCGTCCGCGTGGTCTGGCACTGGTTCT
GAGCAATGTTCATTTTACCGGTGAAAAAGAACTGGAATTTCGTAGCGGTGGTGAT
GTTGATCATAGTACCCTGGTTACCCTGTTTAAACTGCTGGGTTATGACGTTCATGT
TCTGTGTGATCAGACCGCACAAGAAATGCAAGAGAAACTGCAGAATTTTGCACAG
CTGCCTGCACATCGTGTTACCGATAGCTGTATTGTTGCACTGCTGAGCCATGGTG
TTGAAGGTGCAATTTATGGTGTGGATGGCAAACTGCTGCAACTGCAAGAAGTGTT
TCAGCTGTTTGATAATGCAAATTGTCCGAGCCTGCAGAATAAACCGAAAATGTTTT
TTATCCAGGCCTGCCGTGGTGATGAAACCGATCGTGGTGTTGATCAGCAGGATTA
A

SEQ ID No. 8 (nucleotide sequence of cp caspase-2 without tag, with GS linker and CEES<u>A</u>)

ATGGGCAAAAATCATGCAGGTAGTCCGGGTTGTGAAGAAAGCGCAGCAGG
TAAAGAAAAACTGCCGAAAATGCGTCTGCCGACCCGTAGCGATATGATTTGTGGT
TATGCATGTCTGAAAGGCACCGCAGCAATGCGTAATACCAAACGTGGTAGCTGGT
ATATTGAAGCACTGGCACAGGTTTTTAGCGAACGTGCATGTGATATGCATGTTGC
AGATATGCTGGTTAAAGTGAACGCCCTGATTAAAGATCGTGAAGGTTATGCACCG
GGTACAGAATTTCATCGTTGTAAAGAAATGAGCGAGTATTGTAGCACCCTGTGTC
GTCATCTGTACCTGTTTCCGGGTCATCCTCCGACCGGATCCGGTCCGGTTTGTCT
GCAGGTTAAACCGTGTACACCGGAATTTTATCAGACCCATTTTCAGCTGGCATATC
GTCTGCAGAGCCGTCCGCGTGGTCTGGCACTGGTTCTGAGCAATGTTCATTTTAC
CGGTGAAAAAGAACTGGAATTTCGTAGCGGTGGTGATGTTGATCATAGTACCCTG
GTTACCCTGTTTAAACTGCTGGGTTATGACGTTCATGTTCTGTGTGATCAGACCGC
ACAAGAAATGCAAGAGAAACTGCAGAATTTTGCACAGCTGCCTGCACATCGTGTT
ACCGATAGCTGTATTGTTGCACTGCTGAGCCATGGTGTTGAAGGTGCAATTTATG
GTGTGGATGGCAAACTGCTGCAACTGCAAGAAGTGTTTCAGCTGTTTGATAATGC
AAATTGTCCGAGCCTGCAGAATAAACCGAAAATGTTTTTTATCCAGGCCTGCCGT
GGTGATGAAACCGATCGTGGTGTTGATCAGCAGGAT

Fig. 1 continued

SEQ ID No. 9 (amino acid sequence of cp caspase-2 without tag, with GS linker and CEESA)

MGKNHAGSPGCEESAAGKEKLPKMRLPTRSDMICGYACLKGTAAMRNTKRG
SWYIEALAQVFSERACDMHVADMLVKVNALIKDREGYAPGTEFHRCKEMSEYCSTLC
RHLYLFPGHPPTGSGPVCLQVKPCTPEFYQTHFQLAYRLQSRPRGLALVLSNVHFTG
EKELEFRSGGDVDHSTLVTLFKLLGYDVHVLCDQTAQEMQEKLQNFAQLPAHRVTDS
CIVALLSHGVEGAIYGVDGKLLQLQEVFQLFDNANCPSLQNKPKMFFIQACRGDETDR
GVDQQD

SEQ ID No. 10 (nucleotide sequence of human wt caspase-2 with CARD)

ATGGCCGCTGACAGGGGACGCAGGATATTGGGAGTGTGTGGCATGCATC
CTCATCATCAGGAAACTCTAAAAAAGAACCGAGTGGTGCTAGCCAAACAGCTGTT
GTTGAGCGAATTGTTAGAACATCTTCTGGAGAAGGACATCATCACCTTGGAAATG
AGGGAGCTCATCCAGGCCAAAGTGGGCAGTTTCAGCCAGAATGTGGAACTCCTC
AACTTGCTGCCTAAGAGGGGTCCCCAAGCTTTTGATGCCTTCTGTGAAGCACTGA
GGGAGACCAAGCAAGGCCACCTGGAGGATATGTTGCTCACCACCCTTTCTGGGC
TTCAGCATGTACTCCCACCGTTGAGCTGTGACTACGACTTGAGTCTCCCTTTTCC
GGTGTGTGAGTCCTGTCCCCTTTACAAGAAGCTCCGCCTGTCGACAGATACTGTG
GAACACTCCCTAGACAATAAAGATGGTCCTGTCTGCCTTCAGGTGAAGCCTTGCA
CTCCTGAATTTTATCAAACACACTTCCAGCTGGCATATAGGTTGCAGTCTCGGCCT
CGTGGCCTAGCACTGGTGTTGAGCAATGTGCACTTCACTGGAGAGAAAGAACTG
GAATTTCGCTCTGGAGGGGATGTGGACCACAGTACTCTAGTCACCCTCTTCAAGC
TTTTGGGCTATGACGTCCATGTTCTATGTGACCAGACTGCACAGGAAATGCAAGA
GAAACTGCAGAATTTTGCACAGTTACCTGCACACCGAGTCACGGACTCCTGCATC
GTGGCACTCCTCTCGCATGGTGTGGAGGGCGCCATCTATGGTGTGGATGGGAAA
CTGCTCCAGCTCCAAGAGGTTTTTCAGCTCTTTGACAACGCCAACTGCCCAAGCC
TACAGAACAAACCAAAAATGTTCTTCATCCAGGCCTGCCGTGGAGATGAGACTGA
TCGTGGGGTTGACCAACAAGATGGAAAGAACCACGCAGGATCCCCTGGGTGCGA
GGAGAGTGATGCCGGTAAAGAAAAGTTGCCGAAGATGAGACTGCCCACGCGCTC
AGACATGATATGCGGCTATGCCTGCCTCAAAGGGACTGCCGCCATGCGGAACAC
CAAACGAGGTTCCTGGTACATCGAGGCTCTTGCTCAAGTGTTTTCTGAGCGGGCT
TGTGATATGCACGTGGCCGACATGCTGGTTAAGGTGAACGCACTTATCAAGGATC
GGGAAGGTTATGCTCCTGGCACAGAATTCCACCGGTGCAAGGAAATGTCTGAATA
CTGCAGCACTCTGTGCCGCCACCTCTACCTGTTCCCAGGACACCCTCCCACATGA

SEQ ID No. 11 (amino acid sequence of human wt caspase-2 with CARD)

MAAPSAGSWSTFQHKELMAADRGRRILGVCGMHPHHQETLKKNRVVLAKQL
LLSELLEHLLEKDIITLEMRELIQAKVGSFSQNVELLNLLPKRGPQAFDAFCEALRETKQ
GHLEDMLLTTLSGLQHVLPPLSCDYDLSLPFPVCESCPLYKKLRLSTDTVEHSLDNKD
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQDGKNHA
GSPGCEESDAGKEKLPKMRLPTRSDMICGYACLKGTAAMRNTKRGSWYIEALAQVF
SERACDMHVADMLVKVNALIKDREGYAPGTEFHRCKEMSEYCSTLCRHLYLFPGHP
PT

Fig. 1 continued

SEQ ID No. 12 (nucleotide sequence of cp caspase-2 D285E, with *N-terminal His Tag*, GS linker and CEES<u>A</u>)

ATGCACCATCATCACCATCATGGCAAAAATCATGCAGGTAGTCCGGGTTGT
GAAGAAAGCGCAGCAGGTAAAGAAAAACTGCCGAAAATGCGTCTGCCGACCCGT
AGCGATATGATTTGTGGTTATGCATGTCTGAAAGGCACCGCAGCAATGCGTAATA
CCAAACGTGGTAGCTGGTATATTGAAGCACTGGCACAGGTTTTTAGCGAACGTGC
ATGTGATATGCATGTTGCAGATATGCTGGTTAAAGTGAACGCCCTGATTAAAGATC
GTGAAGGTTATGCACCGGGTACAGAATTTCATCGTTGTAAAGAAATGAGCGAGTA
TTGTAGCACCCTGTGTCGTCATCTGTACCTGTTTCCGGGTCATCCTCCGACCGGA
TCCGGTCCGGTTTGTCTGCAGGTTAAACCGTGTACACCGGAATTTTATCAGACCC
ATTTTCAGCTGGCATATCGTCTGCAGAGCCGTCCGCGTGGTCTGGCACTGGTTCT
GAGCAATGTTCATTTTACCGGTGAAAAAGAACTGGAATTTCGTAGCGGTGGTGAT
GTTGATCATAGTACCCTGGTTACCCTGTTTAAACTGCTGGGTTATGACGTTCATGT
TCTGTGTGATCAGACCGCACAAGAAATGCAAGAGAAACTGCAGAATTTTGCACAG
CTGCCTGCACATCGTGTTACCGATAGCTGTATTGTTGCACTGCTGAGCCATGGTG
TTGAAGGTGCAATTTATGGTGTGGATGGCAAACTGCTGCAACTGCAAGAAGTGTT
TCAGCTGTTTGATAATGCAAATTGTCCGAGCCTGCAGAATAAACCGAAAATGTTTT
TTATCCAGGCCTGCCGTGGTGATGAAACCGAGCGTGGTGTTGATCAGCAGGATTA
A

SEQ ID No. 13 (amino acid sequence of cp caspase-2 <u>D285E</u>, with *N-terminal His tag* and GS linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDET<u>E</u>RGVDQQD

SEQ ID No. 14 (amino acid sequence of cp caspase-2 Stop, with *N-terminal His Tag*, GS linker and CEES<u>A</u>)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETD

Fig. 1 continued

SEQ ID No. 15 (amino acid sequence of cp caspase-2 Strep, D292S, with *N-terminal His Tag*, GS Linker, CEESA and *Strep tag*)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQSGS*GWSHPQFEK*

SEQ ID No. 16 (amino acid sequence of cp caspase-2 D285E Strep, D285E, D292S, with *N-terminal His Tag*, GS Linker, CEESA and *Strep tag*

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETERGVDQQSGS*GWSHPQFEK*

SEQ ID No. 17 (amino acid sequence of cp caspase-2 with D282T, N-terminal *His tag*, CEESA, and GS Linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGTETDRGVDQQD

SEQ ID No. 18 (amino acid sequence of cp caspase-2 with H185A and D282T, *N-terminal His tag*, CEESA, and GS Linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDASTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGTETDRGVDQQD

Fig. 1 continued

SEQ ID No. 23 (cp caspase-2 S17 D285E with E105V, C132R, E141G, H200R mutations, CEESA, GS linker, without N-terminal His tag)

GKNHAGSPGCEESAAGKEKLPKMRLPTRSDMICGYACLKGTAAMRNTKRGS
WYIEALAQVFSERACDMHVADMLVKVNALIKDREGYAPGTEFHRCKVMSEYCSTLCR
HLYLFPGHPPTGSGPVRLQVKPCTPGFYQTHFQLAYRLQSRPRGLALVLSNVHFTGE
KELEFRSGGDVDHSTLVTLFKLLGYDVRVLCDQTAQEMQEKLQNFAQLPAHRVTDS
CIVALLSHGVEGAIYGVDGKLLQLQEVFQLFDNANCPSLQNKPKMFFIQACRGDETER
GVDQQD

SEQ ID No. 24 (cp caspase-2 S17 D285E with E105V, C132R, E141G, H200R mutations, N-terminal His tag, CEESA and GS linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVRLQVKPCTPGFYQTHFQLAYRLQSRPRGLALVL
SNVHFTGEKELEFRSGGDVDHSTLVTLFKLLGYDVRVLCDQTAQEMQEKLQNFAQLP
AHRVTDSCIVALLSHGVEGAIYGVDGKLLQLQEVFQLFDNANCPSLQNKPKMFFIQAC
RGDETERGVDQQD

SEQ ID No. 25 (cp caspase-2 S20 D285E with C203Y mutation, CEESA, and GS linker, without His Tag)

GKNHAGSPGCEESAAGKEKLPKMRLPTRSDMICGYACLKGTAAMRNTKRGS
WYIEALAQVFSERACDMHVADMLVKVNALIKDREGYAPGTEFHRCKEMSEYCSTLCR
HLYLFPGHPPTGSGPVCLQVKPCTPEFYQTHFQLAYRLQSRPRGLALVLSNVHFTGE
KELEFRSGGDVDHSTLVTLFKLLGYDVHVLYDQTAQEMQEKLQNFAQLPAHRVTDSC
IVALLSHGVEGAIYGVDGKLLQLQEVFQLFDNANCPSLQNKPKMFFIQACRGDETERG
VDQQD

SEQ ID No. 26 (cp caspase-2 S20 D285E with C203Y mutation, N-terminal His-tag, CEESA, and GS linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLYDQTAQEMQEKLQNFAQLP
AHRVTDSCIVALLSHGVEGAIYGVDGKLLQLQEVFQLFDNANCPSLQNKPKMFFIQAC
RGDETERGVDQQD

Fig. 1 continued

SEQ ID No. 27 (cp caspase-2 SV4 D285E with V201A mutation CEESA, and GS linker, without His Tag)

GKNHAGSPGCEESAAGKEKLPKMRLPTRSDMICGYACLKGTAAMRNTKRGS
WYIEALAQVFSERACDMHVADMLVKVNALIKDREGYAPGTEFHRCKEMSEYCSTLCR
HLYLFPGHPPTGSGPVCLQVKPCTPEFYQTHFQLAYRLQSRPRGLALVLSNVHFTGE
KELEFRSGGDVDHSTLVTLFKLLGYDVHALCDQTAQEMQEKLQNFAQLPAHRVTDS
CIVALLSHGVEGAIYGVDGKLLQLQEVFQLFDNANCPSLQNKPKMFFIQACRGDETER
GVDQQD

SEQ ID No. 28 (cp caspase-2 SV4 D285E with V201A mutation, N-terminal His-tag, CEESA, and GS linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHALCDQTAQEMQEKLQNFAQL
PAHRVTDSCIVALLSHGVEGAIYGVDGKLLQLQEVFQLFDNANCPSLQNKPKMFFIQA
CRGDETERGVDQQD

SEQ ID No. 29 (cp caspase-2 SV30 D285E with E174G mutation, CEESA, and GS linker, without His Tag)

GKNHAGSPGCEESAAGKEKLPKMRLPTRSDMICGYACLKGTAAMRNTKRGS
WYIEALAQVFSERACDMHVADMLVKVNALIKDREGYAPGTEFHRCKEMSEYCSTLCR
HLYLFPGHPPTGSGPVCLQVKPCTPEFYQTHFQLAYRLQSRPRGLALVLSNVHFTGE
KGLEFRSGGDVDHSTLVTLFKLLGYDVHVLCDQTAQEMQEKLQNFAQLPAHRVTDS
CIVALLSHGVEGAIYGVDGKLLQLQEVFQLFDNANCPSLQNKPKMFFIQACRGDETER
GVDQQD

SEQ ID No. 30 (cp caspase-2 SV30 D285E with E174G mutation, N-terminal His-tag, CEESA, and GS linker)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKGLEFRSGGDVDHSTLVTLFKLLGYDVHVLCDQTAQEMQEKLQNFAQL
PAHRVTDSCIVALLSHGVEGAIYGVDGKLLQLQEVFQLFDNANCPSLQNKPKMFFIQA
CRGDETERGVDQQD

Fig. 1 continued

SEQ ID No. 35 (amino acid sequence of cp caspase-2 with N-terminal His-tag, T7A3 tag, CEESA, and GS linker)

M*HHHHHH*LEDPERNKERKEAELEAETAEQGKNHAGSPGCEESAAGKEKLPK
MRLPTRSDMICGYACLKGTAAMRNTKRGSWYIEALAQVFSERACDMHVADMLVKVN
ALIKDREGYAPGTEFHRCKEMSEYCSTLCRHLYLFPGHPPTGSGPVCLQVKPCTPEF
YQTHFQLAYRLQSRPRGLALVLSNVHFTGEKELEFRSGGDVDHSTLVTLFKLLGYDV
HVLCDQTAQEMQEKLQNFAQLPAHRVTDSCIVALLSHGVEGAIYGVDGKLLQLQEVF
QLFDNANCPSLQNKPKMFFIQACRGDETDRGVDQQD

SEQ ID No. 36 (nucleotide sequence of cp caspase-2 with N-terminal His-tag, T7A3 tag, CEESA, and GS linker)

ATG*CACCATCATCACCATCAT*CTGGAGGATCCGGAACGCAACAAAGAGC
GAAAGGAAGCTGAGTTGGAAGCTGAGACCGCTGAGCAAGGCAAAAATCATGCA
GGTAGTCCGGGTTGTGAAGAAAGCGCAGCAGGTAAAGAAAAACTGCCGAAAATG
CGTCTGCCGACCCGTAGCGATATGATTTGTGGTTATGCATGTCTGAAAGGCACCG
CAGCAATGCGTAATACCAAACGTGGTAGCTGGTATATTGAAGCACTGGCACAGGT
TTTTAGCGAACGTGCATGTGATATGCATGTTGCAGATATGCTGGTTAAAGTGAACG
CCCTGATTAAAGATCGTGAAGGTTATGCACCGGGTACAGAATTTCATCGTTGTAAA
GAAATGAGCGAGTATTGTAGCACCCTGTGTCGTCATCTGTACCTGTTTCCGGGTC
ATCCTCCGACCGGATCCGGTCCGGTTTGTCTGCAGGTTAAACCGTGTACACCGG
AATTTTATCAGACCCATTTTCAGCTGGCATATCGTCTGCAGAGCCGTCCGCGTGG
TCTGGCACTGGTTCTGAGCAATGTTCATTTTACCGGTGAAAAAGAACTGGAATTTC
GTAGCGGTGGTGATGTTGATCATAGTACCCTGGTTACCCTGTTTAAACTGCTGGG
TTATGACGTTCATGTTCTGTGTGATCAGACCGCACAAGAAATGCAAGAGAAACTG
CAGAATTTTGCACAGCTGCCTGCACATCGTGTTACCGATAGCTGTATTGTTGCACT
GCTGAGCCATGGTGTTGAAGGTGCAATTTATGGTGTGGATGGCAAACTGCTGCAA
CTGCAAGAAGTGTTTCAGCTGTTTGATAATGCAAATTGTCCGAGCCTGCAGAATAA
ACCGAAAATGTTTTTTATCCAGGCCTGCCGTGGTGATGAAACCGATCGTGGTGTT
GATCAGCAGGATTAA

SEQ ID No. 37 (amino acid sequence of T7A3 tag)

LEDPERNKERKEAELEAETAEQ

SEQ ID No. 38 (nucleotide sequence of T7A3 tag)

CTGGAGGATCCGGAACGCAACAAAGAGCGAAAGGAAGCTGAGTTGGAAG
CTGAGACCGCTGAGCAA

Fig. 1 continued

SEQ ID No. 39 (amino acid sequence of cp caspase-2 with T7A3 tag and *His tag*, CEESA and GS linker)

MLEDPERNKERKEAELEAETAEQ*HHHHHH*GKNHAGSPGCEESAAGKEKLPK
MRLPTRSDMICGYACLKGTAAMRNTKRGSWYIEALAQVFSERACDMHVADMLVKVN
ALIKDREGYAPGTEFHRCKEMSEYCSTLCRHLYLFPGHPPTGSGPVCLQVKPCTPEF
YQTHFQLAYRLQSRPRGLALVLSNVHFTGEKELEFRSGGDVDHSTLVTLFKLLGYDV
HVLCDQTAQEMQEKLQNFAQLPAHRVTDSCIVALLSHGVEGAIYGVDGKLLQLQEVF
QLFDNANCPSLQNKPKMFFIQACRGDETDRGVDQQD

SEQ ID No. 40 (nucleotide sequence of cp caspase-2 with T7A3 tag and *His tag*, CEESA, and GS linker)

ATGCTGGAGGATCCGGAACGCAACAAAGAGCGAAAGGAAGCTGAGTTG
GAAGCTGAGACCGCTGAGCAA*CACCATCATCACCATCAT*GGCAAAAATCATGCA
GGTAGTCCGGGTTGTGAAGAAAGCGCAGCAGGTAAAGAAAAACTGCCGAAAATG
CGTCTGCCGACCCGTAGCGATATGATTTGTGGTTATGCATGTCTGAAAGGCACCG
CAGCAATGCGTAATACCAAACGTGGTAGCTGGTATATTGAAGCACTGGCACAGGT
TTTTAGCGAACGTGCATGTGATATGCATGTTGCAGATATGCTGGTTAAAGTGAACG
CCCTGATTAAAGATCGTGAAGGTTATGCACCGGGTACAGAATTTCATCGTTGTAAA
GAAATGAGCGAGTATTGTAGCACCCTGTGTCGTCATCTGTACCTGTTTCCGGGTC
ATCCTCCGACCGGATCCGGTCCGGTTTGTCTGCAGGTTAAACCGTGTACACCGG
AATTTTATCAGACCCATTTTCAGCTGGCATATCGTCTGCAGAGCCGTCCGCGTGG
TCTGGCACTGGTTCTGAGCAATGTTCATTTTACCGGTGAAAAAGAACTGGAATTTC
GTAGCGGTGGTGATGTTGATCATAGTACCCTGGTTACCCTGTTTAAACTGCTGGG
TTATGACGTTCATGTTCTGTGTGATCAGACCGCACAAGAAATGCAAGAGAAACTG
CAGAATTTTGCACAGCTGCCTGCACATCGTGTTACCGATAGCTGTATTGTTGCACT
GCTGAGCCATGGTGTTGAAGGTGCAATTTATGGTGTGGATGGCAAACTGCTGCAA
CTGCAAGAAGTGTTTCAGCTGTTTGATAATGCAAATTGTCCGAGCCTGCAGAATAA
ACCGAAAATGTTTTTTATCCAGGCCTGCCGTGGTGATGAAACCGATCGTGGTGTT
GATCAGCAGGATTAA

SEQ ID No. 41 (amino acid sequence of cp caspase-2 with T7AC tag and *His tag,* CEESA and GS linker)

MLEDPERNKERKEAELQAQTAEQ*HHHHHH*GKNHAGSPGCEESAAGKEKLP
KMRLPTRSDMICGYACLKGTAAMRNTKRGSWYIEALAQVFSERACDMHVADMLVKV
NALIKDREGYAPGTEFHRCKEMSEYCSTLCRHLYLFPGHPPTGSGPVCLQVKPCTPE
FYQTHFQLAYRLQSRPRGLALVLSNVHFTGEKELEFRSGGDVDHSTLVTLFKLLGYD
VHVLCDQTAQEMQEKLQNFAQLPAHRVTDSCIVALLSHGVEGAIYGVDGKLLQLQEV
FQLFDNANCPSLQNKPKMFFIQACRGDETDRGVDQQD

Fig. 1 continued

SEQ ID No. 42 (nucleotide sequence of cp caspase-2 with T7AC tag and *His tag, CEESA* and GS linker)

ATGCTGGAGGATCCGGAACGCAACAAAGAGCGAAAGGAAGCTGAGTTG CAAGCTCAAACCGCTGAGCAA*CACCATCATCACCATCAT*GGCAAAAATCATGCA GGTAGTCCGGGTTGTGAAGAAAGCGCAGCAGGTAAAGAAAAACTGCCGAAAATG CGTCTGCCGACCCGTAGCGATATGATTTGTGGTTATGCATGTCTGAAAGGCACCG CAGCAATGCGTAATACCAAACGTGGTAGCTGGTATATTGAAGCACTGGCACAGGT TTTTAGCGAACGTGCATGTGATATGCATGTTGCAGATATGCTGGTTAAAGTGAACG CCCTGATTAAAGATCGTGAAGGTTATGCACCGGGTACAGAATTTCATCGTTGTAAA GAAATGAGCGAGTATTGTAGCACCCTGTGTCGTCATCTGTACCTGTTTCCGGGTC ATCCTCCGACCGGATCCGGTCCGGTTTGTCTGCAGGTTAAACCGTGTACACCGG AATTTTATCAGACCCATTTTCAGCTGGCATATCGTCTGCAGAGCCGTCCGCGTGG TCTGGCACTGGTTCTGAGCAATGTTCATTTTACCGGTGAAAAAGAACTGGAATTTC GTAGCGGTGGTGATGTTGATCATAGTACCCTGGTTACCCTGTTTAAACTGCTGGG TTATGACGTTCATGTTCTGTGTGATCAGACCGCACAAGAAATGCAAGAGAAACTG CAGAATTTTGCACAGCTGCCTGCACATCGTGTTACCGATAGCTGTATTGTTGCACT GCTGAGCCATGGTGTTGAAGGTGCAATTTATGGTGTGGATGGCAAACTGCTGCAA CTGCAAGAAGTGTTTCAGCTGTTTGATAATGCAAATTGTCCGAGCCTGCAGAATAA ACCGAAAATGTTTTTTATCCAGGCCTGCCGTGGTGATGAAACCGATCGTGGTGTT GATCAGCAGGATTAA

SEQ ID No. 43 (amino acid sequence of T7AC tag)

LEDPERNKERKEAELQAQTAEQ

SEQ ID No. 44 (nucleotide sequence of T7AC tag)

CTGGAGGATCCGGAACGCAACAAAGAGCGAAAGGAAGCTGAGTTGCAAGC TCAAACCGCTGAGCAA

SEQ ID No. 45 (recognition site)

VDVAD

SEQ ID No. 46 (caspase-2 active site 1)

GEKELEFRSGGDVDH

SEQ ID No. 47 (caspase-2 active site 2)

LLSHGVEGAAIYGVDG

SEQ ID No. 48 (caspase-2 active site 3)

QACRGDET

SEQ ID No. 49 (caspase-2 active site 4)

AAMRNTKR

Fig. 1 continued

SEQ ID No. 50 (caspase-2 active site 5)

EGYAPGTEFHRCK

SEQ ID No. 51 (S9 variant with N-terminal *His Tag*, CEESA, GS linker and E105V substitution)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 52 (mS9 Pro D variant with N-terminal *His Tag*, CEESA, GS linker and E105V, G171D, V225G and D282E substitutions)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTDEKELEFRSGGDVDHSTLVTLFKLLGYDVHVLCDQTAQEMQEKLQNFAQLP
AHRGTDSCIVALLSHGVEGAIYGVDGKLLQLQEVFQLFDNANCPSLQNKPKMFFIQAC
RGEETDRGVDQQD

SEQ ID No. 53 (nucleotide sequence of mS9-Thr-0.8 variant, with N-terminal *His Tag*, CEESA, GS linker and K83E, E105V, E172V, V255M, D285Y mutations)

ATG*CACCATCATCACCATCAT*GGCAAAAATCATGCAGGTAGTCCGGGTTGTGAAG
AAAGCGCAGCAGGTAAAGAAAAACTGCCGAAAATGCGTCTGCCGACCCGTAGCG
ATATGATTTGTGGTTATGCATGTCTGAAAGGCACCGCAGCAATGCGTAATACCAAA
CGTGGTAGCTGGTATATTGAAGCACTGGCACAGGTTTTTAGCGAACGTGCATGTG
ATATGCATGTTGCAGATATGCTGGTTGAAGTGAACGCCCTGATTAAAGATCGTGA
AGGTTATGCACCGGGTACAGAATTTCATCGTTGTAAAGTAATGAGCGAGTATTGTA
GCACCCTGTGTCGACATCTATACCTGTTTCCGGGTCATCCTCCGACCGGATCCGG
TCCGGTTTGTCTGCAGGTTAAACCGTGTACACCGGAATTTTATCAGACCCATTTTC
AGCTGGCATATCGTCTGCAGAGCCGTCCGCGTGGTCTGGCACTGGTTCTGAGCA
ATGTTCATTTTACCGGTGTAAAAGAACTGGAATTTCGTAGCGGTGGTGATGTTGAT
CATAGTACCCTGGTTACCCTGTTTAAACTGCTGGGTTATGACGTTCATGTTCTGTG
TGATCAGACCGCACAAGAAATGCAAGAGAAACTGCAGAATTTTGCACAGCTGCCT
GCACATCGTGTTACCGATAGCTGTATTGTTGCACTGCTGAGCCATGGTGTTGAAG
GTGCAATTTATGGTGTGGATGGCAAACTGCTGCAACTGCAAGAAATGTTTCAGCT
GTTTGATAATGCAAATTGTCCGAGCCTGCAGAATAAACCGAAAATGTTTTTATCC
AGGCCTGCCGTGGTGATGAAACCTATCGGGGTGTGGATCAGCAGGATTAATAA

Fig. 1 continued

SEQ ID No. 54 (amino acid sequence of mS9-Thr-0.8 variant, with *N-terminal His Tag*, CEESA, GS linker and K83E, E105V, E172V, V255M and D285Y mutations)

M*HHHHHH*GKNHAGSPGCEESAAGKEKLPKMRLPTRSDMICGYACLKGTAAMRNTK
RGSWYIEALAQVFSERACDMHVADMLVEVNALIKDREGYAPGTEFHRCKVMSEYCS
TLCRHLYLFPGHPPTGSGPVCLQVKPCTPEFYQTHFQLAYRLQSRPRGLALVLSNVH
FTGVKELEFRSGGDVDHSTLVTLFKLLGYDVHVLCDQTAQEMQEKLQNFAQLPAHRV
TDSCIVALLSHGVEGAIYGVDGKLLQLQEMFQLFDNANCPSLQNKPKMFFIQACRGD
ETYRGVDQQD

SEQ ID No. 64 amino acid sequence of cp caspase-2 derived from *Sarcophilus harrisii* with N-terminal *His tag*, A mutation in propeptide of small subunit, and GS linker)

M*HHHHHH*GKEHMASPGCEQSAAGKEKILKMRLPTRSDMICGYACLKGTAAM
RNTKRGSWYIEALTQVFSERARDMHVADMLVKVNALIKDREGYAPGTEFHRCKEMS
EYSSTLCRHLYLFPGHPPTGSGPPSLQVKPCTSEFYRTHHHLAYRLQSRPRGLALVL
SNVHFNGEKDLEFRSGGDVDHSSLVTLFKLLDYDVHVLRDQTAQEMYEKLQRFAQL
STHQNTDSCVVALLSHGIEGGIYGVDGQLLQLQEVFQLFDNANCPNLQNKPKMFFIQ
ACRGDETDRGVDLRD

SEQ ID No. 65 nucleotide sequence of cp caspase-2 derived from *Sarcophilus harrisii* with N-terminal *His tag*, A mutation in propeptide of small subunit, and GS linker)

ATGATGCACCATCATCATCACCATGGTAAAGAACACATGGCAAGTCCGGGT
TGTGAACAGAGCGCAGCAGGTAAAGAAAAAATTCTGAAAATGCGTCTGCCGACAC
GTAGCGATATGATTTGTGGTTATGCATGTCTGAAAGGCACCGCAGCAATGCGTAA
TACCAAACGTGGTAGCTGGTATATTGAAGCACTGACCCAGGTTTTTAGCGAACGT
GCCCGTGATATGCATGTTGCAGATATGCTGGTTAAAGTGAACGCCCTGATTAAAG
ATCGTGAAGGTTATGCACCGGGTACAGAATTTCATCGTTGTAAAGAAATGAGCGA
GTATAGCAGCACCCTGTGTCGTCATCTGTACCTGTTTCCGGGTCATCCTCCGACC
GGTAGCGGTCCGCCTAGCCTGCAGGTTAAACCGTGTACCAGCGAATTTTATCGTA
CCCATCACCATCTGGCATATCGTCTGCAGAGCCGTCCGCGTGGTCTGGCACTGG
TTCTGAGCAATGTTCATTTTAATGGCGAGAAAGATCTGGAATTTCGTAGCGGTGGT
GATGTTGATCATAGCAGCCTGGTTACCCTGTTTAAACTGCTGGATTATGACGTTCA
TGTTCTGCGTGATCAGACCGCACAAGAAATGTATGAAAAACTGCAGCGTTTTGCA
CAGCTGAGCACCCATCAGAATACCGATAGCTGTGTTGTTGCCCTGCTGAGCCATG
GTATTGAAGGTGGTATTTATGGTGTTGATGGTCAGCTGCTGCAACTGCAAGAAGT
TTTTCAGCTGTTTGATAATGCGAATTGTCCGAACCTGCAGAACAAACCGAAAATGT
TTTTTATCCAGGCATGCCGTGGTGATGAAACCGATCGTGGTGTGGATCTGCGCGA
TTAATAA

Fig. 1 continued

SEQ ID No. 66 amino acid sequence of cp caspase-2 derived from *Anolis carolinensisilus* with N-terminal *His tag*, A mutation in propeptide of small subunit, and GS linker)

M*HHHHHH*GNDCASSPGCEETAANKKENPKLRLPTCSDMICGYACLKGTAAM
RNTKHGSWYVEALTSVFAEDSGHMHVADMLVKVNRLIKLREGHAPGTEFHRCKEMS
EYCSTLCQDLYLFPGYFPGGSGPHYPQVMPCTPEFYRTHEQLAYKLKSQPRGLALIL
SNIHFNKETDLDFRSGGDVDNTALHMLFKHLGYQVVVRQDRTAQEMKEELEIFSKHP
AHRNVDSCIVSLLSHGIEGGIYGIDGKLLQLQEIFRLFDNANCPNLQNKPKMFFVQACR
GDETDHGVDQID

SEQ ID No. 67 nucleotide sequence of cp caspase-2 derived from *Anolis carolinensisilus* with N-terminal *His tag*, A mutation in propeptide of small subunit, and GS linker)

ATGCATCATCACCATCATCATGGCAATGATTGTGCAAGCAGTCCGGGTTGT
GAAGAAACCGCAGCAAACAAAAAAGAAAATCCGAAACTGCGTCTGCCGACCTGTA
GCGATATGATTTGTGGTTATGCATGTCTGAAAGGCACCGCAGCCATGCGTAATAC
CAAACATGGTAGCTGGTATGTTGAAGCACTGACCAGCGTTTTTGCCGAAGATAGC
GGTCACATGCACGTTGCAGATATGCTGGTTAAAGTTAACCGTCTGATTAAACTGC
GTGAAGGTCATGCACCGGGTACAGAATTTCATCGTTGTAAAGAAATGAGCGAGTA
TTGTAGCACCCTGTGTCAGGATCTGTACCTGTTTCCGGGTTATTTTCCTGGTGGTA
GCGGTCCGCATTATCCGCAGGTTATGCCGTGTACACCGGAATTTTATCGTACCCA
TGAACAGCTGGCATACAAACTGAAAAGCCAGCCTCGTGGTCTGGCACTGATTCTG
AGCAATATTCACTTTAACAAAGAAACCGATCTGGATTTTCGTAGCGGTGGTGATGT
TGATAATACCGCACTGCACATGCTGTTCAAACATCTGGGTTATCAGGTTGTTGTTC
GTCAGGATCGCACCGCACAAGAAATGAAAGAAGAACTGGAAATCTTCAGCAAACA
TCCGGCACATCGTAATGTTGATAGCTGTATTGTTAGCCTGCTGAGCCATGGTATT
GAAGGTGGTATTTATGGCATTGATGGTAAACTGCTGCAACTGCAAGAAATCTTTCG
CCTGTTTGATAATGCCAATTGTCCGAATCTGCAGAACAAACCGAAAATGTTTTTTG
TTCAGGCATGCCGTGGTGATGAAACGGATCATGGTGTTGATCAGATCGATTGATA
A

SEQ ID No. 68 amino acid sequence of cp caspase-2 derived from *Callorhinchus milii* with N-terminal *His tag*, A mutation in propeptide of small subunit, and GS linker)

M*HHHHHH*GADAPGCEECAAGKERERTRRGKLPTQSDIICGYACLRGTAALRN
TRQGSWYIQALVKVFTERAHNTHVADMLVQVNAVIRDREGFAPGTDFHRCKEMAEY
SIFEEMEGETQRKQRRRKTAAPGSGSGTFSVRPTTAQFYHEHHKQSYRMASRPRGA
ALIVSNEVFVGEGLGHRPGGAADTGVLRALLSQLGYRVTSVCNSPAQELETRLRDFA
LSADHRRTDSCVVVLLSHGVEGAIYGVDGKLVQIHDIFQLFDNANCPNLQNKPKMFFI
QACRGDRTDRGVDRLD

Fig. 1 continued

SEQ ID No. 69 nucleotide sequence of cp caspase-2 derived from *Callorhinchus milii* with N-terminal *His tag*, A mutation in propeptide of small subunit, and GS linker)

ATGCATCATCACCATCATCATGGTGCAGATGCACCGGGTTGTGAAGAATGT
GCAGCAGGTAAAGAACGTGAACGTACCCGTCGTGGTAAACTGCCGACACAGAGC
GATATTATCTGTGGTTATGCATGTCTGCGTGGCACCGCAGCACTGCGTAATACCC
GTCAAGGTAGCTGGTATATTCAGGCACTGGTTAAAGTTTTTACCGAACGTGCACAT
AATACCCATGTTGCAGATATGCTGGTTCAGGTTAATGCAGTTATTCGTGATCGTGA
AGGTTTTGCTCCGGGTACAGATTTTCATCGTTGTAAAGAAATGGCCGAGTATAGC
ATCTTTGAAGAAATGGAAGGTGAAACCCAGCGTAAACAGCGTCGTCGTAAAACCG
CAGCGCCTGGTAGCGGTAGCGGCACCTTTAGCGTTCGTCCGACCACCGCACAGT
TTTATCATGAACATCATAAACAGAGCTATCGTATGGCAAGCCGTCCGCGTGGTGC
AGCACTGATTGTTAGCAATGAAGTTTTTGTTGGTGAAGGTCTGGGTCATCGTCCT
GGTGGTGCCGCAGATACCGGTGTTCTGCGTGCACTGCTGAGCCAGCTGGGTTAT
CGTGTTACCAGCGTTTGTAATAGTCCGGCACAAGAACTGGAAACCCGTCTGCGTG
ATTTTGCACTGAGCGCAGATCATCGTCGTACCGATAGCTGTGTTGTTGTTCTGCT
GAGTCATGGTGTTGAAGGTGCAATTTATGGTGTGGATGGCAAACTGGTTCAGATC
CATGATATTTTTCAGCTGTTTGATAATGCGAATTGCCCGAATCTGCAGAACAAACC
GAAAATGTTTTTTATCCAGGCATGTCGTGGTGATCGCACCGATCGTGGTGTTGAT
CGTCTGGATTAATAA

SEQ ID No. 70 (mS9 Pro E variant with *N-terminal His tag*, CEESA, GS linker and E105V, G171D, V225G,D282E and D285E substitutions)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTDEKELEFRSGGDVDHSTLVTLFKLLGYDVHVLCDQTAQEMQEKLQNFAQLP
AHRGTDSCIVALLSHGVEGAIYGVDGKLLQLQEVFQLFDNANCPSLQNKPKMFFIQAC
RGEETERGVDQQD

SEQ ID No. 71 (amino acid sequence of mS9 Pro E variant E105V, G171D, V225G, D282E, D285E substitutions with T7AC tag and *His tag,* CEESA, and GS linker)

MLEDPERNKERKEAELQAQTAEQ*HHHHHH*GKNHAGSPGCEESAAGKEKLP
KMRLPTRSDMICGYACLKGTAAMRNTKRGSWYIEALAQVFSERACDMHVADMLVKV
NALIKDREGYAPGTEFHRCKVMSEYCSTLCRHLYLFPGHPPTGSGPVCLQVKPCTPE
FYQTHFQLAYRLQSRPRGLALVLSNVHFTDEKELEFRSGGDVDHSTLVTLFKLLGYD
VHVLCDQTAQEMQEKLQNFAQLPAHRGTDSCIVALLSHGVEGAIYGVDGKLLQLQEV
FQLFDNANCPSLQNKPKMFFIQACRGEETERGVDQQD

Fig. 1 continued

SEQ ID No. 72 (amino acid sequence of mS9 Pro D variant E105V, G171D, V225G, D282E substitutions with T7AC tag and *His tag,* CEESA, and GS linker)

MLEDPERNKERKEAELQAQTAEQ*HHHHHH*GKNHAGSPGCEESAAGKEKLP
KMRLPTRSDMICGYACLKGTAAMRNTKRGSWYIEALAQVFSERACDMHVADMLVKV
NALIKDREGYAPGTEFHRCKVMSEYCSTLCRHLYLFPGHPPTGSGPVCLQVKPCTPE
FYQTHFQLAYRLQSRPRGLALVLSNVHFTDEKELEFRSGGDVDHSTLVTLFKLLGYD
VHVLCDQTAQEMQEKLQNFAQLPAHRGTDSCIVALLSHGVEGAIYGVDGKLLQLQEV
FQLFDNANCPSLQNKPKMFFIQACRGEETDRGVDQQD

SEQ ID No. 73 (amino acid sequence of cp caspase-2 Δ Linker with *N-terminal His Tag*, without linker between subunits and CEESA)

M*HHHHHH*GKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGPVCLQVKPCTPEFYQTHFQLAYRLQSRPRGLALVLSN
VHFTGEKELEFRSGGDVDHSTLVTLFKLLGYDVHVLCDQTAQEMQEKLQNFAQLPAH
RVTDSCIVALLSHGVEGAIYGVDGKLLQLQEVFQLFDNANCPSLQNKPKMFFIQACRG
DETDRGVDQQD

SEQ ID No. 74 (amino acid sequence of cp caspase-2 5 aa Linker with *N-terminal His Tag*, with GGSGG linker and CEESA)

M*HHHHHH*GKNHAGSPGCEESAAGKEKLPKMRLPTRSDMICGYACLKGTAAMRNTK
RGSWYIEALAQVFSERACDMHVADMLVKVNALIKDREGYAPGTEFHRCKEMSEYCS
TLCRHLYLFPGHPPTGGSGGGPVCLQVKPCTPEFYQTHFQLAYRLQSRPRGLALVLS
NVHFTGEKELEFRSGGDVDHSTLVTLFKLLGYDVHVLCDQTAQEMQEKLQNFAQLPA
HRVTDSCIVALLSHGVEGAIYGVDGKLLQLQEVFQLFDNANCPSLQNKPKMFFIQACR
GDETDRGVDQQD

SEQ ID No. 75 (amino acid sequence of cp caspase-2 10 aa Linker with *N-terminal His Tag*, with GSAGSAAGSG linker and CEESA)

M*HHHHHH*GKNHAGSPGCEESAAGKEKLPKMRLPTRSDMICGYACLKGTAAMRNTK
RGSWYIEALAQVFSERACDMHVADMLVKVNALIKDREGYAPGTEFHRCKEMSEYCS
TLCRHLYLFPGHPPTGSAGSAAGSGGPVCLQVKPCTPEFYQTHFQLAYRLQSRPRG
LALVLSNVHFTGEKELEFRSGGDVDHSTLVTLFKLLGYDVHVLCDQTAQEMQEKLQN
FAQLPAHRVTDSCIVALLSHGVEGAIYGVDGKLLQLQEVFQLFDNANCPSLQNKPKM
FFIQACRGDETDRGVDQQD

SEQ ID No. 76 (amino acid sequence of cp caspase-2 Δ SS Prop with *N-terminal His Tag*, GS linker and deletion of small subunit propeptide)

M*HHHHHH*GKEKLPKMRLPTRSDMICGYACLKGTAAMRNTKRGSWYIEALAQVFSER
ACDMHVADMLVKVNALIKDREGYAPGTEFHRCKEMSEYCSTLCRHLYLFPGHPPTG
SGPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQD

Fig. 1 continued

SEQ ID No. 77 (amino acid sequence of cp caspase-2 ½ Δ SS Prop with *N-terminal His Tag*, GS linker and partial deletion of small subunit propeptide)

M*HHHHHH*GCEESAAGKEKLPKMRLPTRSDMICGYACLKGTAAMRNTKRGSWYIEAL AQVFSERACDMHVADMLVKVNALIKDREGYAPGTEFHRCKEMSEYCSTLCRHLYLFP GHPPTGSGPVCLQVKPCTPEFYQTHFQLAYRLQSRPRGLALVLSNVHFTGEKELEFR SGGDVDHSTLVTLFKLLGYDVHVLCDQTAQEMQEKLQNFAQLPAHRVTDSCIVALLS HGVEGAIYGVDGKLLQLQEVFQLFDNANCPSLQNKPKMFFIQACRGDETDRGVDQQ D

SEQ ID No. 78 amino acid sequence of cp caspase-2 E105V, E172V derived from *Sarcophilus harrisii* with N-terminal *His tag*, A mutation in propeptide of small subunit, GS linker and E105V, E172V substitutions)

M*HHHHHH*GKEHMASPGCEQSAAGKEKILKMRLPTRSDMICGYACLKGTAAM RNTKRGSWYIEALTQVFSERARDMHVADMLVKVNALIKDREGYAPGTEFHRCKVMS EYSSTLCRHLYLFPGHPPTGSGPPSLQVKPCTSEFYRTHHHLAYRLQSRPRGLALVL SNVHFNGVKDLEFRSGGDVDHSSLVTLFKLLDYDVHVLRDQTAQEMYEKLQRFAQL STHQNTDSCVVALLSHGIEGGIYGVDGQLLQLQEVFQLFDNANCPNLQNKPKMFFIQ ACRGDETDRGVDLRD

SEQ ID No. 79 amino acid sequence of cp caspase-2 E105V, G171D derived from *Callorhinchus milii* with N-terminal *His tag*, A mutation in propeptide of small subunit, GS linker and E104V, G175D substitutions)

M*HHHHHH*GADAPGCEECAAGKERERTRRGKLPTQSDIICGYACLRGTAALRNTRQG SWYIQALVKVFTERAHNTHVADMLVQVNAVIRDREGFAPGTDFHRCKVMAEYSIFEE MEGETQRKQRRRKTAAPGSGSGTFSVRPTTAQFYHEHHKQSYRMASRPRGAALIVS NEVFVDEGLGHRPGGAADTGVLRALLSQLGYRVTSVCNSPAQELETRLRDFALSAD HRRTDSCVVVLLSHGVEGAIYGVDGKLVQIHDIFQLFDNANCPNLQNKPKMFFIQACR GDRTDRGVDRLD

SEQ ID No. 80 (amino acid sequence of cp caspase-2 with N85C, *N-terminal His tag*, CEESA, and GS Linker)

M*HHHHHH*GKNHAGSPGCEESAAGKEKLPKMRLPTRSDMICGYACLKGTAAM RNTKRGSWYIEALAQVFSERACDMHVADMLVKVCALIKDREGYAPGTEFHRCKEMS EYCSTLCRHLYLFPGHPPTGSGPVCLQVKPCTPEFYQTHFQLAYRLQSRPRGLALVL SNVHFTGEKELEFRSGGDVDHSTLVTLFKLLGYDVHVLCDQTAQEMQEKLQNFAQLP AHRVTDSCIVALLSHGVEGAIYGVDGKLLQLQEVFQLFDNANCPSLQNKPKMFFIQAC RGDETDRGVDQQD

Fig. 1 continued

SEQ ID No. 81 (amino acid sequence of cp caspase-2 SV 19 with *N-terminal His Tag*, GS linker, CEESA and mutated C-terminus)

M*HHHHHH*GKNHAGSPGCEESAAGKEKLPKMRLPTRSDMICGYACLKGTAAMRNTK
RGSWYIEALAQVFSERACDMHVADMLVKVNALIKDREGYAPGTEFHRCKEMSEYCS
TLCRHLYLFPGHPPTGSGPVCLQVKPCTPEFYQTHFQLAYRLQSRPRGLALVLSNVH
FTGEKELEFRSGGDVDHSTLVTLFKLLGYDVHVLCDQTAQEMQEKLQNFAQLPAHRV
TDSCIVALLSHGVEGAIYGVDGKLLQLQEVFQLFDNANCPSLQNKPKMFFIQACRGDE
TDHGAVLRG

SEQ ID No. 82 (amino acid sequence of cp caspase-2 C-term +3 with *N-terminal His Tag*, GS linker and deleted propeptide, 3 N-terminal amino acids of small subunit added to C-terminus of large subunit, with D267E, D274S substitutions)

M*HHHHHH*KLPKMRLPTRSDMICGYACLKGTAAMRNTKRGSWYIEALAQVFSERACD
MHVADMLVKVNALIKDREGYAPGTEFHRCKEMSEYCSTLCRHLYLFPGHPPTGSGP
VCLQVKPCTPEFYQTHFQLAYRLQSRPRGLALVLSNVHFTGEKELEFRSGGDVDHST
LVTLFKLLGYDVHVLCDQTAQEMQEKLQNFAQLPAHRVTDSCIVALLSHGVEGAIYGV
DGKLLQLQEVFQLFDNANCPSLQNKPKMFFIQACRGDETERGVDQQSGKE

SEQ ID No. 83 (amino acid sequence of cp caspase-2 N-term +3 with *N-terminal His Tag*, GS linker and deleted propeptide, 3 C-terminal amino acids of large subunit added to N-terminus of small subunit)

M*HHHHHH*QQDGKEKLPKMRLPTRSDMICGYACLKGTAAMRNTKRGSWYIEALAQVF
SERACDMHVADMLVKVNALIKDREGYAPGTEFHRCKEMSEYCSTLCRHLYLFPGHP
PTGSGPVCLQVKPCTPEFYQTHFQLAYRLQSRPRGLALVLSNVHFTGEKELEFRSGG
DVDHSTLVTLFKLLGYDVHVLCDQTAQEMQEKLQNFAQLPAHRVTDSCIVALLSHGV
EGAIYGVDGKLLQLQEVFQLFDNANCPSLQNKPKMFFIQACRGDETDRGVD

SEQ ID No. 84 (amino acid sequence of cp caspase-2 derived from *Sarcophilus harrisii* with N-terminal T7AC tag and *His tag*, A mutation in propeptide of small subunit and GS linker)

MLEDPERNKERKEAELQAQTAEQ*HHHHHH*GKEHMASPGCEQSAAGKEKILK
MRLPTRSDMICGYACLKGTAAMRNTKRGSWYIEALTQVFSERARDMHVADMLVKVN
ALIKDREGYAPGTEFHRCKEMSEYSSTLCRHLYLFPGHPPTGSGPPSLQVKPCTSEF
YRTHHHLAYRLQSRPRGLALVLSNVHFNGEKDLEFRSGGDVDHSSLVTLFKLLDYDV
HVLRDQTAQEMYEKLQRFAQLSTHQNTDSCVVALLSHGIEGGIYGVDGQLLQLQEVF
QLFDNANCPNLQNKPKMFFIQACRGDETDRGVDLRD

Fig. 1 continued

SEQ ID No. 85 amino acid sequence of cp caspase-2 derived from *Callorhinchus milii* with N-terminal T7AC tag and *His tag*, A mutation in propeptide of small subunit and GS linker)

M*LEDPERNKERKEAELQAQTAEQ**HHHHHH*GADAPGCEECAAGKERERTRRGKLPT
QSDIICGYACLRGTAALRNTRQGSWYIQALVKVFTERAHNTHVADMLVQVNAVIRDR
EGFAPGTDFHRCKEMAEYSIFEEMEGETQRKQRRRKTAAPGSGSGTFSVRPTTAQF
YHEHHKQSYRMASRPRGAALIVSNEVFVGEGLGHRPGGAADTGVLRALLSQLGYRV
TSVCNSPAQELETRLRDFALSADHRRTDSCVVVLLSHGVEGAIYGVDGKLVQIHDIFQ
LFDNANCPNLQNKPKMFFIQACRGDRTDRGVDRLD

SEQ ID No. 86 amino acid sequence of cp caspase-2 E105V, E172V derived from *Sarcophilus harrisii* with N-terminal T7AC tag and *His tag*, A mutation in propeptide of small subunit, GS linker and E105V, E172V substitutions)

MLEDPERNKERKEAELQAQTAEQ*HHHHHH*GKEHMASPGCEQSAAGKEKILK
MRLPTRSDMICGYACLKGTAAMRNTKRGSWYIEALTQVFSERARDMHVADMLVKVN
ALIKDREGYAPGTEFHRCKVMSEYSSTLCRHLYLFPGHPPTGSGPPSLQVKPCTSEF
YRTHHHLAYRLQSRPRGLALVLSNVHFNGVKDLEFRSGGDVDHSSLVTLFKLLDYDV
HVLRDQTAQEMYEKLQRFAQLSTHQNTDSCVVALLSHGIEGGIYGVDGQLLQLQEVF
QLFDNANCPNLQNKPKMFFIQACRGDETDRGVDLRD

SEQ ID No. 87 amino acid sequence of cp caspase-2 E105V, G171D derived from *Callorhinchus milii* with N-terminal T7AC tag and *His tag*, A mutation in propeptide of small subunit, GS linker and E104V, G175D substitutions)

M*LEDPERNKERKEAELQAQTAEQ**HHHHHH*GADAPGCEECAAGKERERTRRGKLPT
QSDIICGYACLRGTAALRNTRQGSWYIQALVKVFTERAHNTHVADMLVQVNAVIRDR
EGFAPGTDFHRCKVMAEYSIFEEMEGETQRKQRRRKTAAPGSGSGTFSVRPTTAQF
YHEHHKQSYRMASRPRGAALIVSNEVFVDEGLGHRPGGAADTGVLRALLSQLGYRV
TSVCNSPAQELETRLRDFALSADHRRTDSCVVVLLSHGVEGAIYGVDGKLVQIHDIFQ
LFDNANCPNLQNKPKMFFIQACRGDRTDRGVDRLD

SEQ ID No. 88 (amino acid sequence of cp caspase-2 with A86C, *N-terminal His tag*, CEESA, and GS Linker)

M*HHHHHH*GKNHAGSPGCEESAAGKEKLPKMRLPTRSDMICGYACLKGTAAM
RNTKRGSWYIEALAQVFSERACDMHVADMLVKVNCLIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

Fig. 1 continued

SEQ ID No. 89 (amino acid sequence of mouse caspase-2 (P29594))

MAAPSGRSQSSLHRKGLMAADRRSRILAVCGMHPDHQETLKKNRVVLAKQLL
LSELLEHLLEKDIITLEMRELIQAKGGSFSQNVELLNLLPKRGPQAFDAFCEALRETRQ
GHLEDLLLTTLSDIQHVLPPLSCDYDTSLPFSVCESCPPHKQLRLSTDATEHSLDNGD
GPPCLLVKPCTPEFYQAHYQLAYRLQSQPRGLALVLSNVHFTGEKDLEFRSGGDVD
HTTLVTLFKLLGYNVHVLHDQTAQEMQEKLQNFAQLPAHRVTDSCVVALLSHGVEGG
IYGVDGKLLQLQEVFRLFDNANCPSLQNKPKMFFIQACRGDETDRGVDQQDGKNHT
QSPGCEESDAGKEELMKMRLPTRSDMICGYACLKGNAAMRNTKRGSWYIEALTQVF
SERACDMHVADMLVKVNALIKEREGYAPGTEFHRCKEMSEYCSTLCQQLYLFPGYP
PT

SEQ ID No. 90 (amino acid sequence of large subunit of mouse caspase-2)

GPPCLLVKPCTPEFYQAHYQLAYRLQSQPRGLALVLSNVHFTGEKDLEFRSG
GDVDHTTLVTLFKLLGYNVHVLHDQTAQEMQEKLQNFAQLPAHRVTDSCVVALLSHG
VEGGIYGVDGKLLQLQEVFRLFDNANCPSLQNKPKMFFIQACRGDETDRGVDQQD

SEQ ID No. 91 (amino acid sequence of small subunit of mouse caspase-2)

AGKEELMKMRLPTRSDMICGYACLKGNAAMRNTKRGSWYIEALTQVFSERAC
DMHVADMLVKVNALIKEREGYAPGTEFHRCKEMSEYCSTLCQQLYLFPGYPPT

SEQ ID No. 92 (amino acid sequence of sheep caspase-2 (W5Q8H6))

MAAPSAGSQSALQPKEQMAADRGRRMLRGCGMHPDHQEALKKNRVVLAKE
LLLSELLEHLLERDIITLEMREHIQAKTGSFGQNVELLNLLPKRGPQAFDAFCVALRET
KQSHLEELLLRTLSGLQPVVPPLSCDYDLSLPFPVCESCAPHKRLRLSPGLCAADAVE
HSLDHGDGPPCLQVKPCTPEFYQTHHQLAYRLQSRPRGLALVLSNVHFTGEKDLEF
RSGGDVDHSTLVTLFKLLGYKVHVLLDQTAQEMQEKLQSFAQLPAPRLTDSTDSCIV
ALLSHGVEGSVYGVDGKLLQQLQEVFRLFDNANCPSLQNKPKMFFIQACRGDETDR
GVDQQDGKNHDRSPECEESDASGEELLKTRLPTRSDMICGYACLRGTAAMRNTKRG
SWYVEALTQVFSERACDMHVADMLVKVNALIKEREGYAPGTEFHRCKEMSEYCSTL
CRHLYLFPGHPPT

SEQ ID No. 93 (amino acid sequence of large subunit of sheep caspase-2)

GPPCLQVKPCTPEFYQTHHQLAYRLQSRPRGLALVLSNVHFTGEKDLEFRSG
GDVDHSTLVTLFKLLGYKVHVLLDQTAQEMQEKLQSFAQLPAPRLTDSTDSCIVALLS
HGVEGSVYGVDGKLLQQLQEVFRLFDNANCPSLQNKPKMFFIQACRGDETDRGVDQ
QD

Fig.1 continued

SEQ ID No. 94 (amino acid sequence of small subunit of sheep caspase-2)

ASGEELLKTRLPTRSDMICGYACLRGTAAMRNTKRGSWYVEALTQVFSERAC
DMHVADMLVKVNALIKEREGYAPGTEFHRCKEMSEYCSTLCRHLYLFPGHPPT

SEQ ID No. 95 (amino acid sequence of Tasmanian Devil caspase-2 (G3VQP7))

SRMLGVWGMEREHQEALKKNRVVLAKQLLLSELLEHLLEKDIITLEMRELIQAK
VGSFSQNVEFLNLLPKRGPHAFGAFCDALRETKQGHLEDLLHKTLYSFQQLLPSLNC
DDDSNLPLPVCESCSPHKQLRLSVETMEHSLDNGDGPPSLQVKPCTSEFYRTHHHL
AYRLQSRPRGLALVLSNVHFNGEKDLEFRSGGDVDHSSLVTLFKLLDYDVHVLRDQT
AQEMYEKLQRFAQLSTHQNTDSCVVALLSHGIEGGIYGVDGQLLQLQEVFQLFDNAN
CPNLQNKPKMFFIQACRGDETDRGVDLRDGKEHMASPGCEQSDAGKEKILKMRLPT
RSDMICGYACLKGTAAMRNTKRGSWYIEALTQVFSERARDMHVADMLVKVNALIKDR
EGYAPGTEFHRCKEMSEYSSTLCRHLYLFPGHPPT

SEQ ID No. 96 (amino acid sequence of large subunit of Tasmanian Devil caspase-2)

GPPSLQVKPCTSEFYRTHHHLAYRLQSRPRGLALVLSNVHFNGEKDLEFRSG
GDVDHSSLVTLFKLLDYDVHVLRDQTAQEMYEKLQRFAQLSTHQNTDSCVVALLSHG
IEGGIYGVDGQLLQLQEVFQLFDNANCPNLQNKPKMFFIQACRGDETDRGVDLRD

SEQ ID No. 97 (amino acid sequence of small subunit of Tasmanian Devil caspase-2)

AGKEKILKMRLPTRSDMICGYACLKGTAAMRNTKRGSWYIEALTQVFSERARD
MHVADMLVKVNALIKDREGYAPGTEFHRCKEMSEYSSTLCRHLYLFPGHPPT

SEQ ID No. 98 (amino acid sequence of Chicken caspase-2 (Q98943))

MLGACGMQRYHQEALKKNRVMLARELVLKELMEHMIEKDIITIEMVEMIQAKS
GSFSQNVEFLNLLPKRGPNAFSAFCEALQETKQQHLAEMILKTESSLRHGIATLEQRY
GSNLPLPLSESCNSKRPRLIVEHSLDSGDGPPIPPVKHCTPEFYRDHQHLAYKLISEP
RGLALILSNIHFSSEKDLEYRSGGDVDCASLELLFKHLGYQVTVFHDQSAEEMESALE
RFSKLPDHQDVDSCIVALLSHGVEGGVYGTDGKLLQLQEAFRLFDNANCPNLQNKPK
MFFIQACRGDETDRGVDQRDGKERSDSPGCEESDANKEENLKLRLPTRSDMICGYA
CLKGTAAMRNTKRGSWYIEALTTVFAEDSRDTHVADMLVKVNRQIKQREGYAPGTEF
HRCKEMSEYCSTLCRDLYLFPGYVPGK

Fig. 1 continued

SEQ ID No. 99 (amino acid sequence of large subunit of chicken caspase-2)

GPPIPPVKHCTPEFYRDHQHLAYKLISEPRGLALILSNIHFSSEKDLEYRSGGDV
DCASLELLFKHLGYQVTVFHDQSAEEMESALERFSKLPDHQDVDSCIVALLSHGVEG
GVYGTDGKLLQLQEAFRLFDNANCPNLQNKPKMFFIQACRGDETDRGVDQRD

SEQ ID No. 100 (amino acid sequence of small subunit of chicken caspase-2)

ANKEENLKLRLPTRSDMICGYACLKGTAAMRNTKRGSWYIEALTTVFAEDSRD
THVADMLVKVNRQIKQREGYAPGTEFHRCKEMSEYCSTLCRDLYLFPGYVPGK

SEQ ID No. 101 (amino acid sequence of Anolis caspase-2 (H9GC58))

MEHVESKFHLCIVICFISRMLGVCGMQKCHQEALKKNRVSLAKQLVLKELMEH
LIEKDVITEEMMEMIQAKAGNFSQNIEFLNLLPKRGPKAFSAFCEALRETKQPHLEEML
LRSVSRHCNGIAKLSHSCEEHLSFPVSESGILQKWPRRNPEPMEHSLDDGDGPHYP
QVMPCTPEFYRTHEQLAYKLKSQPRGLALILSNIHFNKETDLDFRSGGDVDNTALHML
FKHLGYQVVVRQDRTAQEMKEELEIFSKHPAHRNVDSCIVSLLSHGIEGGIYGIDGKLL
QLQEIFRLFDNANCPNLQNKPKMFFVQACRGDETDHGVDQIDGNDCASSPGCEETD
ANKKENPKLRLPTCSDMICGYACLKGTAAMRNTKHGSWYVEALTSVFAEDSGHMHV
ADMLVKVNRLIKLREGHAPGTEFHRCKEMSEYCSTLCQDLYLFPGYFPG

SEQ ID No. 102 (amino acid sequence of large subunit of Anolis caspase-2)

GPHYPQVMPCTPEFYRTHEQLAYKLKSQPRGLALILSNIHFNKETDLDFRSGG
DVDNTALHMLFKHLGYQVVVRQDRTAQEMKEELEIFSKHPAHRNVDSCIVSLLSHGIE
GGIYGIDGKLLQLQEIFRLFDNANCPNLQNKPKMFFVQACRGDETDHGVDQID

SEQ ID No. 103 (amino acid sequence of small subunit of Anolis caspase-2)

ANKKENPKLRLPTCSDMICGYACLKGTAAMRNTKHGSWYVEALTSVFAEDSG
HMHVADMLVKVNRLIKLREGHAPGTEFHRCKEMSEYCSTLCQDLYLFPGYFPG

SEQ ID No. 104 (amino acid sequence of Alligator caspase-2 (A0A1U8D1G6))

MSGACGMQPCHQEALRRHRVPLAKQLVLQELLEHLLARAVLTPEMKEAIQTK
AGSFSQNVEFLSLLPKRGPQAFSAFCEALRETRQEHLEEMLLNAIQHSSNGYVKRGH
DYDSSLPFPVCESYHLSKRPRCIEPFEHSLDNGDGPPYPQVRACTPEFYRTHQRLAY
KLTSDPRGLALVLSNVHFNGEKDLEFRSGGDVDCAALEKLFECLGYKVTVHHDQSAQ
EMQETLQKFSQKPTHQEVDSCIVALLSHGVEGGVYGIDGKLLQLQEVFRLFDNANCL
NLQNKPKMFFIQACRGDETDRGVDQRDGKERSDSPGYEESDANKEENPRLRLPTCS
DMICGYACLKGTAAMRNTKRGSWYIEALTSVFAEDSHNTHVADMLVKVNRMIKHREG
YAPGTEFHRCKEMSEYCSTLCRDLYLFPGYLPGN

Fig. 1 continued

SEQ ID No. 105 (amino acid sequence of large subunit of Alligator caspase-2)

GPPYPQVRACTPEFYRTHQRLAYKLTSDPRGLALVLSNVHFNGEKDLEFRSG
GDVDCAALEKLFECLGYKVTVHHDQSAQEMQETLQKFSQKPTHQEVDSCIVALLSHG
VEGGVYGIDGKLLQLQEVFRLFDNANCLNLQNKPKMFFIQACRGDETDRGVDQRD

SEQ ID No. 106 (amino acid sequence of small subunit of Alligator caspase-2)

ANKEENPRLRLPTCSDMICGYACLKGTAAMRNTKRGSWYIEALTSVFAEDSH
NTHVADMLVKVNRMIKHREGYAPGTEFHRCKEMSEYCSTLCRDLYLFPGYLPGN

SEQ ID No. 107 (amino acid sequence of Xenopus caspase-2 (F6RDY9))

MLGGMQKHHKDALQRLRVTLLHDMIIEELVEHLVSSGILTPIMHSTIMAHRSEY
KQNVTLLTQLPKRGPRAFSEFCNALHATGQRHLAEQLEEEAQQQQMESVTPEVHER
SFPLPVQESTPSRPRRQFCREYNEESIDDGDGPGTVQLCSVDFYLSHHQQAYKMHS
CPRGRALIISNVAFETQDLDHRYGGEVDVTSLEKLFSSLGFQVEVRRNLNAQNMMSQ
LGAFSALPAHSALDSCVVAVLSHGLDGAVYGTDGKLVQLQDVFTAMDNAHCPQLQN
KPKMFFIQACRGEEADRGVDQRDGREQSASPGCEQSDAGREDIKVRLPTQSDMICA
YACLKGTVSLRNTKRGSWFVQDLVSVFSQYSKNTHVADMLVKVNALIKEREGHAPGT
EFHRCKEMSEYCSTLCRDLYLFPGIGPPK

SEQ ID No. 108 (amino acid sequence of large subunit of Xenopus caspase-2)

GPGTVQLCSVDFYLSHHQQAYKMHSCPRGRALIISNVAFETQDLDHRYGGEV
DVTSLEKLFSSLGFQVEVRRNLNAQNMMSQLGAFSALPAHSALDSCVVAVLSHGLD
GAVYGTDGKLVQLQDVFTAMDNAHCPQLQNKPKMFFIQACRGEEADRGVDQRD

SEQ ID No. 109 (amino acid sequence of small subunit of Xenopus caspase-2)

AGREDIKVRLPTQSDMICAYACLKGTVSLRNTKRGSWFVQDLVSVFSQYSKNT
HVADMLVKVNALIKEREGHAPGTEFHRCKEMSEYCSTLCRDLYLFPGIGPPK

SEQ ID No. 110 (amino acid sequence of Danio caspase-2 (Q0PKX3))

MLGECGMTKWERLALRRNSVKMLQDLVVDDLLIQCLQQDGILTDSMAESIMA
KPTSQGRSHQLLFLLPKRGPRAFSTFCSALKETEQHHLCKLLMDFTEKDKCFSEPSL
SLPTQECVTPAKRPRTHESMEMCLDADSPVTTAVLPCTPEFYQSHRPQAYPMRSCP
RGLALVLSNVRFDSANTDLDIRRGGEVDEETLRRLFTELDFKVSLHRDLTAEAMRRCL
EQFAQQQEHAAYDCAVVCLLSHGVEGSVYGTDGQLLELDWVFEVFDNARCPLLQNK
PKMFFIQACRGEEMDNGVDQLDGQERTQSPGCEQRDAGREGERDNREKKEEKERE
RLRVKLPQRSDMICGFATLKGTAAMRNTKKGSWFIQELNTAIRQRANNTHLSDILVQV
NGQIKSREGYAPGSAHHRCKEMSEFTSSLCKDLYLFPKYYPSN

Fig. 1 continued

SEQ ID No. 111 (amino acid sequence of large subunit of Danio caspase-2)

SPVTTAVLPCTPEFYQSHRPQAYPMRSCPRGLALVLSNVRFDSANTDLDIRRG
GEVDEETLRRLFTELDFKVSLHRDLTAEAMRRCLEQFAQQQEHAAYDCAVVCLLSHG
VEGSVYGTDGQLLELDWVFEVFDNARCPLLQNKPKMFFIQACRGEEMDNGVDQLD

SEQ ID No. 112 (amino acid sequence of small subunit of Danio caspase-2)

AGREGERDNREKKEEKERERLRVKLPQRSDMICGFATLKGTAAMRNTKKGS
WFIQELNTAIRQRANNTHLSDILVQVNGQIKSREGYAPGSAHHRCKEMSEFTSSLCKD
LYLFPKYYPSN

SEQ ID No. 113 (amino acid sequence of Ghost Shark caspase-2 (V9KZT1))

MKGKWEMKSAESEALRKVHVTLAKQLVSTEIVHHLLSAEILTEEMVDLLETCR
GTFQKNTELLRLLPKRGPRAFEEFCRALDRTKQSHLTGLLRESVTEEEALCKPTQESE
CVTPAKKFCSLWRVCLDAGDGSGTFSVRPTTAQFYHEHHKQSYRMASRPRGAALIV
SNEVFVGEGLGHRPGGAADTGVLRALLSQLGYRVTSVCNSPAQELETRLRDFALSA
DHRRTDSCVVVLLSHGVEGAIYGVDGKLVQIHDIFQLFDNANCPNLQNKPKMFFIQAC
RGDRTDRGVDRLDGADAPGCEECDAGKERERTRRGKLPTQSDIICGYACLRGTAAL
RNTRQGSWYIQALVKVFTERAHNTHVADMLVQVNAVIRDREGFAPGTDFHRCKEMA
EYSIFEEMEGETQRKQRRRKTAAP

SEQ ID No. 114 (amino acid sequence of large subunit of Ghost Shark caspase-2)

SGTFSVRPTTAQFYHEHHKQSYRMASRPRGAALIVSNEVFVGEGLGHRPGGA
ADTGVLRALLSQLGYRVTSVCNSPAQELETRLRDFALSADHRRTDSCVVVLLSHGVE
GAIYGVDGKLVQIHDIFQLFDNANCPNLQNKPKMFFIQACRGDRTDRGVDRLD

SEQ ID No. 115 (amino acid sequence of small subunit of Ghost Shark caspase-2)

AGKERERTRRGKLPTQSDIICGYACLRGTAALRNTRQGSWYIQALVKVFTERA
HNTHVADMLVQVNAVIRDREGFAPGTDFHRCKEMAEYSIFEEMEGETQRKQRRRKT
AAP

SEQ ID No. 116 (amino acid sequence of Sea squirt caspase-2 (A0A1W2WKB0))

MDDAPSPTDSLSNIRSTASVHSLFSRSDVRTQSNTAINHINTVQSPTSTKAATS
YQINLHQGMDLFDGPTVSDLTVRKSTHQHLMQHTDCYQMTMRGRPKGAALIISVEKF
HPESDLLNREGSEKDRVRLELVLQQIGFQCYVLINGTAEQIVSTLQTFAELEEHYYNS
CSLVAAMSHGDAGCFYGSDGVSVAIDTVVNFFSNQNCHSLQKKPKIFLFQACQGDEY
DMGVDEVDGPVQAPVGDVDNTSTSSSNDHIRNKLPQKSDMLIGQATMKGFAAMRNT
KHGSWYIQAFVRVLARHACDTDLLDMMTKVNNILKHKEGWCPGSVYHRCKVMPEFK
SSLSKKLYFFPGI

Fig. 1 continued

SEQ ID No. 117 (amino acid sequence of large subunit of Sea Squirt caspase-2)

GPTVSDLTVRKSTHQHLMQHTDCYQMTMRGRPKGAALIISVEKFHPESDLLN
REGSEKDRVRLELVLQQIGFQCYVLINGTAEQIVSTLQTFAELEEHYYNSCSLVAAMS
HGDAGCFYGSDGVSVAIDTVVNFFSNQNCHSLQKKPKIFLFQACQGDEYDMGVDEV
D

SEQ ID No. 118 (amino acid sequence of small subunit of Sea Squirt caspase-2)

NTSTSSSNDHIRNKLPQKSDMLIGQATMKGFAAMRNTKHGSWYIQAFVRVLA
RHACDTDLLDMMTKVNNILKHKEGWCPGSVYHRCKVMPEFKSSLSKKLYFFPGI

SEQ ID No. 179 (amino acid sequence of cp caspase-2 Δ SS Prop, with GS linker and G151D substitution (equivalent position in SEQ ID No. 6: G171D)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTDEKELEFRSGGDVDH
STLVTLFKLLGYDVHVLCDQTAQEMQEKLQNFAQLPAHRVTDSCIVALLSHGVEGAIY
GVDGKLLQLQEVFQLFDNANCPSLQNKPKMFFIQACRGDETDRGVDQQD

SEQ ID No. 180 (amino acid sequence of cp caspase-2 Δ SS Prop, with GS linker and E85V substitution (equivalent position in SEQ ID No. 6: E105V)

MAGKEKLPKMRLPTRSDMICGYACLKGTAAMRNTKRGSWYIEALAQVFSERA
CDMHVADMLVKVNALIKDREGYAPGTEFHRCKVMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQD

SEQ ID No. 181 (amino acid sequence of cp caspase-2 Δ SS Prop, with GS linker and E152V substitution (equivalent position in SEQ ID No. 6: E172V)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGVKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQD

Fig. 1 continued

SEQ ID No. 182 (amino acid sequence of cp caspase-2 Δ SS Prop, with GS linker and D262E substitution (equivalent position in SEQ ID No. 6: D282E)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGEETDRGVDQQD

SEQ ID No. 183 (amino acid sequence of cp caspase-2 Δ SS Prop, with GS linker and D262T substitution (equivalent position in SEQ ID No. 6: D282T)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGTETDRGVDQQD

SEQ ID No. 184 (amino acid sequence of cp caspase-2 Δ SS Prop, with GS linker and V205G substitution (equivalent position in SEQ ID No. 6: V225G)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRGTDSCIVALLSHGVEGAI
YGVDGKLLQLQEVFQLFDNANCPSLQNKPKMFFIQACRGDETDRGVDQQD

SEQ ID No. 185 (amino acid sequence of cp caspase-2 Δ SS Prop, with GS linker and K63E substitution (equivalent position in SEQ ID No. 6: K83E)

MAGKEKLPKMRLPTRSDMICGYACLKGTAAMRNTKRGSWYIEALAQVFSERA
CDMHVADMLVEVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQD

SEQ ID No. 186 (amino acid sequence of cp caspase-2 Δ SS Prop, with GS linker and H165A substitution (equivalent position in SEQ ID No. 6: H185A)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
ASTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETDRGVDQQD

Fig. 1 continued

SEQ ID No. 187 (amino acid sequence of cp caspase-2 Δ SS Prop, with GS linker and V235M substitution (equivalent position in SEQ ID No. 6: V255M)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEMFQLFDNANCPSLQNKPKMFFIQACRGDETDRGVDQQD

SEQ ID No. 188 (amino acid sequence of cp caspase-2 Δ SS Prop, with GS linker and D265E substitution (equivalent position in SEQ ID No. 6: D285E)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETERGVDQQD

SEQ ID No. 189 (amino acid sequence of cp caspase-2 Δ SS Prop, with GS linker and D265Y substitution (equivalent position in SEQ ID No. 6: D285Y)

MAGKEKLPKMRLPTRSDMICGYACLKGTAAMRNTKRGSWYIEALAQVFSERA
CDMHVADMLVKVNALIKDREGYAPGTEFHRCKEMSEYCSTLCRHLYLFPGHPPTGS
GPVCLQVKPCTPEFYQTHFQLAYRLQSRPRGLALVLSNVHFTGEKELEFRSGGDVD
HSTLVTLFKLLGYDVHVLCDQTAQEMQEKLQNFAQLPAHRVTDSCIVALLSHGVEGAI
YGVDGKLLQLQEVFQLFDNANCPSLQNKPKMFFIQACRGDETYRGVDQQD

SEQ ID No. 190 (amino acid sequence of cp caspase-2 with His tag and G171D substitution)

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTDEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 191 (amino acid sequence of cp caspase-2 with His tag and D282E substitution)

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGEETDRGVDQQD

Fig. 1 continued

SEQ ID No. 192 (amino acid sequence of cp caspase-2 with His tag and V225G substitution)

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLCDQTAQEMQEKLQNFAQLP
AHRGTDSCIVALLSHGVEGAIYGVDGKLLQLQEVFQLFDNANCPSLQNKPKMFFIQAC
RGDETDRGVDQQD

SEQ ID No. 198 (amino acid sequence of cp caspase-2 with His tag and C203S substitution)

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKEMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLSDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 199 (amino acid sequence of cp caspase-2 with His tag and E105V and C203S substitution)

MHHHHHHGKNHAGSPGCEESAAGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTGEKELEFRSGGDVDHSTLVTLFKLLGYDVHVLSDQTAQEMQEKLQNFAQLP
AHRVTDSCIVALLSHGVEGAIYGVDGKLLQLQEVFQLFDNANCPSLQNKPKMFFIQAC
RGDETDRGVDQQD

Fig. 1 continued

(Substrate Sequences)

SEQ ID No. 31 (nucleotide sequence of fusion protein *6H*_VDVAD_hFGF-2 with GSG Linker)

ATG*CACCATCACCATCACCAT*GGCAGCGGCGTGGATGTGGCGGATgCCGC
TGGTTCGATTACTACCCTGCCTGCTTTACCTGAAGATGGTGGTTCTGGTGCGTTC
CCGCCGGGTCACTTCAAAGACCCAAAACGTTTGTACTGTAAAAACGGTGGCTTTT
TTCTGCGCATCCATCCGGACGGCCGCGTGGATGGTGTCCGTGAAAAGTCCGACC
CGCACATTAAGCTGCAACTGCAGGCCGAGGAGCGTGGTGTTGTTAGCATCAAAG
GCGTGAGCGCAAATCGTTACCTGGCGATGAAAGAGGATGGCCGTCTGCTGGCGA
GCAAGAGCGTTACCGACGAGTGCTTCTTCTTTGAACGCCTGGAGAGCAATAATTA
CAACACCTACCGTAGCCGCAAGTATACCTCTTGGTATGTGGCGCTGAAGCGTACG
GGCCAGTATAAATTGGGTAGCAAAACGGGTCCGGGCCAAAAGGCAATCCTGTTC
CTGCCGATGAGCGCGAAATCCTAA

SEQ ID No. 32 (amino acid sequence of fusion protein *6H*_VDVAD_hFGF with GSG Linker)

M*HHHHHH*GSGVDVADAAGSITTLPALPEDGGSGAFPPGHFKDPKRLYCKNG
GFFLRIHPDGRVDGVREKSDPHIKLQLQAEERGVVSIKGVSANRYLAMKEDGRLLAS
KSVTDECFFFERLESNNYNTYRSRKYTSWYVALKRTGQYKLGSKTGPGQKAILFLPM
SAKS

SEQ ID No. 33 (amino acid sequence of fusion protein *6H*_VDVAD_Ubiquitin-conjugating enzyme E2 L3 with GSG Linker)

MRGS*HHHHHH*GSGVDVADGIRMRARYPSVLDMAASRRLMKELEEIRKCGMK
NFRNIQVDEANLLTWQGLIVPDNPPYDKGAFRIEINFPAEYPFKPPKITFKTKIYHPNID
EKGQVCLPVISAENWKPATKTDQVIQSLIALVNDPQPEHPLRADLAEEYSKDRKKFCK
NAEEFTKKYGEKRPVD

Fig. 1 continued

SEQ ID No. 34 (amino acid sequence of *6H*_VDVAD_β-Galactosidase with <u>GSG Linker</u>)

M*HHHHHH*<u>GSG</u>VDVADMTMITDSLAVVLQRRDWENPGVTQLNRLAAHPPFAS
WRNSEEARTDRPSQQLRSLNGEWRFAWFPAPEAVPESWLECDLPEADTVVVPSNW
QMHGYDAPIYTNVTYPITVNPPFVPTENPTGCYSLTFNVDESWLQEGQTRIIFDGVNS
AFHLWCNGRWVGYGQDSRLPSEFDLSAFLRAGENRLAVMVLRWSDGSYLEDQDM
WRMSGIFRDVSLLHKPTTQISDFHVATRFNDDFSRAVLEAEVQMCGELRDYLRVTVS
LWQGETQVASGTAPFGGEIIDERGGYADRVTLRLNVENPKLWSAEIPNLYRAVVELH
TADGTLIEAEACDVGFREVRIENGLLLLNGKPLLIRGVNRHEHHPLHGQVMDEQTMV
QDILLMKQNNFNAVRCSHYPNHPLWYTLCDRYGLYVVDEANIETHGMVPMNRLTDD
PRWLPAMSERVTRMVQRDRNHPSVIIWSLGNESGHGANHDALYRWIKSVDPSRPVQ
YEGGGADTTATDIICPMYARVDEDQPFPAVPKWSIKKWLSLPGETRPLILCEYAHAMG
NSLGGFAKYWQAFRQYPRLQGGFVWDWVDQSLIKYDENGNPWSAYGGDFGDTPN
DRQFCMNGLVFADRTPHPALTEAKHQQQFFQFRLSGQTIEVTSEYLFRHSDNELLH
WMVALDGKPLASGEVPLDVAPQGKQLIELPELPQPESAGQLWLTVRVVQPNATAWS
EAGHISAWQQWRLAENLSVTLPAASHAIPHLTTSEMDFCIELGNKRWQFNRQSGFLS
QMWIGDKKQLLTPLRDQFTRAPLDNDIGVSEATRIDPNAWVERWKAAGHYQAEAALL
QCTADTLADAVLITTAHAWQHQGKTLFISRKTYRIDGSGQMAITVDVEVASDTPHPARI
GLNCQLAQVAERVNWLGLGPQENYPDRLTAACFDRWDLPLSDMYTPYVFPSENGL
RCGTRELNYGPHQWRGDFQFNISRYSQQQLMETSHRHLLHAEEGTWLNIDGFHMGI
GGDDSWSPSVSAEFQLSAGRYHYQLVWCQK

SEQ ID No. 55 (nucleotide sequence of fusion protein 6H_VDVAD_Ubiquitin-conjugating enzyme E2 L3 with GSG Linker)

ATGAGAGGATCTCACCATCACCATCACCATGGCAGCGGCgtggatgtggcgGAT
GGGATCCGCATGCGAGCTCGGTACCCCAGTGTGCTGGACATGGCGGCCAGCAG
GAGGCTGATGAAGGAGCTTGAAGAAATCCGCAAATGTGGGATGAAAAACTTCCGT
AACATCCAGGTTGATGAAGCTAATTTATTGACTTGGCAAGGGCTTATTGTTCCTGA
CAACCCTCCCTATGATAAGGGAGCCTTCAGAATCGAAATCAACTTTCCAGCAGAG
TACCCATTCAAACCACCGAAGATCACATTTAAAACAAAGATCTATCACCCAAACAT
CGACGAAAAGGGGCAGGTCTGTCTGCCAGTAATTAGTGCCGAAAACTGGAAGCC
AGCAACCAAAACCGACCAAGTAATCCAGTCCCTCATAGCACTGGTGAATGACCCC
CAGCCTGAGCACCCGCTTCGGGCTGACCTAGCTGAAGAATACTCTAAGGACCGT
AAAAAATTCTGTAAGAATGCTGAAGAGTTTACAAAGAAATATGGGGAAAAGCGAC
CTGTGGACTAA SEQ ID No. 56 (amino acid sequence of fusion protein 6H_VDVAD_X_ Ubiquitin-conjugating enzyme E2 L3 with GSG Linker)

MRGSHHHHHHGSGVDVADXIRMRARYPSVLDMAASRRLMKELEEIRKCGMK
NFRNIQVDEANLLTWQGLIVPDNPPYDKGAFRIEINFPAEYPFKPPKITFKTKIYHPNID
EKGQVCLPVISAENWKPATKTDQVIQSLIALVNDPQPEHPLRADLAEEYSKDRKKFCK
NAEEFTKKYGEKRPVD

Fig. 1 continued

SEQ ID No. 57 (amino acid sequence of fusion protein 6H_DEVD_ Ubiquitin-conjugating enzyme E2 L3 with GSG Linker)

MRGSHHHHHHGSGDEVDGIRMRARYPSVLDMAASRRLMKELEEIRKCGMKN
FRNIQVDEANLLTWQGLIVPDNPPYDKGAFRIEINFPAEYPFKPPKITFKTKIYHPNIDE
KGQVCLPVISAENWKPATKTDQVIQSLIALVNDPQPEHPLRADLAEEYSKDRKKFCKN
AEEFTKKYGEKRPVD

SEQ ID No. 58 (amino acid sequence of fusion protein 6H_EISD_ Ubiquitin-conjugating enzyme E2 L3 with GSG Linker)

MRGSHHHHHHGSGEISDGIRMRARYPSVLDMAASRRLMKELEEIRKCGMKNF
RNIQVDEANLLTWQGLIVPDNPPYDKGAFRIEINFPAEYPFKPPKITFKTKIYHPNIDEK
GQVCLPVISAENWKPATKTDQVIQSLIALVNDPQPEHPLRADLAEEYSKDRKKFCKNA
EEFTKKYGEKRPVD

SEQ ID No. 59 (amino acid sequence of fusion protein 6H_EFKD_ Ubiquitin-conjugating enzyme E2 L3 with GSG Linker)

MRGSHHHHHHGSGEFKDGIRMRARYPSVLDMAASRRLMKELEEIRKCGMKN
FRNIQVDEANLLTWQGLIVPDNPPYDKGAFRIEINFPAEYPFKPPKITFKTKIYHPNIDE
KGQVCLPVISAENWKPATKTDQVIQSLIALVNDPQPEHPLRADLAEEYSKDRKKFCKN
AEEFTKKYGEKRPVD

SEQ ID No. 60 (amino acid sequence of fusion protein 6H_VDQQE_ Ubiquitin-conjugating enzyme E2 L3 with GSG Linker)

MRGSHHHHHHGSGVDQQEGIRMRARYPSVLDMAASRRLMKELEEIRKCGMK
NFRNIQVDEANLLTWQGLIVPDNPPYDKGAFRIEINFPAEYPFKPPKITFKTKIYHPNID
EKGQVCLPVISAENWKPATKTDQVIQSLIALVNDPQPEHPLRADLAEEYSKDRKKFCK
NAEEFTKKYGEKRPVD

SEQ ID No. 61 (amino acid sequence of fusion protein 6H_VDQQS_ Ubiquitin-conjugating enzyme E2 L3 with GSG Linker)

MRGSHHHHHHGSGVDQQSGIRMRARYPSVLDMAASRRLMKELEEIRKCGMK
NFRNIQVDEANLLTWQGLIVPDNPPYDKGAFRIEINFPAEYPFKPPKITFKTKIYHPNID
EKGQVCLPVISAENWKPATKTDQVIQSLIALVNDPQPEHPLRADLAEEYSKDRKKFCK
NAEEFTKKYGEKRPVD

SEQ ID No. 62 (amino acid sequence of fusion protein 6H_DETE_R_ Ubiquitin-conjugating enzyme E2 L3 with GSG Linker)

MRGSHHHHHHGSGDETERIRMRARYPSVLDMAASRRLMKELEEIRKCGMKN
FRNIQVDEANLLTWQGLIVPDNPPYDKGAFRIEINFPAEYPFKPPKITFKTKIYHPNIDE
KGQVCLPVISAENWKPATKTDQVIQSLIALVNDPQPEHPLRADLAEEYSKDRKKFCKN
AEEFTKKYGEKRPVD

Fig. 1 continued

SEQ ID No. 63 (amino acid sequence of fusion protein 6H_DETD_R_ Ubiquitin-conjugating enzyme E2 L3 with GSG Linker)

MRGSHHHHHHGSGDETDRIRMRARYPSVLDMAASRRLMKELEEIRKCGMKN
FRNIQVDEANLLTWQGLIVPDNPPYDKGAFRIEINFPAEYPFKPPKITFKTKIYHPNIDE
KGQVCLPVISAENWKPATKTDQVIQSLIALVNDPQPEHPLRADLAEEYSKDRKKFCKN
AEEFTKKYGEKRPVD

SEQ ID No. 19 (amino acid sequence of fusion protein 6H_VDTTD_ Ubiquitin-conjugating enzyme E2 L3 with GSG Linker)

MRGSHHHHHHGSGVDTTDGIRMRARYPSVLDMAASRRLMKELEEIRKCGMK
NFRNIQVDEANLLTWQGLIVPDNPPYDKGAFRIEINFPAEYPFKPPKITFKTKIYHPNID
EKGQVCLPVISAENWKPATKTDQVIQSLIALVNDPQPEHPLRADLAEEYSKDRKKFCK
NAEEFTKKYGEKRPVD

Amino acid sequence of construct 747 pyrI D73E – cp pyrB

SEQ ID No. 20 (MCSI (pyrI D73E))

MGTHDNKLQVEAIKRGTVIDHIPAQIGFKLLSLFKLTETDQRITIGLNLPSGEMG
RKDLIKIENTFLSEDQVEQLALYAPQATVNRIDNYEVVGKSRPSLPERIDNVLVCPNSN
CISHAEPVSSSFAVRKRANDIALKCKYCEKEFSHNVVLAN

SEQ ID No. 21 (MCSII (cp pyrB))

MTRVQKERLDPSEYANVKAQFVLRASDLHNAKANMKVLHPLPRVDEIATDVD
KTPHAWYFQQAGNGIFARQALLALVLNRANPLYQKHIISINDLSRDDLNLVLATAAKLK
ANPQPELLKHKVIASCFFEASTRTRLSFETSMHRLGASVVGFSDSANTSLGKKGETLA
DTISVISTYVDAIVMRHPQEGAARLATEFSGNVPVLNAGDGSNQHPTQTLLDLFTIQET
QGRLDNLHVAMVGDLKYGRTVHSLTQALAKFDGNRFYFIAPDALAMPQYILDMLDEK
GIAWSLHSSIEEVMAEVDILY

SEQ ID No. 22 (amino acid sequence of 6His-GSG-VDVAD-ΔM-X-pyrB)

MHHHHHHGSGVDVADXRVQKERLDPSEYANVKAQFVLRASDLHNAKANMKV
LHPLPRVDEIATDVDKTPHAWYFQQAGNGIFARQALLALVLNRANPLYQKHIISINDLS
RDDLNLVLATAAKLKANPQPELLKHKVIASCFFEASTRTRLSFETSMHRLGASVVGFS
DSANTSLGKKGETLADTISVISTYVDAIVMRHPQEGAARLATEFSGNVPVLNAGDGSN
QHPTQTLLDLFTIQETQGRLDNLHVAMVGDLKYGRTVHSLTQALAKFDGNRFYFIAPD
ALAMPQYILDMLDEKGIAWSLHSSIEEVMAEVDILY

SEQ ID No. 193 (amino acid sequence of 6H_VDVAD_SOD with GSG Linker)

MHHHHHHGSGVDVADGATKAVCVLKGDGPVQGIINFEQKESNGPVKVWGSI
KGLTEGLHGFHVHEFGDNTAGCTSAGPHFNPLSRKHGGPKDEERHVGDLGNVTAD
KDGVADVSIEDSVISLSGDHCIIGRTLVVHEKADDLGKGGNEESTKTGNAGSRLACGV
IGTAQVDDYKDDDDKGGGGSGGGGSWSHPQFEK

Fig. 1 continued

SEQ ID No. 253 (amino acid sequence of cp caspase-2 with with *N-terminal His Tag*, GS linker, CEES<u>A</u> and E105V and G171D substitution)

M*HHHHHH*GKNHAGSPGCEES<u>A</u>AGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTDEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 254 (amino acid sequence of cp caspase-2 with with *N-terminal His Tag*, GS linker, CEES<u>A</u> and E105V and G171V substitution)

M*HHHHHH*GKNHAGSPGCEES<u>A</u>AGKEKLPKMRLPTRSDMICGYACLKGTAAM
RNTKRGSWYIEALAQVFSERACDMHVADMLVKVNALIKDREGYAPGTEFHRCKVMS
EYCSTLCRHLYLFPGHPPTGSGPVCLQVKPCTPEFYQTHFQLAYRLQSRPRGLALVL
SNVHFTVEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 255 (amino acid sequence of cp caspase-2 with with *N-terminal His Tag*, GS linker, CEES<u>A</u> and E105N and G171V substitution)

M*HHHHHH*GKNHAGSPGCEES<u>A</u>AGKEKLPKMRLPTRSDMICGYACLKGTAAM
RNTKRGSWYIEALAQVFSERACDMHVADMLVKVNALIKDREGYAPGTEFHRCKNMS
EYCSTLCRHLYLFPGHPPTGSGPVCLQVKPCTPEFYQTHFQLAYRLQSRPRGLALVL
SNVHFTVEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

SEQ ID No. 256 (amino acid sequence of cp caspase-2 with with *N-terminal His Tag*, GS linker, CEES<u>A</u> and E105H and G171V substitution)

M*HHHHHH*GKNHAGSPGCEES<u>A</u>AGKEKLPKMRLPTRSDMICGYACLKGTAAM
RNTKRGSWYIEALAQVFSERACDMHVADMLVKVNALIKDREGYAPGTEFHRCKHMS
EYCSTLCRHLYLFPGHPPTGSGPVCLQVKPCTPEFYQTHFQLAYRLQSRPRGLALVL
SNVHFTVEKELEFRSGGDVDHSTLVTLFKLLGYDVHVLCDQTAQEMQEKLQNFAQLP
AHRVTDSCIVALLSHGVEGAIYGVDGKLLQLQEVFQLFDNANCPSLQNKPKMFFIQAC
RGDETDRGVDQQD

Fig. 1 continued

SEQ ID No. 257 (amino acid sequence of fusion protein ompA-T7AC-6H-GSG-VDVAD-rhGH)

MKKTAIAIAVALAGFATVAQALEDPERNKERKEAELQAQTAEQHHHHHHGSGVDVAD
FPTIPLSRLFDNAMLRAHRLHQLAFDTYQEFEEAYIPKEQKYSFLQNPQTSLCFSESIP
TPSNREETQQKSNLELLRISLLLIQSWLEPVQFLRSVFANSLVYGASDSNVYDLLKDLE
EGIQTLMGRLEDGSPRTGQIFKQTYSKFDTNSHNDDALLKNYGLLYCFRKDMDKVET
FLRIVQCRSVEGSCGF*

SEQ ID No. 258 (nucleotide sequence of fusion protein ompA-T7AC-6H-GSG-VDVAD-rhGH)

ATGAAAAAGACAGCTATCGCGATTGCAGTGGCACTGGCTGGTTTCGCTACCGTAG
CGCAGGCCCTGGAGGATCCGGAACGCAACAAAGAGCGAAAGGAAGCTGAGTTG
CAAGCTCAAACCGCTGAGCAACACCATCACCATCACCATGGCAGCGGCGTGGAT
GTGGCGGATTTTCCGACCATTCCGCTGAGCCGTCTGTTTGATAATGCAATGCTGC
GTGCACATCGTCTGCATCAGCTGGCATTTGATACCTATCAAGAATTTGAAGAAGC
GTATATCCCGAAAGAGCAGAAATATAGCTTCCTGCAGAATCCGCAGACCAGCCTG
TGTTTTAGCGAAAGCATTCCGACACCGAGCAATCGTGAAGAAACCCAGCAGAAAA
GCAATCTGGAACTGCTGCGTATTAGCCTGCTGCTGATTCAGAGCTGGCTGGAACC
GGTGCAGTTTCTGCGTAGCGTTTTTGCAAATAGCCTGGTTTATGGTGCAAGCGAT
AGCAATGTTTATGATCTGCTGAAAGATCTGGAAGAAGGTATTCAGACCCTGATGG
GTCGTCTGGAAGATGGTTCACCGCGTACCGGTCAGATCTTTAAACAGACCTATAG
CAAATTCGATACCAACAGCCATAATGATGATGCCCTGCTGAAAAACTATGGTCTGC
TGTATTGTTTCCGCAAAGATATGGATAAAGTGGAAACCTTTCTGCGCATTGTTCAG
TGTCGTAGCGTTGAAGGTAGCTGTGGTTTCTAA

SEQ ID No. 259 (amino acid sequence of fusion protein T7AC-6H-GSG-VDVAD-PTH)

MLEDPERNKERKEAELQAQTAEQHHHHHHGSGVDVADSVSEIQLMHNLGKHLNSM
ERVEWLRKKLQDVHNFVALGAPLAPRDAGSQRPRKKEDNVLVESHEKSLGEADKAD
VNVLTKAKSQ*

SEQ ID No. 260 (nucleotide sequence of fusion protein T7AC-6H-GSG-VDVAD-PTH)

ATGCTGGAGGATCCGGAACGCAACAAAGAGCGAAAGGAAGCTGAGTTGCAAGCT
CAAACCGCTGAGCAACACCATCACCATCACCATGGCAGCGGCGTGGATGTGGCG
GATAGCGTTAGCGAAATTCAGCTGATGCATAATCTGGGCAAACATCTGAATAGCA
TGGAACGTGTTGAATGGCTGCGTAAAAAACTGCAGGATGTGCATAATTTTGTTGC
ACTGGGTGCACCGCTGGCACCGCGTGATGCAGGTAGTCAGCGTCCTCGTAAAAA
AGAAGATAACGTTCTGGTTGAAAGCCACGAAAAAAGCCTGGGTGAAGCAGATAAA
GCAGATGTTAATGTTCTGACCAAAGCCAAAAGCCAGTAA

Fig. 1 continued

SEQ ID No. 261 (amino acid sequence of fusion protein T7AC-6H-GSG-VDVAD-G-CSF)

MLEDPERNKERKEAELQAQTAEQHHHHHHGSGVDVADATPLGPASSLPQSFLLKCL
EQVRKIQGDGAALQEKLVSECATYKLCHPEELVLLGHSLGIPWAPLSSCPSQALQLA
GCLSQLHSGLFLYQGLLQALEGISPELGPTLDTLQLDVADFATTIWQQMEELGMAPAL
QPTQGAMPAFASAFQRRAGGVLVASHLQSFLEVSYRVLRHLAQP*

SEQ ID No. 262 (nucleotide sequence of fusion protein T7AC-6H-GSG-VDVAD-G-CSF)

ATGCTGGAGGATCCGGAACGCAACAAAGAGCGAAAGGAAGCTGAGTTGCAAGCT
CAAACCGCTGAGCAACACCATCACCATCACCATGGCAGCGGCGTGGATGTGGCG
GATGCAACACCGCTGGGTCCTGCAAGCAGCCTGCCGCAGAGCTTTCTGCTGAAA
TGTCTGGAACAGGTTCGTAAAATTCAAGGTGATGGCGCAGCACTGCAAGAAAAAC
TGGTTAGCGAATGTGCAACCTATAAACTGTGTCATCCGGAAGAACTGGTTCTGCT
GGGTCATAGCCTGGGTATTCCGTGGGCACCGCTGAGTAGCTGTCCGAGCCAGGC
ACTGCAGCTGGCAGGTTGTCTGAGTCAGCTGCATAGCGGTCTGTTTCTGTATCAG
GGTCTGCTGCAGGCACTGGAAGGTATTAGTCCGGAACTGGGTCCGACACTGGAT
ACCCTGCAACTGGATGTTGCAGATTTTGCAACCACCATTTGGCAGCAGATGGAAG
AATTAGGTATGGCACCAGCGCTGCAGCCGACACAGGGTGCAATGCCTGCATTTG
CAAGCGCATTTCAGCGTCGTGCCGGTGGTGTTCTGGTTGCAAGCCATCTGCAGA
GTTTTCTGGAAGTTAGCTATCGTGTTCTGCGTCATCTGGCACAGCCGTAA

SEQ ID No. 263 (amino acid sequence of fusion protein T7AC-6H-GSG-VDVAD-TNF-alpha)

MLEDPERNKERKEAELQAQTAEQHHHHHHGSGVDVADVRSSSRTPSDKPVAHVVA
NPQAEGQLQWLNRRANALLANGVELRDNQLVVPSEGLYLIYSQVLFKGQGCPSTHV
LLTHTISRIAVSYQTKVNLLSAIKSPCQRETPEGAEAKPWYEPIYLGGVFQLEKGDRLS
AEINRPDYLDFAESGQVYFGIIAL*

SEQ ID No. 264 (nucleotide sequence of fusion protein T7AC-6H-GSG-VDVAD-TNF-alpha)

ATGCTGGAGGATCCGGAACGCAACAAAGAGCGAAAGGAAGCTGAGTTGCAAGCT
CAAACCGCTGAGCAACACCATCACCATCACCATGGCAGCGGCGTGGATGTGGCG
GATGTCCGTTCCAGCAGCCGTACGCCGAGCGATAAACCTGTCGCGCACGTAGTG
GCGAATCCGCAAGCCGAGGGTCAGCTGCAGTGGCTGAATCGTCGCGCGAACGC
GCTGCTGGCCAATGGTGTTGAGCTGCGTGACAACCAACTGGTTGTTCCATCCGAA
GGCCTGTACCTGATTTATTCTCAAGTGCTGTTCAAAGGTCAGGGTTGCCCGAGCA
CGCACGTGTTGCTGACCCATACCATTAGCCGCATCGCAGTCAGCTACCAGACCAA
GGTCAACCTGTTGAGCGCGATCAAGTCCCCGTGTCAACGTGAAACGCCTGAGGG
CGCTGAGGCCAAGCCGTGGTATGAGCCGATCTACCTGGGTGGCGTGTTTCAGCT
GGAGAAAGGTGACCGTCTGAGCGCGGAAATCAACCGCCCGGATTATTTAGATTTT
GCCGAGTCTGGTCAGGTGTACTTCGGCATTATTGCACTGTGA

Fig. 1 continued

SEQ ID No. 265 (amino acid sequence of fusion protein hFGF-2)

MAAGSITTLPALPEDGGSGAFPPGHFKDPKRLYCKNGGFFLRIHPDGRVDGVREKSD
PHIKLQLQAEERGVVSIKGVSANRYLAMKEDGRLLASKSVTDECFFFERLESNNYNTY
RSRKYTSWYVALKRTGQYKLGSKTGPGQKAILFLPMSAKS*

SEQ ID No. 266 (amino acid sequence of fusion protein 6H-hFGF-2)

MHHHHHHAAGSITTLPALPEDGGSGAFPPGHFKDPKRLYCKNGGFFLRIHPDGRVD
GVREKSDPHIKLQLQAEERGVVSIKGVSANRYLAMKEDGRLLASKSVTDECFFFERLE
SNNYNTYRSRKYTSWYVALKRTGQYKLGSKTGPGQKAILFLPMSAKS*

SEQ ID No. 267 (amino acid sequence of fusion protein T7AC-6H-GSG-VDVAD-hFGF-2)

MLEDPERNKERKEAELQAQTAEQHHHHHHGSGVDVADAAGSITTLPALPEDGGSGA
FPPGHFKDPKRLYCKNGGFFLRIHPDGRVDGVREKSDPHIKLQLQAEERGVVSIKGV
SANRYLAMKEDGRLLASKSVTDECFFFERLESNNYNTYRSRKYTSWYVALKRTGQY
KLGSKTGPGQKAILFLPMSAKS*

SEQ ID No. 268 (amino acid sequence of fusion protein T7AC-6H-GSG-VDSAD-hFGF-2)

MLEDPERNKERKEAELQAQTAEQHHHHHHGSGVDSADAAGSITTLPALPEDGGSGA
FPPGHFKDPKRLYCKNGGFFLRIHPDGRVDGVREKSDPHIKLQLQAEERGVVSIKGV
SANRYLAMKEDGRLLASKSVTDECFFFERLESNNYNTYRSRKYTSWYVALKRTGQY
KLGSKTGPGQKAILFLPMSAKS*

SEQ ID No. 269 (amino acid sequence of fusion protein T7A3-6H-GSG-VDVAD-hFGF-2)

MLEDPERNKERKEAELEAETAEQHHHHHHGSGVDVADAAGSITTLPALPEDGGSGA
FPPGHFKDPKRLYCKNGGFFLRIHPDGRVDGVREKSDPHIKLQLQAEERGVVSIKGV
SANRYLAMKEDGRLLASKSVTDECFFFERLESNNYNTYRSRKYTSWYVALKRTGQY
KLGSKTGPGQKAILFLPMSAKS*

SEQ ID No. 270 (amino acid sequence of fusion protein T7AC-6H-VDVAD-hFGF-2 without GSG linker)

MLEDPERNKERKEAELQAQTAEQHHHHHHVDVADAAGSITTLPALPEDGGSGAFPP
GHFKDPKRLYCKNGGFFLRIHPDGRVDGVREKSDPHIKLQLQAEERGVVSIKGVSAN
RYLAMKEDGRLLASKSVTDECFFFERLESNNYNTYRSRKYTSWYVALKRTGQYKLG
SKTGPGQKAILFLPMSAKS*

Fig. 1 continued

SEQ ID No. 271 (amino acid sequence of fusion protein T7AC-6H-GSGSGSG-VDVAD-hFGF-2 with 7 amino acid long linker)

MLEDPERNKERKEAELQAQTAEQHHHHHHGSGSGSGVDVADAAGSITTLPALPEDG
GSGAFPPGHFKDPKRLYCKNGGFFLRIHPDGRVDGVREKSDPHIKLQLQAEERGVVS
IKGVSANRYLAMKEDGRLLASKSVTDECFFFERLESNNYNTYRSRKYTSWYVALKRT
GQYKLGSKTGPGQKAILFLPMSAKS*

SEQ ID No. 272 (amino acid sequence of fusion protein T7AC-6H-GSGSGSG-VDVAD-hFGF-2)

ATGCTGGAGGATCCGGAACGCAACAAAGAGCGAAAGGAAGCTGAGTTGCAAGCT
CAAACCGCTGAGCAACACCATCACCATCACCATGGTAGCGGCTCTGGCAGCGGC
GTGGATGTGGCGGATGCCGCTGGTTCGATTACTACCCTGCCTGCTTTACCTGAAG
ATGGTGGTTCTGGTGCGTTCCCGCCGGGTCACTTCAAAGACCCAAAACGTTTGTA
CTGTAAAAACGGTGGCTTTTTTCTGCGCATCCATCCGGACGGCCGCGTGGATGGT
GTCCGTGAAAAGTCCGACCCGCACATTAAGCTGCAACTGCAGGCCGAGGAGCGT
GGTGTTGTTAGCATCAAAGGCGTGAGCGCAAATCGTTACCTGGCGATGAAAGAG
GATGGCCGTCTGCTGGCGAGCAAGAGCGTTACCGACGAGTGCTTCTTCTTTGAA
CGCCTGGAGAGCAATAATTACAACACCTACCGTAGCCGCAAGTATACCTCTTGGT
ATGTGGCGCTGAAGCGTACGGGCCAGTATAAATTGGGTAGCAAAACGGGTCCGG
GCCAAAAGGCAATCCTGTTCCTGCCGATGAGCGCGAAATCCTAA

SEQ ID No. 273 (amino acid sequence of fusion protein ompA-6H-GSG-VDVAD-TNF-alpha)

MKKTAIAIAVALAGFATVAQAHHHHHHGSGVDVADVRSSSRTPSDKPVAHVVANPQA
EGQLQWLNRRANALLANGVELRDNQLVVPSEGLYLIYSQVLFKGQGCPSTHVLLTHTI
SRIAVSYQTKVNLLSAIKSPCQRETPEGAEAKPWYEPIYLGGVFQLEKGDRLSAEINR
PDYLDFAESGQVYFGIIAL*

SEQ ID No. 274 (nucleotide sequence of fusion protein ompA-6H-GSG-VDVAD-TNF-alpha)

ATGAAAAAGACAGCTATCGCGATTGCAGTGGCACTGGCTGGTTTCGCTACCGTAG
CGCAGGCCCACCATCACCATCACCATGGCAGCGGCGTGGATGTGGCGGATGTCC
GTTCCAGCAGCCGTACGCCGAGCGATAAACCTGTCGCGCACGTAGTGGCGAATC
CGCAAGCCGAGGGTCAGCTGCAGTGGCTGAATCGTCGCGCGAACGCGCTGCTG
GCCAATGGTGTTGAGCTGCGTGACAACCAACTGGTTGTTCCATCCGAAGGCCTGT
ACCTGATTTATTCTCAAGTGCTGTTCAAAGGTCAGGGTTGCCCGAGCACGCACGT
GTTGCTGACCCATACCATTAGCCGCATCGCAGTCAGCTACCAGACCAAGGTCAAC
CTGTTGAGCGCGATCAAGTCCCCGTGTCAACGTGAAACGCCTGAGGGCGCTGAG
GCCAAGCCGTGGTATGAGCCGATCTACCTGGGTGGCGTGTTTCAGCTGGAGAAA
GGTGACCGTCTGAGCGCGGAAATCAACCGCCCGGATTATTTAGATTTTGCCGAGT
CTGGTCAGGTGTACTTCGGCATTATTGCACTGTGA

Fig. 1 continued

SEQ ID No. 275 (amino acid sequence of fusion protein 6H-GSG-VDVAD-BIWA4)

MHHHHHHGSGVDVADEIVLTQSPATLSLSPGERATLSCSASSSINYIYWYQQKPGQA
PRLLIYLTSNLASGVPARFSGSGSGTDFTLTISSLEPEDFAVYYCLQWSSNPLTFGGG
TKVEIKRGGGGSGGGGSGGGGSEVQLVESGGGLVKPGGSLRLSCAASGFTFSSYD
MSWVRQAPGKGLEWVSTISSGGSYTYYLDSIKGRFTISRDNAKNSLYLQMNSLRAED
TAVYYCARQGLDYWGRGTLVTVSS*

SEQ ID No. 276 (nucleotide sequence of fusion protein 6H-GSG-VDVAD-BIWA4)

ATGCACCATCACCATCACCATGGCAGCGGCGTGGATGTGGCGGATGAAATTGTG
CTGACCCAGAGCCCGGCGACCCTGAGCCTGAGCCCGGGTGAACGTGCCACCCT
GAGCTGTAGCGCGAGCAGCAGCATTAACTATATCTATTGGTATCAGCAGAAACCG
GGCCAGGCGCCGCGTCTGCTGATTTATCTGACCAGCAACCTGGCCAGCGGTGTT
CCGGCGCGTTTTAGCGGCAGCGGTAGCGGCACCGATTTTACCCTGACCATTAGC
AGCCTGGAACCGGAAGATTTTGCGGTGTATTATTGCCTGCAGTGGAGCAGCAATC
CGCTGACCTTTGGCGGTGGCACCAAAGTGGAAATTAAACGTGGCGGCGGTGGCA
GCGGTGGTGGTGGTAGCGGCGGTGGCGGCAGCGAAGTGCAGCTGGTTGAAAGC
GGTGGCGGCCTGGTGAAACCGGGTGGCAGCCTGCGTCTGAGCTGTGCGGCGAG
CGGCTTTACCTTTAGCAGCTATGATATGAGCTGGGTGCGTCAGGCGCCGGGCAA
AGGCCTGGAATGGGTGAGCACCATCAGCAGCGGCGGCAGCTATACCTATTATCT
GGATAGCATCAAAGGCCGTTTTACCATTAGCCGTGATAACGCGAAAAACAGCCTG
TATCTGCAGATGAACAGCCTGCGTGCGGAAGATACCGCGGTTTATTATTGCGCGC
GTCAGGGCCTGGATTATTGGGGCCGTGGCACCCTGGTTACCGTGAGCAGCTAA

SEQ ID No. 282 (DsbA (Thiol:disulfide interchange protein)

MKKIWLALAGLVLAFSASA

SEQ ID No. 283 (Endoxylanase from Bacillus sp.)

MFKFKKKFLVGLTAAFMSISMFSATASA

SEQ ID No. 284 (LamB (λ receptor protein)

MMITLRKLPLAVAVAAGVMSAQAMA

SEQ ID No. 285 (Lpp (murein lipoprotein))

MKATKLVLGAVILGSTLLAG

SEQ ID No. 286 (LTB (heat-labile enterotoxin subunit B))

MNKVKCYVLFTALLSSLYAHG

Fig. 1 continued

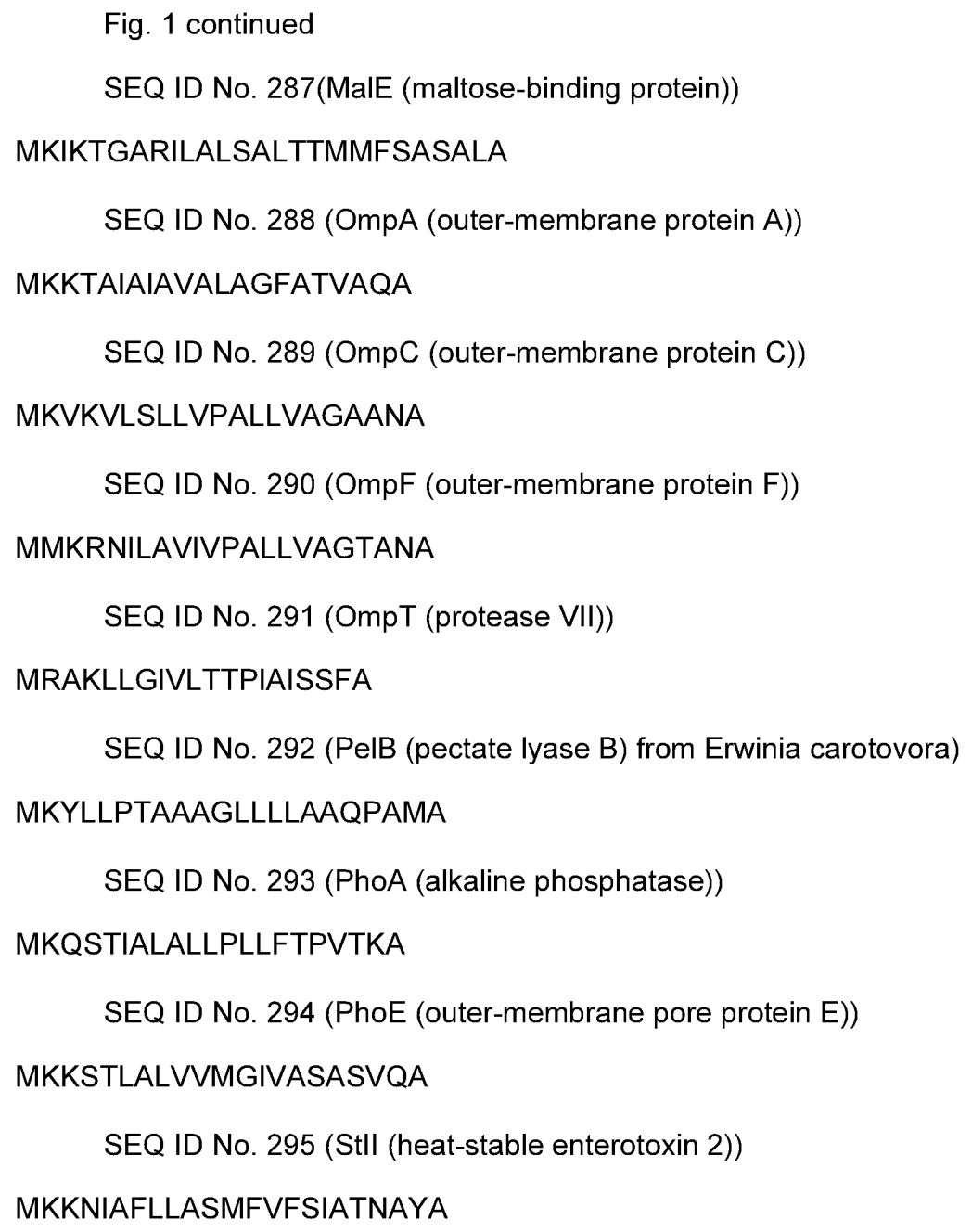

SEQ ID No. 287(MalE (maltose-binding protein))

MKIKTGARILALSALTTMMFSASALA

SEQ ID No. 288 (OmpA (outer-membrane protein A))

MKKTAIAIAVALAGFATVAQA

SEQ ID No. 289 (OmpC (outer-membrane protein C))

MKVKVLSLLVPALLVAGAANA

SEQ ID No. 290 (OmpF (outer-membrane protein F))

MMKRNILAVIVPALLVAGTANA

SEQ ID No. 291 (OmpT (protease VII))

MRAKLLGIVLTTPIAISSFA

SEQ ID No. 292 (PelB (pectate lyase B) from Erwinia carotovora)

MKYLLPTAAAGLLLLAAQPAMA

SEQ ID No. 293 (PhoA (alkaline phosphatase))

MKQSTIALALLPLLFTPVTKA

SEQ ID No. 294 (PhoE (outer-membrane pore protein E))

MKKSTLALVVMGIVASASVQA

SEQ ID No. 295 (StII (heat-stable enterotoxin 2))

MKKNIAFLLASMFVFSIATNAYA

Fig. 4
A
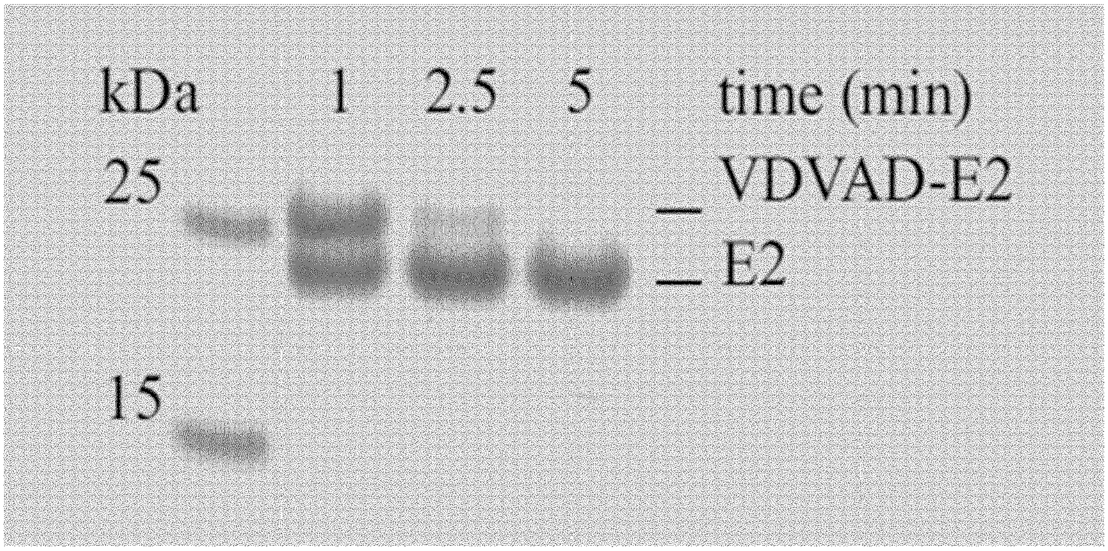
B
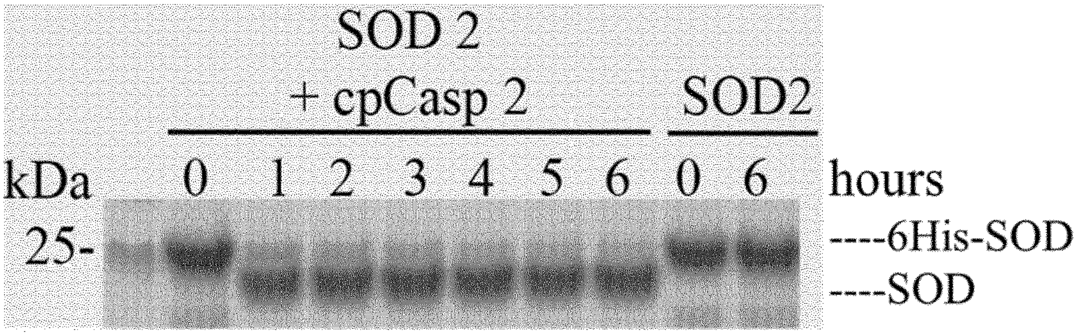
Fig. 5
| | | | 280 | | |
|---|---|---|---|---|---|
| **cp caspase-2** | **(SEQ ID No.6)** | PKMFFIQACR | GDETDRGVDQQD | 292 | |
| **cp caspase-2 D285E** | **(SEQ ID No.13)** | PKMFFIQACR | GDETERGVDQQD | 292 | |
| **cp caspase-2 Stop** | **(SEQ ID No.14)** | PKMFFIQACR | GDETD** | 285 | |
| **cp caspase-2 Strep D292S** | **(SEQ ID No.15)** | PKMFFIQACR | GDETDRGVDQQ**S** | GSGWSHPQFEK | 303 |
| **cp caspase-2 Strep D292S D285E** | **(SEQ ID No.16)** | PKMFFIQACR | GDETERGVDQQ**S** | GSGWSHPQFEK | 303 |

| Active site | Large Subunit | | | | | | Small Subunit | | | | |
|---|---|---|---|---|---|---|---|---|---|---|---|
| | 1 | SEQ ID No. | 2 | SEQ ID No. | 3 | SEQ ID No. | 4 | SEQ ID No. | 5 | SEQ ID No. |
| Human P41976 | G--EKDLEFRSGGDVDH | 119 | LLSHGVEGALYGVDG | 130 | QACRGDEY | 141 | AAMRNTRR | 152 | EGYAPGTEFHRCK | 163 |
| Mouse P29704 | G-EKDLEFRSGEDVDH | 120 | LLSHGVEGSLYGVDG | 131 | QACRGDEY | 142 | AAMRNTKR | 153 | EGYAPGTEFHRCK | 164 |
| Sheep W5Q0H6 | G--EKDLEFRSGGDVDH | 121 | LLSHGVEGSVYGVDG | 132 | QACRGDEY | 143 | AAMRNTKR | 154 | EGYAPGTEFHRCK | 165 |
| Tasman Devil G3VQ27 | G--EKDLEFRSGGDVDH | 122 | LLSHGIEGSLYGVDG | 133 | QACRGDEY | 144 | AAMRNTKR | 155 | EGYAPGTEFHRCK | 166 |
| Chicken Q5ZM43 | G--EKDLEYRSGGDVDC | 123 | LLSHGIEGSVYGVDG | 134 | QACRGDEY | 145 | AAMRNTRR | 156 | EGYAPGTEFHRCK | 167 |
| Anolis H9GC56 | K--VTDLEFRSGGDVDN | 124 | LLSHGIEGSIYGIDG | 135 | QACRGDEY | 146 | AAMRNTRH | 157 | EGHAPGTEFHRCK | 168 |
| Alligator A0A1U8DAG8 | G--EKDLEFRSGGDVDC | 125 | LLSHGVEGSVYGVDG | 136 | QACRGDEY | 147 | AAMRNTRR | 158 | EGYAPGTEFHRCK | 169 |
| Xenopus F6SDY9 | P--QDLDHRVGGEVDV | 126 | VLSRGLLGAVYGHDG | 137 | QACRGEEA | 148 | VSLRNTKR | 159 | EGHAPGTEFHRCK | 170 |
| Danio Q6PBX3 | SAVDLDIRRGGEVDE | 127 | LLSHGVEGSVYGVDG | 138 | QACRGEEM | 149 | AAMRNTKR | 160 | EGYAPGSAEHRCK | 171 |
| Ghost Shark V9KZ71 | G--EGLARPGAADT | 128 | LLSHGVEGALYGVDG | 139 | QACRGDRH | 150 | AALRNTRQ | 161 | EGYAPGTDFHRCK | 172 |
| Sea squirt A0A1W2WPB0 | P--ESDLNRGGSRDR | 129 | AMSHGDAGSIYGSDG | 140 | QACQGDEY | 151 | AAMRNTKH | 162 | EGMDPGSVYHRCK | 173 |
| Consensus | G--EKDLEFRSGGDVDH | 174 | LLSHGVEGSVYGVDG | 175 | QACRGDEH | 176 | AAMRNTRR | 177 | EGYAPGTEFHRCK | 178 |
| Identity | 25 % | | 53.3 % | | 50 % | | 37.5 % | | 61.5 % | |

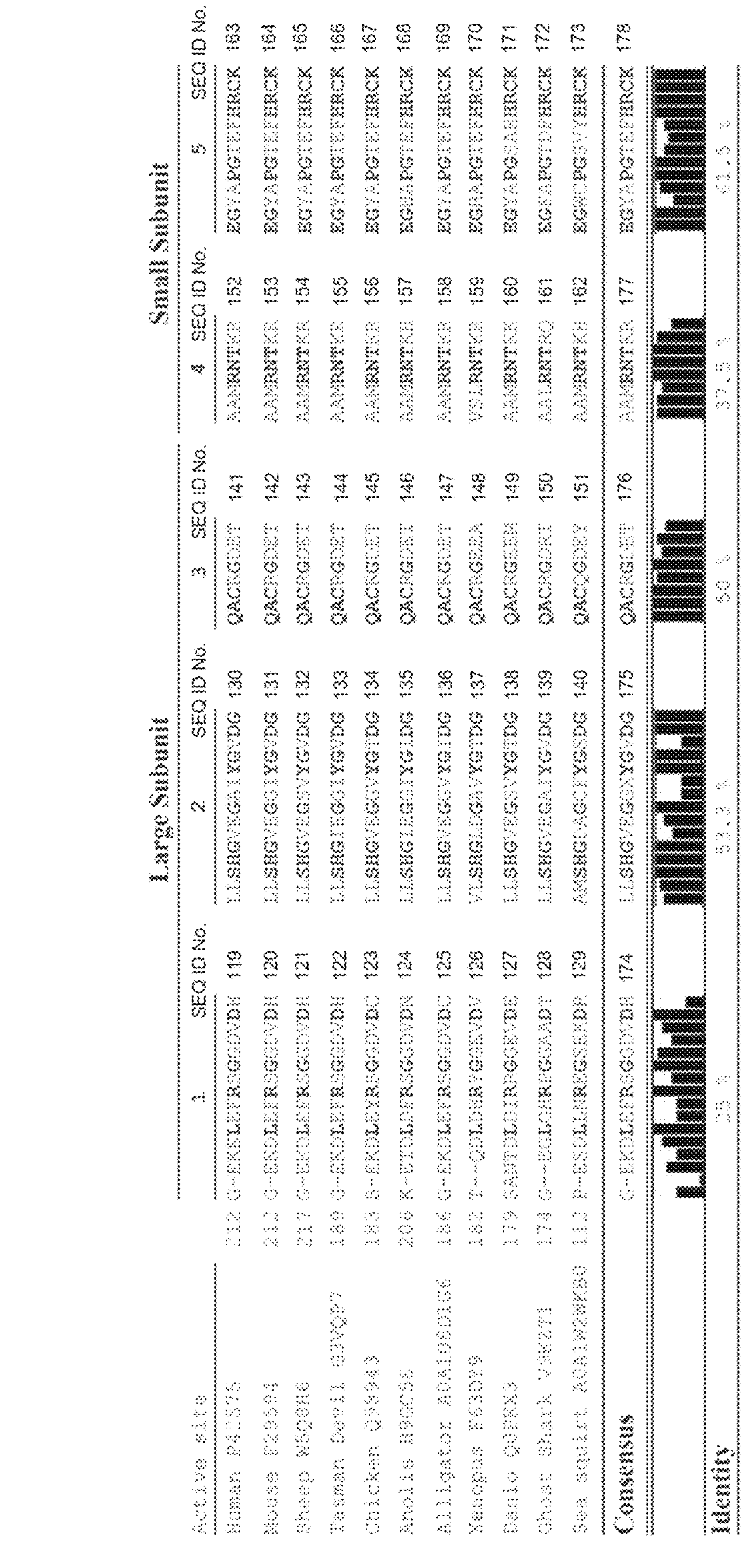

Fig. 7

| | | DEVD |
|---|---|---|
| cp caspase-2 | x̄ | 140 |
| | σ | ± 27 |
| wt caspase-2 | x̄ | 44 |
| | σ | ± 8 |

Fig. 23
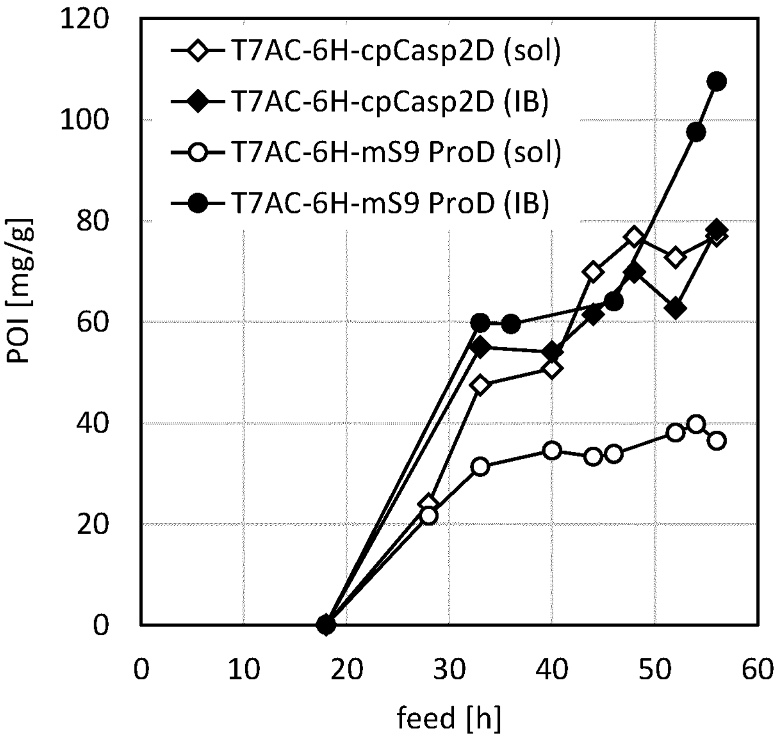
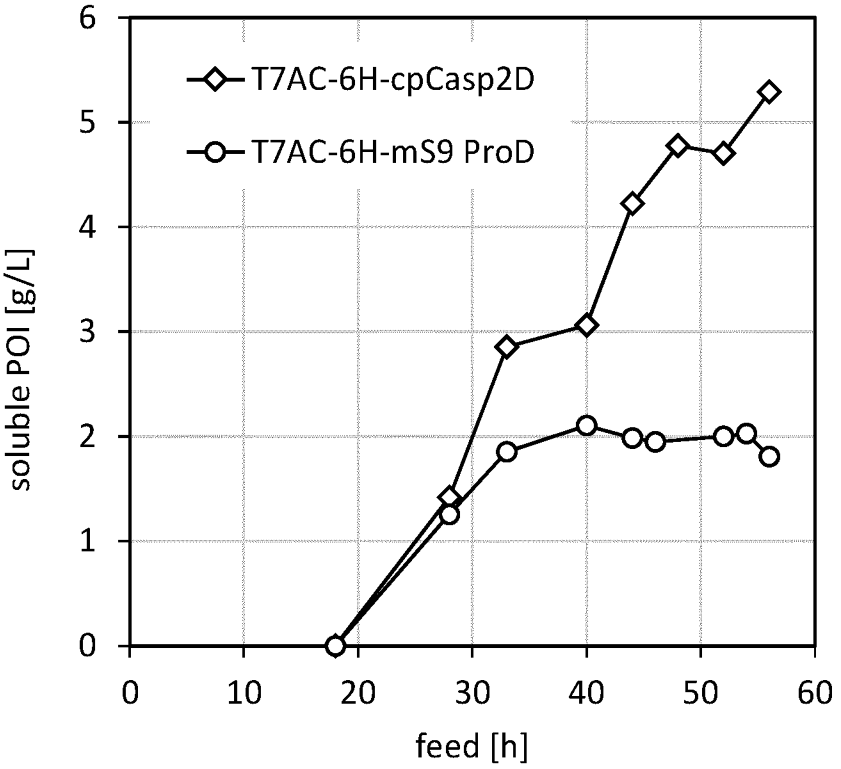

Comparison VDVAD vs VDSAD (T7AC_6H_GSG_VDXAD-hFGF2 w T7AC_6H_mS9ProD)

6H_GSG_VDVAD-hFGF2 vs T7AC_6H_GSG_VDVAD-hFGF2
w T7AC_6H_mS9ProD

6H_GSG_VDVAD-hFGF2 vs T7AC_6H_GSG_VDVAD-hFGF2
w T7AC_6H_mS9ProE

CASPASE-2 VARIANTS

FIELD OF THE INVENTION

The invention relates generally to the field of molecular biology, biotechnology or bioprocess engineering for the production and use of a modified caspase-2, specifically a circularly permuted caspase-2. The invention further relates to the production and isolation of recombinant protein constructs, specifically using modified caspase-2 for the maturation of recombinant fusion proteins or polypeptides comprising a caspase recognition site.

SEQUENCE LISTING

The instant application contains a Sequence Listing which has been submitted electronically in ASCII format and is hereby incorporated by reference in its entirety. Said ASCII copy, created on Feb. 3, 2026, is named 12-0435-US-1_SL.txt and is 356,820 bytes in size.

BACKGROUND OF THE INVENTION

Despite all the recent advances in biotechnology the production of proteins is still challenging due to their diverse characteristics. Protocols usually have to be optimized for every protein, which is especially problematic for large scale production.

The diverse characteristics of proteins makes their purification challenging and impede a general protocol. This is why proteins are often fused to tags with special binding properties. Already the first human proteins recombinantly expressed in *E. coli*, somatostatin [1] and insulin [2], were fusion proteins. Even today protein tags are still widely used in recombinant protein production, not only to facilitate purification and detection but also to enhance expression and solubility. Popular tags to stabilize expression and increase solubility are for example GST (Glutathione S-transferase), MBP (Maltose-binding protein), SUMO (Small ubiquitin-related modifier), or DsbA (Protein disulfide isomerase 1). Tags for affinity purification include among others His, HA (hemaglutinin antigen), Strep II, and FLAG tag.

However, as versatile and useful tags are, as difficult can be their removal. For many—especially medical—applications a tag-free protein is essential. Tags can influence the structure and characteristics of proteins and therefore also alter the response to immunogens or trigger an immune reaction themselves [3]. Especially for biopharmaceutical applications a protease which efficiently cleaves tags from the product is essential [4].

A variety of proteases for tag removal are available. They all cleave at defined recognition sequences which are inserted between the tag and the protein of interest. Usually the protease has a tag itself and is subsequently removed in a second purification step. The most commonly used are endopeptidases like factor Xa, thrombin, TEV (tobacco etch virus protease), and enterokinase. However, all of these proteases have one or several downsides: they cleave inefficiently or unspecifically, do not accept all residues in the P1' position, leave overhang residues at the N-terminus, or they need special buffer conditions that are not favorable to the target protein. Another major drawback for industrial application is the high cost of these proteases [5].

Despite the fact, that caspases have been studied more intensively than other protease classes, and have a quite high specificity, they have hardly ever been considered for biotechnological purposes like tag cleavage.

Caspase is the acronym for cysteinyl aspartate-specific protease, a class of proteases that is defined by a conserved catalytic cysteine and their strong preference to cleave their substrates after aspartate residues [6]. The first caspase was described in the early 1990s, since then a total of fifteen have been discovered in mammalia, thirteen of which are found in humans [7]. They are well known for their role in regulated cell death [8] and inflammatory reactions [9]. More recently it has been discovered, that they are also involved in other processes like cell differentiation [10], cell cycle regulation [11], and maybe even cell motility [12]. MacKenzie and Clark investigated the role of dimerization in the ability of caspases to form fully functional proteases and describe that dimerization is necessary for active site formation because both caspase monomers contribute residues that enable the formation of a fully functional active site (MacKenzie and Clark, *Adv Exp Med Biol.* (2012); 747:55-73).

In recent years, reversed caspases, where the small subunit of the caspase is N-terminal to the large subunit of the caspase have been developed (U.S. Pat. No. 6,379,950).

Srinivasa et al. for example describe recombinant caspases 3 and 6 precursors, which are constitutively active and have their small subunit preceding their large subunit (Srinivasa et al. *Journal of Biological Chemistry, American Society for Biochemistry and Molecular Biology* (1998), 273(17):10107-10111).

Circular Permutation may provide potential benefits by reorganizing the polypeptide chain of a protein, however, by connecting the native protein termini via a covalent linker and introducing new ends through the cleavage of an existing peptide bond, circular permutation can also perturb local tertiary structure and protein dynamics, as well as introduce possible quaternary structure changes and problems (Yu and Lutz, *Trends in Biotechnology* (2011), 29(1):18-25).

WO2009/044988A1 describes a method of producing a caspase, using a recombinant caspase expression vector capable of being over-expressed without cytotoxicity because the auto-activation recognition site of caspase is replaced with a non-cysteine protease recognition site to nullify the auto-activation activity during the mass-expression in *E. coli.*

Three systems employing caspases for tag removal have been published, which are difficult to compare because different fusion proteins, buffers, substrate to enzyme ratios, and incubation temperatures were used.

Caspase-3 and an engineered caspase-3 with uncleavable propeptide (but wild-type order of subunits) have been used to cleave GST tags from fusion proteins. The modified caspase was able to achieve complete tag cleavage at 25° C. in about three hours (molar caspase to substrate ratio 1:80, mass ratio 1:100) [13]. In another system which also uses caspase-3 to cleave GST tags (caspase to substrate mass ratio 1:200) processing was complete to over 90% in 45 min, but incubation was at 30° C. [14].

A system with caspase-6 has also been published, it is more effective and manages complete cleavage of substrates in about thirty minutes (molar caspase to substrate ratio 1:500) [15].

Even though these caspase-based tag cleaving systems have been published more than ten years ago, they have not been adopted into the common repertoire of protein purifications. Use of the caspase-3 based system has only been published once, for the expression of interleukins [16]. The caspase-6 system also has been used by merely two other groups, both from the Indian Institute of Immunology, for the purification of *Mycobacterium tuberculosis* [17] and *Helicobacter pylori* proteins [18].

EP1597369B1, for example, discloses a method of protein production using a fusion protein, comprising a protein of interest and a protease recognition site, wherein a protease, such as a caspase, is used to cleave the fusion protein at the recognition site.

U.S. Pat. No. 7,604,980B2 also uses a fusion protein comprising a protein of interest and a caspase recognition site to produce a protein of interest. In this disclosure, caspase-6 is preferably used to cleave the fusion protein.

A main reason why caspases have not become more popular in biotechnology might be the challenges during their recombinant production. Native caspases are synthesized as inactive zymogens, thus to obtain an active enzyme there are two main possibilities. The subunits can be expressed separately and then mixed after purification, which makes their production very complex [19]. Or, the procaspase is expressed which causes autocatalytic activation. This process, however, is often not complete [20], therefore enzyme activity can vary between batches [21]. Furthermore, as caspases are active in *E. coli* they can also cleave bacterial proteins [22] and negatively influence growth and yield. In addition, the substrate specificities of both caspase-3 [23] and caspase-6 [24] have been described as rather promiscuous. They are very likely to cleave fusion proteins at undesired sites.

Therefore, there is an urgent need for an industrially applicable platform technology which enables efficient and specific tag removal to improve purification of recombinant protein products.

SUMMARY OF THE INVENTION

In the production of recombinant proteins, processing of fusion proteins with state-of-the-art enzymes to remove tags often generates a non-authentic N- or C-terminus since these enzymes lack specificity. Such lack of specificity can also lead to unspecific cleavage or proteolytic degradation of the protein of interest.

It is the objective of the present invention to provide an improved system for the production of recombinant proteins employing a modified caspase-2, specifically a circular permuted caspase-2.

The objective is solved by the present invention.

Specifically provided herein is a modified caspase-2, specifically a circularly permuted caspase-2, with significantly improved P1' tolerance. The caspase-2 variants provided herein are specifically used in the production of recombinant proteins to generate a protein of interest comprising an authentic N-terminus by target specific cleavage of N-terminal tags.

According to the invention, there is provided a single-chain circular permuted caspase-2 (cp caspase-2) comprising the following structure from N- to C-terminus:

i. a small subunit of a caspase-2, or a functionally active variant thereof; and ii. a large subunit of a caspase-2, or a functionally active variant thereof, wherein said cp caspase-2 comprises one or more amino acid substitutions increasing P1' tolerance of said cp caspase-2 compared to a cp caspase-2 without said amino acid substitutions.

Specifically, the cp caspase-2 provided herein is catalytically active, specifically upon dimerization. Specifically, the cp caspase-2 described herein is catalytically active and capable of catalyzing peptide bond cleavage upon dimerization. Specifically, the cp caspase-2 described herein is a single-chain caspase-2 that does not require cleavage by initiator caspases for activation.

Specifically, the caspase-2 or cp caspase-2 provided herein is a functionally active variant of wild-type caspase-2 comprising improved P1' tolerance. Specifically, said functionally active variant is capable of cleaving a substrate with high efficiency and specificity.

Specifically, provided herein is a single chain caspase-2 comprising the following structure from N- to C-terminus:

i. a small subunit of a caspase-2 comprising SEQ ID NO:3, or a functionally active variant thereof comprising SEQ ID No. 91, SEQ ID No. 94, SEQ ID No. 97, SEQ ID No. 100, SEQ ID No. 103, SEQ ID No. 106, SEQ ID No. 109, SEQ ID No. 112, SEQ ID No. 115, or SEQ ID No. 118 and optionally up to 8, 9, or 10 amino acid substitutions, insertions and/or deletions; and ii. a large subunit of a caspase-2 comprising SEQ ID NO:4, or a functionally active variant thereof comprising SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No. 114, or SEQ ID No. 117 and optionally up to 8, 9, or 10 amino acid substitutions, insertions and/or deletions, wherein said single chain caspase-2 comprises one or more amino acid substitutions increasing proteolytic activity of said single chain caspase-2 compared to a caspase-2 comprising the same sequence as said single chain caspase-2 but without said amino acid substitutions. Optionally, said single chain caspase-2 comprises one or more further amino acid substitutions, insertions or deletions.

Specifically, said variant is of animal origin, specifically of mammalian, reptile or fish origin, more specifically from human, marsupial, iguana or cartilaginous fish, ghost shark or tasman devil origin.

According to a specific embodiment, the cp caspase-2 provided herein comprises one or more amino acid substitutions at positions 171, 105, 172, 282, 225, 83, 185, 255, or 285 of SEQ ID No. 6 or at a position functionally equivalent to any of positions 171, 105, 172, 282, 225, 83, 185, 255, or 285 of SEQ ID No. 6 or any combination thereof. Specifically, a cp caspase-2 comprising one or more of said amino acid substitutions, also referred to as "cp caspase-2 variant", comprises improved P1' tolerance compared to a cp caspase-2 not comprising said substitutions. Specifically, the cp caspase-2 variants provided herein comprise improved P1' tolerance for at least one amino acid other than glycine.

According to a further specific embodiment, the cp caspase-2 provided herein comprises a propeptide of a small caspase-2 subunit (SS propeptide), fused to the N-terminus of the small subunit. Specifically, the SS propeptide comprises one or more amino acid substitutions at the C-terminus of the SS propeptide. Specifically, the SS propeptide of the cp caspase-2 described herein is modified to prevent cleavage at its C-terminus. Specifically, the SS propeptide comprises an amino acid substitution at position $Asp^{14}$ of SEQ ID No. 2 or at a position functionally equivalent to $Asp^{347}$ of SEQ ID No. 11, specifically Asp is substituted to Ala.

According to a specific embodiment, the SS propeptide described herein comprises the amino acid sequence of SEQ ID No. 2, wherein X can be any amino acid except D or E, specifically it is A, or a variant thereof having 1, 2, 3, 4, or 5 point mutations or deletions. Specifically, said variant is a functionally active variant. Preferably, the SS propeptide sequence comprises the amino acid sequence of SEQ ID No. 2, wherein X is not D or E.

According to a further specific embodiment, the cp caspase-2 provided herein comprises one or more linker sequences, specifically consisting of 1, 2, 3, 4, 5, 6, 7, 8, 9, 10, 11 or 12 or even more amino acid residues. Specifically, the linker can comprise more than 20 or 30 or even more amino acids, as long as the caspase retains its functional activity as described herein. Specifically, the linker sequence comprises glycine, alanine and/or serine residues. Specifically, the linker comprises at least one glycine and serine residue, more specifically the linker is GS, GSG, GGSGG (SEQ ID NO:278), GSGSGSGS (SEQ ID NO:280 having an extra serine at the C terminus) and/or GSAGSAAGSG (SEQ ID NO:279).

Specifically, the cp caspase-2 comprises a subunit-linker sequence, which is a linker sequence between the small subunit and the large subunit of the cp caspase-2 described herein.

According to a further specific embodiment, the cp caspase-2 provided herein comprises one or more C-terminal or N-terminal tags, specifically selected from the group consisting of affinity tags, solubility enhancement tags and monitoring tags.

Specifically, any tag known in the art can be fused to the cp caspase-2.

Specifically, the affinity tag is selected from the group consisting of poly-histidine tag, poly-arginine tag, peptide substrate for antibodies, chitin binding domain, RNAse S peptide, protein A, β-galactosidase, FLAG tag, Strep II tag, streptavidin-binding peptide (SBP) tag, calmodulin-binding peptide (CBP), glutathione S-transferase (GST), maltose-binding protein (MBP), S-tag, HA tag, c-Myc tag, SUMO tag, *E. coli* thioredoxin, NusA, chitin binding domain CBD, chloramphenicol acetyl transferase CAT, LysRS, ubiquitin, calmodulin, and lambda gpV, specifically the tag is a His tag comprising one or more His, more specifically it is a hexahistidine tag.

Specifically, the solubility enhancement tag is selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T7AC, T3, N1, N2, N3, N4, N5, N6, N7, calmodulin-binding peptide (CBP), poly Arg, poly Lys, G B1 domain, protein D, Z domain of Staphylococcal protein A, DsbA, DsbC and thioredoxin.

Preferably, the solubility enhancement tag is selected from the group consisting of T7A3 tag and T7AC tag.

Specifically, the monitoring tag is selected from the group consisting of m-Cherry, GFP and f-Actin.

According to a specific embodiment, the cp caspase-2 described herein comprises more than one tag sequences, specifically it comprises an affinity tag and a solubility enhancement tag. Specifically, it comprises an affinity tag, a solubility enhancement tag and a monitoring tag. Specifically, it comprises more than one tag of the same functionality, specifically it comprises more than one affinity tag, more than one solubility enhancement tag and/or more than one monitoring tag, and any combination thereof. Specifically, the cp caspase-2 described herein comprises a C-terminal and an N-terminal tag, each comprising one or more tag sequences, preferably selected from affinity tag, solubility enhancement tag and monitoring tag Specifically, the affinity tag is a hexahistidine (SEQ ID NO:315) tag and the solubility enhancement tag is a T7AC tag.

According to a further specific embodiment, the cp caspase-2 provided herein comprises a tag-linker sequence, which is a linker sequence between two tags or a tag and the small subunit, the large subunit or the SS propeptide of the cp caspase-2. Specifically, the cp caspase-2 provided herein comprises one or more N-terminal tags and optionally one or more tag-linker sequences between the tags or between a tag and the N-terminus of the small subunit or the SS propeptide. Specifically, the cp caspase-2 provided herein comprises one or more C-terminal tags and optionally one or more tag-linker sequences, which are linker sequences between the tags or between a tag and the C-terminus of the large subunit.

According to a further embodiment, herein provided is a functionally active variant of the cp caspase-2 or caspase-2, wherein i. the small subunit of a caspase-2 comprises
   a) a first conserved region of the active center with at least 37.5% amino acid sequence identity to SEQ ID No. 177 (1st consensus: AAMRNTKR) or 100% sequence identity to XXXRNTXX (SEQ ID No. 200), wherein X is any amino acid,
   b) a second conserved region of the active center with at least 61.5% amino acid sequence identity to SEQ ID No. 178 (2nd consensus: EGYAPGTEFHRCK) or 100% sequence identity to EGXXPGXXXHRCK (SEQ ID No. 194), wherein X is any amino acid, and
ii. the large subunit of a caspase-2 comprises
   a) a third conserved region of the active center with at least 25.0% amino acid sequence identity to SEQ ID No. 174 (3rd consensus: G-EKDLEFRSGGDVDH) or 100% sequence identity to X-XXXLXXRXGXXXDX (SEQ ID No. 195), wherein X is any amino acid,
   b) a fourth conserved region of the active center with at least 53.3% amino acid sequence identity to SEQ ID No. 175 (4th consensus: LLSHGVEGGXYGVDG) or 100% sequence identity to XXSHGXXGXX-YGXDG (SEQ ID No. 196), wherein X is any amino acid, and
   c) a fifth conserved region of the active center with at least 50.0% amino acid sequence identity to SEQ ID No. 176 (5th consensus: QACRGDET) or 100% sequence identity to QACXGXXX (SEQ ID No. 197), wherein X is any amino acid.

According to a specific embodiment, the cp caspase-2 provided herein comprises an N-terminal and/or C-terminal truncation of at least 1, 2, 3, 4, 5 and up to 10 or even more, as long as the caspase retains its functional activity as described herein. According to a further specific embodiment, the cp caspase-2 provided herein comprises an N-terminal and/or C-terminal extension of at least 1, 2, 3, 4, 5 and up to 10 or even more, as long as the caspase retains its functional activity as described herein. Specifically, the cp caspase-2 may comprise a truncation and an extension.

Specifically, the small subunit of the cp caspase-2 described herein comprises the amino acid sequence of SEQ ID No. 3, SEQ ID No. 91, SEQ ID No. 94, SEQ ID No. 97, SEQ ID No. 100, SEQ ID No. 103, SEQ ID No. 106, SEQ ID No. 109, SEQ ID No. 112, SEQ ID No. 115, SEQ ID No. 118 or a functionally active variant thereof comprising at least 70, 75, 80, 85, 90, 91, 92, 93, 94, 95, 96, 97 or 98% sequence identity. Specifically, the large subunit of the cp caspase-2 described herein comprises the amino acid sequence of SEQ ID No. 4, SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No.

114, SEQ ID No. 117, or a functionally active variant thereof comprising at least 70, 75, 80, 85, 90, 91, 92, 93, 94, 95, 96, 97 or 98% sequence identity.

According to a specific embodiment, the cp caspase-2 variant provided herein comprises one or more amino acid substitutions, selected from i. $Gly^{171}$, substituted with D or an amino acid selected from the group consisting of R, K, E, Q, N, A, S, T, P, H, Y;
ii. $Glu^{105}$, substituted with V or an amino acid selected from the group consisting of C, L, I, M, F, W, R, K, D, Q, N;
iii. $Glu^{172}$, substituted with V or an amino acid selected from the group consisting of C, L, I, M, F, W, R, K, D, Q, N;
iv. $Asp^{282}$, substituted with E or T or an amino acid selected from the group consisting of R, K, Q, N, G, A, S, P, H, Y;
v. $Val^{225}$, substituted with G or an amino acid selected from the group consisting of A, S, T, P, H, Y, C, L, I, M, F, W;
vi. $Lys^{83}$, substituted with E or an amino acid selected from the group consisting of R, D, Q, N,
vii. $His^{185}$, substituted with A or an amino acid selected from the group consisting of G, S, T, P, Y;
viii. $Val^{255}$, substituted with M or an amino acid selected from the group consisting of C, L, I, F, W; and/or
ix. $Asp^{285}$, substituted with E or Y or an amino acid selected from the group consisting of R, K, Q, N, G, A, S, T, P, H;

with reference to the positions of SEQ ID No. 6, or positions functionally equivalent to positions of SEQ ID No. 6.

Specifically, selection of alternative amino acid exchanges at a given position with a high potential for resulting in similar effects as in the described selected variants is based on the categorization of all amino acids into distinct, not overlapping groups according to their hydrophobicity attributes: polar (R, K, E, D, Q, N), neutral (G, A, S, T, P, H, Y), hydrophobic (C, V, L, I, M, F, W), as determined by Stapor et al. (Stapor K, et al. Machine Learning Paradigms—Advances in Data Analytics. Tsihrintzis G A, Sotiropoulos D N and Jain L C (eds.), Springer 2019 (ISSN 1868-4394), pp 101-128).

Specifically, the cp caspase-2 provided herein comprises amino acid substitutions at positions of SEQ ID No. 6, or at positions functionally equivalent to positions of SEQ ID No. 6, selected from i. $His^{185}$ and $Asp^{282}$, specifically comprising H185A and D282T substitutions;
ii. $Glu^{105}$ and $Asp^{285}$, specifically comprising E105V and D285E substitutions;
iii. $Glu^{105}$, $Gly^{171}$, $Val^{225}$ and $Asp^{282}$, specifically comprising E105V, G171D, V225G and D282E substitutions;
iv. $Glu^{105}$, $Gly^{171}$, $Val^{225}$, $Asp^{282}$ and $Asp^{285}$, specifically comprising E105V, G171D, V225G, D282E and D285E substitutions;
v. $Lys^{83}$, $Glu^{105}$, $Glu^{172}$, $Val^{255}$ and $Asp^{285}$, specifically comprising K83E, E105V, E172V, V255M and D285Y substitutions;
vi. $Glu^{105}$ and $Gly^{171}$, specifically comprising E105V and G171D substitutions;
vii. $Glu^{105}$ and $Glu^{172}$, specifically comprising E105V and E172V substitutions; and
viii. $Gly^{171}$ and $Glu^{172}$, specifically comprising G171 D and E172V substitutions, wherein said cp caspase-2 has increased P1' tolerance compared to a cp caspase-2 without the respective amino acid substitution, optionally wherein said cp caspase-2 comprises an SS propeptide comprising an amino acid substitution to Ala at position $Asp^{14}$ of SEQ ID No. 2 or at a position functionally equivalent to position $Asp^{347}$ of SEQ ID No. 11.

Specifically, the cp caspase-2 variant ms9 ProD comprising E105V, G171D, V225G and D282E substitutions displays excellent P1' tolerance.

Specifically, the cp caspase-2 variant E105V G171D comprising E105V and G171 D substitutions displays excellent P1' tolerance, which is increased compared to the cp caspase-2 variant ms9 ProD. Specifically, the highest tolerance of the cp caspase-2 variant E105V G171 D is for the amino acid residue proline.

According to a specific embodiment, the cp caspase-2 described herein comprises at least 70, 75, 80, 85, 90, 91, 92, 93, 94, 95, 96, 97 or 98% sequence identity to SEQ ID No. 9 (*Homo sapiens*), SEQ ID No. 64 (*Sarcophilus harrisii*, Tasmanian Devil), SEQ ID No. 66 (*Anolis carolinensisilus*), SEQ ID No. 68 (*Callorhinchus milii*, Ghost Shark), SEQ ID No. 76 or SEQ ID No. 77 (*Homo sapiens*) and comprises one or more amino acid substitutions at a position functionally equivalent to any of positions 171, 105, 172, 282, 225, 83, 185, 255, or 285 of SEQ ID No. 6 or any combination thereof.

Specifically, the cp caspase-2 variant described herein comprises SEQ ID No. 6 and one or more amino acid substitutions at position 171, 105, 172, 282, 225, 83, 185, 255, or 285 of SEQ ID No. 6 or at a position functionally equivalent to position 171, 105, 172, 282, 225, 83, 185, 255, or 285 of SEQ ID No. 6, or any combination thereof.

Specifically, the cp caspase-2 variant described herein comprises any one or more of amino acid substitutions G171 D, E105V, E172V, D282E, D282T, V225G, K83E, H185A, V255M, D285Y and D285E, with reference to the numbering according to SEQ ID No. 6.

According to a further specific embodiment, the cp caspase-2 variant described herein comprises SEQ ID No. 6 or has at least 70, 75, 80, 85, 90, 91, 92, 93, 94, 95, 96, 97 or 98% sequence identity with SEQ ID No. 6, and comprises amino acid substitutions E105V, G171 D, V225G, D282E, and/or D285E, with reference to the numbering of SEQ ID No. 6, wherein said cp caspase-2 has increased P1' tolerance.

According to a further specific embodiment, the cp caspase-2 variant described herein comprises SEQ ID No. 6 or has at least 70, 75, 80, 85, 90, 91, 92, 93, 94, 95, 96, 97 or 98% sequence identity with SEQ ID No. 6, and comprises amino acid substitutions K83E, E105V, E172V, V255M and/or D285Y, with reference to the numbering of SEQ ID No. 6, wherein said cp caspase-2 has increased P1' tolerance.

According to a further specific embodiment, the cp caspase-2 variant described herein comprises SEQ ID No. 6 or has at least 70, 75, 80, 85, 90, 91, 92, 93, 94, 95, 96, 97 or 98% sequence identity with SEQ ID No. 6, and comprises amino acid substitutions H185A and/or D282T, with reference to the numbering of SEQ ID No. 6, wherein said cp caspase-2 has increased P1' tolerance, specifically for branched P1' amino acid residues.

Specifically, the cp caspase-2 variant described herein comprises an amino acid sequence selected from the group consisting of SEQ ID No. 1, 13, 17, 18, 23, 24, 51, 52, 54, 70, 71, 72, 78, 79, 86, 87, 179, 180, 181, 182, 183, 184, 185, 186, 187, 188, 189, 190, 191 and 192 or an amino acid sequence having at least 70%, 75%, 80%, 85%, 90%, specifically at least 95%, specifically at least 99% sequence identity with any one of SEQ ID No. 1, 13, 17, 18, 23, 24, 51, 52, 54, 70, 71, 72, 78, 79, 86, 87, 179, 180, 181, 182, 183, 184, 185, 186, 187, 188, 189, 190, 191 and 192.

According to a specific embodiment, the cp caspase-2 described herein comprises a C-terminal tag and an amino acid substitution at positions 285 and 292 of SEQ ID No. 6 or at a position functionally equivalent to positions 285 and 292 of SEQ ID No. 6, specifically comprising substitutions to Glu and Ser, respectively (D285E and D292S).

Specifically, the caspase-2 or cp caspase-2 described herein is recruited by a recognition site for proteolytic cleavage, comprising 5 amino acids of the sequence P5 P4 P3 P2 P1, wherein P1 can be any amino acid, preferably it is D or E, P2 can be any amino acid, preferably it is A, P3 can be any amino acid, preferably it is V, P4 can be any amino acid, preferably it is D, and P5 can be any amino acid, preferably it is V.

Specifically, the caspase-2 variant or cp caspase-2 variant described herein has increased specificity, specifically to the recognition site VDVAD (SEQ ID NO:45) wherein P5 is V, P4 is D, P3 is V, P2 is A and P1 is D, compared to wild-type (wt) caspase-2 comprising the amino acid sequence of SEQ ID No. 11.

Specifically, the caspase-2 or cp caspase-2 described herein recognizes or can be further modified to recognize a variety of recognition sites. According to a specific example, the caspase-2 variant or cp caspase-2 variant described herein recognizes any one or more of the recognitions sites LDESD (SEQ ID NO:204), DVAD (SEQ ID NO:205), DEVD (SEQ ID NO:206), DEVE (SEQ ID NO:207), ADVAD (SEQ ID NO:208), VDTTD (SEQ ID NO:209), DTTD (SEQ ID NO:210), DVPD (SEQ ID NO:211), VDVPD (SEQ ID NO:212), VDQQD (SEQ ID NO:213), or TDTSD (SEQ ID NO:214). Preferably, the caspase-2 or cp caspase-2 described herein recognizes and has high specifity for one recognition site.

According to a further specific example, the variants of caspase-2 or cp caspase-2 described herein recognizes the recognition site DRKD (SEQ ID NO:215), DAVD (SEQ ID NO:216), VKVD (SEQ ID NO:217), DTLD (SEQ ID NO:218), EEPD (SEQ ID NO:219), DETD (SEQ ID NO:220), DATD (SEQ ID NO:221), NKVD (SEQ ID NO:222), DALD (SEQ ID NO:223), DSVD (SEQ ID NO:224), NAID (SEQ ID NO:225), DKPD (SEQ ID NO:226), IQLD (SEQ ID NO:227), DNAD (SEQ ID NO:228), DVVD (SEQ ID NO:229), ENPD (SEQ ID NO:230), DMAD (SEQ ID NO:231), DLID (SEQ ID NO:232), DGAD (SEQ ID NO:233), DVKD (SEQ ID NO:234), GYND (SEQ ID NO:235), ELPD (SEQ ID NO:236), DSTD (SEQ ID NO:237), DRQD (SEQ ID NO:238), HAVD (SEQ ID NO:239), QERLD (SEQ ID NO:240), LERD (SEQ ID NO:241), MMPD (SEQ ID NO:242), EEPD (SEQ ID NO:243), VESID (SEQ ID NO:244), EAMD (SEQ ID NO:245), EDAD (SEQ ID NO:246), EEED (SEQ ID NO:247), AVLD (SEQ ID NO:248), and/or EEGD (SEQ ID NO:249).

According to a further specific example, the variants of caspase-2 or cp caspase-2 described herein recognizes the recognition site TDTSD (SEQ ID NO:214), LDEPD (SEQ ID No. 250), and/or KDEVD (SEQ ID No. 251).

Specifically, the recognition site can be selected from the group consisting of DEXD (SEQ ID No. 202) and DVXD (SEQ ID No. 203), wherein X is any amino acid.

Specifically, the recognition site comprises the sequence P5 P4 P3 P2 P1, wherein P5 is V, P4 is D, P3 is Q, P2 is Q and P1 is D. Specifically, the V on position P5 can be replaced with I, Y, L, T, N, or A, and/or the D on position P4 can be replaced with S, and/or the Q on position P3 can be replaced with V, E or T, and/or the Q on position P2 can be replaced with A, S, K, V, M, or L Testing of a recognition site library (P4-P1) for Caspase 2 resulted in the following predominant amino acids: position P4: D, V; position P3: V, E, T; position P2: S, T and position P1: D.

Specifically, the caspase-2 or cp caspase-2 described herein is capable of cleaving at a cleavage site P1/P1', wherein P1' can be any amino acid.

Further provided herein is a caspase-2 comprising one or more amino acid substitutions at positions 212, 431, 213, 323, 266, 409, 226, 296 or 326 of SEQ ID No. 11 or at a position functionally equivalent to any of positions 212, 431, 213, 323, 266, 409, 226, 296 or 326 of SEQ ID No. 11 or a combination thereof, also referred to as "caspase-2 variant", and wherein said amino acid substitution increases P1' tolerance compared to a caspase-2 which has the same sequence but does not comprise said substitutions. In other words, the caspase-2 that the caspase-2 variant is compared to has an identical sequence as the caspase-2 variant, except that it does not comprise any of the amino acid substitutions at positions 212, 431, 213, 323, 266, 409, 226, 296 or 326 of SEQ ID No. 11, or at a position functionally equivalent to any of positions 212, 431, 213, 323, 266, 409, 226, 296 or 326 of SEQ ID No. 11, which increase the P1' tolerance according to the invention.

Specifically, the caspase-2 variant provided herein comprises improved P1' tolerance for at least one amino acid other than glycine compared to a caspase-2 not comprising the respective amino acid substitution.

Specifically, the caspase-2 variant described herein comprises at least 70, 75, 80, 85, 90, 91, 92, 93, 94, 95, 96, 97 or 98% sequence identity to SEQ ID No. 11, SEQ ID No. 89, SEQ ID No. 92, SEQ ID No. 95, SEQ ID No. 98, SEQ ID No. 101, SEQ ID No. 104, SEQ ID No. 107, SEQ ID No. 110, SEQ ID No. 113 or SEQ ID No. 116 and comprises one or more amino acid substitutions at positions 409, 431, 212, 213, 266, 296, 226, 323 or 326 of SEQ ID No. 11 or at a position functionally equivalent to any of positions 409, 431, 212, 213, 266, 296, 323 or 326 of SEQ ID No. 11 or a combination thereof.

Specifically, the caspase-2 described herein comprises at least a small caspase-2 subunit and a large caspase-2 subunit.

Specifically, the small subunit of the caspase-2 described herein comprises the amino acid sequence of SEQ ID No. 3, SEQ ID No. 91, SEQ ID No. 94, SEQ ID No. 97, SEQ ID No. 100, SEQ ID No. 103, SEQ ID No. 106, SEQ ID No. 109, SEQ ID No. 112, SEQ ID No. 115, SEQ ID No. 118, or a functionally active variant thereof comprising at least at least 70, 75, 80, 85, 90, 91, 92, 93, 94, 95, 96, 97 or 98% sequence identity. Specifically, the large subunit of the caspase-2 described herein comprises the amino acid sequence of SEQ ID No. 4, SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No. 114, SEQ ID No. 117, or a functionally active variant thereof comprising at least 70, 75, 80, 85, 90, 91, 92, 93, 94, 95, 96, 97 or 98% sequence identity.

According to a specific embodiment, the caspase-2 provided herein comprises one or more linker sequences, specifically consisting of 1, 2, 3, 4, 5, 6, 7, 8, 9, 10, 11 or 12 or even more amino acid residues. Specifically, the linker can comprise more than 20 or 30 or even more amino acids, as long as the caspase retains its functional activity as described herein. Specifically, the linker sequence comprises glycine, alanine and/or serine residues. Specifically, the linker comprises at least one glycine and serine residue, more specifically the linker is GS, GGSGG (SEQ ID NO:278) and/or GSAGSAAGSG (SEQ ID NO:279).

Specifically, the caspase-2 comprises a subunit-linker sequence, which is a linker sequence between the small subunit and the large subunit of the caspase-2 described herein.

According to a further specific embodiment, the caspase-2 provided herein comprises one or more C-terminal or N-terminal tags, specifically selected from the group consisting of affinity tags, solubility enhancement tags and monitoring tags described herein. Specifically, any tag known in the art can be fused to the caspase-2.

According to a specific embodiment, the caspase-2 provided herein comprises an N-terminal and/or C-terminal truncation of at least 1, 2, 3, 4, 5 and up to 10 or even more, as long as the caspase retains its functional activity as described herein. According to a further specific embodiment, the caspase-2 provided herein comprises an N-terminal and/or C-terminal extension of at least 1, 2, 3, 4, 5 and up to 10 or even more, as long as the caspase retains its functional activity as described herein. Specifically, the caspase-2 may comprise a truncation and an extension.

According to a specific embodiment, the caspase-2 variant provided herein comprises one or more amino acid substitutions, selected from i. $Gly^{212}$, substituted with D or an amino acid selected from the group consisting of R, K, E, Q, N, A, S, T, P, H, Y
ii. $Glu^{431}$, substituted with V or an amino acid selected from the group consisting of C, L, I, M, F, W, R, K, D, Q, N
iii. $Glu^{213}$, substituted with V or an amino acid selected from the group consisting of C, L, I, M, F, W, R, K, D, Q, N
iv. $Asp^{323}$, substituted with E or T or an amino acid selected from the group consisting of R, K, Q, N, G, A, S, P, H, Y
v. $Val^{266}$, substituted with G or an amino acid selected from the group consisting of A, S, T, P, H, Y, C, L, I, M, F, W
vi. $Lys^{409}$, substituted with E or an amino acid selected from the group consisting of R, D, Q, N,
vii. $His^{226}$, substituted with A or an amino acid selected from the group consisting of G, S, T, P, Y,
viii. $Val^{296}$, substituted with M or an amino acid selected from the group consisting of C, L, I, F, W, and/or
ix. $Asp^{326}$, substituted with E or Y or an amino acid selected from the group consisting of R, K, Q, N, G, A, S, T, P, H, with reference to the positions of SEQ ID No. 11, or positions functionally equivalent to positions of SEQ ID No. 11.

Specifically, the caspase-2 variant provided herein comprises amino acid substitutions at positions of SEQ ID No. 11, or at positions functionally equivalent to positions of SEQ ID No. 11, selected from i. $His^{226}$ and $Asp^{323}$, specifically comprising H226A and D323T substitutions;
ii. $Glu^{431}$, specifically comprising a E431V substitution;
iii. $Glu^{431}$ and $Asp^{326}$, specifically comprising E431V and D326E substitutions;
iv. $Glu^{431}$, $Gly^{212}$, $Val^{266}$ and $Asp^{323}$, specifically comprising E431V, G212D, V266G and D323E substitutions;
v. $Glu^{431}$, $Gly^{212}$, $Val^{266}$, $Asp^{323}$ and $Asp^{326}$, specifically comprising E431V, G212D, V266G, D323E and D326E substitutions;
vi. $Lys^{409}$, $Glu^{431}$, $Glu^{213}$, $Val^{296}$ and $Asp^{326}$, specifically comprising K409E, E431V, E213V, V296M and D326Y substitutions;
vii. $Glu^{431}$ and $Gly^{212}$, specifically comprising E431V and G212D substitutions;
viii. $Glu^{431}$ and $Glu^{213}$, specifically comprising E431V and E213V substitutions; and
ix. $Gly^{212}$ and $Glu^{213}$, specifically comprising G212D and E213V substitutions.

Further provided herein is a method of producing a caspase variant, specifically a caspase-2, even more specifically the circular permuted caspase-2, comprising increased P1' tolerance.

Specifically, a wild-type cp caspase-2 or a cp caspase-2 variant as described herein, or a functionally active variant thereof, is produced by a method comprising the steps of i. cloning a nucleotide sequence encoding a caspase-2, specifically a circular permuted caspase-2 into a vector, specifically said sequence is under the control of a promoter,
ii. transforming a host cell with said vector,
iii. culturing the transformed host cell under conditions wherein the caspase is expressed,
iv. isolating the caspase from the host cell culture, optionally by disintegrating the host cells, and
v. optionally purifying the caspase.

Specifically, the nucleic acid sequence encoding the caspase-2 described herein is operably linked to a promoter. Specifically, the promoter is an inducible or a constitutive promoter. Specifically, the promoter is selected from the group consisting of T7, lac, tac, trc, lacUV5, trp, phoA, pL, XylS/Pm regulator/promoter system, Pm-promoter, Pm-promoter variants, araBAD, T3, T5, T4, T7A1, T7A2, T7A3, hybrid promoters and the strong constitutive HCD promoter. Specifically, the promoter is associated with one or more lac operators or respective other operators or regulators or further regulation elements or the promoter is not associated with such regulatory elements. In a preferred embodiment, the promoter/regulator is a promoter/regulator selected from the group consisting of T7 promoter/operator, XylS/Pm regulator/promoter, functionally active variants of the Pm promoter, araBAD promoter/operator, T5, T7A1, T7A2, T7A3 promoter/operator, phoA promoter/regulator, and the trp promoter/operator system. Specifically, the promoter/regulator is of the T7 promoter/operator system.

Specifically, the host cell is a eukaryotic or a prokaryotic microbial host cell. Specifically, host cells are selected from the group consisting of bacterial cells, yeast cells, insect cells, mammalian cells and plant cells, preferably the host cells are bacterial or yeast cells selected from the group consisting of *E. coli*, *Pseudomonas* sp., *Bacillus* sp., *Streptomyces* sp., *Saccharomyces* sp., *Schizosaccharomyces* sp., *Pichia* sp., *Kluyveromyces* sp. and *Hansenula* sp.

Even more specifically, the host cell is of an *E. coli* B or K strain, such as but not limited to BL21 or HMS174. Specifically, the host cell has integrated in its genome a nucleotide sequence encoding the T7 RNA polymerase and is capable of constitutive of inducible expression of the caspase-2 described herein. as According to a specific example, the host cell is an *E. coli* BL21 (DE3), or HMS 174 (DE3) cell or a cell derived from BL21 (DE3), or HMS 174 (DE3) comprising a deletion of at least one essential lambda phage protein.

The caspase-2 or cp caspase-2 described herein may comprise a tag sequence, within its sequence or fused to its N- or C-terminus.

The circular permuted caspase-2 can optionally have an affinity tag, preferably fused to its N- or C-terminus, preferably the affinity tag is a 6His (SEQ ID NO:315)Tag. In a preferred embodiment the 6His (SEQ ID NO:315) tag is N-terminal. Specifically, in order to increase the expression of soluble cp caspase-2 the cp caspase-2 is fused with a solubility enhancement tag at its C- or N-terminus. In a preferred embodiment, the solubility enhancement tag is N-terminal to the cp caspase-2. Preferably the solubility tag is based on highly charged peptides of bacteriophage genes. Exemplary solubility tags and their sequences are listed in Table 1 of U.S. Pat. No. 8,535,908 B2. Specifically, the solubility tag is selected from the group consisting of the tags, T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T7AC, T3, N1, N2, N3, N4, N5, N6, N7, calmodulin-binding peptide (CBP), DsbA, DsbC, poly Arg, poly Lys, G B1 domain, protein D, Z domain of Staphylococcal protein A, and thioredoxin tag, preferably it comprises a T7AC or a T7A3 tag. According to a specific example, the tag is a modified T7A3 tag, herein referred to as T7AC (SEQ ID No. 43). Preferably, one or more T7A3 (SEQ ID No. 37) and/or T7AC (SEQ ID No. 43) tags or functional variants thereof having 1-5 amino acid substitutions, additions, dilutions or the like, are used.

Specifically, the caspase produced according to the method described herein has one or more affinity tags and one or more solubility enhancement tags fused to its N-terminus with or without linker sequences between the tags or between a tag and the N-terminus of the cp caspase-2. Specifically, said caspase has a T7AC or a T7A3 tag and a 6His (SEQ ID NO:315) tag fused to its N-terminus, whereas from N- to C-terminus the 6 His (SEQ ID NO:315) Tag is the first and the T7AC or T7A3 tag is the second tag, or the T7AC or T7A3 tag is the first and the 6His (SEQ ID NO:315) tag is the second tag.

It has surprisingly been found that production of a cp caspase-2 described herein can be significantly improved using a solubility enhancement tag, such as T7A3 or T7AC, fused to the N-terminus of the enzyme. Use of such tag significantly increases the titer of the enzyme by about 2.5-fold or more.

According to a specific embodiment, the cp caspase-2 produced according to the method described herein, thus comprises the following elements fused to its N-terminus, in the order from N- to C-terminus:

a. affinity tag, preferably 6-His (SEQ ID NO:315) tag;
b. optionally a linker;
c. solubility enhancement tag, preferably T7AC or T7A3; and
d. cp caspase-2, wild-type or variant as described herein.

According to a further specific embodiment, the cp caspase-2 produced according to the method described herein, comprises the following elements fused to its N-terminus, in the order from N- to C-terminus:

a. solubility enhancement tag, preferably T7AC or T7A3;
b. optionally a linker;
c. affinity tag, preferably 6-His (SEQ ID NO:315) tag; and
d. cp caspase-2, wild-type or variant as described herein.

Specifically, the expression cassette for expression of the cp caspase-2 comprises the nucleotide sequence encoding the cp caspase-2 under control of a promoter. Optionally, the expression cassette further comprises the nucleotide sequences encoding the affinity tag, in a preferred embodiment the 6 His (SEQ ID NO:315) tag and/or a nucleotide sequence encoding the T7AC or T7A3 tag and nucleotide sequences encoding linker sequences between the tags and/or between a tag and the cp-caspase-2. In another embodiment, the expression cassette is flanked by two sequences homologous to a sequence in the genome of the host cell, preferably a microbial cell, more preferably a bacterial cell, more preferably *E. coli*, for integration of the expression cassette by homologous recombination into the genome of the host cell.

Specifically, the cell is transformed by a vector comprising the expression cassette. Specifically, the cp caspase-2, with or without tags as described herein, is expressed from one or more plasmids or from one or two copies of a nucleic acid sequence integrated in the genome of the host cell.

Specifically, the cp caspase-2 with or without tags as described herein, can be produced by cultivation of the host cell and induction of expression by addition of an inducer, such as e.g. IPTG when using the T7 promoter/operator system, in a bioreactor (fermenter).

Specifically, culturing of step (iii) of the method to produce a cp caspase-2 as described herein comprises a fed-batch phase for expression of the cp caspase-2 comprising a specific growth rate and induction of expression, preferably using IPTG.

Specifically, culturing of step (iii) of the method to produce a cp caspase-2 as described herein comprises a fed-batch phase for expression of the cp caspase-2, said fed batch phase specifically comprising a specific growth rate, μ of about 0.01-0.1 $h^{-1}$, and induction of expression of the cp caspase-2 by addition of IPTG at a concentration of about 0.01-1.5 μmol/g of actual CDM (cell dry mass). Specifically, concentration of IPTG of μmol/g of actual CDM means the concentration of IPTG in the fermenter at a certain time point during the feed phase related to the CDM in g at that certain time point.

According to a specific embodiment, growth rate p is about 0.01-0.07 $h^{-1}$, preferably it is about 0.01-0.03 $h^{-1}$ or 0.01-0.05 $h^{-1}$ or 0.02-0.05 $h^{-1}$ or 0.03-0.05 $h^{-1}$ or 0.03-0.07 $h^{-1}$ or 0.05-0.07 $h^{-1}$, preferably it is any of about 0.03, 0.05 or 0.07 $h^{-1}$.

According to a further specific embodiment, the IPTG concentration is about 0.1-1.5 μmol/g or 0.1-1.3 μmol/g or 0.2-1.3 μmol/g or 0.3-1.3 μmol/g or 0.5-1.3 μmol/g of actual CDM, preferably it is about 0.5-0.9 μmol/g actual CDM or about 0.9-1.3 μmol/g actual CDM, preferably it is about 0.5, 0.9 or about 1.3 μmol/g CDM.

According to yet a further specific embodiment, culturing of step (ii) further comprises a first fed-batch phase for the production of biomass, prior to the fed-batch phase for the expression of the cp caspase-2, said first fed-batch phase comprising a growth rate, μ of about 0.05-0.5 $h^{-1}$ or 0.05-0.4 $h^{-1}$ or 0.07-0.3 $h^{-1}$. Specifically, the growth rate μ is about 0.1-0.3 $h^{-1}$ or 0.1-0.2 $h^{-1}$, or 0.10, 0.11, 0.12, 0.13, 0.14, 0.15, 0.16, 0.17, 0.18, 0.19 or 0.20 $h^{-1}$. preferably about 0.13-0.21 $h^{-1}$, even more preferably about 0.16-0.18 $h^{-1}$ and most preferably it is about 0.17 $h^{-1}$. Specifically, said first fed-batch phase is followed by a second fed-batch phase for expression of the recombinant protein, preferably started by addition of an inducer of expression, such as IPTG, and typically comprising a lower growth rate.

Specifically provided herein is a fusion protein comprising the following structure from N- to C-terminus:

i. a tag sequence comprising a caspase recognition site specifically recognized by the cp caspase-2 or caspase2 described herein, ii. a cleavage site P1/P1', and iii. a protein or polypeptide of interest (POI).

Specifically, P1' is the N-terminal amino acid of the protein of interest (POI).

Specifically, the tag sequence of the fusion protein described herein further comprises one or more tags selected from the group consisting of affinity tags, solubility enhancement tags and monitoring tags. Specifically, any tag with any function known in the art can be fused to the POI. Specifically, the fusion protein further comprises one or more linker sequences. Specifically, the fusion protein comprises a caspase recognition site comprising 5 amino acids of the sequence P5 P4 P3 P2 P1, and a cleavage site P1/P1', wherein P1' is the N-terminal amino acid of the POI.

According to a specific embodiment, the fusion protein provided herein comprises the cp caspase-2 or caspase 2 described herein within its sequence. Specifically, the fusion protein comprises the cp caspase-2 or caspase 2 described herein fused to the N- or the C-terminus of the fusion protein.

Specifically, such fusion protein is used to produce a POI comprising an authentic N-terminus by cleavage of the fusion protein at the N-terminus of the POI using the cp caspase-2 or caspase-2 described herein.

In one embodiment, the POI comprises an N-terminal tag which comprises at least a caspase recognition site, wherein the C-terminal amino acid of the recognition site, P1, is the last (C-terminal) amino acid residue of the tag and the N-terminal amino acid of the POI is the P1' residue of the caspase cleavage site. In this embodiment, the tag sequence including the recognition site is released from the POI through proteolytic cleavage by the caspase, generating a POI comprising an authentic N-terminus.

Further provided herein are methods of producing a protein or polypeptide of interest (POI) using the cp caspase-2 or caspase-2 described herein. Specifically, the cp caspase-2 described herein is used for the production of a POI comprising an authentic N-terminus Specifically provided herein are methods of producing a POI comprising an authentic N-terminus, using the fusion protein described herein and the caspase-2 or the cp caspase-2 described herein.

Specifically provided herein are methods of producing a POI comprising an authentic N-terminus, using the fusion protein described herein, wherein the fusion protein comprises the caspase-2 or the cp caspase-2 described herein at its N- or C-terminus.

Specifically, the fusion protein used in the methods described herein comprises the following structure from N- to C-terminus:

i. one or more N-terminal tags, ii. optionally one or more tag-linker sequences and iii. a caspase recognition site comprising 5 amino acids of the sequence P5 P4 P3 P2 P1, iv. a cleavage site P1/P1', and v. a POI, wherein said recognition site is specifically recognized by the caspase-2 or the cp caspase-2 described herein. Specifically, P1' is the N-terminal amino acid of the POI.

Specifically provided herein is a method of producing a POI in vivo.

Specifically, the in vivo method of producing a POI comprising an authentic N-terminus comprises the steps of:

i. expressing the fusion protein comprising from N- to C-terminus optionally one or more tags, optionally one or more tag-linker sequences and a caspase recognition site N-terminally fused to the POI; and the caspase-2 or cp caspase-2 described herein specifically recognizing the recognition site of the fusion protein, in the same host cell, ii. optionally, wherein said fusion protein and caspase-2 or cp caspase-2 are under the same promoter, iii. culturing the host cell, wherein said caspase-2 or cp caspase-2 cleaves the fusion protein in culture, and iv. isolating the POI from the cell and optionally purifying the POI.

Specifically, the host cell is selected from the group consisting of bacterial cells, yeast cells, insect cells, mammalian cells and plant cells, preferably the host cells are bacterial or yeast cells selected from the group consisting of *E. coli, Pseudomonas* sp., *Bacillus* sp., *Streptomyces* sp., *Saccharomyces* sp., *Schizosaccharomyces* sp., *Pichia* sp., *Kluyveromcyes* sp. and *Hansenula* sp.

According to a specific embodiment, the fusion protein and the caspase described herein are under transcriptional control of different promoters and the expression of the caspase is induced after expression of the fusion protein. According to a different embodiment, the fusion protein and the caspase are under transcriptional control of the same promoter, specifically they are expressed at the same time.

Specifically, the caspase comprises an N- or C-terminal tag, which may be used to separate the caspase and the POI.

According to a further specific embodiment, the caspase described herein is part of the fusion protein expressed in the host cell and cleaves the fusion protein releasing a POI comprising an authentic N-terminus in the host cell.

Specifically, the fusion protein, the POI and/or the caspase are isolated using a column, specifically a chromatography column, more specifically an immobilized metal affinity chromatography column (IMAC).

Specifically provided herein is a method of producing a POI in vitro.

Specifically, the in vitro method of producing a protein of interest (POI) comprising an authentic N-terminus comprises the steps of:

i. providing a fusion protein comprising from N- to C-terminus one or more tags, optionally one or more tag-linker sequences and a caspase recognition site N-terminally fused to the POI, wherein said caspase recognition site is specifically recognized by the caspase-2 or cp caspase-2 described herein, ii. contacting said fusion protein with said caspase-2 or cp caspase-2 for a period of time sufficient for said caspase-2 or cp caspase-2 to cleave the fusion protein, and iii. optionally purifying the POI.

Specifically, the method of producing a POI as described herein, comprises the steps of:

i. expressing a fusion protein in a host cell comprising the following structure from N- to C-terminus:

a. an N-terminal affinity tag, b. optionally a linker sequence, c. a caspase recognition site, d. a cleavage site P1/P1', and e. a POI, wherein P1' is the N-terminal amino acid of the POI, and wherein said recognition site is specifically recognized by the caspase-2 or cp caspase-2 described herein (caspase);

ii. isolating said fusion protein;

iii. purifying said fusion protein using the N-terminal affinity tag;

iv. providing the caspase described herein specifically recognizing the recognition site of the fusion protein;

v. contacting said fusion protein with said caspase for a period of time sufficient for said caspase to cleave the fusion protein;

vi. optionally removing the cleaved affinity tag, and optionally the non-cleaved fusion protein using the affinity tag and the caspase; and vii. optionally further purifying the POI.

Specifically, the caspase used in such method comprises at its N- or C-terminus an affinity tag identical or similar to the affinity tag of the fusion protein. Specifically, the caspase, the cleaved affinity tag and any un-cleaved fusion protein are removed in step vi. using said affinity tag.

Specifically, said fusion protein is purified using the tag, for example using affinity chromatography, more specifically immobilized metal affinity chromatography. Specifically, the captured fusion protein is released and the N-terminal tag is removed in solution or in immobilized enzyme reactor, wherein the caspase is immobilized in a column or on a carrier.

According to a further specific embodiment, the fusion protein and the caspase are bound on a column.

Specifically, the method of producing a POI comprising an authentic N-terminus using a column comprises the following steps:

i. expressing a fusion protein comprising one or more N-terminal affinity tags, optionally one or more tag-linker sequences, a caspase recognition site and a cleavage site P1/P1', wherein P1' is the N-terminal amino acid of the POI, and a POI, in a host cell, ii. isolating the fusion protein from the host cell and capturing/binding the fusion protein on a solid support using the affinity tag, iii. providing a caspase-2 or cp caspase-2 described herein (caspase) specifically recognizing the recognition site of the fusion protein, iv. contacting said caspase with the bound fusion protein for a period of time sufficient for said caspase to cleave the fusion protein releasing the POI from the solid support whereas tag and optionally the uncleaved fusion protein remain bound, and v. isolating and optionally further purifying the POI.

Specifically, the caspase comprises a tag sequence, specifically an affinity tag, to allow separation of the caspase from the POI after cleavage.

In a specific embodiment, the caspase-2 or cp caspase-2 described herein comprises an affinity tag and is immobilized on a solid support or column and the fusion protein is brought into contact with the immobilized caspase. Specifically, the fusion protein is brought into contact with the caspase immobilized in a column by flowing the fusion protein through the column. Specifically, the cleaved tag is separated from the POI using the affinity tag in the tag sequence.

In a further specific embodiment, the caspase and the fusion protein comprise an identical N-terminal affinity tag, allowing immobilization of the fusion protein and the caspase on the solid support. Upon cleavage of the POI by the caspase, the POI is released from the column and the tag sequence is retained in the column as well as the caspase and optional uncleaved fusion protein.

Specifically, the solid support is a column, specifically a chromatography column, more specifically an immobilized metal affinity chromatography column (IMAC) or an activated NHS column allowing immobilization of a polypeptide through amine coupling.

Specifically, a flow-through reactor is used comprising immobilized caspase-2, cp caspase-2 or fusion protein described herein. Specifically, the flow-through reactor is a plug flow reactor.

Further provided herein is an isolated nucleotide sequence encoding the caspase-2 or cp caspase-2 described herein.

Further provided herein is a vector comprising the isolated nucleotide sequence described herein, specifically said vector is a bacterial expression vector. More specifically the vector is a plasmid. In another embodiment, the vector is a linear vector flanked with homology regions for homologous integration of the nucleotide sequence encoding the caspase-2 or cp caspase-2 described herein into the chromosome of the host cell.

Further provided herein is an expression cassette comprising the nucleotide sequence operably linked to regulatory elements such as promoter, operator, terminator and the like. Specifically, said regulatory elements are one or more promoters or expression enhancing elements.

Further provided herein is a host cell or a host cell line expressing the caspase-2 or cp caspase-2 described herein, wherein the host cells are selected from the group consisting of bacterial cells, yeast cells, insect cells, mammalian cells and plant cells, preferably the host cells are bacterial or yeast cells selected from the group consisting of *E. coli, Bacillus* sp., *Streptomyces* sp., *Saccharomyces* sp., *Schizosaccharomyces* sp., *Kluyveromyces* sp. and *Pichia* sp.

According to a specific embodiment, the expression cassette and the host cell or host cell line described herein are comprised in an expression system. Further provided herein is an expression system comprising the expression cassette and the host cell or host cell line described herein.

Further described herein is the use of the caspase-2 or cp caspase-2 described herein for the in vivo cleavage of a substrate in a non-human organism. Specifically, the non-human organism is a prokaryotic organism, specifically it is *E. coli.*

Further provided herein is a kit, comprising i. the caspase-2 or cp caspase-2 described herein, and ii. an expression vector, optionally comprising an affinity tag, preferably a 6His (SEQ ID NO:315) tag, a linker sequence, and/or a nucleotide sequence coding for a recognition site, preferably VDVAD (SEQ ID NO:45).

The kit may optionally further comprise chromatography material for affinity chromatography, preferably an IMAC (immobilized metal affinity chromatography) material, preferably Ni-NTA (Ni-Nitrilotriacetic acid) chromatography material, preferably pre-packed in a chromatography column.

Further optionally comprised in the kit is a plasmid comprising the nucleotide sequence from 5' to 3' encoding an affinity tag, preferably a 6His (SEQ ID NO:315) tag, optionally a linker sequence and a nucleotide sequence coding for the recognition site, preferably VDVAD (SEQ ID NO:45). Via a multiple cloning site, a DNA sequence encoding a POI can be inserted into the plasmid directly fused to the nucleotide sequence encoding the recognition site.

Further described herein is a pharmaceutical composition comprising the caspase-2 or cp caspase-2 provided herein and optionally one or more excipients.

Further described herein is use of the caspase-2 or cp caspase-2 provided herein for preparing a pharmaceutical composition.

Specifically, the caspase-2 or cp caspase-2 described herein is provided for use in the treatment of a disease. Specifically, the caspase-2 or cp caspase-2 described herein is provided for use in the treatment of cancer, osteoporosis, Alzheimer's disease, Parkinson's disease, inflammatory disease, or auto-immune diseases, specifically via proteolytically attacking respective disease relevant proteins.

Specifically, the caspase-2 or cp caspase-2 described herein is provided for the manufacture of a medicament for the treatment of cancer, Alzheimer's disease, Parkinson's disease or inflammatory disease. Further provided herein is a protein tag for enhanced expression of a POI, comprising a solubility enhancement tag and the amino acid sequence VDVAD (SEQ ID NO:45). Specifically, the sequence VDVAD (SEQ ID NO:45) is at the C-terminus of the protein tag described herein, specifically directly linked to the N-terminus of the POI.

It has been surprisingly found that by including the amino acid sequence VDVAD (SEQ ID NO:45) in a protein tag, the expression of a protein of interest fused to the protein tag can be significantly increased. Importantly, this increase in expression persists, despite addition of a histidine tag sequence to the protein tag. Using a histidine affinity tag, such as 6-His (SEQ ID NO:315), typically decreases the expression rate of a protein of interest significantly. The inventors have surprisingly found that by including the sequence VDVAD (SEQ ID NO:45) in the protein tag this effect is reversed, and increased expression titers can be provided.

According to a specific embodiment, the solubility enhancement tag is selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T3, N1, N2, N3, N4, N5, N6, N7, T7AC, calmodulin-binding peptide (CBP), DsbA, DsbC, poly Arg, poly Lys, G B1 domain, protein D, Z domain of Staphylococcal protein A, and thioredoxin tag. Specifically, the solubility enhancement tag is T7AC or T7A3.

According to a further specific embodiment, the protein tag described herein further comprises a histidine tag sequence, preferably comprising 1-20 histidine residues, even more preferably it is a 1-His, 2-His, 3-His, 4-His (SEQ ID NO:317), 5-His (SEQ ID NO:316), 6-His(SEQ ID NO:315), 7-His (SEQ ID NO:314), 8-His (SEQ ID NO:313), 9-His(SEQ ID NO:312), 10-His (SEQ ID NO:311), 11-His (SEQ ID NO:310), 12-His (SEQ ID NO:309), 13-His (SEQ ID NO:308), 14-His (SEQ ID NO:307), 15-His (SEQ ID NO:306), 16-His (SEQ ID NO:305), 17-His (SEQ ID NO:304), 18-His (SEQ ID NO:303), 19-His (SEQ ID NO:302) or 20-His (SEQ ID NO:301) tag sequence.

Specifically, the solubility enhancement tag is located at the N-terminus of the protein tag described herein.

Specifically, the histidine tag sequence is located at the N-terminus of the protein tag described herein.

According to a specific embodiment, the protein tag described herein further comprises one or more linker sequences comprising one or more amino acid residues. Specifically, said linker sequence comprises 1, 2, 3, 4, 5, 6, 7, 8, 9, 10, 11, 12, 13, 14, 15, 16, 17, 18, 19 or 20 or more amino acid residues. Specifically, the linker can comprise more than 20 or 30 or even more amino acids, as long as the caspase retains its functional activity as described herein. Specifically, the one or more amino acid residues of the linker sequence are any of the naturally occurring amino acids or derivatives thereof, preferably selected from the group consisting of G, S, T, N, A. Specifically, the linker sequence comprises glycine, alanine and/or serine residues. Specifically, the linker comprises at least one glycine and serine residue, more specifically the linker is GS, GSG, GGSGG (SEQ ID NO:278), GSGSGSG (SEQ ID NO:280) and/or GSAGSAAGSG (SEQ ID NO:279).

Specifically, said one or more linker sequences are located between the VDVAD (SEQ ID NO:45) sequence and the solubility enhancement tag or the histidine tag sequence.

According to a specific embodiment, the protein tag described herein further comprises a signal peptide at its N-terminus. Signal peptides are known to the person skilled in the art, and comprise for example those described by Choi and Lee, Appl Microbiol Biotechnol (2004); 64:625-635 or Karyolaimos et al. Frontiers in Microbiology (2019); 10:1-11. Specifically, the signal peptide is selected from the group consisting of ompA (outer membrane protein A), DsbA (Thiol:disulfide interchange protein), MalE (maltose-binding protein), PelB (pectate lyase B) from *Erwinia carotovora*, PhoA (alkaline phosphatase), OmpC (outer-membrane protein C), OmpF (outer-membrane protein F), OmpT (protease VII), Endoxylanase from *Bacillus* sp., LamB (A receptor protein), Lpp (murein lipoprotein), LTB (heat-labile enterotoxin subunit B), PhoE (outer-membrane pore protein E), and StII (heat-stable enterotoxin 2).

Using a signal sequence, also herein referred to as signal peptide, leader sequence or leader peptide, such as the ompA signal peptide, which guides the protein through the inner membrane into the periplasma of bacteria, e.g, *E. coli*, which has been fused to the N-terminus of the protein tag described herein allows successful production of the POI and the fusion proteins described herein in the periplasma of *E. coli*. This is surprising since expression enhancers are usually located at the N-terminus of the whole fusion protein (respectively the expression construct, respectively the gene encoding the fusion protein), as described herein. As demonstrated in Example 10.2, and FIG. 31, a very high titer of a recombinant protein expressed in the periplasma of *E. coli* of more than 5 g/L could be achieved using a signal peptide located at the N-terminus of the protein tag.

Specifically, the protein tag described herein comprises one of the following structures from N- to C-terminus:

a. T7AC-6-His (SEQ ID NO:315)-VDVAD (SEQ ID NO:45);
b. T7A3-6-His (SEQ ID NO:315)-VDVAD (SEQ ID NO:45);
c. T7AC-6-His (SEQ ID NO:315)-GSG-VDVAD (SEQ ID NO:45);
d. T7A3-6-His (SEQ ID NO:315)-GSG-VDVAD (SEQ ID NO:45);
e. T7AC-6-His (SEQ ID NO:315)-GSGSGSG (SEQ ID NO:280)-VDVAD (SEQ ID NO:45);
f. T7A3 (SEQ ID NO:37)-6-His-GSGSGSG (SEQ ID NO:280)-VDVAD (SEQ ID NO:45);
g. 6-His (SEQ ID NO:315)-T7AC-VDVAD (SEQ ID NO:45);
h. 6-His (SEQ ID NO:315)-T7A3-VDVAD (SEQ ID NO:45);
i. 6-His (SEQ ID NO:315)-T7AC-GSG-VDVAD (SEQ ID NO:45);
j. 6-His (SEQ ID NO:315)-T7A3-GSG-VDVAD (SEQ ID NO:45);
k. 6-His (SEQ ID NO:315)-T7AC-GSG-VDVAD (SEQ ID NO:45);
l. 6-His (SEQ ID NO:315)-T7A3-GSG-VDVAD (SEQ ID NO:45).

Specifically, the protein tag described herein comprises one of the following structures from N- to C-terminus:

a. ompA signal peptide-T7AC-6-His (SEQ ID NO:315)-VDVAD (SEQ ID NO:45);

b. ompA signal peptide-T7A3-6-His (SEQ ID NO:315)-VDVAD (SEQ ID NO:45);
c. ompA signal peptide-T7AC-6-His (SEQ ID NO:315)-GSG-VDVAD(SEQ ID NO:45);
d. ompA signal peptide-T7A3-6-His (SEQ ID NO:315)-GSG-VDVAD (SEQ ID NO:45);
e. ompA signal peptide-T7AC-6-His (SEQ ID NO:315)-GSGSGSG (SEQ ID NO:280)-VDVAD (SEQ ID NO:45);
f. ompA signal peptide-T7A3-6-His (SEQ ID NO:315)-GSGSGSG (SEQ ID NO:280)-VDVAD (SEQ ID NO:45);
g. ompA signal peptide-6-His (SEQ ID NO:315)-T7AC-VDVAD (SEQ ID NO:45);
h. ompA signal peptide-6-His (SEQ ID NO:315)-T7A3-VDVAD (SEQ ID NO:45);
i. ompA signal peptide-6-His(SEQ ID NO:315)-T7AC-GSG-VDVAD (SEQ ID NO:45);
j. ompA signal peptide-6-His(SEQ ID NO:315)-T7A3-GSG-VDVAD (SEQ ID NO:45);
k. ompA signal peptide-6-His(SEQ ID NO:315)-T7AC-GSGSGSG (SEQ ID NO:280)-VDVAD (SEQ ID NO:45);
l. ompA signal peptide-6-His(SEQ ID NO:315)-T7A3-GSGSGSG(SEQ ID NO:280)-VDVAD (SEQ ID NO:45).

Further provided herein is a fusion protein comprising the protein tag described herein and a POI. Specifically, the N-terminus of the POI is fused to the C-terminus of said protein tag. Even more specifically, the N-terminus of the POI is directly fused to the C-terminus of the protein tag, which C-terminus is the sequence VDVAD (SEQ ID NO:45), i.e., the N-terminal amino acid of the POI is directly linked to the C-terminal D of the VDVAD (SEQ ID NO:45) sequence of the protein tag.

With regard to the POI there is no limitation. The POI may be any polypeptide, including e.g. the caspases described herein.

Further also provided herein is a method of producing a POI, comprising the steps of:

i. providing the fusion protein described herein comprising the protein tag described herein comprising a POI,
ii. contacting said fusion protein with a circular permuted caspase-2 (cp caspase-2) for a period of time sufficient for said cp caspase-2 to cleave the fusion protein thereby releasing the POI, and
iii. optionally purifying the POI.

According to a specific embodiment, the method of producing a POI as described herein comprises the following steps:

i. cloning a nucleotide sequence encoding the fusion protein described herein comprising the protein tag described herein, under the control of a promoter into an expression vector,
ii. transforming a host cell with said vector,
iii. culturing the transformed host cell under conditions wherein said fusion protein is expressed,
iv. optionally isolating said fusion protein from the host cell culture, optionally by disintegrating the host cells, and
v. purifying said fusion protein using IMAC chromatography,
vi. contacting said fusion protein with a circular permuted caspase-2 (cp caspase-2) for a period of time sufficient for said cp caspase-2 to cleave the fusion protein thereby releasing the POI, and
vii. optionally further purifying the POI,
viii. optionally modifying the POI and
ix. optionally formulating the POI.

Specifically, the promoter is selected from the group consisting of T7 promoter/operator, XylS/Pm regulator/promoter or variants of the Pm promoter, araBAD promoter/operator, T5, T7A1, T7A2, T7A3 promoter/operator, phoA promoter/regulator and the trp promoter/operator system.

FIGURES

FIG. 1: SEQ ID Nos. of amino acid and nucleotide sequences referred to herein. Bold and/or underlined letters in amino acid sequences refer to amino acid substitutions.

FIG. 2: Schematic representation of wild-type and circularly permuted caspase-2 structures. (A) human wild-type procaspase-2 (not processed) (SEQ ID No. 11), (B) the standard cp-caspase-2 including a modified SS pro-peptide, a His Tag and a GS linker between the SS and LS (SEQ ID No. 6), based on human wt caspase-2, (C) the standard cp-caspase-2 including a modified SS pro-peptide and a GS linker between the SS and LS (SEQ ID No. 9) and (D) the standard cp-caspase-2 including a His Tag and a GS linker between the SS and LS (SEQ ID No. 76).

FIG. 3: Schematic representation of mature enzymes of (A) human wild-type caspase 2, processed, (B) the standard cp-caspase-2 including a modified SS pro-peptide and a His Tag and a GC linker between SS and LS (SEQ ID No. 6), based on human wt caspase-2, (C) the standard cp-caspase-2 including a modified SS pro-peptide and a GS linker between the SS and LS (SEQ ID No. 9) and (D) the standard cp-caspase-2 including a His Tag and a GS linker between the SS and LS (SEQ ID No. 76).

FIG. 4: A Standard cleavage assay with cp caspase-2 (SEQ ID No. 6) and VDVAD-E2 (SEQ ID NO:33) with a P1' glycine (SEQ ID No. 33). Lane 1: Molecular weight marker, Lane 2: cleavage of the substrate after 1 minute reaction time, Lane 3: cleavage of the substrate after 2.5 minutes reaction time, Lane 4: cleavage of the substrate after 5 minutes reaction time. E2: E2 without tag. B: Standard cleavage assay with cp caspase-2 (SEQ ID No. 6) and VDVAD-SOD (SEQ ID No. 193). Lane 1: Molecular weight marker, Lanes 2-8: cleavage of the substrate after 0, 2, 3, 4, 5, 6 hours reaction time, respectively. Lane 9-10: Substrate VDVAD-SOD (SEQ ID No. 193) without caspase incubated for 0 and 6 hours respectively. 6His (SEQ ID NO:315)-SOD: SOD with N-terminal 6His (SEQ ID NO:315) tag and the recognition site VDVAD (SEQ ID NO:45) directly fused to the N-terminus of SOD; SOD: SOD without tag.

FIG. 5: Graphic representation of C-terminal sequences of cp caspases-2.

FIG. 6: Alignment of natural sequences of homologue caspases-2 of different species (01 Human (SEQ ID No. 11), 02 Mouse (SEQ ID No. 89), 03 Sheep (SEQ ID No. 92), 04 Tasmanian Devil (SEQ ID No. 95), 05 Chicken (SEQ ID No. 98), 06 *Anolis* (SEQ ID No. 101), 07 Alligator (SEQ ID No. 104), 08 *Xenopus* (SEQ ID No. 107), 09 *Danio* (SEQ ID No. 110), 10 Ghost Shark (SEQ ID No. 113), 11 Sea Squirt (SEQ ID No. 116). Unprocessed proteins consist of CARD domain, large subunit (LS) containing the two catalytic centers, small subunit propeptide (SS Propept.) and small subunit (SS). Active sites 1-5 interact with substrates.

FIG. 7: Alignment of active sites of natural sequences of caspases-2 from different species. Active sites interact with substrates and are relatively conserved. Definition of subunits and active sites see Tables 3 and 4. Numbers before the first active site represent the starting position of the first active site. Bold letters in amino acid sequences refer to amino acids that are equal for all species in the respective active site.

FIG. 8: Michaelis-Menten kinetic parameter $k_{cat}/K_M$ for cp caspase-2 and variants thereof: cpCasp2D (SEQ ID No.6), T7AC_cpCasp2D (SEQ ID No. 41), S9 (SEQ ID No. 51), G171D (SEQ ID No. 190), T7AC_mS9ProE (SEQ ID No. 71), T7AC_mS9ProD (SEQ ID No. 72).

FIG. 9: Cleavage of DEVD-E2 (SEQ ID No.57) by cp caspase-2 (SEQ ID No. 6) and wild-type caspase-2: Decrease of activity when using DEVD (SEQ ID NO:206) instead of VDVAD (SEQ ID NO:45) as recognition site (DEVD-E2 (SEQ ID NO:57) instead of VDVAD-E2 (SEQ ID NO:33) as substrate) for cp caspase-2 and wild-type caspase.

FIG. 10: Lab-scale fermentations of *E. coli* BL21(DE3) (pET30a_6H-cpCasp2D)(SEQ ID NO:6) (A, two graphs on the left) and BL21(DE3)(pET30a_T7AC-6H-cpCasp2D) (SEQ ID No. 41) (B, two graphs on the right): expression of soluble and insoluble 6H-cp caspase-2D (cpCasp2) (SEQ ID NO:6) (A) and T7AC-6H-cp caspase-2D (T7AC-6H-cp-Casp2)(SEQ ID NO:41) (B) in the course of time as specific yield [mg/g] and volumetric yield [g/L]: with (T7AC_6H-cpCasp2 (SEQ ID NO:41), B) and without (cpCasp2, A) solubility tag, T7AC.

FIG. 11: Lab-scale fermentations of *E. coli* BL21(DE3) (pET30a_6H-cpCasp2D) (SEQ ID NO:6) and BL21(DE3) (pET30a_T7AC-6H-cpCasp2D) (SEQ ID No. 41): biomass course.

FIG. 12: Biomass course of lab-scale fermentations of three cp caspases-2 (cp caspase-2, mS9 Pro D285E and mS9 Pro D285) with and without T7AC solubility tag in *E. coli* BL21(DE3) with pET30a vectors. The total CDM is shown as average of all 6 fermentations including standard deviation compared to expected growth (calc. CDM).

FIG. 13: Normalized soluble production of three different cp caspases-2 (cp caspase-2 (cpCasp2D), mS9 Pro D285E (mS9ProE) and mS9 Pro (mS9ProD)) with and without T7AC solubility tag in *E. coli* BL21(DE3) with pET30a vectors.

FIG. 14: Growth kinetics of *E. coli* BL21(DE3)(pET30a-T7AC_6H-cpCasp2) (SEQ ID NO:41) during carbon limited 2 phase fed-batch cultivation (μ=0.17 followed by 0.03 h-1 during induction) with three different IPTG induction strengths; coarse of CDM production; CDM in [g/L]

FIG. 15: *E. coli* BL21(DE3)(pET30a-T7AC_6H-cp-Casp2) (SEQ ID NO:6) during carbon limited 2 phase fed-batch cultivation (μ=0.17 and followed by 0.03 $h^{-1}$ during induction) with three different IPTG induction strengths. Volumetric soluble cp caspase-2 titers (sol. POI [g/L]) obtained cultivating at the lowest growth rate (μ=0.03 $h^{-1}$) and inducing with different IPTG levels. cp caspase-2 was quantified by SDS-PAGE. The mean values and standard deviations for individual determinations are shown (n=3).

FIG. 16: Example Michaelis-Menten kinetic measured by FRET assay.

FIG. 17: Cleavage kinetic for 2.9 g/L hFGF-2 fusion protein incubated with 0.055 g/L of T7AC_cpCasp2D (SEQ ID No. 41), T7AC_mS9ProE (SEQ ID No. 71) and T7AC_mS9ProD (SEQ ID No. 72).

FIG. 18: Cleavage kinetic for hFGF-2 fusion protein incubated at varying concentrations with cp caspase-2 (cp-Casp2, SEQ ID No. 6).

FIG. 19: Cleavage kinetic for 2.4 g/L TNF-alpha fusion protein incubated with 0.046 g/L cp caspase-2 (T7AC-cpCasp2D, SEQ ID No. 41) or the variant mS9 Pro D285E (T7AC_mS9ProE, SEQ ID No. 71).

FIG. 20: Cleavage kinetic for 9.1 g/L GFP fusion protein incubated with 0.11 g/L of the cp caspase-2 variant mS9 Pro D285E. (T7AC_mS9ProE, SEQ ID No. 71).

FIG. 21: Percentage of cleavage as described in Example 9.3.6 with varying residence times, performed with hFGF-2 fusion protein as substrate with a concentration of 50 μM.

FIG. 22: Direct comparison between T7AC-6H-cpCasp2D (SEQ ID No. 41) and T7AC-6H-mS9 ProD (SEQ ID NO:72) production during carbon limited 2 phase fed-batch cultivation (μ=0.17 and followed by 0.03 h-1 during induction) with constant 0.9 μmol IPTG/g CDM: biomass course.

FIG. 23: Direct comparison between T7AC-6H-cpCasp2D (SEQ ID No. 41) and T7AC-6H-mS9 ProD (SEQ ID NO:72) production during carbon limited 2 phase fed-batch cultivation (μ=0.17 and followed by 0.03 h-1 during induction) with constant 0.9 μmol IPTG/g CDM: expression of soluble (sol) and insoluble (IB) cp caspases-2 in the course of time as specific yield [mg/g] (top) and volumetric titer [g/L] (below).

FIG. 24: Direct comparison between T7AC-6H-cpCasp2D (SEQ ID No. 41) and T7AC-6H-mS9 ProD (SEQ ID NO:72) production during carbon limited 2 phase fed-batch cultivation (μ=0.17 and followed by 0.05 h-1 during induction) with constant 0.9 μmol IPTG/g CDM: biomass course.

FIG. 25: Direct comparison between T7AC-6H-cpCasp2D (SEQ ID No. 41) and T7AC-6H-mS9 ProD (SEQ ID NO:72) production during carbon limited 2 phase fed-batch cultivation (μ=0.17 and followed by 0.03 $h^{-1}$ during induction) with constant 0.9 μmol IPTG/g CDM: expression of soluble and insoluble cp caspases-2 in the course of time as specific yield [mg/g] (left) and volumetric titer [g/L] (right).

FIG. 26: Lab-scale fermentations of *E. coli* BL21(DE3) (pET30a_casp2-6H)(SEQ ID NO:6): expression of soluble and insoluble wild-type caspase-2 in the course of time (23 h and 29 h after induction) estimated via western blot with anti-Caspase-2 antibody. Lane 6: positive control 6H-cpCasp2D (SEQ ID NO:6) (29 h after induction, diluted 1:4).

FIG. 27: Biomass course of lab-scale fermentations of 6H-cpCasp2D (6H-cp caspase-2D) (SEQ ID NO:6) and wt caspase2-6H (SEQ ID NO:315) in *E. coli* BL21(DE3) with pET30a vector.

FIG. 28: Biomass course in benchtop fermentations of 4 different cp caspase homologues.

FIG. 29: benchtop fermentations of 2 different cp caspase homologues: expression of soluble (Soluble) and insoluble (IB) cp caspase-2 homologues in the course of time. Left: the wild-type like homologue, T7AC-6H-cpCasp2_sar (SEQ ID NO:64); right: the P1'tolerable cp caspase-2 variant, T7AC-6H-cpCasp2_sat_mut (SEQ ID NO:78)

FIG. 30: Comparison of different fermentation conditions and expression tags for the production of cp caspase-2D (see Table 40): soluble POI is the titer (volumetric yield) of the respective cp caspase-2D with 6H (SEQ ID NO:315) or T7AC-6H (SEQ ID NO:315) tag in [g/L]. 6H cpCasp2D (SEQ ID NO:6): 6H-cp caspase-2D (SEQ ID NO:6) fermented as described in Example 9, section 9.1.2.2; T7AC_6H_cpCasp2D (SEQ ID NO:41): T7AC-6H-cp caspase-2D (SEQ ID NO:41) fermented as described in Example 9, section 9.1.2.2; DoE: T7AC-6H-cp caspase-2D (SEQ ID NO:41) fermented as described in Example 9, section 9.1.2.3; optimization run: T7AC-6H-cp caspase-2D (SEQ ID NO:41) fermented as described in Example 9, section 9.1.2.9.

FIG. 31: Course of fermentation of the fusion protein T7AC-6H-GSG-VDVAD-rhGH (SEQ ID NO:257) performed as described in Example 10, section 10.2 (the fusion protein is expressed with an N-terminal signal peptide (leader peptide), ompA leader peptide, to guide the fusion protein into the periplasma of the host cell): left: formation of biomass (as CDM (cell dry mass) in [g/L] compared to calculated CDM, right: volumetric titer in [g/L] of the soluble fusion protein.

FIG. 32: Course of fermentation of the fusion protein T7AC-6H-GSG-VDVAD-PTH (SEQ ID NO:259) performed as described in Example 10, section 10.2 and table 53; left: formation of biomass (as CDM (cell dry mass) in [g/L] compared to calculated CDM, right: volumetric titer in [g/L] of the soluble fusion protein.

FIG. 33: Course of fermentation of the fusion protein T7AC-6H-GSG-VDVAD-TNFα (SEQ ID NO:263) performed as described in Example 19, section 19.2 and table 53; left: formation of biomass (as CDM (cell dry mass) in [g/L] compared to calculated CDM, right: volumetric titer in [g/L] of the soluble fusion protein.

FIG. 34: Course of fermentation of the fusion protein 6H-GSG-VDVAD (SEQ ID NO:45)-TNFα performed as described in Example 19, section 19.2 and table 53; left: formation of biomass (as CDM (cell dry mass) in [g/L] compared to calculated CDM, right: volumetric titer in [g/L] of the soluble and the insoluble (IB) fusion protein.

FIG. 35: Course of fermentation of the fusion protein 6H-GSG-VDVAD-BIWA4 (scFv)(SEQ ID NO:275) performed as described in Example 19, section 19.2 and table 53; left: formation of biomass (as CDM (cell dry mass) in [g/L] compared to calculated CDM, right: volumetric titer in [g/L] of insoluble (IB) fusion protein.

FIG. 36: Course of fermentation of the fusion protein 6H-GSG-VDVAD (SEQ ID NO:45)-GFPmut3.1 (=6H-GSG-VDVAD (SEQ ID NO:45)-GFP) performed as described in Example 19, section 19.2 and table 53; left: formation of biomass (as CDM (cell dry mass) in [g/L] compared to calculated CDM, right: volumetric titer in [g/L] of the soluble and the insoluble (IB) fusion protein.

FIG. 37: Course of fermentation of the protein hFGF-2 and the fusion proteins 6H-hFGF-2 (SEQ ID NO:266), 6H-GSG-VDVAD-hFGF-2 (SEQ ID NO:32), T7AC-6H-GSG-VDVAD-hFGF-2 (SEQ ID NO:267) and T7A3-6H-GSG-VDVAD-hFGF-2 (SEQ ID NO:271) performed as described in Example 19, section 19.2 and table 53; biomass (as CDM (cell dry mass) in [g/L] compared to calculated CDM.

FIG. 38: Course of fermentation of the protein hFGF-2 and the fusion proteins 6H-hFGF-2 (SEQ ID NO:266), 6H-GSG-VDVAD-hFGF-2 (SEQ ID NO:32), T7AC-6H-GSG-VDVAD-hFGF-2 (SEQ ID NO:267) and T7A3-6H-GSG-VDVAD-hFGF-2 (SEQ ID NO:269) performed as described in Example 19, section 19.2 and table 53; volumetric titer in [g/L] of the soluble protein resp.fusion protein FIG. 39: Course of fermentation of the fusion protein T7AC-6H-GSG-VDVAD-GCSF (SEQ ID NO:261) performed as described in Example 19, section 19.2 and table 53; left: formation of biomass (as CDM (cell dry mass) in [g/L] compared to calculated CDM, right: volumetric titer in [g/L] of the soluble fusion protein FIG. 40: Comparison of Michaelis-Menten kinetics depending on the recognition site of the cleavage tag with T7AC-6H-mS9ProD (SEQ ID NO:72). The grey traces and data points correspond to the cleavage kinetics of T7AC-6H-GSG-VDVAD-hFGF2 (SEQ ID NO:269). The black traces and data points correspond to the cleavage kinetics of T7AC-6H-GSG-VDSAD-hFGF2 (SEQ ID NO:268). The circles denote the measured data, the solid lines denote the model fit and the dashed lines denote the 95% confidence interval of the model fit.

FIG. 41: IMAC capture of 6H (SEQ ID NO:315)_GSG_VDVAD(SEQ ID NO:45)-TNFα. 3 L of cell lysis supernatant were loaded.

FIG. 42: SDS-PAGE of 6H(SEQ ID NO:315)_GSG_VDVAD (SEQ ID NO:45)-TNFα IMAC Capture. 1: marker; 2: cell lysis supernatant (1:5); 3: flow-through (1:5); 4: wash; 5-17: elution fractions.

FIG. 43: IMAC capture of T7AC_6H_GSG_VDVAD-TNFα (SEQ ID NO:263). 3 L of cell lysis supernatant were loaded.

FIG. 44: SDS-PAGE of T7AC_6H_GSG_VDVAD-TNFα (SEQ ID NO:263) IMAC Capture. 1: marker; 2: cell lysis supernatant (1:5); 3: flow-through (1:5); 4: wash; 5-6: elution fractions; 7: elution fraction (1:2); 8-17: elution fractions. The main peak in lanes 5-17 represents the fusion protein T7AC-6H-GSG-VDVAD-TNFα (SEQ ID NO:263).

FIG. 45: Comparison of Michaelis-Menten kinetics depending on the cleavage tag with 6H-cpCasp2D (SEQ ID NO:6). The grey traces and data points correspond to the cleavage kinetics of T7AC-6H-GSG-VDVAD-hFGF2 (SEQ ID NO:267). The black traces and data points correspond to the cleavage kinetics of 6H-GSG-VDVAD-hFGF2(SEQ ID NO:32). The circles denote the measured data, the solid lines denote the model fit and the dashed lines denote the 95% confidence interval of the model fit.

FIG. 46: Comparison of Michaelis-Menten kinetics depending on the cleavage tag with T7AC-6H-cpCasp2D (SEQ ID No. 41). The grey traces and data points correspond to the cleavage kinetics of T7AC-6H-GSG-VDVAD-hFGF2 (SEQ ID NO:267). The black traces and data points correspond to the cleavage kinetics of 6H-GSG-VDVAD-hFGF2 (SEQ ID NO:32). The circles denote the measured data, the solid lines denote the model fit and the dashed lines denote the 95% confidence interval of the model fit.

FIG. 47: Comparison of Michaelis-Menten kinetics depending on the cleavage tag with T7AC-6H-mS9ProD (SEQ ID NO:72). The grey traces and data points correspond to the cleavage kinetics of T7AC-6H-GSG-VDVAD-hFGF2 (SEQ ID NO:267). The black traces and data points correspond to the cleavage kinetics of 6H-GSG-VDVAD-hFGF2 (SEQ ID NO:32). The circles denote the measured data, the solid lines denote the model fit and the dashed lines denote the 95% confidence interval of the model fit.

FIG. 48: Comparison of Michaelis-Menten kinetics depending on the cleavage tag with T7AC-6H-mS9ProE (SEQ ID No. 71). The grey traces and data points correspond to the cleavage kinetics of T7AC-6H-GSG-VDVAD-hFGF2 (SEQ ID NO:267). The black traces and data points correspond to the cleavage kinetics of 6H-GSG-VDVAD-hFGF2 (SEQ ID NO:32). The circles denote the measured data, the solid lines denote the model fit and the dashed lines denote the 95% confidence interval of the model fit.

FIG. 49: Comparison of Michaelis-Menten kinetics depending on the cleavage tag with T7AC-6H-mS9ProD (SEQ ID NO:72). The light grey traces and triangle shaped data points correspond to the cleavage kinetics of T7AC-6H-GSGSGSG-VDVAD-hFGF2 (SEQ ID NO:271). The dark grey traces and box shaped data points correspond to the cleavage kinetics of T7AC-6H-GSG-VDVAD-hFGF2 (SEQ ID NO:267). The black traces and round data points correspond to the cleavage kinetics of T7AC-6H-VDVAD-hFGF 2 (SEQ ID NO:270). The measured data is shown as circles, boxes or triangles, the solid lines denote the model fit and the dashed lines denote the 95% confidence interval of the model fit.

FIG. 50: Cleavage reaction of T7AC_6H_GSG_VDVAD-hFGF2 (SEQ ID NO:267) and T7AC_6H_GSG_VDVAD-TNFα (SEQ ID NO:263) with T7AC_6H-cpCasp2D (SEQ ID No. 41), T7AC_6H-mS9ProE(SEQ ID No. 71), T7AC_6H-mS9ProD (SEQ ID NO:72). Lane 1: marker; lane 2: T7AC_6H_GSG_VDVAD-hFGF2 (SEQ ID NO:267); lane 3: T7AC_6H_GSG_VDVAD-hFGF2 (SEQ ID NO:267)+T7AC_6H-cpCasp2D (SEQ ID No. 41) 100:1 (M/M) 1h; lane 4: T7AC_6H_GSG_VDVAD-hFGF2 (SEQ ID NO:267)+T7AC_6H-mS9ProE (SEQ ID No. 71) 100:1 (M/M) 1h; lane 5: T7AC_6H_GSG_VDVAD-hFGF2 (SEQ ID NO:267)+T7AC_6H-mS9ProD (SEQ ID NO:72) 100:1 (M/M) 1h; lane 6: T7AC_6H_GSG_VDVAD-TNFα (SEQ ID NO:263); lane 7: T7AC_6H_GSG_VDVAD-TNFα (SEQ ID NO:263)+T7AC_6H-cpCasp2D (SEQ ID No. 41) 100:1 (M/M) 1h; lane 8: T7AC_6H_GSG_VDVAD-TNFα (SEQ ID NO:263)+T7AC_6H-mS9ProE(SEQ ID No. 71) 100:1 (M/M) 1h; lane 9: T7AC_6H_GSG_VDVAD-TNFα (SEQ ID NO:263)+T7AC_6H-mS9ProD (SEQ ID NO:72) 100:1 (M/M) 1h; lane 10: T7AC_6H-cpCasp2D (SEQ ID No. 41), T7AC_6H-mS9ProD (SEQ ID NO:72), T7AC_6H-mS9ProE. (SEQ ID No. 71); The main peak in lane 2 represents the uncleaved fusion protein, T7AC_6H_GSG_VDVAD-hFGF2 (SEQ ID NO:267); the peak of lane 3-5 that has the same migration as the main peak of lane 2 represents the uncleaved fusion protein, T7AC_6H_GSG_VDVAD-hFGF2 (SEQ ID NO:267); the peak below in lanes 3-5, having a migration between 14 and 17 kDa represents the released protein of interest, hFGF-2. The main peak in lane 6 represents the uncleaved fusion protein, T7AC_6H_GSG_VDVAD-TNFα (SEQ ID NO:263); the peak of lanes 7-9 that has the same migration as the main peak of lane 6 represents the uncleaved fusion protein, T7AC_6H_GSG_VDVAD-TNFα (SEQ ID NO:263); the peak below in lanes 7-9, having a migration between 14 and 17 kDa represents the released protein of interest, TNFα.

FIG. 51: Cleavage reaction of T7AC_6H_GSG_VDVAD-rhGH (SEQ ID NO:257) and T7AC_6H_GSG_VDVAD-GCSF (SEQ ID NO:261) with T7AC_6H-cpCasp2D (SEQ ID No. 41), T7AC_6H-mS9ProE (SEQ ID No. 71), T7AC_6H-mS9ProD (SEQ ID NO:72). Lane 1: marker; lane 2: T7AC_6H_GSG_VDVAD-rHGH (SEQ ID NO:257); lane 3: T7AC_6H_GSG_VDVAD-rHGH (SEQ ID NO:257)+T7AC_6H-cpCasp 2D (SEQ ID No. 41) 100:1 (M/M) 2h; lane 4: T7AC_6H_GSG_VDVAD-rHGH (SEQ ID NO:257)+T7AC_6H-mS9ProE (SEQ ID No. 71) 100:1 (M/M) 2h; lane 5: T7AC_6H_GSG_VDVAD-rHGH (SEQ ID NO:257)+T7AC_6H-mS9ProD (SEQ ID NO:72) 100:1 (M/M) 2h; lane 6: T7AC_6H_GSG_VDVAD-GCSF (SEQ ID NO:261); lane 7: T7AC_6H_GSG_VDVAD-GCSF (SEQ ID NO:261)+T7AC_6H-cpCasp2D (SEQ ID No. 41) 100:1 (M/M) 2h; lane 8: T7AC_6H_GSG_VDVAD-GCSF (SEQ ID NO:261)+T7AC_6H-mS9ProE (SEQ ID No. 71) 100:1 (M/M) 2h; lane 9: T7AC_6H_GSG_VDVAD-GCSF (SEQ ID NO:261)+T7AC_6H-mS9ProD (SEQ ID NO:72) 100:1 (M/M) 2h; lane 10: T7AC_6H-cpCasp2D (SEQ ID No. 41), T7AC_6H-mS9ProD (SEQ ID NO:72), T7AC_6H-mS9ProE (SEQ ID No. 71). The main peak in lane 2 represents the uncleaved fusion protein, T7AC_6H_GSG_VDVAD-rhGH (SEQ ID NO:257); the peak of lane 3-5 that has the same migration as the main peak of lane 2 represents the uncleaved fusion protein, T7AC_6H_GSG_VDVAD-rhGH (SEQ ID NO:257); the peak below in lanes 3-5, having a migration of about 17 kDa represents the released protein of interest, rhGH. The main peak in lane 6 represents the uncleaved fusion protein, T7AC_6H_GSG_VDVAD-GCSF (SEQ ID NO:261) the peak of lanes 7-9 that has the same migration as the main peak of lane 6 represents the uncleaved fusion protein, T7AC_6H_GSG_VDVAD-GCSF (SEQ ID NO:261) the peak below in lanes 7-9, having a migration between 14 and 17 kDa represents the released protein of interest, GCSF.

FIG. 52: Cleavage reaction of T7AC_6H_GSG_VDVAD-GCSF (SEQ ID NO:261) and T7AC_6H_GSG_VDVAD-PTH (SEQ ID NO:259) with T7AC_6H-cpCasp2D (SEQ ID No. 41), T7AC_6H-mS9ProE (SEQ ID No. 71), T7AC_6H-mS9ProD (SEQ ID NO:72). Lane 1: marker; lane 2: T7AC_6H_GSG_VDVAD-GCSF (SEQ ID NO:261); lane 3: T7AC_6H_GSG_VDVAD-GCSF (SEQ ID NO:261)+T7AC_6H-cpCasp2D (SEQ ID No. 41) 50:1 (M/M) 2h; lane 4: T7AC_6H_GSG_VDVAD-GCSF (SEQ ID NO:261)+T7AC_6H-mS9ProE (SEQ ID No. 71) 50:1 (M/M) 2h; lane 5: T7AC_6H_GSG_VDVAD-GCSF (SEQ ID NO:261)+T7AC_6H-mS9ProD (SEQ ID NO:72) 50:1 (M/M) 2h; lane 6: T7AC_6H_GSG_VDVAD-PTH (SEQ ID NO:259); lane 7: T7AC_6H_GSG_VDVAD-PTH (SEQ ID NO:259)+T7AC_6H-cpCasp2D (SEQ ID No. 41) 50:1 (M/M) 2h; lane 8: T7AC_6H_GSG_VDVAD-PTH (SEQ ID NO:259)+T7AC_6H-mS9ProE (SEQ ID No. 71) 50:1 (M/M) 2h; lane 9: T7AC_6H_GSG_VDVAD-PTH (SEQ ID NO:259)+T7AC_6H-mS9ProD (SEQ ID NO:72) 50:1 (M/M) 2h; lane 10: T7AC_6H-cpCasp2D (SEQ ID No. 41), T7AC_6H-mS9ProD (SEQ ID NO:72), T7AC_6H-mS9ProE (SEQ ID No. 71). The main peak in lane 2 represents the uncleaved fusion protein, T7AC_6H_GSG_VDVAD-GCSF (SEQ ID NO:261); the peak of lane 3-5 that has the same migration as the main peak of lane 2 represents the uncleaved fusion protein, T7AC_6H_GSG_VDVAD-GCSF (SEQ ID NO:261); the peak below in lanes 3-5, having a migration of about 14 and 17 kDa represents the released protein of interest, GCSF. The main peak in lane 6 represents the uncleaved fusion protein, T7AC_6H_GSG_VDVAD-PTH (SEQ ID NO:259) the peak of lanes 7-9 that has the same migration as the main peak of lane 6 represents the uncleaved fusion protein, T7AC_6H_GSG_VDVAD-PTH (SEQ ID NO:259), the peak below in lanes 7-9, having a migration between 6 and 14 kDa represents the released protein of interest, PTH.

FIG. 53: IMAC capture of 6H_GSG_VDVAD_hFGF-2 (SEQ ID NO:32). Elution can be seen between 80 and 100 mL. A split peak was observed, but SDS-PAGE analysis revealed that both peak halves contained mostly the fusion protein, 6H-GSG-VDVAD-hFGF-2 (SEQ ID NO:32).

FIG. 54: Subtractive IMAC polish of 6H_GSG_VDVAD_hFGF-2 (SEQ ID NO:32). The product elutes during loading (from −0 to 15 mL).

FIG. 55: SDS-PAGE of hFGF-2 platform process. M: marker; SN: clarified lysis supernatant; CF: capture IMAC flow through; CWA: capture IMAC wash; CEL: capture IMAC eluate; BX: UF/DF buffer exchange; ETR: enzymatic tag removal; SFT: subtractive IMAC flow-through; SWA: wash of subtractive IMAC; SEL: subtractive IMAC eluate. The main peak in CEL and BX represents the uncleaved fusion protein 6H-GSG-VDVAD-hFGF2 (SEQ ID NO:32), the main peak in ETR and SFT represents the hFGF-2 with the native N-terminus from which the tag was cleaved off.

FIG. 56: Intact mass spectrum of hFGF-2 after tag removal and flow through IMAC purification. (A) shows the total deconvoluted MS spectrum and (B) shows the zoomed spectrum.

FIG. 57: Sequence logo of 79 selected recognition sites. The size of the letter represents the probability of occurrence of an amino acid at the positions P1-P5 of the caspase recognition site.

FIG. 58: Course of fermentation of the fusion protein T7AC-6H-GSG-VDVAD-BIWA4 (scFv) (SEQ ID NO:275) performed as described in Example 19, section 19.2 and table 53; left: formation of biomass (as CDM (cell dry mass) in [g/L] compared to calculated CDM, right: volumetric titer in [g/L] of insoluble (IB) fusion protein.

FIG. 59: Cleavage of 1 mg/ml VDVAD-β-galactosidase (SEQ ID No. 34) fusion protein incubated with 0.1 mg/ml cp caspase-2 (SEQ ID No. 6) for 24 hours. "+" means incubation with cp-caspase, "−" means incubation without cp caspase. No unspecific cleavage since no additional bands compared to the lanes "−" can be seen in the lanes "+". The cleavage of the β-galactosidase fusion protein cannot be seen in this SDS-Page since the migration difference between the cleaved and the uncleaved fusion protein cannot be detected by this SDS-Page method.

FIG. 60: Cleavage of 1 mg/ml VDTTD-E2 (SEQ ID No. 19) fusion protein and 1 mg/ml VDVAD-E2 (SEQ ID No. 33) fusion protein incubated with 0.003 mg/ml cp caspase-2 (SEQ ID No. 6) for 30 minutes.

DETAILED DESCRIPTION

Unless indicated or defined otherwise, all terms used herein have their usual meaning in the art, which will be clear to the skilled person. Reference is for example made to standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Janeway et al, "Immunobiology" (5th Ed., or more recent editions, Garland Science, New York, 2001).

The subject matter of the claims specifically refers to artificial products or methods employing or producing such artificial products, which may be variants of native (wild-type) products. Though there can be a certain degree of sequence identity to the native structure, it is well understood that the materials, methods and uses of the invention, e.g., specifically referring to isolated nucleic acid sequences, amino acid sequences, fusion constructs, expression constructs, transformed host cells and modified proteins including enzymes, are "man-made" or synthetic, and are therefore not considered as a result of "laws of nature".

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein, amino acids refer to twenty naturally occurring amino acids encoded by sixty-one triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).

The "positively" charged amino acids are:
Arginine: (Arg, R) polar, positive; and
Lysine: (Lys, K) polar, positive.

The "negatively" charged amino acids are:
Aspartic acid: (Asp, D) polar, negative; and
Glutamic acid: (Glu, E) polar, negative.

Caspases are the key enzymes in the initiation and execution of apoptosis and inflammation, hence their activity has to be tightly controlled. Although the sequences of caspases do differ (e.g. human caspase-1 and -2 have only 27% amino acid identity and 52% similarity), their active sites and tertiary structure are highly conserved. All caspases are synthesized as relatively inactive single-chain zymogens (procaspases), which comprise a prodomain (2-25 kDa), as well as a large and a small subunit of 17-21 kDa and 10-13 kDa respectively. The executioner caspases (caspases-3, -6, -7) and caspase-14 have a short, while all other caspases have a long prodomain. To get fully active, wild-type caspases first need to dimerize through hydrophobic interactions, then their intersubunit linker is cut and the prodomain is removed by proteolytic cleavages after aspartate residues. A main difference between the activation of executioner and initiator caspases is that the latter are already active after dimerization and the autocatalytic separation of their subunits is only necessary for stabilization. Active wild-type caspases are homodimers of heterodimers. Each heterodimer consists of a large and small subunit derived from a single protein chain. The enzyme is formed by a central twelve-stranded β-sheet, to which each of the four subunits contributes. From this core four loops protrude which contain the active site and form the binding pockets. In all caspases the catalytic center is in the large subunit. The substrate recognition site is formed by amino acids from both subunits, though the small subunit contributes the main residues which are responsible for differing substrate specificity between caspases. The cleavage of the inter-subunit linker causes a rearrangement of the active site loops, allowing the binding pockets to form and to make the active cysteine solvent accessible.

As used herein the term "recognition site" or "caspase recognition site" refers to an amino acid sequence of at least 3, preferably at least 4 or 5, amino acid residues of a substrate, which is specifically recognized by the caspase-2 or cp caspase-2 described herein. Specifically, the at least three substrate amino acids which are targeted and bound by the caspase provided herein and which form the recognition site are termed P3-P1 or P3 P2 P1, P4-P1 or P4 P3 P2 P1 for a recognition site comprising 4 substrate amino acids, P5-P1 or P5 P4 P3 P2 P1 for a recognition site comprising 5 substrate amino acids, P6-P1 or P6 P5 P4 P3 P2 P1 for a recognition site comprising 6 substrate amino acids, P7-P1 or P7 P6 P5 P4 P3 P2 P1 for a recognition site comprising 7 substrate amino acids, and so on. As described herein, the caspase provided herein interacts with its substrate in a target-specific manner by specifically recognizing and binding the recognition site comprising at least 3, 4, 5, 6, 7, 8, 9, 10 or more amino acid residues comprised in the sequence of the substrate. The recognition site amino acid residues occupy specific pockets on the caspase, numbered with the matching S designation (S1, S2, S3, S4, S5 etc; S1', S2' etc), each of which may be constructed of several amino acid residues. The objective of this interaction mode, which almost always binds the cleavage region in an extended peptide conformation, is to align the substrate accurately into register with the catalytic machinery.

Specifically, the caspase-2 or cp caspase-2 provided herein is not limited to the recognition site of wild-type caspase-2, VDVAD (SEQ ID No. 45). Further provided herein are variants of caspase-2, which target recognition sites other than VDVAD (SEQ ID NO:45) with high specificity and efficiency. Specifically provided herein are caspase-2 variants which target any one or more of the recognition sites described herein.

Preferably, the caspases described herein have high specificity towards a single recognition site, but embodiments are envisioned wherein a caspase recognizes more than one recognition site, for example for cleavage of one protein at multiple sites or for simultaneous cleavage of different proteins comprising different recognition sites.

Using the selection method described herein, caspase-2 variants can be selected which specifically recognize any one or more recognition sites. Specifically, any of the caspase variants described herein, comprising any one or more of the amino acid substitutions increasing P1' tolerance as described herein can be subjected to the selection method described herein. In such a way, for example, caspase-2 variants comprising increased P1' tolerance and target specificity towards a certain recognition site can be selected.

According to a further specific embodiment, recognition site specificity of the caspase variants described herein can be influenced, by introduction of amino acid substitutions, additions or deletions which are known to increase or decrease specificity to a certain recognition site.

Specifically, the caspase-2 or cp caspase-2 described herein recognizes a recognition site comprising the sequence XDXXD (SEQ ID No. 201), wherein X can be any amino acid. Specifically, the recognition site can be selected from the group consisting of DEXD (SEQ ID No. 202) and DVXD (SEQ ID No. 203), wherein X is any amino acid.

According to a specific example, the caspase-2 or cp caspase-2 described herein recognizes any one or more of the recognitions sites LDESD (SEQ ID No. 204), DVAD (SEQ ID No. 205), DEVD (SEQ ID No. 206), DEVE (SEQ ID No. 207), ADVAD (SEQ ID No. 208), VDTTD (SEQ ID No. 209), DTTD (SEQ ID No. 210), DVPD (SEQ ID No. 211), VDVPD (SEQ ID No. 212), VDQQD (SEQ ID No. 213), or TDTSD (SEQ ID No. 214).

According to a further specific example, the caspase-2 or cp caspase-2 described herein recognizes the recognition site DRKD (SEQ ID No. 215), DAVD (SEQ ID No. 216), VKVD (SEQ ID No. 217), DTLD (SEQ ID No. 218), EEPD (SEQ ID No. 219), DETD (SEQ ID No. 220), DATD (SEQ ID No. 221), NKVD (SEQ ID No. 222), DALD (SEQ ID No. 223), DSVD (SEQ ID No. 224), NAID (SEQ ID No. 225), DKPD (SEQ ID No. 226), IQLD (SEQ ID No. 227), DNAD (SEQ ID No. 228), DVVD (SEQ ID No. 229), ENPD (SEQ ID No. 230), DMAD (SEQ ID No. 231), DLID (SEQ ID No. 232), DGAD (SEQ ID No. 233), DVKD(SEQ ID No. 234), GYND (SEQ ID No. 235), ELPD (SEQ ID No. 236), DSTD (SEQ ID No. 237), DRQD (SEQ ID No. 238), HAVD (SEQ ID No. 239), QERLD (SEQ ID No. 240), LERD (SEQ ID No. 241), MMPD (SEQ ID No. 242), EEPD (SEQ ID No. 243), VESID (SEQ ID No. 244), EAMD (SEQ ID No. 245), EDAD (SEQ ID No. 246), EEED (SEQ ID No. 247), AVLD (SEQ ID No. 248), and/or EEGD (SEQ ID No. 249).

According to yet a further specific example, the caspase-2 or cp caspase-2 described herein recognizes the recognition site TDTSD (SEQ ID No. 214), LDEPD (SEQ ID No. 250), and/or KDEVD (SEQ ID No. 251).

As used herein the term “cleavage site” refers to the amino residues P1/P1' wherein cleavage occurs at the residue of the amino terminal scissile bond P1 and the one to the carboxy-terminal side P1'.

Proteolytic cleavage of the substrate happens after the P1 residue. Specifically, the amino acids following the P1 residue are referred to as P1'-P4' residues, also termed the prime side. The prime side of the substrate is important for substrate processing, specifically the P1' residue. The P1'-P4' residues can under certain circumstances influence binding by steric hindrance. The P1' residue is close to the active site and in particular branched (e. g. leucine or valine) and polar amino acids (e. g. threonine or aspartate) in this position can compete for space with the catalytic cysteine and negatively influence the cleavage.

Wild-type caspases have a high preference for aspartate in the P1 position. The P2 and P3 positions are less selective and a variety of residues is accommodated, although many caspases have the highest activity with a glutamate residue at the P3 position. The P4 position is crucial for distinction between caspase classes: Inflammatory caspases and caspase-14 prefer hydrophobic residues, initiator caspases and caspase-6 aliphatic residues, and executioner caspases as well as wild-type caspase-2 favor aspartate. The prime side positions of substrates have not been investigated as intensively, although studies have shown that the P1' site has an influence on cleavage, as certain residues can reduce the activity up to 1000-fold. All wild-type caspases prefer substrates with small residues (glycine, serine, alanine), but large hydrophobic amino acids (phenylalanine, tyrosine) are also surprisingly well tolerated. Most likely the P1' site is not necessary for efficient binding of the substrate, but certain residues can hinder it. The prime sites further away (P2'-P4') from the cleavage site have little influence. However, whether a substrate is cleaved by a caspase or not, does not only depend on the mere presence or absence of a recognition site, as many proteins are processed at non-canonical sites. Secondary and tertiary structures of the substrate are very important for recognition. In vivo proteins are preferably cleaved at solvent accessible loops, but a significant amount is also cleaved within α-helices.

Specifically, wildtype caspase-2 highly prefers a glycine residue at the P1' site.

According to a specific embodiment, variants of cp caspase-2 and/or caspase-2 can be selected for increased P1' tolerance as described herein. Specifically, functionally active variants of cp caspase-2 having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 6, preferably at least 85, 90 or 95% sequence identity with SEQ ID No. 6, comprise improved tolerance for P1' residues other than glycine. According to a further specific embodiment, caspase-2 variants as described herein can be selected for specific cleavage of recognition sites other than VDVAD (SEQ ID NO:45).

Hence there are no limitations regarding the substrate. Substrates of the caspase provided herein can be any protein or polypeptide, a naturally occurring protein or polypeptide naturally comprising a recognition site specifically targeted by the caspase described herein, or heterologous proteins or polypeptides engineered to comprise a recognition site within their sequence or at or near their N-terminus or C-terminus.

According to a specific embodiment, the substrate comprises a protein of interest as described herein.

Caspase-2 was first described as apoptotic protein in 1994, due to its similarity with CED-3, a cell death protein in *Caenorhabditis elegans*, and human caspase-1. Procaspase-2 consists of a CARD followed by a large and a small subunit (see FIG. 2A). Its structure is most similar to caspase-9, although unlike other initiator caspases, caspase-2 does not activate executioner caspases. Instead it triggers apoptosis by releasing cytochrome c from mitochondria and thereby initiates the intrinsic pathway for caspase-9 activation. Like all caspases the active caspase-2 is a dimer of heterodimers. A large (p19) and small (p12) subunit form a caspase heterodimer, and two of these compose the complete enzyme. Wild-type caspase-2 contains two active sites, one in each heterodimer. The two wt heterodimers are linked by a disulfide bridge formed by two cysteines of the small subunits ($Cys^{436}$ of SEQ ID No. 11). No other caspase has such an intermolecular covalent linkage, which enables it to exist as stable dimer in solution. Interestingly the disulfide bridge can only form after the separation of large and small subunit via cleavage.

The substrate binding site of wild-type caspase-2 is mainly formed by three protein loops. The first loop (residues 212-221 of SEQ ID No. 11, large subunit) interacts with the prime site of the substrate (P1'-P4'), while the second loop (residues 373-382 of SEQ ID No. 11, small subunit) binds to the whole substrate (P5-P4'), and the third loop (residues 419-431 of SEQ ID No. 11, small subunit) interacts with the recognition site (P5-P1). Wild-type caspase-2 has a near absolute requirement for aspartate residues on both P1 and P4 positions of the recognition site, while many residues are accepted in the P2 and P3 positions. The S1 pocket is positively charged and the substrate residue stabilized by two arginine residues. The S4 pocket is also deep and narrow and therefore very specific. Likewise, the P3 and P5 residues bind to their unique pockets, only the P2 residue is not bound individually. Wild-type caspase-2 is unique in recognizing a pentapeptide and not a tetrapeptide like all other caspases. VDVAD (SEQ ID NO:45) is considered the preferred cleavage site of wild-type caspase-2.

As used herein, the term "wild-type" generally refers to a phenotype, genotype, or gene that predominates in a natural population of organisms or strain of organisms in contrast to that of natural or recombinant mutant variants. In other words, "wild-type" refers to the form or forms of a gene commonly occurring in nature in a given species. The term "wild-type" with respect to caspase-2 and cp caspase-2 as used herein, refers to amino acid or nucleotide sequences of caspase-2, or domains thereof such as e.g. small and large subunit, originating from different species and commonly occurring in nature.

Within the context of this invention, it should be understood that the term "caspase" generally refers to "caspase-2" and functionally active variants thereof.

The term "cp-caspase-2" as used herein refers to a circular permuted caspase-2, as described herein, which is a single chain caspase-2 comprising the small subunit N-terminal of the large subunit of a caspase-2 as further described herein.

"cp-caspase-2" comprises the small subunit and large subunit of caspases 2 originating from different species as well as functionally active variants thereof. Specifically, wild type caspase-2 of the different species comprises several, specifically 4, domains.

The terms "wild-type caspase-2" or "wt caspase-2" and "wild-type cp caspase-2" or "wt cp caspase-2" encompass wild-type caspase-2 sequences originating from different species and functionally active variants thereof. Wild-type caspase-2 described herein, may comprise one or more amino acid substitutions, deletions and/or insertions, which are conservative modifications and do not alter the enzyme's protease function. The wild-type caspase-2 and wild-type cp caspase-2 as described herein, do not comprise amino acid substitutions increasing P1' tolerance.

The terms "caspase-2 variant" and "cp caspase-2 variant" as used herein refer to variants of the wild-type caspase-2 or wild-type cp caspase-2 which have increased proteolytic activity, specifically increased P1' tolerance, and comprise specific amino acid substitutions as described herein.

The terms "caspase-2" and "cp caspase-2" encompass both the wild-type version of the enzyme, circularly permuted or not circularly permuted, and the variant version of the enzyme, circularly permuted or not circularly permuted, comprising increased P1' tolerance as described herein, unless otherwise specified.

The boundaries of the small subunit and the large subunit, as well as the other domains, are identified either experimentally by amino acid sequence analysis of the mature caspase or by inspection of structural homology (e.g., the conserved Asp-X cleavage site, in human for example $Asp^{14}$ of SEQ ID No. 2 or $Asp^{347}$ of SEQ ID No. 11). For exemplary purposes, the Table below presents the boundaries of the 4 domains including prodomain (CARD), large Subunit (LS), intervening sequence (small subunit propeptide), and small subunit (SS) of caspase-2 in different species. The amino acid positions of the table below refer to the amino acid positions in SEQ ID Nos. 11, 89, 92, 95, 98, 101, 104, 107, 110, 113, 116.

| | Prodomain (CARD) | Large Subunit | Intervening Sequence (Propeptide Small Subunit) | Small Subunit |
|---|---|---|---|---|
| Human P42575 | 1-169 | 170-333 | 334-347 | 348-452 |
| Mouse P29594 | 1-169 | 170-333 | 334-347 | 348-452 |
| Sheep W5Q86 | 1-174 | 175-342 | 343-356 | 357-461 |
| Tasman Devil G3VQP7 | 1-146 | 147-310 | 311-324 | 325-429 |
| Chicken Q98943 | 1-140 | 141-304 | 305-318 | 319-424 |
| Anolis H9GC58 | 1-163 | 164-327 | 328-341 | 342-446 |
| Alligator A0A1U8D1G6 | 1-143 | 144-307 | 308-321 | 322-427 |
| Xenopus F6RDY9 | 1-141 | 142-302 | 303-316 | 317-421 |
| Danio Q0PKX3 | 1-136 | 137-301 | 302-315 | 316-435 |
| Ghost Shark V9KZT1 | 1-131 | 132-294 | 295-305 | 306-417 |
| Sea squirt A0A1W2WKB0 | 1-67 | 68-234 | 235-245 | 246-351 |

The caspase described herein comprises at least a portion of the caspase-2 small subunit and at least a portion of the caspase-2 large subunit. In preferred embodiments, the propeptide of the small caspase-2 subunit is also present. The prodomain (CARD) is generally not required for enzyme activity and is normally released in vivo. Caspases of the present invention optionally have a prodomain or portion thereof. The propeptide of the small subunit is optional for inclusion in the cp-caspase-2. Although it is preferred that both subunits are derived from the same species, combinations of subunits from different species may be used.

As noted above, a portion of the large subunit and a portion of the small subunit may be used in the caspase described herein, but when designing the caspase-2 and/or the cp caspase-2 described herein, active sites are preferably not deleted.

Caspase-2 is unique in the caspase-family in that it comprises the following consensus sequence (SEQ ID NO:277):

```
QXXRXCSSPRXCALVXSXVTXDPXXADPLDHXKXGEXXEEVXXKVXTEX

DFVXSVHRXXXAQAMRXCIEQFCQLPXHRTADGXVXXXXXXXVDXAVYS

XDXELLQXDWVFEAXDNSHXPLXQNXXXXXFVXXXXXEXMXXXVVQDTX

PERTGSPSXEQRDAGREGEGDPGSRRPVSLGRPRIXLXQRSXMICGFAS

LKXQRLSTAAMXXTXRXXXXVXEXNEAXRLRSRDTHLADXXVQXXARIK

XRXGXAPGTPHXRCXEMSEFTXSXCNDXFLF
```

Caspase-2 is an initiator caspase, while caspase-3 and caspase-6 are effector caspases. The structure of caspase-2 is stabilized by a disulfide bond and wt caspase-2 is the only caspase with a recognition site comprising 5 amino acid residues (Grinshpon et al., AC. Biochem J. 2019; 476(22): 3475-3492).

In a preferred embodiment, the caspase-2 variants described herein, that are not circularly permuted, comprise at least a portion of a small caspase-2 subunit and at least a portion of a large caspase-2 subunit and amino acid substitutions at any one or more of positions 212, 431, 213, 323, 266, 409, 226, 296 or 326 of SEQ ID No. 11, or at a position functionally equivalent to positions 212, 431, 213, 323, 266, 409, 226, 296 or 326 of SEQ ID No. 11. Specifically, said caspase-2 variant comprises improved P1' tolerance, specifically for amino acids other than glycine in the P1' position, compared to the respective wildtype caspase-2.

The person skilled in the art will readily understand that the respective wildtype caspase-2 is a protein comprising the amino acid sequence of the caspase-2 from which the caspase-2 variant originates. For example, a caspase-2 variant as described herein which is of human origin, comprises improved P1' tolerance compared to human wildtype caspase-2 comprising SEQ ID No. 11. According to a further specific example, a caspase-2 variant as described herein which is of ghost shark origin and comprises amino acid substitutions at any one or more of positions 369, 391, 174, 187, 227, 257, 284 or 287 of SEQ ID No. 113, comprises improved P1' tolerance compared to ghost shark wildtype caspase-2 comprising SEQ ID No. 113. According to a further specific example, a caspase-2 variant as described herein which is of Tasmanian devil origin and comprises amino acid substitutions at any one or more of positions 386, 408, 189, 190, 203, 243, 273, 300, or 303 of SEQ ID No. 95, comprises improved P1' tolerance compared to Tasmanian devil wildtype caspase-2 comprising SEQ ID No. 95.

Additionally, the caspase-2 variants described herein can comprise the amino acid sequence of the homologous wildtype caspase 2 of several different species, such as but not limited to Mouse, Sheep, Tasman Devil, Chicken, *Anolis*, Alligator, *Xenopus, Danio*, Ghost Shark, Sea Squirt or any other species, as shown in SEQ ID Nos. 11, 89, 92, 95, 98, 101, 104, 107, 110, 113, 116 and FIG. 6.

Circular permutation (CP) has first been discovered in natural proteins in 1979. Circularly permuted (cp) proteins arise by covalent linkage of native N- and C-terminus and the introduction of new termini by cleavage elsewhere in the protein. In nature this either happens by duplication/deletion or fission/fusion events at the gene level. The new variants have an altered order of amino acids but maintain the same tertiary structure. Despite one published variant, an uncleavable reversed caspase-3, all described reverse variants still cleave themselves at the intersubunit linker, to make their structure more similar to the wild-type variants. Circularly permuted, constitutively active forms of caspase-7 and -14 have been published but all of them cleave their intersubunit linker. It was not expected that circular permutation of caspase-2 would be successful. As the structure of the N-terminus of the large subunit has not been completely determined, it was unclear if the two subunits of caspase-2 could be joined. It was thus surprising to see that the circular permuted variants of caspase-2 provided herein were active and it was even more surprising that they depicted significantly improved characteristics, in particular higher P1' tolerance, higher specificity, higher catalytic efficiencies, increase in heat tolerance and tolerance to chaotropic conditions and significantly improved manufacturability over wild-type caspase-2.

As used herein the term "circular permuted caspase-2" or "cp caspase-2" refers to a modified variant of caspase-2 comprising an altered order of amino acids, specifically, the order of amino acids is altered compared to order of amino acids in wildtype caspase-2. The cp caspase-2 referred to herein is a protease in which a small subunit of a caspase-2 is N-terminal to a large subunit of a caspase-2. Specifically, the amino acid order is altered by linkage of the native N-terminus of the LS and the C-terminus of the SS and the introduction of new termini by cleavage elsewhere in the protease. The cp caspase-2 provided herein comprises the following structure from N- to C-terminus: a small caspase-2 subunit, or a functionally active variant thereof, covalently linked, either via a linker or directly, to a large caspase-2 subunit, or a functionally active variant thereof. The structure of the cp caspase-2 described herein is exemplified in FIGS. 2B, 2C and 2D. Optionally, the two subunits are linked via a linker sequence of up to 12 amino acids or even more, as long as the remaining cp caspase 2 is still a functional active variant of caspase 2 or cp caspase 2.

Hence a caspase-2 was designed whose scaffold was changed by circular permutation, i.e. covalent ligation of the wild type N- and C-termini and intramolecular cut of the protein backbone at a different position to create new N- and C-termini, which leads to swapped domains, i.e. exchange of the positioning of the small and large caspase subunits, and which are active without the need of processing steps as in wild-type executioner or apoptotic caspases.

Circular permuted caspase-2 as described herein includes wildtype caspase-2 sequences without amino acid alterations, albeit in altered order, and circular permuted variants of wildtype caspase-2, which differ from wildtype caspase-2 sequences in one or more amino acid substitutions, deletions, additions and the like and comprise increased proteolytic activity, specifically increased P1' tolerance.

Variants of caspase and cp-caspase genes provided herein may be engineered from natural variants (e.g., polymorphisms, splice variants, mutants), synthesized or constructed. Many methods have been developed for generating mutants (see, generally, Sambrook et al., Supra; Ausubel, et al., Supra). Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, typically *E. coli*, but alternatively, other prokaryotes, yeast or other eukaryotes may be used. Standard screening and vector growth protocols are used to identify mutant sequences and obtain high yields. Similarly, deletions and/or insertions of the caspase-2 or cp caspase-2 genes may be constructed by any of a variety of known methods, such as discussed herein. For example, the gene can be digested with restriction enzymes and re-ligated such that a sequence is deleted or re-ligated with additional sequences such that an insertion or large substitution is made. Other means of generating variant sequences may be employed with methods known in the art. Verification of variant sequences is typically accomplished by restriction enzyme mapping, sequence analysis, or probe hybridization.

Specifically, the cp caspases of the present invention are generated by rearranging the gene sequence of a caspase-2 gene such that the nucleic acid sequence encoding the small subunit precedes (is 5' to) the nucleic acid sequence encoding the large subunit.

Specifically, the wild-type cp caspase-2 or cp caspase-2 variant described herein is of animal origin, specifically it is of mammalian, reptile or fish origin. Specifically, is derived from Human (SEQ ID No. 11), Mouse (SEQ ID No. 89), Sheep (SEQ ID No. 92), Tasmanian Devil (SEQ ID No. 95), Chicken (SEQ ID No. 98), *Anolis* (SEQ ID No. 101), Alligator (SEQ ID No. 104), *Xenopus* (SEQ ID No. 107), *Danio* (SEQ ID No. 110), Ghost Shark (SEQ ID No. 113), or Sea Squirt (SEQ ID No. 116) caspase-2. Preferably, the cp caspase-2 described herein is derived from human, marsupial, iguana, Tasmanian devil, ghost shark or cartilaginous fish caspase-2.

According to a specific embodiment, the wild-type cp caspase-2 or cp caspase-2 variant described herein comprises a sequence having more than 80 or 90%, specifically at least 80, 81, 82, 83, 84, 85, 86, 87, 88, 89, 90, 91, 92, 93, 94, 95, 96, 97, 98, 99% sequence identity compared to an active site, e.g. comprising SEQ ID No. 46, SEQ ID No. 47, SEQ ID No. 48, SEQ ID No. 49 and SEQ ID No 50. Preferably, the cp caspase-2 described herein has at least 90, 95% or more sequence identity with SEQ ID Nos. 46-50.

According to a further specific embodiment, the wild-type cp caspase-2 or cp caspase-2 variant described herein comprises at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 64 (*Sarcophilus harrisii*, tasman devil), SEQ ID No. 66 (*Anolis carolinensisilus*) or SEQ ID No. 68 (*Callorhinchus milii*, ghost shark).

According to a preferred embodiment, the wild-type cp caspase-2 or cp caspase-2 variant described herein comprises the amino acid sequence of SEQ ID No. 9 or is a functional variant thereof having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 9. Specifically, the cp caspase-2 described herein has the amino acid sequence of SEQ ID No. 9, or it is a functional active variant thereof comprising one or more amino acid substitutions or deletions, preferably comprising 1, 2, 3, 4, 5, 6, 7, 8, 9 or 10 amino acid substitutions, additions or deletions or the like.

According to a further preferred embodiment, the wild-type cp caspase-2 or cp caspase-2 variant described herein comprises the amino acid sequence of SEQ ID No. 6 or is a functional variant thereof having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 6. Specifically, the cp caspase-2 described herein has the amino acid sequence of SEQ ID No. 6, or it is a functional active variant thereof comprising one or more amino acid substitutions or deletions, preferably comprising 1, 2, 3, 4, 5, 6, 7, 8, 9 or 10 amino acid substitutions, additions or deletions or the like.

According to a further preferred embodiment, the wild-type cp caspase-2 or cp caspase-2 variant described herein comprises the amino acid sequence of SEQ ID No. 74, SEQ ID No. 75, SEQ ID No. 76 or SEQ ID No. 77 or is a functional variant thereof having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 74, SEQ ID No. 75, SEQ ID No. 76 or SEQ ID No. 77. Specifically, the cp caspase-2 described herein has the amino acid sequence of SEQ ID No. 74, SEQ ID No. 75, SEQ ID No. 76 or SEQ ID No. 77, or it is a functional active variant thereof comprising one or more amino acid substitutions or deletions, preferably comprising 1, 2, 3, 4, 5, 6, 7, 8, 9 or 10 amino acid substitutions, additions or deletions or the like.

According to a specific embodiment, the caspase-2 variant described herein comprises one or more amino acid substitutions at positions 171, 105, 172, 282, 225, 83, 185, 255, or 285 of SEQ ID No. 6 or at a position functionally equivalent to any of positions 171, 105, 172, 282, 225, 83, 185, 255, or 285 of SEQ ID No. 6 such as positions 409, 431, 212, 213, 266, 226, 296, 323 or 326 of SEQ ID No. 11.

The term "functionally equivalent" as used in respect of amino acid substitutions herein refers to amino acids at positions corresponding to the position in the sequence of caspase-2 of a different species. Specifically, by "functionally equivalent" it is meant that variants of the caspase-2 or cp caspase-2 described herein comprise an amino acid substitution at a position considered to concur with the substitutions described herein numbered with respect to SEQ ID No. 6 and that have the same functional role in the variant. Specifically, an amino acid substitution at a position functionally equivalent to the amino acid substitutions described herein confer improved P1' tolerance upon the variant.

Generally, functionally equivalent substitution mutations occur at homologous amino acid positions in the amino acid sequences of caspase-2. Hence, use herein of the term "functionally equivalent" also encompasses mutations that are "positionally equivalent" or "homologous" to a given mutation, regardless of whether or not the particular function of the mutated amino acid is known. It is possible to identify positionally equivalent or homologous amino acid residues on the basis of sequence alignment and/or molecular modelling.

By way of example, the residues shown in the table 63 below are identified as positionally equivalent and/or functionally equivalent to positions 171, 105, 172, 282, 225, 83, 185, 255, and 285 of SEQ ID No. 6. It will be readily known by one of ordinary skill in the art how to identify positionally equivalent and/or functionally equivalent positions for the amino acid substitutions described herein in caspase-2 sequences of other species.

TABLE 63

| Position in wt human caspse-2 (UniProt ID P42575, SEQ ID No. 11) | Position in human cp caspase-2 (SEQ ID No. 6) | Position in wild-type Callorhinchus milii (UniProt ID V9KZT1, SEQ ID No. 113) | Position in Callorhinchus cp caspase-2 (SEQ ID No. 68) | Position in wild-type Sarcophilus harrisii (UniProt ID G3VQP7, SEQ ID No. 95) | Position in Sarcophilus cp caspase-2 (SEQ ID No. 64) |
|---|---|---|---|---|---|
| Asp 347 | 21 | Asp 305 | 18 | Asp 324 | 21 |
| Lys 409 | 83 | Gln 369 | 82 | Lys 386 | 83 |
| Glu 431 | 105 | Glu 391 | 104 | Glu 408 | 105 |
| Gly 212 | 171 | Gly 174 | 175 | Gly 189 | 171 |
| Glu 213 | 172 | — | — | Glu 190 | 172 |
| His 226 | 185 | Thr 187 | 188 | His 203 | 185 |
| Val 266 | 225 | Arg 227 | 228 | Asn 243 | 225 |
| Val 296 | 255 | Ile 257 | 258 | Val 273 | 255 |
| Asp 323 | 282 | Asp 284 | 285 | Asp 300 | 282 |
| Asp 326 | 285 | Asp 287 | 288 | Asp 303 | 285 |

According to a specific example, homologues of the caspase-2 and the cp caspase-2 described herein are constructed analogue to the caspase-2 or cp caspase-2 of human origin. For example, using the wildtype sequence of caspase-2 in the respective species, such as e.g. Tasmanian devil caspase-2 (*Sarcophilus harrisii*, UniProtKB14 ID G3VQP7) and Ghost shark caspase-2 (*Callorhinchus milii*, UniProtKB14 ID V9KZT1), the caspase-2 subunits are determined (see FIG. 6: Alignment: initiating region of the domains). Depending on the desired caspase structure, the order of large and small subunit may be exchanged to create a constitutively active circular permuted caspase. Specifically, to ensure expression of as a single chain protein, in the cases where the caspase is a cp caspase comprising the small subunit propeptide, the aspartate in the propeptide of the small subunit (corresponding to $Asp^{343}$ in the wild-type sequence of human caspase-2) is mutated, e.g. to alanine, to avoid cleavage of the propeptide. Additionally, the protein sequence may be codon optimized for expression in the desired prokaryotic host, such as e.g. *E. coli*, and linker and/or tag sequences may be added. Resulting exemplary variants are *Sarcophilus* cp caspase-2 (SEQ ID No. 64) and *Callorhinchus* cp caspase-2 (SEQ ID No. 68). In this specific example, mutations at positions corresponding to residues $Glu^{105}$ and $Glu^{172}$ in cp caspase-2 (SEQ ID No. 6) were inserted in Sarcophilus cp caspase-2, generating variant Sarcophilus cp caspase-2 E105V, E172V (SEQ ID No. 78). In a further specific example, mutations at positions corresponding to $Glu^{105}$ and $Gly^{171}$ in cp caspase-2 (SEQ ID No. 6) were inserted in *Callorhinchus* cp caspase-2, generating variant *Callorhinchus* cp caspase-2 E105V, G171 D (SEQ ID No. 79).

Surprisingly, the amino acid substitutions described herein confer improved P1' tolerance upon the caspase-2 and cp caspase-2 described herein. As used herein, the term "improved P1' tolerance" refers to increased proteolytic activity of a caspase regarding one or more P1' residues. For example, while wildtype human caspase-2 prefers glycine in the P1' position, the caspases and cp caspases described herein are capable of proteolytic cleavage at a cleavage site comprising a P1' residue other than glycine with increased activity compared to wildtype caspase-2 or to a cp caspase-2 not comprising the amino acid substitutions described herein. Specifically, the caspase-2 variants described herein comprise improved P1' tolerance compared to the respective wildtype caspase-2. The person skilled in the art will readily understand that the respective wildtype caspase-2 is a protein comprising the amino acid sequence of the caspase-2 from which the caspase-2 variant originates. For example, a caspase-2 variant as described herein which is of human origin, specifically a cp caspase-2 as described herein, e.g. a cp caspase-2 comprising SEQ ID No. 70, comprises improved P1' tolerance compared to human cp caspase-2 comprising SEQ ID No. 6. Specifically, the caspases of the present invention comprise at least 5, 10, 25, 50, 75 or 100% or more increase in proteolytic activity for at least one amino acid residue in the P1' position compared to a cp caspase-2 not comprising the amino acid substitutions described herein.

As described above, the cp caspase-2 and the caspase-2 provided herein comprise at least a small caspase-2 subunit and a large caspase-2 subunit.

The term "small caspase-2 subunit" as used herein, refers to a small subunit, derived from caspase-2, which is covalently linked to a large caspase-2 subunit also derived from caspase-2, optionally the two subunits are linked via a linker sequence comprising one or more and up to 12 amino acids or more, as long as the remaining cp caspase 2 is still a functional active variant of caspase 2 or cp caspase 2. According to a specific example, the small subunit of cp caspase-2 is derived from wild-type caspase-2 spanning amino acid residues 348 to 452 of the amino acid sequence of wild-type caspase-2 (SEQ ID No. 11). Specifically, the small caspase-2 subunit comprises the amino acid sequence of SEQ ID No. 3 or a variant thereof having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 3.

Specifically, a variant of the small caspase-2 subunit described herein is functionally active, when direct or indirect fusion or combination with a large caspase-2 subunit or variant thereof results in a functionally active caspase-2 variant.

Specifically, the small subunit of the cp caspase-2 described herein comprises the amino acid sequence of SEQ ID No. 3, SEQ ID No. 91, SEQ ID No. 94, SEQ ID No. 97, SEQ ID No. 100, SEQ ID No. 103, SEQ ID No. 106, SEQ ID No. 109, SEQ ID No. 112, SEQ ID No. 115, SEQ ID No. 118, or a functionally active variant thereof comprising at least 70, 75, 80, 85, 90, 91, 92, 93, 94, 95, 96, 97 or 98% sequence identity.

The term "modified small caspase-2 subunit pro-peptide" as used herein refers to the pro-peptide of the small subunit of caspase-2, which has been modified at its C-terminus. According to a specific example, the pro-peptide of the small subunit of cp caspase-2 is derived from wild-type caspase-2 spanning amino acid residues 334 to 347 of the amino acid sequence of wild-type caspase-2 (SEQ ID No. 11), comprising an amino acid substitution or deletion of at least one residue at its C-terminus. Specifically, the pro-peptide of the small subunit as described herein comprises the amino acid sequence of SEQ ID No. 2, wherein X can be any amino acid, preferably it is not D and preferably it is not E, even more preferably it is A, or a variant thereof having 1, 2 or 3 amino acid substitutions or 1, 2 or 3 amino acid deletions or additions.

The term "large caspase-2 subunit" as used herein, refers to a large subunit, derived from caspase-2, which is covalently linked to a small caspase-2 subunit also derived from caspase-2, optionally linked via a linker sequence. According to a specific example, the large subunit of cp caspase-2 is derived from wild-type caspase-2 spanning amino acid residues 170 to 333 of the amino acid sequence of wild-type caspase-2 (SEQ ID No. 11). Specifically, the large caspase-2 subunit comprises the amino acid sequence of SEQ ID No. 4 or a variant thereof having at least 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% sequence identity with SEQ ID No. 4.

Specifically, a variant of the large caspase-2 subunit described herein is functionally active, when direct or indirect fusion to or combination with a small caspase-2 subunit or variant thereof results in a functionally active caspase-2 variant.

Specifically, the large subunit of the cp caspase-2 described herein comprises the amino acid sequence of SEQ ID No. 4, SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No. 114, SEQ ID No. 117, or a functionally active variant thereof comprising at least at least 70, 75, 80, 85, 90, 91, 92, 93, 94, 95, 96, 97 or 98% sequence identity.

Further provided herein is a functionally active variant of the cp caspase-2 as described herein, which is essentially identical to the cp caspase-2 described above, but differs from its polypeptide or the nucleotide sequence, respectively, in that it is derived from a homologous sequence of a different species.

As used herein the term "catalytically active" refers to the ability of the caspase described herein to catalyze the hydrolysis of the substrate's peptide bond. Caspases are endopeptidases capable of forcing formation of a tetrahedral intermediate by promotion of a cysteine residue to act as a nucleophile in order to cleave its substrate. Specifically, the cp caspase-2 described herein is catalytically active and is capable of specifically cleaving its substrate at the caspase recognition site as described herein. Specifically, the cp caspase-2 described herein is catalytically active upon dimerization, comprising two single chain cp caspase-2 units as described herein. Specifically, the cp caspase-2 described herein is catalytically active irrespective of proteolytic cleavage of its subunits or pro-peptide, more specifically its small caspase-2 subunit pro-peptide is not cleaved at its C-terminus. Therefore, the cp caspase-2 described herein is not a zymogen, since it does not require activation through cleavage, neither through an activating enzyme nor through autocatalytic cleavage.

Activation of wild-type caspase-2 requires cleavage at the C-terminus of the large subunit and consequent separation of the small and large subunit. In mature wild-type caspase-2, the pro-peptide of the small subunit is removed by cleavage at its C-terminus. Surprisingly, the cp caspase-2 described herein, does not require cleavage between the subunits for activation. Despite modifications that prevent cleavage between the subunits as well as separation of the C-terminus of the propeptide of its small subunit, single-chain cp caspase-2 as described herein is catalytically active.

Specifically, two single-chain cp caspases-2 as described herein dimerize via covalent linkage, specifically via one or more disulfide bonds. Specifically, dimerization, however, can also be independent of disulfide bond linkage.

Specifically, the catalytic efficiency of a protease is defined as the rate of hydrolysis and can be determined using the Michaelis-Menten equation ($k_{cat}/K_M$). The Michaelis constant, $K_M$, is equal to the substrate concentration at which the enzyme converts substrates into products at half its maximal rate and hence is related to the affinity of the substrate for the enzyme. The catalytic constant ($k_{cat}$) is the rate of product formation when the enzyme is saturated with substrate and therefore reflects the enzyme's maximum rate. The rate of product formation is dependent on both how well the enzyme binds substrate and how fast the enzyme converts substrate into product once substrate is bound. An equation with a low $K_M$ value indicates a large binding affinity, as the reaction will approach Vmax, the maximal rate of the reaction, more rapidly. An equation with a high $K_M$ indicates that the enzyme does not bind as efficiently with the substrate, and Vmax will only be reached if the substrate concentration is high enough to saturate the enzyme. The catalyst rate constant ($k_{cat}$) measures the number of substrate molecules turned over by enzyme per second. The reciprocal of $k_{cat}$ is then the time required by an enzyme to turn over a substrate molecule. The higher the $k_{cat}$ is, the more substrates get turned over in one second. When $k_{cat}$ is divided by $K_M$, a measure of enzyme efficiency is obtained. The enzyme efficiency can be increased as $k_{cat}$ has high turnover and a small number of $K_M$.

Specifically, a comparison of catalytic efficiency constants is used as a measure of the preference of an enzyme for different substrates, i.e. substrate specificity. The higher the specificity constant, the more the enzyme "prefers" that substrate.

Specifically, catalytic activity of the caspase-2 or cp caspase-2 described herein can be measured by examining cleavage of the caspase substrate. Specifically, cleavage activity of the caspase described herein can be examined by methods well known in the art. According to a specific example but not limited thereto, cleavage of the caspase substrate can be examined by eye on an SDS-PAGE gel or by densitometric scanning. Specifically, catalytic activity of the caspase described herein is analyzed with SDS-PAGE to separate cleaved and uncut substrate from the caspase and band intensities of cleaved substrate are determined to evaluate the percentage of cleavage product at a specific time point. Specifically, caspase and substrate are mixed and at timed intervals samples are taken and the reaction is stopped. Preferably, to standardize the process only samples with about 50% of cleaved substrate are used.

According to a further specific example, cleavage activity of the caspases described herein is determined using a Förster resonance energy transfer (FRET) assay.

According to another specific example but not limited thereto, cleavage of the caspase substrate can be examined by measuring the increase in fluorescence when a peptide substrate, encompassing a recognition sequence for the caspase described herein, a fluorophore and a quencher, is cleaved by said caspase. Specifically, caspase and substrate are mixed at defined concentrations and the increase in fluorescence is monitored for a certain time. This fluorescence increase can be used to calculate the rate of product generation, which is then used to fit a Michaelis-Menten kinetic. The resulting Michaelis-Menten parameters $k_{cat}$ and $K_M$ can be used to define the catalytic efficiency of the caspase.

The term "single-chain" as used herein refers to a polypeptide comprising a linear chain of amino acids. A protein contains at least one long polypeptide, specifically a polypeptide comprising a linear chain of more than 100 amino acids. Short polypeptides, containing less than 20-30 residues are commonly called peptides, or sometimes oligopeptides. The individual amino acid residues are bonded together by peptide bonds and adjacent amino acid residues. The sequence of amino acid residues in a protein is defined by the sequence of a gene, which is encoded in the genetic code. Specifically, as used herein, the term "single-chain" refers to a protein which is active irrespective of proteolytic cleavage within its amino acid sequence.

In the fully mature wild-type caspase-2 the small subunit is reduced from a p14 to a p12 chain by cleavage after the recognition site CEESD (residues 343 to 347 of SEQ ID No. 11, residues 17 to 21 of SEQ ID No. 6). The pro-peptide of the small subunit of wild-type caspase-2 is thus separated from the small subunit by proteolytic cleavage after the recognition site CEESD. According to a specific embodiment, the C-terminal amino acid of the small subunit propeptide of the cp caspase-2 is modified to prevent separation of the pro-peptide of the small subunit of cp caspase-2 from the small subunit. Specifically, amino acid residue 21 of SEQ ID No. 6 is substituted with any amino acid but aspartic acid (D) or glutamic acid (E). Specifically, amino acid residue 21 of SEQ ID No. 6 is selected from the group consisting of alanine (A), arginine (R), asparagine (N), cysteine (C), glutamine (Q), glycine (G), histidine (H), isoleucine (I), leucine (L), lysine (K), methionine (M), phenylalanine (F), proline (P), serine (S), threonine (T), tryptophan (W), tyrosine (Y) and valine (V). Specifically, the C-terminal aspartic acid of the propeptide of the small subunit of cp caspase-2 is substituted with any amino acid residue but aspartic acid or glutamic acid, preferably with alanine, to ensure expression of the cp caspase-2 described herein as a single protein chain.

As described herein, the caspases of the invention may be used to produce a protein of interest (POI) comprising an authentic N-terminus. The term “authentic N-terminus” as used herein refers to the desired N-terminus of a protein to be produced using the means provided herein. In other words, a protein comprises an authentic N-terminus if it comprises the N-terminus that was designed to be generated by the method of recombinant protein production described herein. The authentic N-terminus may be the N-terminus naturally occurring in the protein that is to be produced, or it may be designed artificially, i.e. an N-terminal sequence not naturally occurring in said protein. In a specific example, the P1' residue is the N-terminal amino acid of the POI and cleavage by the caspase described herein generates an authentic N-terminus.

Low cleavage efficiencies of substrates with sub-optimal P1' residues or recognition sites can be an issue for applications, in particular large-scale applications, where an authentic N-terminus of the product is desired. Specifically, the caspase described herein has such high activity and efficiency that substrates with all P1' residues are still cleaved within a reasonable time frame, even for large scale processes. Histidine, for example, is tolerated fifty times less than glycine, still the cp caspase-2 described herein is capable of cleaving 90% of a substrate comprising histidine at the P1' site at 25° C. within two hours. According to a further specific example, when the concentration of cp caspase-2 is increased, even 50% of a substrate with an isoleucine P1' residue can be cleaved within two hours.

According to a specific example, variants of caspase-2 comprising improved P1' tolerance of increased specificity for a predetermined recognition site as described herein can be produced by screening for cp caspase-2 variants capable of efficiently cleaving substrates comprising amino residues at their P1' site which are not well tolerated by cp caspase-2 such as for example branched (Thr, Leu, Val, Ile) and acidic (Asp, Glu) residues as well as Gln and Pro.

For example, a circularly permuted catalytic subunit of aspartate transcarbamoylase (cpATCase) which harbors its new N-terminus in a beta strand located in the interior of the protein is used for the selection of variants of the caspase described herein comprising desired characteristics such as for example increased P1' tolerance or different or improved recognition site specificity. The respective *E. coli* gene is named pyrB, the gene product of which forms a complex quaternary structure with the regulatory subunit pyrI in a stoichiometry of 3 regulatory subunit dimers and 2 catalytic subunit trimers. This cp enzyme is used to detect specific proteases via the growth of *E. coli*, because fusion of any stretch of amino acids towards this new N-terminus renders the enzyme inactive as it can no longer fold properly due to space limitations in the interior of the protein. However, if a protease is provided that can exactly cleave off this additional stretch of amino acids, the enzyme gets reactivated. As this is an essential enzyme of the pyrimidine synthesis in *E. coli*, it is possible to use this reactivation for applying a strong selection pressure. An *E. coli* mutant that lacks the original ATCase (e.g. by deleting pyrB and pyrI) and carries a plasmid encoding a cpATCase, e.g. cp-pyrB and pyrI provided on a single vector, that is inhibited by a N-terminal fusion sequence harboring a protease recognition site is provided. Thus the *E. coli* mutant becomes a pyrimidine auxotroph strain which can only survive in media supplemented with pyrimidines or when the cells are complemented with a vector encoding ATCase. The cpATCase can be activated by catalytic (in vivo) cleavage of the N-terminal fusion sequence. If a respective protease is provided via an additional plasmid, the *E. coli* can grow. Thereby, proteases can be selected that specifically recognize the recognition sites in the N-terminal fusion and/or that have increased tolerance for specific P1' residues, such as e.g. proline (P).

According to a specific embodiment, the caspase-2 or cp caspase-2 described herein comprises significantly improved specificity for a recognition site other than VDVAD (SEQ ID NO:45), compared to wild-type caspase-2.

The term “linker” as used herein refers to any amino acid sequence that does not interfere with the function of elements being linked. Linkers may connect e.g., nucleotide sequences, or amino acid sequences. Linkers can be used between the small and large subunit of cp caspase-2 or between caspase-2 or cp caspase-2 and N-terminal or C-terminal tags or between tag sequences. Linkers can also be used in the fusion protein described herein. The linkers may be used to engineer appropriate amounts of flexibility. Preferably, the linkers are short, e.g., 1-20 nucleotides or amino acids or even more and are typically flexible. Amino acid linkers commonly used consist of a number of glycine, serine, and optionally alanine, in any order. Such linkers usually have a length of at least any one of 1, 2, 3, 4, 5, 6, 7, 8, 9, 10, 11, 12, 13, 14, 15, or 20 amino acids, as required. Preferably, the linker comprises 1 to 12 amino acid residues, preferably it is a short linker. Preferably the linker is a GS, GGSGG (SEQ ID NO:278), GSAGSAAGSG (SEQ ID NO:279), $(GS)_n$, GSGSGSG (SEQ ID NO:280), GSG or GGGGS (SEQ ID NO:281) linker or any combination thereof. In some embodiments, the linker comprises one or more units, repeats or copies of a motif, such as for example GS, GSG or G4S (SEQ ID NO:281).

According to a specific embodiment, the caspase described herein and/or the fusion protein as described herein comprises one or more N-terminal and/or C-terminal tag sequences. Such tag sequence may comprise any number of amino acids of more than 2, 5 or 10 amino acids and up to 20, 50, 100, 200 or more amino acids. Specifically, tag sequences used herein may be any tag sequence known to the person skilled in the art. Specifically, tag sequences used herein are selected from affinity tags, solubility enhancement tags or monitoring tags. Specifically, any tag with any function known in the art can be fused to caspase2 or cp-caspase-2.

Affinity tags are amino acid sequences that can be used for example for the purification of proteins where they are attached to (fusion proteins with affinity tag e.g. at its N-terminus). These affinity tags have high affinity to appropriate ligands of a solid support, like chromatography resins or directly to the resins. By selectively binding of the fusion protein having the affinity tag to the particular resin the fusion protein and/or the caspase (caspase-2, cp cspase-2) can be purified highly effective by only one chromatography step. According to a specific embodiment, affinity tag sequences used herein are selected from histidine (His) tag, specifically a poly-histidine tag, arginine-tag, specifically a poly-arginine tag, peptide substrate for antibodies, chitin binding domain, RNAse S peptide, protein A, β-galactosidase, FLAG tag, Strep II tag, streptavidin-binding peptide (SBP) tag, calmodulin-binding peptide (CBP), glutathione S-transferase (GST), maltose-binding protein (MBP), S-tag, HA tag, or c-Myc tag or any other tag known to be useful for the efficient purification of a protein it is fused to. Preferably, the tag is a His tag comprising one or more H, specifically a hexahistidine (SEQ ID NO:315) tag. Specifically, fusion proteins comprising a poly-, or hexa-histidine tag (SEQ ID NO:315) (His-tag) can be captured and purified by IMAC, preferably using a Ni-NTA chromatography material.

Solubility enhancement tags can be fused C- or N-terminal to a POI and/or the caspase (caspase-2, cp cspase-2, wild-type or variant) described herein. Solubility enhancement tags can increase the titer of the soluble fusion protein and/or the caspase (caspase-2, cp cspase-2) when expressed in a host cell, e.g. a bacterial cell, e.g. *E. coli* significantly, e.g. in the cytosol of *E. coli*, compared to expression of the proteins without the tag. According to a further specific embodiment, solubility enhancement tag sequences used herein are selected from calmodulin-binding peptide (CBP), poly Arg, poly Lys, G B1 domain, protein D, Z domain of Staphylococcal protein A, and thioredoxin or any other tag known to improve the solubility of the protein it is fused to e.g. during expression in a host cell. Preferably the solubility tag is based on highly charged peptides of bacteriophage genes, for example such as those listed in U.S. Pat. No. 8,535,908 B2. Specifically, the solubility enhancement tag is selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T7AC T3, N1, N2, N3, N4, N5, N6, N7, calmodulin-binding peptide (CBP), poly Arg, poly Lys, G B1 domain, protein D, Z domain of Staphylococcal protein A, DsbA, DsbC and thioredoxin.

Preferably, the solubility enhancement tag is selected from the group consisting of T7A3 tag and T7AC tag. According to a specific example, the tag is a modified T7A3 tag, herein referred to as T7AC (SEQ ID No. 43). Preferably, one or more T7A3 (SEQ ID No. 37) and/or T7AC (SEQ ID No. 43) tags or functional variants thereof having 1-5 amino acid substitutions, additions, dilutions or the like, are used.

According to a further specific embodiment, the monitoring tag sequence used herein is m-Cherry, GFP or f-Actin or any other tag useful for detection or quantification of the caspase and/or the fusion protein during production of the caspase and/or the fusion protein including fermentation, isolation and purification by simple in-situ, inline online or atline detectors, like UV, IR, Raman, Fluorescence and the like.

The caspase described herein and the fusion protein described herein may comprise any number of tag sequences in any order and any combination. Specifically, the caspase described herein and the fusion protein described herein may comprise one or more tag sequences of the same functionality, for example more than one affinity tag, e.g. two or more T7AC tags, or of different functionality, e.g. a T7AC affinity tag and an m-Cherry monitoring tag. Specifically, the caspase or the fusion protein described herein may comprise an affinity tag, a solubility enhancement tag and a monitoring tag in any order, optionally separated by linker sequences. For example, the caspase or the fusion protein described herein may comprise an affinity tag and a solubility enhancement tag, wherein the affinity tag preferably is a hexahistidine (SEQ ID NO:315) tag and the solubility enhancement tag preferably is a T7AC tag. According to a further example, the tag sequences may be separated by a linker sequence as described herein and said linker sequence may optionally comprise a recognition site for specific cleavage by the caspase described herein.

The term "functional variant" or "functionally active variant" also includes naturally occurring allelic variants, as well as mutants or any other non-naturally occurring variants. As is known in the art, an allelic variant, or also referred to as homologue, is an alternate form of a nucleic acid or peptide that is characterized as having a substitution, deletion, or addition of one or more nucleotides or amino acids that does essentially not alter the biological function of the nucleic acid or polypeptide. Specifically, a functional variant may comprise a substitution, deletion and/or addition of 1, 2, 3, 4, 5, 6, 7, 8, 9, 10, 11, 12, 13, 14, 15, 16, 17, 18, 19 or 20 amino acid residues, or a combination thereof, which substitutions, deletions and/or additions are conservative modifications and do not alter the enzyme's function. Specifically, a functional variant as described herein comprises no more than or up to 1, 2, 3, 4, 5, 6, 7, 8, 9, 10, 11, 12, 13, 14, 15, 16, 17, 18, 19 or 20 amino acid substitutions, deletions and/or additions, which are conservative modifications and do not alter the enzyme's function. Specifically, a functionally active variant as described herein comprises up to 15, preferably up to 10 or 5, amino acid substitutions, deletions and/or additions, which are conservative modifications and do not alter the enzyme's function.

Specifically, a functionally active variant described herein comprises at least 5% or at least 10, 20, 30 or 40, 50, 60, 70, 80 or 90% or even more of the proteolytic activity of cp caspase-2 comprising SEQ ID No. 6 for the recognition site VDVAD (SEQ ID NO:45), wherein glycine (G) is in the P1' position. Specifically, functionally active variants described herein comprise at least 5%, 10%, 15%, 20%, 25%, 30%, 35%, 40%, 45%, 50%, 55%, 60%, 65%, 70%, 75%, 80%, 85%, or at least 90% or more of the proteolytic activity of cp caspase-2 comprising SEQ ID No. 6 for the recognition site VDVAD (SEQ ID NO:45) of the substrate VDVAD-E2 (SEQ ID No. 33). Specifically, the proteolytic activity is determined using a Förster resonance energy transfer (FRET) assay.

Functional variants may be obtained by sequence alterations in the polypeptide or the nucleotide sequence, e.g. by one or more point mutations, wherein the sequence alterations retain or improve a function of the unaltered polypeptide or the nucleotide sequence, when used in combination of the invention. Such sequence alterations can include, but are not limited to, (conservative) substitutions, additions, deletions, mutations and insertions. Conservative substitutions are those that take place within a family of amino acids that are related in their side chains and chemical properties.

Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

The term "sequence identity" as used herein is understood as the relatedness between two amino acid sequences or between two nucleotide sequences and described by the degree of sequence identity or sequence complementarity. The sequence identity of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or polynucleotides by detecting excess similarity, and statistically significant similarity that reflects common ancestry. Homologues may encompass orthologues, which are herein understood as the same protein in different organisms, e.g., variants of such protein in different organisms or species.

To determine the % complementarity of two complementary sequences, one of the two sequences needs to be converted to its complementary sequence before the % complementarity can then be calculated as the % identity between the first sequence and the second converted sequences using the above-mentioned algorithm.

"Percent (%) identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences can be determined using NCBI BLAST, specifically NCBI BLAST+2.9.0 program version (Apr-02-2019).

"Percent (%) identity" with respect to a nucleotide sequence e.g., of a nucleic acid molecule or a part thereof, in particular a coding DNA sequence, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software.

Those skilled in the art can determine appropriate parameters for measuring alignment, including any algorithms needed to achieve maximal alignment over the full length of the sequences being compared.

Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomies.org.cn), and Maq (available at maq.sourceforge.net).

According to a specific embodiment, the caspase provided herein is used for the production of a mature and/or functional protein or polypeptide of interest. Specifically described herein is a process for the production of a mature protein or polypeptide by producing it as a fusion protein comprising an N-terminal fusion sequence, wherein the fusion sequence comprises an engineered recognition site specifically recognized by the caspase described herein and wherein upon proteolytic cleavage by the caspase a mature and/or functional protein of interest is released.

Fusion protein strategies for enhancing expression level, improving solubility and facilitating purification of a protein of interest have been around since 1983 and before. However, these strategies are not used widely and adaptation of a fusion protein strategy for large-scale process development is difficult in regard of the specificity, activity, availability and purity of the protease enzyme used. The specificity needs to be high enough to at least allow a number of proteins to be cleaved only at the engineered cleavage site in the connecting linker sequence. The activity of the enzyme needs to be high enough to allow sufficient cleavage in a short period of time. This avoids hold-up time during the production and minimizes degradation of the protein of interest during incubation. The protease needs to be available at low cost, so an efficient expression system and a low-cost production method are necessary. The protease should also be sufficiently pure, especially free of even trace contamination of non-specific proteases from the host organism. No protease will fit these requirements for all possible proteins of interest, therefore an easy and effective way of adapting proteases to different POIs is necessary.

Specifically described herein is a method for producing a POI having a predetermined N-terminal amino acid residue, comprising: expressing the POI in a host cell as a fusion protein, wherein the N-terminus of the POI is fused to fusion sequence comprising a caspase recognition site, the fusion protein being specifically cleavable by the cp caspase-2 described herein at the junction of the linker with the N-terminal amino acid residue of the POI. Specifically, the host cell does not express an endogenous functional protease capable of cleaving the fusion protein at the recognition site. According to the method specifically described herein the fusion protein is isolated from the host cell and the fusion protein is contacted with an extract containing the cp caspase-2 described herein which cleaves the fusion protein exactly at the junction of the linker and the N-terminal amino acid residue of the POI, thereby producing a mature POI. Specifically, said extract comprising the caspase is derived from cells which produce said caspase by recombinant DNA methods.

With regard to the protein or polypeptide of interest (POI) there are no limitations. More specifically, the protein may either be a polypeptide not naturally occurring in the host cell, i.e. a heterologous protein, or else may be native to the host cell, i.e. a homologous protein to the host cell, but is produced, for example, upon integration by recombinant techniques of one or more copies of the nucleic acid sequence encoding the homologous POI into the genome or chromosome of the host cell, or by recombinant modification of the promoter sequence controlling the expression of the gene encoding the POI. According to a further example, the POI can also be expressed in a host using a vector, more specifically a plasmid. The POI can be a monomer, dimer or multimer, it can be a homomer or heteromer. Examples for proteins that can be produced by the method of the invention are, without limitation, enzymes, regulatory proteins, receptors, growth factors, hormones, peptides, e.g. peptide hormones, cytokines, membrane or transport proteins. The POIs may also be antigens as used for vaccination, vaccines, antigen-binding proteins, immune stimulatory proteins, interleukins, interferons, allergens, full-length antibodies or antibody fragments or derivatives or affinity scaffolds. Antibody derivatives may be for example, but not limited to single chain variable fragments (scFv), Fab fragments or single domain antibodies or camelid antibodies or heavy chain antibodies or derivatives thereof such as $V_{HH}$ fragments or the like.

As used herein the term "fusion protein" refers to a POI comprising at its N- or C-terminus an engineered fusion sequence comprising a caspase recognition site as described herein. Specifically, the fusion sequence described herein comprises at least one caspase recognition site, one or more tag sequences as described herein and optionally one or more linker sequences as described herein. According to a specific example, the fusion protein comprises one or more tag sequences, optionally linked via linker sequences, one or more caspase recognition sites and one or more POIs.

According to a specific embodiment, the fusion protein provided herein comprises a first part, comprising one or more tag sequences optionally linked via linker sequences, a second part, comprising a recognition site for target-specific proteolytic cleavage using the cp caspase-2 described herein and a third part, comprising a POI. Specifically, the fusion protein described herein may comprise each part more than once and in different order. For example, the fusion protein provided herein may comprise a first part comprising a tag sequence, a second part comprising a caspase recognition site, another first part comprising the same or a different tag sequence, another second part comprising the same or a different recognition site and a third part comprising a POI. According to a further example, the fusion protein described herein may comprise more than one POI separated by one or more fusion sequences comprising one or more recognition sites.

The cp caspase-2 or caspase-2 itself as described herein can be part of a fusion protein as the POI or part of the fusion sequence to e.g. facilitate production of the capase itself.

The fusion protein described herein is encoded by a heterologous gene which is engineered in such a way that it is translated into protein by a host organism. As a host organism, any living cell or organism applies. Living cells or organisms can be of prokaryotic or eukaryotic nature. Common cells that serve as hosts for expression of recombinant genes are e.g. *Escherichia coli, Bacillus species, Streptomyces* species, Yeast strains such as *Saccharomyces, Schizosaccharomyces, Pichia, Kluyveromcyes* or *Hansenula* strains, insect cells, mammalian cell lines, plant cells. Expression hosts can also be at the level of a multicellular organism such as transgenic plants, sheep, goat, cow, chicken and rabbit, whereby the product can be isolated either from organs or from body fluids such as milk, blood or eggs. Alternatively, the gene can be translated into protein using cell free translation systems, possibly coupled to an in vitro transcription system. These systems provide all steps necessary to obtain protein from DNA by supplying the necessary enzymes and substrates in an in vitro reaction. In principle, any living cell or organism can provide the necessary enzymes for this process and extraction protocols for obtaining such enzyme systems are known in the art. Common systems used for in vitro transcription/translation are extracts or lysates from reticulocytes, wheat germ or *Escherichia coli.*

According to a specific embodiment, the fusion protein is isolated and purified before cleavage with the cp caspase-2 described herein. The physicochemical features of the fusion sequence, comprising one or more tag sequences, can be used for uniform, streamlined and highly specific purification of the fusion protein. The characteristics of the fusion sequence towards adsorption chromatographic medium, or specific affinity purification methods should be considered. For example, tag sequences can be included that increase the binding to ion exchange columns (e.g. poly-arginine), hydrophobic interaction columns (e.g. poly-phenylalanine), or immobilized metal chelating chromatography (e.g. poly-histidine). Other non-limiting examples are fusion protein or domains that have an affinity for a substrate or ligand e.g. maltose binding protein MBP, glutathione S transferase GST, protein A, biotinylated peptides or domains, chitin binding domains CBD. Further non-limiting examples are the use of tag sequences that increase solubility at higher temperatures (e.g. thioredoxin), or will reversibly precipitate at certain conditions. A purification scheme based on the properties of the fusion sequence will most probably be applicable to the complete fusion protein. A combination of such specific purification methods can be used if the fusion sequence comprises different tag sequences with different functionalities, or when they show a different selective behavior on different chromatography media.

According to a specific embodiment the number of steps needed in the maturation of the fusion protein, subsequent removal of the enzyme and removal of the fusion sequence cut from the fusion protein can be reduced. If an affinity tag is incorporated in the fusion sequence, the same affinity tag can be fused, e.g. by recombinant DNA technology, to the caspase. Using this strategy, the fusion protein can be captured on a solid support, for example a chromatographic column, and then incubated with the cp caspase-2 described herein fused to an affinity tag that shows affinity for the same solid support. After an appropriate incubation time, the liquid phase of the reaction vessel will contain the protein of interest, while both the fusion part and the enzyme are adsorbed on the solid phase.

According to a further specific embodiment, cleavage of the fusion protein is induced in vivo. Cleavage in the cell has the advantage that no post-productional processing is needed. However, the advantage of a specific affinity purification based on the properties of the fusion part is lost in this case. Specifically, two alternative strategies can be applied. First, the caspase may be induced at the same time as the fusion protein, e.g. using an expression cassette comprising both the caspase and the fusion protein, or by engineering a fusion protein including the caspase as part of the fusion protein, or by using expression vectors comprising the caspase and the fusion protein under separate promoters which are induced at the same time. The latter can be realized by using the same promoter in two transcriptional cassettes, or by using two promoters that are induced with the same inducer (e.g. IPTG/lactose), or by using two promoters, that are inducible with different agents, whereby both agents are added at the same time. Alternatively, the caspase enzyme can be induced at a different time point than the onset of production of the fusion protein. The caspase can be produced before or more preferably after the production onset of the fusion protein. In the latter case, the protein of interest will more likely fold to a soluble, active protein.

The terms "mature form" or "mature protein" of interest refer to the polypeptide of interest in its desired form, without pre-peptides, leader sequences or fusion sequences. Preferably, in its mature form the protein is starting with the amino terminal amino acid or ending with the carboxy terminal amino acid of the POI occurring under its biological active or functional form. Specifically, the mature protein comprises an authentic N- or C-terminus, which is the desired N- or C-terminus.

Further provided herein is a method of producing a cp caspase-2 or a fusion protein as described herein. The cp caspase-2 produced according to the method described herein may comprise SEQ ID No. 6 or comprises amino acid substitutions with reference to SEQ ID No. 6. Specifically, said cp caspase-2 may be derived from wild type caspase-2.

Specifically, the fusion protein comprises a POI, which may be a caspase-2 as described herein, and a protein tag as described herein. Use of the protein tag as described herein significantly increases expression of the fusion protein and improves production of the POI.

Specifically, the method of producing a cp caspase-2 described herein, allows more efficient production of the caspase and the caspase produced according to said method comprises improved characteristics, such as e.g. improved P1' tolerance or improved target specificity.

According to a specific example, but not limited thereto, wild-type or variant caspase-2 or cp caspase-2 or a fusion protein as described herein is produced in a fermentation process comprising 2 phases. Specifically, the 2 phases comprise:

i. Biomass production: For biomass production to a certain concentration of biomass, the first fed-batch phase can be performed with an exponential feed (exponential substrate feed) at a specific growth rate (p) of 0.05-0.5 $h^{-1}$ or 0.05-0.4 $h^{-1}$ preferably at a p of 0.07-0.3 $h^{-1}$ or 0.1-0.3 $h^{-1}$ or 0.1-0.2 $h^{-1}$, even more preferably at a p of 0.10, 0.11, 0.12, 0.13, 0.14, 0.15, 0.16, 0.17, 0.18, 0.19 or 0.20 $h^{-1}$. preferably about 0.13-0.21 $h^{-1}$, even more preferably about 0.16-0.18 $h^{-1}$ and most preferably it is about 0.17 $h^{-1}$ Also, any other feed mode appropriate for the formation of a certain amount of biomass can be applied, such as but not limited to step-feed, linear increasing feed, or constant feed. The substrate feed can be controlled by increasing pump speed according to the exponential growth algorithm, X=X0*eμt, with superimposed feedback control of weight loss in the substrate tank. Specifically, the substrate feed comprises glucose or glycerin or any other carbon-source and optionally comprises $Ca^{2+}$, $Mg^{2+}$ and/or trace elements. In a preferred embodiment, the first fed-batch phase was performed for 0.5-2.5 generations, more preferred for 0.7-2.3 generations.

ii. In a second feed-phase with an exponential feed (exponential substrate feed) at a specific growth rate (μ) a lower growth rate, a μ of 0.01-0.1 $h^{-1}$ or 0.01-0.07 $h^{-1}$, preferably a p of 0.01-0.03 $h^{-1}$ or 0.01-0.05 $h^{-1}$ or 0.02-0.05 $h^{-1}$ or 0.03-0.05 $h^{-1}$ or 0.03-0.07 $h^{-1}$0.05-0.07 $h^{-1}$, and even more preferably a μ of about 0.03, 0.05 or 0.07 $h^{-1}$, can be applied. For adaption to the low growth conditions, the cells can initially be grown at the low μ without induction, e.g. for about 0.10, 0.15, 0.20, 0.25, 0.30, 0.35, 0.40, 0.45 or 0.50 generations. Subsequently an inducer, e.g. IPTG for the T7 promoter/operator system can be added. Isopropyl β-d-1-thiogalactopyranoside (IPTG) is a molecular biology reagent. This compound is a molecular mimic of allolactose, a lactose metabolite that triggers transcription of the lac operon, and is used to induce protein expression where the gene is under the control of the lac operator. Induction can be done with different or varying IPTG concentrations ranging from 0.01-1.5 or 0.1-1.5 μmol/g CDM (cell dry mass) more preferably 0.1-1.3 or 0.2-1.3 or 0.3-1.3 or 0.5-1.3 μmol/g CDM even more preferably ranging from about 0.5-0.9 μmol/g CDM or about 0.9-1.3 μmol/g actual CDM, preferably it is about 0.5, 0.9 or about 1.3 μmol/g CDM. for one or two or even more generations. Specifically, the fed-batch phases are performed at 30° C.

Thus, induction can be performed as follows: Induction starts with fed-batch phase by adding feed medium including IPTG (so called "over feed" induction, table 20) to achieve a final IPTG concentration as described above in μmol IPTG/g theoretical CDM at the end of the fermentation.

In another embodiment IPTG corresponding to the CDM at induction time (μmol/g DCM), can be injected into the reactor and then IPTG calculated to the actual CDM can be fed into the fermenter within the feed medium. To that end the needed IPTG can be transferred into the feed bottle calculated to the IPTG needed until the theoretical CDM at the end of fermentation. Thus, the IPTG concentration related to the theoretical CDM is constant throughout the whole fermentation.

The produced caspase or fusion protein can be isolated by cell disintegration e.g. by high pressure homogenization, centrifugation of the cell debris, concentration of the supernatant by tangential flow micro-filtration or the like. Further purification can be done by chromatography, such as ion exchange chromatography, hydrophobic interaction chromatography, size exclusion chromatography, isoelectric focusing, mixed mode chromatography reversed phase high performance chromatography, tangential flow microfiltration, depth filtration, ammonium sulphate, -cloride, -citrate precipitation heat precipitation, solubilization, crystallization, centrifugation or the like. Specifically, when the cp caspase-2 comprises an affinity tag, it can be purified highly effectively by only one chromatography step, which is an affinity chromatography step. Preferably, the affinity tag is a 6His (SEQ ID NO:315) tag and the affinity chromatography is an IMAC, more specifically a Ni-NTA chromatography.

Specifically, using said method the cp caspase-2 with or without tags and/or linkers as described herein can be produced. Specifically, the cp caspase-2 produced according to the method described herein comprises significantly improved specificity for the recognition site VDVAD (SEQ ID No. 45) compared to wild-type caspase-2. Specifically, a cp caspase-2 comprising the exemplary amino acid sequence of SEQ ID No. 6, SEQ ID No. 9, SEQ ID No. 13, SEQ ID No. 35, SEQ ID No. 39 or SEQ ID No. 41 recognizes and cleaves substrates comprising the recognition site VDVAD (SEQ ID NO:45) with significantly improved specificity compared to wild-type caspase-2. Such increased specificity has the distinct advantage that it leads to a significant reduction of off-target effects and avoids proteolytic cleavage of the target substrate or other proteins within the host at sites other than the recognition site. Specifically, the cp caspase-2 described herein is at least 2 times, preferably at least 3 times, more specific for the recognition site VDVAD (SEQ ID NO:45) than wild-type caspase-2.

Further provided herein is a method of producing a POI using the protein tag described herein. Specifically, the POI is fused to the protein tag and cloned into an expression vector under operable linkage to a promoter, which may be an inducible promoter. Said expression vector is integrated into a host cell and the host cell is cultured under conditions allowing expression of the fusion protein, optionally following a growth phase for the accumulation of biomass before the recombinant protein is expressed. The POI may be produced employing a fed-batch process as described herein, comprising an expression phase as described herein and optionally a growth phase as described herein.

According to a specific embodiment of the method of producing a POI as described herein, the fusion protein is contacted with a caspase-2 or cp caspase-2 as described herein after expression, to produce a POI comprising the desired N-terminus, i.e. the natural or designed N-terminus without any unwanted tags attached. Specifically, the fusion protein is contacted with the caspase enzyme after isolation of the fusion protein from the host cell culture.

After production of the POI according to the method described herein, the POI may be further modified, purified and/or formulated.

The methods described herein specifically refer to the production of heterologous compounds. Such term used with respect to a nucleotide or amino acid sequence or protein, refers to a compound which is either foreign, i.e. “exogenous”, such as not found in nature, to a given host cell; or that is naturally found in a given host cell, e.g., is “endogenous”, however, in the context of a heterologous construct, e.g., employing a heterologous nucleic acid, thus “not naturally-occurring”. The heterologous nucleotide sequence as found endogenously may also be produced in an unnatural, e.g., greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature (i.e., “not natively associated”). Any recombinant or artificial nucleotide sequence is understood to be heterologous.

As used herein the term “host cell” refers to one or more cells which can be used in the methods described herein. Typically, the term refers to viable cells, capable of growing in a cell culture, into which a heterologous nucleic acid sequence or amino acid sequence is introduced. Specifically, the host cells are selected from the group consisting of bacterial cells, yeast cells, insect cells, mammalian cells and plant cells. Mammalian cells used in accordance with the present disclosure typically are human or rodent cells, such as mouse, rat or hamster cells, such as for example Chinese Hamster Ovary (CHO) cells. Preferably the host cells are bacterial or yeast cells selected from the group consisting of *E. coli, Pseudomonas* sp., *Bacillus* sp., *Streptomyces* sp., *Saccharomyces* sp., *Schizosaccharomyces* sp., *Pichia* sp., *Kluyveromyces* sp. and *Hansenula* sp.

The term “expression” is understood in the following way. Nucleic acid molecules containing a desired coding sequence of an expression product such as e.g., a fusion protein as described herein or a cp caspase-2 as described herein may be used for expression purposes. Hosts transformed or transfected with these sequences are capable of producing the encoded proteins. In order to effect transformation, the expression system may be included in a vector; however, the relevant DNA may also be integrated into the host chromosome. Specifically, the term refers to a host cell and compatible vector under suitable conditions, e.g., for the expression of a protein coded for by foreign DNA carried by the vector and introduced to the host cell.

Coding DNA is a DNA sequence that encodes a particular amino acid sequence for a particular polypeptide or protein. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors often include one or more replication systems for cloning or expression, one or more markers for selection in the host, e.g., antibiotic resistance, one or more nuclear localization signals (NLS) and one or more expression cassettes.

“Expression vectors” or “vectors” as used herein are defined as DNA sequences that are required for the transcription of cloned recombinant nucleotide sequences, i.e. of recombinant genes and the translation of their mRNA in a suitable host organism. To obtain expression, a sequence encoding a desired expression product, such as e.g. the fusion protein described herein or the cp caspase-2 described herein, is typically cloned into an expression vector that contains a promoter to direct transcription. Suitable bacterial and eukaryotic promoters are well known in the art. The promoter used to direct expression of a nucleic acid depends on the particular application. For example, a strong constitutive promoter is typically used for expression and purification of fusion proteins. In contrast, when the expression product is to be administered in vivo for gene regulation, either a constitutive or an inducible promoter can be used, depending on the particular use of the expression product. In addition, a preferred promoter for administration can be a weak promoter. The promoter can also include elements that are responsive to transactivation, e.g., hypoxia response elements, Gal4 response elements and lac repressor response elements. Expression vectors comprise the expression cassette and additionally usually comprise an origin for autonomous replication in the host cells or a genome integration site, one or more selectable markers (e.g., an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together.

An “expression cassette” refers to a DNA coding sequence or segment of DNA coding for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a “DNA construct”.

The term “vector” as used herein includes autonomously replicating nucleotide sequences as well as genome integrating nucleotide sequences. A common type of vector is a “plasmid”, which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g., a foreign gene) can be introduced into a host cell, so as to transform the host and promote expression (e.g., transcription and translation) of the introduced sequence.

Expression products, such as the caspase-2 or cp caspase-2 described herein, can be expressed from an autonomously replicating nucleotide sequence, or from nucleotide sequences stably integrated into the genome of a host cell.

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al.).

According to specific embodiments, the fusion protein or the cp caspase-2 described herein are expressed as inclusion body. Methods for the purification of recombinant proteins expressed as inclusion bodies are well known in the art. Typically, 70 to 80% of recombinant proteins expressed in bacteria, such as e.g. *E. coli*, are contained in inclusion bodies. Specifically, the purification of the expressed proteins from the inclusion bodies requires two main steps: extraction of inclusion bodies from the bacteria, for example via cell lysis followed by affinity purification, followed by solubilization and optionally refolding of the purified inclusion bodies.

Further described herein is a pharmaceutical composition comprising the cp caspase-2 or caspase-2 provided herein. According to a specific embodiment, such pharmaceutical composition comprising the cp caspase-2 or its variants as described herein is used for the treatment of for example cancer, Alzheimer's disease, Parkinson's disease or inflammatory disease. Specifically, the pharmaceutical composition described herein further comprises pharmaceutically acceptable carriers or excipients, such as for example bulking agents, when used for diagnosis or therapy. These pharmaceutical compositions can be administered in accordance with the present invention as a bolus injection or infusion or by continuous infusion. Pharmaceutical carriers suitable for facilitating such means of administration are well-known in the art.

Pharmaceutically acceptable carriers generally include any and all suitable solvents, dispersion media, coatings, isotonic and absorption delaying agents, and the like that are physiologically compatible with a caspase provided by the invention. Further examples of pharmaceutically acceptable carriers include sterile water, saline, phosphate buffered saline, dextrose, glycerol, ethanol, and the like, as well as combinations of any thereof.

Additional pharmaceutically acceptable carriers are known in the art and described in, e.g., Remington's Pharmaceutical Sciences (Gennaro, AR, ed., Mack Publishing Co, 1985). Liquid formulations can be solutions, emulsions or suspensions and can include excipients such as suspending agents, solubilizers, surfactants, preservatives, and chelating agents.

Exemplary formulations as used for parenteral administration include those suitable for subcutaneous, intramuscular or intravenous injection as, for example, a solution, emulsion or suspension.

The caspase-2 or cp caspase-2 described herein is specifically administered at a therapeutically effective amount, meaning a quantity or activity sufficient to effect beneficial or desired results, including clinical results, when administered to a subject, e.g. a patient suffering from cancer. As such, an effective amount or synonymous quantity thereof depends upon the context in which it is being applied. An effective amount is intended to mean that amount of a compound that is sufficient to treat, prevent or inhibit such diseases or disorders.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The caspase-2, variants and dimers thereof described herein are particularly provided in the isolated form, which are substantially pure, meaning free of other proteins or enzymes. Still, such isolated enzyme may be comprised in a combination preparation, containing a combination of the isolated cp caspase-2, e.g., with at least one other enzyme or protein or antibody, such as monoclonal antibodies or antibody fragments. The term "substantially pure" or "purified" as used herein shall refer to a preparation comprising at least 50% (w/w), preferably at least 60%, 70%, 80%, 90%, or 95% of a compound, such as a caspase or a POI. Purity is measured by methods appropriate for the compound (e.g., chromatographic methods, polyacrylamide gel electrophoresis, HPLC analysis, and the like).

The following items are particular embodiments described herein.

1. A single-chain circular permuted caspase-2 (cp caspase-2) comprising the following structure from N- to C-terminus:
   i. a small subunit of a caspase-2, or a functionally active variant thereof, and
   ii. a large subunit of a caspase-2, or a functionally active variant thereof, wherein said cp caspase-2 comprises one or more amino acid substitutions increasing P1' tolerance of said cp caspase-2 compared to a cp caspase-2 without said amino acid substitutions.
2. The cp caspase-2 of item 1 comprising one or more amino acid substitutions at positions 171, 105, 172, 282, 225, 83, 185, 255, or 285 of SEQ ID No. 6 or at a position functionally equivalent to any of positions 171, 105, 172, 282, 225, 83, 185, 255, or 285 of SEQ ID No. 6 or any combination thereof.
3. The cp caspase-2 of item 1 or 2, comprising a propeptide of a small caspase-2 subunit (SS propeptide), fused to the N-terminus of the small subunit.
4. The cp caspase-2 of item 3, wherein the SS propeptide comprises one or more amino acid substitutions at the C-terminus of the SS propeptide.
5. The cp caspase-2 of item 3 or 4, wherein the SS propeptide comprises an amino acid substitution at position $Asp^{14}$ of SEQ ID No. 2 or at a position functionally equivalent to $Asp^{347}$ of SEQ ID No. 11, specifically Asp is substituted to Ala.

6. The cp caspase-2 of any one of items 1 to 5, further comprising one or more linker sequences, specifically consisting of 1, 2, 3, 4, 5, 6, 7, 8, 9, 10, 11 or 12 amino acid residues.
7. The cp caspase-2 of item 6, wherein the linker sequence comprises glycine and/or serine residues, more specifically the linker is GS, GGSGG (SEQ ID NO:278), GSAGSAAGSG (SEQ ID NO:280), $(GS)_n$, GSG or G4S (SEQ ID NO:281).
8. The cp caspase-2 of items 6 or 7, wherein the linker sequence is a subunit-linker sequence between the small subunit and the large subunit.
9. The cp caspase-2 of any one of items 1 to 8, comprising one or more C-terminal or N-terminal tags, specifically selected from the group consisting of affinity tags, solubility enhancement tags and monitoring tags.
10. The cp caspase-2 of item 9, wherein the affinity tag is selected from the group consisting of poly-histidine tag, poly-arginine tag, peptide substrate for antibodies, chitin binding domain, RNAse S peptide, protein A, β-galactosidase, FLAG tag, Strep II tag, streptavidin-binding peptide (SBP) tag, calmodulin-binding peptide (CBP), glutathione S-transferase (GST), maltose-binding protein (MBP), S-tag, HA tag, c-Myc tag, SUMO tag, *E. coli* thioredoxin, NusA, chitin binding domain CBD, chloramphenicol acetyl transferase CAT, LysRS, ubiquitin, calmodulin, and lambda gpV, specifically the tag is a His tag comprising one or more His, more specifically it is a hexahistidine (SEQ ID NO:315) tag.
11. The cp caspase-2 of item 9, wherein the solubility enhancement tag is selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T3, N1, N2, N3, N4, N5, N6, N7, T7AC, calmodulin-binding peptide (CBP), DsbA, DsbC, poly Arg, poly Lys, G B1 domain, protein D, Z domain of Staphylococcal protein A, and thioredoxin.
12. The cp caspase-2 of item 9, wherein the monitoring tag is selected from the group consisting of m-Cherry, GFP and f-Actin.
13. The cp caspase-2 of any one of items 9 to 12, comprising more than one tags, specifically comprising an affinity tag and a solubility enhancement tag.
14. The cp caspase-2 of item 13, wherein the affinity tag is a hexahistidine (SEQ ID NO:315) tag and the solubility enhancement tag is a T7AC or a T7A3 tag.
15. The cp caspase-2 of any one of items 6 to 14, wherein the linker sequence is a tag-linker sequence, linking two tags or linking a tag and the small subunit, the large subunit or the SS propeptide of the cp caspase-2.
16. The cp caspase-2 of any one of items 1 to 15, comprising one or more N-terminal tags and optionally one or more tag-linker sequences between the tags or between a tag and the N-terminus of the small subunit or the SS propeptide.
17. The cp caspase-2 of any one of items 1 to 16, comprising one or more C-terminal tags and optionally one or more tag-linker sequences, which are linker sequences between the tags or between a tag and the C-terminus of the large subunit.
18. A functionally active variant of the cp caspase-2 of any one of items 1-17, wherein
   i. the small subunit of a caspase-2 comprises
      a) a first conserved region of the active center with at least 37.5% amino acid sequence identity to SEQ ID No. 177 (1st consensus: AAMRNTKR) or 100% sequence identity to XXXRNTXX (SEQ ID No. 200), wherein X is any amino acid,
      b) a second conserved region of the active center with at least 61.5% amino acid sequence identity to SEQ ID No. 178 (2nd consensus: EGYAPGTEFHRCK) or 100% sequence identity to EGXXPGXXXHRCK (SEQ ID No. 194), wherein X is any amino acid, and
   ii. the large subunit of a caspase-2 comprises
      a) a third conserved region of the active center with at least 25.0% amino acid sequence identity to SEQ ID No. 174 (3rd consensus: G-EKDLEFRSGGDVDH) or 100% sequence identity to X-XXXLXXRXGXXXDX (SEQ ID No. 195), wherein X is any amino acid,
      b) a fourth conserved region of the active center with at least 53.3% amino acid sequence identity to SEQ ID No. 175 (4th consensus: LLSHGVEGGXYGVDG) or 100% sequence identity to XXSHGXXGXX-YGXDG (SEQ ID No. 196), wherein X is any amino acid, and
      c) a fifth conserved region of the active center with at least 50.0% amino acid sequence identity to SEQ ID No. 176 (5th consensus: QACRGDET) or 100% sequence identity to QACXGXXX (SEQ ID No. 197), wherein X is any amino acid.
19. A functionally active variant of the cp caspase-2, comprising at least 70, 75, 80, 85, 90, 91, 92, 93, 94, 95, 96, 97 or 98% sequence identity to the cp caspase-2 of any one of items 1 to 18.
20. The functionally active variant of item 19, comprising at least 70, 75, 80, 85, 90, 91, 92, 93, 94, 95, 96, 97 or 98% sequence identity to SEQ ID No. 9, 6, 14, 15, 16, 80, 88, 25, 26, 27, 28, 29, 30, 35, 39, 41, 64, 66, 68, 73, 74, 75, 76, 77, 81, 82, 83, 84, or 85.
21. The cp caspase-2 of any one of items 1 to 20, wherein the
   i. small subunit is selected from the group consisting of SEQ ID No. 3, SEQ ID No. 91, SEQ ID No. 94, SEQ ID No. 97, SEQ ID No. 100, SEQ ID No. 103, SEQ ID No. 106, SEQ ID No. 109, SEQ ID No. 112, SEQ ID No. 115, SEQ ID No. 118 or functionally active variants thereof having at least 70, 75, 80, 85, 90, 91, 92, 93, 94, 95, 96, 97 or 98% sequence identity, and/or
   ii. the large subunit is selected from the group consisting of SEQ ID No. 4, SEQ ID No. 90, SEQ ID No. 93, SEQ ID No. 96, SEQ ID No. 99, SEQ ID No. 102, SEQ ID No. 105, SEQ ID No. 108, SEQ ID No. 111, SEQ ID No. 114, SEQ ID No. 117, or functionally active variants thereof having at least 70, 75, 80, 85, 90, 91, 92, 93, 94, 95, 96, 97 or 98% sequence identity.
22. The cp caspase-2 of any one of items 1 to 21, comprising
   i. an N-terminal and/or C-terminal truncation, and/or
   ii. an N-terminal and/or C-terminal extension.
23. The cp caspase-2 of any one of items 1 to 22, comprising one or more amino acid substitutions, selected from
   i. $Gly^{171}$, substituted with D, or an amino acid selected from the group consisting of R, K, E, Q, N, A, S, T, P, H, Y
   ii. $Glu^{105}$, substituted with V, or an amino acid selected from the group consisting of C, L, I, M, F, W, R, K, D, Q, N iii. $Glu^{172}$, substituted with V, or an amino acid selected from the group consisting of C, L, I, M, F, W, R, K, D, Q, N
iv. $Asp^{282}$, substituted with E, or T, or an amino acid selected from the group consisting of R, K, Q, N, G, A, S, P, H, Y
v. $Val^{225}$, substituted with G, or an amino acid selected from the group consisting of A, S, T, P, H, Y, C, L, I, M, F, W
vi. $Lys^{83}$, substituted with E, or an amino acid selected from the group consisting of R, D, Q, N,
vii. $His^{185}$, substituted with A, or an amino acid selected from the group consisting of G, S, T, P, Y,
viii. $Val^{255}$, substituted with M, or an amino acid selected from the group consisting of C, L, I, F, W, and/or
ix. $Asp^{285}$, substituted with E, or Y, or an amino acid selected from the group consisting of R, K, Q, N, G, A, S, T, P, H, with reference to the positions of SEQ ID No. 6, or positions functionally equivalent to positions of SEQ ID No. 6.

24. The cp caspase-2 of any one of items 1 to 22 comprising amino acid substitutions at positions of SEQ ID No. 6, or at positions functionally equivalent to positions of SEQ ID No. 6, selected from the group consisting of
i. $His^{185}$ and $Asp^{282}$, specifically comprising H185A and D282T substitutions;
ii. $Glu^{105}$ and $Asp^{285}$, specifically comprising E105V and D285E substitutions;
iii. $Glu^{105}$, $Gly^{171}$, $Val^{225}$ and $Asp^{282}$, specifically comprising E105V, G171D, V225G and D282E substitutions;
iv. $Glu^{105}$, $Gly^{171}$, $Val^{225}$, $Asp^{282}$ and $Asp^{285}$, specifically comprising E105V, G171 D, V225G, D282E and D285E substitutions;
v. $Lys^{83}$, $Glu^{105}$, $Glu^{172}$, $Val^{255}$ and $Asp^{285}$, specifically comprising K83E, E105V, E172V, V255M and D285Y substitutions:
vi. $Glu^{105}$ and $Gly^{171}$, specifically comprising E105V and G171D substitutions;
vii. $Glu^{105}$ and $Glu^{172}$, specifically comprising E105V and E172V substitutions; and
viii. $Gly^{171}$ and $Glu^{172}$, specifically comprising G171D and E172V substitutions, wherein said cp caspase-2 has increased P1' tolerance compared to a cp caspase-2 without the respective amino acid substitution, optionally wherein said cp caspase-2 comprises an SS propeptide comprising an amino acid substitution to Ala at position $Asp^{14}$ of SEQ ID No. 2 or at a position functionally equivalent to position $Asp^{347}$ of SEQ ID No. 11.

25. The cp caspase-2 of any one of items 1 to 22, comprising SEQ ID No. 6 and one or more amino acid substitutions at position 171, 105, 172, 282, 225, 83, 185, 255, or 285 of SEQ ID No. 6 or at a position functionally equivalent to position 171, 105, 172, 282, 225, 83, 185, 255, or 285 of SEQ ID No. 6, or any combination thereof.

26. The cp caspase-2 of item 25, comprising any one or more of amino acid substitutions G171D, E105V, E172V, D282E, D282T, V225G, K83E, H185A, V255M, D285Y and D285E.

27. The cp caspase-2 of any one of items 1 to 26, comprising an amino acid sequence selected from the group consisting of SEQ ID No. 1, 13, 17, 18, 23, 24, 51, 52, 54, 70, 71, 72, 78, 79, 86, 87, 179, 180, 181, 182, 183, 184, 185, 186, 187, 188, 189 190, 191 and 192 or an amino acid sequence having at least 70%, 75%, 80%, 85%, 90%, specifically at least 95%, specifically at least 99% sequence identity with any one of SEQ ID No. 1, 13, 17, 18, 23, 24, 51, 52, 54, 70, 71, 72, 78, 79, 86, 87, 179, 180, 181, 182, 183, 184, 185, 186, 187, 188, 189, 190, 191 and 192.

28. The cp caspase-2 of any one of items 1 to 27, comprising a C-terminal tag and an amino acid substitution at positions 285 and 292 of SEQ ID No. 6 or at a position functionally equivalent to positions 285 and 292 of SEQ ID No. 6, specifically comprising substitutions to Glu and Ser (D285E and D292S).

29. The cp caspase-2 of any one of items 1 to 28, wherein said cp caspase-2 is recruited by a recognition site for proteolytic cleavage, comprising 5 amino acids of the sequence P5 P4 P3 P2 P1, wherein
P1 can be any amino acid, preferably it is D or E,
P2 can be any amino acid, preferably it is A,
P3 can be any amino acid, preferably it is V,
P4 can be any amino acid, preferably it is D, and
P5 can be any amino acid, preferably it is V.

30. A method of producing a circular permuted caspase-2 (cp caspase-2) comprising the steps of
i. cloning a nucleotide sequence encoding a cp caspase-2, under the control of a promoter into an expression vector,
ii. transforming a host cell with said vector,
iii. culturing the transformed host cell under conditions wherein the cp caspase-2 is expressed,
iv. optionally isolating the cp caspase-2 from the host cell culture, optionally by disintegrating the host cells, and
v. optionally purifying the cp caspase-2.

31. The method of item 30, wherein the cp caspase-2 is the cp caspase-2 of any one of items 1 to 29.

32. The method of item 30 or 31, wherein the promoter is selected from the group consisting of T7 promoter/operator, XylS/Pm regulator/promoter or variants of the Pm promoter, araBAD promoter/operator, T5, T7A1, T7A2, T7A3 promoter/operator, phoA promoter/regulator and the trp promoter/operator system.

33. The method of any one of items 30 to 32, wherein the cp caspase-2 comprises an solubility enhancement tag, selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T7AC, T3, N1, N2, N3, N4, N5, N6,N7, calmodulin-binding peptide (CBP), DsbA, DsbC, poly Arg, poly Lys, G B1 domain, protein D, Z domain of Staphylococcal protein A, and thioredoxin tag, preferably it comprises a T7AC or a T7A3 tag.

34. The method of any one of items 30 to 33, wherein the cp caspase-2 comprises an affinity tag, preferably a His tag, and even more preferably a 6-His (SEQ ID NO:315) tag.

35. The method of any one of items 30 to 34, wherein the host cell is a eukaryotic or prokaryotic host cell, preferably a yeast cell or a bacterial cell, and even more preferably an *E. coli* cell.

36. The method of any one of items 30 to 35, wherein the cp caspase-2 comprises an N-terminal tag comprising an affinity tag, preferably a His tag and even more preferably a 6-His (SEQ ID NO:315) tag, and a solubility enhancement tag, preferably T7AC or T7A3.

37. The method of item 36, wherein the cp caspase-2 further comprises a linker between the affinity tag and the solubility enhancement tag.
38. The method of items 36 or 37, wherein the cp caspase-2 comprises the following elements fused to its N-terminus, in the order from N- to C-terminus:
  a. affinity tag, preferably 6-His (SEQ ID NO:315) tag;
  b. optionally a linker;
  c. solubility enhancement tag, preferably T7AC or T7A3;
  d. optionally a linker; and
  e. cp caspase-2.
39. The method of items 36 or 37, wherein the cp caspase-2 comprises the following elements fused to its N-terminus, in the order from N- to C-terminus:
  a. solubility enhancement tag, preferably T7AC or T7A3;
  b. optionally a linker;
  c. affinity tag, preferably 6-His (SEQ ID NO:315) tag;
  d. optionally a linker and
  e. cp caspase-2.
40. The method of any one of items 30 to 39, wherein culturing of step (iii) comprises a fed-batch phase for expression of the cp-caspase-2, said fed batch phase specifically comprising a growth rate, μ of about 0.01-0.1 $h^{-1}$, and induction of expression of the cp caspase-2 by addition of IPTG at a concentration of about 0.01-1.5 μmol/g actual CDM (cell dry mass).
41. The method of item 40, wherein the growth rate μ is about 0.03-0.07 $h^{-1}$, preferably it is about 0.05-0.07 $h^{-1}$ or 0.03-0.05$h^{-1}$, preferably it is any of about 0.03, 0.05 or 0.07$h^{-1}$.
42. The method of item 40 or 41, wherein the IPTG concentration is about 0.5-1.3 μmol/g CDM, preferably it is about 0.5-0.9 μmol/g CDM or about 0.9-1.3 μmol/g CDM, preferably it is about 0.5, 0.9 or about 1.3 μmol/g CDM.
43. The method of any one of items 40 to 42, wherein culturing of step (iii) further comprises a first fed-batch phase for the production of biomass, prior to the fed-batch phase for the expression of the cp caspase-2, said first fed-batch phase comprising a growth rate, μ of about 0.07-0.3 $h^{-1}$.
44. The method of item 43, wherein the growth rate μ is about 0.1-0.2 $h^{-1}$, preferably about 0.13-0.21 $h^{-1}$, even more preferably about 0.16-0.18 $h^{-1}$ and most preferably it is about 0.17 $h^{-1}$.
45. The method of any one of items 30 to 44, wherein the cp caspase-2 is purified using affinity chromatography, preferably IMAC.
46. A cp caspase-2 obtained by the method of any one of items 30 to 45.
47. A method of producing a protein of interest (POI) comprising an authentic N-terminus, comprising the steps of:
  i. providing a fusion protein comprising from N- to C-terminus one or more tags, optionally one or more tag-linker sequences and a caspase recognition site N-terminally fused to the POI, wherein said caspase recognition site is specifically recognized by the cp caspase-2 of any one of items 1 to 29,
  ii. contacting said fusion protein with said cp caspase-2 for a period of time sufficient for said cp caspase-2 to cleave the fusion protein, and
  iii. optionally purifying the POI.
48. A method of producing a protein of interest (POI) comprising an authentic N-terminus, comprising the steps of:
  i. expressing the fusion protein comprising from N- to C-terminus optionally one or more tags, optionally one or more tag-linker sequences and a caspase recognition site N-terminally fused to the POI, wherein said caspase recognition site is specifically recognized by the cp caspase-2 of any one of items 1 to 29; and the cp caspase-2 of any one of items 1 to 29 specifically recognizing the recognition site of the fusion protein, in the same host cell,
  ii. optionally, wherein said fusion protein and cp caspase-2 are under the same promoter,
  iii. cultivating the host cell, wherein said cp caspase-2 cleaves the fusion protein in vivo in the cell, and
  iv. optionally isolating the POI from the cell and optionally purifying the POI.
49. The method of item 47 or 48, wherein the fusion protein comprises a caspase recognition site comprising 5 amino acids of the sequence P5 P4 P3 P2 P1, and a cleavage site P1/P1', wherein P1' is the N-terminal amino acid of the POI.
50. The method of item 47 or 48, wherein the fusion protein and the cp caspase-2 are under transcriptional control of different promoters and wherein the expression of the cp caspase-2 is induced after expression of the fusion protein.
51. The method of any one of items 47 to 50, wherein the fusion protein comprises the cp caspase-2 of any one of items 1 to 29, specifically wherein the fusion protein comprises the cp caspase-2 of any one of items 1 to 29 at its N- or C-terminus and wherein the fusion protein comprises the following structure from N- to C-terminus:
  i. one or more N-terminal tags,
  ii. optionally one or more tag-linker sequences and
  iii. a caspase recognition site comprising 5 amino acids of the sequence P5 P4 P3 P2 P1,
  iv. a cleavage site P1/P1',
  v. a POI, and wherein P1' is the N-terminal amino acid of said POI and said cp caspase-2 specifically recognizes said recognition site.
52. The method of any one of items 47 to 51, comprising the steps of:
  i. expressing a fusion protein in a host cell comprising the following structure from N- to C-terminus:
    a. an N-terminal affinity tag,
    b. optionally a linker sequence,
    c. a caspase recognition site,
    d. a cleavage site P1/P1', and
    e. a POI, wherein P1' is the N-terminal amino acid of the POI, and wherein said recognition site is specifically recognized by the cp caspase-2 of any one of items 1 to 29,
  ii. isolating said fusion protein
  iii. purifying said fusion protein using the N-terminal affinity tag,
  iv. providing a cp caspase-2 of any one of items 1 to 29, specifically recognizing the recognition site of the fusion protein,
  v. contacting said fusion protein with said cp caspase-2 for a period of time sufficient for said cp caspase-2 to cleave the fusion protein, vi. optionally removing the cleaved affinity tag, and optionally the non-cleaved fusion protein using the affinity tag and the cp caspase-2, and vii. optionally further purifying the POI.

53. The method of item 52, wherein the cp caspase-2 comprises at its N- or C-terminus an affinity tag identical to the affinity tag of the fusion protein and wherein the cp caspase-2 is removed in step vi. using said affinity tag.

54. The method of item 52 or 53, comprising the steps of i. expressing a fusion protein comprising one or more N-terminal affinity tags, optionally one or more tag-linker sequences, a caspase recognition site and a cleavage site P1/P1', wherein P1' is the N-terminal amino acid of the POI, and a POI, wherein said recognition site is specifically recognized by the cp caspase-2 of any one of items 1 to 29, in a host cell, and ii. isolating the fusion protein and binding/capturing the fusion protein on a solid support using the affinity tag, iii. providing a cp caspase-2 of any one of items 1 to 29, specifically recognizing the recognition site of the fusion protein, iv. contacting said cp caspase-2 with the bound/captured fusion protein for a period of time sufficient for said cp caspase-2 to cleave the fusion protein, v. releasing the POI from the solid support, and vi. isolating and optionally further purifying the POI.

55. The method of item 54, wherein the cp caspase-2 and the fusion protein comprise an identical affinity tag, allowing binding of the fusion protein and the caspase on the solid support and release of the POI upon cleavage by the caspase.

56. The method of item 54 or 55, wherein the solid support is a column, specifically a chromatography column, more specifically an immobilized metal affinity chromatography column (IMAC).

57. The method of any one of items 47 to 56, wherein a flow-through reactor comprising immobilized cp caspase-2 of any one of items 1 to 29 is used.

58. An isolated nucleotide sequence encoding the cp caspase-2 of any one of items 1 to 29.

59. A vector comprising the nucleotide sequence of item 58, specifically it is a bacterial expression vector.

60. An expression cassette comprising the nucleotide sequence of item 58 operably linked to regulatory elements.

61. A host cell or a host cell line expressing the cp caspase-2 of any one of items 1 to 29, wherein the host cells are selected from the group consisting of bacterial cells, yeast cells, insect cells, mammalian cells and plant cells, preferably the host cells are bacterial or yeast cells selected from the group consisting of *E. coli*, *Pseudomonas* sp., *Bacillus* sp., *Streptomyces* sp., *Saccharomyces* sp., *Schizosaccharomyces* sp., *Pichia* sp., *Kluyveromyces* sp. and *Hansenula* sp.

62. An expression system comprising the vector of item 59 or the expression cassette of item 60 and a host cell of item 61.

63. Use of the cp caspase-2 of any one of items 1 to 29 for the in vivo cleavage of a substrate in a non-human organism.

64. The use of item 63, wherein the non-human organism is a prokaryotic organism, specifically it is *E. coli.*

65. Use of the cp caspase-2 of any one of items 1 to 29 for the production of a protein of interest (POI).

66. The use of item 65, wherein the POI comprises an authentic N-terminus.

67. A fusion protein comprising the following structure from N- to C-terminus:

i. a tag sequence comprising a caspase recognition site comprising 5 amino acids of the sequence P5 P4 P3 P2 P1, specifically recognized by the cp caspase-2 of any one of items 1 to 29, ii. a cleavage site P1/P1', wherein P1' is the N-terminal amino acid of the protein of interest (POI), and iii. a POI.

68. The fusion protein of item 67, wherein the tag sequence further comprises one or more tags selected from the group consisting of affinity tags, solubility enhancement tags and monitoring tags.

69. The fusion protein of item 68, further comprising one or more tag-linker sequences.

70. A kit comprising i. the caspase-2 of item 74 or the cp caspase-2 of any one of items 1 to 29, specifically for cleaving a fusion protein of any one of items 67 to 69 or the fusion protein of item 90 or 91.

71. The kit of item 70, further comprising an expression vector, comprising a polynucleotide encoding the protein tag of items 75 to 89.

72. The cp caspase-2 of any one of items 1 to 29, for use in the treatment of a disease.

73. The cp caspase-2 of any one of items 1 to 29, for use in the treatment of cancer, Alzheimer's disease, Parkinson's disease or inflammatory disease.

74. A caspase-2 comprising one or more amino acid substitutions at positions 409, 431, 212, 213, 266, 226, 296, 323 or 326 of SEQ ID No. 11 or at a position functionally equivalent to any of positions 409, 431, 212, 213, 266, 226, 296, 323 or 326 of SEQ ID No. 11 or a combination thereof, wherein said amino acid substitution increases P1' tolerance compared to a caspase-2 comprising the same sequence but not comprising said amino acid substitutions.

75. A protein tag for enhanced expression of a POI, comprising a solubility enhancement tag and the amino acid sequence VDVAD (SEQ ID NO:45), wherein the sequence VDVAD (SEQ ID NO:45) is located at the C-terminus of the protein tag.

76. The tag of item 75, wherein the solubility enhancement tag is selected from the group consisting of T7C, T7B, T7B1, T7B2, T7B3, T7B3, T7B4, T7B5, T7B6, T7B6, T7B7, T7B8, T7B9, T7B10, T7B11, T7B12, T7B13, T7A, T7A1, T7A2, T7A3, T7A4, T7A5, T3, N1, N2, N3, N4, N5, N6, N7 and T7AC.

77. The tag of item 76, wherein the solubility enhancement tag is T7AC or T7A3.

78. The tag of any one of items 75 to 77, further comprising a histidine tag sequence, preferably comprising 1-20 histidine residues, even more preferably it is a 3-His, 6-His (SEQ ID NO:315) or 9-His tag (SEQ ID NO:312) sequence.

79. The tag of any one of items 75 to 78, wherein the solubility enhancement tag is located at the N-terminus of said protein tag.

80. The tag of any one of item 78, wherein the histidine tag sequence is located at the N-terminus of said protein tag.

81. The tag of any one of items 75 to 80, further comprising one or more linker sequences comprising one or more amino acid residues.

82. The tag of item 81, wherein said one or more linker sequences are located between the VDVAD (SEQ ID NO:45) sequence and the solubility enhancement tag and/or the histidine tag sequence.
83. The tag of item 81 or 82, wherein the one or more amino acid residues of the linker sequence are any of the naturally occurring amino acids or derivatives thereof, preferably selected from the group consisting of G, S, A, T and N.
84. The tag of any one of items, 81 to 83, wherein the linker sequence is GSG.
85. The tag of any one of items 81 to 83, wherein the linker sequence is GSGSGSG (SEQ ID NO:280).
86. The tag of any one of items 75 to 85, further comprising a signal peptide at the N-terminus of said protein tag.
87. The tag of item 86, wherein the signal peptide is selected from the group consisting of ompA (outer membrane protein A), DsbA (Thiol:disulfide interchange protein), MalE (maltose-binding protein), PelB (pectate lyase B) from *Erwinia carotovora*, PhoA (alkaline phosphatase), OmpC (outer-membrane protein C), OmpF (outer-membrane protein F), OmpT (protease VII), Endoxylanase from *Bacillus* sp., LamB (A receptor protein), Lpp (murein lipoprotein), LTB (heat-labile enterotoxin subunit B), PhoE (outer-membrane pore protein E), and StII (heat-stable enterotoxin 2).
88. The tag of any one of items 75 to 87, wherein the tag comprises one of the following structures from N- to C-terminus:
   a. T7AC-6-His (SEQ ID NO:315)-VDVAD (SEQ ID NO:45);
   b. T7A3-6-His(SEQ ID NO:315)-VDVAD (SEQ ID NO:45);
   c. T7AC-6-His(SEQ ID NO:315)-GSG-VDVAD (SEQ ID NO:45);
   d. T7A3-6-His(SEQ ID NO:315)-GSG-VDVAD (SEQ ID NO:45);
   e. T7AC-6-His (SEQ ID NO:315)-GSGSGSG (SEQ ID NO:280)-VDVAD (SEQ ID NO:45);
   f. T7A3-6-His (SEQ ID NO:315)-GSGSGSG (SEQ ID NO:280)-VDVAD (SEQ ID NO:45);
   g. 6-His (SEQ ID NO:315)-T7AC-VDVAD (SEQ ID NO:45);
   h. 6-His (SEQ ID NO:315)-T7A3-VDVAD (SEQ ID NO:45);
   i. 6-His(SEQ ID NO:315)-T7AC-GSG-VDVAD (SEQ ID NO:45);
   j. 6-His (SEQ ID NO:315)-T7A3-GSG-VDVAD (SEQ ID NO:45);
   k. 6-His (SEQ ID NO:315)-T7AC-GSGSGSG (SEQ ID NO:280)-VDVAD (SEQ ID NO:45);
   l. 6-His (SEQ ID NO:315)-T7A3-GSGSGSG (SEQ ID NO:280)-VDVAD (SEQ ID NO:45).
89. The tag of item 86 or 87, wherein the tag comprises one of the following structures from N- to C-terminus:
   a. ompA signal peptide-T7AC-6-His (SEQ ID NO:315)-VDVAD (SEQ ID NO:45);
   b. ompA signal peptide-T7A3-6-His (SEQ ID NO:315)-VDVAD (SEQ ID NO:45);
   c. ompA signal peptide-T7AC-6-His (SEQ ID NO:315)-GSG-VDVAD (SEQ ID NO:45);
   d. ompA signal peptide -T7A3-6-His (SEQ ID NO:315)-GSG-VDVAD (SEQ ID NO:45);
   e. ompA signal peptide-T7AC-6-His (SEQ ID NO:315)-GSGSGSG (SEQ ID NO:280)-VDVAD (SEQ ID NO:45);
   f. ompA signal peptide-T7A3-6-His (SEQ ID NO:315)-GSGSGSG (SEQ ID NO:280)-VDVAD (SEQ ID NO:45);
   g. ompA signal peptide-6-His (SEQ ID NO:315)-T7AC-VDVAD (SEQ ID NO:45);
   h. ompA signal peptide-6-His (SEQ ID NO:315)-T7A3-VDVAD (SEQ ID NO:45);
   i. ompA signal peptide-6-His (SEQ ID NO:315)-T7AC-GSG-VDVAD (SEQ ID NO:45);
   j. ompA signal peptide-6-His (SEQ ID NO:315)-T7A3-GSG-VDVAD (SEQ ID NO:45);
   k. ompA signal peptide-6-His (SEQ ID NO:315)-T7AC-GSGSGSG (SEQ ID NO:280)-VDVAD (SEQ ID NO:45);
   l. ompA signal peptide-6-His (SEQ ID NO:315)-T7A3-GSGSGSG (SEQ ID NO:280)-VDVAD (SEQ ID NO:45).
90. A fusion protein comprising the protein tag of any one of items 75 to 89 and a POI, wherein the N-terminus of the POI is fused to the C-terminus of said protein tag.
91. The fusion protein of item 90, wherein the N-terminus of the POI is directly fused to the C-terminus of the protein tag, which C-terminus is the sequence VDVAD (SEQ ID NO:45).
92. A method of producing a POI, comprising the steps of:
   i. providing the fusion protein of item 90 or 91 comprising a POI,
   ii. contacting said fusion protein with a circular permuted caspase-2 (cp caspase-2) for a period of time sufficient for said cp caspase-2 to cleave the fusion protein thereby releasing the POI, and
   iii. optionally purifying the POI.
93. The method of item 92, further comprising the following steps:
   i. cloning a nucleotide sequence encoding the fusion protein of item 90 or 91, under the control of a promoter into an expression vector,
   ii. transforming a host cell with said vector,
   iii. culturing the transformed host cell under conditions wherein said fusion protein is expressed,
   iv. optionally isolating said fusion protein from the host cell culture, optionally by disintegrating the host cells, and
   v. purifying said fusion protein using IMAC chromatography,
   vi. contacting said fusion protein with a circular permuted caspase-2 (cp caspase-2) for a period of time sufficient for said cp caspase-2 to cleave the fusion protein thereby releasing the POI, and
   vii. optionally further purifying the POI,
   viii. optionally modifying the POI and
   ix. optionally formulating the POI.
94. The method of item 92 or 93, wherein the promoter is selected from the group consisting of T7 promoter/operator, XylS/Pm regulator/promoter or variants of the Pm promoter, araBAD promoter/operator, T5, T7A1, T7A2, T7A3 promoter/operator, phoA promoter/regulator and the trp promoter/operator system.
95. The method of items 65-66, wherein the host cell is a eukaryotic or prokaryotic host cell, preferably a yeast or a bacterial cell, preferably it is an *E. coli* cell.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: General Materials and Methods 1.1 *Escherichia coli* Strains

*E. coli* BL21 (DE3) was used for all standard protein expressions.

For plasmid extractions and for cloning experiments *E. coli* strain NovaBlue (Novagen, Madison, WI, USA) was used as a host.

1.2 Culture Media

TY (tryptone-yeast) medium (1% peptone, 0.7% yeast extract, 0.25% (w/v) NaCl).

TB medium (1.2% peptone, 2.4% yeast extract, 0.4% glycerol, 17 mM $KH_2PO_4$, 72 mM $K_2HPO_4$).

SOC (super optimal broth with catabolite repression) (2% (w/v) tryptone, 0.5% (w/v) yeast extract, 10 mM NaCl, 2.5 mM KCl, 10 mM $MgCl_2$ and 20 mM glucose, pH 7.0).

Medium for the recovery of cells after transformation.

Optimized M9 minimal medium (50 mM $Na_2HPO_4$, 20 mM $KH_2PO_4$ 10 mM NaCl, 1 mM $MgSO_4$, 0.1 mM $CaCl_2$, 0.4% Glucose, 20 mM $NH_4Cl$, 0.5% (w/v) casamino acids, 10 μg/ml $FeSO_4$, vitamins (0.001 mg/ml of each biotin, thiamine, riboflavin, pyridoxine, niacinamide). For induction 0.1 to 0.4 mM IPTG were used.

1.3 Recombinant Protein Expression

Standard Expression Protocol: Substrate proteins were expressed in TY medium, induction with 1 mM IPTG, at OD600 1.0 and executed at 37° C., 220 rpm, for 4 h.

Expression protocol for caspases: Caspases were expressed in TB medium, induction was at OD600 1.2 with 0.4 mM IPTG, 25° C., for 4 h.

1.4 Cell Lysis and Protein Purification

Substrates and caspases were purified using Immobilized Metal Affinity Purification (IMAC).

The harvested cell pellets were suspended in Tris-Buffer (50 mM Tris, 50 mM NaCl, pH 7.5), disrupted with a French press and the clarified supernatant applied to an IMAC column (HisTrap FF Crude, 1 ml, GE Healthcare). Washing was executed for five column volumes with running buffer (50 mM Tris/HCl, pH 7.4, 300 mM NaCl, 20 mM Imidazole), the fifth wash fraction had an increased imidazole concentration (40 mM). Elution was conducted for five column volumes with buffer containing 250 mM imidazole.

After affinity-chromatography imidazole and excess NaCl were exchanged to Tris-buffer with a sepharose column (HiTrap Desalting, 5 ml, GE Healthcare). All elution fractions were pooled, the concentration determined with a BCA assay, and the proteins stored in Tris-Buffer with 2 mM DTT at −80 C.

1.5 Testing of Caspases—In Vitro Cleavage Assay

The activity of purified caspases was assessed with an in vitro cleavage assay. The samples were analyzed with SDS-PAGE to separate cleaved and unprocessed substrate. The band intensities were measured with ImageQuant TL 1 D software, version 8.1 (GE Healthcare) and used for statistical analysis and calculation of cleavage efficiency. To standardize the process samples with about 50% of cleaved substrate were used for calculations.

Standard conditions where defined as: enzyme to substrate mass ratio of 1:100 (1 mg/ml substrate and 0.01 mg/ml caspase, molar ratio 1:170) in caspase assay buffer (20 mM PIPES, 100 mM NaCl, 10% sucrose, 0.1% CHAPS, 1 mm EDTA, 10 mM DTT, pH 7.2) and incubation at 25° C. For slowly proceeding reactions the caspase concentration was increased to 0.1 mg/ml (enzyme to substrate mass ratio 1:10).

cp caspase-2 (0.01 mg/ml) (SEQ ID No. 6) cleaved 50% of the substrate VDVAD-E2 with a P1' glycine (1 mg/ml) (SEQ ID No. 33) at 25° C., in caspase assay buffer within 1 min (FIG. 4). These conditions were defined as standard activity to which all other reactions were compared.

By N-terminal Edman sequencing of the processed substrate, it was proven, that it was only cleaved between the VDVAD (SEQ ID NO:45) recognition site and the P1' glycine.

FIG. 4A shows a standard cleavage assay with cp caspase-2 (SEQ ID No. 6) and VDVAD-E2 (SEQ ID NO:33) with a P1' glycine (SEQ ID No. 33). Cleavage of 1 mg/ml VDVAD-E2 (SEQ ID No. 33) with 0.01 mg/ml cp caspase-2 at 25° C. is shown, samples taken after 1.0, 2.5 and 5 min. After 2.5 min 90% of substrate were cleaved and processing was completed in less than 5 min.

For in vitro cleavages that compared the activity to commercially available caspase-2 about 0.005 mg/ml wt caspase-2 (Caspase-2 (human), recombinant, active, Enzo Life Sciences Inc.; Farmingdale (NY), USA) were used to cleave 1 mg/ml VDVAD-E2 (SEQ ID NO:33) with a P1' glycine (mass ratio 1:200, molar ratio 1:340).

Example 2: Designed Cp Caspase-2 Constructs and Substrates 2.1 Cloning of Constructs To create specific changes like deletions, insertions, substitutions, site mutations or the like in initial proteins, caspases-2 or cp caspases-2 (e.g.: SEQ ID No. 6) in plasmid DNA, site directed mutageneses were performed.

The specific primers were designed back-to-back and used for an exponential amplification with a high-fidelity DNA Polymerase.

After amplification a KLD (kinase ligase DpnI) reaction was performed. In this treatment the PCR product was incubated with a Kinase, a Ligase and DpnI restriction enzyme, so that the PCR fragments were phosphorylated and ligated to a circular plasmid and the template DNA was removed. Constructs were transformed into NovaBlue heat shock cells and a fraction of the cell suspension was plated on TY agar containing the appropriate antibiotic. Successful cloning was verified by sequencing of single colonies.

All substrates and caspases were expressed and purified as described in sections 1.3 and 1.4, Example 1.

Protein and nucleotide sequences of all constructs are listed in FIG. 1.

2.2 Caspase Substrates

Human ubiquitin-conjugating enzyme E2 L3 (E2; UniProt ID P6803612) as fusion protein was used as standard caspase substrate. A fusion protein (VDVAD-E2) (SEQ ID NO:33) with N-terminal His tag, short GSG-linker and VDVAD (SEQ ID No. 45) caspase-2 recognition site was designed. The first amino acid after the cleavage site (P1') was a glycine (VDVAD-E2, SEQ ID No. 33). The whole protein has a size of 21.3 kDa, whereas when the tag is cleaved off, the E2 protein itself has 19.5 kDa. This difference is big enough to visualize the cleavage activity on an SDS-PAGE.

As the P1' site is known to influence cleavage activity, E2 was expressed and purified with all twenty possible residues after the VDVAD (SEQ ID NO:45) cleavage site. E2 was also cloned with cleavage sites differing from VDVAD (SEQ ID NO:45). All tested tag sequences fused to E2-protein are listed in Table 1.

TABLE 1

E2 fusion proteins used as cp caspase-2 substrates

| Substrate name | Substrate sequence | Tested for | SEQ ID No. |
|---|---|---|---|
| VDVAD-E2 | 6H-GSG-VDVAD-G-E2 | standard substrate G on P1' position | 33 |
| Xxx-E2 | 6H-GSG-VDVAD-X-E2 | 19 different AA on P1' position, to test P1' influence | 56 |
| DEVD-E2 | 6H-GSG-DEVD-G-E2 | P5 influence | 57 |

β-galactosidase was chosen as a model protein, because due to its large size (116 kDa) it is vulnerable to unspecific cleavage. An N-terminal His tag as well as a GSG linker and the caspase-2 cleavage site VDVAD (SEQ ID NO:45) were added (SEQ ID No. 34).

Superoxide Dismutase, SOD, was used as an additional model fusion protein with an N-terminal 6His (SEQ ID NO:315) Tag and the recognition site, VDVAD (SEQ ID NO:45), directly fused to the N-terminus of SOD (SEQ ID No. 193).

hFGF (Human Fibroblast Growth Factor) was used to evaluate the influence of His tag and VDVAD (SEQ ID NO:45) cleavage site on protein expression. Three pET30a constructs (hFGF, 6H-Hfgf (SEQ ID NO:266), and 6H-VD-VAD-hFGF (SEQ ID No. 32) were cloned.

Recombinant expressions of wild-type (hFGF), His tagged (6H-hFGF)(SEQ ID NO:266), and 6H-hFGF (SEQ ID NO:266) with caspase-2 cleavage site VDVAD (6H-VDVAD-hFGF)(SEQ ID NO:32) were compared. The expression of both variants with His tag was reduced. This effect was less pronounced in the 6H-VDVAD-hFGF (SEQ ID NO:32) variant. Total expression was significantly reduced, but, interestingly, the amount of soluble protein remained the same for 6H-Hfgf (SEQ ID NO:266) and was even increased for 6H-VDVAD-hFGF (SEQ ID NO:32) compared to wild-type hFGF.

It has been described that His tags can influence the rate of both total and soluble production of recombinant proteins. The important result is, that the VDVAD (SEQ ID NO:45) sequence itself does not seem to have a negative influence on production or solubility of recombinant proteins. For proteins whose yield is reduced by a His tag, the caspase cleavage site can easily be combined with other tags.

2.3 Designed Variants of Circularly Permuted Caspase-2

Circularly permuted caspase-2: Circularly permuted caspase-2 variants (cp caspases-2) were designed. based on the sequence of human caspase-2 (UniProtKB14 ID P42575, SEQ ID No. 11) the N-terminal CARD was removed and the order of large (LS) and small subunit (SS) exchanged to create a constitutively active caspase. The SS was linked to the N-terminus of the LS via a GS-linker. Optionally the SS pro-peptide was linked to the N-terminus of the SS. In this case to ensure expression as a single chain protein, an aspartate ($Asp^{343}$ in the wild-type sequence of caspase-2, $Asp^{21}$ in the cp caspase-2) was mutated to alanine, to avoid cleavage of the small subunit from a p14 to a p12 chain. This resulted in the cp caspase-2 variants SEQ ID No.9, SEQ ID No. 6 and, SEQ ID No. 76, both of the latter having additionally an N-terminal 6 His tag. The basic structures of these variants are shown in FIG. 2 B, C, D and FIG. 3 B, C, D.

The protein sequence was codon optimized for *E. coli* with the GeneArt™ online tool (Thermo Fisher Scientific). Between the small and the large subunit, a glycine-serine linker was added which also forms a BamHI restriction site. This enables the separate cloning of the subunits and facilitates the creation of chimera consisting of subunits from different caspases. The N-terminal His tag enabled IMAC-purification.

FIG. 2 shows a schematic representation of wild-type (SEQ ID No. 11) and cp caspase-2 (e.g. SEQ ID No. 9) structures. The annotations are taken from UniProtKB Database (P42575). The structure of the active enzymes (caspase dimer) is depicted in FIG. 3. FIG. 3 shows a schematic representation of mature enzymes of wild-type and circularly permuted caspase-2 structures. Disulfide bonds between small subunits, linkers, as well as N- and C-termini are depicted. While the mature wild-type caspase-2 consists of four protein chains, the cp caspase-2 has only two.

All cp-caspase-2 variants described under this chapter 2.3 were constructed based on SEQ ID No. 6, except otherwise described. The amino acid positions of the mutations indicated correspond to SEQ ID No. 6, unless explicitly stated otherwise. All variants have 6His (SEQ ID NO:315) Tag, except otherwise described.

cp caspase-2 Stop and cp caspase-2 D285E: To test the influence of the propeptide annotated in UniProtKB14 (ID P42575) within the C-terminus of the large subunit, a truncated version was produced by deleting amino acids 286-292 in the cp caspase-2 of SEQ ID No. 6, thereby creating the cp caspase-2 Stop variant (SEQ ID No. 14), and an uncleavable variant (cp caspase-2 D285E) (SEQ ID No. 13) was created.

cp caspase-2 with C-terminal Strep tag: Strep tags were fused C-terminal to create cp caspase-2 Strep and cp caspase-2 D285E Strep variants (SEQ ID No. 15 and SEQ ID No. 16, respectively).

In SEQ ID No. 15, a Strep tag was fused to the C-terminus of the cp caspase 2 (SEQ ID No. 6), which was mutated to VDQQS (the substitution: D292S) (SEQ ID NO:15), as experiments had shown that VDQQE (D to E substitution of VDQQD (SEQ ID NO:213)) is recognized as a cleavage site. Despite the VDQQS (SEQ ID NO:15) mutation, the Strep tag was partially cleaved from the caspase. The cleavage product had the same size as the Stop variant (31.9 kDa), indicating that it had been cleaved at the DETD-R (between $Asp^{285}$ and $Arg^{286}$) (SEQ ID No. 220) and not at the VDQQS (SEQ ID NO:15) site.

Therefore, a Strep tag was added to the C-terminus of cp caspase-2 with the D285E and the E292S mutations. This variant (SEQ ID No. 16) was expressed as a single chain with 33.9 kDa. Proving that the mutation of $Asp^{285}$ to Glu prevents cleavage. The C-terminal Strep-tag did not influence the cleavage activity of this variant. FIG. 5 shows a graphic representation of C-terminal sequences of cp caspase-2 variants.

cp caspase-2 D282T and cp caspase-2 H185A D282T: Two cp caspase-2 variants were generated, the first with a D282T mutation and the second with an additional H185A mutation in cp caspase-2 (SEQ ID No. 6) comprising SEQ ID No. 17 and SEQ ID No. 18, respectively.

cp caspase-2 G171D, cp caspase-2 V225G, and cp caspase-2 D282E: cp caspase-2 (SEQ ID No. 6) was mutated at positions 171, 225, or 282 respectively resulting in amino acid exchanges G171D, V225G, or D282E resulting in the variants having SEQ ID No. 190, 192 and 191, respectively.

cp caspase-2 with different linkers between small and large subunit: The GS linker between small and large subunit of cp caspase-2 (SEQ ID No. 6) was mutated. Resulting variants contained no linker (cp caspase-2 A Linker, SEQ ID No. 73), a GGSGG linker (cp caspase-2 5 aa Linker, SEQ ID No. 74), and a GSAGSAAGSG linker (cp caspase-2 10 aa Linker, SEQ ID No. 75).

cp caspase-2 with partial and without small subunit propeptide: The propeptide of the small subunit of cp caspase-2 (SEQ ID No. 6) was mutated by site directed mutagenesis. Deletion of residues 8-22 produced a variant without propeptide (cp caspase-2 Δ SS Prop, SEQ ID No. 76, see also FIG. 2 D and FIG. 3 D), deletion of residues 8-15 produced a variant with partial deleted propeptide (cp caspase-2½ Δ SS Prop, SEQ ID No. 77).

cp caspase-2 with shifted circular permutation: cp caspase-2 Δ SS Prop (SEQ ID No. 76) was used to generate variants with shifted circular permutation. At the N-terminus of the small subunit three amino acids were deleted and added to the C-terminus of the large subunit. Because of possible auto-cleavage, detected when adding a Strep-tag to the C-terminal end of cp caspase-2, additionally the mutations D267E and D274S according to SEQ ID No.76 were inserted. The resulting variant cp caspase-2 C-term +3 (SEQ ID No. 82) was expressed, purified and tested as described above.

In parallel, a variant was generated by deletion of the 3 C-terminal residues of the large subunit and insertion of those residues to the N-terminus of the small subunit of cp caspase-2 Δ SS Prop (SEQ ID No. 76). The resulting variant cp caspase-2 N-term +3 (SEQ ID No. 83) was expressed, purified and tested as described in the standard protocol in Example 1.

cp caspase-2 C203S: The variant was created by insertion of the C203S mutation in cp caspase-2 (SEQ ID No. 6) resulting in SEQ ID No. 198.

cp caspase-2 S9 C203S: The substitution C203S was inserted in cp caspase-2 S9 (SEQ ID No. 51), resulting in SEQ ID No. 199.

cp caspase-2 N85C and cp caspase-2 A86C: The variants were created by insertion of the mutations N85C (SEQ ID No. 80) and A86C (SEQ ID No. 88) in cp caspase-2 (SEQ ID No. 6).

Homologue Cp Caspase-2 Variants:

The cp caspase-2 variants from different species were constructed analogue to the cp caspase-2 of human origin (SEQ ID No. 6).

Based on the sequence of Tasmanian devil caspase-2 (*Sarcophilus harrisii*, UniProtKB14 ID G3VQP7, SEQ ID No. 95) and Ghost shark caspase-2 (*Callorhinchus* mil UniProtKB14 ID V9KZT1, SEQ ID No. 113) the N-terminal CARD was removed and the order of large and small subunit exchanged to create a constitutively active caspase. The SS was linked to the N-terminus of the LS via a GS-linker. The SS pro-peptide was linked to the N-terminus of the SS. To ensure expression as a single chain protein, an aspartate (corresponding to $Asp^{343}$ in the wild-type sequence of human caspase-2, $Asp^{21}$ in the cp protein) was mutated to alanine, to avoid cleavage of the small subunit propeptide.

The protein sequence was codon optimized for *E. coli* with the GeneArt™ online tool (Thermo Fisher Scientific). Between the small and the large subunit, a glycine-serine linker was added which also forms a BamHI restriction site. This enables the separate cloning of the subunits and facilitates the creation of chimera consisting of subunits from different caspases. The N-terminal His tag enabled IMAC-purification.

Resulting variants are Sarcophilus cp caspase-2 (SEQ ID No. 64) and *Callorhinchus* cp caspase-2 (SEQ ID No. 68).

Mutations at positions corresponding to (at positions functionally equivalent to) residues $Glu^{105}$ and $Glu^{172}$ in cp caspase-2 (SEQ ID No. 6) were inserted in Sarcophilus cp caspase-2, generating variant Sarcophilus cp caspase-2 E105V E172V (SEQ ID No. 78).

Mutations at positions corresponding to $Glu^{105}$ and $Gly^{171}$ in cp caspase-2 (SEQ ID No. 6) were inserted in *Callorhinchus* cp caspase-2, generating variant *Callorhinchus* cp caspase-2 E105V G171 D (SEQ ID No. 79).

Additionally, the variants were cloned containing an N-terminal T7AC tag (SEQ ID No. 84, 85, 86, 87).

Functionally equivalent positions are listed in Table 2.

TABLE 2

Corresponding functionally equivalent positions of homologous caspase-2 variants

| Position in wt human caspse-2 (UniProt ID P42575, SEQ ID No. 11) | Position in human cp caspase-2 (SEQ ID No. 6) | Position in wild-type Callorhinchus milii (UniProt ID V9KZT1, SEQ ID No. 113) | Position in Callorhinchus cp caspase-2 (SEQ ID No. 68) | Position in wild-type Sarcophilus harrisii (UniProt ID G3VQP7, SEQ ID No. 95) | Position in Sarcophilus cp caspase-2 (SEQ ID No. 64) |
|---|---|---|---|---|---|
| Asp 347 | 21 | Asp 305 | 18 | Asp 324 | 21 |
| Lys 409 | 83 | Gln 369 | 82 | Lys 386 | 83 |
| Glu 431 | 105 | Glu 391 | 104 | Glu 408 | 105 |
| Gly 212 | 171 | Gly 174 | 175 | Gly 189 | 171 |
| Glu 213 | 172 | — | — | Glu 190 | 172 |
| His 226 | 185 | Thr 187 | 188 | His 203 | 185 |
| Val 266 | 225 | Arg 227 | 228 | Asn 243 | 225 |
| Val 296 | 255 | Ile 257 | 258 | Val 273 | 255 |
| Asp 323 | 282 | Asp 284 | 285 | Asp 300 | 282 |
| Asp 326 | 285 | Asp 287 | 288 | Asp 303 | 285 |

FIG. 6 shows an alignment of natural sequences of homologue caspase-2 from different species. Unprocessed proteins consist of CARD domain, large subunit (LS) containing the two catalytic centers, small subunit propeptide (SS Propept.) and small subunit (SS). Active sites 1-5 interact with substrates. Definition of subunits and active sites see Tables 3 and 4.

UniProt IDs: Human (P42575), Mouse (P29594), Sheep (WQ81-6), Tasmanian Devil (G3VQP7), Chicken (098943), *Anolis* (H9GC38), Alligator (AA1U8D1G6), *Xenopus* (F6RDY9), *Danio* (QPKX3), Ghost Shark (V9KZT1), Sea squirt (A0A1 W2WKB0)

FIG. 7 shows an alignment of active sites of natural sequences of caspases-2 from different species (sequences and SEQ ID Nos. see Table 24). Active sites interact with substrates and are relatively conserved. Definition of subunits and active sites see Tables 3 and 4. Numbers represent the starting position of the first active site.

TABLE 3

Definition of positions of caspase-2 subunits of different species.

| | Prodomain (CARD) | Large Subunit | Intervening Sequence (Propeptide Small Subunit) | Small Subunit |
|---|---|---|---|---|
| Human P42575 | 1-169 | 170-333 | 334-347 | 348-452 |
| Mouse P29594 | 1-169 | 170-333 | 334-347 | 348-452 |
| Sheep W5Q86 | 1-174 | 175-342 | 343-356 | 357-461 |
| Tasman Devil G3VQP7 | 1-146 | 147-310 | 311-324 | 325-429 |

TABLE 3-continued

Definition of positions of caspase-2 subunits of different species.

| | Prodomain (CARD) | Large Subunit | Intervening Sequence (Propeptide Small Subunit) | Small Subunit |
|---|---|---|---|---|
| Chicken Q98943 | 1-140 | 141-304 | 305-318 | 319-424 |
| Anolis H9GC58 | 1-163 | 164-327 | 328-341 | 342-446 |
| Alligator A0A1U8D1G6 | 1-143 | 144-307 | 308-321 | 322-427 |
| Xenopus F6RDY9 | 1-141 | 142-302 | 303-316 | 317-421 |
| Danio Q0PKX3 | 1-136 | 137-301 | 302-315 | 316-435 |
| Ghost Shark V9KZT1 | 1-131 | 132-294 | 295-305 | 306-417 |
| Sea squirt A0A1W2WKB0 | 1-67 | 68-234 | 235-245 | 246-351 |

TABLE 4

Definition of active sites in caspases-2 of different species.

| | Active Site | | | | |
|---|---|---|---|---|---|
| | 1 | 2 | 3 | 4 | 5 |
| Human P42575 | 212-226 | 274-285 | 318-325 | 375-382 | 418-430 |
| Mouse P29594 | 212-226 | 274-285 | 318-325 | 375-382 | 418-430 |
| Sheep W5Q8H6 | 217-231 | 282-293 | 327-334 | 384-391 | 427-439 |
| Tasman Devil G3VQP7 | 189-203 | 251-262 | 295-302 | 352-359 | 395-407 |
| Chicken Q98943 | 183-197 | 245-256 | 289-296 | 346-353 | 389-401 |
| Anolis H9GC58 | 206-236 | 268-279 | 312-319 | 368-376 | 412-424 |
| Alligator A0A1U8D1G6 | 186-200 | 248-259 | 292-299 | 349-356 | 392-404 |
| Xenopus F6RDY9 | 182-195 | 243-257 | 287 -294 | 343-350 | 386-398 |
| Danio Q0PKX3 | 179-194 | 242-256 | 286-293 | 357-364 | 400-412 |
| Ghost Shark V9KZT1 | 174-187 | 235-249 | 279-286 | 335-342 | 378-390 |
| Sea squirt A0A1W2WKB0 | 112-127 | 175-189 | 219-226 | 277-284 | 320-332 |

TABLE 5 active sites of natural sequences of caspases-2 from different species

| | Active Site | | | | |
|---|---|---|---|---|---|
| | 1 | 2 | 3 | 4 | 5 |
| Human P42575 | GEKELEFRSGGD VDH (SEQ ID No. 119) | LLSHGVEGAIYGV DG (SEQ ID No. 130) | QACRGD ET (SEQ ID No. 141) | AAMRNT KR (SEQ ID No. 152) | EGYAPGTEFH RCK (SEQ ID No. 163) |
| Mouse P29594 | GEKDLEFRSGGD VDH (SEQ ID No. 120) | LLSHGVEGGIYG VDG (SEQ ID No. 131) | QACRGD ET (SEQ ID No. 142) | AAMRNT KR (SEQ ID No. 153) | EGYAPGTEFH RCK (SEQ ID No. 164) |
| Sheep W5Q8H6 | GEKDLEFRSGGD VDH (SEQ ID No. 121) | LLSHGVEGSVYG VDG (SEQ ID No. 132) | QACRGD ET (SEQ ID No. 143) | AAMRNT KR (SEQ ID No. 154) | EGYAPGTEFH RCK (SEQ ID No. 165) |
| Tasman Devil G3VQP7 | GEKDLEFRSGGD VDH (SEQ ID No. 122) | LLSHGIEGGIYGV DG (SEQ ID No. 133) | QACRGD ET (SEQ ID No. 144) | AAMRNT KR (SEQ ID No. 155) | EGYAPGTEFH RCK (SEQ ID No. 166) |
| Chicken Q98943 | SEKDLEYRSGGD VDC (SEQ ID No. 123) | LLSHGVEGGVYG TDG (SEQ ID No. 134) | QACRGD ET (SEQ ID No. 145) | AAMRNT KR (SEQ ID No. 156) | EGYAPGTEFH RCK (SEQ ID No. 167) |
| Anolis H9GC58 | KETDLDFRSGGD VDN (SEQ ID No. 124) | LLSHGIEGGIYGI DG (SEQ ID No. 135) | QACRGD ET (SEQ ID No. 146) | AAMRNT KH (SEQ ID No. 157) | EGHAPGTEFH RCK (SEQ ID No. 168) |
| Alligator A0A1U8D1G6 | GEKDLEFRSGGD VDC (SEQ ID No. 125) | LLSHGVEGGVYG IDG (SEQ ID No. 136) | QACRGD ET (SEQ ID No. 147) | AAMRNT KR (SEQ ID No. 158) | EGYAPGTEFH RCK (SEQ ID No. 169) |
| Xenopus F6RDY9 | TQDLDHRYGGE VDV (SEQ ID No. 126) | VLSHGLDGAVYG TDG (SEQ ID No. 137) | QACRGE EA (SEQ ID No. 148) | VSLRNT KR (SEQ ID No. 159) | EGHAPGTEFH RCK (SEQ ID No. 170) |
| Danio Q0PKX3 | SANTDLDIRRGG EVDE (SEQ ID No. 127) | LLSHGVEGSVYG TDG (SEQ ID No. 138) | QACRGE EM (SEQ ID No. 149) | AAMRNT KK (SEQ ID No. 160) | EGYAPGSAHH RCK (SEQ ID No. 171) |
| Ghost Shark V9KZT1 | GEGLGHRPGGA ADT (SEQ ID No. 128) | LLSHGVEGAIYGV DG (SEQ ID No. 139) | QACRGD RT (SEQ ID No. 150) | AALRNT RQ (SEQ ID No. 161) | EGFAPGTDFH RCK (SEQ ID No. 172) |

TABLE 5-continued active sites of natural sequences of caspases-2 from different species

| | Active Site | | | | |
|---|---|---|---|---|---|
| | 1 | 2 | 3 | 4 | 5 |
| Sea squirt A0A1W2WKB0 | PESDLLNREGSE KDR (SEQ ID No. 129) | AMSHGDAGCFY GSDG (SEQ ID No. 140) | QACQGD EY (SEQ ID No. 151) | AAMRNT KH (SEQ ID No. 162) | EGWCPGSVYH RCK (SEQ ID No. 173) |

Example 3: Selection of Cp Caspase-2 and all Found Mutations by Selection

Selection System to Detect Variants with Improved P1' Tolerance

A selection system was used for the improvement of cp caspase-2. It is based on a circularly permuted ATCase (aspartate transcarbamoylase) catalytic subunit and a pyrimidine auxotroph strain. The pyrBI operon (encoding regulatory pyrI and catalytic pyrB subunits of ATCase) was deleted in *E. coli* BL21(DE3), so this knock-out strain can only survive in media containing pyrimidines or when the cells are complemented with a vector encoding ATCase. A cp catalytic subunit of ATCase (cp-pyrB), which harbors its new N-terminus in the interior of the protein, is used to detect specific proteases via the growth of *E. coli*, because fusion of any stretch of amino acids to its N-terminus renders the enzyme inactive as it can no longer fold properly due to space limitations in the interior of the protein. However, if a protease is provided that can exactly cleave off this additional stretch of amino acids, the enzyme gets reactivated.

3.1 Design of Constructs and Caspase Mutant Libraries

Selection medium: Optimized M9 medium (see Example 1, section 1.2)

Strain: *E. coli* BL21(DE3) with pyrBI operon exchanged to kanamycin resistance (id est: pyrBI is deleted)

Vectors: expressions of the ATCase subunits, cp-pyrB and pyrI from pETDuet™-1 vector using T7 promoters and the ampicillin-resistance as selection marker, expressions of the diverse caspase variants from pACYCDuet™-1 vector using a T7 promoter and the chloramphenicol resistance marker. Selection protocol was performed with respective cotransformations with simultaneous use of ampicillin, kanamycin and chloramphenicol in the above selection medium.

VDVAD (SEQ ID NO:45)-cpATCase

The used pETDuet-1 plasmid (substrate plasmid), contained a pyrI gene in MCSI (SEQ ID No. 20) and cp-pyrB gene in MCSII (SEQ ID No. 21). In pyrI the potential caspase cleavage site DQVD (SEQ ID NO:206, where the $2^{nd}$ residue is E to Q) was changed to DQVE (SEQ ID NO:207, where the $2^{nd}$ residue is E to Q) by mutation of $Asp^{73}$. A 6His (SEQ ID NO:315) tag followed by a GSG linker and a caspase recognition site were fused to the N-terminus of cp pyrB c227 [25]. This hinders the correct folding of the enzyme and makes it inactive, but proteolytic cleavage of this tag can restore its function. The first Met of cp pyrB was deleted. The amino acid after Met is Thr. The cpATCase is still active when this residue is substituted. Only mutations to His, Lys, Phe, Tyr, and Trp render it inactive. This enables the selection for caspases with improved or altered recognition site specificity and/or improved P1' tolerance. CpATCase constructs with 6His-GSG-VDVAD-ΔM-X-pyrB (SEQ ID No. 22) were used for in vivo selection of altered P1' tolerance.

Construction of Caspase Mutant Library—Ep PCR and Oe PCR

Mutant gene libraries of different cp caspase-2 variants were generated by error prone (ep) PCR and overlap extension (oe) PCR of vector and the mutated caspase gene. The linear DNA fragments were ligated using T4 DNA ligase. The amount of mutations can be modified by changing the Mg(II) and Mn(II) ion concentrations in the PCR buffer. The used concentrations caused in average one to three amino acid exchanges in the caspase. The cp caspase-2 variants, of which mutant libraries were made of, are indicated in Table 5 in the column "Mutated Caspase".

3.2 Selection of Caspase Libraries

The caspase mutant libraries were transformed into *E. coli* BL21(DE3) ΔpyrBI electro competent cells that already contained the cpATCase plasmid with the desired protease cleavage site and P1' residue. Selection was executed either in optimized M9 medium or on M9 agar plates at 30° C. for 24-48 h. Liquid cultures were used to enrich mutants with improved growth. IPTG concentrations in liquid culture and in agar plates between 0.025 and 1 mM were used.

Mutant libraries in *E. coli* BL21(DE3) ΔpyrBI cells were selected with VDVAD (SEQ ID NO:45)-cpATCase with different P1' residues. Selections were executed with Pro, Met, Thr, and Val. Selections with P1' Met were executed with cp ATCase without deletion of the native methionine, all other selections were executed with constructs comprising SEQ ID No. 22. Selection with Met, Thr, and Val as P1' lead to hundreds of positive variants, thus only the largest colonies were analyzed.

All together 77 clones with a total of 263 mutations were analyzed from all selections combined. Some mutations were found several times in independent experiments. The mutations of resulting variants in comparison to SEQ ID No. 6 are shown in Table 5 below. P1' amino acids used for selection are indicated under "P1'McpATease".

Mutations of variants were analyzed and several were selected for expression and characterization by in vitro cleavages. Variants were chosen when they had been enriched in liquid culture or contained mutations that were found several times independently. Description of those variants can be found in Example 4.

TABLE 5

| cp caspase-2 variants resulting from the selection screen | | | | | |
|---|---|---|---|---|---|
| Variant | P1' cp ATCase | IPTG mM | Mutated caspase | Small Subunit 1-128 | Large Subunit 129-292 |
| SM1 | Met | 0.025 | cp caspase-2 D285E | L45Q | K136R |
| SM2 | Met | 0.025 | cp caspase-2 D285E | E105V | |
| SM5 | Met | 0.025 | cp caspase-2 D285E | | T126S |
| SM6 | Met | 0.025 | cp caspase-2 D285E | R35S | Q144R |
| SM7 | Met | 0.025 | cp caspase-2 D285E | E105V | |
| SM8 | Met | 0.025 | cp caspase-2 D285E | | F147L |
| S9 D285E | Met | 0.025 | cp caspase-2 D285E | E105V | |
| SM10 | Met | 0.025 | cp caspase-2 D285E | E105V | |
| SM11 | Met | 0.025 | cp caspase-2 D285E | | L149R V201A |
| SM13 | Met | 0.025 | cp caspase-2 D285E | K26R | |
| SM17 | Met | 0.1 | cp caspase-2 D285E | E105V | C132R E141G H200R |
| SM18 | Met | 0.1 | cp caspase-2 D285E | H4R K46R M75L E105V | |
| SM19 | Met | 0.1 | cp caspase-2 D285E | | C132W Q144R L149Q S186N |
| SM20 | Met | 0.1 | cp caspase-2 D285E | | C203Y |
| SM31 | Met | 0.1 | cp caspase-2 D285E | K83R | |
| SM32 | Met | 0.1 | cp caspase-2 D285E | Y94H | T226S |
| SM34 | Met | 0.1 | cp caspase-2 D285E | K24R R115S | K136E V189A C194Q H200Q |
| SM37 | Met | 0.1 | cp caspase-2 D285E | G8D C37S | |
| SM38 | Met | 0.1 | cp caspase-2 D285E | | L164M |
| SM39 | Met | 0.1 | cp caspase-2 D285E | | C203R E209D |
| SM42 | Met | 0.1 | cp caspase-2 D285E | G93D C114R | |
| SM44 | Met | 0.1 | cp caspase-2 D285E | | P265T |
| SM45 | Met | 0.1 | cp caspase-2 D285E | | Q148P |
| SM47 | Met | 0.1 | cp caspase-2 D285E | | C203Y |
| ST22 | Thr | 0.1 | cp caspase-2 D285E | | T140A |
| ST23 | Thr | 0.1 | cp caspase-2 D285E | | F148I |
| ST24 | Thr | 0.1 | cp caspase-2 D285E | Y42F | Q155R |
| ST28 | Thr | 0.1 | cp caspase-2 D285E | R35C L45V V82F L87V | |
| ST29 | Thr | 0.1 | cp caspase-2 D285E | N10D | |
| S9-ST47 | Thr | 0.25 | S9 D285E | | H185Q P221L T284A |
| S9-ST50 | Thr | 0.25 | S9 D285E | | Q215H |
| S9-ST51 | Thr | 0.25 | S9 D285E | F68I | E172A |
| S9-ST57 | Thr | 0.25 | S9 D285E | R71C | |
| S9-ST58 | Thr | 0.25 | S9 D285E | | V135A |
| S9-ST59 | Thr | 0.25 | S9 D285E | | F142S L152Q |
| mS9 Thr 0.8 | Thr | 0.8 | S9 D285 | K83E | E172V V225M D285Y |
| S9-ST61 | Thr | 0.25 | S9 D285 | | T284S |
| S9-ST62 | Thr | 0.25 | S9 D285 | C114R | L133Q E283G |
| S9-ST63 | Thr | 0.25 | S9 D285 | C44G | |
| S9-ST65 | Thr | 0.4 | S9 D285 | I61V | V231L |
| S9-ST67 | Thr | 0.4 | S9 D285 | C103G F120L | C132R |
| SV4 | Val | 0.1 | cp caspase-2 D285E | | V201A |
| SV5 | Val | 0.1 | cp caspase-2 D285E | E92V | |
| SV6 | Val | 0.1 | cp caspase-2 D285E | L27P | |
| SV7 | Val | 0.1 | cp caspase-2 D285E | E99V | F147S T170S |
| SV9 | Val | 0.1 | cp caspase-2 D285E | | Q134K |
| SV10 | Val | 0.1 | cp caspase-2 D285E | | V201A |
| SV12 | Val | 0.1 | cp caspase-2 D285E | | C132S Q211R N216D |
| SV13 | Val | 0.1 | cp caspase-2 D285E | | V201D |
| SV28a | Val | 0.1 | cp caspase-2 D285E | | T190S T226S |
| SV30 | Val | 0.1 | cp caspase-2 D285E | | E174G |
| SV31 | Val | 0.1 | cp caspase-2 D285E | | C203Y |
| SV32 | Val | 0.1 | cp caspase-2 D285E | | E174G |
| SV33 | Val | 0.1 | cp caspase-2 D285E | | E174G |
| SV34 | Val | 0.1 | cp caspase-2 D285E | | K193R Q205L T284A |
| SV36 | Val | 0.1 | cp caspase-2 D285E | | G129S T284A |
| SV37 | Val | 0.1 | cp caspase-2 D285E | | L153Q E239D |
| SV47 | Val | 0.25 | cp caspase-2 D285E | E105V | T226A |
| SV48 | Val | 0.25 | cp caspase-2 D285E | E105V | |
| SV49 | Val | 0.25 | cp caspase-2 D285E | T48S A49S S69I | |
| SV50 | Val | 0.25 | cp caspase-2 D285E | E105V | |
| SV51 | Val | 0.25 | cp caspase-2 D285E | | Q154R |
| SV53 | Val | 0.1 | cp caspase-2 D285E | E141D | |
| SV54 | Val | 0.1 | cp caspase-2 D285E | | H185R |
| SV56 | Val | 0.1 | cp caspase-2 D285E | | H155R S235T |

TABLE 5-continued cp caspase-2 variants resulting from the selection screen

| Variant | P1' cp ATCase | IPTG mM | Mutated caspase | Small Subunit 1-128 | Large Subunit 129-292 |
|---|---|---|---|---|---|
| SV57 | Val | 0.1 | cp caspase-2 D285E | N116S | T284A |
| SV58 | Val | 0.1 | cp caspase-2 D285E | A49V | Q148R |
| SV60 | Val | 0.1 | cp caspase-2 D285E | K55E | R157Q V189G Q215L |
| SV63 | Val | 0.1 | cp caspase-2 D285E | | E254D |
| S9-SV65 | Val | 0.1 | S9 D285E | K46E | |
| S9-SV66 | Val | 0.1 | S9 D285E | V105A C110R | C138S T190N |
| S9-SV67 | Val | 0.1 | S9 D285E | Y94F | L149Q |
| S9-SV68 | Val | 0.1 | S9 D285E | | Y143F R156L S165I E176V |
| S9-SV71 | Val | 0.25 | S9 D285E | | L258Q |
| S9-SV72 | Val | 0.25 | S9 D285 | Q66K | A150V |
| S9-SV75 | Val | 0.25 | S9 D285 | | F259Y |
| S9-SV77 | Val | 0.4 | S9 D285 | | S186C |
| SP2 | Pro | 0.1 | cp caspase-2 D285E | E99V H123N | |
| SP4 | Pro | 0.1 | cp caspase-2 D285E | M51I | |
| mS9 Pro D285E | Pro | 0.1 | S9 D285E | G171D | V225G D282E |
| S9-SP8 | Pro | 0.1 | S9 D285E | G171D | V225G D282E |
| S9-SP9 | Pro | 0.1 | S9 D285E | G171D | V225G D282E |
| S9-SP10 | Pro | 0.1 | S9 D285E | G171D | V225G D282E |
| S9-SP11 | Pro | 0.1 | S9 D285E | G171D | V225G D282E |
| S9-SP12 | Pro | 0.1 | S9 D285E | | A222T |
| S9-SP14 | Pro | 0.25 | S9 D285 | C110S | K173E D198E K248I |

Example 4: Characterization of Variants Found by Selection cp caspase-2 S9 D285E and S9 D285: Selection of a cp caspase-2 D285E (SEQ ID No. 13) library, containing about 5,500 variants, was performed, with VDVAD (SEQ ID NO:45)-cpATCase that contained a methionine as P1' and with an induction strength of 0.025 mM IPTG. The E105V mutation was found repeatedly among 16 analyzed clones. One selected variant with this mutation (cp caspase-2 S9 D285E, SEQ ID No. 1) was expressed, purified and tested as described in Example 1.

The selected cp caspase-2 S9 D285E was mutated to generate the cp caspase-2 S9 D285 variant (SEQ ID No. 51). The variant was expressed, purified and tested as described above (Example 1).

cp caspase-2 mS9 Pro D285E and cp caspase-2 mS9 Pro D285: The cp caspase-2 S9 D285E (SEQ ID No. 1) variant was used for a further round of mutation because of its improved P1' tolerance. The new mutant library contained about 10.000 variants and was selected with VDVAD(SEQ ID NO:45)-ΔM-Pro-cpATCase. Selection in liquid culture enriched a variant (mS9 Pro D285E, SEQ ID No. 70) with the mutations E105V, G171D, V225G, D282E and D285E. The caspase was expressed and purified as described above.

The selected cp caspase-2 mS9 Pro D285E (SEQ ID No. 70) was mutated to generate the cp caspase-2 mS9 Pro D285 variant (SEQ ID No. 52). The variant was expressed, purified and tested as described above.

cp caspase-2 mS9 Thr 0.8: The variant with K83E, E105V, E172V, V255M, and D285Y mutations was selected from mutated cp caspase-2 S9 D285 (SEQ ID No. 51). The new variant (SEQ ID No. 53 and SEQ ID No. 54) was enriched in liquid culture in a selection with VDVAD (SEQ ID NO:45)-Thr-cpATCase and 0.8 mM IPTG. It was expressed, purified and tested as described in Example 1.

cp caspase-2 S17: Variant with E105V, C132R, E141G, H200R, and D285E mutations that was selected from mutated cp caspase-2 D285E (SEQ ID No. 13) with VDVAD (SEQ ID NO:45)-cpATCase with Met as P1' and 0.1 mM IPTG. The variant was never purified and tested in vitro, mutations at positions 105, 132 and 105 were found repeatedly in different experiments.

cp caspase-2 S20: The variant with C203Y and D285E mutations (SEQ ID No. 26) was selected from mutated cp caspase-2 D285E (SEQ ID No. 13) with VDVAD (SEQ ID NO:45)-cpATCase with Met as P1' and 0.1 mM IPTG.

cp caspase-2 D285E SV4: The variant with V201A and D285E mutations (SEQ ID No. 28) was selected from mutated cp caspase-2 D285E (SEQ ID No. 13) with VDVAD (SEQ ID NO:45)-Val-cpATCase and 0.1 mM IPTG. The mutation V201A was found several times independently.

cp caspase-2 SV19: The cp caspase-2 SV 19 (SEQ ID No. 81) was selected from variants with mutated C-terminus with VDVAD (SEQ ID NO:45)-Val-cpATCase and 0.1 mM IPTG.

The sequence equals the consensus-sequence of 13 active variants with mutated C-terminus.

cp caspase-2 D285E SV30: The variant with E174G and D285E mutations (SEQ ID No. 30) was selected from mutated cp caspase-2 D285E (SEQ ID No. 13) with VDVAD (SEQ ID NO:45)-Val-cpATCase and 0.1 mM IPTG. The variant was enriched in liquid culture.

Example 5: Cleavage Activity of Generated Caspases and their Variants

5.1 β-Galactosidase

The model substrate β-galactosidase contains four DXXD and one DXXE sites, three of which are on the surface and could be accessible to the caspase.

After incubating 1 mg/ml β-galactosidase fusion protein (with N-terminal tag including the recognition site VDVAD (SEQ ID NO:45) with 0.1 mg/ml cp caspase-2 (SEQ ID No. 6) for 24 hours, no unspecific cleavage was observed. Correct cleavage of the His tag was confirmed by N-terminal protein sequencing.

5.2 VDVAD-SOD (SEQ ID No. 193) Cleavage

FIG. 4 B shows the cleavage of the substrate 6His-VDVAD-SOD (SEQ ID No. 193) by cp caspase-2, SEC ID No. 6: within 1 hour: almost 100% of the substrate was cleaved, whereas no cleavage was observed without cp caspase-2 after 6 hours.

5.3 VDVAD (SEQ ID NO:45)-Gly-E2 Cleavage Values of all Tested Cp Caspase-2 Variants Cp caspase-2 (0.01 mg/m) (SEQ ID No. 6) cleaved 50% of the substrate VDVAD-E2 (SEQ ID NO:33) with a P1' glycine (1 mg/mm) at 25° C., in caspase assay buffer within 1 min. These conditions were defined as standard activity to which all other reactions were compared (FIG. 4A).

Not all tested variants cleaved the standard substrate to 50% in 1 m. A list of all cleavages with a P1' Gly is given in Table 6.

TABLE 6

Cleavage activity of cp caspase-2 variants. Time required to cleave 50% of the VDVAD-E2 substrate with P1' Gly which is used as the standard substrate. Cleavage of 1 mg/ml substrate by 0.01 mg/ml caspase at 25° C.

| Caspase Variant | Minutes | SEQ ID No. |
|---|---|---|
| cp caspase-2 | 1 min | 6 |
| cp caspase-2 D285E | 1 min | 13 |
| cp caspase-2 D282T | 1 min | 17 |
| cp caspase-2 H185A D282T | 1 min | 18 |
| cp caspase-2 S9 D285<br>E105V | 1 min | 51 |
| cp caspase-2 S9 D285E<br>E105V, D285E | 1 min | 1 |
| cp caspase-2 mS9 Pro D285<br>E105V, G171D, V225G, D282E | 1 min | 52 |
| cp caspase-2 mS9 Pro D285E<br>E105V, G171D, V225G, D282E, D285E | 1 min | 70 |
| cp caspase-2 G171D | 1 min | 190 |
| cp caspase-2 V225G | 1 min | 192 |
| cp caspase-2 D282E | 1 min | 191 |
| cp caspase-2 Thr 0.8<br>K83E E105V, E172V, V255M, D285Y | 4 min | 54 |
| cp caspase-2 Δ Linker<br>without linker between small and large subunit | 1 min | 73 |
| cp caspase-2 5 aa Linker<br>GGSGG linker between small and large subunit | 1 min | 74 |
| cp caspase-2 10 aa Linker<br>GSAGSAAGSG linker between small and large subunit | 1 min | 75 |
| cp caspase-2 ½ Δ SS Prop<br>partial deletion of small subunit propeptide | 1 min | 77 |
| cp caspase-2 Δ SS Prop<br>deletion of small subunit propeptide | 1 min | 76 |
| Stop Variant | 60 min | 14 |
| cp caspase-2 S20<br>C203Y, D285E | 3 min | 26 |
| cp caspase-2 C203S | 2 min | 198 |

TABLE 6-continued

Cleavage activity of cp caspase-2 variants. Time required to cleave 50% of the VDVAD-E2 substrate with P1' Gly which is used as the standard substrate. Cleavage of 1 mg/ml substrate by 0.01 mg/ml caspase at 25° C.

| Caspase Variant | Minutes | SEQ ID No. |
|---|---|---|
| cp caspase-2 S9 C203S<br>E105V, C203S | 2 min | 199 |
| cp caspase-2 SV19<br>C-terminal sequence DETDHGAVLRG | 2 min | 81 |
| cp caspase-2 D285E SV4<br>V201A, D285E | 3 min | 28 |
| cp caspase-2 D285E SV30<br>E174G, D285E | 3 min | 30 |
| cp Caspase 2 N85C | 2 min | 80 |
| cp Caspase 2 A86C | 1 min | 88 |
| cp Caspase-2 D285E Strep<br>C-terminal Strep-taq, D285E, D292S | 1 min | 16 |

5.4 P1' Tolerance

Cleavage site specificity and P1' tolerance of caspases have been studied using peptide substrates, degradome analysis, and phage libraries. Peptides are not ideal for this purpose, as structure influences the cleavage activity. Degradome studies, on the other hand, are influenced by the sequences occurring in the analyzed cells. To our knowledge, so far no study has systematically tested caspase specificity and P1' tolerance with protein substrates. Therefore, we permuted the P1' residue after the cleavage site in the fusion protein VDVAD-E2 (SEQ ID NO:33) (Example 2, section 2.2) to evaluate the cleavage efficiency of cp caspase-2 in dependency of the P1' residue.

Glycine was highly preferred in the P1' position, cleavage before all other residues was at least five-times less efficient. The group of amino acids that was reasonably well tolerated comprised small, basic, and aromatic residues, as well as Asn and Met.

Table 7 (Table 7.1 and Table 7.2) shows cleavage of E2 substrates with VDVAD (SEQ ID NO:45) recognition site and different P1' residues by cp caspase-2 variants. Activity is given in percent of activity for cleavage of VDVAD-E2 (SEQ ID NO:33) with a P1' glycine for each cp-caspase-2 variant. Thus Table 7 shows the P1'tolerance of the respective cp caspase-2 variant. All values (means±standard deviation) were determined with at least three independent experiments, executed with 1 mg/ml E2. For Asp-E2, Glu-E2, Ile-E2, Pro-E2 and Val-E2 cp caspase-2 concentration was 0.1 mg/ml, for all others 0.01 mg/ml. The given values already consider these concentration differences.

Table 8 (Table 8.1 and Table 8.2) further below shows the cleavage activity of all cpcaspase-2 variants for all P1'amino acids related to the cleavage activity of the standard cp caspase-2 (SEQ ID No. 6) in %. Thus Table 8 shows the extent of increase (or decrease) of P1'tolerance.

TABLE 7.1

Cleavage of E2 substrates with VDVAD recognition site and different P1' residues by cp caspase-2 variants. Activity is given in percent of activity for cleavage of VDVAD-E2 with a P1' glycine for each cp-caspase-2 variant. Average Values (Av.) and Standard Deviation (Dev.) are shown. All experiments were executed with 1 mg/ml E2 substrate. For P1' D, E, I, P, and V cp caspase-2 concentration was 0.1 mg/ml, for all others 0.01 mg/ml cp caspase-2 at 25° C.

| Caspase variants | P1' | A | C | D | E | F | H | I | K | L | M |
|---|---|---|---|---|---|---|---|---|---|---|---|
| cp caspase-2 | Av. | 2.24 | 17.8 | 0.140 | 0.033 | 4.85 | 1.91 | 0.08 | 4.09 | 0.25 | 2.80 |
| | Dev. | 0.59 | 2.15 | 0.047 | 0.009 | 1.53 | 0.40 | 0.02 | 1.19 | 0.07 | 0.18 |
| cp caspase-2 D285E | Av. | 1.82 | 7.58 | 0.086 | 0.025 | 1.76 | 0.62 | 0.06 | 1.40 | 0.10 | 1.29 |
| | Dev. | 0.60 | 1.61 | 0.015 | 0.004 | 0.29 | 0.26 | 0.02 | 0.05 | 0.01 | 0.24 |

TABLE 7.1-continued

Cleavage of E2 substrates with VDVAD recognition site and different P1' residues by cp caspase-2 variants. Activity is given in percent of activity for cleavage of VDVAD-E2 with a P1' glycine for each cp-caspase-2 variant. Average Values (Av.) and Standard Deviation (Dev.) are shown. All experiments were executed with 1 mg/ml E2 substrate. For P1' D, E, I, P, and V cp caspase-2 concentration was 0.1 mg/ml, for all others 0.01 mg/ml cp caspase-2 at 25° C.

| Caspase variants | P1' | A | C | D | E | F | H | I | K | L | M |
|---|---|---|---|---|---|---|---|---|---|---|---|
| cp caspase-2 D282T | Av. | 4.56 | 30.0 | 0.143 | 0.039 | 5.18 | 2.50 | 0.19 | 2.50 | 0.34 | 4.56 |
| | Dev. | 0.42 | 0.00 | 0.046 | 0.003 | 0.78 | 0.00 | 0.03 | 0.00 | 0.07 | 0.42 |
| cp caspase-2 H185A | Av. | 5.76 | 26.7 | 0.178 | 0.042 | 5.76 | 2.88 | 0.20 | 3.67 | 0.61 | 4.44 |
| D282T | Dev. | 0.30 | 3.82 | 0.036 | 0.000 | 0.30 | 0.15 | 0.06 | 0.30 | 0.20 | 0.64 |
| cp caspase-2 S9 D285 | Av. | 7.14 | 40.3 | 0.252 | 0.127 | 12.2 | 4.82 | 0.16 | 7.94 | 1.12 | 7.23 |
| E105V | Dev. | 1.55 | 0.48 | 0.081 | 0.025 | 1.94 | 1.51 | 0.01 | 1.59 | 0.15 | 1.47 |
| cp caspase-2 S9 D285E | Av. | 3.69 | | 0.21 | 0.17 | 14.5 | 21.8 | 0.16 | | 0.7 | 3.2 |
| E105V, D285E | Dev. | | | | | | | | | | |
| cp caspase-2 S9 Pro | Av. | 39.8 | 58.8 | 0.750 | 0.439 | 31.3 | 31.2 | 2.39 | 43.8 | 6.21 | 27.5 |
| D285 E105V, G171D, | Dev. | 6.84 | 20.3 | 0.160 | 0.145 | 11.0 | 11.9 | 0.81 | 5.15 | 2.03 | 8.63 |
| V225G, D282E | | | | | | | | | | | |
| cp caspase-2 S9 Pro | Av. | 34.1 | 43.9 | 1.400 | 0.961 | 20.1 | 12.1 | 1.48 | 21.7 | 4.03 | 24.2 |
| D285E E105V, G171D, | Dev. | 6.12 | 5.36 | 0.351 | 0.070 | 6.06 | 3.66 | 0.22 | 5.64 | 0.87 | 0.74 |
| V225G, D282E, D285E | | | | | | | | | | | |
| cp caspase-2 G171D | Av. | 12.5 | 43.0 | 0.292 | 0.148 | 9.49 | 6.18 | 0.64 | 15.5 | 1.81 | 12.5 |
| | Dev. | 0.00 | 14.4 | 0.050 | 0.026 | 2.68 | 0.46 | 0.17 | 2.03 | 0.09 | 2.04 |
| cp caspase-2 V225G | Av. | 2.98 | 13.1 | 0.173 | 0.036 | 2.67 | 2.45 | 0.10 | 3.49 | 0.28 | 2.65 |
| | Dev. | 0.67 | 1.53 | 0.059 | 0.002 | 0.18 | 0.76 | 0.02 | 0.88 | 0.03 | 0.60 |
| cp caspase-2 D282E | Av. | 2.59 | 16.0 | 0.080 | 0.047 | 3.80 | 1.90 | 0.10 | 3.75 | 0.28 | 2.44 |
| | Dev. | 0.32 | 2.74 | 0.009 | 0.011 | 0.35 | 0.17 | 0.01 | 0.42 | 0.00 | 0.30 |
| cp caspase-2 Thr 0.8 | Av. | 28.1 | 70.4 | 3.178 | 3.309 | 21.7 | 17.9 | 1.01 | 21.3 | 3.08 | 20.4 |
| K83E, E105V, E172V, | Dev. | 1.70 | 8.47 | 0.168 | 0.561 | 3.18 | 3.82 | 0.45 | 5.91 | 1.45 | 2.46 |
| V255M, D285Y | | | | | | | | | | | |

TABLE 7.2

Cleavage of E2 substrates with VDVAD recognition site and different P1' residues by cp caspase-2 variants. Activity is given in percent of activity for cleavage of VDVAD-E2 with a P1' glycine for each cp-caspase-2 variant. Average Values (Av.) and Standard Deviation (Dev.) are shown. All experiments were executed with 1 mg/ml E2 substrate. For P1' D, E, I, P, and V cp caspase-2 concentration was 0.1 mg/ml, for all others 0.01 mg/ml cp caspase-2 at 25° C.

| Caspase variants | P1' | N | P | Q | R | S | T | V | W | Y |
|---|---|---|---|---|---|---|---|---|---|---|
| cp caspase-2 | Av. | 4.41 | 0.0025 | 0.48 | 4.95 | 8.01 | 0.56 | 0.16 | 3.47 | 2.65 |
| | Dev. | 0.97 | 0.0009 | 0.16 | 0.68 | 1.08 | 0.00 | 0.02 | 0.12 | 0.13 |
| cp caspase-2 D285E | Av. | 2.97 | 0.0006 | 0.41 | 4.27 | 4.48 | 0.55 | 0.11 | 0.77 | 0.79 |
| | Dev. | 0.89 | 0.0002 | 0.12 | 0.24 | 0.28 | 0.09 | 0.01 | 0.07 | 0.04 |
| cp caspase-2 D282T | Av. | 4.93 | 0.0035 | 0.52 | 6.75 | 12.7 | 1.72 | 0.36 | 3.33 | 3.03 |
| | Dev. | 0.38 | 0.0000 | 0.10 | 0.55 | 0.76 | 0.49 | 0.05 | 0.38 | 0.29 |
| cp caspase-2 H185A D282T | Av. | 5.08 | 0.0028 | 0.61 | 6.91 | 12.5 | 2.36 | 0.42 | 4.06 | 3.17 |
| | Dev. | 0.39 | 0.0002 | 0.11 | 0.51 | 1.25 | 0.38 | 0.10 | 0.58 | 0.20 |
| cp caspase-2 S9 D285 | Av. | 11.7 | 0.0065 | 0.90 | 14.6 | 17.3 | 1.67 | 0.46 | 9.83 | 6.87 |
| E105V | Dev. | 0.00 | 0.0013 | 0.11 | 3.94 | 3.44 | 0.33 | 0.09 | 2.42 | 1.25 |
| cp caspase-2 S9 D285E | Av. | | 0.005 | 0.80 | | | 1.75 | 0.32 | | |
| E105V, D285E | Dev. | | | | | | | | | |
| cp caspase-2 S9 Pro D285 | Av. | 40.0 | 0.1380 | 10.9 | 62.1 | 55.5 | 16.0 | 5.25 | 22.7 | 28.6 |
| E105V, G171D, V225G, | Dev. | 0.00 | 0.0483 | 3.48 | 15.9 | 16.4 | 4.88 | 1.74 | 7.05 | 0.00 |
| D282E | | | | | | | | | | |
| cp caspase-2 S9 Pro D285E | Av. | 21.0 | 0.0651 | 2.10 | 45.2 | 39.9 | 15.1 | 3.66 | 16.4 | 12.3 |
| E105V, G171D, V225G, | Dev. | 3.61 | 0.0142 | 0.76 | 4.30 | 3.88 | 2.16 | 0.45 | 3.44 | 2.52 |
| D282E, D285E | | | | | | | | | | |
| cp caspase-2 G171D | Av. | 12.8 | 0.0331 | 3.74 | 24.6 | 23.8 | 5.21 | 1.03 | 8.41 | 3.65 |
| | Dev. | 4.19 | 0.0126 | 0.69 | 4.83 | 4.32 | 0.88 | 0.08 | 0.45 | 0.52 |
| cp caspase-2 V225G | Av. | 4.82 | 0.0019 | 0.56 | 4.68 | 5.31 | 0.63 | 0.14 | 3.81 | 2.54 |
| | Dev. | 0.99 | 0.0006 | 0.00 | 1.17 | 1.33 | 0.03 | 0.02 | 1.17 | 0.78 |
| cp caspase-2 D282E | Av. | 4.22 | 0.0034 | 0.51 | 5.19 | 5.93 | 0.95 | 0.20 | 4.19 | 3.52 |
| | Dev. | 0.17 | 0.0005 | 0.08 | 0.52 | 0.85 | 0.06 | 0.02 | 0.21 | 0.21 |
| cp caspase-2 Thr 0.8 | Av. | 26.9 | 0.0332 | 17.3 | 35.2 | 51.2 | 13.1 | 3.26 | 17.41 | 13.2 |
| K83E, E105V, E172V, | Dev. | 3.01 | 0.0015 | 1.10 | 4.23 | 7.67 | 1.79 | 0.45 | 4.29 | 0.81 |
| V255M, D285Y | | | | | | | | | | |

TABLE 8.1

Cleavage activity of all cpcaspase-2 variants for all P1' amino acids related to the cleavage activity of the standard cp caspase-2 (SEQ ID No. 6) in %. Average Values (Av.) and Standard Deviation (Dev.) values are normed to the activity of the respective caspase with VDVAD-E2 with P1' Gly at 25° C. and compared to the activity of cp caspase-2.

| Caspase variants | P1' | A | C | D | E | F | H | I | K | L | M |
|---|---|---|---|---|---|---|---|---|---|---|---|
| cp caspase-2 | Av. | 100% | 100% | 100% | 100% | 100% | 100% | 100% | 100% | 100% | 100% |
| | Dev. | 26% | 12% | 34% | 27% | 37% | 21% | 27% | 29% | 29% | 6% |
| cp caspase-2 | Av. | 81% | 43% | 62% | 76% | 40% | 32% | 79% | 34% | 41% | 46% |
| D285E | Dev. | 27% | 9% | 11% | 11% | 7% | 14% | 22% | 1% | 3% | 8% |
| cp caspase-2 | Av. | 204% | 169% | 102% | 118% | 119% | 131% | 240% | 61% | 135% | 163% |
| D282T | Dev. | 19% | 0% | 33% | 8% | 18% | 0% | 34% | 0% | 29% | 15% |
| cp caspase-2 | Av. | 258% | 150% | 127% | 125% | 132% | 151% | 257% | 90% | 242% | 159% |
| H185A, D282T | Dev. | 14% | 22% | 26% | 0% | 7% | 8% | 70% | 7% | 80% | 23% |
| cp caspase-2 | Av. | 319% | 227% | 180% | 381% | 281% | 252% | 203% | 194% | 447% | 258% |
| S9 D285 | Dev. | 69% | 3% | 58% | 76% | 45% | 79% | 15% | 39% | 58% | 52% |
| E105V | | | | | | | | | | | |
| cp caspase-2 | Av. | 166% | | 150% | 512% | | | 203% | | 288% | 114% |
| S9 D285E | Dev. | | | | | | | | | | |
| E105V, D285E | | | | | | | | | | | |
| cp caspase-2 | Av. | 1781% | 331% | 535% | 1321% | 720% | 1568% | 2965% | 1070% | 2484% | 982% |
| S9 Pro D285 | Dev. | 306% | 114% | 114% | 436% | 253% | 436% | 952% | 126% | 813% | 309% |
| E105V G171D | | | | | | | | | | | |
| V225G D282E | | | | | | | | | | | |
| cp caspase-2 | Av. | 1523% | 247% | 999% | 2894% | 462% | 634% | 1877% | 530% | 1611% | 865% |
| S9 Pro D285E | Dev. | 274% | 30% | 250% | 210% | 139% | 191% | 278% | 138% | 347% | 26% |
| E105V, G171D, | | | | | | | | | | | |
| V225G, D282E, | | | | | | | | | | | |
| D285E | | | | | | | | | | | |
| cp caspase-2 | Av. | 559% | 242% | 208% | 445% | 218% | 324% | 808% | 379% | 722% | 447% |
| G171D | Dev. | 0% | 81% | 36% | 78% | 62% | 24% | 214% | 49% | 37% | 73% |
| cp caspase-2 | Av. | 133% | 74% | 124% | 107% | 61% | 128% | 130% | 85% | 113% | 95% |
| V225G | Dev. | 30% | 9% | 42% | 6% | 4% | 40% | 23% | 21% | 13% | 21% |
| cp caspase-2 | Av. | 116% | 90% | 57% | 142% | 87% | 99% | 123% | 92% | 111% | 87% |
| D282E | Dev. | 14% | 15% | 6% | 33% | 8% | 9% | 12% | 10% | 0% | 11% |
| cp caspase-2 | Av. | 1258% | 397% | 2268% | 9960% | 498% | 940% | 1285% | 519% | 1232% | 728% |
| Thr 0.8 | Dev. | 76% | 48% | 120% | 1688% | 73% | 200% | 571% | 144% | 581% | 88% |
| K83E, E105V, | | | | | | | | | | | |
| E172V, V255M, | | | | | | | | | | | |
| D285Y | | | | | | | | | | | |

TABLE 8.2

Cleavage activity of all cpcaspase-2 variants for all P1'amino acids related to the cleavage activity of the standard cp caspase-2 (SEQ ID No. 6) in %. Average Values (Av.) and Standard Deviation (Dev.) values are normed to the activity of the respective caspase with VDVAD-E2 with P1' Gly at 25° C. and compared to the activity of cp caspase-2.

| Caspase variants | P1' | N | P | Q | R | S | T | V | W | Y |
|---|---|---|---|---|---|---|---|---|---|---|
| cp caspase-2 | Av. | 100% | 100% | 100% | 100% | 100% | 100% | 100% | 100% | 100% |
| | Dev. | 22% | 38% | 34% | 14% | 13% | 0% | 16% | 4% | 5% |
| cp caspase-2 | Av. | 67% | 22% | 87% | 86% | 56% | 99% | 68% | 22% | 30% |
| D285E | Dev. | 20% | 10% | 26% | 5% | 4% | 16% | 4% | 2% | 1% |
| cp caspase-2 | Av. | 112% | 141% | 108% | 136% | 158% | 310% | 224% | 96% | 114% |
| D282T | Dev. | 9% | 0% | 21% | 11% | 10% | 88% | 33% | 11% | 11% |
| cp caspase-2 | Av. | 115% | 115% | 127% | 140% | 156% | 425% | 265% | 117% | 120% |
| H185A, D282T | Dev. | 9% | 10% | 23% | 10% | 16% | 68% | 61% | 17% | 7% |
| cp caspase-2 S9 | Av. | 265% | 265% | 188% | 295% | 216% | 300% | 291% | 283% | 260% |
| D285 | Dev. | 0% | 52% | 22% | 80% | 43% | 59% | 56% | 70% | 47% |
| E105V | | | | | | | | | | |
| cp caspase-2 S9 | Av. | | 407% | 167% | | | 315% | 202% | | |
| D285E | Dev. | | | | | | | | | |
| E105V, D285E | | | | | | | | | | |
| cp caspase-2 S9 | Av. | 907% | 5617% | 2275% | 1255% | 692% | 2883% | 3314% | 654% | 1079% |
| Pro D285 | Dev. | 0% | 1964% | 728% | 322% | 204% | 878% | 1101% | 203% | 0% |
| E105V G171D | | | | | | | | | | |
| V225G D282E | | | | | | | | | | |

TABLE 8.2-continued

Cleavage activity of all cpcaspase-2 variants for all P1'amino acids related to the cleavage activity of the standard cp caspase-2 (SEQ ID No. 6) in %. Average Values (Av.) and Standard Deviation (Dev.) values are normed to the activity of the respective caspase with VDVAD-E2 with P1' Gly at 25° C. and compared to the activity of cp caspase-2.

| Caspase variants | P1' | N | P | Q | R | S | T | V | W | Y |
|---|---|---|---|---|---|---|---|---|---|---|
| cp caspase-2 S9 | Av. | 476% | 2650% | 440% | 914% | 498% | 2717% | 2308% | 472% | 466% |
| Pro D285E E105V, G171D, V225G, D282E, D285E | Dev. | 82% | 579% | 160% | 87% | 48% | 388% | 283% | 99% | 95% |
| cp caspase-2 | Av. | 290% | 1348% | 782% | 497% | 296% | 937% | 650% | 242% | 138% |
| G171D | Dev. | 95% | 512% | 143% | 98% | 54% | 159% | 48% | 13% | 20% |
| cp caspase-2 | Av. | 109% | 77% | 116% | 95% | 66% | 114% | 89% | 110% | 96% |
| V225G | Dev. | 23% | 26% | 0% | 24% | 17% | 6% | 11% | 34% | 30% |
| cp caspase-2 | Av. | 96% | 138% | 108% | 105% | 74% | 171% | 127% | 121% | 133% |
| D282E | Dev. | 4% | 19% | 18% | 11% | 11% | 12% | 15% | 6% | 8% |
| cp caspase-2 Thr | Av. | 610% | 1350% | 3609% | 712% | 639% | 2355% | 2057% | 501% | 497% |
| 0.8 K83E, E105V, E172V, V255M, D285Y | Dev. | 68% | 61% | 229% | 86% | 96% | 322% | 283% | 123% | 31% |

Taken together, these data show that variants of a cp caspase-2, comprising amino acid substitutions at any one or more of positions 83, 105, 171, 172, 185, 225, 255, 282, 285 of SEQ ID No. 6, display significantly improved P1' tolerance for at least one amino acid. In most cases, these variants comprise significantly improved P1' tolerance for multiple amino acids.

Furthermore, these data show that even though amino acid substitutions at positions 85, 86, 132, 141, 174, 200, 201, 203 of SEQ ID No. 6 do not improve P1' tolerance, they do not hamper caspase activity significantly. Table 6, for example, shows that variants comprising amino acid substitutions at positions 85, 86, 132, 141, 174, 200, 201, or 203 of SEQ ID No. 6 still cleave about 50% of the substrate VDVAD-E2 (SEQ ID NO:33) within 2 or 3 minutes. These represent examples for functionally active variants of cp-caspases-2 of the present invention. Furthermore, all variants selected using the selection system as described in Example 3 and as shown in Table 24 are further examples of functionally active variants of cp-caspases-2, since they all have catalytic activity for the cleavage of the VDVAD (SEQ ID NO:45) P1' motif (a caspase-2 cleavage site). Otherwise the colonies/clones would not have grown.

Example 6: cp caspase-2 Variants Recognizing Different Recognition Sites than VDVAD (SEQ ID NO:45)

6.1 System for In Vivo Selection of Cp Caspase-2 Variants, Similar as 3.1

The selection system described in section 3.1 of Example 3 is used for the selection of caspases that tolerate different cleavage sites than VDVAD (SEQ ID NO:45).

A gene library of 6His-GSG-XDXXD-AM-Thr-pyrB (SEQ ID No. 22) cpATCase constructs was cloned with degenerate primers to insert random mutations in the caspase recognition sequence at the positions P5, P3, and P2.

*E. coli* BL21(DE3) ΔpyrBI cells were generated that contain the cp caspase-2 construct (SEQ ID No. 7) in a pACYCDuet vector. After transformation of the cpATCase library into the cells the selection, as described above, was executed either in M9 medium or on M9 agar plates at 30° C. for 24-48 h.

Several single colonies were sequenced and the nucleotide sequence of the cpATCase was analyzed detecting alternative cleavage sites tolerated by cp caspase-2.

The alternative cleavage sites were cloned into the substrate proteins and the activity of different cp caspase-2 variants were tested as described above in Example 1.

Example 7: Simultaneous Mutation of Residues $Val^{105}$ and $Gly^{171}$

7.1 Design of Constructs and Selection

Saturated mutagenesis with degenerate primers, designed to create all possible 19 amino acid substitutions in the protein, was performed with cp caspase-2 S9 (SEQ ID No. 51), comprising the additional G171 D substitution, as a template. The gene library containing all 400 variants with possible combinations of mutations in positions 105 and 171 were transformed in *E. coli* BL21(DE3) ΔpyrBI cells that contained the VDVAD (SEQ ID NO:45)-cpATCase substrate with P1' Thr (SEQ ID No. 22). The selection, as described in Example 3 above, was executed either in M9 medium or on M9 agar plates at 30° C. for 24-48 h.

The DNA of several single colonies was analyzed, detecting combinations of mutations in active variants.

The combinatorial mutants were expressed, purified and tested as described above in Example 1.

Example 8: Comparison of Generated Variants to Wild-Type Caspase-2

DEVD-E2 (SEQ ID No. 57)

DEVD (SEQ ID NO:206) is the preferred cleavage site of caspases-3 and -7. DEVD-E2 (SEQ ID NO:57) was used to evaluate the influence of the P5 residue, because the influence of the amino acids in the P2 and P3 positions on caspase-2 activity are considered insignificant. The substrate was processed 140 times slower than VDVAD-E2 (SEQ ID No. 33) by cp caspase-2 (SEQ ID No. 6) showing that the recognition of the P5 residue is very important for caspase-2 and cp caspase-2.

This is in accordance with results from fluorescent peptides [26, 24], and proves the initial assumption of this study that caspase-2 was more specific than other caspases, because of its pentapeptidic recognition site. This seems to be even more pronounced in the circularly permuted variant, as the literature only describes a 35-fold increase in activity with VDVAD (SEQ ID NO:45) over DEVD (SEQ ID NO:206) [26].

8.1 Comparison of Specificity with Wild-Type Caspase-2

The specificity of cp caspase-2 (SEQ ID No. 6) was compared with commercially available wild-type caspase-2 (human, recombinant, active Caspase-2, Enzo Life Sciences, Farmingdale, NY, USA). 72 U/ml of the wild-type caspase-2 were used for cleavage reactions, according to the specifications, this equals about 0.005 mg/ml enzyme, half the concentration used in standard reactions with cp caspase-2. But the wild-type caspase was even six times less active than cp caspase-2 under the same conditions (1 mg/ml VDVAD-E2 (SEQ ID NO:33) was processed to 50% in 6 min).

While the absolute activities of the enzymes might be difficult to compare, because of different purity and concentration, a clear discrepancy could be found between their specificities. Wild-type caspase-2 cleaved DEVD-E2 (SEQ ID NO:57) only 44 times slower than VDVAD-E2 (SEQ ID NO:33), while cp caspase-2 has a 140-fold preference for VDVAD (SEQ ID NO:45) over DEVD (SEQ ID NO:206). Thus, the cp caspase-2 is three times more specific than the wild-type enzyme (FIG. 9). FIG. 9 shows cleavage of DEVD-E2 (SEQ ID NO:57) by cp caspase-2 (SEQ ID No. 6) and wild-type caspase-2. Reduction of cleavage activity with DEVD-E2 (SEQ ID NO:57) substrate, given in x-fold decrease in comparison to VDVAD-E2 (SEQ ID NO:33) processing. The graph shows means±standard deviation of at least three independent experiments. (*) indicates statistical significance at level $p \leq 0.05$, () at level $p \leq 0.01$, and (*) at level $p \leq 0.001$.

8.2.: Production and Characterization of a Wild Type Caspase-2

For comparison of wild-type caspase-2 with cp-caspase-2 variants a human caspase-2 was produced.

Production of Wt Caspase-2:

Production of wt caspase-2 was performed in a 30 L (23 L net volume, 5 L batch volume) computer-controlled bioreactor (Bioengineering; Wald, Switzerland) equipped with standard control units (Siemens PS7, Intellution iFIX). The pH was maintained at a set-point of 7.0±0.05 by addition of 25% ammonia solution (w/w), the temperature was set to 37° C.±0.5° C. in the batch phase and 30° C.±0.5° C. in the fed-batch phase. To avoid oxygen limitation the DO level was held above 30% saturation by adjusting the stirrer speed and the aeration rate of the process air. The maximum overpressure in the head space was 1.1 bar.

Pre-cultures for inoculation were grown in synthetic media calculated to produce 3 g/L. For incubation 1 mL of a deep frozen MCB was aseptically transferred to 400 mL medium and cultivated in two 2000 mL shaking flasks at 37° C. and 180 rpm until an OD of approx. 4 was reached.

For cultivation, minimal media calculated to produce 64 g cell dry mass (CDM) in the batch phase and 890 g CDM during feed phase were used. The batch medium was prepared volumetrically; the components were dissolved in 8 L RO—$H_2O$. The fed-batch medium was prepared gravimetrically; the final weight was 8.45 kg. All components for the fed-batch medium were weighed in and dissolved in RO—$H_2O$ separately. All components (obtained from MERCK), were added in relation to the theoretical grams of cell dry mass to be produced: The composition of the batch and the fed-batch medium is as follows: 94.1 mg/g $KH_2PO_4$, 31.8 mg/g $H_3PO_4$ (85%), 41.2 mg/g $C_6H_5Na_3O_7$*$2H_2O$, 45.3 mg/g $NH_4SO_4$, 46.0 mg/g $MgCl_2$*$2H_2O$, 20.2 mg/g $CaCl_2$)*2 $H_2O$, 50 μL trace element solution, and 3.3 g/g $C_6H_{12}O_6$*H2O. The trace element solution was prepared in 5 N HCl and included 40 g/L $FeSO_4$·*$7H_2O$, 10 g/L $MnSO_4$·*$H_2O$, 10 g/L $AlCl_3$·*6 $H_2O$, 4 g/L $CoCl_2$, 2 g/L $ZnSO_4$·*$7H_2O$, 2 g/L $Na_2MoO_2$·*$2H_2O$, 1 g/L $CuCl_2$·*2 $H_2O$, and 0.5 g/L $H_3BO_3$. To accelerate initial growth of the population, the complex component yeast extract (150 mg/g calculated CDM) was added to the batch medium. Nitrogen level was maintained by adding 25% ammonium hydroxide solution (w/w) for pH control. Antifoam (PPG 2000) 0.5 mL/L total volume was added at the beginning.

The fed-batch phase (29 h) was performed at 30° C. with an exponential feeding strategy with a consistent growth rate of p=0.1 h-1. The substrate feed was controlled by increasing pump speed according to the exponential growth algorithm, X=X0·eμt, with superimposed feedback control of weight loss in the substrate tank. Induction started with fed-batch phase by adding 0.5 μmol IPTG/g CDM directly to the feed-media to achieve a protein production for 4 generations. IPTG concentration was calculated with the theoretical final CDM.

| Component | Quantity |
|---|---|
| Batch medium components | |
| $KH_2PO_4$ | 0.094 g/g final CDM |
| 85% $H_3PO_4$ | 0.032 g/g final CDM |
| Yeast extract | 0.15 g/g CDM (batch) |
| $C_6H_5Na_3O$ $2H_2O$ | 0.25 g/g final CDM |
| $MgCl_2$•$7H_2O$ | 0.1 g/g CDM (batch) |
| $CaCl_2$•$2H_2O$ | 0.02 g/g CDM (batch) |
| $(NH_4)_2SO_4$ | 0.046 g/g final CDM |
| Trace element solution | 50 μL/g CDM (batch) |
| $C_6H_{12}O_6$•$H_2O$ | 3.3 g/g CDM (batch) |
| Fed batch medium components | |
| $MgCl_2$•$7H_2O$ | 0.1 g/g CDM (fed-batch) |
| $CaCl_2$•$2H_2O$ | 0.02 g/g CDM (fed-batch) |
| Trace element solution | 50 uL/g CDM (fed-batch) |
| $C_6H_{12}O_6$•$H_2O$ | 3.3 g/g CDM (fed-batch) |

In addition to standard online monitoring (pH, stirrer speed, temperature and p02) the concentration of p02 and 02 in the outlet air was measured with a BlueSens gas analyzer. Sampling of the standard offline process parameters started after one generation in fed-batch mode. The first sample was withdrawn from the bioreactor prior to induction. Optical density (OD600) was measured with a spectrophotometer at wavelength λ=600 nm. Samples were diluted in PBS to ensure a measurement at a linear range from 0.1 to 0.8. Cell dry mass (CDM) was determined by centrifugation of 10 mL of cell suspension for 8 min at 8500 rpm. The supernatant was discarded and cells were resuspended with RO—$H_2O$ and centrifuged. Water was discarded and cell were resuspended again with RO—$H_2O$. Cell suspension was transferred into a beaker, which was weighted before. Beakers were dried for at least 24 h at 105° C. and weighted again. The difference in weight account for the CDM.

For the determination of the content of cp caspase-2 and variants, aliquots of approximately 1.0 mg CDM of the samples were centrifuged (10 min. at 13200 rpm); the supernatants were discarded, the insides of the tubes were carefully blotted dry and the samples were stored at −20° C. The *E. coli* cell mass was harvested by centrifugation at 18,590 rcf for 15 minutes and the supernatant was discarded. The *E. coli* cell harvest was solubilized using homogenization buffer (50 mM sodium phosphate, 300 mM NaCl, pH 8.0). The cells were re suspended at a concentration of 400 g wet cell mass per L. Cell lysis was performed through high pressure homogenization at 1400 bar/140 bar with two passages with an in-line counter current chiller set to 10° C. The homogenate was centrifuged at 18,590 rcf for 2.5 hours at 4° C. The pellet was discarded and the supernatant used. Before chromatography the supernatant was filtered through a 0.22 μm membrane.

The wt caspase-2 carrying a poly-his-tag was captured using immobilized metal affinity chromatography (IMAC). The following buffers were used: equilibration buffer: 50 mM sodium phosphate, 300 mM NaCl, 20 mM imidazole, pH 8.0. Elution buffer: 50 mM sodium phosphate, 300 mM NaCl, 500 mM imidazole, pH 8.0.

Imidazole was added to the clarified supernatant before IMAC, to a final concentration of 20 mM imidazole. 57 CV clarified supernatant were loaded to an equilibrated Ni-Sepharose 6 Fast Flow column (50×18 mm, 35 mL). A residence time of 7 minutes was used during loading and 3 minutes for subsequent steps. After loading was completed the column was washed for 10 CV with equilibration buffer. The bound wt caspase 2 was eluted using a step gradient to 100% elution buffer for 10 CV.

The elution fractions were analyzed using SDS-PAGE and all fractions containing wt caspase-2 were used for the next purification step.

The capture eluate of wt caspase-2 was buffer exchanged before the polishing chromatography step. Tangential flow ultra-/diafiltration with a 5 kDa cut off membrane was used with a sample buffer of 50 mM sodium citrate, pH 5.0. In total 5 volumes were exchanged.

The capture step used cation exchange chromatography on SP Sepharose HP (5×24 mm, 0.5 mL) using the following buffers: equilibration buffer A: 50 mM sodium citrate, pH 5.0. Elution buffer B: 50 mM sodium citrate, 1 M NaCl, pH 5.0.

Buffer exchanged capture eluate was loaded on the equilibrated polishing column. The residence time was held constant at 5 minutes. The column was loaded with 37 CV of buffer exchanged capture eluate. Wt caspase-2 was eluted in a linear gradient from 0-100% B in 10 CV. The elution fractions were analyzed using Western blot and SDS PAGE and the fractions positive for the small sub unit of wt caspase-2 were combined and stored at −80° C. Before performing enzyme kinetic measurements, oxidation induced activity losses were reversed by incubating wt caspase-2 with 100 mM DTT for 15 minutes.

Characterization of Wt Caspase-2

FRET Assay

Michaelis Menten kinetic was determined for wt caspase-2 and cp caspase-2 for the following substrates: VDVADFA (SEQ ID NO:318), VDVADGA (SEQ ID NO:319), VDVADQA (SEQ ID NO:320) and VDVADVA (SEQ ID NO:321), where the P1' amino acid is indicated by bold and underlined font.

TABLE 9

FRET results for wt and cp caspase-2.

| | P1' | F | G | Q | V |
|---|---|---|---|---|---|
| wt caspase-2 | $K_M$ (M) | 7.9E−05 | 9.7E−05 | 1.1E−04 | 8.6E−05 |
| | 95% confidence interval $K_M$ (M) | 1.1E−05 | 1.2E−05 | 9.8E−06 | 8.9E−06 |
| | $k_{cat}$ ($s^{-1}$) | 8.4E−04 | 3.2E−02 | 5.7E−04 | 2.3E−04 |
| | 95% confidence interval $k_{cat}$ ($s^{-1}$) | 5.3E−05 | 1.9E−03 | 2.4E−05 | 1.1E−05 |
| | $k_{cat}/K_M$ ($M^{-1}s^{-1}$) | 11 | 335 | 5.0 | 2.7 |

TABLE 9-continued

FRET results for wt and cp caspase-2.

| | P1' | F | G | Q | V |
|---|---|---|---|---|---|
| cp caspase-2 | $K_M$ (M) | 5.8E−05 | 4.9E−05 | 1.3E−04 | 7.3E−05 |
| | 95% confidence interval $K_M$ (M) | 1.5E−05 | 1.3E−05 | 2.4E−05 | 1.8E−05 |
| | $k_{cat}$ ($s^{-1}$) | 7.9E−03 | 2.7E−01 | 4.6E−03 | 1.7E−03 |
| | 95% confidence interval $k_{cat}$ ($s^{-1}$) | 8.1E−04 | 2.7E−02 | 4.6E−04 | 1.9E−04 |
| | $k_{cat}/K_M$ ($M^{-1}s^{-1}$) | 136 | 5542 | 36 | 24 |

The FRET results in Table 9 show significant differences between the two proteases. Cp caspase-2 exhibits catalytic efficiencies approximately one order of magnitude higher than wt caspase-2. While the Michaelis constant KM appears mostly unaffected by circular permutation, the turnover number kcat is the cause for the stark differences in catalytic efficiency kcat/KM between wt caspase-2 and cp caspase-2. The produced wt caspase-2 seems to exhibit slightly better P1' tolerance compared to cp caspase-2 (both not comprising the amino acid substitutions for improved P1' tolerance described herein), e.g. F as P1' is cleaved with 2.5% catalytic efficiency in cp caspase 2 compared to 3.2% in wt caspase-2. This slight increase in P1' (1.3 to 2.3-fold increase) is overshadowed by the, on average eleven times lower catalytic efficiency and eight times lower turnover number of wt caspase-2.

Tolerance for Elevated Temperatures

Cleavage of a heat stable model fusion tag protein, namely GFP, was used to quantify the tolerance of caspase-2 towards elevated temperatures.

TABLE 10

Cleavage of GFP carrying the fusion tag at different temperatures

| | Temperature (° C.) | 25 | 50 |
|---|---|---|---|
| wt caspase-2 | Time (min) | 7 | 7 |
| | $v_0$ ($s^{-1}$) | 2.2E−03 | 4.3E−03 |
| | Standard deviation $v_0$ ($s^{-1}$) | 1.7E−04 | 6.4E−05 |
| cp caspase-2 | Time (min) | 7 | 7 |
| | $v_0$ ($s^{-1}$) | 3.5E−03 | 9.8E−03 |
| | Standard deviation $v_0$ ($s^{-1}$) | 6.7E−05 | 6.0E−04 |

The GFP cleavage results in Table 10 show comparable heat tolerance between the two proteases. The cleavage reaction with cp caspase-2 is 1.6-fold faster, than with wt caspase-2 at 25° C. This difference increases to 2.3-fold at 50° C., showcasing the increased stability of cp caspase-2 at elevated temperatures. In general, the cleavage reaction at 50° C. is 1.9 times faster for wt caspase-2 and 2.8 times faster for cp caspase 2. This is a clear benefit if a heat stable target protein has to be processed.

Tolerance to Chaotropic Conditions

Cleavage of a model fusion tag protein stable in 4 M urea, namely FGF2, was used to quantify the tolerance of caspase-2 towards chaotropic conditions.

TABLE 11

Cleavage of FGF2 carrying the fusion tag at different urea concentrations.

| | Urea concentration (M) | 0 | 4 |
|---|---|---|---|
| wt caspase-2 | Time (min) | 5 | 90 |
| | $v_0$ ($s^{-1}$) | 4.7E−02 | 5.7E−04 |
| | Standard deviation $v_0$ ($s^{-1}$) | 5.6E−03 | 1.4E−05 |

TABLE 11-continued

Cleavage of FGF2 carrying the fusion tag at different urea concentrations.

| | Urea concentration (M) | 0 | 4 |
|---|---|---|---|
| cp caspase-2 | Time (min) | 5 | 90 |
| | $v_0$ ($s^{-1}$) | 1.5E−01 | 2.0E−03 |
| | Standard deviation $v_0$ ($s^{-1}$) | 2.0E−03 | 6.0E−05 |

The FGF2 cleavage results in Table 11 show comparable tolerance for chaotropic conditions between the two proteases. In order to quantify the cleavage product in the linear range, the reaction had to be stopped at differing time points. Both proteases show almost identical behavior in the presence of 4 M urea, were the reaction rate is reduced to 1.2% and 1.3% for wt caspase-2 and cp caspase-2 respectively. For this particular model protein, cp caspase-2 exhibited a 3.2-fold increased reaction rate relative to wt caspase-2.

Manufacturability

Perhaps the biggest observable difference between the two proteases, is in their ease of manufacture. In order to express the difference in manufacturability between wt caspase-2 and cp caspase-2, we calculated the amount of dry cell mass required to produce one milligram of purified enzyme. This takes into account the differences in specific protein content of the *E. coli* fermentation and the differences in downstream processing yields. It does not take into account differences in biomass yield between fermentations. In order to produce 1 mg of wt caspase-2, 70 g of cell dry mass (CDM) were required. For the production of cp caspase-2, only 34 mg of CDM were needed per milligram pure enzyme. This corresponds to a difference in manufacturability of a factor of 2,033.

Conclusion

FRET assay results with 4 different P1' amino acids showed a general trend of tenfold higher catalytic efficiencies of the cp caspase-2 compared to wt caspase-2. The cleavage of non peptide substrates, showed two to three-fold faster cleavage reaction depending on the protein substrate. The circular permutation of caspase-2 has apparently lead to an increase in heat tolerance, showcased by the larger increase in turnover rate at 50° C. The tolerance to chaotropic conditions also appears slightly higher The largest differentiating factor between wt and cp enzymes is their manufacturability. While the expression level of wt caspase-2 is very low (under the limit of quantification), cp caspase-2 reaches expression levels of 80 mg specific protein content per g CDM. This also results in much lower losses during DSP, where a process yield of about 35% can be achieved for cp caspase-2.

Example 9: Production Process for Cp Caspase-2 and Variants

9.1 Upstream Processing of Cp Caspase-2 and Variants

For the production of cp caspase-2 and variants with and without solubility tag lab-scale fermentations were performed as described below. Different expression clones were compared regarding cell growth and soluble recombinant protein production. For final process optimization, a series of cultivation runs were conducted according to a Design of experiments (DoEs) approach.

9.1.1 Bacterial Strain, Plasmid and Cp Caspase-2 and Variants

The *E. coli* strain BL21(DE3) [$F^-$, fhuA2, Ion, ompT, gal, dcm, ΔhsdS λ DE3 [λ sBamHIo, ΔEcoRI-B int::(lacI::

PlacUV5::T7 gene1) i21 Δnin5], purchased from Novagen, was transformed with a pET30a vector carrying the gene for cp caspase-2 or variants with and without solubility tag under the T7 promoter/operator system. The expression systems cultivated in lab-scale bioreactors are listed in Table 12.

TABLE 12

Expression clones for cp caspase-2 and variants with and without solubility tag

| Name of Expression clone | Caspase variant | SEQ ID |
|---|---|---|
| BL21(DE3)(pET30a_6H-cpCasp2D) | cp caspase-2 D | SEQ ID No. 6 |
| BL21(DE3)(pET30a_T7AC-6H-cpCasp2D) | cp caspase-2 D | SEQ ID No. 41 |
| BL21(DE3)(pET30a_6H-mS9ProE) | mS9 Pro E285 | SEQ ID No. 70 |
| BL21(DE3)(pET30a_T7AC-6H-mS9ProE) | mS9 Pro E285 | SEQ ID No. 71 |
| BL21(DE3)(pET30a_6H-mS9ProD) | mS9 Pro D285 | SEQ ID No. 52 |
| BL21(DE3)(pET30a_T7AC-6H-mS9ProD) | mS9 Pro D285 | SEQ ID No. 72 |

9.1.2 Lab-Scale Fermentation of Cp Caspase-2 and Variants.

9.1.2.1 Fermentation Media

For high cell density (HCD) cultivation experiments minimal media calculated to produce 80 g cell dry mass (CDM) in the batch phase and 1450 g CDM during feed phase were used. The batch medium was prepared volumetrically; the components were dissolved in 10 L RO—$H_2O$. The fed-batch medium was prepared gravimetrically; the final weight was 10.1 kg. All components for the fed-batch medium were weighed in and dissolved in RO—$H_2O$ separately. All components (obtained from MERCK), were added in relation to the theoretical grams of cell dry mass to be produced: The composition of the batch and the fed-batch medium is as follows: 94.1 mg/g $KH_2PO_4$, 31.8 mg/g $H_3P_4$ (85%), 41.2 mg/g $C_6H_5Na_3O_7$*2 $H_2O$, 45.3 mg/g $NH_4SO_4$, 46.0 mg/g $MgCl_2$*2 $H_2O$, 20.2 mg/g $CaCl_2$*2 $H_2O$, 50 µL trace element solution, and 3.3 g/g $C_6H_{12}O_6$*$H_2O$. The trace element solution was prepared in 5 N HCl and included 40 g/L $FeSO_4$·*7$H_2O$, 10 g/L $MnSO_4$·*$H_2O$, 10 g/L $AlCl_3$·*6 $H_2$, 4 g/L $CoCl_2$, 2 g/L $ZnSO_4$·*7$H_2O$, 2 g/L $Na_2MoO_2$·*2 $H_2O$, 1 g/L $CuCl_2$*2 $H_2O$, and 0.5 g/L $H_3BO_3$. To accelerate initial growth of the population, the complex component yeast extract (150 mg/g calculated CDM) was added to the batch medium. Nitrogen level was maintained by adding 25% ammonium hydroxide solution (w/w) for pH control. Antifoam (PPG 2000) 0.5 mL/L total volume was added at the beginning. Pre-cultures for inoculation were grown in synthetic media calculated to produce 3 g/L).

TABLE 13

Batch medium components

| Component | Quantity |
|---|---|
| $KH_2PO_4$ | 0.094 g/g final CDM |
| 85% $H_3PO_4$ | 0.032 g/g final CDM |
| Yeast extract | 0.15 g/g CDM (batch) |
| $C_6H_5Na_3O_7$•$2H_2O$ | 0.25 g/g final CDM |
| $MgCl_2$•$7H_2O$ | 0.1 g/g CDM (batch) |
| $CaCl_2$•$2H_2O$ | 0.02 g/g CDM (batch) |
| $(NH_4)_2SO_4$ | 0.046 g/g final CDM |
| Trace element solution | 50 µL/g CDM (batch) |
| $C_6H_{12}O_6$•$H_2O$ | 3.3 g/g CDM (batch) |

TABLE 14

| Fed batch medium components | |
|---|---|
| Component | Quantity |
| $MgCl_2$•$7H_2O$ | 0.1 g/g CDM (fed-batch) |
| $CaCl_2$•$2H_2O$ | 0.02 g/g CDM (fed-batch) |
| Trace element solution | 50 μL/g CDM (fed-batch) |
| $C_6H_{12}O_6$•$H_2O$ | 3.3 g/g CDM (fed-batch) |

9.1.2.2 Cultivation and Induction Conditions for Standardized Lab-Scale Fermentations All HCD fermentations were performed in a 30 L (23 L net volume, 5 L batch volume) computer-controlled bioreactor (Bioengineering; Wald, Switzerland) equipped with standard control units (Siemens PS7, Intellution iFIX). The pH was maintained at a set-point of 7.0±0.05 by addition of 25% ammonia solution (w/w), the temperature was set to 37° C.±0.5° C. in the batch phase and 30° C.±0.5° C. in the fed-batch phase. To avoid oxygen limitation the DO level was held above 30% saturation by adjusting the stirrer speed and the aeration rate of the process air. The maximum overpressure in the head space was 1.1 bar. Foaming was suppressed by addition of 0.5 mL/L antifoam (PPG 2000 Sigma Aldrich) to the batch medium and by pulsed addition of antifoam during the fed-batch phase. The cultivation was inoculated with an overnight pre-culture. The pre-culture was set-up by inoculating 200 mL LB media with 1 mL of a deep frozen WCB in 2000 mL shake flasks. Cells were grown on an orbital shaker at 180 rpm and at 37° C. until the $OD_{600}$ reached a value of approx. 4. Thereafter, batch was inoculated with the pre-culture to an initial OD600 of 0.10 and cultivated at 37 C. At the end of the batch phase as soon as cells entered the stationary growth phase, an exponential substrate feed was started. The fed-batch phase (29 h) was performed at 30° C. with an exponential feeding strategy with a consistent growth rate of p=0.1 $h^{-1}$. The substrate feed was controlled by increasing pump speed according to the exponential growth algorithm, $X=X_0 \cdot e^{\mu t}$, with superimposed feedback control of weight loss in the substrate tank. Induction started with fed-batch phase by adding 0.5 μmol IPTG/g CDM directly to the feed-media to achieve a protein production for 4 generations. IPTG concentration was calculated with the theoretical final CDM.

9.1.2.3 Cultivation and Induction Conditions for DoE Approach

Pre-cultivation and batch phase were identical to the previously described standardized fermentations. The fed-batch phases were performed at 30° C. For biomass production the first fed-batch phase was performed with an exponential feed (μ=of 0.17 $h^{-1}$) for 1.72 generations. As previously described, the substrate feed was controlled by increasing pump speed according to the exponential growth algorithm, $X=X_0*e^{\mu t}$, with superimposed feedback control of weight loss in the substrate tank. In a second feed-phase a lower growth rate (0.03, 0.05 and 0.07 $h^{-1}$) was adjusted resulting in a total feed time of 60.5 h, 39 h and 30 h. The calculated CDM was 70 g/L. To ensure sufficient adaption to the low growth conditions, the cells grew for 0.25 generations without induction. Then induction was performed with three different IPTG concentrations (0.5, 0.9 and 1.3 μmol/g CDM) for two generations. 9 DoE fermentations were performed.

9.1.2.4 Fermentation Monitoring

In addition to standard online monitoring (pH, stirrer speed, temperature and $pO_2$) the concentration of $pO_2$ and $O_2$ in the outlet air was measured with a BlueSens gas analyzer. Sampling of the standard offline process parameters started after one generation in fed-batch mode. The first sample was withdrawn from the bioreactor prior to induction. Optical density (OD600) was measured with a spectrophotometer at wavelength λ=600 nm. Samples were diluted in PBS to ensure a measurement at a linear range from 0.1 to 0.8. Cell dry mass (CDM) was determined by centrifugation of 10 mL of cell suspension for 8 min at 8500 rpm. The supernatant was discarded and cells were resuspended with RO—$H_2O$ and centrifuged. Water was discarded and cell were resuspended again with RO—$H_2O$. Cell suspension was transferred into a beaker, which was weighted before. Beakers were dried for at least 24 h at 105° C. and weighted again. The difference in weight account for the CDM.

For the determination of the content of cp caspase-2 and variants, aliquots of approximately 1.0 mg CDM of the samples were centrifuged (10 min. at 13200 rpm); the supernatants were discarded, the insides of the tubes were carefully blotted dry and the samples were stored at −20° C.

9.1.2.5 Determination of Cp Caspase-2 and Variants in Fermentation Samples

Cell disintegration, fractionation of soluble and insoluble recombinant protein and IB dissolving: Cell disintegration was performed from fermentation samples containing approximately 1.0 mg CDM. 200 μL of cell integration buffer was added to the cell pellet and vortexed until the pellet was completely resuspended. For cell disruption 50 μL Lysozyme and 50 μL Benzonase were added and incubated while shaking at room temperature. 100 μL Triton X-100 was added and samples were incubated again while shaking. Then, samples were centrifuged at 4° C. and 13000 rpm to separate soluble proteins and inclusion bodies (IB). The supernatant was transferred into a new reaction tube for direct analysis (SDS-PAGE) or stored at −20° C.

The remaining pellet (IBs and cell debris) was washed two times by resuspending with 1 mL Tris/HCL (100 mM). After resuspending the pellet was centrifuged at 4° C. and 13000 rpm for 10 min. The supernatant was discarded. Afterwards, 400 μL IB solvent buffer was added and incubated at room temperature for 30 min. while shaking. Finally, the sample was centrifuged again and the supernatant containing dissolved IBs was used for analysis (SDS-PAGE) or stored at −20° C.

TABLE 15

| Cell disintegration solutions | |
|---|---|
| Tris/HCl (pH = 8.2) | 30 mM |
| EDTA | 0.5 M |
| $MgCl_2 \times 6H_2O$ | 200 mM |
| Triton X-100 | 6% |
| Lysozym | 2 mg/mL |
| Benzonase | 50 units/mL |

TABLE 16

| Cell disintegration buffer 3 mL | |
|---|---|
| Tris/HCl (pH = 8.2) 30 mM | 2.7 mL |
| EDTA | 150 μL |
| $MgCl_2 \times 6H_2O$ | 150 μL |
| Sample reducing Agent (10×) | 24 μL |

TABLE 17

| IB solvent buffer | |
|---|---|
| Tris/HCl (pH = 8.2) | 100 mM |
| urea | 8 M |
| Sample reducing agent (10×) | 28 μl/mL IB solution buffer |

SDS-PAGE

Sodium dodecyl sulfate polyacrylamide gel electrophoresis (SDS-PAGE) was used to separate and analyze the recombinant proteins. Electrophoresis was performed by using precast gels with an acrylamide gradient (NuPAGE 4-12% BisTris, Thermo Fisher Scientific, Waltham, MA, USA) and NuPAGE® MES SDS Running buffer. Loading samples were prepared by mixing 13 μL of the supernatant (soluble fraction) or IB supernatant (insoluble fraction) with 5 μL LDS sample buffer (4×) and 2 μL NuPAGE® reducing agent (10×) and incubating the mixture in a thermos mixer at 70° C. for 10 minutes. A ready-to-use molecular weight marker (Mark12™, Unstained Standard, Invitrogen) was directly loaded as size marker. For quantification, purified T7AC_6H_cpCasp2 (SEQ ID NO:41) standards (75, 50 and 25 μg/mL) listed in Table 12, produced as described in Example 9 (see sections 9.1, and 9.2), were used. Electrophoresis settings were 200 V and 400 mA for 40 to 50 minutes in a XCell SureLock™ Electrophoresis Cell chamber (Thermo Fisher Scientific). After electrophoresis the SDS Gels were fixed in fixing solution (40% ethanol; 50% $_dH_2O$; 10% acetic acid) for 30 minutes and stained afterwards with Coomassie brilliant blue R250 staining solution for 30 minutes. Finally, the gel was decolorized in a destaining solution (25% acetic acid; 8% ethanol; 67% $_dH_2O$) for at least two hours. Gels were transferred in water and scanned with a desktop scanner, converted to grey-scale and analysed using the software ImageQuant TL (7.0). The concentration of cp caspase-2 and variants was quantified via a linear regression curve.

9.1.2.6 Comparison of production of cp caspase-2 and variants with and without solubility tag in fermentations with a $\mu$=0.1 $h^{-1}$ and an IPTG concentration of 0.5 μmol IPTG/g CDM during induction.

While overexpression of cp caspase-2 was possible in *E. coli*, the expression rate of soluble cp caspase-2 was generally low. In order to increase the fermentation titer, a solubility tag was added to the enzyme. The tag T7A3 (SEQ ID No. 37) is based on a highly negatively charged peptide from the T7 bacteriophage. When used on the cp caspase-2 variants we noticed autocatalytic cleavage of the tag and subsequently modified the tag, using a cleavage site prediction algorithm. The altered solubility tag was coined T7AC (SEQ ID No. 43) and was able to double the expression level of soluble cp caspase-2. For this solubility- and His-tagged enzyme, we developed a downstream process based on an IMAC capture step and a cation exchange chromatography (CEX) polishing step. With this downstream process we were able to produce highly pure (>99% protein purity by reversed phase HPLC) cp caspase-2 in the hundreds of mg scale.

For evaluation of the production of cp caspase-2 and variants with and without solubility tag (T7AC), standardized lab-scale fermentations were performed. Expression clones were compared regarding cell growth and soluble and insoluble recombinant protein production.

Comparing the production of 6H-cpCasp2D (SEQ ID NO:6) and T7AC-6H-cpCasp2D (SEQ ID No. 41) in lab-scale fermentations, we observed that the production of 6H-cpCasp2D (SEQ ID NO:6) without solubility tag lead predominantly to inclusion body formation (FIG. 10 A). In the end of the cultivation the calculated CDM was not reached due to too high expression levels (FIG. 11). The addition of the T7AC solubility tag N-terminal of the caspase increased soluble expression (FIG. 10 B), whereby the overall recombinant protein expression was slightly lower. Cell growth followed the calculated CDM (FIG. 11). The final CDM was about 77.5 g/L respectively 1549 g in total. The solubility tag did not negatively influence the subsequent metal affinity chromatography.

FIG. 10 shows lab-scale fermentations of *E. coli* BL21 (DE3)(pET30a_6H-cpCasp2D) (SEQ ID NO:6) (A, two graphs on the left) and BL21(DE3)(pET30a_T7AC-6H-cpCasp2D) (SEQ ID No. 41) (B, two graphs on the right): expression of soluble and insoluble 6H-cp caspase-2D (SEQ ID NO:6)(cpCasp2) (A) and T7AC-6H-cp caspase-2D (T7AC-6H-cpCasp2) (SEQ ID NO:41) (B) in the course of time as specific yield [mg/g] and volumetric yield [g/L]: with (T7AC_6H-cpCasp2 (SEQ ID NO:41), B) and without (cpCasp2, A) solubility tag, T7AC.

FIG. 11 shows lab-scale fermentations of *E. coli* BL21 (DE3)(pET30a_6H-cpCasp2D) (SEQ ID NO:6) and BL21 (DE3) (pET30a_T7AC-6H-cpCasp2D) (SEQ ID No. 41): biomass course.

Comparing the production of three cp caspase-2 variants (cp caspase-2, mS9Pro E285 and mS9 Pro D285) with and without T7AC solubility tag, it turned out that the variant itself has no influence on the performance, no significant differences in cell growth and soluble cp caspase-2 expression. By means of the T7AC solubility tag the soluble expression of all three variants was significantly improved.

Cell growth kinetics off all cultivations were almost the same (VC<4%). Only at the end of the fermentations slight deviations were observed (FIG. 12). The fermentation strategy and the low induction level (0.5 μmol IPTG/g CDM) did not overburden the host metabolism. The addition of the T7AC solubility tag N-terminal of all cp caspase-2 variants increased the soluble expression levels (FIG. 13). The final soluble product titers were up to 1.2 g/L.

FIG. 12 shows biomass course of lab-scale fermentations of three cp caspase-2 variants (cp caspase-2 (cpCasp2D), mS9 Pro E285 (mS9ProE) and mS9 Pro D285 (mS9ProD)) with and without T7AC solubility tag in *E. coli* BL21(DE3) with pET30a vectors; the mean values and the standard deviation for these six cultivations are shown. The total CDM is shown as average of all 6 fermentations including standard deviation compared to expected growth (calc. CDM).

FIG. 13 shows normalized soluble production of cp caspase-2 of three different cp caspase-2 variants (cp caspase-2 (cpCasp2D), mS9 Pro E285 (mS9ProE) and mS9 Pro D285 (mS9ProD)) with and without T7AC solubility tag in *E. coli* BL21(DE3) with pET30a vectors.

9.1.2.7 DoE Approach for Process Optimization

For final process optimization, a series of cultivation runs were conducted according to a Design of experiments (DoEs) approach described previously. The production clone BL21(DE3)(pET30a-T7AC_6H_cpCasp2)(SEQ ID NO:41) was used. The influence of different growth rates ($\mu$=0.03, 0.05 and 0.07 $h^{-1}$) and induction strengths (0.5, 0.9 and 1.3 μmol IPTG/g CDM) were investigated regarding cell growth and soluble and insoluble recombinant protein production. The results are shown in Table 18.

TABLE 18

DoE approach for process optimisation: biomass and recombinant protein levels at the end of cultivation

| Cultivation [#] | growth rate [$h^{-1}$] | induction [μmol/g CDM] | feed [h] | CDM [g] | cal. CDM [g] | achieved CDM [%] |
|---|---|---|---|---|---|---|
| Cas_DoE_03 | 0.03 | 0.5 | 60.5 | 750 | 1133 | 66 |
| Cas_DoE_02 | 0.05 | 0.5 | 39.0 | 1026 | 1163 | 88 |
| Cas_DoE_01 | 0.07 | 0.5 | 30.0 | 1102 | 1131 | 97 |
| Cas_DoE_05 | 0.03 | 0.9 | 60.5 | 691 | 1145 | 60 |
| Cas_DoE_04 | 0.05 | 0.9 | 39.0 | 924 | 1126 | 82 |
| Cas_DoE_06 | 0.07 | 0.9 | 30.0 | 1048 | 1136 | 92 |
| Cas_DoE_07 | 0.03 | 1.3 | 60.5 | 639 | 1130 | 57 |
| Cas_DoE_08 | 0.05 | 1.3 | 39.0 | 903 | 1127 | 80 |
| Cas_DoE_09 | 0.07 | 1.3 | 30.0 | 981 | 1135 | 86 |

| Cultivation [#] | spec. yield soluble [mg/g] | spec. yield IB [mg/g] | spec. yield total [mg/g] | vol. yield soluble [g/L] | vol. yield IB [g/L] | vol. yield total [g/L] |
|---|---|---|---|---|---|---|
| Cas_DoE_03 | 100.68 | 50.86 | 151.53 | 4.71 | 2.38 | 7.09 |
| Cas_DoE_02 | 56.31 | 45.39 | 101.69 | 3.54 | 2.85 | 6.39 |
| Cas_DoE_01 | 35.92 | 52.25 | 88.18 | 2.43 | 3.53 | 5.96 |
| Cas_DoE_05 | 105.24 | 94.30 | 199.54 | 4.56 | 4.09 | 8.65 |
| Cas_DoE_04 | 52.84 | 54.01 | 106.85 | 3.07 | 3.14 | 6.21 |
| Cas_DoE_06 | 45.27 | 103.11 | 148.38 | 2.98 | 6.78 | 9.76 |
| Cas_DoE_07 | 63.22 | 70.29 | 133.51 | 2.59 | 2.88 | 5.47 |
| Cas_DoE_08 | 67.5 | 55.6 | 123.1 | 3.9 | 3.2 | 7.0 |
| Cas_DoE_09 | 50.2 | 92.0 | 142.2 | 3.06 | 5.60 | 8.65 |

It was observed that the specific yield of soluble cp caspase-2 was higher at low growth rates and IB formation decreased. The calculated CDM was not reached at the end of fermentation with p=0.03 h-1 due to too high expression levels (FIG. 14). FIG. 14 shows growth kinetics of *E. coli* BL2i(DE3)(pET30a-T7AC_6H-cpCasp2)(SEQ ID NO:4i) during carbon limited 2 phase fed-batch cultivation (μ=0.17 followed by 0.03 h-1 during induction) with three different IPTG induction strengths.

Nevertheless, the highest volumetric soluble yield was reached with μ=0.03 $h^{-1}$ and 0.9 or 0.5 μmol IPTG/g CDM (FIG. 15).

FIG. 15 shows *E. coli* BL2i1(DE3)(pET30a-T7AC_6H-cpCasp2)(SEQ ID NO:4i) during carbon limited 2 phase fed-batch cultivation (μ=0.17 and followed by 0.03 h-1 during induction) with three different IPTG induction strengths. Volumetric soluble cp caspase-2 titers (sol. POI [g/L]) obtained cultivating at the lowest growth rate (μ=0.03 $h^{-1}$) and inducing with different IPTG levels. cp caspase-2 was quantified by SDS-PAGE. The mean values and standard deviations for individual determinations are shown (n=3).

This process can be applied to all cp caspase-2 variants irrespective if it includes or not mutations at positions that increase the P1' tolerance.

9.2 Downstream Processing of Cp Caspase-2 and Variants 9.2.1 Downstream Processing of Cp Caspase-2 without Solubility Tag The *E. coli* cell mass from fermentations as described under 10.1 was harvested by centrifugation at 18,590 rcf for 15 minutes and the supernatant was discarded. The *E. coli* cell harvest was solubilized using homogenization buffer (50 mM sodium phosphate, 500 mM NaCl, 20 mM imidazole, pH 7.0). The cells were resuspended at a concentration of 150 g wet cell mass per L. Cell lysis was performed through high pressure homogenization at 700 bar/70 bar with two passages. The homogenate was centrifuged at 18,590 rcf for 2 hours. The pellet was discarded and the supernatant used. Before chromatography the supernatant was filtered through a 0.22 pm membrane.

The cp caspase-2 carrying a poly-his-tag was captured using immobilized metal affinity chromatography. The following buffers were used: equilibration buffer: 50 mM sodium phosphate, 500 mM NaCl, 20 mM imidazole, pH 7.0. Wash buffer: 50 mM sodium phosphate, 500 mM NaCl, 20 mM imidazole, 30% iso-propanol, pH 7.0. Elution buffer: 50 mM sodium phosphate, 500 mM NaCl, 500 mM imidazole, pH 7.0.

Clarified supernatant was loaded to an equilibrated Ni-Sepharose 6 Fast Flow column to a capacity of ~40 mg/mL. A residence time of 3-5 minutes was used. After loading was completed the column was washed for 5 column volumes (5 CV) with equilibration buffer, 10 CV with wash buffer and 5 CV of equilibration buffer. The bound cp caspase-2 was eluted using a linear gradient from 0-100% elution buffer in 10 CV, with a 10 CV hold step to fully elute all protein.

The elution fractions were analyzed using SDS-PAGE and all fractions containing cp caspase-2 were used for the next purification step.

The capture eluate of cp caspase-2 was buffer exchanged before the polishing chromatography step. Tangential flow ultra-/diafiltration with a 5 kDa cut off membrane was used with a sample buffer of 50 mM sodium citrate, pH 5.0. In total 5 volumes were exchanged.

The capture step used cation exchange chromatography on SOURCE 30S using the following buffers: equilibration buffer A: 50 mM sodium citrate, pH 5.0. Elution buffer B: 50 mM sodium citrate, 1 M NaCl, pH 5.0.

Buffer exchanged capture eluate was loaded on the equilibrated polishing. The residence time was held constant at 5 minutes. The column was loaded to a capacity of ~100 mg/ml. cp caspase-2 was eluted in a linear gradient from 0-100% B in 20 CV. The elution fractions were analyzed using RP-HPLC as described under 10.3 and the fractions showing a purity of ~99% were combined and stored at −80° C.

9.2.2 Downstream Processing of Cp Caspase-2 with Solubility Tag

Lysis was executed as described in section 9.2.1 but cells were resuspended at a concentration of 200 g wet cell mass per L.

IMAC was executed as described above, but the column was loaded to a capacity of ~30 mg/ml and a residence time of 2-3 minutes was chosen. After loading was completed the column was washed for 5 column volumes (5 CV) with equilibration buffer, 5 CV with wash buffer and 1 CV of equilibration buffer. The bound cp caspase-2 was eluted using a linear gradient from 0-50% elution buffer in 5 CV, followed by a gradient from 50-100% B in 1 CV, followed by a 2 CV hold step at 100% to fully elute all protein.

The elution peak fraction was used for the next purification step. Buffer exchange of the capture eluate was executed as described above.

The capture step used cation exchange chromatography on SP Sepharose High Performance using the following buffers: equilibration buffer A: 50 mM sodium citrate, pH 5.0. Elution buffer B: 50 mM sodium citrate, 1 M NaCl, pH 5.0.

Buffer exchanged capture eluate was loaded on the equilibrated polishing. The residence time was held constant at 1-2 minutes. The column was loaded to a capacity of ~50 mg/ml. The column was washed for 5 column volumes (5 CV) with 30% B, cp caspase-2 was eluted with 10 CV of 45% B and the column was stripped with 3 CV of 100% B. The elution fraction was aliquoted and stored at −80° C. The purity was determined by RP-HPLC and was ~99% (98.6-99.4%).

9.3 Characterization of Cp Caspase-2 and Variants 9.3.1 Purity Determination of Cp Caspase-2 and Variants (HPLC)

Experiments were performed on a Tosoh TSKgel Protein C4-300, L×I.D. 5 cm×4.6 mm, 3 μm column with a guard column on a Waters e2695 HPLC. Mobile phase A was water with 0.15% trifluoroacetic acid (TFA) and mobile phase B was acetonitrile with 0.15% TFA. The flowrate was 1 ml/min. Temperature of the column oven was 40° C., temperature of the autosampler 10° C. The following gradient was used as shown in Table 19.

TABLE 19

RP-HPLC method for purity determination.

| Step | Cumulative time [min] | % B |
|---|---|---|
| Injection | 0 | 2 |
| Wash | 1 | 2 |
| Gradient 1 | 2 | 25 |
| Gradient 2 | 8 | 50 |
| Gradient 3 | 15 | 55 |
| Gradient 4 | 16 | 90 |
| Hold | 18 | 90 |
| Re-equilibration | 19 | 2 |

200 μL of purified cp caspase-2 (or variant) sample (~4 g/L) was diluted with 100 μL PBS and 100 μL 2 M Dithiothreitol (DTT). 10 μl of 0.22 μm filtered sample were injected. The outlet was monitored at 214 nm and 280 nm. The HCP peaks eluted between retention times 3.8 and 9 minutes. The cp caspase-2 peaks eluted between 9.2 and 12.4 minutes. The peak areas in the 214 nm signal were used to calculate the purity of the protein of interest.

9.3.2 Quantification of Released Fusion Tag with RP-HPLC

The calibration curve was generated mixing the substrate protein, e.g. human fibroblast growth factor 2 (hFGF-2), and cp caspase-2 in a ratio 10:1 (in triplicates) and incubated for 4 hours at 25° C. while shaking. The reaction was stopped by adding formic acid to a final concentration of 0.3% or by adding cystamine to a final concentration of 10 mM. Each triplet was diluted with PBS buffer to get six different concentrations (100 μM, 46 μM, 21 μM, 10 μM, 4 μM, 2 μM).

10 μL of 0.22 μm filtered sample were injected to a reversed phase high pressure liquid chromatography (RP-HPLC) using a method outlined below. The outlet was monitored at 214 nm. The fusion tag peaks eluted between retention times 3.9 and 5.6 minutes. The peak areas in the 214 nm signal were used to calculate the quantity of the fusion tag using a linear calibration function.

Experiments were performed on a Tosoh TSKgel Protein C4-300, L×I.D. 5 cm×4.6 mm, 3 μm column with a guard column on a Waters e2695 HPLC. Mobile phase A was water with 0.15% trifluoroacetic acid (TFA) and mobile phase B was acetonitrile with 0.15% TFA. The flowrate was 1 mL/min. Temperature of the column oven was 40° C., temperature of the autosampler 10° C. The following gradient was used (Table 20):

TABLE 20

| Step | Cumulative time [min] | % B |
|---|---|---|
| Injection | 0 | 2 |
| Wash | 1 | 2 |
| Gradient 1 | 7 | 28.2 |
| Gradient 2 | 8 | 90 |
| Hold | 10 | 90 |
| Re-equilibration | 11 | 2 |

9.3.3 Determination of Enzymatic Activity with FRET Assay

A Förster resonance energy transfer (FRET) assay for the determination of the Michaelis-Menten enzymatic activity parameters was performed in the following way.

The substrates were obtained from Bachem AG and were of the general structure of Abz-VDVAD(SEQ ID NO:45)-XA-Dap(Dnp), where all 20 amino acids were substituted for X (the P1' position). All substrates were dissolved in 10 mM HEPES, pH 7.5 to a concentration of 750 μM. Abz means 2-Aminobenzoyl, Dap(Dnp) means α,β-diamino-propionic acid (2,4-Dinitrophenyl).

The buffer for the assay was 50 mM HEPES, 150 mM NaCl, pH 7.2.

The calibration curve was generated by incubating varying amounts of substrate (20 μM, 6.9 μM, 2.4 μM, 0.8 μM, 0.3 μM, 0.1 μM) with 72 μM cp caspase-2 D285E in phosphate buffered saline (PBS) and incubated at room temperature for up to 24 hours. 100% conversion was assumed. Fluorescence was measured in black 96 well plates on a Tecan Infinite M200 Pro plate reader. Excitation wavelength was 320 nm, emission wavelength 420 nm.

Michaelis-Menten kinetics were measured by varying substrate concentrations (200 μM, 100 μM, 50 μM, 20 μM, 10 μM) at constant enzyme concentration ([E]=1 μM). The initial slope was measured by measuring the fluorescence for 3-15 minutes (or 3 to 20 hours for proline as P1') and calculating the slope of the initial measurement in μM product generated per second. Fluorescence was measured in black 96 well plates on a Tecan Infinite M200 Pro plate reader. Excitation wavelength was 320 nm, emission wavelength 420 nm. In the FRET assay all substrates, except for proline as P1' showed excellent linearity for at least a few minutes.

Evaluation of the data was performed by fitting the data in the TableCurve 2D v5 software to a Michaelis-Menten kinetic:

Where v is the initial slope, $V_{max}$ is the maximum rate, $K_M$ is the Michaelis constant and [5] is the substrate concentration. The parameters $V_{max}$ and $K_M$ were fitted. $k_{cat}$ was calculated by dividing $V_{max}$ by the enzyme concentration [E].

An example kinetic curve can be seen in FIG. 16.

The results are shown in Table 21 and 22 and FIG. 8. FIG. 8 shows an example Michaelis-Menten kinetic measured by FRET assay. The measured substrate was Abz-VDVADHA (SEQ ID NO:3i8 Phe to His at position 6)-Dap(Dnp) at concentrations given on the x-axis. The y-axis gives the measured initial slope values. Shaded circles represent measured data points, the full line represents the model fit and the dashed lines represent upper and lower 95% confidence intervals of the model fit.

TABLE 21

FRET assay results for caspase variants with varying P1' positions as the substrate, n.d. = not determined, ci = 95% confidence interval. Caspase 1 = 6H_cpCasp2 (SEQ ID NO:6), 2 = T7AC_6H_cpCasp2 (SEQ ID NO:41), 3 = 6H_cpCasp2_G171D (SEQ ID NO:190), 4 = 6H_cpCasp2_S9_E105V(SEQ ID NO:51), 5 = T7AC_6H_mS9ProE (SEQ ID NO:71, 6 = T7AC_6H_mS9ProD (SEQ ID NO:72).

| Casp. | | A | C | D | E | F | G | H | I | K | L |
|---|---|---|---|---|---|---|---|---|---|---|---|
| 1 | $K_M$ [$M^{-1}$] | 8.9 E−5 | 3.8 E−5 | 1.6 E−4 | 1.7 E−4 | 6.0 E−5 | 1.1 E−4 | 1.2 E−4 | 7.1 E−5 | 1.2 E−4 | 2.9 E−4 |
| | $K_M$ ci [$M^{-1}$] | 1.1 E−5 | 1.0 E−5 | 5.6 E−5 | 7.2 E−5 | 1.6 E−5 | 3.7 E−5 | 2.1 E−5 | 2.5 E−5 | 1.6 E−5 | 9.6 E−5 |
| | $k_{cat}$ [$s^{-1}$] | 7.1 E−3 | 2.1 E−2 | 6.1 E−4 | 1.5 E−4 | 3.6 E−3 | 1.9 E−1 | 5.8 E−3 | 9.3 E−4 | 1.5 E−2 | 2.2 E−3 |
| | $k_{cat}$ ci [$s^{-1}$] | 4.2 E−4 | 2.0 E−3 | 1.2 E−4 | 3.7 E−5 | 4.0 E−4 | 3.1 E−2 | 5.1 E−4 | 1.4 E−4 | 1.1 E−3 | 4.8 E−4 |
| | $k_{cat}/K_M$ [$M^{-1}s^{-1}$] | 8.0 E+1 | 5.6 E+2 | 3.9 E+0 | 8.9 E−1 | 6.1 E+1 | 1.7 E+3 | 4.7 E+1 | 1.3 E+1 | 1.3 E+2 | 7.5 E+0 |
| 2 | $K_M$ [$M^{-1}$] | 1.2 E−4 | n.d. | 1.8 E−4 | 2.0 E−4 | 5.8 E−5 | 4.9 E−5 | 1.1 E−4 | 6.2 E−5 | 1.1 E−4 | 1.6 E−4 |
| | $K_M$ ci [$M^{-1}$] | 1.2 E−5 | n.d. | 4.3 E−5 | 6.1 E−5 | 1.5 E−5 | 1.3 E−5 | 2.2 E−5 | 1.4 E−5 | 2.9 E−5 | 2.6 E−5 |
| | $k_{cat}$ [$s^{-1}$] | 1.6 E−2 | n.d. | 1.7 E−3 | 5.7 E−4 | 7.9 E−3 | 2.7 E−1 | 9.1 E−3 | 1.6 E−3 | 2.6 E−2 | 4.1 E−3 |
| | $k_{cat}$ ci [$s^{-1}$] | 8.6 E−4 | n.d. | 2.3 E−4 | 1.0 E−4 | 8.1 E−4 | 2.7 E−2 | 8.9 E−4 | 1.5 E−4 | 3.4 E−3 | 3.9 E−4 |
| | $k_{cat}/K_M$ [$M^{-1}s^{-1}$] | 1.4 E+2 | n.d. | 9.0 E+0 | 2.8 E+0 | 1.4 E+2 | 5.5 E+3 | 8.2 E+1 | 2.6 E+1 | 2.4 E+2 | 2.6 E+1 |
| 3 | $K_M$ [$M^{-1}$] | 1.2 E−4 | n.d. | 1.5 E−4 | 2.1 E−4 | 8.6 E−5 | 7.5 E−5 | 1.7 E−4 | 7.8 E−5 | 9.4 E−5 | 3.0 E−4 |
| | $K_M$ ci [$M^{-1}$] | 1.7 E−5 | n.d. | 5.9 E−5 | 8.0 E−5 | 1.6 E−5 | 2.7 E−5 | 6.0 E−5 | 1.6 E−5 | 2.3 E−5 | 5.0 E−5 |
| | $k_{cat}$ [$s^{-1}$] | 4.5 E−2 | n.d. | 8.1 E−4 | 7.1 E−4 | 4.8 E−2 | 3.8 E−1 | 6.0 E−2 | 5.9 E−3 | 1.0 E−1 | 2.4 E−2 |
| | $k_{cat}$ ci [$s^{-1}$] | 3.2 E−3 | n.d. | 1.7 E−4 | 1.6 E−4 | 3.9 E−3 | 5.9 E−2 | 1.2 E−2 | 5.4 E−4 | 1.1 E−2 | 2.7 E−3 |
| | $k_{cat}/K_M$ [$M^{-1}s^{-1}$] | 3.7 E+2 | n.d. | 5.3 E+0 | 3.4 E+0 | 5.6 E+2 | 5.1 E+3 | 3.5 E+2 | 7.6 E+1 | 1.1 E+3 | 7.9 E+1 |
| 4 | $K_M$ [$M^{-1}$] | 1.1 E−4 | n.d. | 2.0 E−4 | 1.8 E−4 | 7.7 E−5 | 5.7 E−5 | 1.6 E−4 | 7.0 E−5 | 9.7 E−5 | 3.0 E−4 |
| | $K_M$ ci [$M^{-1}$] | 2.1 E−5 | n.d. | 3.4 E−5 | 2.2 E−5 | 1.5 E−5 | 8.6 E−6 | 2.1 E−5 | 9.1 E−6 | 1.5 E−5 | 6.9 E−5 |
| | $k_{cat}$ [$s^{-1}$] | 9.2 E−2 | n.d. | 1.4 E−2 | 3.2 E−3 | 5.2 E−2 | 8.2 E−1 | 7.7 E−2 | 8.0 E−3 | 1.1 E−1 | 2.5 E−2 |
| | $k_{cat}$ ci [$s^{-1}$] | 8.7 E−3 | n.d. | 1.4 E−3 | 2.3 E−4 | 4.3 E−3 | 4.9 E−2 | 5.7 E−3 | 4.4 E−4 | 7.9 E−3 | 3.9 E−3 |
| | $k_{cat}/K_M$ [$M^{-1}s^{-1}$] | 8.2 E+2 | n.d. | 6.9 E+1 | 1.8 E+1 | 6.8 E+2 | 1.4 E+4 | 4.8 E+2 | 1.1 E+2 | 1.1 E+3 | 8.4 E+1 |
| 5 | $K_M$ [$M^{-1}$] | 1.1 E−4 | n.d. | 1.5 E−4 | 1.1 E−4 | 8.0 E−5 | 4.3 E−5 | 1.6 E−4 | 1.3 E−4 | 9.2 E−5 | 4.1 E−4 |
| | $K_M$ ci [$M^{-1}$] | 1.0 E−5 | n.d. | 3.7 E−5 | 1.7 E−5 | 1.3 E−5 | 1.7 E−5 | 1.5 E−5 | 1.5 E−5 | 1.9 E−5 | 1.4 E−4 |
| | $k_{cat}$ [$s^{-1}$] | 8.1 E−2 | n.d. | 7.0 E−3 | 6.1 E−3 | 7.8 E−2 | 4.1 E−1 | 1.2 E−1 | 1.2 E−2 | 1.6 E−1 | 6.7 E−2 |
| | $k_{cat}$ ci [$s^{-1}$] | 3.9 E−3 | n.d. | 9.0 E−4 | 4.6 E−4 | 5.7 E−3 | 5.8 E−2 | 6.3 E−3 | 7.3 E−4 | 1.5 E−2 | 1.7 E−2 |
| | $k_{cat}/K_M$ [$M^{-1}s^{-1}$] | 7.6 E+2 | n.d. | 4.5 E+1 | 5.4 E+1 | 9.8 E+2 | 9.5 E+3 | 7.2 E+2 | 9.5 E+1 | 1.7 E+3 | 1.6 E+2 |
| 6 | $K_M$ [$M^{-1}$] | 1.0 E−4 | n.d. | 1.9 E−4 | 1.6 E−4 | 1.2 E−4 | 6.5 E−5 | 1.7 E−4 | 1.1 E−4 | 7.9 E−5 | 4.0 E−4 |
| | $K_M$ ci [$M^{-1}$] | 2.3 E−5 | n.d. | 3.6 E−5 | 3.9 E−5 | 3.4 E−5 | 1.4 E−5 | 5.3 E−5 | 2.3 E−5 | 2.7 E−5 | 6.8 E−5 |
| | $k_{cat}$ [$s^{-1}$] | 1.2 E−1 | n.d. | 3.8 E−3 | 3.2 E−3 | 2.2 E−1 | 7.3 E−1 | 2.0 E−1 | 2.0 E−2 | 3.0 E−1 | 1.1 E−1 |
| | $k_{cat}$ ci [$s^{-1}$] | 1.3 E−2 | n.d. | 4.3 E−4 | 4.3 E−4 | 3.2 E−2 | 6.3 E−2 | 3.5 E−2 | 2.1 E−3 | 4.5 E−2 | 1.4 E−2 |
| | $k_{cat}/K_M$ [$M^{-1}s^{-1}$] | 1.2 E+3 | n.d. | 2.0 E+1 | 1.9 E+1 | 1.8 E+3 | 1.1 E+4 | 1.2 E+3 | 1.9 E+2 | 3.8 E+3 | 2.9 E+2 |

TABLE 22

FRET assay results for caspase variants with varying P1' positions as the substrate, n.d. = not determined, conf int = 95% confidence interval. Caspase 1 = 6H_cpCasp2 (SEQ ID NO:6), 2 = T7AC_6H_cpCasp2 (SEQ ID NO:41), 3 = 6H_cpCasp2_G171D (SEQ ID NO:190), 4 = 6H_cpCasp2_S9_E105V (SEQ ID NO:51), 5 = T7AC_6H_mS9ProE (SEQ ID NO:71), 6 = T7AC_6H_mS9ProD (SEQ ID NO:72).

| Casp. | | M | N | P | Q | R | S | T | V | W | Y |
|---|---|---|---|---|---|---|---|---|---|---|---|
| 1 | $K_M$ [$M^{-1}$] | 3.8 E−4 | 7.8 E−5 | 3.0 E−4 | 1.2 E−4 | 5.8 E−5 | 2.0 E−4 | 7.5 E−5 | 6.4 E−5 | 4.6 E−5 | 3.4 E−4 |
| | $K_M$ ci [$M^{-1}$] | 1.2 E−4 | 1.6 E−5 | 1.5 E−4 | 2.4 E−5 | 1.0 E−5 | 3.5 E−5 | 2.0 E−5 | 2.3 E−5 | 2.0 E−5 | 5.3 E−5 |
| | $k_{cat}$ [$s^{-1}$] | 2.8 E−2 | 9.2 E−3 | 8.1 E−6 | 2.1 E−3 | 2.1 E−2 | 8.9 E−3 | 3.4 E−3 | 5.4 E−4 | 1.4 E−2 | 1.7 E−2 |
| | $k_{cat}$ ci [$s^{-1}$] | 6.1 E−3 | 8.5 E−4 | 2.6 E−6 | 2.1 E−4 | 1.4 E−3 | 9.5 E−4 | 4.0 E−4 | 8.1 E−5 | 2.3 E−3 | 1.8 E−3 |
| | $K_{cat}/K_M$ [$M^{-1}s^{-1}$] | 7.4 E+1 | 1.2 E+2 | 2.6 E−2 | 1.7 E+1 | 3.6 E+2 | 4.5 E+1 | 4.5 E+1 | 8.5 E+0 | 3.2 E+2 | 4.8 E+1 |
| 2 | $K_M$ [$M^{-1}$] | 3.4 E−4 | 8.7 E−5 | 1.5 E−4 | 1.3 E−4 | 5.6 E−5 | 1.3 E−4 | 8.9 E−5 | 7.3 E−5 | 3.6 E−5 | 3.0 E−4 |
| | $K_M$ ci [$M^{-1}$] | 7.7 E−5 | 1.9 E−5 | 6.6 E−5 | 2.4 E−5 | 1.2 E−5 | 1.9 E−5 | 2.8 E−5 | 1.8 E−5 | 1.4 E−5 | 4.4 E−5 |
| | $k_{cat}$ [$s^{-1}$] | 6.5 E−2 | 2.0 E−2 | 9.9 E−6 | 4.6 E−3 | 5.7 E−2 | 1.7 E−2 | 6.3 E−3 | 1.7 E−3 | 2.8 E−2 | 3.3 E−2 |
| | $k_{cat}$ ci [$s^{-1}$] | 1.0 E−2 | 2.0 E−3 | 2.4 E−6 | 4.6 E−4 | 4.8 E−3 | 1.3 E−3 | 9.0 E−4 | 1.9 E−4 | 3.6 E−3 | 3.4 E−3 |
| | $K_{cat}/K_M$ [$M^{-1}s^{-1}$] | 1.9 E+2 | 2.3 E+2 | 6.5 E−2 | 3.6 E+1 | 1.0 E+3 | 1.3 E+2 | 7.1 E+1 | 2.4 E+1 | 7.6 E+2 | 1.1 E+2 |
| 3 | $K_M$ [$M^{-1}$] | 6.1 E−4 | 1.1 E−4 | 3.9 E−4 | 1.6 E−4 | 6.5 E−5 | 2.2 E−4 | 1.4 E−4 | 9.6 E−5 | 5.6 E−5 | 3.5 E−4 |
| | $K_M$ ci [$M^{-1}$] | 1.5 E−4 | 1.5 E−5 | 2.7 E−4 | 3.3 E−5 | 1.8 E−5 | 6.0 E−5 | 3.4 E−5 | 2.6 E−5 | 1.5 E−5 | 1.2 E−4 |
| | $k_{cat}$ [$s^{-1}$] | 3.8 E−1 | 3.4 E−2 | 8.0 E−5 | 2.0 E−2 | 2.1 E−1 | 1.5 E−2 | 1.7 E−2 | 6.8 E−3 | 8.2 E−2 | 1.2 E−1 |
| | $k_{cat}$ ci [$s^{-1}$] | 7.5 E−2 | 2.3 E−3 | 4.0 E−5 | 2.2 E−3 | 2.4 E−2 | 2.6 E−3 | 2.2 E−3 | 8.8 E−4 | 8.3 E−3 | 2.9 E−2 |
| | $k_{cat}/K_M$ [$M^{-1}s^{-1}$] | 6.2 E+2 | 3.2 E+2 | 2.1 E−1 | 1.2 E+2 | 3.3 E+3 | 7.0 E+1 | 1.2 E+2 | 7.1 E+1 | 1.5 E+3 | 3.5 E+2 |
| 4 | $K_M$ [$M^{-1}$] | 8.3 E−4 | 1.0 E−4 | 2.5 E−4 | 1.3 E−4 | 4.8 E−5 | 2.0 E−4 | 1.5 E−4 | 8.1 E−5 | 5.1 E−5 | 3.4 E−4 |
| | $K_M$ ci [$M^{-1}$] | 2.8 E−4 | 1.9 E−5 | 1.2 E−4 | 2.3 E−5 | 1.1 E−5 | 4.2 E−5 | 2.7 E−5 | 1.4 E−5 | 1.6 E−5 | 6.0 E−5 |
| | $k_{cat}$ [$s^{-1}$] | 6.5 E−1 | 1.0 E−1 | 1.3 E−4 | 2.3 E−2 | 1.9 E−1 | 7.8 E−2 | 3.1 E−2 | 9.2 E−3 | 1.7 E−1 | 1.6 E−1 |
| | $k_{cat}$ ci [$s^{-1}$] | 1.9 E−1 | 8.7 E−3 | 3.9 E−5 | 2.1 E−3 | 1.6 E−2 | 9.8 E−3 | 3.2 E−3 | 7.0 E−4 | 2.0 E−2 | 2.0 E−2 |
| | $k_{cat}/K_M$ [$M^{-1}s^{-1}$] | 7.8 E+2 | 9.6 E+2 | 5.1 E−1 | 1.7 E+2 | 3.9 E+3 | 3.8 E+2 | 2.2 E+2 | 1.1 E+2 | 3.3 E+3 | 4.6 E+2 |
| 5 | $K_M$ [$M^{-1}$] | 3.7 E−4 | 1.2 E−4 | 1.2 E−4 | 1.2 E−4 | 6.8 E−5 | 1.2 E−4 | 1.0 E−4 | 9.0 E−5 | 5.6 E−5 | 4.2 E−4 |
| | $K_M$ ci [$M^{-1}$] | 1.2 E−4 | 3.8 E−5 | 3.3 E−5 | 1.8 E−5 | 1.6 E−5 | 2.8 E−5 | 1.6 E−5 | 1.5 E−5 | 2.4 E−5 | 3.1 E−4 |
| | $k_{cat}$ [$s^{-1}$] | 5.8 E−1 | 5.5 E−2 | 1.3 E−4 | 4.7 E−2 | 3.6 E−1 | 2.7 E−2 | 3.1 E−2 | 1.1 E−2 | 1.7 E−1 | 3.0 E−1 |
| | $k_{cat}$ ci [$s^{-1}$] | 1.4 E−1 | 8.6 E−3 | 1.9 E−5 | 3.6 E−3 | 3.5 E−2 | 3.2 E−3 | 2.4 E−3 | 8.6 E−4 | 2.8 E−2 | 1.6 E−1 |
| | $k_{cat}/K_M$ [$M^{-1}s^{-1}$] | 1.6 E+3 | 4.4 E+2 | 1.1 E+0 | 3.9 E+2 | 5.3 E+3 | 2.2 E+2 | 3.1 E+2 | 1.2 E+2 | 3.1 E+3 | 7.2 E+2 |
| 6 | $K_M$ [$M^{-1}$] | 4.8 E−4 | 1.3 E−4 | 1.0 E−4 | 1.2 E−4 | 4.7 E−5 | 1.8 E−4 | 1.2 E−4 | 1.0 E−4 | 5.3 E−5 | 9.0 E−4 |
| | $K_M$ ci [$M^{-1}$] | 1.4 E−4 | 4.4 E−5 | 1.8 E−5 | 2.2 E−5 | 1.8 E−5 | 2.4 E−5 | 3.9 E−5 | 2.2 E−5 | 2.3 E−5 | 4.6 E−4 |
| | $k_{cat}$ [$s^{-1}$] | 1.1 E+0 | 1.3 E−1 | 2.9 E−4 | 5.4 E−2 | 5.1 E−1 | 4.8 E−2 | 5.3 E−2 | 2.3 E−2 | 2.4 E−1 | 1.1 E+0 |
| | $k_{cat}$ ci [$s^{-1}$] | 2.4 E−1 | 2.2 E−2 | 2.4 E−5 | 5.0 E−3 | 7.2 E−2 | 3.8 E−3 | 9.1 E−3 | 2.3 E−3 | 3.9 E−2 | 4.9 E−1 |
| | $kcat/K_M$ [$M^{-1}s^{-1}$] | 2.3 E+3 | 9.8 E+2 | 2.8 E+0 | 4.4 E+2 | 1.1 E+4 | 2.7 E+2 | 4.5 E+2 | 2.2 E+2 | 4.6 E+3 | 1.2 E+3 |

9.3.4 Determination of Enzymatic Activity with Model Proteins

Purified model proteins carrying a fusion tag e.g. MHHHHHHGSGVDVAD (SEQ ID No. 252) fused to the N-terminus of the POI were used as the substrate for a kinetic assay. All model protein substrates were formulated in PBS. The model proteins used were human fibroblast growth factor 2 (FGF-2) which was produced as a soluble protein in the cytosol of *E. coli*, human tumor necrosis factor alpha (TNFα) which was produced as a soluble protein in the periplasma of *E. coli*, and a single chain variable fragment, BIWA4 (scFv) which was produced as an inclusion body in the cytosol of *E. coli*. The buffer for the digestion was PBS.

To determine a Michaelis-Menten kinetics six different concentrations (100 μM, 384 μM, 668 μM, 952 μM, 1236

μM, 1520 μM) of the model protein hFGF-2 were incubated with 1 μM of different cp caspase-2 variants (in triplicates). The reaction was stopped by adding formic acid to a final concentration of 0.1% after 45 seconds.

To determine a Michaelis-Menten kinetics five different concentrations (50, 101, 135, 220, 305 μM) of the model protein BIWA4 were incubated with 10 μM of mS9ProD/E (in triplicates). The reaction was stopped by adding formic acid to a final concentration of 0.2% after 420 seconds.

To determine a Michaelis-Menten kinetics six different concentrations (100 μM, 299 μM, 498 μM, 697 μM, 896 μM, 1093 μM) of the model protein tumor necrosis factor α were incubated with 10 μM of different cp caspase-2 variants (in duplicates). The reaction was stopped by adding formic acid to a final concentration of 0.1% after 420 seconds.

Product generation was determined using the RP-HPLC method outlined in section 9.3.2. Initial rate (v0) in μM/s of each concentration was calculated using the fusion tag peak area at the time points of the initial slope. This data was transferred to TableCurve 2D to fit a Michaelis-Menten kinetics in order to get values for $V_{max}$ and $K_M$.

TABLE 23

Model protein kinetic results n.d. = not determined, conf int = 95% confidence interval.

| Caspase | | hFGF-2 | BIWA4 | TNFa |
|---|---|---|---|---|
| 6H_cpCasp2D | $K_M$ [$M^{-1}$] | 5.9 E−4 | n.d. | n.d. |
| (SEQ ID No: | KM ci [M − 1] | 1.7 E−4 | n.d. | n.d. |
| 6) | $k_{cat}$ [$s^{-1}$] | 6.2 E−1 | n.d. | n.d. |
| | kcat ci [s − 1] | 6.8 E−2 | n.d. | n.d. |
| | kcat/KM [M − 1s − 1] | 1.1 E+3 | n.d. | n.d. |
| T7AC_6H_ | $K_M$ [$M^{-1}$] | 6.5 E−4 | n.d. | 2.8 E−4 |
| cpCasp2D | KM ci [M − 1] | 2.3 E−4 | n.d. | 6.5 E−5 |
| (SEQ ID NO: | $k_{cat}$ [$s^{-1}$] | 1.7 E+0 | n.d. | 1.3 E−2 |
| 41) | kcat ci [s − 1] | 2.4 E−1 | n.d. | 9.8 E−4 |
| | $k_{cat}/K_M$ [$M^{-1}s^{-1}$] | 2.6 E+3 | n.d. | 4.7 E+1 |
| T7AC_6H_ | $K_M$ [$M^{-1}$] | 2.9 E−4 | 1.6 E−4 | 5.2 E−4 |
| mS9ProE | KM ci [M − 1] | 4.8 E−5 | 1.4 E−4 | 1.7 E−4 |
| (SEQ ID NO: | $k_{cat}$ [$s^{-1}$] | 1.3 E+0 | 5.8 E−3 | 7.9 E−2 |
| 71) | kcat ci [s − 1] | 6.0 E−2 | 1.0 E−2 | 1.1 E−2 |
| | $k_{cat}/K_M$ [$M^{-1}s^{-1}$) | 4.5 E+3 | 3.6 E+1 | 1.5 E+2 |
| T7AC_6H_ | $K_M$ [$M^{-1}$] | 2.7 E−4 | 2.3 E−4 | n.d. |
| mS9ProD | KM ci [M − 1] | 4.1 E−5 | 4.7 E−5 | n.d. |
| (SEQ ID NO: | $k_{cat}$ [$s^{-1}$] | 1.9 E+0 | 3.2 E−3 | n.d. |
| 72) | kcat ci [s − 1] | 7.6 E−2 | 3.6 E−4 | n.d. |
| | $k_{cat}/K_M$ [$M^{-1}s^{-1}$] | 6.9 E+3 | 1.4 E+1 | n.d. |

9.3.5 Protein Cleavage in Solution

The fusion proteins as described in section 9.3.4 were used substrates for a kinetic assay. All model protein substrates were formulated in PBS. The buffer for the digestion was PBS.

Product generation was determined using the RP-HPLC method outlined in section 9.3.2.

For the digestion of fusion protein, a certain concentration of fusion protein was incubated under agitation at room temperature with a defined concentration of cp caspase-2. For the digestion of hFGF-2, 2.9 g/L hFGF-2 fusion protein was incubated with 0.055 g/L cp caspase-2 or the variant mS9 Pro D285E or mS9 Pro D. The cleavage of FGF-2 fusion protein was also performed with varying concentrations of FGF-2 (2 g/L and 10 g/L) and cp caspase-2 (0.02 g/L, 0.1 g/L) and the product generation was determined over time. For the digestion of TNF-alpha, 2.4 g/L TNF-alpha fusion protein was incubated with 0.046 g/L cp caspase-2 or the variant mS9 Pro D285E. For the digestion of GFP, 9.1 g/L GFP fusion protein was incubated with 0.11 g/L cp caspase-2 or the variant mS9 Pro D285E.

Tag cleavage from FGF-2 with cp caspase-2 and variants thereof showed very fast processing. Complete removal of the tag for hFGF-2 was measured after 15 minutes for mS9 Pro D285E and mS9 Pro D and after 180 minutes for cp caspase-2 as shown in FIG. 17. Cleavage kinetic for 2.9 g/L hFGF-2 fusion protein incubated with 0.055 g/L of T7AC_cpCasp2D (SEQ ID No. 41), T7AC_mS9ProE (SEQ ID No. 71) and T7AC_mS9ProD (SEQ ID No. 72).

FIG. 18 shows the cleavage kinetic for hFGF-2 fusion protein incubated at varying concentrations with cp caspase-2 (cpCasp2, SEQ ID No. 6)

FIG. 18 shows the influence of fusion protein and enzyme concentration in the example of FGF-2 cleavage with cp caspase-2. The cleavage appears similarly fast when the ratio of fusion protein to enzyme is kept constant. At high substrate concentrations, i.e. high concentrations of fusion protein, the reaction is still fast even when cp caspas-2 is only used at a 1:500 dilution.

TNF-alpha is a more difficult substrate, due to its N-terminal valine. The cleavage reaction is slower compared to FGF-2, but high yields are still possible. TNF-alpha fusion protein could be cleaved efficiently with either cp caspase-2 or mS9 Pro D285E variant, with the variant producing up to 98% cleaved protein of interest (FIG. 19).

The cleavage of GFP fusion protein is slower, but up to 60% of GFP can be processed as shown in FIG. 20.

9.3.6 Protein Cleavage with Immobilized Enzyme

Enzyme immobilization was performed through amine coupling. The primary amino groups of the lysine residues on the enzyme were coupled to activated NHS-groups, placed on spacer arms in the resin. The coupling forms a stable amide bond. Cp caspase-2 was immobilized at the following concentrations 1 μM, 10 μM, 50 μM and 100 μM. The enzyme was diluted in coupling buffer (0.2 M $NaHCO_3$, 0.5 M NaCl, pH 8.3) to reach the desired concentration. For a 500 μl column, around 1.5-2 ml of resin slurry in 100% isopropanol was transferred to a 15 ml centrifuge tube. The first step was to wash the resin for removal of the isopropanol. This was done with 10 to 15 resin volumes of cold 1 mM HCl. Immediately after the washing step, the resin and the coupling buffer with enzyme were mixed using a vortex. The sample was left at 4° C. overnight for the coupling reaction. After the coupling the samples were mixed with blocking buffer (0.1 M Tris-HCl, pH 8.5) and kept in the buffer for 2 to 4 hours to block all non-reacted NHS groups in the resin. The samples were then washed alternating two buffers with high (0.1 M Tris-HCl, pH 8.5) respectively low (0.1 M HAc, 0.5 M NaCl, pH 4.7) pH using 3 medium volumes each time and repeating the procedure for 3 to 6 times. In each step, the buffer was added, the sample vortexed, thereafter centrifuged (1.000×g, 1 min, 4° C.) and the supernatant was discarded. The immobilized resin was then stored at 4° C. in either 20% EtOH or 0.01% $NaN_3$ in 1×PBS to prevent microbial contamination before packed in columns.

To determine the kinetics and activity of the immobilized cp caspase-2, the columns were tested with different concentrations of the model protein, hFGF-2 at varying residence times in the column. The flow through from the sample application and first column wash was collected in fractions in 96 deep well plates containing 1/1000 formic acid to deactivate any leaked enzyme and to stop the reaction. The amount of product was quantified using the RP-HPLC method outlined in section 9.3.2.

The amount of cleavage varied with residence time (See FIG. 21). At low residence times, less cleavage was observed, due to mass transfer limitation of the stationary phase.

Example 10: General Materials and Methods for Examples 2-7 and 11-16 (Unless Otherwise Stated)

10.1 *Escherichia coli* Strains

*E. coli* BL21 (DE3) was used for all standard protein expressions and for the selection system as outlined in Example 3.

For plasmid extractions and for cloning experiments *E. coli* strain NovaBlue (Novagen, Madison, WI, USA) was used as a host.

10.2 Culture Media

TY (tryptone-yeast) medium (1% peptone, 0.7% yeast extract, 0.25% (w/v) NaCl).

TB medium (1.2% peptone, 2.4% yeast extract, 0.4% glycerol, 17 mM $KH_2PO_4$, 72 mM $K_2HPO_4$).

SOC (super optimal broth with catabolite repression) (2% (w/v) tryptone, 0.5% (w/v) yeast extract, 10 mM NaCl, 2.5 mM KCl, 10 mM $MgCl_2$ and 20 mM glucose, pH 7.0). Medium for the recovery of cells after transformation.

Optimized M9 minimal medium (50 mM $Na_2HPO_4$, 20 mM $KH_2PO_4$ 10 mM NaCl, 1 mM $MgSO_4$, 0.1 mM $CaCl_2$), 0.4% Glucose, 20 mM $NH_4Cl$, 0.5% (w/v) casamino acids, 10 μg/ml $FeSO_4$, vitamins (0.001 mg/ml of each biotin, thiamine, riboflavin, pyridoxine, niacinamide). For induction 0.1 to 0.4 mM IPTG were used.

10.3 Recombinant Protein Expression

Standard Expression Protocol: Fusion proteins, which are substrates (hereinafter "fusion proteins" or "substrates") for caspases, caspase-2 variants, cp caspases-2 with (hereinafter "P1'tolerable cp caspases-2") and without mutations (hereinafter "wild-type cp caspases-2") for increased tolerability for the amino acid in P1'position, as described in Example 2, Section 2.2 were expressed in TY medium in shaking flasks. A 20 ml preculture was prepared by inoculation with a single colony and incubated shaking at 220 rpm, 37° C. overnight. The next day the culture was diluted 1:50 in 1000 ml fresh TY medium and incubated shaking at 220 rpm, 37° C. until induction at OD600 1.0 with 1 mM IPTG, at 37° C., 220 rpm, for 4 h.

Expression protocol for wild-type cp caspases-2 and P1'tolerable cp caspases-2: The cp caspases-2 were expressed in TB medium in shaking flasks. A 20 ml preculture was prepared by inoculation with a single colony and incubated shaking at 220 rpm, 37° C. overnight. The next day the culture was diluted 1:50 in 1000 ml fresh TB medium and incubated shaking at 220 rpm, 37° C. until induction at OD600 1.2 with 0.4 mM IPTG, 25° C., 220 rpm, for 4 h.

10.4 Cell Lysis and Protein Purification

Fusion proteins, wild-type cp caspases-2 and P1'tolerable cp-caspase-2 variants were purified using Immobilized Metal Affinity Purification (IMAC).

The harvested cell pellets were suspended in Tris-Buffer (50 mM Tris, 50 mM NaCl, pH 7.5), disrupted with a French press and the clarified supernatant applied to an IMAC column (HisTrap FF Crude, 1 ml, GE Healthcare). Washing was executed for five column volumes with running buffer (50 mM Tris/HCl, pH 7.4, 300 mM NaCl, 20 mM Imidazole), the fifth wash fraction had an increased imidazole concentration (40 mM). Elution was conducted for five column volumes with buffer containing 250 mM imidazole.

After affinity-chromatography imidazole and excess NaCl were exchanged to Tris-buffer with a sepharose column (HiTrap Desalting, 5 ml, GE Healthcare). All elution fractions were pooled, the concentration determined with a BCA assay, and the proteins stored in Tris-Buffer with 2 mM DTT at −80° C.

10.5 Testing of Wild-Type Cp Caspases-2 and P1'Tolerable Cp Caspases-2 (Hereinafter Together "Cp Caspases-2")—In Vitro Cleavage Assay The activity of purified caspases was assessed with an in vitro cleavage assay. The samples were analyzed with SDS-PAGE to separate cleaved and unprocessed substrate. The band intensities were measured with ImageQuant TL 1 D software, version 8.1 (GE Healthcare) and used for statistical analysis and calculation of cleavage efficiency. To standardize the process samples with about 50% of cleaved fusion protein were used for calculations.

Standard conditions where defined as: enzyme to fusion protein mass ratio of 1:100 (1 mg/ml substrate and 0.01 mg/ml caspase, molar ratio 1:170) in caspase assay buffer (20 mM PIPES, 100 mM NaCl, 10% sucrose, 0.1% CHAPS, 1 mm EDTA, 10 mM DTT, pH 7.2) and incubation at 25° C. For slowly proceeding reactions the caspase concentration was increased to 0.1 mg/ml (enzyme to fusion protein mass ratio 1:10). Fusion proteins are described in Example 2, section 2.2.

cp caspase-2 (0.01 mg/ml) (SEQ ID No. 6) cleaved 50% of the substrate VDVAD-E2 (SEQ ID NO:33) with a P1' glycine (1 mg/ml) (SEQ ID No. 33) at 25° C., in caspase assay buffer within 1 min (FIG. 4 A). These conditions were defined as standard activity to which all other reactions were compared.

By N-terminal Edman sequencing of the processed fusion protein, it was proven, that it was only cleaved between the VDVAD (SEQ ID NO:45) recognition site and the P1' glycine.

FIG. 4A shows a standard cleavage assay with cp caspase-2 (SEQ ID No. 6) and VDVAD-E2 (SEQ ID NO:33) with a P1' glycine (SEQ ID No. 33). Cleavage of 1 mg/ml VDVAD-E2 (SEQ ID NO:33) with 0.01 mg/ml cp caspase-2 at 25° C. is shown, samples taken after 1.0, 2.5 and 5 min. After 2.5 min 90% of substrate were cleaved and processing was completed in less than 5 min.

For in vitro cleavages that compared the activity to commercially available caspase-2 about 0.005 mg/ml wt caspase-2 (Caspase-2 (human), recombinant, active, Enzo Life Sciences Inc.; Farmingdale (NY), USA) were used to cleave 1 mg/ml VDVAD-E2 (SEQ ID NO:33) with a P1' glycine (mass ratio 1:200, molar ratio 1:340).

Example 11: Designed Wild-Type Cp Caspases-2, P1'Tolerable Cp-Caspases-2 and Fusion Proteins 11.1 Cloning of Constructs To create specific changes like deletions, insertions of linkers or tags, substitutions, site mutations of single bases or the like in initial proteins, site directed mutagenesis was performed.

The specific primers containing the desired mutations were designed with 5' ends annealing back-to-back and were used for an exponential amplification of the whole plasmid with a high-fidelity DNA polymerase in a polymerase chain reaction (PCR).

After amplification a KLD (kinase ligase DpnI) reaction was performed. In this treatment the PCR product was incubated with a Kinase, a Ligase and DpnI restriction enzyme, so that the PCR fragments were phosphorylated and ligated to a circular plasmid and the bacterial derived, methylated template DNA was digested. NovaBlue heat shock cells were transformed with the constructs and a fraction of the cell suspension was plated on TY agar containing the appropriate antibiotic. Successful cloning was verified by sequencing of single colonies.

All fusion proteins and cp caspases-2 as described here were expressed and purified as described in Example 10, sections 10.3 and 10.4 unless otherwise stated.

Protein and nucleotide sequences of all constructs are listed in FIG. 1.

11.2 Fusion Proteins as Substrates for Caspases, Caspase-2 Variants and Cp Caspases-2

Human ubiquitin-conjugating enzyme E2 L3 (E2; Uni-Prot ID P6803612) as fusion protein was used as standard caspase substrate. A fusion protein (VDVAD-E2) with N-terminal His tag, short GSG-linker and VDVAD (SEQ ID NO:45) caspase-2 recognition site was designed (SEQ ID NO:33). The first amino acid after the cleavage site (P1') was a glycine (VDVAD-E2, SEQ ID No. 33). The whole protein has a size of 21.3 kDa, whereas when the tag is cleaved off, the E2 protein itself has 19.5 kDa. This difference is big enough to visualize the cleavage activity on an SDS-PAGE.

As the P1' site is known to influence cleavage activity, E2 was expressed and purified with all twenty possible residues after the VDVAD (SEQ ID NO:45) cleavage site. E2 was also cloned with cleavage sites differing from VDVAD (SEQ ID NO:45). All tested tag sequences fused to E2-protein are listed in Table 1.

β-galactosidase was chosen as a model protein, because due to its large size (116 kDa) it is vulnerable to unspecific cleavage. An N-terminal His tag as well as a GSG linker and the caspase-2 cleavage site VDVAD (SEQ ID NO:45) were added (SEQ ID No. 34). The first amino acid after the cleavage site (P1'=the N-terminal amino acid of the β-ga-lactosidase) is a methionine (M, Met).

Superoxide Dismutase, SOD, was used as a model fusion protein with an N-terminal 6His (SEQ ID NO:315)Tag, a GSG linker and the recognition site, VDVAD (SEQ ID NO:45), fused to the N-terminus of SOD (SEQ ID No. 193). The first amino acid after the cleavage site (P1'=the N-ter-minal amino acid of Superoxide Dismutase) is glycine (g, Gly).

11.3 Designed Wild-Type Cp Caspases-2 and P1 Tolerable Cp-Caspase-2 Variants

Circularly permuted caspase-2: Circularly permuted caspase-2 variants (cp caspases-2) were designed. based on the sequence of human caspase-2 (UniProtKB14 ID P42575, SEQ ID No. 11); the N-terminal CARD was removed and the order of large (LS) and small subunit (SS) exchanged to create a constitutively active caspase. The SS was linked to the N-terminus of the LS via a GS-linker. Optionally the SS pro-peptide was linked to the N-terminus of the SS. In this case to ensure expression as a single chain protein, an aspartate (Asp$^{343}$ in the wild-type sequence of caspase-2, Asp$^{21}$ in the cp caspase-2) was mutated to alanine, to avoid cleavage of the small subunit from a p14 to a p12 chain. This resulted in the cp caspases-2 SEQ ID No.9, SEQ ID No. 6 and, SEQ ID No. 76, both of the latter having additionally an N-terminal 6 His tag. The basic structures of these variants are shown in FIG. 2 B, C, D and FIG. 3 B, C, D.

The protein sequence was codon optimized for E. coli with the GeneArt™ online tool (Thermo Fisher Scientific). Between the small and the large subunit, a glycine-serine linker was added which also forms a BamHI restriction site.

This enables the separate cloning of the subunits and facilitates the creation of chimera consisting of subunits from different caspases. The N-terminal His tag enabled IMAC-purification.

FIG. 2 shows a schematic representation of wild-type (SEQ ID No. 11) and cp caspase-2 (e.g. SEQ ID No. 9) structures. The annotations are taken from UniProtKB Database (P42575). The structure of the active enzymes (caspase dimer) is depicted in FIG. 3. FIG. 3 shows a schematic representation of mature enzymes of wild-type and circularly permuted caspase-2 structures. Disulfide bonds between small subunits, linkers, as well as N- and C-termini are depicted. While the mature wild-type caspase-2 consists of four protein chains, the cp caspase-2 has only two.

All cp-caspase-2 variants described under this chapter 2.3 were constructed based on SEQ ID No. 6, except otherwise described. The amino acid positions of the mutations indicated correspond to SEQ ID No. 6, unless explicitly stated otherwise. All variants have 6His (SEQ ID NO:315) Tag, except otherwise described.

cp caspase-2 Stop and cp caspase-2 D285E: To test the influence of the propeptide annotated in UniProtKB14 (ID P42575) within the C-terminus of the large subunit, a truncated version was produced by deleting amino acids 286-292 in the cp caspase-2 of SEQ ID No. 6, thereby creating the cp caspase-2 Stop variant (SEQ ID No. 14), and an uncleavable variant (cp caspase-2 D285E) (SEQ ID No. 13) was created.

cp caspase-2 with C-terminal Strep tag: Strep tags were fused C-terminal to create cp caspase-2 Strep and cp caspase-2 D285E Strep variants (SEQ ID No. 15 and SEQ ID No. 16, respectively).

In SEQ ID No. 15, a Strep tag was fused to the C-terminus of the cp caspase 2 (SEQ ID No. 6), which was mutated to VDQQS (the substitution: D292S), as experiments had shown that VDQQE is recognized as a cleavage site. Despite the VDQQS mutation, the Strep tag was partially cleaved from the caspase. The cleavage product had the same size as the Stop variant (31.9 kDa), indicating that it had been cleaved at the DETD-R (between Asp$^{285}$ and Arg$^{286}$) and not at the VDQQS site.

Therefore, a Strep tag was added to the C-terminus of cp caspase-2 with the D285E and the E292S mutations. This variant (SEQ ID No. 16) was expressed as a single chain with 33.9 kDa. Proving that the mutation of Asp$^{285}$ to Glu prevents cleavage. The C-terminal Strep-tag did not influence the cleavage activity of this variant. FIG. 5 shows a graphic representation of C-terminal sequences of cp caspases-2.

cp caspase-2 D282T and cp caspase-2 H185A D282T: Two cp caspases-2 were generated, the first with a D282T mutation and the second with an additional H185A mutation in cp caspase-2 (SEQ ID No. 6) comprising SEQ ID No. 17 and SEQ ID No. 18, respectively.

cp caspase-2 G171D, cp caspase-2 V225G, and cp caspase-2 D282E: cp caspase-2 (SEQ ID No. 6) was mutated at positions 171, 225, or 282 respectively resulting in amino acid exchanges G171D, V225G, or D282E resulting in the variants having SEQ ID No. 190, 192 and 191, respectively.

cp caspase-2 with different linkers between small and large subunit: The GS linker between small and large subunit of cp caspase-2 (SEQ ID No. 6) was mutated. Resulting variants contained no linker (cp caspase-2 A Linker, SEQ ID No. 73), a GGSGG linker (cp caspase-2 5 aa Linker, SEQ ID No. 74), and a GSAGSAAGSG linker (cp caspase-2 10 aa Linker, SEQ ID No. 75).

cp caspase-2 with partial and without small subunit propeptide: The propeptide of the small subunit of cp caspase-2 (SEQ ID No. 6) was mutated by site directed mutagenesis. Deletion of residues 8-22 produced a variant without propeptide (cp caspase-2 Δ SS Prop, SEQ ID No. 76, see also FIG. 2 D and FIG. 3 D), deletion of residues 8-15 produced a variant with partial deleted propeptide (cp caspase-2½ Δ SS Prop, SEQ ID No. 77).

cp caspase-2 with shifted circular permutation: cp caspase-2 Δ SS Prop (SEQ ID No. 76) was used to generate variants with shifted circular permutation. At the N-terminus of the small subunit three amino acids were deleted and added to the C-terminus of the large subunit. Because of possible auto-cleavage, detected when adding a Strep-tag to the C-terminal end of cp caspase-2, additionally the mutations D267E and D274S according to SEQ ID No.76 were inserted. The resulting variant cp caspase-2 C-term +3 (SEQ ID No. 82) was expressed, purified and tested as described above in Example 10, sections 10.3, 10.4 and 10.5.

In parallel, a variant was generated by deletion of the 3 C-terminal residues of the large subunit and insertion of those residues to the N-terminus of the small subunit of cp caspase-2 Δ SS Prop (SEQ ID No. 76). The resulting variant cp caspase-2 N-term +3 (SEQ ID No. 83) was expressed, purified and tested as described in the standard protocol in Example 10.

Both variants were expressed with an N-terminal 6His (SEQ ID NO:315)-tag.

cp caspase-2 C203S: The variant was created by insertion of the C203S mutation in cp caspase-2 (SEQ ID No. 6) resulting in SEQ ID No. 198.

cp caspase-2 S9 C203S: The substitution C203S was inserted in cp caspse-2 S9 (SEQ ID No. 51), resulting in SEQ ID No. 199.

cp caspase-2 N85C and cp caspase-2 A86C: The variants were created by insertion of the mutations N85C (SEQ ID No. 80) and A86C (SEQ ID No. 88) in cp caspase-2 (SEQ ID No. 6).

Homologous Cp Caspases-2:

The cp caspases-2 from different species were constructed analogue to the cp caspase-2 of human origin (SEQ ID No. 6).

Based on the sequence of Tasmanian devil caspase-2 (*Sarcophilus harrisii*, UniProtKB14 ID G3VQP7, SEQ ID No. 95) and Ghost shark caspase-2 (*Callorhinchus* mil UniProtKB14 ID V9KZT1, SEQ ID No. 113) the N-terminal CARD was removed and the order of large and small subunit exchanged to create a constitutively active caspase. The SS was linked to the N-terminus of the LS via a GS-linker. The SS pro-peptide was linked to the N-terminus of the SS. To ensure expression as a single chain protein, an aspartate (corresponding to $Asp^{343}$ in the wild-type sequence of human caspase-2, $Asp^{21}$ in the cp protein) was mutated to alanine, to avoid cleavage of the small subunit propeptide.

The protein sequence was codon optimized for *E. coli* with the GeneArt™ online tool (Thermo Fisher Scientific). Between the small and the large subunit, a glycine-serine linker was added which also forms a BamHI restriction site. This enables the separate cloning of the subunits and facilitates the creation of chimera consisting of subunits from different caspases. The N-terminal His tag enabled IMAC-purification.

Resulting variants are Sarcophilus cp caspase-2 (SEQ ID No. 64) and *Callorhinchus* cp caspase-2 (SEQ ID No. 68).

Mutations at positions corresponding to (at positions functionally equivalent to) residues $Glu^{105}$ and $Glu^{172}$ in cp caspase-2 (SEQ ID No. 6) were inserted in Sarcophilus cp caspase-2, generating variant Sarcophilus cp caspase-2 E105V E172V (SEQ ID No. 78).

Mutations at positions corresponding to $Glu^{105}$ and $Gly^{171}$ in cp caspase-2 (SEQ ID No. 6) were inserted in *Callorhinchus* cp caspase-2, generating variant *Callorhinchus* cp caspase-2 E105V G171 D (SEQ ID No. 79).

Additionally, the variants were cloned containing an N-terminal T7AC-6His tag (SEQ ID No. 84, 85, 86, 87).

Functionally equivalent positions are listed in Table 2.

FIG. 6 shows an alignment of natural sequences of homologue caspase-2 from different species. Unprocessed proteins consist of CARD domain, large subunit (LS) containing the two catalytic centers, small subunit propeptide (SS Propept.) and small subunit (SS). Active sites 1-5 interact with substrates. Definition of subunits and active sites see Tables 3 and 4.

UniProt IDs: Human (P42575), Mouse (P29594), Sheep (W5Q8H6), Tasmanian Devil (G3VQP7), Chicken (Q98943), *Anolis* (H9GC58), Alligator (A0A1U8D1G6), *Xenopus* (F6RDY9), *Danio* (QOPKX3), Ghost Shark (V9KZT1), Sea squirt (A0A1W2WKB0)

FIG. 7 shows an alignment of active sites of natural sequences of caspases-2 from different species (sequences and SEQ ID Nos. see Table 21). Active sites interact with substrates and are relatively conserved. Definition of subunits and active sites see Tables 3, 4 and 5. Numbers represent the starting position of the first active site. Table 5 active sites of natural sequences of caspases-2 from different species The homologous cp caspases-2 described above were fermented in benchtop fermentations.

TABLE 24

Expression clones for the homologous cp caspases-2 and variants thereof with solubility tag

| Name of Expression clone | Caspase variant | SEQ ID |
|---|---|---|
| BL21(DE3)(pET30a_T7AC-6H-cpCasp2_cal) | Callorhinchus cp caspase-2 | SEQ ID No. 68 resp. 85 |
| BL21(DE3)(pET30a_T7AC-6H-cpCasp2_sar) | Sarcophilus cp caspase-2 | SEQ ID No. 64 resp. 84 |
| BL21(DE3)(pET30a_T7AC-6H-cpCasp2_cal_E105V, G171D) | Callorhinchus cp caspase-2 E105V G171D | SEQ ID No. 79 resp. 87 |
| BL21(DE3)(pET30a_T7AC-6H-cpCasp2_sar_E105V, E172V) | Sarcophilus cp caspase-2 E105V E172V | SEQ ID No. 78 resp. 86 |

For the benchtop fed-batch cultivations, a DASGIP® parallel bioreactor system (Eppendorf AG, Germany) enabling four parallel cultivations was used. The total vessel volume was 2.1 L with a maximum working volume of 1.8 L The bioreactors were equipped with a pH probe (Hamilton Bonaduz AG, Switzerland), an optical DO probe (Hamilton Bonaduz AG), and a DASGIP® GA4X-module (Eppendorf AG) for online off-gas monitoring. Pre-cultivation and batch phase were identical to the standardized fermentations as described in Example 18 (section 18.1.2.2) unless stated otherwise. The fed-batch phases were performed at 30° C. For biomass production the fed-batch phase was performed with an exponential feed (μ=of 0.05 $h^{-1}$) for 2.74 generations resulting in a total feed time of 39 h. The calculated CDM was 34 g/L.

Induction started with fed-batch phase by adding feed medium including IPTG (so called "over feed" induction) to achieve a final IPTG concentration of 0.5 μmol IPTG/g theoretical CDM at the end of the fermentation and a protein production for 4 generations.

The production of two different cp caspase-2 homologous and variants thereof, T7AC-6H-cpCasp2_cal (SEQ ID No. 68, also called "cpCasp2-cal"), T7AC-6H-cpCasp2_sar (SEQ ID No. 64, also called "cpCasp2_sar"), T7AC-6H-cpCasp2_cal_E105V, G171D (SEQ ID No. 79, also called: "T7AC-6H-cpCasp2_cal_mut" or cpCasp2_cal_mut") and T7AC-6H-cpCasp2_sar_E105V, E172V (SEQ ID No. 78, also called: "T7AC-6H-cpCasp2_sar_mut" or cpCasp2_sar_mut"), were investigated in benchtop fermentations with a p=0.05 $h^{W}$ and an IPTG concentration of 0.9 μmol IPTG/g CDM during induction. The cell growth kinetics of all production clones were comparable (FIG. 28). For the cp caspases-2 derived from the tasmanian devil (*Sarcophilus harrisii*), a wild-type like cp caspase-2 variant, T7AC-6H-cpCasp2_sar (SEQ ID NO:64) and a P1'tolarable cp caspase-2 variant, T7AC-6H-cpCasp2_sar(SEQ ID NO:64)_E105V, E172V, titers of up to 1.6 g/l soluble cp caspases-2 were obtained (FIG. 29).

Purification of the homologous cp caspases-2 was performed as described in section 18.2.2.

Michaelis Menten kinetic was determined as described under section: kinetic and P1'tolerability were tested as described in 18.3.3.

Michaelis Menten kinetic was determined for the homologous cp caspases-2 for the following substrates: VDVADFA (SEQ ID NO:318), VDVADGA (SEQ ID NO:319), VDVADQA (SEQ ID NO:320) and VDVADVA (SEQ ID NO:321), where the P1' amino acid is indicated by bold and underlined font.

TABLE 25

FRET results for cpCasp2 homologs from S. harrisii.

| | P1' | F | G | Q | V |
|---|---|---|---|---|---|
| cpCasp2_sar | $K_M$ (M) | 4.4E−5 | 4.8E−5 | 9.4E−5 | 3.4E−5 |
| | 95% confidence interval $K_M$ (M) | 1.2E−5 | 1.1E−5 | 1.8E−5 | 1.0E−5 |
| | $k_{cat}$ ($s^{-1}$) | 3.4E−3 | 1.4E−1 | 2.0E−3 | 5.5E−4 |
| | 95% confidence interval $k_{cat}$ ($s^{-1}$) | 3.3E−4 | 1.2E−2 | 1.8E−4 | 5.5E−5 |
| | $k_{cat}/K_M$ ($M^{-1}s^{-1}$) | 77 | 2874 | 22 | 16 |
| cpCasp2_sar_mut | $K_M$ (M) | 5.2E−5 | 3.1E−5 | 1.2E−4 | 6.9E−5 |
| | 95% confidence interval $K_M$ (M) | 1.7E−5 | 8.8E−6 | 1.7E−5 | 1.5E−5 |
| | $k_{cat}$ ($s^{-1}$) | 1.2E−2 | 3.2E−1 | 5.6E−3 | 2.3E−3 |
| | 95% confidence interval $k_{cat}$ ($s^{-1}$) | 1.5E−3 | 3.0E−2 | 4.1E−4 | 2.1E−4 |
| | $k_{cat}/K_M$ ($M^{-1}s^{-1}$) | 235 | 10607 | 49 | 34 |

The FRET results in Table 25 show a drastic difference in catalytic efficiency between the two proteases. Adding the mutations E105V and E172V into the cpCasp2 of *S. harrisii*, greatly increases the catalytic efficiency kcat/KM by a factor of 2 to 4. This increase is mostly driven by an increase in the turnover number kcat, while the Michaelis constant KM remains mostly unchanged.

TABLE 26

FRET results for cpCasp2 homologs from C. milii. The values for the P1' amino acids G and F was determined at a single substrate concentration of 100 μM

| | P1' | F | G |
|---|---|---|---|
| cpCasp2_cal | $v_0$ (μM $s^{-1}$) | 7.7E−6 | 6.1E−5 |
| | $v_0$ standard deviation (uM $s^{-1}$) | 3.8E−6 | 3.5E−6 |
| cpCasp2_cal_mut | $v_0$ (μM $s^{-1}$) | 2.4E−5 | 1.1E−4 |
| | $v_0$ standard deviation (uM $s^{-1}$) | 1.4E−6 | 5.5E−7 |

As can be seen in Table 26, cpCasp2_cal_mut with the two mutations E105V and G171 D shows a higher activity for both G and F at the P1' site compared to cpCasp2_cal. In detail, the $v_0$ for the VDVADFA (SEQ ID NO:318) substrate was three times higher for cpCasp2_cal_mut. The $v_0$ for the VDVADGA (SEQ ID NO:319) substrate was two times higher for cpCasp2_cal_mut. This corresponds to an increase in P1' tolerability of 173%.

Example 12: Selection of Cp Caspases-2 and all Found Mutations by Selection

Selection system to detect variants with improved P1' tolerance A selection system was used for the improvement of cp caspase-2. It is based on a circularly permuted ATCase (aspartate transcarbamoylase) catalytic subunit and a pyrimidine auxotroph strain. The pyrBI operon (encoding regulatory pyrI and catalytic pyrB subunits of ATCase) was deleted in *E. coli* BL21(DE3), so this knock-out strain can only survive in media containing pyrimidines or when the cells are complemented with a vector encoding ATCase. A cp catalytic subunit of ATCase (cp-pyrB), which harbors its new N-terminus in the interior of the protein, is used to detect specific proteases via the growth of *E. coli*, because fusion of any stretch of amino acids to its N-terminus renders the enzyme inactive as it can no longer fold properly due to space limitations in the interior of the protein. However, if a protease is provided that can exactly cleave off this additional stretch of amino acids, the enzyme gets reactivated.

12.1 Design of Constructs and Cp Caspase-2 Mutant Libraries

Selection medium: Optimized M9 medium (see Example 10, section 10.2)

Strain: *E. coli* BL21(DE3) with pyrBI operon exchanged to kanamycin resistance (id est: pyrBI is deleted)

Vectors: expressions of the ATCase subunits, cp-pyrB and pyrI from pETDuet™-1 vector using T7 promoters and the ampicillin-resistance as selection marker, expressions of the diverse caspase variants from pACYCDuet™-1 vector using a T7 promoter and the chloramphenicol resistance marker. Selection protocol was performed with respective cotransformations with simultaneous use of ampicillin, kanamycin and chloramphenicol in the above selection medium.

VDVAD (SEQ ID NO:45)-cpATCase

The used pETDuet-1 plasmid (substrate plasmid), contained a pyrI gene in MCSI (SEQ ID No. 20) and cp-pyrB gene in MCSII (SEQ ID No. 21). In pyrI the potential caspase cleavage site DQVD (SEQ ID NO:206, where the $2^{nd}$ residue is E to Q) was changed to DQVE (SEQ ID NO:207, where the $2^{nd}$ residue is E to Q) by mutation of $Asp^{73}$. A 6His(SEQ ID NO:315) tag followed by a GSG linker and a caspase recognition site were fused to the N-terminus of cp pyrB c227 [25]. This hinders the correct folding of the enzyme and makes it inactive, but proteolytic cleavage of this tag can restore its function. The first Met of cp pyrB was deleted. The amino acid after Met is Thr. The cpATCase is still active when this residue is substituted. Only mutations to His, Lys, Phe, Tyr, and Trp render it inactive. This enables the selection for caspases with improved or altered recognition site specificity and/or improved P1' tolerance. CpATCase constructs with 6His-GSG-VDVAD-ΔM-X-pyrB (SEQ ID No. 22) were used for in vivo selection of altered P1' tolerance.

Construction of Cp Caspase-2 Mutant Library—Ep PCR and Oe PCR

Mutant gene libraries of different cp caspases-2 were generated by error prone (ep) PCR and overlap extension (oe) PCR of vector and the mutated caspase gene. The linear DNA fragments were ligated using T4 DNA ligase. The amount of mutations can be modified by changing the Mg(II) and Mn(II) ion concentrations in the PCR buffer. The used concentrations caused in average one to three amino acid exchanges in the caspase. The cp caspases-2, of which mutant libraries were made of, are indicated in Table 5 in the column "Mutated Caspase".

12.2 Selection of Cp Caspase-2 Mutant Libraries

The caspase mutant libraries were transformed into *E. coli* BL21(DE3) ΔpyrBI electro competent cells that already contained the cpATCase plasmid with the desired protease cleavage site and P1' residue. Selection was executed either in optimized M9 medium or on M9 agar plates at 30° C. for 24-48 h. Liquid cultures were used to enrich mutants with improved growth. IPTG concentrations in liquid culture and in agar plates between 0.025 and 1 mM were used.

Mutant libraries in *E. coli* BL21(DE3) ΔpyrBI cells were selected with VDVAD (SEQ ID NO:45)-cpATCase with different P1' residues. Selections were executed with Pro, Met, Thr, and Val. Selections with P1' Met were executed with cp ATCase without deletion of the native methionine, all other selections were executed with constructs comprising SEQ ID No. 22. Selection with Met, Thr, and Val as P1' lead to hundreds of positive variants, thus only the largest colonies were analyzed.

All together 77 clones with a total of 263 mutations were analyzed from all selections combined. Some mutations were found several times in independent experiments. The mutations of resulting variants in comparison to SEQ ID No. 6 are shown in Table 5 below. P1' amino acids used for selection are indicated under "P1'cpATCase".

Mutations of variants were analyzed and several were selected for expression (clones harboring those variants were cultivated and variants expressed and purified as described in Example 10, Sections 10.3 and 10.4) and characterization by in vitro cleavages (as described in Example 10, Section 10.5). Variants were chosen when they had been enriched in liquid culture or contained mutations that were found several times independently. Description of those variants can be found in Example 13.

TABLE 27 cp caspases-2 resulting from the selection as described in this Example

| Variant | P1' cp ATCase | IPTG mM | Mutated caspase | Small Subunit 1-128 | Large Subunit 129-292 |
|---|---|---|---|---|---|
| SM1 | Met | 0.025 | cp caspase-2 D285E | L45Q | K136R |
| SM2 | Met | 0.025 | cp caspase-2 D285E | E105V | |
| SM5 | Met | 0.025 | cp caspase-2 D285E | | T126S |
| SM6 | Met | 0.025 | cp caspase-2 D285E | R35S | Q144R |
| SM7 | Met | 0.025 | cp caspase-2 D285E | E105V | |
| SM8 | Met | 0.025 | cp caspase-2 D285E | | F147L |
| S9 D285E | Met | 0.025 | cp caspase-2 D285E | E105V | |
| SM10 | Met | 0.025 | cp caspase-2 D285E | E105V | |
| SM11 | Met | 0.025 | cp caspase-2 D285E | | L149R<br>V201A |
| SM13 | Met | 0.025 | cp caspase-2 D285E | K26R | |
| SM17 | Met | 0.1 | cp caspase-2 D285E | E105V | C132R<br>E141G<br>H200R |

TABLE 27-continued cp caspases-2 resulting from the selection as described in this Example

| Variant | P1' cp ATCase | IPTG mM | Mutated caspase | Small Subunit 1-128 | Large Subunit 129-292 |
|---|---|---|---|---|---|
| SM18 | Met | 0.1 | cp caspase-2 D285E | H4R<br>K46R<br>M75L<br>E105V | |
| SM19 | Met | 0.1 | cp caspase-2 D285E | | C132W<br>Q144R<br>L149Q<br>S186N |
| SM20 | Met | 0.1 | cp caspase-2 D285E | | C203Y |
| SM31 | Met | 0.1 | cp caspase-2 D285E | K83R | |
| SM32 | Met | 0.1 | cp caspase-2 D285E | Y94H | T226S |
| SM34 | Met | 0.1 | cp caspase-2 D285E | K24R<br>R115S | K136E<br>V189A<br>C194Q<br>H200Q |
| SM37 | Met | 0.1 | cp caspase-2 D285E | G8D<br>C37S | |
| SM38 | Met | 0.1 | cp caspase-2 D285E | | L164M |
| SM39 | Met | 0.1 | cp caspase-2 D285E | | C203R<br>E209D |
| SM42 | Met | 0.1 | cp caspase-2 D285E | G93D<br>C114R | |
| SM44 | Met | 0.1 | cp caspase-2 D285E | | P265T |
| SM45 | Met | 0.1 | cp caspase-2 D285E | | Q148P |
| SM47 | Met | 0.1 | cp caspase-2 D285E | | C203Y |
| ST22 | Thr | 0.1 | cp caspase-2 D285E | | T140A |
| ST23 | Thr | 0.1 | cp caspase-2 D285E | | F148I |
| ST24 | Thr | 0.1 | cp caspase-2 D285E | Y42F | Q155R |
| ST28 | Thr | 0.1 | cp caspase-2 D285E | R35C<br>L45V<br>V82F<br>L87V | |
| ST29 | Thr | 0.1 | cp caspase-2 D285E | N10D | |
| S9-ST47 | Thr | 0.25 | S9 D285E | | H185Q<br>P221L<br>T284A |
| S9-ST50 | Thr | 0.25 | S9 D285E | | Q215H |
| S9-ST51 | Thr | 0.25 | S9 D285E | F68I | E172A |
| S9-ST57 | Thr | 0.25 | S9 D285E | R71C | |
| S9-ST58 | Thr | 0.25 | S9 D285E | | V135A |
| S9-ST59 | Thr | 0.25 | S9 D285E | | F142S<br>L152Q |
| mS9 Thr 0.8 | Thr | 0.8 | S9 D285 | K83E | E172V<br>V225M<br>D285Y |
| S9-ST61 | Thr | 0.25 | S9 D285 | | T284S |
| S9-ST62 | Thr | 0.25 | S9 D285 | C114R | L133Q<br>E283G |
| S9-ST63 | Thr | 0.25 | S9 D285 | C44G | |
| S9-ST65 | Thr | 0.4 | S9 D285 | I61V | V231L |
| S9-ST67 | Thr | 0.4 | S9 D285 | C103G<br>F120L | C132R |
| SV4 | Val | 0.1 | cp caspase-2 D285E | | V201A |
| SV5 | Val | 0.1 | cp caspase-2 D285E | E92V | |
| SV6 | Val | 0.1 | cp caspase-2 D285E | L27P | |
| SV7 | Val | 0.1 | cp caspase-2 D285E | E99V | F147S<br>T170S |
| SV9 | Val | 0.1 | cp caspase-2 D285E | | Q134K |
| SV10 | Val | 0.1 | cp caspase-2 D285E | | V201A |
| SV12 | Val | 0.1 | cp caspase-2 D285E | | C132S<br>Q211R<br>N216D |
| SV13 | Val | 0.1 | cp caspase-2 D285E | | V201D |
| SV28a | Val | 0.1 | cp caspase-2 D285E | | T190S<br>T226S |
| SV30 | Val | 0.1 | cp caspase-2 D285E | | E174G |
| SV31 | Val | 0.1 | cp caspase-2 D285E | | C203Y |
| SV32 | Val | 0.1 | cp caspase-2 D285E | | E174G |
| SV33 | Val | 0.1 | cp caspase-2 D285E | | E174G |
| SV34 | Val | 0.1 | cp caspase-2 D285E | | K193R<br>Q205L<br>T284A |

TABLE 27-continued cp caspases-2 resulting from the selection as described in this Example

| Variant | P1' cp ATCase | IPTG mM | Mutated caspase | Small Subunit 1-128 | Large Subunit 129-292 |
|---|---|---|---|---|---|
| SV36 | Val | 0.1 | cp caspase-2 D285E | | G129S<br>T284A |
| SV37 | Val | 0.1 | cp caspase-2 D285E | | L153Q<br>E239D |
| SV47 | Val | 0.25 | cp caspase-2 D285E | E105V | T226A |
| SV48 | Val | 0.25 | cp caspase-2 D285E | E105V | |
| SV49 | Val | 0.25 | cp caspase-2 D285E | T48S<br>A49S<br>S69I | |
| SV50 | Val | 0.25 | cp caspase-2 D285E | E105V | |
| SV51 | Val | 0.25 | cp caspase-2 D285E | | Q154R |
| SV53 | Val | 0.1 | cp caspase-2 D285E | E141D | |
| SV54 | Val | 0.1 | cp caspase-2 D285E | | H185R |
| SV56 | Val | 0.1 | cp caspase-2 D285E | | H155R<br>S235T |
| SV57 | Val | 0.1 | cp caspase-2 D285E | N116S | T284A |
| SV58 | Val | 0.1 | cp caspase-2 D285E | A49V | Q148R |
| SV60 | Val | 0.1 | cp caspase-2 D285E | K55E | R157Q<br>V189G<br>Q215L |
| SV63 | Val | 0.1 | cp caspase-2 D285E | | E254D |
| S9-SV65 | Val | 0.1 | S9 D285E | K46E | |
| S9-SV66 | Val | 0.1 | S9 D285E | V105A<br>C110R | C138S<br>T190N |
| S9-SV67 | Val | 0.1 | S9 D285E | Y94F | L149Q |
| S9-SV68 | Val | 0.1 | S9 D285E | | Y143F<br>R156L<br>S165I<br>E176V |
| S9-SV71 | Val | 0.25 | S9 D285E | | L258Q |
| S9-SV72 | Val | 0.25 | S9 D285 | Q66K | A150V |
| S9-SV75 | Val | 0.25 | S9 D285 | | F259Y |
| S9-SV77 | Val | 0.4 | S9 D285 | | S186C |
| SP2 | Pro | 0.1 | cp caspase-2 D285E | E99V<br>H123N | |
| SP4 | Pro | 0.1 | cp caspase-2 D285E | M51I | |
| mS9 Pro D285E | Pro | 0.1 | S9 D285E | G171D | V225G<br>D282E |
| S9-SP8 | Pro | 0.1 | S9 D285E | G171D | V225G<br>D282E |
| S9-SP9 | Pro | 0.1 | S9 D285E | G171D | V225G<br>D282E |
| S9-SP10 | Pro | 0.1 | S9 D285E | G171D | V225G<br>D282E |
| S9-SP11 | Pro | 0.1 | S9 D285E | G171D | V225G<br>D282E |
| S9-SP12 | Pro | 0.1 | S9 D285E | | A222T |
| S9-SP14 | Pro | 0.25 | S9 D285 | C110S | K173E<br>D198E<br>K248I |

Example 13: Characterization of Variants Found by Selection as Described in Example 12 cp caspase-2 S9 D285E and S9 0285: Selection of a cp caspase-2 D285E (SEQ ID No. 13) library, containing about 5,500 variants, was performed, with VDVAD (SEQ ID NO:45)-cpATCase that contained a methionine as P1' and with an induction strength of 0.025 mM IPTG. The E105V mutation was found repeatedly among 16 analyzed clones. One selected variant with this mutation (cp caspase-2 S9 D285E, SEQ ID No. 1) was expressed, purified and tested as described in Example 10.

The selected cp caspase-2 S9 D285E was mutated to generate the cp caspase-2 S9 D285 variant (SEQ ID No. 51). The variant was expressed, purified and tested as described above (Example 10).

cp caspase-2 mS9 Pro D285E and cp caspase-2 mS9 Pro 0285: The cp caspase-2 S9 D285E (SEQ ID No. 1) variant was used for a further round of mutation because of its improved P1' tolerance. The new mutant library contained about 10.000 variants and was selected with VDVAD(SEQ ID NO-45)-AM-Pro-cpATCase. Selection in liquid culture enriched a variant (mS9 Pro D285E, SEQ ID No. 70) with the mutations E105V, G171D, V225G, D282E and D285E. The caspase was expressed and purified as described above.

The selected cp caspase-2 mS9 Pro D285E (SEQ ID No. 70) was mutated to generate the cp caspase-2 mS9 Pro D285 variant (SEQ ID No. 52). The variant was expressed, purified and tested as described above.

cp caspase-2 mS9 Thr 0.8: The variant with K83E, E105V, E172V, V255M, and D285Y mutations was selected from mutated cp caspase-2 S9 D285 (SEQ ID No. 51). The new variant (SEQ ID No. 53 and SEQ ID No. 54) was enriched in liquid culture in a selection with VDVAD (SEQ ID NO:45)-Thr-cpATCase and 0.8 mM IPTG. It was expressed, purified and tested as described in Example 10.

cp caspase-2 S17: Variant with E105V, C132R, E141G, H200R, and D285E mutations that was selected from mutated cp caspase-2 D285E (SEQ ID No. 13) with VDVAD (SEQ ID NO:45)-cpATCase with Met as P1' and 0.1 mM IPTG. The variant was never purified and tested in vitro, mutations at positions 105, 132 and 105 were found repeatedly in different experiments.

cp caspase-2 S20: The variant with C203Y and D285E mutations (SEQ ID No. 26) was selected from mutated cp caspase-2 D285E (SEQ ID No. 13) with VDVAD (SEQ ID NO:45)-cpATCase with Met as P1' and 0.1 mM IPTG.

cp caspase-2 D285E SV4: The variant with V201A and D285E mutations (SEQ ID No. 28) was selected from mutated cp caspase-2 D285E (SEQ ID No. 13) with VDVAD (SEQ ID NO:45)-Val-cpATCase and 0.1 mM IPTG. The mutation V201A was found several times independently.

cp caspase-2 SV19: The cp caspase-2 SV 19 (SEQ ID No. 81) was selected from variants with mutated C-terminus with VDVAD (SEQ ID NO:45)-Val-cpATCase and 0.1 mM IPTG.

The sequence equals the consensus-sequence of 13 active variants with mutated C-terminus.

cp caspase-2 D285E SV30: The variant with E174G and D285E mutations (SEQ ID No. 30) was selected from mutated cp caspase-2 D285E (SEQ ID No. 13) with VDVAD (SEQ ID NO:45)-Val-cpATCase and 0.1 mM IPTG. The variant was enriched in liquid culture.

Example 14: Cleavage Activity of Wild-Type Like Cp-Caspase-2 Variants and P1'Tolerable Cp Caspases-2: Designed and Selected Variants 14.1 β-Galactosidase (as Described in Example 11, Section 11.2)

The model substrate β-galactosidase contains four DXXD and one DXXE sites, three of which are on the surface and could be accessible to the caspase.

After incubating 1 mg/ml β-galactosidase fusion protein (with N-terminal tag including the recognition site VDVAD (SEQ ID NO:45) with 0.1 mg/ml cp caspase-2 (SEQ ID No. 6) for 24 hours, no unspecific cleavage was observed(FIG. 59: The cp caspase-2 cleavage cannot be seen since the difference between the cleaved and the uncleaved β-galactosidase fusion protein is too small for a resolution in this SDS-Page). Correct cleavage of the His tag was confirmed by N-terminal protein sequencing.

14.2 SOD (as Described in Example 11, Section 11.2)

FIG. 4 B shows the cleavage of the substrate 6His-VDVAD-SOD (SEQ ID No. 193) by cp caspase-2, SEC ID No. 6: within 1 hour: almost 100% of the substrate was cleaved, whereas no cleavage was observed without cp caspase-2 after 6 hours.

14.3 VDVAD (SEQ ID NO:45)-Gly-E2 (as Described in Example 11, Section 11.2) Cleavage Values of all Tested Cp Caspases-2 (of Examples 10-13 and 16)

Cp caspase-2 (0.01 mg/ml) (SEQ ID No. 6) cleaved 50% of the substrate VDVAD-E2 (SEQ ID NO:33) with a P1' glycine (1 mg/ml) at 25° C., in caspase assay buffer within 1 min. These conditions were defined as standard activity to which all other reactions were compared (FIG. 4A).

The activity of all cp caspases-2 with the fusion protein (substrate), VDVAD-E2 (SEQ ID NO:33) with P1'glycine, was tested as described in Example 10, section 10.5 to compare their standard proteolytic activities. Not all tested variants cleaved this standard substrate to 50% in 1 min. A list of the activities of all cp caspases-2 is given in Table 28.

TABLE 28

Cleavage activity of cp caspases-2 (of Examples 10-13 and 16). Time required to cleave 50% of the VDVAD-E2 fusion protein with P1' Gly (as described in Example 11, Section 11.2) which is used as the standard substrate. Cleavage of 1 mg/ml substrate by 0.01 mg/ml cp caspase-2 variant at 25° C.

| Caspase Variant | Minutes | SEQ ID No. |
|---|---|---|
| cp caspase-2 = cp caspase2D | 1 min | 6 |
| cp caspase-2 D285E = cp caspase-2E | 1 min | 13 |
| cp caspase-2 D282T | 1 min | 17 |
| cp caspase-2 H185A D282T | 1 min | 18 |
| cp caspase-2 S9 D285<br>E105V | 1 min | 51 |
| cp caspase-2 S9 D285E<br>E105V, D285E | 1 min | 1 |
| cp caspase-2 mS9 Pro D285<br>E105V, G171D, V225G, D282E = mS9 ProD | 1 min | 52 |
| cp caspase-2 mS9 Pro D285E<br>E105V, G171D, V225G, D282E, D285E = mS9 ProE | 1 min | 70 |
| cp caspase-2 G171D | 1 min | 190 |
| cp caspase-2 V225G | 1 min | 192 |
| cp caspase-2 D282E | 1 min | 191 |
| cp caspase-2 Thr 0.8<br>K83E E105V, E172V, V255M, D285Y | 4 min | 54 |
| cp caspase-2 Δ Linker<br>without linker between small and large subunit | 1 min | 73 |
| cp caspase-2 5 aa Linker<br>GGSGG linker between small and large subunit | 1 min | 74 |
| cp caspase-2 10 aa Linker<br>GSAGSAAGSG linker between small and large subunit | 1 min | 75 |
| cp caspase-2½ Δ SS Prop<br>partial deletion of small subunit propeptide | 1 min | 77 |
| cp caspase-2 Δ SS Prop<br>deletion of small subunit propeptide | 1 min | 76 |
| Stop Variant | 60 min | 14 |
| cp caspase-2 S20<br>C203Y, D285E | 3 min | 26 |
| cp caspase-2 C203S | 2 min | 198 |
| cp caspase-2 S9 C203S<br>E105V, C203S | 2 min | 199 |
| cp caspase-2 SV19<br>C-terminal sequence DETDHGAVLRG | 2 min | 81 |
| cp caspase-2 D285E SV4<br>V201A, D285E | 3 min | 28 |
| cp caspase-2 D285E SV30<br>E174G, D285E | 3 min | 30 |
| cp Caspase 2 N85C | 2 min | 80 |
| cp Caspase 2 A86C | 1 min | 88 |

TABLE 28-continued

Cleavage activity of cp caspases-2 (of Examples 10-13 and 16). Time required to cleave 50% of the VDVAD-E2 fusion protein with P1' Gly (as described in Example 11, Section 11.2) which is used as the standard substrate. Cleavage of 1 mg/ml substrate by 0.01 mg/ml cp caspase-2 variant at 25° C.

| Caspase Variant | Minutes | SEQ ID No. |
|---|---|---|
| cp Caspase-2 D285E Strep<br>C-terminal Strep-tag, D285E, D292S | 1 min | 16 |
| cp caspase-2 N-term + 3<br>3 C-terminal aa added to N-terminus of small subunit | 1 min | 83 |
| cp caspase-2 C-term + 3<br>3 N-terminal aa added to C-terminus of large subunit | 7 min | 82 |
| cp caspase-2 E105V G171D | 1 min | 253 |
| cp caspase-2 E105V G171V | 1 min | 254 |
| cp caspase-2 E105H G171V | 3 min | 256 |

14.4 P1' Tolerance

Cleavage site specificity and P1' tolerance of caspases have been studied using peptide substrates, degradome analysis, and phage libraries. Peptides are not ideal for this purpose, as structure influences the cleavage activity. Degradome studies, on the other hand, are influenced by the sequences occurring in the analyzed cells. To our knowledge, so far no study has systematically tested caspase specificity and P1' tolerance with protein substrates. Therefore, we permuted the P1' residue after the cleavage site in the fusion protein VDVAD-E2 (SEQ ID NO:33) (Example 11, section 11.2) to evaluate the cleavage efficiency of cp caspase-2 in dependency of the P1' residue.

Glycine was highly preferred in the P1' position, cleavage before all other residues was at least five-times less efficient. The group of amino acids that was reasonably well tolerated comprised small, basic, and aromatic residues, as well as Asn and Met.

Table 29 (Table 29.1 and Table 29.2) shows cleavage of E2 substrates with VDVAD (SEQ ID NO:45) recognition site and different P1' residues (Example 11, section 11.2) by cp caspases-2 (of Examples 10-13 and 16). Cleavage was carried out as described in 10.5. Activity is given in percent of activity for cleavage of VDVAD-E2 (SEQ ID NO:33) with a P1' glycine for each cp-caspase-2 variant. Thus Table 29 (29.1 and 29. 2) shows the P1'tolerance of the respective cp caspase-2 variant. All values (means±standard deviation) were determined with at least three independent experiments, executed with 1 mg/ml E2. For Asp-E2, Glu-E2, Ile-E2, Pro-E2 and Val-E2 cp caspase-2 concentration was 0.1 mg/ml, for all others 0.01 mg/ml. The given values already consider these concentration differences.

Table 30 (Table 30.1 and Table 30.2) further below shows the cleavage activity of all cpcaspase-2 variants for all P1'amino acids related to the cleavage activity of the standard cp caspase-2 (SEQ ID No. 6) in %. Thus Table 30 shows the extent of increase (or decrease) of P1'tolerance.

TABLE 29.1

Cleavage of E2 substrates with VDVAD (SEQ ID NO:45) recognition site and different P1' residues (as described in Example 11, Section 11.2) by cp caspases-2 (of Examples 10-13 and 16). Activity is given in percent of activity for cleavage of VDVAD-E2 (SEQ ID NO:33) with a P1' glycine for the respective cp-caspase-2 variant. Average Values (Av.) and Standard Deviation (Dev.) are shown. All experiments were executed with 1 mg/ml E2 substrate. For P1' = D, E, I, P, and V cp caspase-2 concentration was 0.1 mg/ml, for all others 0.01 mg/ml cp caspase-2 at 25° C..

| Caspase variants | P1' | A | C | D | E | F | H | I | K | L | M |
|---|---|---|---|---|---|---|---|---|---|---|---|
| cp caspase-2 | Av. | 2.24 | 17.8 | 0.140 | 0.033 | 4.85 | 1.91 | 0.08 | 4.09 | 0.25 | 2.80 |
| | Dev. | 0.59 | 2.15 | 0.047 | 0.009 | 1.53 | 0.40 | 0.02 | 1.19 | 0.07 | 0.18 |
| cp caspase-2 D285E | Av. | 1.82 | 7.58 | 0.086 | 0.025 | 1.76 | 0.62 | 0.06 | 1.40 | 0.10 | 1.29 |
| | Dev. | 0.60 | 1.61 | 0.015 | 0.004 | 0.29 | 0.26 | 0.02 | 0.05 | 0.01 | 0.24 |
| cp caspase-2 D282T | Av. | 4.56 | 30.0 | 0.143 | 0.039 | 5.18 | 2.50 | 0.19 | 2.50 | 0.34 | 4.56 |
| | Dev. | 0.42 | 0.00 | 0.046 | 0.003 | 0.78 | 0.00 | 0.03 | 0.00 | 0.07 | 0.42 |
| cp caspase-2 H185A D282T | Av. | 5.76 | 26.7 | 0.178 | 0.042 | 5.76 | 2.88 | 0.20 | 3.67 | 0.61 | 4.44 |
| | Dev. | 0.30 | 3.82 | 0.036 | 0.000 | 0.30 | 0.15 | 0.06 | 0.30 | 0.20 | 0.64 |
| cp caspase-2 S9 D285 | Av. | 7.14 | 40.3 | 0.252 | 0.127 | 12.2 | 4.82 | 0.16 | 7.94 | 1.12 | 7.23 |
| E105V | Dev. | 1.55 | 0.48 | 0.081 | 0.025 | 1.94 | 1.51 | 0.01 | 1.59 | 0.15 | 1.47 |
| cp caspase-2 S9 D285E | Av. | 3.69 | | 0.21 | 0.17 | 14.5 | 21.8 | 0.16 | | 0.7 | 3.2 |
| E105V, D285E | Dev. | | | | | | | | | | |
| cp caspase-2 S9 Pro D285 | Av. | 39.8 | 58.8 | 0.750 | 0.439 | 31.3 | 31.2 | 2.39 | 43.8 | 6.21 | 27.5 |
| E105V, G171D, V225G, D282E | Dev. | 6.84 | 20.3 | 0.160 | 0.145 | 11.0 | 11.9 | 0.81 | 5.15 | 2.03 | 8.63 |
| cp caspase-2 S9 Pro D285E | Av. | 34.1 | 43.9 | 1.400 | 0.961 | 20.1 | 12.1 | 1.48 | 21.7 | 4.03 | 24.2 |
| E105V, G171D, V225G, D282E, D285E | Dev. | 6.12 | 5.36 | 0.351 | 0.070 | 6.06 | 3.66 | 0.22 | 5.64 | 0.87 | 0.74 |
| cp caspase-2 G171D | Av. | 12.5 | 43.0 | 0.292 | 0.148 | 9.49 | 6.18 | 0.64 | 15.5 | 1.81 | 12.5 |
| | Dev. | 0.00 | 14.4 | 0.050 | 0.026 | 2.68 | 0.46 | 0.17 | 2.03 | 0.09 | 2.04 |
| cp caspase-2 V225G | Av. | 2.98 | 13.1 | 0.173 | 0.036 | 2.67 | 2.45 | 0.10 | 3.49 | 0.28 | 2.65 |
| | Dev. | 0.67 | 1.53 | 0.059 | 0.002 | 0.18 | 0.76 | 0.02 | 0.88 | 0.03 | 0.60 |
| cp caspase-2 D282E | Av. | 2.59 | 16.0 | 0.080 | 0.047 | 3.80 | 1.90 | 0.10 | 3.75 | 0.28 | 2.44 |
| | Dev. | 0.32 | 2.74 | 0.009 | 0.011 | 0.35 | 0.17 | 0.01 | 0.42 | 0.00 | 0.30 |
| cp caspase-2 Thr 0.8 | Av. | 28.1 | 70.4 | 3.178 | 3.309 | 21.7 | 17.9 | 1.01 | 21.3 | 3.08 | 20.4 |
| K83E, E105V, E172V, V255M, D285Y | Dev. | 1.70 | 8.47 | 0.168 | 0.561 | 3.18 | 3.82 | 0.45 | 5.91 | 1.45 | 2.46 |
| cp caspase-2 N-term +3 | Av. | | | | | 4.85 | | | | | |
| | Dev. | | | | | 0.53 | | | | | |
| cp caspase-2 C-term +3 | Av. | | | | | 1.98 | | | | | |
| | Dev. | | | | | 0.14 | | | | | |
| cp caspase-2 E105V G171D | Av. | | | | | 23.8 | | | | | |
| | Dev. | | | | | 3.8 | | | | | |
| cp caspase-2 E105V G171V | Av. | | | | | 22.7 | | | | | |
| | Dev. | | | | | 3.5 | | | | | |
| cp caspase-2 E105H G171V | Av. | | | | | 11.3 | | | | | |
| | Dev. | | | | | 0.5 | | | | | |

TABLE 29.2

Cleavage of E2 substrates with VDVAD (SEQ ID NO:45) recognition site and different P1' residues (as described in Example 11, section 11.2) by cp caspases-2 (of Examples 10-13 and 16). Activity is given in percent of activity for cleavage of VDVAD-E2 with a P1' glycine for the respective cp-caspase-2 variant. Average Values (Av.) and Standard Deviation (Dev.) are shown. All experiments were executed with 1 mg/ml E2 substrate. For P1' D, E, I, P, and V cp caspase-2 concentration was 0.1 mg/ml, for all others 0.01 mg/ml cp caspase-2 at 25° C..

| Caspase variants | P1' | N | P | Q | R | S | T | V | W | Y |
|---|---|---|---|---|---|---|---|---|---|---|
| cp caspase-2 | Av. | 4.41 | 0.0025 | 0.48 | 4.95 | 8.01 | 0.56 | 0.16 | 3.47 | 2.65 |
| | Dev. | 0.97 | 0.0009 | 0.16 | 0.68 | 1.08 | 0.00 | 0.02 | 0.12 | 0.13 |
| cp caspase-2 D285E | Av. | 2.97 | 0.0006 | 0.41 | 4.27 | 4.48 | 0.55 | 0.11 | 0.77 | 0.79 |
| | Dev. | 0.89 | 0.0002 | 0.12 | 0.24 | 0.28 | 0.09 | 0.01 | 0.07 | 0.04 |
| cp caspase-2 D282T | Av. | 4.93 | 0.0035 | 0.52 | 6.75 | 12.7 | 1.72 | 0.36 | 3.33 | 3.03 |
| | Dev. | 0.38 | 0.0000 | 0.10 | 0.55 | 0.76 | 0.49 | 0.05 | 0.38 | 0.29 |
| cp caspase-2 H185A D282T | Av. | 5.08 | 0.0028 | 0.61 | 6.91 | 12.5 | 2.36 | 0.42 | 4.06 | 3.17 |
| | Dev. | 0.39 | 0.0002 | 0.11 | 0.51 | 1.25 | 0.38 | 0.10 | 0.58 | 0.20 |
| cp caspase-2 S9 D285 | Av. | 11.7 | 0.0065 | 0.90 | 14.6 | 17.3 | 1.67 | 0.46 | 9.83 | 6.87 |
| E105V | Dev. | 0.00 | 0.0013 | 0.11 | 3.94 | 3.44 | 0.33 | 0.09 | 2.42 | 1.25 |
| cp caspase-2 S9 D285E | Av. | | 0.005 | 0.80 | | | 1.75 | 0.32 | | |
| E105V, D285E | Dev. | | | | | | | | | |
| cp caspase-2 S9 Pro D285 | Av. | 40.0 | 0.1380 | 10.9 | 62.1 | 55.5 | 16.0 | 5.25 | 22.7 | 28.6 |
| E105V, G171D, V225G, D282E | Dev. | 0.00 | 0.0483 | 3.48 | 15.9 | 16.4 | 4.88 | 1.74 | 7.05 | 0.00 |
| cp caspase-2 S9 Pro D285E | Av. | 21.0 | 0.0651 | 2.10 | 45.2 | 39.9 | 15.1 | 3.66 | 16.4 | 12.3 |

TABLE 29.2-continued

Cleavage of E2 substrates with VDVAD (SEQ ID NO:45) recognition site and different P1' residues (as described in Example 11, section 11.2) by cp caspases-2 (of Examples 10-13 and 16). Activity is given in percent of activity for cleavage of VDVAD-E2 with a P1' glycine for the respective cp-caspase-2 variant. Average Values (Av.) and Standard Deviation (Dev.) are shown. All experiments were executed with 1 mg/ml E2 substrate. For P1' D, E, I, P, and V cp caspase-2 concentration was 0.1 mg/ml, for all others 0.01 mg/ml cp caspase-2 at 25° C..

| Caspase variants | P1' | N | P | Q | R | S | T | V | W | Y |
|---|---|---|---|---|---|---|---|---|---|---|
| E105V, G171D, V225G, D282E, D285E | Dev. | 3.61 | 0.0142 | 0.76 | 4.30 | 3.88 | 2.16 | 0.45 | 3.44 | 2.52 |
| cp caspase-2 G171D | Av. | 12.8 | 0.0331 | 3.74 | 24.6 | 23.8 | 5.21 | 1.03 | 8.41 | 3.65 |
| | Dev. | 4.19 | 0.0126 | 0.69 | 4.83 | 4.32 | 0.88 | 0.08 | 0.45 | 0.52 |
| cp caspase-2 V225G | Av. | 4.82 | 0.0019 | 0.56 | 4.68 | 5.31 | 0.63 | 0.14 | 3.81 | 2.54 |
| | Dev. | 0.99 | 0.0006 | 0.00 | 1.17 | 1.33 | 0.03 | 0.02 | 1.17 | 0.78 |
| cp caspase-2 D282E | Av. | 4.22 | 0.0034 | 0.51 | 5.19 | 5.93 | 0.95 | 0.20 | 4.19 | 3.52 |
| | Dev. | 0.17 | 0.0005 | 0.08 | 0.52 | 0.85 | 0.06 | 0.02 | 0.21 | 0.21 |
| cp caspase-2 Thr 0.8 | Av. | 26.9 | 0.0332 | 17.3 | 35.2 | 51.2 | 13.1 | 3.26 | 17.41 | 13.2 |
| K83E, E105V, E172V, V255M, D285Y | Dev. | 3.01 | 0.0015 | 1.10 | 4.23 | 7.67 | 1.79 | 0.45 | 4.29 | 0.81 |
| cp caspase-2 N-term +3 | Av. | | | 1.04 | | | | 0.23 | | |
| | Dev. | | | 0.10 | | | | 0.07 | | |
| cp caspase-2 C-term +3 | Av. | | | 4.44 | | | | 0.10 | | |
| | Dev. | | | 0.97 | | | | 0.00 | | |
| cp caspase-2 E105V G171D | Av. | | 0.1937 | 7.44 | | | 20.0 | 6.86 | | |
| | Dev. | | 0.0321 | 0.77 | | | 0.0 | 0.57 | | |
| cp caspase-2 E105V G171V | Av. | | 0.1362 | 5.26 | | | 4.8 | 1.63 | | |
| | Dev. | | 0.0476 | 0.31 | | | 0.4 | 0.13 | | |
| cp caspase-2 E105H G171V | Av. | | 0.0170 | 2.45 | | | 1.8 | 0.43 | | |
| | Dev. | | 0.0026 | 0.21 | | | 0.2 | 0.03 | | |

TABLE 30.1

Cleavage activity of all cp caspases-2 (of Examples 10-13 and 16) for the E2 substrates with VDVAD (SEQ ID NO:45) recognition site with all P1' residues (Example 11, section 11.2) related to the cleavage activity of the standard cp caspase-2 (SEQ ID No. 6) in %. Average Values (Av.) and Standard Deviation (Dev.) values are normed to the activity of the respective caspase with VDVAD-E2 (SEQ ID NO:33) with P1' Gly at 25° C. and compared to the activity of cp caspase-2.

| Caspase variants | P1' | A | C | D | E | F | H | I | K | L | M |
|---|---|---|---|---|---|---|---|---|---|---|---|
| cp caspase-2 | Av. | 100% | 100% | 100% | 100% | 100% | 100% | 100% | 100% | 100% | 100% |
| | Dev. | 26% | 12% | 34% | 27% | 37% | 21% | 27% | 29% | 29% | 6% |
| cp caspase-2 | Av. | 81% | 43% | 62% | 76% | 40% | 32% | 79% | 34% | 41% | 46% |
| D285E | Dev. | 27% | 9% | 11% | 11% | 7% | 14% | 22% | 1% | 3% | 8% |
| cp caspase-2 | Av. | 204% | 169% | 102% | 118% | 119% | 131% | 240% | 61% | 135% | 163% |
| D282T | Dev. | 19% | 0% | 33% | 8% | 18% | 0% | 34% | 0% | 29% | 15% |
| cp caspase-2 | Av. | 258% | 150% | 127% | 125% | 132% | 151% | 257% | 90% | 242% | 159% |
| H185A, D282T | Dev. | 14% | 22% | 26% | 0% | 7% | 8% | 70% | 7% | 80% | 23% |
| cp caspase-2 | Av. | 319% | 227% | 180% | 381% | 281% | 252% | 203% | 194% | 447% | 258% |
| S9 D285 E105V | Dev. | 69% | 3% | 58% | 76% | 45% | 79% | 15% | 39% | 58% | 52% |
| cp caspase-2 | Av. | 166% | | 150% | 512% | | | 203% | | 288% | 114% |
| S9 D285E E105V, D285E | Dev. | | | | | | | | | | |
| cp caspase-2 | Av. | 1781% | 331% | 535% | 1321% | 720% | 1568% | 2965% | 1070% | 2484% | 982% |
| S9 Pro D285 E105V G171D V225G D282E | Dev. | 306% | 114% | 114% | 436% | 253% | 436% | 952% | 126% | 813% | 309% |
| cp caspase-2 | Av. | 1523% | 247% | 999% | 2894% | 462% | 634% | 1877% | 530% | 1611% | 865% |
| S9 Pro D285E E105V, G171D, V225G, D282E, D285E | Dev. | 274% | 30% | 250% | 210% | 139% | 191% | 278% | 138% | 347% | 26% |
| cp caspase-2 | Av. | 559% | 242% | 208% | 445% | 218% | 324% | 808% | 379% | 722% | 447% |
| G171D | Dev. | 0% | 81% | 36% | 78% | 62% | 24% | 214% | 49% | 37% | 73% |
| cp caspase-2 | Av. | 133% | 74% | 124% | 107% | 61% | 128% | 130% | 85% | 113% | 95% |
| V225G | Dev. | 30% | 9% | 42% | 6% | 4% | 40% | 23% | 21% | 13% | 21% |
| cp caspase-2 | Av. | 116% | 90% | 57% | 142% | 87% | 99% | 123% | 92% | 111% | 87% |
| D282E | Dev. | 14% | 15% | 6% | 33% | 8% | 9% | 12% | 10% | 0% | 11% |
| cp caspase-2 | Av. | 1258% | 397% | 2268% | 9960% | 498% | 940% | 1285% | 519% | 1232% | 728% |

TABLE 30.1-continued

Cleavage activity of all cp caspases-2 (of Examples 10-13 and 16) for the E2 substrates with VDVAD (SEQ ID NO:45) recognition site with all P1' residues (Example 11, section 11.2) related to the cleavage activity of the standard cp caspase-2 (SEQ ID No. 6) in %. Average Values (Av.) and Standard Deviation (Dev.) values are normed to the activity of the respective caspase with VDVAD-E2 (SEQ ID NO:33) with P1' Gly at 25° C. and compared to the activity of cp caspase-2.

| Caspase variants | P1' | A | C | D | E | F | H | I | K | L | M |
|---|---|---|---|---|---|---|---|---|---|---|---|
| Thr 0.8 K83E, E105V, E172V, V255M, D285Y | Dev. | 76% | 48% | 120% | 1688% | 73% | 200% | 571% | 144% | 581% | 88% |
| cp caspase-2 | Av. | | | | | 111% | | | | | |
| N-term +3 | Dev. | | | | | 12% | | | | | |
| cp caspase-2 | Av. | | | | | 46% | | | | | |
| C-term +3 | Dev. | | | | | 3% | | | | | |
| cp caspase-2 | Av. | | | | | 548% | | | | | |
| E105V G171D | Dev. | | | | | 86% | | | | | |
| cp caspase-2 | Av. | | | | | 522% | | | | | |
| E105V G171V | Dev. | | | | | 79% | | | | | |
| cp caspase-2 | Av. | | | | | 259% | | | | | |
| E105H G171V | Dev. | | | | | 12% | | | | | |

TABLE 30.2

Cleavage activity of all cpcaspase-2 variants (of Examples 10-13 and 16) for the E2 substrates with VDVAD (SEQ ID NO:45) recognition site with all P1' residues (Example 11, section 11.2) related to the cleavage activity of the standard cp caspase-2 (SEQ ID No. 6) in %. Average Values (Av.) and Standard Deviation (Dev.) values are normed to the activity of the respective caspase with VDVAD-E2 (SEQ ID NO:33) with P1' Gly at 25° C. and compared to the activity of cp caspase-2.

| Caspase variants | P1' | N | P | Q | R | S | T | V | W | Y |
|---|---|---|---|---|---|---|---|---|---|---|
| cp caspase-2 | Av. | 100% | 100% | 100% | 100% | 100% | 100% | 100% | 100% | 100% |
| | Dev. | 22% | 38% | 34% | 14% | 13% | 0% | 16% | 4% | 5% |
| cp caspase-2 | Av. | 67% | 22% | 87% | 86% | 56% | 99% | 68% | 22% | 30% |
| D285E | Dev. | 20% | 10% | 26% | 5% | 4% | 16% | 4% | 2% | 1% |
| cp caspase-2 | Av. | 112% | 141% | 108% | 136% | 158% | 310% | 224% | 96% | 114% |
| D282T | Dev. | 9% | 0% | 21% | 11% | 10% | 88% | 33% | 11% | 11% |
| cp caspase-2 | Av. | 115% | 115% | 127% | 140% | 156% | 425% | 265% | 117% | 120% |
| H185A, D282T | Dev. | 9% | 10% | 23% | 10% | 16% | 68% | 61% | 17% | 7% |
| cp caspase-2 S9 | Av. | 265% | 265% | 188% | 295% | 216% | 300% | 291% | 283% | 260% |
| D285 E105V | Dev. | 0% | 52% | 22% | 80% | 43% | 59% | 56% | 70% | 47% |
| cp caspase-2 S9 | Av. | | 407% | 167% | | | 315% | 202% | | |
| D285E E105V, D285E | Dev. | | | | | | | | | |
| cp caspase-2 S9 | Av. | 907% | 5617% | 2275% | 1255% | 692% | 2883% | 3314% | 654% | 1079% |
| Pro D285 E105V G171D V225G D282E | Dev. | 0% | 1964% | 728% | 322% | 204% | 878% | 1101% | 203% | 0% |
| cp caspase-2 S9 | Av. | 476% | 2650% | 440% | 914% | 498% | 2717% | 2308% | 472% | 466% |
| Pro D285E E105V, G171D, V225G, D282E, D285E | Dev. | 82% | 579% | 160% | 87% | 48% | 388% | 283% | 99% | 95% |
| cp caspase-2 | Av. | 290% | 1348% | 782% | 497% | 296% | 937% | 650% | 242% | 138% |
| G171D | Dev. | 95% | 512% | 143% | 98% | 54% | 159% | 48% | 13% | 20% |
| cp caspase-2 | Av. | 109% | 77% | 116% | 95% | 66% | 114% | 89% | 110% | 96% |
| V225G | Dev. | 23% | 26% | 0% | 24% | 17% | 6% | 11% | 34% | 30% |
| cp caspase-2 | Av. | 96% | 138% | 108% | 105% | 74% | 171% | 127% | 121% | 133% |
| D282E | Dev. | 4% | 19% | 18% | 11% | 11% | 12% | 15% | 6% | 8% |
| cp caspase-2 Thr | Av. | 610% | 1350% | 3609% | 712% | 639% | 2355% | 2057% | 501% | 497% |
| 0.8 K83E, E105V, E172V, V255M, D285Y | Dev. | 68% | 61% | 229% | 86% | 96% | 322% | 283% | 123% | 31% |
| cp caspase-2 N- | Av. | | | 218% | | | | 145% | | |
| term +3 | Dev. | | | 21% | | | | 43% | | |
| cp caspase-2 C- | Av. | | | 929% | | | | 63% | | |
| term +3 | Dev. | | | 204% | | | | 2% | | |
| cp caspase-2 | Av. | | 7882% | 1557% | | | 3600% | 4328% | | |
| E105V G171D | Dev. | | 1306% | 162% | | | 0% | 362% | | |
| cp caspase-2 | Av. | | 5541% | 1100% | | | 859% | 1027% | | |
| E105V G171V | Dev. | | 1938% | 65% | | | 70% | 83% | | |

TABLE 30.2-continued

Cleavage activity of all cpcaspase-2 variants (of Examples 10-13 and 16) for the E2 substrates with VDVAD (SEQ ID NO:45) recognition site with all P1' residues (Example 11, section 11.2) related to the cleavage activity of the standard cp caspase-2 (SEQ ID No. 6) in %. Average Values (Av.) and Standard Deviation (Dev.) values are normed to the activity of the respective caspase with VDVAD-E2 (SEQ ID NO:33) with P1' Gly at 25° C. and compared to the activity of cp caspase-2.

| Caspase variants | P1' | N | P | Q | R | S | T | V | W | Y |
|---|---|---|---|---|---|---|---|---|---|---|
| cp caspase-2 | Av. | | 693% | 513% | | | 323% | 273% | | |
| E105H G171V | Dev. | | 106% | 45% | | | 44% | 18% | | |

Taken together, these data show that variants of a cp caspase-2, comprising amino acid substitutions at any one or more of positions 83, 105, 171, 172, 185, 225, 255, 282, 285 of SEQ ID No. 6, display significantly improved P1' tolerance for at least one amino acid. In most cases, these variants comprise significantly improved P1' tolerance for multiple amino acids.

Furthermore, these data show that even though amino acid substitutions at positions 85, 86, 132, 141, 174, 200, 201, 203 of SEQ ID No. 6 do not improve P1' tolerance, they do not hamper caspase activity significantly. Table 6, for example, shows that variants comprising amino acid substitutions at positions 85, 86, 132, 141, 174, 200, 201, or 203 of SEQ ID No. 6 still cleave about 50% of the substrate VDVAD-E2 (SEQ ID NO:33) within 2 or 3 minutes. These represent examples for functionally active variants of cp-caspases-2 of the present invention. Furthermore, all variants selected using the selection system as described in Example 12 and as shown in Table 27 are further examples of functionally active variants of cp-caspases-2, since they all have catalytic activity for the cleavage of the VDVAD (SEQ ID NO:45) P1' motif (a caspase-2 cleavage site). Otherwise the colonies/clones would not have grown.

Example 15: Selection of Alternative Caspase-2 Recognition Sites for Cleavagecp Caspases-2

15.1 System for In Vivo Selection of Alternative Caspase Recognition Sites

The selection system described in Section 12.1 of Example 12 is used for the selection of recognition sites different to VDVAD (SEQ ID NO:45) that are accepted by cp caspase-2 mS9 Pro with a 6His-tag (SEQ ID No. 70).

A gene library of 6His-GSG-XDXXD-AM-Thr-pyrB (SEQ ID No. 22) cpATCase constructs was cloned with degenerate primers to insert random mutations in the caspase recognition sequence at the positions P5, P3, and P2 (Forward primer sequence: nnnnnnGATACCCGCGTGCAAAAAG (nnnnnn-(SEQ ID NO:322)), reverse primer sequence: ATCnnnGCCGCTGCCATGATGATG) (ATCnnn-SEQ ID NO:323). The primers were designed with their 5' ends back-to-back for a PCR with a high-fidelity DNA polymerase which generates a linear DNA fragment of the whole vector (described in Section 11.1, Example 11). After KLD reaction NovaBlue heat shock cells were transformed with the gene library and diluted in an overnight culture, which was used for a DNA preparation. Sequencing of the pooled gene library was used to control the quality of the DNA preparation before selection to ensure a diverse mutant library.

*E. coli* BL21(DE3) ΔpyrBI cells were generated that contain the cp caspase-2 mS9 Pro construct (SEQ ID No. 70) in a pACYCDuet-1 vector.

The cells were transformed with the XDXXD-cpATCase library and after recovery in SOC medium the cells were either diluted in optimized M9 minimal medium or plated on optimized M9 agar plates containing 0.1 mM IPTG and incubated at 30° C. for 24-48 h.

15.2 Selected and Identified Alternative Caspase-2 Recognition Sites for Cleavage cp caspases-2: 79 single colonies were sequenced and the nucleotide sequence of the cpATCase was analyzed detecting alternative recognition sites tolerated by cp caspase-2 mS9 Pro.

The list of all found cleavage sites, as described in Table 31, Section 15.2, Example 15, was used to generate a sequence logo for the consensus sequence. FIG. 57 shows that the cleavage site VDVAD (SEQ ID NO:45) is recognized with very high probability, in position P2 also a Ser is well accepted. Though Val is mostly accepted in positions P3 and P5, also Thr occurs with a high probability in P5, as well as an Arg in P3. Overall, many amino acids are accepted in all 3 randomly mutated positions and the optimal recognition site detected with our selection system for cp caspase-2 is VDVAD (SEQ ID NO:45).

In a similar experiment the influence of the P1' residue on the recognition site selection was tested.

*E. coli* BL21(DE3) ΔpyrBI cells were generated that contain the cp caspase-2 construct (SEQ ID No. 6) in a pACYCDuet-1 vector.

A cpATCase substrate library with an XDXXD recognition site and Pro as P1' was generated as described above. After transformation of the cells with the gene library, the selection was executed in an optimized M9 liquid culture to enrich an optimal recognition site. After plating of the incubated culture 22 single colonies were sequenced. Four sequences could not be analyzed because of contaminations, one YDVPD site (VDVPD (SEQ ID NO:212) with V-to-Y substitution at the 1st amino acid residue) was found, all 17 other sequences showed a VDSAD (SEQ ID NO: 45 with V-to-S substitution at the 3rd amino acid residue) recognition site.

TABLE 31

List of all found recognition sites in selections with P1' Thr and cp caspase-2 mS9 Pro (SEQ ID No. 70). Selection was performed as described in Example 3.

| No. | P5 | P4 | P3 | P2 | P1 |
|---|---|---|---|---|---|
| 1 | E | D | C | R | D |
| 2 | F | D | L | C | D |
| 3 | F | D | R | K | D |
| 4 | F | D | S | G | D |
| 5 | F | D | T | S | D |
| 6 | F | D | V | S | D |
| 7 | H | D | T | S | D |
| 8 | I | D | C | C | D |

TABLE 31-continued

List of all found recognition sites in selections with P1' Thr and cp caspase-2 mS9 Pro (SEQ ID No. 70). Selection was performed as described in Example 3.

| No. | P5 | P4 | P3 | P2 | P1 |
|---|---|---|---|---|---|
| 9 | I | D | E | S | D |
| 10 | I | D | L | S | D |
| 11 | I | D | L | S | D |
| 12 | I | D | S | K | D |
| 13 | I | D | T | I | D |
| 14 | I | D | T | Q | D |
| 15 | I | D | V | A | D |
| 16 | I | D | V | P | D |
| 17 | K | D | V | D | D |
| 18 | L | D | Q | M | D |
| 19 | L | D | Q | S | D |
| 20 | L | D | R | A | D |
| 21 | L | D | R | A | D |
| 22 | L | D | R | V | D |
| 23 | L | D | V | C | D |
| 24 | M | D | K | S | D |
| 25 | N | D | E | R | D |
| 26 | N | D | R | P | D |
| 27 | P | D | T | A | D |
| 28 | Q | D | E | R | D |
| 29 | Q | D | K | S | D |
| 30 | Q | D | R | R | D |
| 31 | Q | D | R | S | D |
| 32 | Q | D | R | S | D |
| 33 | Q | D | T | S | D |
| 34 | R | D | K | V | D |
| 35 | R | D | S | V | D |
| 36 | R | D | T | P | D |
| 37 | R | D | V | C | D |
| 38 | R | D | Y | P | D |
| 39 | S | D | Q | T | D |
| 40 | S | D | S | T | D |
| 41 | S | D | T | A | D |
| 42 | T | D | A | A | D |
| 43 | T | D | A | A | D |
| 44 | T | D | E | C | D |
| 45 | T | D | E | R | D |
| 46 | T | D | K | Q | D |
| 47 | T | D | M | T | D |
| 48 | T | D | Q | A | D |
| 49 | T | D | R | A | D |
| 50 | T | D | R | L | D |
| 51 | T | D | R | S | D |
| 52 | T | D | S | T | D |
| 53 | T | D | V | A | D |
| 54 | T | D | V | S | D |
| 55 | T | D | V | S | D |
| 56 | V | D | A | I | D |
| 57 | V | D | C | T | D |
| 58 | V | D | E | L | D |
| 59 | V | D | E | V | D |
| 60 | V | D | K | A | D |
| 61 | V | D | R | T | D |
| 62 | V | D | R | T | D |
| 63 | V | D | S | L | D |
| 64 | V | D | S | S | D |
| 65 | V | D | S | S | D |
| 66 | V | D | V | A | D |
| 67 | V | D | V | C | D |
| 68 | V | D | V | K | D |
| 69 | V | D | V | L | D |
| 70 | V | D | V | R | D |
| 71 | V | D | V | T | D |
| 72 | V | D | V | W | D |
| 73 | Y | D | F | P | D |
| 74 | Y | D | M | L | D |
| 75 | Y | D | R | A | D |
| 76 | Y | D | S | A | D |
| 77 | Y | D | S | S | D |
| 78 | Y | D | S | S | D |
| 79 | Y | D | V | A | D |

15.3 Cleavage of Fusion Proteins (Substrates) with Alternative Caspase-2 Recognition Sites for Cleavage cp caspases-2Human fibroblast growth factor-2 was expressed with a modified tag. The tag T7AC-6H (SEQ ID NO-315)-GSG-VDSAD(SEQ ID NO-45) was attached on the N-terminus of the POI, resulting in the fusion protein T7AC-6H-GSG-VDSAD-hFGF2 (SEQ ID NO:268). The protein was expressed in a shaker culture as described in Example 10, section 10.3. The purification of the fusion protein was performed as described in Example 19, section 19.3. After IMAC capture and buffer exchange into PBS using UF/DF, the fusion protein was stored in aliquots at −80° C. until further use.

A Michaelis-Menten type enzyme kinetic was performed as described in Example 20 and the results were compared to the cleavage of substrate T7AC-6H-GSG-VDVAD-hFGF2 (SEQ ID NO:267) (Example 20). The experiment was performed with T7AC-6H-mS9ProD (SEQ ID NO:72) as the enzyme. As shown in FIG. 40, the cleavage kinetics of the two recognition sites are different, since the confidence intervals do not overlap. The reaction with the canonical recognition site VDVAD (SEQ ID NO:45) has a lower $K_M$, and a higher $k_{cat}$ and $k_{cat}/K_M$ value as shown in Table 32.

TABLE 32

Michaelis-Menten kinetic parameters of the cleavage of T7AC-6H-GSG-VDSAD-hFGF2 ("VDSAD") (SEQ ID NO:268) and T7AC-6H-GSG-VDVAD-hFGF2 (SEQ ID NO:267) ("VDVAD") with T7AC-6H-mS9ProD (SEQ ID NO:72).

| | VDSAD | VDVAD |
|---|---|---|
| $K_M$ (μM) | 865 | 329 |
| $k_{cat}$ (1/s) | 1.4 | 1.9 |
| $k_{cat}/K_M$ ($s^{-1}$*$\mu M^{-1}$) | 1670 | 5724 |

A further recommended recognition site for cp-caspases-2 resp caspases-2 was tested: VDTTD (SEQ ID No. 209) (Kitevska, T., Roberts, S. J., Pantaki-eimany, D., Boyd, S. E., Scott, F. L., and Hawkins, C. J. Analysis of the minimal specificity of caspase-2 and identification of Ac-VDTTD (SEQ ID No. 209)-AFC as a caspase-2-selective peptide substrate Bioscience Reports. Bioscience Reports 34 (2014)): It had been reported that a fluorogenic substrate with VDTTD (SEQ ID No. 209) was cleaved four times more efficiently than the VDVAD (SEQ ID NO:45) substrate by wild type caspase-2.

The cleavage of 6His-GSG-VDTTD-E2 (SEQ ID NO:19) was tested. This experiment also shows that the residues at positions P2 and P3 have a minor influence on activity (FIG. 60)

Example 16: Simultaneous Mutation of Residues $Glu^{105}$ and $Gly^{171}$ of SEQ ID No. 6 or Functionally Equivalent to Positions of SEQ ID No. 6

16.1 Design of Constructs and Selection

Saturation mutagenesis with degenerate primers, designed to create all possible 19 amino acid substitutions at one site in the protein, was performed with cp caspase-2 E105V G171 D (SEQ ID No. 200) in a pACYCDuet-1 vector as a template.

For the site-specific random mutation, a PCR reaction was performed with a high-fidelity DNA polymerase, as described in Section 11.1, Example 11. The primers were designed with their 5' ends back-to-back to create a linear DNA fragment of the whole vector. Mutations at positions Val$^{105}$ and Asp$^{171}$ were inserted sequentially in two separate PCR reactions.

Primers were designed with the degenerate codon NNS at the site of mutation which generates all 20 amino acids with 32 codons and reduces codon redundancy.

For the PCR different annealing temperatures between 58 and 62° C. were used to ensure optimal binding of all codon combinations. Depending on the random codon the temperature can vary up to 4° C. For the mutation at position Val$^{105}$ the forward primer TCGTTGTAAAnnsATGAGCGAGTATTG (SEQ ID NO:282) and the reverse primer TGAAATTCTGTACCCGGTG (SEQ ID NO:283) were used. To ligate the linear fragments a KLD reaction was performed as described in Section 11.1 of Example 11. The ligated product was purified and used as a template for the following mutagenesis to insert mutations at position Asp$^{171}$. The forward primer CATTTTACCnnsGAAAAAGAACTG (SEQ ID NO:284) and the reverse primer AACATTGCTCAGAACCAG (SEQ ID NO:285) were used. Sequencing of the pooled gene library was used to control the quality of the DNA preparation. A clear preference for the nucleotide G was observed at the degenerate position which only produced a reduced sequence space. An additional set of primers was used to exclude all codons with G nucleotides already found in the previous PCR reaction to introduce mutations for amino acids that were not found with the NNS codon. The forward primers CATTTTACChhcGAAAAAGAACTG (SEQ ID NO:286) and CATTTTACChhgGAAAAAGAACTG (SEQ ID NO:287) and for both the same reverse primer AACATTGCTCAGAACCAG (SEQ ID NO:288) were used.

Following this, a KLD reaction was performed. NovaBlue heat shock cells were transformed with the ligated product and the cells were diluted into an overnight culture which was used for a DNA preparation. Sequencing of the pooled gene library from primers with NNS, HHC and HHG codons was used to control the quality of the library before selection. All nucleotides were represented in the first two degenerate positions to theoretically produce all 400 possible variants.

*E. coli* BL21(DE3) ΔpyrBI cells that contained the VDVAD (SEQ ID NO:45)-cpATCase substrate with P1' Thr and Pro (SEQ ID No. 22) were transformed with the gene library. The selection, as described in Example 3, was executed either in optimized M9 medium or on optimized M9 agar plates at 30° C. for 24-48 h.

16.2 Selected and Identified Cp Caspases-2 Having Mutations in Positions Glu$^{105}$ and Gly$^{171}$ The DNA of 161 single colonies was analyzed, detecting combinations of mutations in active variants, as shown in Table 33, Section 16.2 in Example 16.

TABLE 33

List of all identified cp caspases-2 with simultaneous mutations at positions Glu$^{105}$ and Gly$^{171}$. Variants were selected as described in Example 12.

| Amino acid in position 105 | Amino acid in position 171 | Found in selection with P1' Thr | Found in selection with P1' Pro | Enriched during selection |
|---|---|---|---|---|
| A | D | | x | |
| A | E | x | x | |
| A | G | x | | |
| A | V | x | | |
| C | E | x | | |
| C | G | x | | |
| E | A | x | | |
| E | C | x | | |
| E | G | x | | x |
| E | K | x | | |
| G | A | x | | |
| G | G | x | | |
| G | V | x | | x |
| G | W | x | | |
| I | G | x | | |
| L | A | x | | |
| L | E | x | | |
| L | G | x | | |
| L | R | x | | |
| L | S | x | | |
| L | V | x | | |
| M | A | x | x | x |
| M | E | x | x | |
| M | G | x | | |
| M | V | x | | |
| N | V | x | | |
| P | E | x | | |
| P | G | x | | |
| Q | G | x | | x |
| Q | V | x | | |
| R | G | x | | |
| S | R | x | | |
| T | G | x | | |
| T | V | x | | x |
| V | A | x | x | |
| V | C | | x | |
| V | D | | x | x |
| V | E | x | x | x |
| V | G | x | x | x |
| V | N | | x | |
| V | R | | x | |
| V | V | x | x | x |
| W | G | x | | |
| W | V | x | | |

16.3 Characterization of Cp Caspases-2 Having Mutations in Positions Glu$^{105}$ and Gly$^{171}$ Three combinatorial mutants were expressed, purified and tested as described in Sections 10.3, 10.4 and 10.5 of Example 10.

Variant cp caspase-2 E105V G171D (SEQ ID No. 253) was chosen for further tests because the mutations E105V and G171D showed the highest influence on the cp caspase-2 properties when tested separately. The combination of both mutations was also found repeatedly during selections of the combinatorial library with P1' Pro and the variant was enriched in liquid culture. The specific activity of cp caspase-2 E105V G171D was the same as for the other caspase variants, 50% of 1 mg/ml VDVAD-E2 (SEQ ID NO:33) were cleaved in 1 min by 0.01 mg/ml cp caspase, as shown in Table 28, Example 14. The P1' tolerance was even increased compared to cp caspase-2 mS9 ProD, the highest tolerance was observed for proline in the P1' position, as shown in Tables 29.1, 29.2, 30.1 and 30.2, Example 14.

Variant cp caspase-2 E105V G171V (SEQ ID No. 254) was found repeatedly in selections with P1' Thr and Pro and was also enriched in liquid culture. The specific activity of the variant was the same as for the other caspase variants, 50% of 1 mg/ml VDVAD-E2 (SEQ ID NO:33) cleaved in 1 min by 0.01 mg/ml caspase, as shown in Table 28, Example 14. The values for P1' cleavage activities are higher than for the variant with the single mutation E105V (cp caspase-2 S9, SEQ ID No. 51), the tolerance for P1' Pro was even increased to the level of variant mS9 ProD, as shown in Tables 29.1, 29.2, 30.1 and 30.2, Example 5.

The variant cp caspase-2 E105H G171V (SEQ ID No. 256) was suggested by the molecular modelling group and was never found in a selection. It was cloned as described in Section 11.1, Example 11 and expressed, purified and tested. Its specific activity was slightly decreased, 1 mg/ml VDVAD-E2 (SEQ ID NO:33) were cleaved by 0.01 mg/ml caspase in about 3 min, as shown in Table 28, Example 14. Though the variant's P1' tolerance was lower compared to cp caspase-2 E105V G171V, it was increased compared to cp caspase-2. The highest increase was observed for P1' Pro, as shown in Tables 29.1, 29.2, 30.1 and 30.2.

Example 17.: Comparison of Generated Variants to Wild-Type Caspase-2 DEVD-E2 (SEQ ID No. 57)

DEVD (SEQ ID NO:206) is the preferred cleavage site of caspases-3 and -7. DEVD-E2 (SEQ ID NO:57) (Example 11, section 11.2) was used to evaluate the influence of the P5 residue, because the influence of the amino acids in the P2 and P3 positions on caspase-2 activity are considered insignificant. The substrate was processed 140 times slower than VDVAD-E2 (SEQ ID No. 33; Example 11, section 11.2) by cp caspase-2 (SEQ ID No. 6) showing that the recognition of the P5 residue is very important for caspase-2 and cp caspase-2.

This is in accordance with results from fluorescent peptides [26, 24], and proves the initial assumption of this study that caspase-2 was more specific than other caspases, because of its pentapeptidic recognition site. This seems to be even more pronounced in the circularly permuted variant, as the literature only describes a 35-fold increase in activity with VDVAD (SEQ ID NO:45) over DEVD (SEQ ID NO:206) [26].

17.1 Comparison of Specificity with Wild-Type Caspase-2

The specificity of cp caspase-2 (SEQ ID No. 6) was compared with commercially available wild-type caspase-2 (human, recombinant, active Caspase-2, Enzo Life Sciences, Farmingdale, NY, USA). 72 U/ml of the wild-type caspase-2 were used for cleavage reactions, according to the specifications, this equals about 0.005 mg/ml enzyme, half the concentration used in standard reactions with cp caspase-2. But the wild-type caspase was even six times less active than cp caspase-2 under the same conditions (1 mg/ml VDVAD-E2 (SEQ ID No. 33) was processed to 50% in 6 min).

While the absolute activities of the enzymes might be difficult to compare, because of different purity and concentration, a clear discrepancy could be found between their specificities. Wild-type caspase-2 cleaved DEVD-E2 only 44 times slower than VDVAD-E2 (SEQ ID No. 33), while cp caspase-2 has a 140-fold preference for VDVAD (SEQ ID NO:45) over DEVD (SEQ ID NO:206). Thus, the cp caspase-2 is three times more specific than the wild-type enzyme (FIG. 9). FIG. 9 shows cleavage of DEVD-E2 (SEQ ID NO:57) by cp caspase-2 (SEQ ID No. 6) and wild-type caspase-2. Reduction of cleavage activity with DEVD-E2 (SEQ ID NO:57) substrate, given in x-fold decrease in comparison to VDVAD-E2 (SEQ ID No. 33) processing. The graph shows means±standard deviation of at least three independent experiments. (*) indicates statistical significance at level $p \leq 0.05$, () at level $p \leq 0.01$, and (*) at level $p \leq 0.001$.

17.2.: Production and Characterization of a Wild Type Caspase-2

For comparison of wild-type caspase-2 with cp-caspase-2 variants a human caspase-2 was produced.

Production of Wt Caspase-2:

Production of wt caspase-2 was performed in a 30 L (23 L net volume, 5 L batch volume) computer-controlled bioreactor (Bioengineering; Wald, Switzerland) equipped with standard control units (Siemens PS7, Intellution iFIX). The pH was maintained at a set-point of 7.0±0.05 by addition of 25% ammonia solution (w/w), the temperature was set to 37° C.±0.5° C. in the batch phase and 30° C.±0.5° C. in the fed-batch phase. To avoid oxygen limitation the DO level was held above 30% saturation by adjusting the stirrer speed and the aeration rate of the process air. The maximum overpressure in the head space was 1.1 bar.

Pre-cultures for inoculation were grown in synthetic media calculated to produce 3 g/L. For incubation 1 mL of a deep frozen MCB was aseptically transferred to 400 mL medium and cultivated in two 2000 mL shaking flasks at 37° C. and 180 rpm until an OD of approx. 4 was reached.

For cultivation, minimal media calculated to produce 64 g cell dry mass (CDM) in the batch phase and 890 g CDM during feed phase were used. The batch medium was prepared volumetrically; the components were dissolved in 8 L RO—$H_2O$. The fed-batch medium was prepared gravimetrically; the final weight was 8.45 kg. All components for the fed-batch medium were weighed in and dissolved in RO—$H_2O$ separately. All components (obtained from MERCK), were added in relation to the theoretical grams of cell dry mass to be produced: The composition of the batch and the fed-batch medium is as follows: 94.1 mg/g $KH_2PO_4$, 31.8 mg/g $H_3PO_4$ (85%), 41.2 mg/g $C_6H_5Na_3O_7$*2 $H_2O$, 45.3 mg/g $NH_4SO_4$, 46.0 mg/g $MgCl_2$*2 $H_2O$, 20.2 mg/g $CaCl_2$*2 $H_2O$, 50 µL trace element solution, and 3.3 g/g C6H1206*$H_2O$. The trace element solution was prepared in 5 N HCl and included 40 g/L $FeSO_4$·*7$H_2O$, 10 g/L $MnSO_4$·*$H_2O$, 10 g/L $AlCl_3$·*6 $H_2O$, 4 g/L $CoCl_2$, 2 g/L $ZnSO_4$·*7$H_2O$, 2 g/L $Na_2MoO_2$·*2 $H_2O$, 1 g/L $CuCl_2$·*2 $H_2O$, and 0.5 g/L $H_3BO_3$. To accelerate initial growth of the population, the complex component yeast extract (150 mg/g calculated CDM) was added to the batch medium. Nitrogen level was maintained by adding 25% ammonium hydroxide solution (w/w) for pH control. Antifoam (PPG 2000) 0.5 mL/L total volume was added at the beginning.

The fed-batch phase (29 h) was performed at 30° C. with an exponential feeding strategy with a consistent growth rate of µ=0.1 h-1. The substrate feed was controlled by increasing pump speed according to the exponential growth algorithm, X=X0·eµt, with superimposed feedback control of weight loss in the substrate tank. Induction started with fed-batch phase by adding 0.5 µmol IPTG/g CDM directly to the feed-media to achieve a protein production for 4 generations. IPTG concentration was calculated with the theoretical final CDM.

| Component | Quantity |
|---|---|
| Batch medium components | |
| $KH_2PO_4$ | 0.094 g/g final CDM |
| 85% $H_3PO_4$ | 0.032 g/g final CDM |
| Yeast extract | 0.15 g/g CDM (batch) |
| $C_6H_5Na_3O$ $2H_2O$ | 0.25 g/g final CDM |
| $MgCl_2$••$7H_2O$ | 0.1 g/g CDM (batch) |
| $CaCl_2$•$2H_2O$ | 0.02 g/g CDM (batch) |
| $(NH_4)_2SO_4$ | 0.046 g/g final CDM |

-continued

| Component | Quantity |
|---|---|
| Trace element solution | 50 μL/g CDM (batch) |
| $C_6H_{12}O_6$••$H_2O$ | 3.3 g/g CDM (batch) |
| Fed batch medium components | |
| Component | Quantity |
| $MgCl_2$••••$7H_2O$ | 0.1 g/g CDM (fed-batch) |
| $CaCl_2$••$2H_2O$ | 0.02 g/g CDM (fed-batch) |
| Trace element solution | 50 μL/g CDM (fed-batch) |
| $C_6H_{12}O_6$•$H_2O$ | 3.3 g/g CDM (fed-batch) |

In addition to standard online monitoring (pH, stirrer speed, temperature and $pO_2$) the concentration of $pO_2$ and $O_2$ in the outlet air was measured with a BlueSens gas analyzer. Sampling of the standard offline process parameters started after one generation in fed-batch mode. The first sample was withdrawn from the bioreactor prior to induction. Optical density (OD600) was measured with a spectrophotometer at wavelength λ=600 nm. Samples were diluted in PBS to ensure a measurement at a linear range from 0.1 to 0.8. Cell dry mass (CDM) was determined by centrifugation of 10 mL of cell suspension for 8 min at 8500 rpm. The supernatant was discarded and cells were resuspended with RO—$H_2O$ and centrifuged. Water was discarded and cell were resuspended again with RO—$H_2O$. Cell suspension was transferred into a beaker, which was weighted before. Beakers were dried for at least 24 h at 105° C. and weighted again. The difference in weight account for the CDM.

For the determination of the content of wt caspase-2, aliquots of approximately 1.0 mg CDM of the samples were centrifuged (10 min. at 13200 rpm); the supernatants were discarded, the insides of the tubes were carefully blotted dry and the samples were stored at −20° C.

Comparison of wt caspase-2 production with cp caspase-2 production in fermentations with a μ=0.1 $h^{-1}$ and an IPTG concentration of 0.5 μmol IPTG/g CDM during induction (standard fermentations as described in section 18.1.2.2). Whereas overexpression of cp caspase-2 was possible in *E. coli*, the expression of soluble wt caspase-2-6H (SEQ ID NO:6) was generally low and only detectable with western blot (FIG. 26). Additionally, no inclusion body formation was observed. Cell growth followed the calculated CDM. Final CDM was about 69.61 g/L respectively 1111 g in total. (FIG. 27). Manufacturability of wt caspase-2 is much worse compared with cp caspase-2.

Figure 2:
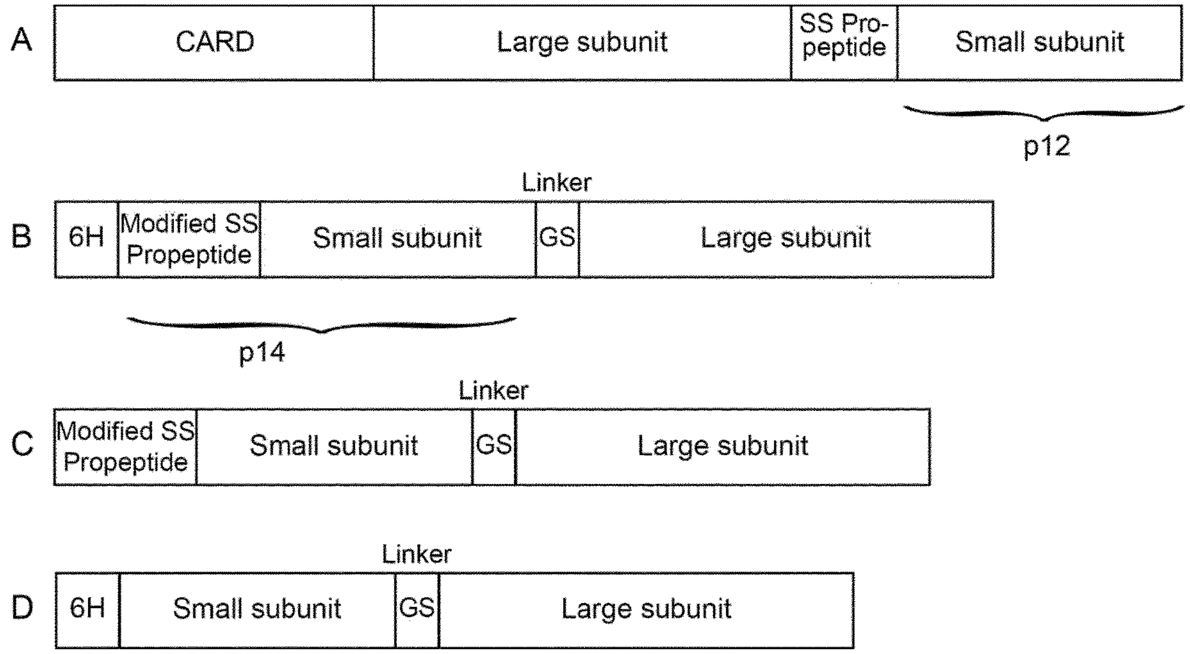
Figure 3:
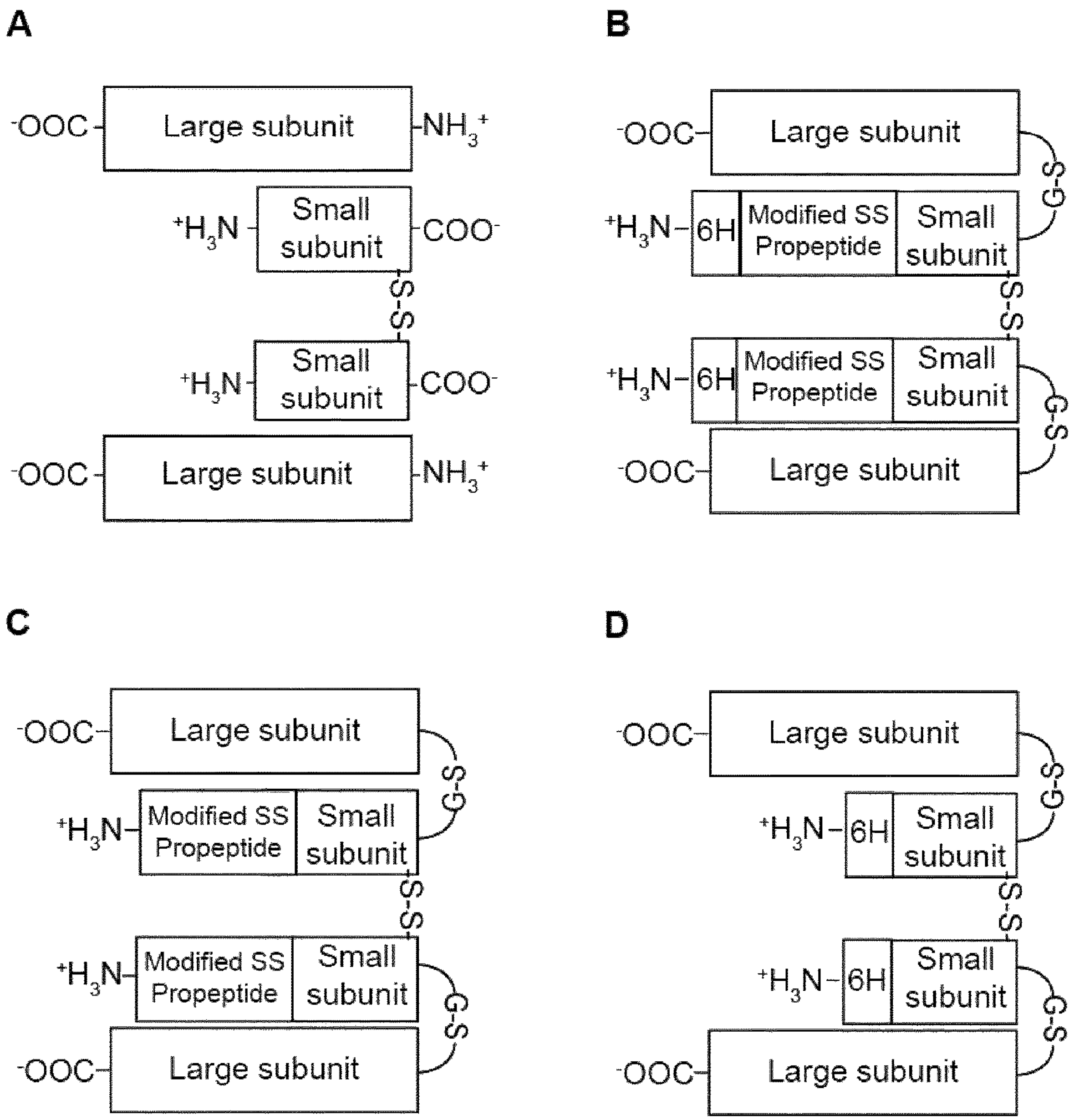
Figure 6:
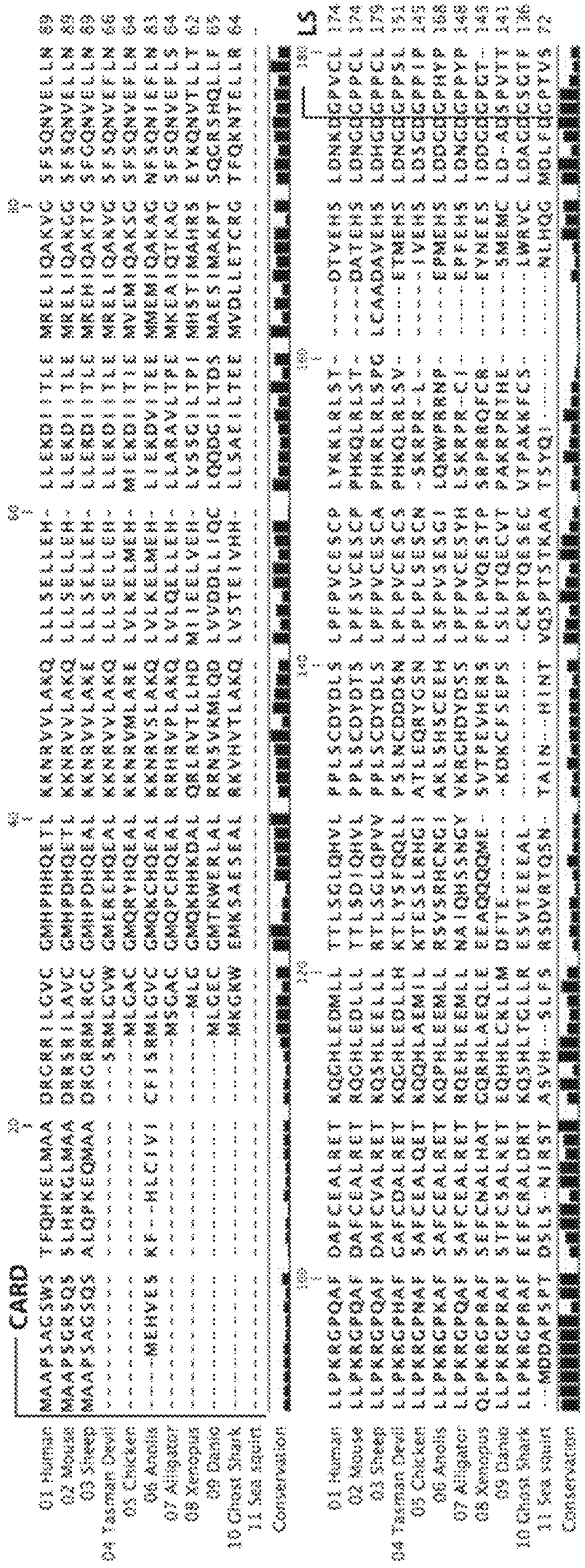
Figure 6:
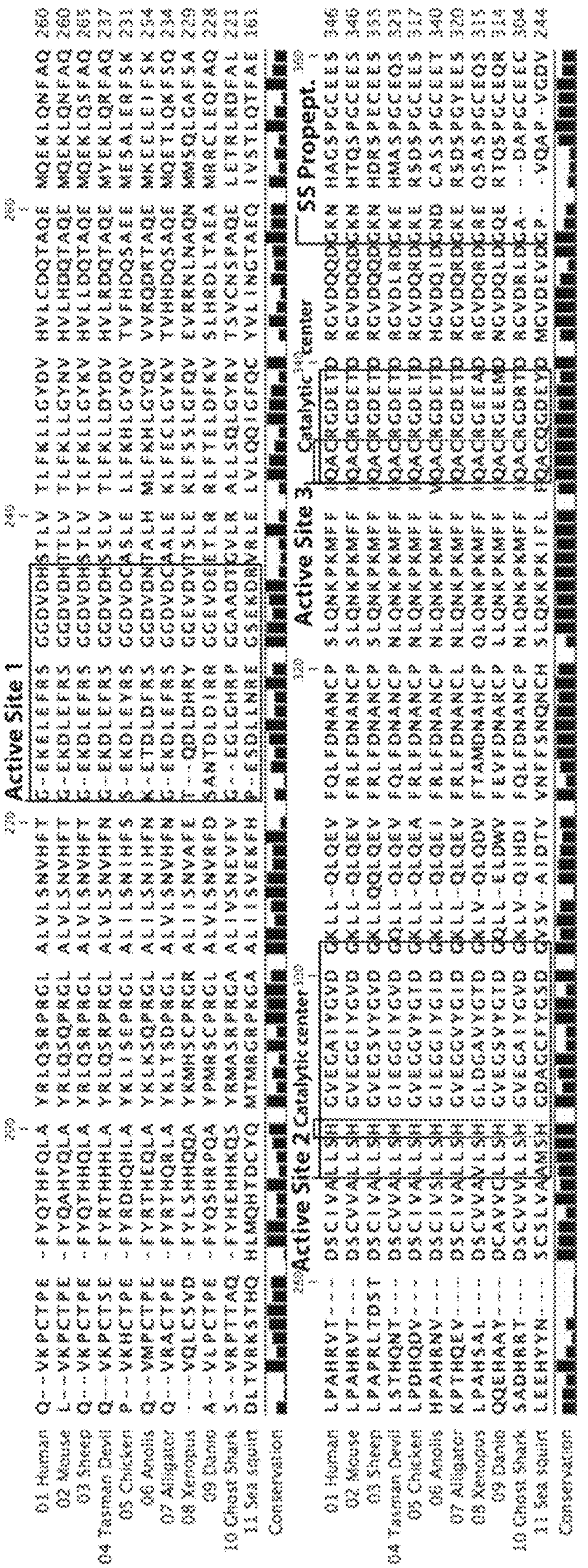
Figure 6:
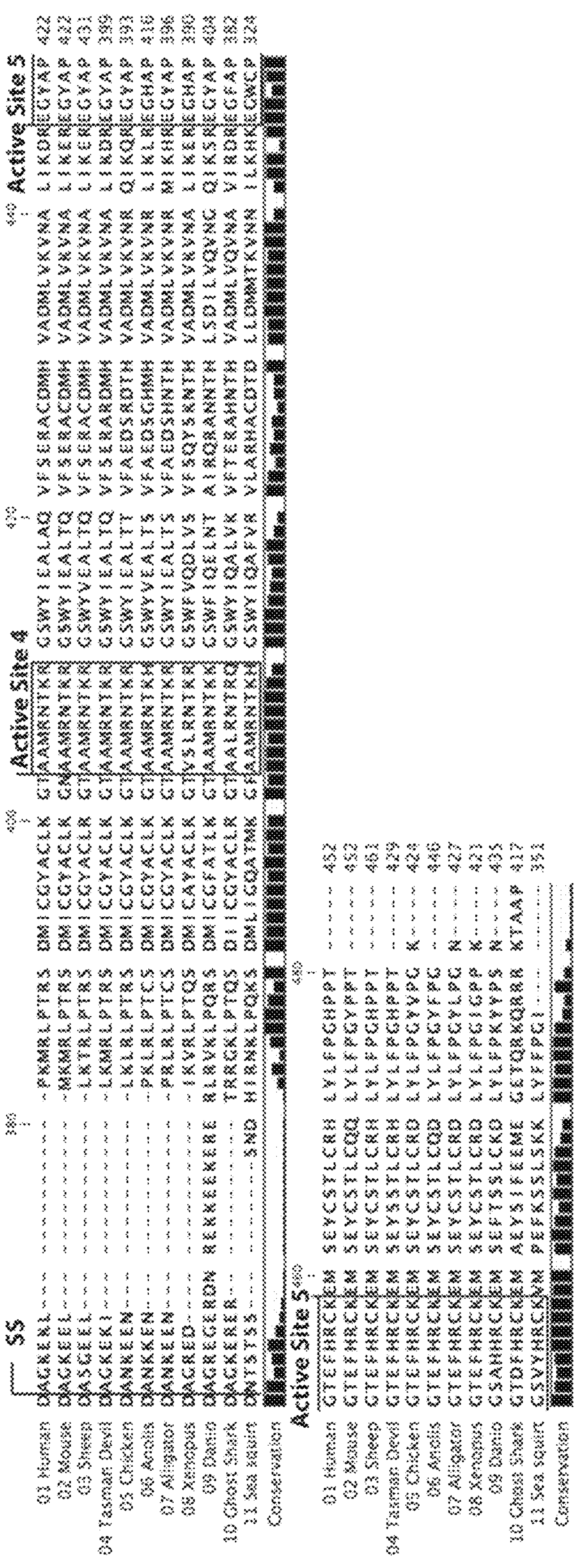

For recovery the *E. coli* cell mass was harvested by centrifugation at 18,590 rcf for 15 minutes and the supernatant was discarded. The *E. coli* cell harvest was solubilized using homogenization buffer (50 mM sodium phosphate, 300 mM NaCl, pH 8.0). The cells were re suspended at a concentration of 400 g wet cell mass per L. Cell lysis was performed through high pressure homogenization at 1400 bar/140 bar with two passages with an in-line counter current chiller set to 10° C. The homogenate was centrifuged at 18,590 rcf for 2.5 hours at 4° C. The pellet was discarded and the supernatant used. Before chromatography the supernatant was filtered through a 0.22 μm membrane.

The wt caspase-2 carrying a poly-his-tag was captured using immobilized metal affinity chromatography (IMAC). The following buffers were used: equilibration buffer: 50 mM sodium phosphate, 300 mM NaCl, 20 mM imidazole, pH 8.0. Elution buffer: 50 mM sodium phosphate, 300 mM NaCl, 500 mM imidazole, pH 8.0.

Imidazole was added to the clarified supernatant before IMAC, to a final concentration of 20 mM imidazole. 57 CV clarified supernatant were loaded to an equilibrated Ni-Sepharose 6 Fast Flow column (50×18 mm, 35 mL). A residence time of 7 minutes was used during loading and 3 minutes for subsequent steps. After loading was completed the column was washed for 10 CV with equilibration buffer. The bound wt caspase 2 was eluted using a step gradient to 100% elution buffer for 10 CV.

The elution fractions were analyzed using SDS-PAGE and all fractions containing wt caspase-2 were used for the next purification step.

The capture eluate of wt caspase-2 was buffer exchanged before the polishing chromatography step. Tangential flow ultra-/diafiltration with a 5 kDa cut off membrane was used with a sample buffer of 50 mM sodium citrate, pH 5.0. In total 5 volumes were exchanged.

The capture step used cation exchange chromatography on SP Sepharose HP (5×24 mm, 0.5 mL) using the following buffers: equilibration buffer A: 50 mM sodium citrate, pH 5.0. Elution buffer B: 50 mM sodium citrate, 1 M NaCl, pH 5.0.

Buffer exchanged capture eluate was loaded on the equilibrated polishing column. The residence time was held constant at 5 minutes. The column was loaded with 37 CV of buffer exchanged capture eluate. Wt caspase-2 was eluted in a linear gradient from 0-100% B in 10 CV. The elution fractions were analyzed using Western blot and SDS PAGE and the fractions positive for the small sub unit of wt caspase-2 were combined and stored at −80° C. Before performing enzyme kinetic measurements, oxidation induced activity losses were reversed by incubating wt caspase-2 with 100 mM DTT for 15 minutes.

Characterization of Wt Caspase-2

FRET Assay (as Described in Example 9, Section 9.3.3)

Michaelis Menten kinetic was determined for wt caspase-2 and cp caspase-2 for the following substrates: VDVADFA (SEQ ID NO:318), VDVADGA (SEQ ID NO:319), VDVADQA (SEQ ID NO:320) and VDVADVA (SEQ ID NO:321), where the P1' amino acid is indicated by bold and underlined font.

TABLE 34

FRET results for wt and cp caspase-2.

| | P1' | F | G | Q | V |
|---|---|---|---|---|---|
| wt caspase-2 | $K_M$ (M) | 7.9E−05 | 9.7E−05 | 1.1E−04 | 8.6E−05 |
| | 95% confidence interval $K_M$ (M) | 1.1E−05 | 1.2E−05 | 9.8E−06 | 8.9E−06 |
| | $k_{cat}$ ($s^{-1}$) | 8.4E−04 | 3.2E−02 | 5.7E−04 | 2.3E−04 |
| | 95% confidence interval $k_{cat}$ ($s^{-1}$) | 5.3E−05 | 1.9E−03 | 2.4E−05 | 1.1E−05 |
| | $k_{cat}/K_M$ ($M^{-1}s^{-1}$) | 11 | 335 | 5.0 | 2.7 |
| cp caspase-2 | $K_M$ (M) | 5.8E−05 | 4.9E−05 | 1.3E−04 | 7.3E−05 |
| | 95% confidence interval $K_M$ (M) | 1.5E−05 | 1.3E−05 | 2.4E−05 | 1.8E−05 |

TABLE 34-continued

| FRET results for wt and cp caspase-2. | | | | |
|---|---|---|---|---|
| P1' | F | G | Q | V |
| $k_{cat}$ ($s^{-1}$) | 7.9E−03 | 2.7E−01 | 4.6E−03 | 1.7E−03 |
| 95% confidence interval $k_{cat}$ ($s^{-1}$) | 8.1E−04 | 2.7E−02 | 4.6E−04 | 1.9E−04 |
| $k_{cat}/K_M$ ($M^{-1}s^{-1}$) | 136 | 5542 | 36 | 24 |

The FRET results in Table 34 show significant differences between the two proteases. Cp caspase-2 exhibits catalytic efficiencies approximately one order of magnitude higher than wt caspase-2. While the Michaelis constant $K_M$ appears mostly unaffected by circular permutation, the turnover number $k_{cat}$ is the cause for the stark differences in catalytic efficiency $k_{cat}/K_M$ between wt caspase-2 and cp caspase-2. The produced wt caspase-2 seems to exhibit slightly better P1' tolerance compared to cp caspase-2 (both not comprising the amino acid substitutions for improved P1' tolerance described herein), e.g. F as P1' is cleaved with 2.5% catalytic efficiency in cp caspase 2 compared to 3.2% in wt caspase-2. This slight increase in P1' (1.3 to 2.3-fold increase) is overshadowed by the, on average eleven times lower catalytic efficiency and eight times lower turnover number of wt caspase-2.

Tolerance for Elevated Temperatures

Cleavage of a heat stable model fusion tag protein, 6H-GSG-VDVAD (SEQ ID NO-45)-GFPmut3.1 (GFP with P1'=M), was used to quantify the tolerance of caspase-2 towards elevated temperatures.

TABLE 35

| Cleavage of GFP carrying the fusion tag at different temperatures | | | |
|---|---|---|---|
| | | Temperature (° C.) | |
| | | 25 | 50 |
| wt caspase-2 | Time (min) | 7 | 7 |
| | $v_0$ ($s^{-1}$) | 2.2E−03 | 4.3E−03 |
| | Standard deviation $v_0$ ($s^{-1}$) | 1.7E−04 | 6.4E−05 |
| cp caspase-2 | Time (min) | 7 | 7 |
| | $v_0$ ($s^{-1}$) | 3.5E−03 | 9.8E−03 |
| | Standard deviation $v_0$ ($s^{-1}$) | 6.7E−05 | 6.0E−04 |

The GFP cleavage results in Table 35 show comparable heat tolerance between the two proteases. The cleavage reaction with cp caspase-2 is 1.6-fold faster, than with wt caspase-2 at 25° C. This difference increases to 2.3-fold at 50° C., showcasing the increased stability of cp caspase-2 at elevated temperatures. In general, the cleavage reaction at 50° C. is 1.9 times faster for wt caspase-2 and 2.8 times faster for cp caspase 2. This is a clear benefit if a heat stable target protein has to be processed.

Tolerance to Chaotropic Conditions

Cleavage of a model fusion tag protein stable in 4 M urea, namely 6H-GSG-VDVAD-hFGF-2 (SEQ ID NO:32) (P1'=A), was used to quantify the tolerance of caspase-2 towards chaotropic conditions.

TABLE 36

| Cleavage of FGF2 carrying the fusion tag at different urea concentrations. | | | |
|---|---|---|---|
| | | Urea concentration (M) | |
| | | 0 | 4 |
| wt caspase-2 | Time (min) | 5 | 90 |
| | $v_0$ ($s^{-1}$) | 4.7E−02 | 5.7E−04 |
| | Standard deviation $v_0$ ($s^{-1}$) | 5.6E−03 | 1.4E−05 |
| cp caspase-2 | Time (min) | 5 | 90 |
| | $v_0$ ($s^{-1}$) | 1.5E−01 | 2.0E−03 |
| | Standard deviation $v_0$ ($s^{-1}$) | 2.0E−03 | 6.0E−05 |

The FGF2 cleavage results in Table 36 show comparable tolerance for chaotropic conditions between the two proteases. In order to quantify the cleavage product in the linear range, the reaction had to be stopped at differing time points. Both proteases show almost identical behavior in the presence of 4 M urea, were the reaction rate is reduced to 1.2% and 1.3% for wt caspase-2 and cp caspase-2 respectively. For this particular model protein, cp caspase-2 exhibited a 3.2-fold increased reaction rate relative to wt caspase-2.

Manufacturability

Perhaps the biggest observable difference between the two proteases, is in their ease of manufacture. In order to express the difference in manufacturability between wt caspase-2 and cp caspase-2, we calculated the amount of dry cell mass required to produce one milligram of purified enzyme. This takes into account the differences in specific protein content of the *E. coli* fermentation and the differences in downstream processing yields. It does not take into account differences in biomass yield between fermentations. In order to produce 1 mg of wt caspase-2, 70 g of cell dry mass (CDM) were required. For the production of cp caspase-2, only 34 mg of CDM were needed per milligram pure enzyme. This corresponds to a difference in manufacturability of a factor of 2033.

Conclusion

FRET assay results with 4 different P1' amino acids showed a general trend of tenfold higher catalytic efficiencies of the cp caspase-2 compared to wt caspase-2. The cleavage of non peptide substrates, showed two to three-fold faster cleavage reaction depending on the protein substrate. The circular permutation of caspase-2 has apparently lead to an increase in heat tolerance, showcased by the larger increase in turnover rate at 50° C. The tolerance to chaotropic conditions also appears slightly higher The largest differentiating factor between wt and cp enzymes is their manufacturability. While the expression level of wt caspase-2 is very low (under the limit of quantification), cp caspase-2 reaches expression levels of 80 mg specific protein content per g CDM. This also results in much lower losses during DSP, where a process yield of about 35% can be achieved for cp caspase-2.

Example 18: Production Process for Wild-Type Cp Caspases-2 and P1 Tolerable Cp Caspases-2

18.1 Upstream Processing of Cp Caspase-2 and Variants

For the production of cp caspase-2 and variants with and without solubility tag lab-scale fermentations were performed as described below. Different expression clones were compared regarding cell growth and soluble recombinant protein production. For further process optimization, a series of cultivation runs was conducted.

18.1.1 Bacterial Strain, Plasmid and Wild-Type Cp Caspases-2 and P1 Tolerable Cp Caspases-2

The *E. coli* strain BL21(DE3) [$F^-$, fhuA2, Ion, ompT, gal, dcm, ΔhsdS λ DE3 [λ sBamHlo, ΔEcoRI-B int::(lacI:: PlacUV5::T7 gene1) i21 Δnin5], purchased from Novagen, was transformed with a pET30a vector carrying the gene for the respective cp caspase-2 variant with and without solubility tag under the T7 promoter/operator system. The expression clones cultivated in lab-scale bioreactors are listed in Table 37.

TABLE 37

Expression clones for cp caspase-2 and variants with and without solubility tag

| Name of Expression clone | Caspase variant | SEQ ID |
|---|---|---|
| BL21(DE3)(pET30a_ 6H-cpCasp2D) | cp caspase-2 D | SEQ ID No. 6 |
| BL21(DE3)(pET30a_ T7A3-6H-cpCasp2D) | cp caspase-2 D | — |
| BL21(DE3)(pET30a_ 6H-T7A3-cpCasp2D) | cp caspase-2 D | — |
| BL21(DE3)(pET30a_ T7AC-6H-cpCasp2D) | cp caspase-2 D | SEQ ID No. 41 |
| BL21(DE3)(pET30a_ 6H-mS9ProE) | mS9 Pro E285 | SEQ ID No. 70 |
| BL21(DE3)(pET30a_ T7AC-6H-mS9ProE) | mS9 Pro E285 | SEQ ID No. 71 |
| BL21(DE3)(pET30a_ 6H-mS9ProD) | mS9 Pro D285 | SEQ ID No. 52 |
| BL21(DE3)(pET30a_ T7AC-6H-mS9ProD) | mS9 Pro D285 | SEQ ID No. 72 |

18.1.2 Lab-Scale Fermentation of Cp Caspase-2 and Variants.

18.1.2.1 Fermentation Media

For high cell density (HCD) cultivation experiments minimal media calculated to produce 80 g cell dry mass (CDM) in the batch phase and 1450 g CDM during feed phase were used. The batch medium was prepared volumetrically; the components were dissolved in 10 L RO—$H_2O$. The fed-batch medium was prepared gravimetrically; the final weight was 10.1 kg. All components for the fed-batch medium were weighed in and dissolved in RO—$H_2O$ separately. All components (obtained from MERCK), were added in relation to the theoretical grams of cell dry mass to be produced: The composition of the batch and the fed-batch medium is as follows: 94.1 mg/g $KH_2PO_4$, 31.8 mg/g $H_3PO_4$ (85%), 41.2 mg/g $C_6H_5Na_3O_7$*2 $H_2O$, 45.3 mg/g $NH_4SO_4$, 46.0 mg/g $MgCl_2$*2 $H_2O$, 20.2 mg/g $CaCl_2$*2 $H_2O$, 50 μL trace element solution, and 3.3 g/g $C_6H_{12}O_6$*$H_2O$. The trace element solution was prepared in 5 N HCl and included 40 g/L $FeSO_4$·*7$H_2O$, 10 g/L $MnSO_4$·*$H_2O$, 10 g/L $AlCl_3$·*6 $H_2O$, 4 g/L $CoCl_2$, 2 g/L $ZnSO_4$·*7$H_2O$, 2 g/L $Na_2MoO_2$·*2 $H_2O$, 1 g/L $CuCl_2$·*2 $H_2O$, and 0.5 g/L $H_3BO_3$. To accelerate initial growth of the population, the complex component yeast extract (150 mg/g calculated CDM) was added to the batch medium. Nitrogen level was maintained by adding 25% ammonium hydroxide solution (w/w) for pH control. Antifoam (PPG 2000) 0.5 mL/L total volume was added at the beginning. Pre-cultures for inoculation were grown in synthetic media calculated to produce 3 g/L).

TABLE 38

Batch medium components

| Component | Quantity |
|---|---|
| $KH_2PO_4$ | 0.094 g/g final CDM |
| 85% $H_3PO_4$ | 0.032 g/g final CDM |
| Yeast extract | 0.15 g/g CDM (batch) |
| $C_6H_5Na_3O_7$••2$H_2O$ | 0.25 g/g final CDM |
| $MgCl_2$•7$H_2O$ | 0.1 g/g CDM (batch) |
| $CaCl_2$•2$H_2O$ | 0.02 g/g CDM (batch) |
| $(NH_4)_2SO_4$ | 0.046 g/g final CDM |
| Trace element solution | 50 μL/g CDM (batch) |
| $C_6H_{12}O_6$•$H_2O$ | 3.3 g/g CDM (batch) |

TABLE 39

Fed batch medium components

| Component | Quantity |
|---|---|
| $MgCl_2$•7$H_2O$ | 0.1 g/g CDM (fed-batch) |
| $CaCl_2$•2$H_2O$ | 0.02 g/g CDM (fed-batch) |
| Trace element solution | 50 μL/g CDM (fed-batch) |
| $C_6H_{12}O_6$•$H_2O$ | 3.3 g/g CDM (fed-batch) |

18.1.2.2 Cultivation and Induction Conditions for (Standard) Lab-Scale Fermentations of Wild-Type Cp Caspases-2 and P1'Tolerable Cp Caspases-2.

All high cell densities (HCD) fermentations were performed in a 30 L (23 L net volume, 5 L batch volume) computer-controlled bioreactor (Bioengineering; Wald, Switzerland) equipped with standard control units (Siemens PS7, Intellution iFIX). The pH was maintained at a set-point of 7.0±0.05 by addition of 25% ammonia solution (w/w), the temperature was set to 37° C.±0.5° C. in the batch phase and 30° C.±0.5° C. in the fed-batch phase. To avoid oxygen limitation the DO level was held above 30% saturation by adjusting the stirrer speed and the aeration rate of the process air. The maximum overpressure in the head space was 1.1 bar. Foaming was suppressed by addition of 0.5 mL/L antifoam (PPG 2000 Sigma Aldrich) to the batch medium and by pulsed addition of antifoam during the fed-batch phase. The cultivation was inoculated with an overnight pre-culture. The pre-culture was set-up by inoculating 200 mL LB media with 1 mL of a deep frozen WCB in 2000 mL shake flasks. Cells were grown on an orbital shaker at 180 rpm and at 37 C until the $OD_{600}$ reached a value of approx. 4. Thereafter, batch was inoculated with the pre-culture to an initial OD600 of 0.10 and cultivated at 37° C. At the end of the batch phase as soon as cells entered the stationary growth phase, an exponential substrate feed was started. The fed-batch phase (29 h, unless otherwise stated in table 40) was performed at 30° C., unless otherwise stated in table 40, with an exponential feeding strategy with a consistent growth rate of p=0.1 $h^{-1}$, unless otherwise stated in table 40. The substrate feed was controlled by increasing pump speed according to the exponential growth algorithm, $X=X_0—e^{\mu t}$, with superimposed feedback control of weight loss in the substrate tank. Induction was as follows, unless otherwise stated in table 40: Induction started with fed-batch phase by adding feed medium including IPTG (so called "overfeed" induction, table 40) to achieve a final IPTG concentration of 0.5 μmol IPTG/g theoretical CDM at the end of the fermentation and a protein production for 4 generations.

18.1.2.3 Further Cultivation and Induction Conditions:

Pre-cultivation and batch phase were identical to the previously described standardized fermentations. The fed-batch phases were performed at 30° C. For biomass production the first fed-batch phase was performed with an exponential feed (μ =of 0.17 $h^{-1}$) for 1.72 generations. As previously described, the substrate feed was controlled by increasing pump speed according to the exponential growth algorithm, $X=X_0*e^{\mu t}$, with superimposed feedback control of weight loss in the substrate tank. In a second feed-phase a lower growth rate (0.03, 0.05 and 0.07 $h^{-1}$) was adjusted resulting in a total feed time of 60.5 h, 39 h and 30 h. The calculated CDM was 70 g/L. To ensure sufficient adaption to the low growth conditions, the cells grew for 0.25 generations without induction. Then induction was performed with three different IPTG concentrations (0.5, 0.9 and 1.3 μmol/g actual CDM) for two generations. IPTG corresponding to the CDM at induction time, as mentioned before, was injected into the reactor and then IPTG calculated to the actual CDM was fed into the fermenter within the feed medium. To that end the needed IPTG was transferred into the feed bottle calculated to the IPTG needed until the theoretical CDM at the end of fermentation. Thus, the IPTG concentration related to the theoretical CDM was constant throughout the whole fermentation. 9 fermentations were performed. The results are described in 18.1.2.7

TABLE 40

Summary of all cultivation and induction conditions for cp caspase-2 and cp caspases-2: IPTG over feed was according to 18.1.2.2 except *: was performed as described in 18.1.2.3

| | | Fermentation strategy | | | | | | | | | | | | |
|---|---|---|---|---|---|---|---|---|---|---|---|---|---|---|
| | | Batch | | | | Fed-Betch | | | | | | | | IPTG over |
| Experiment | cp casgase-2 and cp caspase-2 variants | Temp. [° C.] | total CDM [g] | V [l] | CDM [g/l] | Temp. [° C.] | total V [l] | total CDM [g] | CDM [g/l] | μ [$h^{-1}$] | Gen. | feed [h] | production [h] | feed [μmol/gCDM] |
| Cas_F11 | 6H-cpCasp2D | 37 | 80.0 | 10.00 | 8.0 | 30 | 18.6 | 1453.0 | 78.3 | 0.1 | 4.18 | 29 | 29 | 0.5 |
| Cas_F17 | 6H-T7A3-cpCasp2D | 37 | 80.0 | 10.00 | 8.0 | 30 | 18.6 | 1453.0 | 78.0 | 0.1 | 4.18 | 29 | 29 | 0.5 |
| Cas_F18 | T7A3-6H-cpCasp2D | 37 | 80.0 | 10.00 | 8.0 | 30 | 18.6 | 1453.0 | 78.0 | 0.1 | 4.18 | 29 | 29 | 1.0 |
| Cas_F22 | 6H-mS9 ProD | 37 | 80.0 | 10.00 | 8.0 | 30 | 18.6 | 1453.0 | 78.0 | 0.1 | 4.18 | 29 | 29 | 0.5 |
| Cas_F24 | T7AC-6H-cpCasp2D | 37 | 80.0 | 10.00 | 8.0 | 30 | 18.6 | 1453.0 | 78.0 | 0.1 | 4.18 | 29 | 29 | 0.5 |
| Cas_F25 | 6H-mS9 ProE | 37 | 80.0 | 10.00 | 8.0 | 30 | 18.6 | 1453.0 | 78.0 | 0.1 | 4.18 | 29 | 29 | 0.5 |
| Cas_F26 | T7AC-6H-mS9 ProE | 37 | 80.0 | 10.0 | 8.0 | 30 | 18.6 | 1453 | 78.0 | 0.1 | 4.18 | 29 | 29 | 0.5 |
| Cas_F28 | T7AC-6H-cpCasp2D | 37 | 80.0 | 10.0 | 8.0 | 30 | 18.6 | 1453 | 78.0 | 0.05 | 4.18 | 32 | 17 | 0.5 |
| Cas_F30 | T7AC-6H-mS9 ProD | 37 | 80.0 | 10.0 | 8.0 | 30 | 18.6 | 1453 | 79.0 | 0.1 | 4.18 | 29 | 29 | 0.5 |
| Cas_F31 | T7AC-6H-mS9 ProE | 37 | 64.0 | 8.0 | 8.0 | 30 | 15.3 | 1163 | 76.0 | 0.1 | 4.18 | 29 | 29 | 0.5 |
| Cas_F34_ confDoE | T7AC-6H-cpCasp2D | 37 | 64.0 | 8.0 | 8.0 | 30 | 14.8 | 1601 | 108.8 | 0.17, 0.03 | 4.65 | 56 | 38 | 0.9* |
| Cas_F35_wt | wtCasp2-6H | 37 | 64.0 | 8.0 | 8.0 | 30 | 14.8 | 952 | 64.0 | 0.1 | 3.90 | 27 | 27 | 0.5 |
| DAS_Cas01 R1 | T7AC-6H-cpCasp2_cal | 37 | 6.0 | 0.6 | 10.0 | 30 | 1.2 | 40 | 34.0 | 0.05 | 2.74 | 39 | 39 | 0.9 |
| DAS_Cas01 R2 | T7AC-6H-cpCasp2_sar | 37 | 6.0 | 0.6 | 10.0 | 30 | 1.2 | 40 | 34.0 | 0.05 | 2.74 | 39 | 39 | 0.9 |
| DAS_Cas01 R3 | T7AC-6H-cpCasp2_ cal_E105V, G171D | 37 | 6.0 | 0.6 | 10.0 | 30 | 1.2 | 40 | 34.0 | 0.05 | 2.74 | 39 | 39 | 0.9 |
| DAS_Cas01 R4 | T7AC-6H-cpCasp2_ sar_E105V, E172V | 37 | 6.0 | 0.6 | 10.0 | 30 | 1.2 | 40 | 34.0 | 0.05 | 2.74 | 39 | 39 | 0.9 |
| Cas_F42 | T7AC-6H-mS9 ProD | 37 | 64.0 | 8.0 | 8.0 | 30 | 14.8 | 1601 | 108.8 | 0.17, 0.03 | 4.65 | 56 | 38 | 0.9* |
| Cas_F44 | T7AC-6H-mS9 ProD | 37 | 64.0 | 8.0 | 3.0 | 30 | 15.4 | 1042 | 67.5 | 0.17, 0.05 | 4.03 | 39 | 28 | 0.9* |

All fermentation results for the fermentations as described in table 40 can be seen in Table 41.

TABLE 41

Summary of all fermentations of cp caspases-2 with and without solubility tag: biomass and recombinant protein levels at the end of cultivation.

| | | Growth | | | | | | | | | | |
|---|---|---|---|---|---|---|---|---|---|---|---|---|
| | cp caspase-2 | | Total | cpCaspase-2 Titers | | | | | | | | |
| Experiment | and cp caspase-2 variants | CDM [g/l] | CDM [g] | soluble [mg/g] | IBs [mg/g] | total [mg/g] | soluble [g] | IBs [g] | total [g] | soluble [g/L] | IBs [g/L] | total [g/L] |
| Cas_F11 | 6H-cpCasp2D | 68.4 | 1383 | 6.31 | 112.95 | 119.26 | 8.7 | 156.1 | 164.9 | 0.43 | 7.73 | 8.16 |
| Cas_F17 | 6H-T7A3-cpCasp2D | 72.1 | 1445 | 13.27 | 84.61 | 97.89 | 19.2 | 122.3 | 141.5 | 0.96 | 6.10 | 7.05 |
| Cas_F18 | T7A3-6H-cpCasp2D | 74.1 | 1452 | 13.21 | 70.54 | 83.75 | 19.2 | 102.4 | 121.6 | 0.98 | 5.29 | 6.21 |
| Cas_F22 | 6H-mS9 ProD | 76.1 | 1491 | 9.72 | 31.27 | 40.99 | 19.4 | 49.4 | 64.8 | 0.78 | 2.51 | 3.29 |
| Cas_F24 | T7AC-6H-cpCasp2D | 77.5 | 1549 | 12.62 | 87.85 | 100.47 | 19.5 | 136.1 | 155.6 | 0.98 | 6.82 | 7.79 |
| Cas_F25 | 6H-mS9 ProE | 76.6 | 1546 | 4.63 | 81.49 | 86.13 | 7.2 | 126.0 | 133.2 | 0.36 | 6.25 | 6.61 |
| Cas_F26 | T7AC-6H-mS9 ProE | 78.7 | 1557.4 | 7.54 | 24.58 | 32.12 | 11.7 | 38.3 | 50.0 | 0.59 | 1.94 | 2.59 |
| Cas_F28 | T7AC-6H-cpCasp2D | 77.9 | 1593.3 | 15.79 | 34.34 | 50.13 | 25.2 | 54.7 | 79.9 | 1.23 | 2.68 | 3.91 |

TABLE 41-continued

Summary of all fermentations of cp caspases-2 with and without solubility tag: biomass and recombinant protein levels at the end of cultivation.

| Experiment | cp caspase-2 and cp caspase-2 variants | Growth CDM [g/l] | Total CDM [g] | cpCaspase-2 Titers soluble [mg/g] | IBs [mg/g] | total [mg/g] | soluble [g] | IBs [g] | total [g] | soluble [g/L] | IBs [g/L] | total [g/L] |
|---|---|---|---|---|---|---|---|---|---|---|---|---|
| Cas_F30 | T7AC-6H-mS9 ProD | 76.6 | 1573.9 | 15.10 | 41.69 | 56.79 | 23.8 | 69.6 | 89.4 | 1.16 | 3.19 | 4.35 |
| Cas_F31 | T7AC-6H-mS9 ProE | 81.8 | 1347.0 | 9.37 | 34.61 | 43.98 | 12.6 | 46.6 | 59.2 | 0.77 | 2.83 | 3.60 |
| Cas_F34_confDoE | T7AC-6H-cpCasp2D | 68.8 | 1081.0 | 76.96 | 78.72 | 155.18 | 83.2 | 84.6 | 167.8 | 3.29 | 5.38 | 10.67 |
| Cas_F35_wt | wtCasp2-6H | 69.6 | 1110.9 | NQ | NQ | NQ | NQ | NQ | NQ | NQ | NQ | NQ |
| DAS_Cas01 R2 | T7AC-6H-cpCasp2_sar | 35.0 | 40.2 | 47.75 | 18.27 | 66.02 | 1.9 | 0.7 | 2.7 | 1.53 | 0.58 | 2.11 |
| DAS_Cas01 R4 | T7AC-6H-cpCasp2_sar_ E105V, E172V | 34.1 | 40.2 | 50.48 | 20.46 | 70.94 | 2.1 | 0.8 | 2.9 | 1.67 | 0.68 | 2.34 |
| Cas_F42 | T7AC-6H-mS9 ProD | 49.6 | 804.3 | 36.44 | 107.50 | 143.94 | 29.3 | 86.5 | 115.8 | 1.81 | 5.34 | 7.15 |
| Cas_F44 | T7AC-6H-mS9 ProD | 60.9 | 994.6 | 30.45 | 70.28 | 100.74 | 90.3 | 69.9 | 100.2 | 1.86 | 4.30 | 6.16 |

NQ cold not be quantified 18.1.2.4 Fermentation Monitoring

In addition to standard online monitoring (pH, stirrer speed, temperature and $pO_2$) the concentration of $pO_2$ and $O_2$ in the outlet air was measured with a BlueSens gas analyzer. Sampling of the standard offline process parameters started after one generation in fed-batch mode. The first sample was withdrawn from the bioreactor prior to induction. Optical density ($OD_{600}$) was measured with a spectrophotometer at wavelength λ=600 nm. Samples were diluted in PBS to ensure a measurement at a linear range from 0.1 to 0.8. Cell dry mass (CDM) was determined by centrifugation of 10 mL of cell suspension for 8 min at 8500 rpm. The supernatant was discarded and cells were resuspended with RO—$H_2O$ and centrifuged. Water was discarded and cell were resuspended again with RO—$H_2O$. Cell suspension was transferred into a beaker, which was weighted before. Beakers were dried for at least 24 h at 105° C. and weighted again. The difference in weight account for the CDM.

For the determination of the content of cp caspase-2 and variants, aliquots of approximately 1.0 mg CDM of the samples were centrifuged (10 min. at 13200 rpm); the supernatants were discarded, the insides of the tubes were carefully blotted dry and the samples were stored at −20° C.

18.1.2.5 Determination of Titer and Specific Titer of Cp Caspase-2 Variants and Fusion Proteins in Fermentation Samples Cell disintegration, fractionation of soluble and insoluble recombinant protein and IB dissolving: Cell disintegration was performed from fermentation samples containing approximately 1.0 mg CDM. 200 μL of cell integration buffer was added to the cell pellet and vortexed until the pellet was completely resuspended. For cell disruption 50 μL Lysozyme and 50 μL Benzonase were added and incubated while shaking at room temperature. 100 μL Triton X-100 was added and samples were incubated again while shaking. Then, samples were centrifuged at 4° C. and 13000 rpm to separate soluble proteins and inclusion bodies (IB). The supernatant was transferred into a new reaction tube for direct analysis (SDS-PAGE) or stored at −20° C.

The remaining pellet (IBs and cell debris) was washed two times by resuspending with 1 mL Tris/HCL (100 mM). After resuspending the pellet was centrifuged at 4° C. and 13000 rpm for 10 min. The supernatant was discarded. Afterwards, 400 μL IB solvent buffer was added and incubated at room temperature for 30 min. while shaking. Finally, the sample was centrifuged again and the supernatant containing dissolved IBs was used for analysis (SDS-PAGE) or stored at −20° C.

TABLE 42

| Cell disintegration solutions | |
|---|---|
| Tris/HCl (pH = 8.2) | 30 mM |
| EDTA | 0.5M |
| $MgCl_2$ x $6H_20$ | 200 mM |
| Triton X-100 | 6% |
| Lysozym | 2 mg/mL |
| Benzonase | 50 units/mL |

TABLE 43

| Cell disintegration buffer 3 mL | |
|---|---|
| Tris/HCl (pH = 8.2) 30 mM | 2.7 mL |
| EDTA | 150 μL |
| $MgCl_2$ × $6H_20$ | 150 μL |
| Sample reducing Agent (10×) | 24 μL |

TABLE 44

| IB solvent buffer | |
|---|---|
| Tris/HCl (pH = 8.2) | 100 mM |
| urea | 8 M |
| Sample reducing agent (10×) | 28 μl/mL IB solution buffer |

SDS-PAGE:

Sodium dodecyl sulfate polyacrylamide gel electrophoresis (SDS-PAGE) was used to separate and analyze the recombinant proteins. Electrophoresis was performed by using precast gels with an acrylamide gradient (NuPAGE 4-12% BisTris, Thermo Fisher Scientific, Waltham, MA, USA) and NuPAGE® MES SDS Running buffer.

Loading samples were prepared by mixing 13 μL of the supernatant (soluble fraction) or IB supernatant (insoluble fraction) with 5 μL LDS sample buffer (4×) and 2 μL NuPAGE® reducing agent (10×) and incubating the mixture in a thermos mixer at 70° C. for 10 minutes. A ready-to-use molecular weight marker (Mark12™, Unstained Standard, Invitrogen) was directly loaded as size marker. For quantification, purified T7AC_6H_cpCasp2 (SEQ ID NO:6) standards (75, 50 and 25 μg/mL) listed in Table 9, produced as described in Example 9 (see sections 9.1, and 9.2), were used. For fusion proteins BSA (bovine serum albumin) served as a standard. Electrophoresis settings were 200 V and 400 mA for 40 to 50 minutes in a XCell SureLock™ Electrophoresis Cell chamber (Thermo Fisher Scientific). After electrophoresis the SDS Gels were fixed in fixing solution (40% ethanol; 50% $_dH_2O$; 10% acetic acid) for 30 minutes and stained afterwards with Coomassie brilliant blue R250 staining solution for 30 minutes. Finally, the gel was decolorized in a destaining solution (25% acetic acid; 8% ethanol; 67% $_dH_2O$) for at least two hours. Gels were transferred in water and scanned with a desktop scanner, converted to grey-scale and analysed using the software ImageQuant TL (7.0). The concentration of cp caspase-2 and variants was quantified via a linear regression curve.

18.1.2.6 Comparison of production of wild-type cp caspases-2 and P1'tolerablecp caspases-2 with and without solubility tag in fermentations with a p=0.1 $h^{-1}$ and an IPTG concentration of 0.5 μmol IPTG/g CDM during induction (standard fermentations as described in section 9.1.2.2).

While overexpression of cp caspase-2 was possible in *E. coli*, the expression rate of soluble cp caspase-2 was generally low. In order to increase the fermentation titer, a solubility tag was added to the enzyme. The tag T7A3 (SEQ ID No. 37) is based on a highly negatively charged peptide from the T7 bacteriophage. When used on the cp caspases-2 we noticed autocatalytic cleavage of the tag and subsequently modified the tag, using a cleavage site prediction algorithm. The altered solubility tag was coined T7AC (SEQ ID No. 43)

For evaluation of the production of cp caspase-2 and variants with and without solubility tag (T7AC), standardized lab-scale fermentations (section 18.1.2.2) were performed. Expression clones were compared regarding cell growth and soluble and insoluble recombinant protein production.

Figure 10:
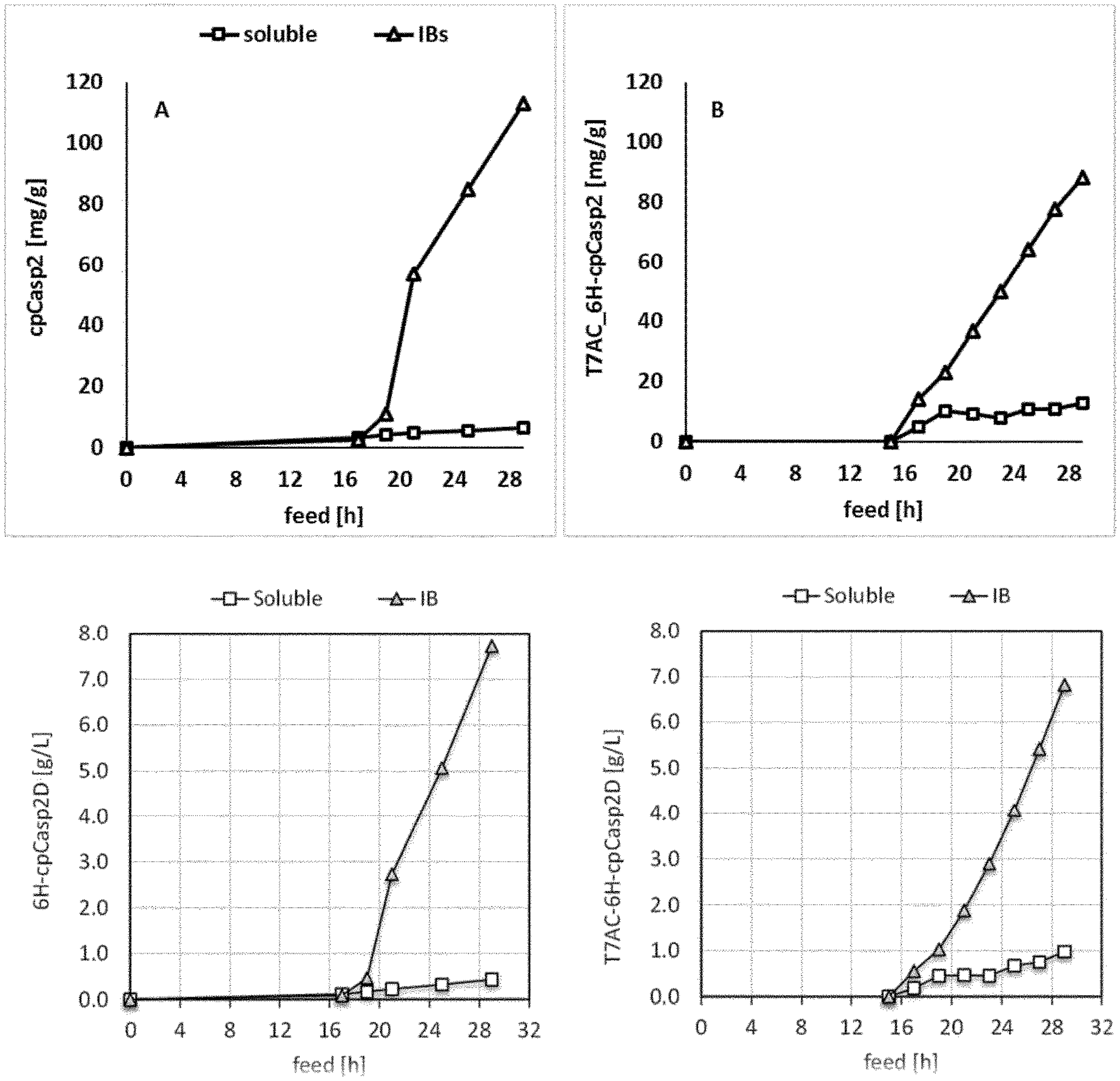
Figure 11:
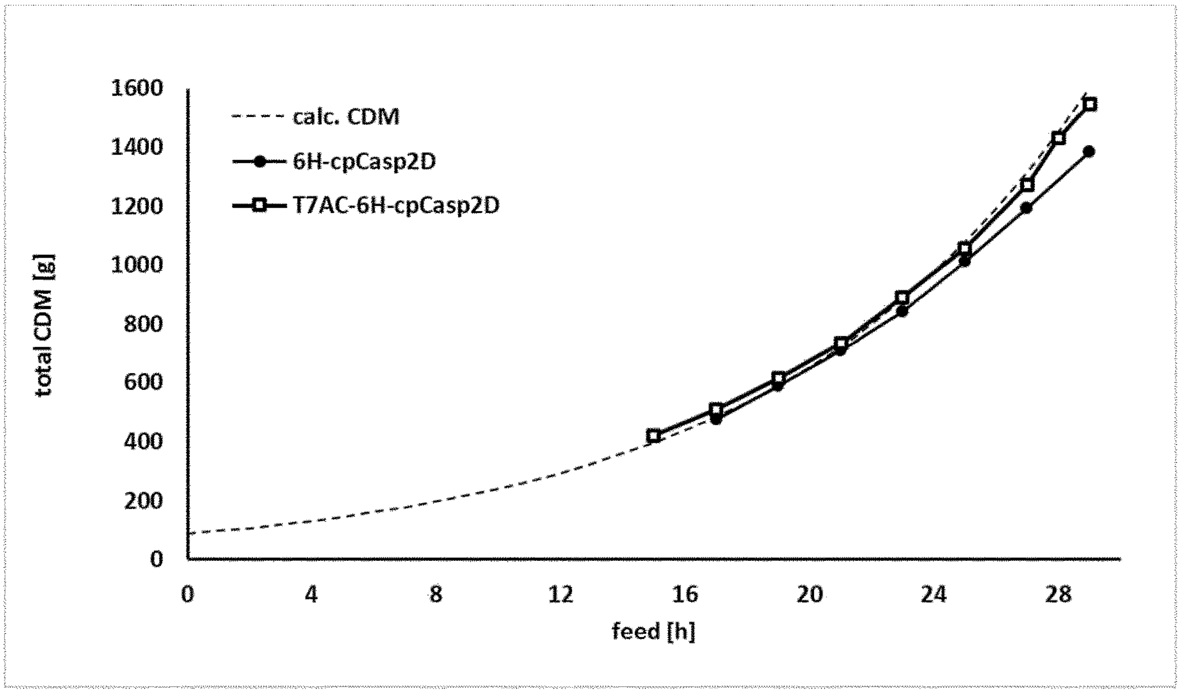

Comparing the production of 6H-cpCasp2D (SEQ ID NO:6) and T7AC-6H-cpCasp2D (SEQ ID No. 41) in lab-scale fermentations, we observed that the production of 6H-cpCasp2D (SEQ ID NO:6) without solubility tag lead predominantly to inclusion body formation (FIG. 10 A). In the end of the cultivation the calculated CDM was not reached due to too high expression levels (FIG. 11). The addition of the T7AC solubility tag N-terminal of the caspase increased soluble expression (FIG. 10 B), whereby the overall recombinant protein expression was slightly lower. Cell growth followed the calculated CDM (FIG. 11). The final CDM was about 77.5 g/L respectively 1549 g in total. The solubility tag did not negatively influence the subsequent metal affinity chromatography.

FIG. 10 shows lab-scale fermentations of *E. coli* BL21 (DE3)(pET30a_6H-cpCasp2D) (SEQ ID NO:6) (A) and BL21(DE3)(pET30a_T7AC-6H-cpCasp2D (SEQ ID No. 41) (B). Expression of soluble and insoluble cp caspase-2 is shown in the course of time. At beginning of feed, expression was induced with IPTG (0.5 μmol/g CDM).

FIG. 11 shows lab-scale fermentations of *E. coli* BL21 (DE3)(pET30a_6H-cpCasp2D) (SEQ ID NO:6) and BL21 (DE3) (pET30a_T7AC-6H-cpCasp2D(SEQ ID No. 41)): biomass course.

Comparing the production of three cp caspases-2 (cp caspase-2, mS9Pro E285 and mS9 Pro D285) with and without T7AC solubility tag, it turned out that the variant itself has no influence on the performance, no significant differences in cell growth and soluble cp caspase-2 expression. By means of the T7AC solubility tag the soluble expression of all three variants was significantly improved.

Figure 12:
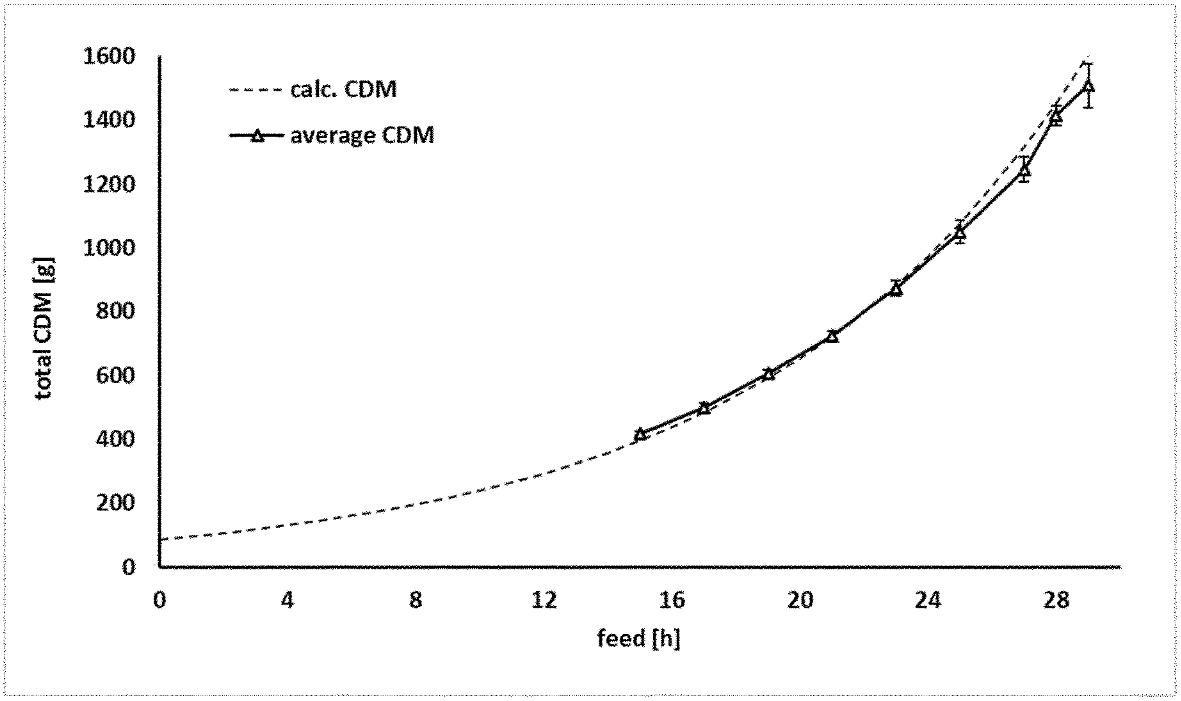
Figure 13:
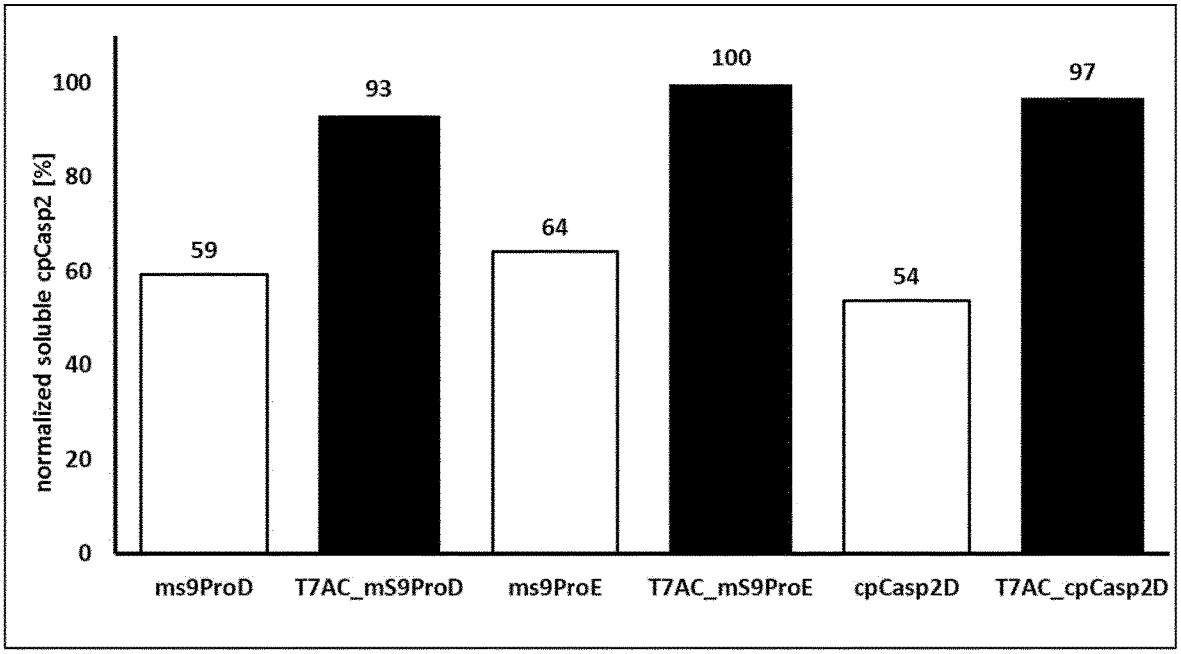

Cell growth kinetics off all cultivations were almost the same (VC<4%). Only at the end of the fermentations slight deviations were observed (FIG. 12). The fermentation strategy and the low induction level (0.5 μmol IPTG/g CDM) did not overburden the host metabolism. The addition of the T7AC solubility tag N-terminal of all cp caspases-2 increased the soluble expression levels (FIG. 13 and Tables 20 and 22). The final soluble product titers were up to 1.2 g/L. FIG. 12 shows biomass course of lab-scale fermentations of three cp caspases-2 (cp caspase-2 (cpCasp2D), mS9 Pro E285 (mS9ProE) and mS9 Pro D285 (mS9ProD), see also Table 17) with and without T7AC solubility tag in *E. coli* BL21(DE3) with pET30a vectors; the mean values and the standard deviation for these six cultivations are shown. The total CDM is shown as average of all 6 fermentations including standard deviation compared to expected growth (calc. CDM).

FIG. 13 shows normalized soluble production of cp caspase-2 of three different cp caspases-2 (cp caspase-2 (cpCasp2D), mS9 Pro E285 (mS9ProE) and mS9 Pro D285 (mS9ProD)) with and without T7AC solubility tag in *E. coli* BL21(DE3) with pET30a vectors.

Furthermore, a T7A3 tag could increase the soluble titer of cp-caspase-2D as can be seen in Table 40 and 41.

18.1.2.7 Further fermentation processes for wild-type like cpcaspase-2 variants and P1'tolerable cp caspases-2.

For testing further process conditions, a series of cultivation runs were conducted according to 18.1.2.3. The production clone BL21(DE3)(pET30a-T7AC_6H_cpCasp2D) (SEQ ID NO:6) was used. The influence of different growth rates (μ=0.03, 0.05 and 0.07 $h^{-1}$) and induction strengths (0.5, 0.9 and 1.3 μmol IPTG/g CDM) were investigated regarding cell growth and soluble and insoluble recombinant protein production. The results are shown in Table 45.

TABLE 45 fermentations as described under section 9.1.2.3: biomass and recombinant protein levels at the end of cultivation

| Cultivation [#] | growth rate [$h^{-1}$] | induction [umol/g CDM] | feed [h] | CDM [g] | cal. CDM [g] | achieved CDM |
|---|---|---|---|---|---|---|
| Cas_DoE_03 | 0.03 | 0.5 | 60.5 | 750 | 1133 | 66 |
| Cas_DoE_02 | 0.05 | 0.5 | 39.0 | 1026 | 1163 | 88 |
| Cas_DoE_01 | 0.07 | 0.5 | 30.0 | 1102 | 1131 | 97 |
| Cas_DoE_05 | 0.03 | 0.9 | 60.5 | 691 | 1145 | 60 |
| Cas_DoE_04 | 0.05 | 0.9 | 39.0 | 924 | 1126 | 82 |
| Cas_DoE_06 | 0.07 | 0.9 | 30.0 | 1048 | 1136 | 92 |
| Cas_DoE_07 | 0.03 | 1.3 | 60.5 | 639 | 1130 | 57 |

TABLE 45-continued

| | | | | | | |
|---|---|---|---|---|---|---|
| Cas_DoE_08 | 0.05 | 1.3 | 39.0 | 903 | 1127 | 80 |
| Cas_DoE_09 | 0.07 | 1.3 | 30.0 | 981 | 1135 | 86 |

| Cultivation [#] | spec. yield soluble [mg/g] | spec. yield IB [mg/g] | spec. yield total [mg/g] | vol. yield soluble [g/L] | vol. yield IB [g/L] | vol. yield total [g/L] |
|---|---|---|---|---|---|---|
| Cas_DoE_03 | 100.68 | 50.86 | 151.53 | 4.71 | 2.38 | 7.09 |
| Cas_DoE_02 | 56.31 | 45.39 | 101.69 | 3.54 | 2.85 | 6.39 |
| Cas_DoE_01 | 35.92 | 52.25 | 88.18 | 2.43 | 3.53 | 5.96 |
| Cas_DoE_05 | 105.24 | 94.30 | 199.54 | 4.56 | 4.09 | 8.65 |
| Cas_DoE_04 | 52.84 | 54.01 | 106.85 | 3.07 | 3.14 | 6.21 |
| Cas_DoE_06 | 45.27 | 103.11 | 148.38 | 2.98 | 6.78 | 9.76 |
| Cas_DoE_07 | 63.22 | 70.29 | 133.51 | 2.59 | 2.88 | 5.47 |
| Cas_DoE_08 | 67.5 | 55.6 | 123.1 | 3.9 | 3.2 | 7.0 |
| Cas_DoE_09 | 50.2 | 92.0 | 142.2 | 3.06 | 5.60 | 8.65 |

Figure 14:
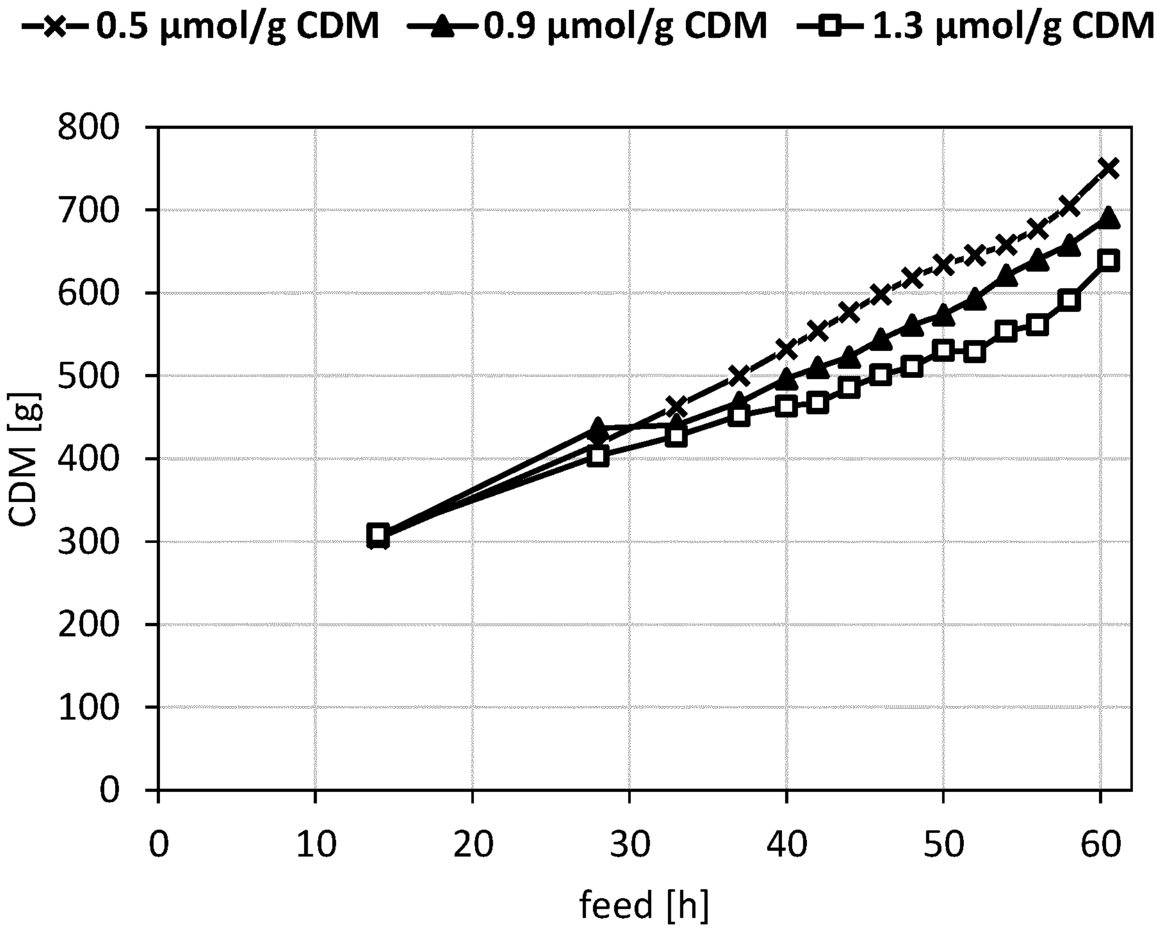

It was observed that the specific yield of soluble cp caspase-2 was higher at low growth rates and IB formation decreased. The calculated CDM was not reached at the end of fermentation with μ=0.03 h-1 due to too high expression levels (FIG. 14). FIG. 14 shows growth kinetics of *E. coli* BL2i(DE3)(pET30a-T7AC_6H-cpCasp2D) (SEQ ID No. 4i) during carbon limited 2 phase fed-batch cultivation (μ=0.17 followed by 0.03 h-1 during induction) with three different IPTG induction strengths.

Figure 15:
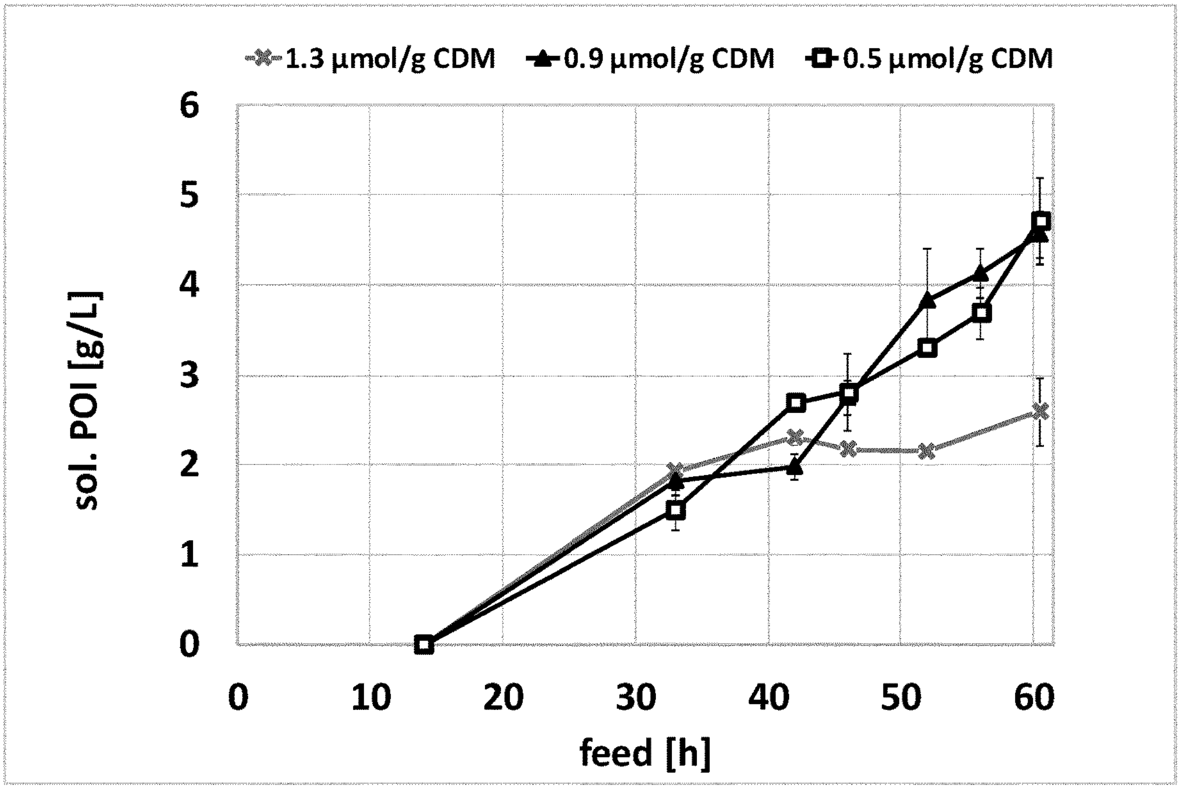

Nevertheless, the highest volumetric soluble yield was reached with p=0.03 $h^{-1}$ and 0.9 or 0.5 μmol IPTG/g CDM (FIG. 15).

FIG. 15 shows *E. coli* BL2i(DE3)(pET30a-T7AC_6H-cpCasp2D) (SEQ ID No. 41) during carbon limited 2 phase fed-batch cultivation (μ=0.17 and followed by 0.03 h-1 during induction) with three different IPTG induction strengths. Volumetric soluble cp caspase-2 titers (sol. POI [g/L]) obtained cultivating at the lowest growth rate (μ=0.03 $h^{-1}$) and inducing with different IPTG levels are shown. cp caspase-2 was quantified by SDS-PAGE. The mean values and standard deviations for individual determinations are shown (n=3).

Surprisingly the combination of using a T7AC or a T7A3 tag and low specific growth rates during induction (expression phase) and dosed IPTG concentration for tuning the expression rate, led to a titer of >5 g/L for cp-caspases-2

18.1.2.8: Application of Fermentation Processes for Production of Cp-Caspase-2 Variants Direct comparison between fermentations of T7AC-6H-cpCasp2D (SEQ ID No. 41) and T7AC-6H-mS9 ProD (SEQ ID NO:72) is shown with two different 2-phase fed-batch cultivations, μ=0.17 followed by 0.03 $h^{-1}$ for production and p=0.17 followed by 0.05 $h^{-1}$ for production with constant 0.9 μmol IPTG/g CDM as described in 18.1.2.3 and tables 40 and 41, Experiment Numbers F42 and F44, in FIG. 22-25.

The processes as outlined in 18.1.2.2 to 18.1.2.8 can be applied to all cp caspases-2 irrespective if it includes or not mutations at positions that increase the P1' tolerance.

Figure 30:
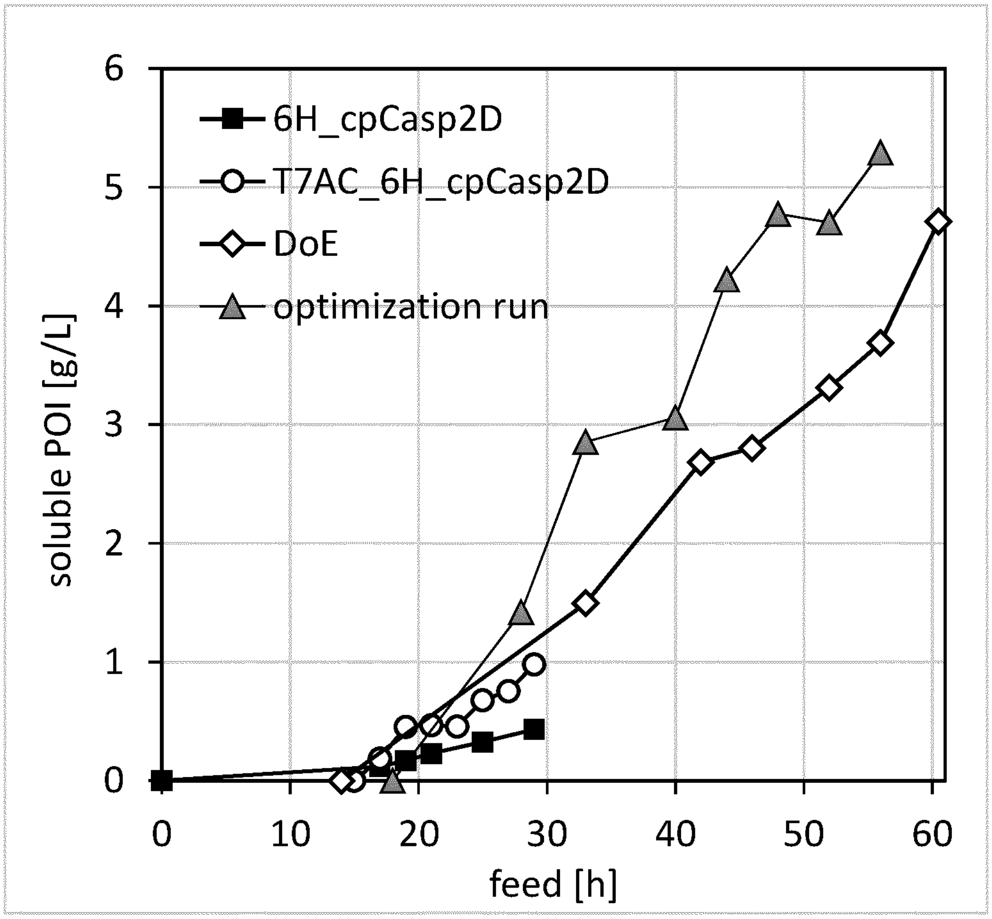
Figure 31:
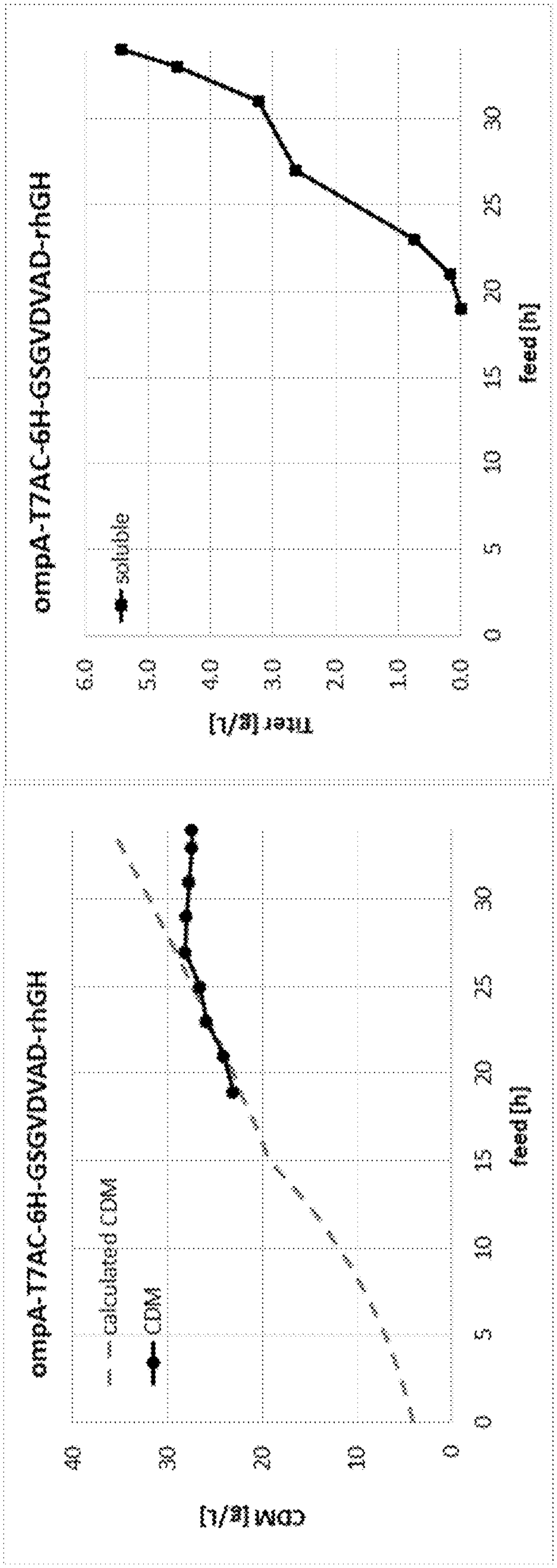
Figure 32:
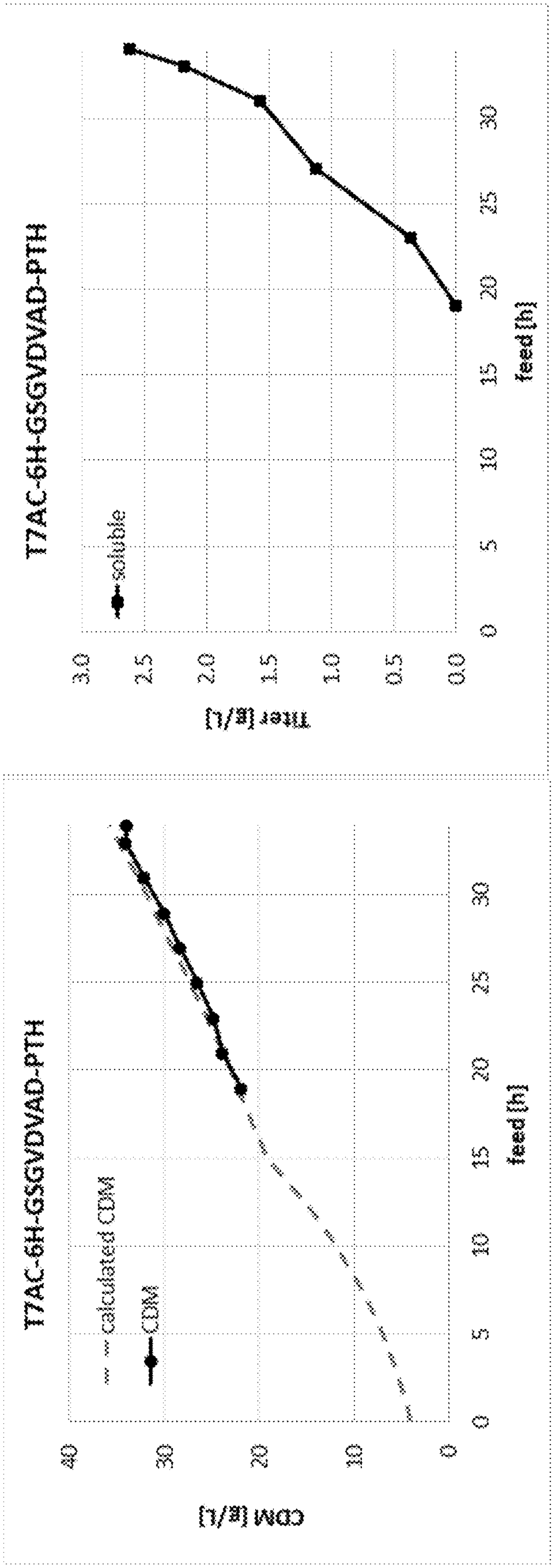
Figure 33:
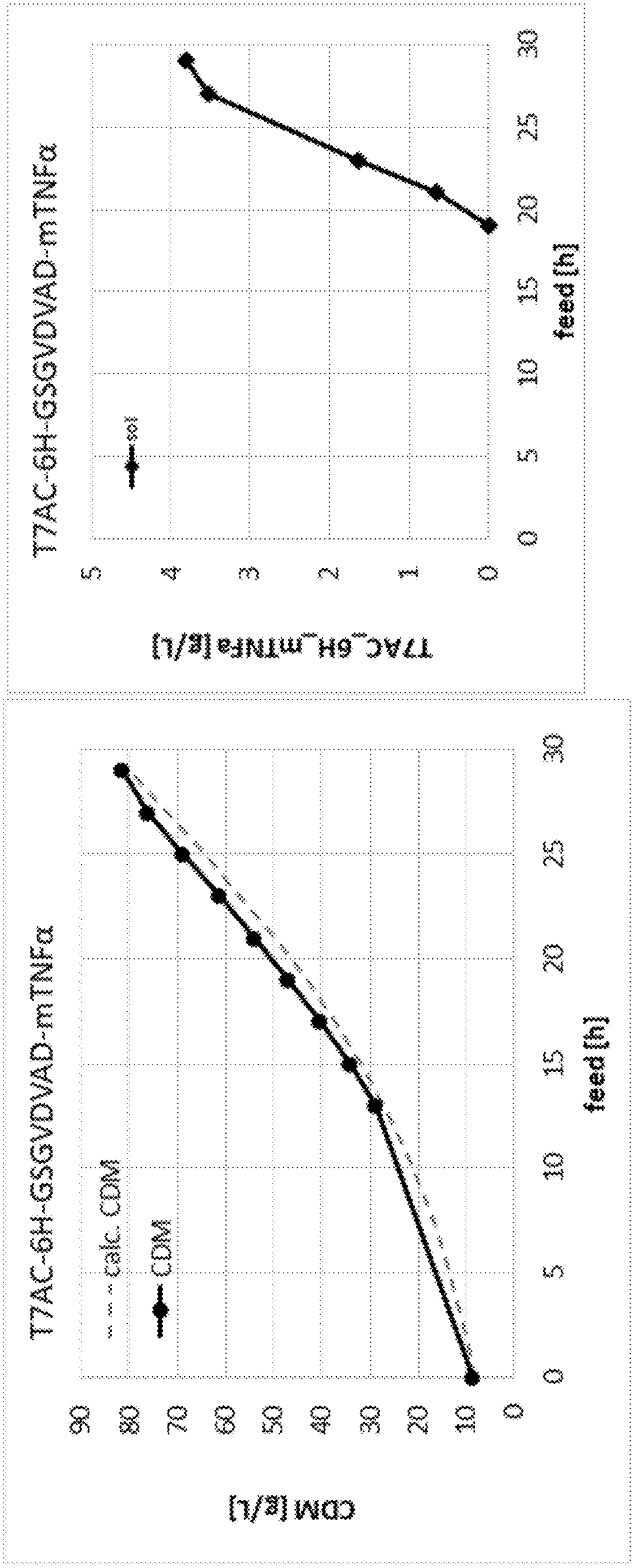
Figure 34:
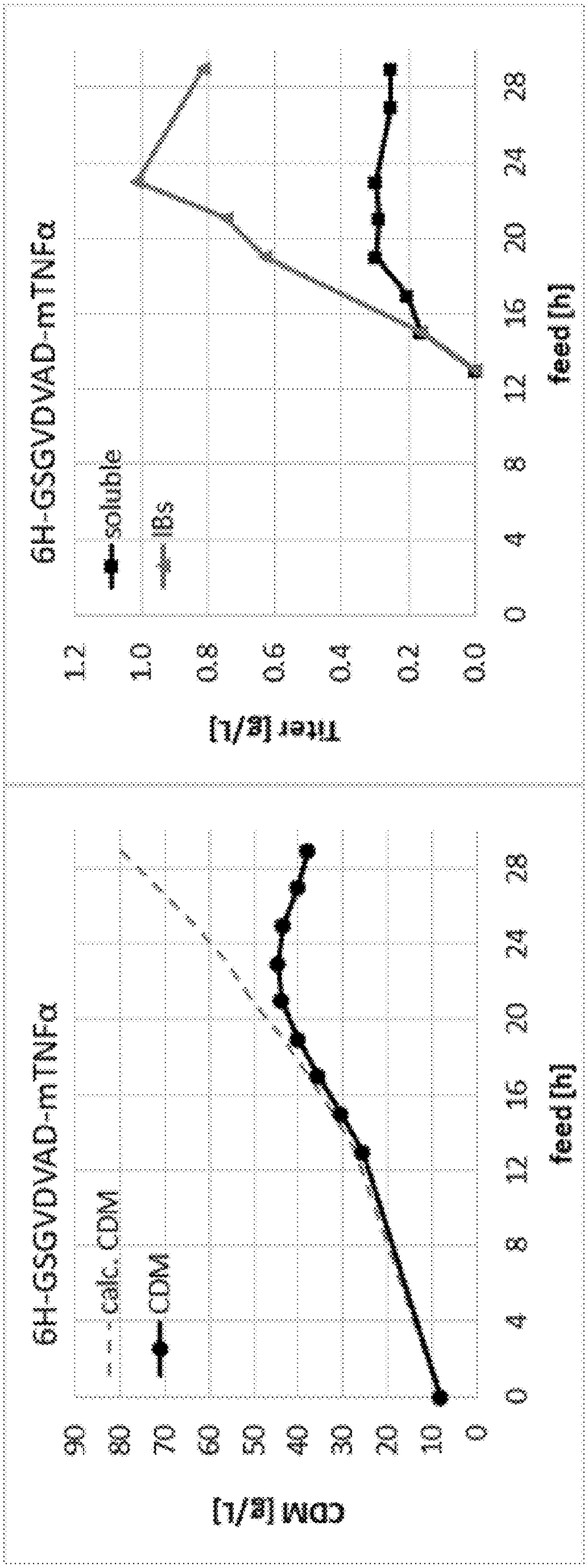

18.1.2.9: Another preferred fermentation process for the production of a cp-caspase2, cp-caspase-2D as described in table 40 and 41 (Experiment Number F34) resulted in surprisingly high titer of soluble cp caspase 2D of 5.28 g/L as can be seen in FIG. 30

18.2 Downstream Processing of Wild-Type Cp Caspases-2 and P1 Tolerable Cp Caspases-2

18.2.1 Downstream Processing without Solubility Tag

The *E. coli* cell mass from fermentations as described under 18.1 or shake flask as described under section 10.3 was harvested by centrifugation at 18,590 rcf for 15 minutes and the supernatant was discarded. The *E. coli* cell harvest was solubilized using homogenization buffer (50 mM sodium phosphate, 500 mM NaCl, 20 mM imidazole, pH 7.0). The cells were resuspended at a concentration of 150 g wet cell mass per L. Cell lysis was performed through high pressure homogenization at 700 bar/70 bar with two passages. The homogenate was centrifuged at 18,590 rcf for 2 hours. The pellet was discarded and the supernatant used. Before chromatography the supernatant was filtered through a 0.22 μm membrane.

The cp caspase-2 carrying a poly-his-tag was captured using immobilized metal affinity chromatography. The following buffers were used: equilibration buffer: 50 mM sodium phosphate, 500 mM NaCl, 20 mM imidazole, pH 7.0. Wash buffer: 50 mM sodium phosphate, 500 mM NaCl, 20 mM imidazole, 30% iso-propanol, pH 7.0. Elution buffer: 50 mM sodium phosphate, 500 mM NaCl, 500 mM imidazole, pH 7.0.

Clarified supernatant was loaded to an equilibrated Ni-Sepharose 6 Fast Flow column to a capacity of ~40 mg/mL. A residence time of 3-5 minutes was used. After loading was completed the column was washed for 5 column volumes (5 CV) with equilibration buffer, 10 CV with wash buffer and 5 CV of equilibration buffer. The bound cp caspase-2 was eluted using a linear gradient from 0-100% elution buffer in 10 CV, with a 10 CV hold step to fully elute all protein.

The elution fractions were analyzed using SDS-PAGE and all fractions containing cp caspase-2 were used for the next purification step.

The capture eluate of cp caspase-2 was buffer exchanged before the polishing chromatography step. Tangential flow ultra-/diafiltration with a 5 kDa cut off membrane was used with a sample buffer of 50 mM sodium citrate, pH 5.0. In total 5 volumes were exchanged.

The capture step used cation exchange chromatography on SOURCE 30S using the following buffers: equilibration bufferA: 50 mM sodium citrate, pH 5.0. Elution buffer B: 50 mM sodium citrate, 1 M NaCl, pH 5.0.

Buffer exchanged capture eluate was loaded on the equilibrated polishing. The residence time was held constant at 5 minutes. The column was loaded to a capacity of ~100 mg/ml. cp caspase-2 was eluted in a linear gradient from 0-100% B in 20 CV. The elution fractions were analyzed using RP-HPLC as described under 9.3.1 and the fractions showing a purity of ~99% were combined and stored at −80° C.

18.2.2 Downstream Processing with Solubility Tag

The *E. coli* cell harvest was solubilized using homogenization buffer (50 mM sodium phosphate, 500 or 300 mM NaCl, pH 7.0 or 8.0, see Table 46). The cells were re suspended at a concentration of 300 g wet cell mass per L. Cell lysis was performed through high pressure homogenization at 1400 bar/140 bar with two passages with an in line counter current chiller set to 10° C. The homogenate was centrifuged at 18,590 rcf for 2 hours at 4° C. The pellet was discarded and the supernatant used. Before chromatography the supernatant was filtered through a 0.22 μm membrane.

TABLE 46

Conditions used for cell lysis of cp caspase 2 variants.

| Enzyme | NaCl concentration, pH |
|---|---|
| T7AC_6H-cpCasp2D (SEQ ID No. 41) | 500 mM NaCl, pH 7.0 |
| T7AC_6H-mS9ProD (SEQ ID No. 72) | 500 mM NaCl, pH 7.0 |
| T7AC_6H-mS9ProE (SEQ ID No. 71) | 500 mM NaCl, pH 7.0 |
| T7AC_6H_cpCasp2D_sar (SEQ ID No. 64) | 300 mM NaCl, pH 8.0 |
| T7AC_6H_cpCasp2D_sar_mut (SEQ ID No. 78) | 300 mM NaCl, pH 8.0 |
| T7AC_6H_cpCasp2D_cal (SEQ ID No. 79) | 300 mM NaCl, pH 8.0 |
| T7AC_6H_cpCasp2D_cal_mut (SEQ ID No. 79) | 300 mM NaCl, pH 8.0 |

The T7AC_6H-tagged cp caspase-2 (SEQ ID NO:41) and cp caspases-2 were captured using immobilized metal affinity chromatography (IMAC). The following buffers were used: equilibration buffer A1: 50 mM sodium phosphate, 500 or 300 mM NaCl, 20 mM imidazole, pH 7.0 or 8.0. Wash bufferA2: 50 mM sodium phosphate, 500 mM NaCl, 20 mM imidazole, pH 7.0, 30% isopropanol. Elution buffer: 50 mM sodium phosphate, 500 or 300 mM NaCl, 500 mM imidazole, pH 7.0 or 8. See Table 27 for details on concentrations.

Imidazole was added to the clarified supernatant before IMAC, to a final concentration of 20 mM imidazole. The clarified supernatant was loaded to an equilibrated Ni-Sepharose 6 Fast Flow column. A residence time of 7 minutes was used during loading and 3 minutes for subsequent steps. After loading was completed the column was washed as shown in Table 47. The bound cp caspase 2 or cp caspase 2 variant was eluted using a step gradient to 100% elution buffer for 10 CV or a linear gradient from 0-100% B over 5 CV with a 5 CV hold step.

TABLE 47

Conditions used for IMAC capture of cp caspase 2 variants.

| Enzyme | Column dimension | NaCl concentration, pH | Wash | Elution |
|---|---|---|---|---|
| T7AC_6H-cpCasp2D (SEQ ID No. 41) | 50 × 18 mm | 500 mM NaCl, pH 7.0 | 5 CV A1, 5 CV A2, 1 CV A1 | Linear 0-50% B 5 CV, 50-100% B in 1 CV |
| T7AC_6H-mS9ProD (SEQ ID No. 72) | 50 × 12 mm | 500 mM NaCl, pH 7.0 | 5 CV A1, 5 CV A2, 1 CV A1 | Linear 0-50% B 5 CV, 50-100% B in 1 CV |
| T7AC_6H-mS9ProE (SEQ ID No. 71) | 50 × 12 mm | 500 mM NaCl, pH 7.0 | 5 CV A1, 5 CV A2, 1 CV A1 | Linear 0-50% B 5 CV, 50-100% B in 1 CV |
| T7AC_6H_cpCasp2D_sar (SEQ ID No. 74) | 26 × 60 mm | 300 mM NaCl, pH 8.0 | 10 CV A1 | Step 100% B 10 CV |
| T7AC_6H_cpCasp2D_sar_mut (SEQ ID No. 78) | 26 × 60 mm | 300 mM NaCl, pH 8.0 | 10 CV A1 | Step 100% B 10 CV |
| T7AC_6H_cpCasp2D_cal (SEQ ID No. 68) | 26 × 60 mm | 300 mM NaCl, pH 8.0 | 10 CV A1 | Step 100% B 10 CV |
| T7AC_6H_cpCasp2D_cal_mut (SEQ ID No. 79) | 26 × 60 mm | 300 mM NaCl, pH 8.0 | 10 CV A1 | Step 100% B 10 CV |

The elution fractions were analyzed using SDS-PAGE and all fractions containing cp caspase 2 or cp caspase 2 variants were used for the next purification step, a cation exchange chromatography (CEX) polishing step. Only for T7AC_6H-cpCasp2_cal (SEQ ID NO:68) and T7AC_6H-cpCasp2_cal_mut (SEQ ID NO:79) the capture eluate was buffer exchanged to phosphate buffered saline (PBS) using UF/DF, omitting the CEX polishing step, due to the low yield in the capture step. UF/DF for cpCasp2_cal and cpCasp2_cal_mut was performed in Amicon centrifugal filter vials with a 10 kDa nominal membrane cut off. In total 5 volumes were exchanged.

The capture eluate of cp caspase 2 or cp caspase 2 variants were buffer exchanged before the polishing chromatography step. Tangential flow ultra-/diafiltration with a 5 kDa cut off PES membrane was used with a sample buffer of 50 mM sodium citrate, pH 5.0. In total 5 volumes were exchanged.

The polishing step was CEX on SP Sepharose HP (10×85 mm, 6.7 mL) using the following buffers: equilibration bufferA: 50 mM sodium citrate, pH 5.0. Elution buffer B: 50 mM sodium citrate, 1 M NaCl, pH 5.0.

Buffer exchanged capture eluate was loaded on the equilibrated polishing column. The residence time was constant at 1.5 minutes. The column was loaded with buffer exchanged capture eluate. T7AC_6H-cpCasp2D (SEQ ID No. 41), T7AC_6H-mS9ProD (SEQ ID NO:72) and T7AC_6H-mS9ProE (SEQ ID No. 71) were eluted in a 5 CV step gradient at 45% B. The elution pools were analyzed using RP-HPLC as described under 9.3.1 and showed a purity of ~99%. T7AC_6H_cpCasp2D_sar (SEQ ID NO:64) and T7AC_6H_cpCasp2D_sar_mut (SEQ ID NO:78) were eluted in a linear gradient from 0-100% B in 10 CV. The elution fractions were analyzed using SDS PAGE and the fractions positive for cpCasp2 were combined and stored at −80° C.

18.3 Characterization of Wild-Type Cp Caspases-2 and P1 Tolerable Cp Caspases-2

18.3.1 Purity Determination (HPLC) for Cp Caspases-2 Purified as Described in Section 18.2.1 and 18.2.2

Experiments were performed on a Tosoh TSKgel Protein C4-300, L×I.D. 5 cm×4.6 mm, 3 μm column with a guard column on a Waters e2695 HPLC. Mobile phase A was water with 0.15% trifluoroacetic acid (TFA) and mobile phase B was acetonitrile with 0.15% TFA. The flowrate was 1 ml/min. Temperature of the column oven was 40° C., temperature of the autosampler 10° C. The following gradient was used as shown in Table 48.

TABLE 48

RP-HPLC method for purity determination.

| Step | Cumulative time [min] | % B |
|---|---|---|
| Injection | 0 | 2 |
| Wash | 1 | 2 |
| Gradient 1 | 2 | 25 |
| Gradient 2 | 8 | 50 |
| Gradient 3 | 15 | 55 |
| Gradient 4 | 16 | 90 |
| Hold | 18 | 90 |
| Re-equilibration | 19 | 2 |

200 μL of purified cp caspase-2 (or variant) sample (~4 g/L) was diluted with 100 μL PBS and 100 μL 2 M Dithiothreitol (DTT). 10 μl of 0.22 μm filtered sample were injected. The outlet was monitored at 214 nm and 280 nm. The HCP peaks eluted between retention times 3.8 and 9 minutes. The cp caspase-2 peaks eluted between 9.2 and 12.4 minutes. The peak areas in the 214 nm signal were used to calculate the purity of the protein of interest.

18.3.2 Quantification of Released Fusion Tag with RP-HPLC

The calibration curve was generated mixing the substrate protein, e.g. human fibroblast growth factor 2 (hFGF-2: T7AC-6H-GSG-VDVAD-hFGF-2) (SEQ ID NO:267), and cp caspase-2 (T7AC-6H-cp-caspase2D)(SEQ ID NO:6) in a ratio 10:1 (in triplicates) and incubated for 4 hours at 25° C. while shaking. The reaction was stopped by adding formic acid to a final concentration of 0.3% or by adding cystamine to a final concentration of 10 mM. Each triplet was diluted with PBS buffer to get six different concentrations (100 μM, 46 μM, 21 μM, 10 μM, 4 μM, 2 μM).

10 μL of 0.22 μm filtered sample were injected to a reversed phase high pressure liquid chromatography (RP-HPLC) using a method outlined below. The outlet was monitored at 214 nm. The fusion tag peaks eluted between retention times 3.9 and 5.6 minutes. The peak areas in the 214 nm signal were used to calculate the quantity of the fusion tag using a linear calibration function.

Experiments were performed on a Tosoh TSKgel Protein C4-300, L×I.D. 5 cm×4.6 mm, 3 μm column with a guard column on a Waters e2695 HPLC. Mobile phase A was water with 0.15% trifluoroacetic acid (TFA) and mobile phase B was acetonitrile with 0.15% TFA. The flowrate was 1 mL/min. Temperature of the column oven was 40° C., temperature of the autosampler 10° C. The following gradient was used (Table 49):

TABLE 49

Conditions of HPLC for detection of released fusion tag

| Step | Cumulative time [min] | % B |
|---|---|---|
| Injection | 0 | 2 |
| Wash | 1 | 2 |
| Gradient 1 | 7 | 28.2 |
| Gradient 2 | 8 | 90 |
| Hold | 10 | 90 |
| Re-equilibration | 11 | 2 |

18.3.3 Determination of Enzymatic Activity of Wild-Type Like Cp-Caspases-2 and P1'Tolerable Cp Caspases-2 (Prepared as Described in Example 18, Section 18.1 and 18.2) with FRET Assay A Förster resonance energy transfer (FRET) assay for the determination of the Michaelis-Menten enzymatic activity parameters was performed in the following way.

The substrates were obtained from Bachem AG and were of the general structure of Abz-VDVAD (SEQ ID NO:45)-XA-Dap(Dnp), where all 20 amino acids were substituted for X (the P1' position). All substrates were dissolved in 10 mM HEPES, pH 7.5 to a concentration of 750 μM.

The buffer for the assay was 50 mM HEPES, 150 mM NaCl, pH 7.2.

The calibration curve was generated by incubating varying amounts of substrate (20 μM, 6.9 μM, 2.4 μM, 0.8 μM, 0.3 μM, 0.1 μM) with 72 μM cpCasp2 in PBS and incubated at room temperature for up to 24 hours. 100% conversion was assumed. Fluorescence was measured in black 96 well plates on a Tecan Infinite M200 Pro plate reader. Excitation wavelength was 320 nm, emission wavelength 420 nm.

Michaelis-Menten kinetics were measured by varying substrate concentrations (200 μM, 100 μM, 50 μM, 20 μM, 10 μM) at constant enzyme concentration ([E]=1 μM).

The initial slope was measured by measuring the fluorescence for 3-15 minutes (or 3 to 20 hours for proline as P1') and calculating the slope of the initial measurement in μM product generated per second. Fluorescence was measured in black 96 well plates on a Tecan Infinite M200 Pro plate reader. Excitation wavelength was 320 nm, emission wavelength 420 nm. In the FRET assay all substrates, except for proline as P1' showed excellent linearity for at least a few minutes.

Evaluation of the data was performed by fitting the data in the TableCurve 2D v5 software to a Michaelis-Menten kinetic:

$$v=V_{max}*[S]/K_M+[S]$$

Where v is the initial slope, Vmax is the maximum rate, KM is the Michaelis constant and [S] is the substrate concentration. The parameters Vmax and KM were fitted. kcat was calculated by dividing Vmax by the enzyme concentration [E].

Figure 16:
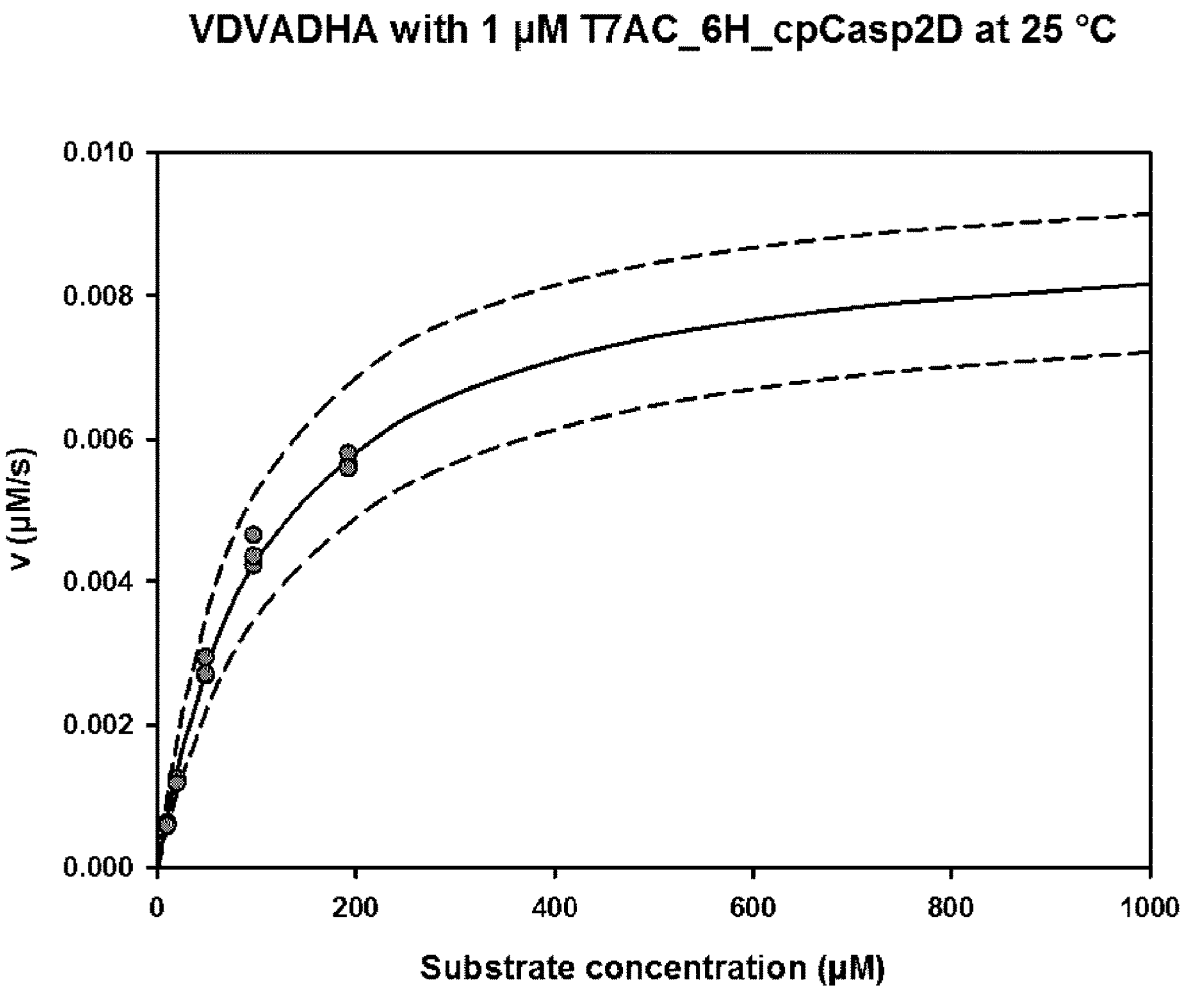
Figure 17:
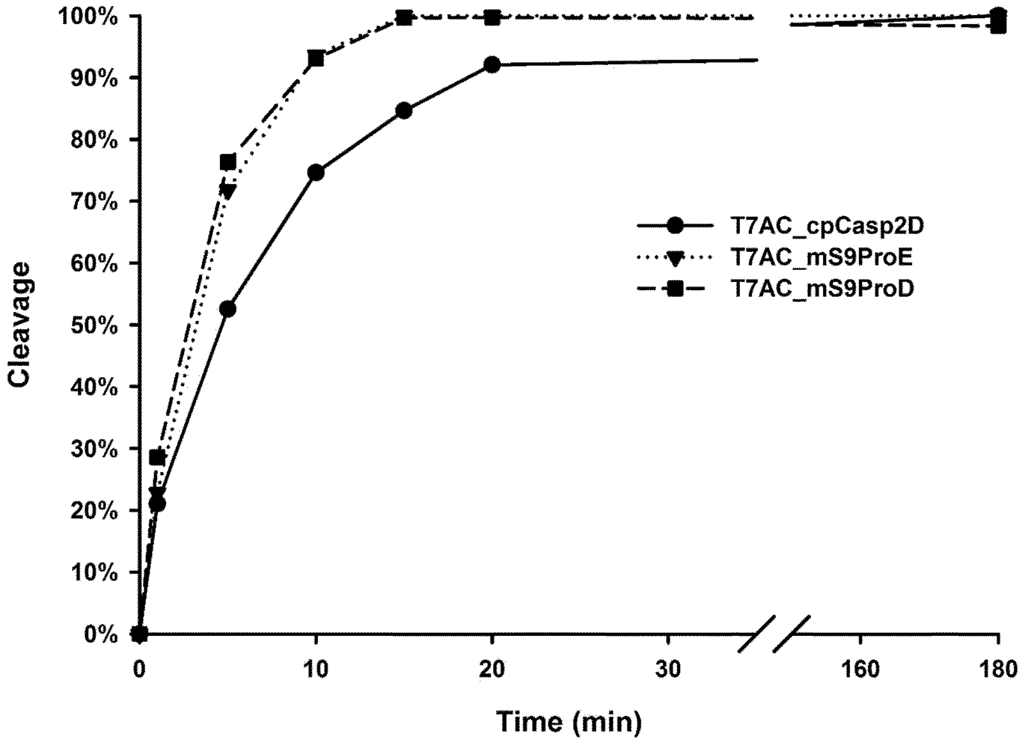
Figure 18:
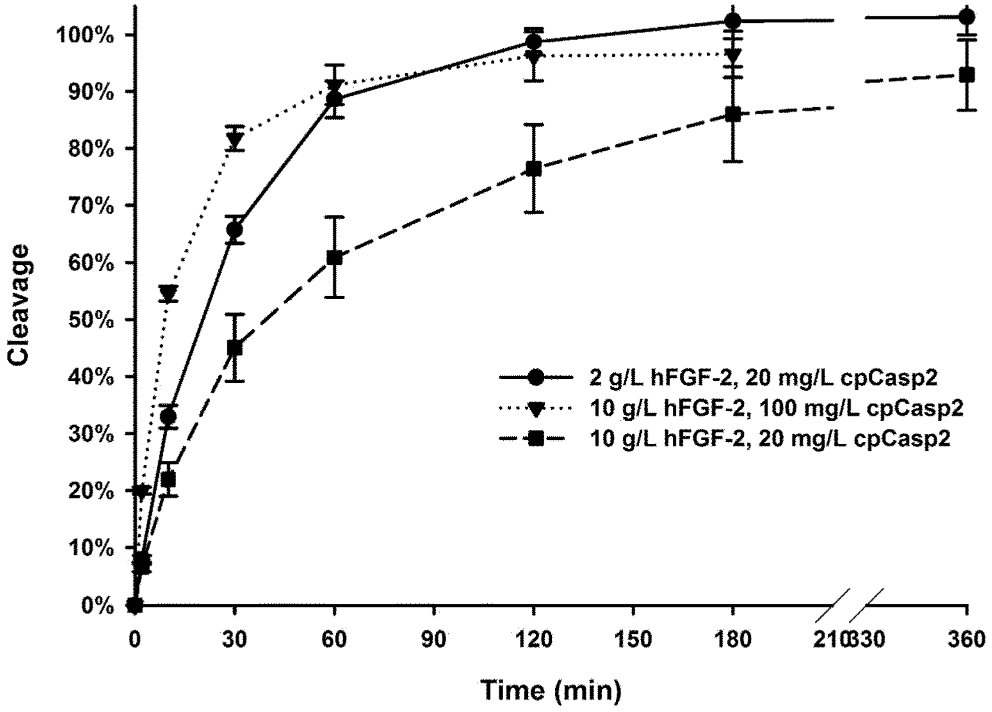
Figure 19:
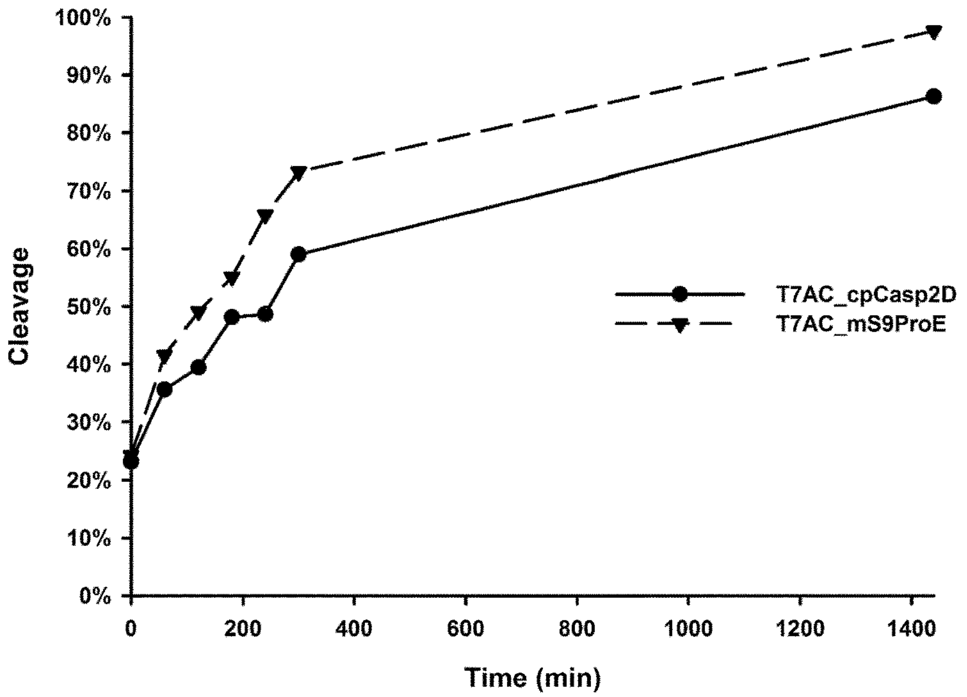
Figure 20:
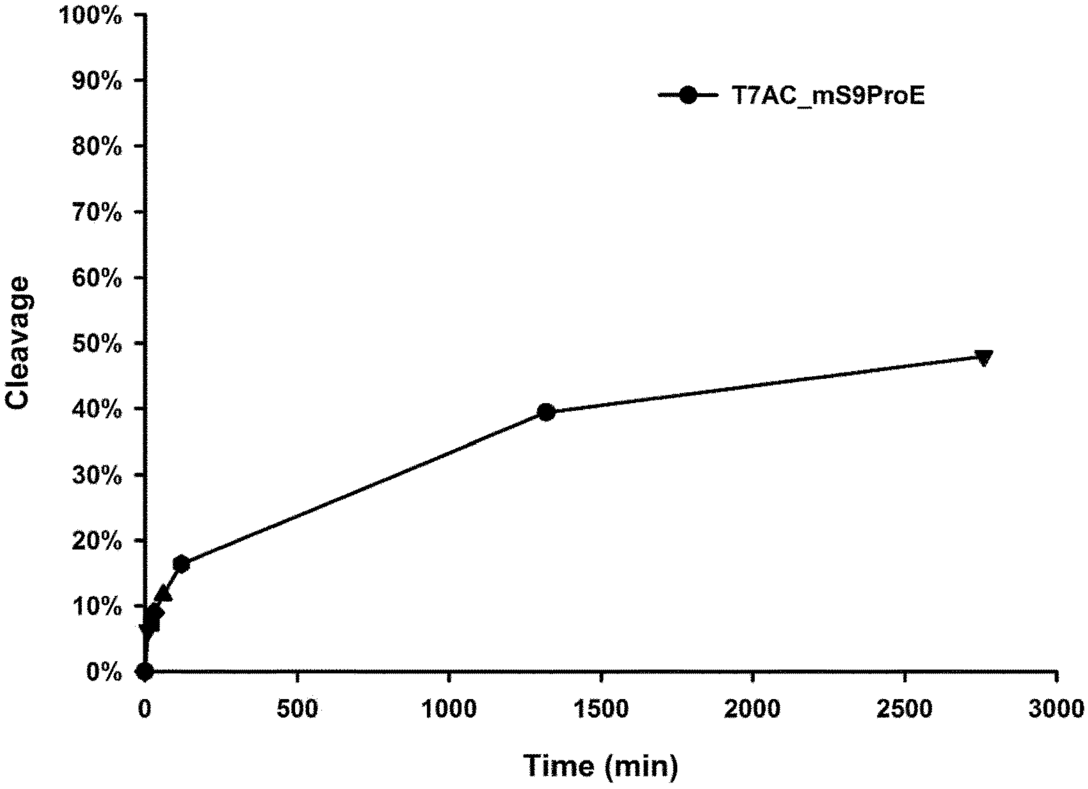

An example kinetic curve can be seen in FIG. 16.

FIG. 16 shows an example Michaelis-Menten kinetic measured by FRET assay. The measured substrate was Abz-VDVADHA (SEQ ID NO:318 Phe to His at position 6)-Dap(Dnp) at concentrations [μM/s] given on the x-axis. The y-axis gives the measured initial slope values (v [μM/s]). Shaded circles represent measured data points, the full line represents the model fit and the dashed lines represent upper and lower 95% confidence intervals of the model fit.

Figure 8:
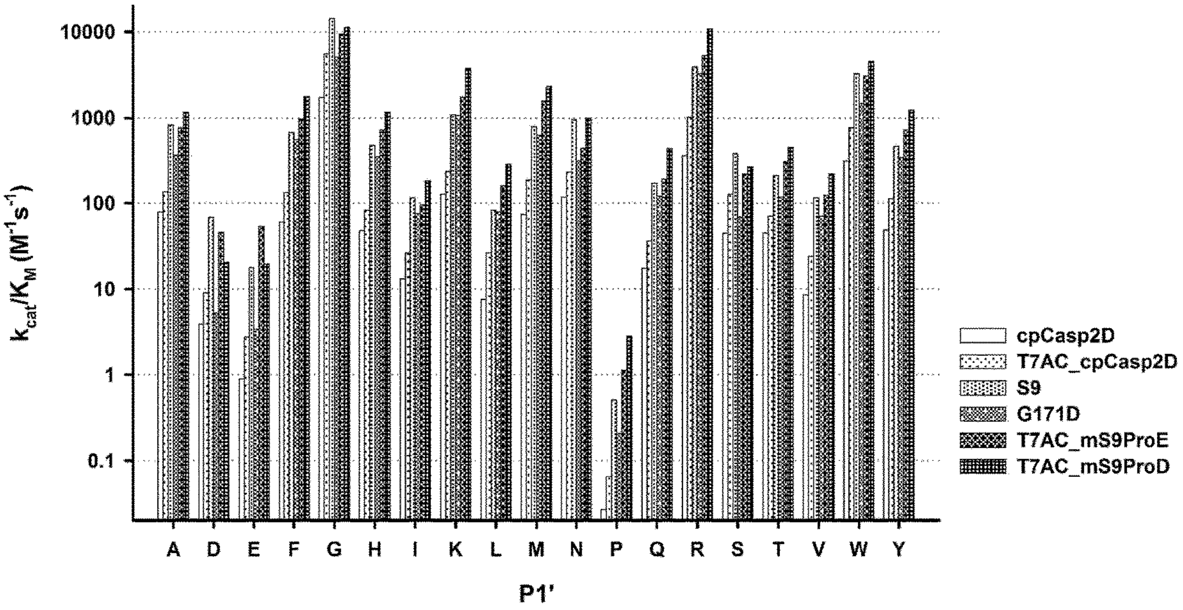
Figure 9:
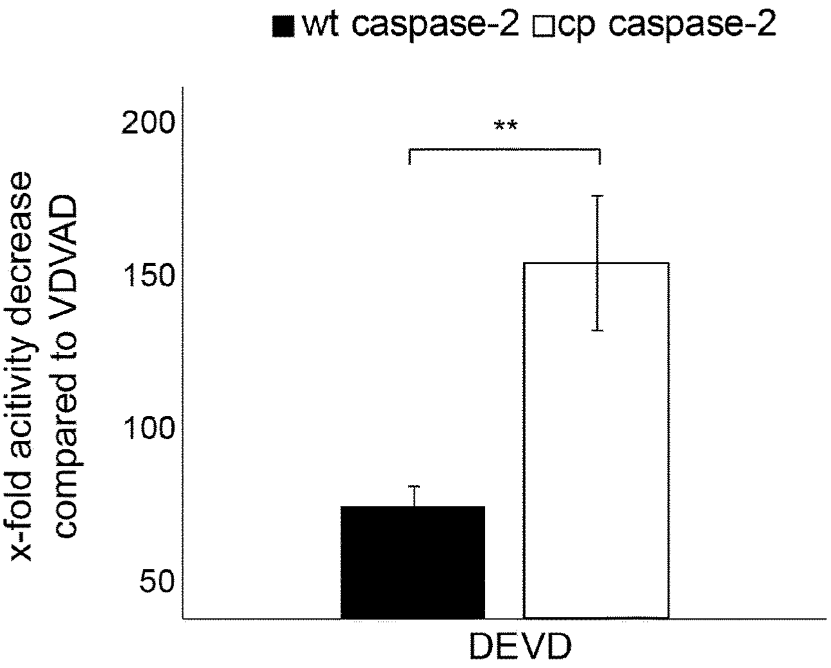

The results of all measurements are shown in Table 50 and 51 and FIG. 8.

TABLE 50

FRET assay results for cp caspases-2 (prepared as described in section 10.3, 18.1 and18.2) with varying P1' positions in the peptide substrates, n.d. = not determined, ci = 95% confidence interval. Cp-caspase-2 variants: 1 = 6H_cpCasp2D (SEQ ID No. 6), 2 = T7AC_6H_cpCasp2D (SEQ ID NO: 41), 3 = 6H_cpCasp2_G171D (SEQ ID NO: 190), 4 = 6H_cpCasp2_S9_E105V (SEQ ID NO: 180), 5 = T7AC_6H_mS9ProE (SEQ ID NO: 70), 6 = T7AC_6H_mS9ProD (SEQ ID NO: 72) (3 = 6H_cpCasp2_G171D (SEQ ID NO: 190) and 4 = 6H_cpCasp2_S9_E105V (SEQ ID NO: 180) were expressed as described in Example 10, section 10.3 and purified as described in 18.2.1).

| Casp. | | A | C | D | E | F | G | H | I | K | L |
|---|---|---|---|---|---|---|---|---|---|---|---|
| 1 | $K_M$ [$M^{-1}$] | 8.9 E−5 | 3.8 E−5 | 1.6 E−4 | 1.7 E−4 | 6.0 E−5 | 1.1 E−4 | 1.2 E−4 | 7.1 E−5 | 1.2 E−4 | 2.9 E−4 |
| | $K_M$ ci [$M^{-1}$] | 1.1 E−5 | 1.0 E−5 | 5.6 E−5 | 7.2 E−5 | 1.6 E−5 | 3.7 E−5 | 2.1 E−5 | 2.5 E−5 | 1.6 E−5 | 9.6 E−5 |
| | $k_{cat}$ [$s^{-1}$] | 7.1 E−3 | 2.1 E−2 | 6.1 E−4 | 1.5 E−4 | 3.6 E−3 | 1.9 E−1 | 5.8 E−3 | 9.3 E−4 | 1.5 E−2 | 2.2 E−3 |
| | $k_{cat}$ ci [$s^{-1}$] | 4.2 E−4 | 2.0 E−3 | 1.2 E−4 | 3.7 E−5 | 4.0 E−4 | 3.1 E−2 | 5.1 E−4 | 1.4 E−4 | 1.1 E−3 | 4.8 E−4 |
| | $k_{cat}/K_M$ [$M^{-1}s^{-1}$] | 8.0 E+1 | 5.6 E+2 | 3.9 E+0 | 8.9 E−1 | 6.1 E+1 | 1.7 E+3 | 4.7 E+1 | 1.3 E+1 | 1.3 E+2 | 7.5 E+0 |
| 2 | $K_M$ [$M^{-1}$] | 1.2 E−4 | n.d. | 1.8 E−4 | 2.0 E−4 | 5.8 E−5 | 4.9 E−5 | 1.1 E−4 | 6.2 E−5 | 1.1 E−4 | 1.6 E−4 |
| | $K_M$ ci [$M^{-1}$] | 1.2 E−5 | n.d. | 4.3 E−5 | 6.1 E−5 | 1.5 E−5 | 1.3 E−5 | 2.2 E−5 | 1.4 E−5 | 2.9 E−5 | 2.6 E−5 |
| | $k_{cat}$ [$s^{-1}$] | 1.6 E−2 | n.d. | 1.7 E−3 | 5.7 E−4 | 7.9 E−3 | 2.7 E−1 | 9.1 E−3 | 1.6 E−3 | 2.6 E−2 | 4.1 E−3 |
| | $k_{cat}$ ci [$s^{-1}$] | 8.6 E−4 | n.d. | 2.3 E−4 | 1.0 E−4 | 8.1 E−4 | 2.7 E−2 | 8.9 E−4 | 1.5 E−4 | 3.4 E−3 | 3.9 E−4 |
| | $k_{cat}/K_M$ [$M^{-1}s^{-1}$] | 1.4 E+2 | n.d. | 9.0 E+0 | 2.8 E+0 | 1.4 E+2 | 5.5 E+3 | 8.2 E+1 | 2.6 E+1 | 2.4 E+2 | 2.6 E+1 |
| 3 | $K_M$ [$M^{-1}$] | 1.2 E−4 | n.d. | 1.5 E−4 | 2.1 E−4 | 8.6 E−5 | 7.5 E−5 | 1.7 E−4 | 7.8 E−5 | 9.4 E−5 | 3.0 E−4 |
| | $K_M$ ci [$M^{-1}$] | 1.7 E−5 | n.d. | 5.9 E−5 | 8.0 E−5 | 1.6 E−5 | 2.7 E−5 | 6.0 E−5 | 1.6 E−5 | 2.3 E−5 | 5.0 E−5 |
| | $k_{cat}$ [$s^{-1}$] | 4.5 E−2 | n.d. | 8.1 E−4 | 7.1 E−4 | 4.8 E−2 | 3.8 E−1 | 6.0 E−2 | 5.9 E−3 | 1.0 E−1 | 2.4 E−2 |
| | $k_{cat}$ ci [$s^{-1}$] | 3.2 E−3 | n.d. | 1.7 E−4 | 1.6 E−4 | 3.9 E−3 | 5.9 E−2 | 1.2 E−2 | 5.4 E−4 | 1.1 E−2 | 2.7 E−3 |
| | $k_{cat}/K_M$ [$M^{-1}s^{-1}$] | 3.7 E+2 | n.d. | 5.3 E+0 | 3.4 E+0 | 5.6 E+2 | 5.1 E+3 | 3.5 E+2 | 7.6 E+1 | 1.1 E+3 | 7.9 E+1 |
| 4 | $K_M$ [$M^{-1}$] | 1.1 E−4 | n.d. | 2.0 E−4 | 1.8 E−4 | 7.7 E−5 | 5.7 E−5 | 1.6 E−4 | 7.0 E−5 | 9.7 E−5 | 3.0 E−4 |
| | $K_M$ ci [$M^{-1}$] | 2.1 E−5 | n.d. | 3.4 E−5 | 2.2 E−5 | 1.5 E−5 | 8.6 E−6 | 2.1 E−5 | 9.1 E−6 | 1.5 E−5 | 6.9 E−5 |
| | $k_{cat}$ [$s^{-1}$] | 9.2 E−2 | n.d. | 1.4 E−2 | 3.2 E−3 | 5.2 E−2 | 8.2 E−1 | 7.7 E−2 | 8.0 E−3 | 1.1 E−1 | 2.5 E−2 |
| | $k_{cat}$ ci [$s^{-1}$] | 8.7 E−3 | n.d. | 1.4 E−3 | 2.3 E−4 | 4.3 E−3 | 4.9 E−2 | 5.7 E−3 | 4.4 E−4 | 7.9 E−3 | 3.9 E−3 |
| | $k_{cat}/K_M$ [$M^{-1}s^{-1}$] | 8.2 E+2 | n.d. | 6.9 E+1 | 1.8 E+1 | 6.8 E+2 | 1.4 E+4 | 4.8 E+2 | 1.1 E+2 | 1.1 E+3 | 8.4 E+1 |
| 5 | $K_M$ [$M^{-1}$] | 1.1 E−4 | n.d. | 1.5 E−4 | 1.1 E−4 | 8.0 E−5 | 4.3 E−5 | 1.6 E−4 | 1.3 E−4 | 9.2 E−5 | 4.1 E−4 |
| | $K_M$ ci [$M^{-1}$] | 1.0 E−5 | n.d. | 3.7 E−5 | 1.7 E−5 | 1.3 E−5 | 1.7 E−5 | 1.5 E−5 | 1.5 E−5 | 1.9 E−5 | 1.4 E−4 |
| | $k_{cat}$ [$s^{-1}$] | 8.1 E−2 | n.d. | 7.0 E−3 | 6.1 E−3 | 7.8 E−2 | 4.1 E−1 | 1.2 E−1 | 1.2 E−2 | 1.6 E−1 | 6.7 E−2 |
| | $k_{cat}$ ci [$s^{-1}$] | 3.9 E−3 | n.d. | 9.0 E−4 | 4.6 E−4 | 5.7 E−3 | 5.8 E−2 | 6.3 E−3 | 7.3 E−4 | 1.5 E−2 | 1.7 E−2 |
| | $k_{cat}/K_M$ [$M^{-1}s^{-1}$] | 7.6 E+2 | n.d. | 4.5 E+1 | 5.4 E+1 | 9.8 E+2 | 9.5 E+3 | 7.2 E+2 | 9.5 E+1 | 1.7 E+3 | 1.6 E+2 |
| 6 | $K_M$ [$M^{-1}$] | 1.0 E−4 | n.d. | 1.9 E−4 | 1.6 E−4 | 1.2 E−4 | 6.5 E−5 | 1.7 E−4 | 1.1 E−4 | 7.9 E−5 | 4.0 E−4 |
| | $K_M$ ci [$M^{-1}$] | 2.3 E−5 | n.d. | 3.6 E−5 | 3.9 E−5 | 3.4 E−5 | 1.4 E−5 | 5.3 E−5 | 2.3 E−5 | 2.7 E−5 | 6.8 E−5 |
| | $k_{cat}$ [$s^{-1}$] | 1.2 E−1 | n.d. | 3.8 E−3 | 3.2 E−3 | 2.2 E−1 | 7.3 E−1 | 2.0 E−1 | 2.0 E−2 | 3.0 E−1 | 1.1 E−1 |
| | $k_{cat}$ ci [$s^{-1}$] | 1.3 E−2 | n.d. | 4.3 E−4 | 4.3 E−4 | 3.2 E−2 | 6.3 E−2 | 3.5 E−2 | 2.1 E−3 | 4.5 E−2 | 1.4 E−2 |
| | $k_{cat}/K_M$ [$M^{-1}s^{-1}$] | 1.2 E+3 | n.d. | 2.0 E+1 | 1.9 E+1 | 1.8 E+3 | 1.1 E+4 | 1.2 E+3 | 1.9 E+2 | 3.8 E+3 | 2.9 E+2 |

TABLE 51

FRET assay results for cp caspases-2 (prepared as described in section 10.3, 18.1 and18.2) with varying P1' positions in the peptide substrates, n.d. = not determined, ci = 95% confidence interval. Cp-caspase-2 variants: 1 = 6H_cpCasp2D, 2 = T7AC_6H_cpCasp2D (SEQ ID NO: 41), 3 = 6H_cpCasp2_G171D (SEQ ID NO: 190), 4 = 6H_cpCasp2_S9_E105V (SEQ ID NO: 180), 5 = T7AC_6H_mS9ProE (SEQ ID NO: 71), 6 = T7AC_6H_mS9ProD (SEQ ID NO: 72) (3 = 6H_cpCasp2_G171D (SEQ ID NO: 190) and 4 = 6H_cpCasp2_S9_E105V (SEQ ID NO: 180) were expressed as described in Example 10, section 10.3 and purified as described in 18.2.1).

| Casp. | | M | N | P | Q | R | S | T | V | W | Y |
|---|---|---|---|---|---|---|---|---|---|---|---|
| 1 | $K_M$ [$M^{-1}$] | 3.8 E−4 | 7.8 E−5 | 3.0 E−4 | 1.2 E−4 | 5.8 E−5 | 2.0 E−4 | 7.5 E−5 | 6.4 E−5 | 4.6 E−5 | 3.4 E−4 |
| | $K_M$ ci [$M^{-1}$] | 1.2 E−4 | 1.6 E−5 | 1.5 E−4 | 2.4 E−5 | 1.0 E−5 | 3.5 E−5 | 2.0 E−5 | 2.3 E−5 | 2.0 E−5 | 5.3 E−5 |
| | $k_{cat}$ [$s^{-1}$] | 2.8 E−2 | 9.2 E−3 | 8.1 E−6 | 2.1 E−3 | 2.1 E−2 | 8.9 E−3 | 3.4 E−3 | 5.4 E−4 | 1.4 E−2 | 1.7 E−2 |
| | $k_{cat}$ ci [$s^{-1}$] | 6.1 E−3 | 8.5 E−4 | 2.6 E−6 | 2.1 E−4 | 1.4 E−3 | 9.5 E−4 | 4.0 E−4 | 8.1 E−5 | 2.3 E−3 | 1.8 E−3 |
| | $k_{cat}/K_M$ [$M^{-1}s^{-1}$] | 7.4 E+1 | 1.2 E+2 | 2.6 E−2 | 1.7 E+1 | 3.6 E+2 | 4.5 E+1 | 4.5 E+1 | 8.5 E+0 | 3.2 E+2 | 4.8 E+1 |
| 2 | $K_M$ [$M^{-1}$] | 3.4 E−4 | 8.7 E−5 | 1.5 E−4 | 1.3 E−4 | 5.6 E−5 | 1.3 E−4 | 8.9 E−5 | 7.3 E−5 | 3.6 E−5 | 3.0 E−4 |
| | $K_M$ ci [$M^{-1}$] | 7.7 E−5 | 1.9 E−5 | 6.6 E−5 | 2.4 E−5 | 1.2 E−5 | 1.9 E−5 | 2.8 E−5 | 1.8 E−5 | 1.4 E−5 | 4.4 E−5 |
| | $k_{cat}$ [$s^{-1}$] | 6.5 E−2 | 2.0 E−2 | 9.9 E−6 | 4.6 E−3 | 5.7 E−2 | 1.7 E−2 | 6.3 E−3 | 1.7 E−3 | 2.8 E−2 | 3.3 E−2 |
| | $k_{cat}$ ci [$s^{-1}$] | 1.0 E−2 | 2.0 E−3 | 2.4 E−6 | 4.6 E−4 | 4.8 E−3 | 1.3 E−3 | 9.0 E−4 | 1.9 E−4 | 3.6 E−3 | 3.4 E−3 |
| | $k_{cat}/K_M$ [$M^{-1}s^{-1}$] | 1.9 E+2 | 2.3 E+2 | 6.5 E−2 | 3.6 E+1 | 1.0 E+3 | 1.3 E+2 | 7.1 E+1 | 2.4 E+1 | 7.6 E+2 | 1.1 E+2 |
| 3 | $K_M$ [$M^{-1}$] | 6.1 E−4 | 1.1 E−4 | 3.9 E−4 | 1.6 E−4 | 6.5 E−5 | 2.2 E−4 | 1.4 E−4 | 9.6 E−5 | 5.6 E−5 | 3.5 E−4 |
| | $K_M$ ci [$M^{-1}$] | 1.5 E−4 | 1.5 E−5 | 2.7 E−4 | 3.3 E−5 | 1.8 E−5 | 6.0 E−5 | 3.4 E−5 | 2.6 E−5 | 1.5 E−5 | 1.2 E−4 |
| | $k_{cat}$ [$s^{-1}$] | 3.8 E−1 | 3.4 E−2 | 8.0 E−5 | 2.0 E−2 | 2.1 E−1 | 1.5 E−2 | 1.7 E−2 | 6.8 E−3 | 8.2 E−2 | 1.2 E−1 |
| | $k_{cat}$ ci [$s^{-1}$] | 7.5 E−2 | 2.3 E−3 | 4.0 E−5 | 2.2 E−3 | 2.4 E−2 | 2.6 E−3 | 2.2 E−3 | 8.8 E−4 | 8.3 E−3 | 2.9 E−2 |
| | $k_{cat}/K_M$ [$M^{-1}s^{-1}$] | 6.2 E+2 | 3.2 E+2 | 2.1 E−1 | 1.2 E+2 | 3.3 E+3 | 7.0 E+1 | 1.2 E+2 | 7.1 E+1 | 1.5 E+3 | 3.5 E+2 |
| 4 | $K_M$ [$M^{-1}$] | 8.3 E−4 | 1.0 E−4 | 2.5 E−4 | 1.3 E−4 | 4.8 E−5 | 2.0 E−4 | 1.5 E−4 | 8.1 E−5 | 5.1 E−5 | 3.4 E−4 |
| | $K_M$ ci [$M^{-1}$] | 2.8 E−4 | 1.9 E−5 | 1.2 E−4 | 2.3 E−5 | 1.1 E−5 | 4.2 E−5 | 2.7 E−5 | 1.4 E−5 | 1.6 E−5 | 6.0 E−5 |
| | $k_{cat}$ [$s^{-1}$] | 6.5 E−1 | 1.0 E−1 | 1.3 E−4 | 2.3 E−2 | 1.9 E−1 | 7.8 E−2 | 3.1 E−2 | 9.2 E−3 | 1.7 E−1 | 1.6 E−1 |
| | $k_{cat}$ ci [$s^{-1}$] | 1.9 E−1 | 8.7 E−3 | 3.9 E−5 | 2.1 E−3 | 1.6 E−2 | 9.8 E−3 | 3.2 E−3 | 7.0 E−4 | 2.0 E−2 | 2.0 E−2 |
| | $k_{cat}/K_M$ [$M^{-1}s^{-1}$] | 7.8 E+2 | 9.6 E+2 | 5.1 E−1 | 1.7 E+2 | 3.9 E+3 | 3.8 E+2 | 2.2 E+2 | 1.1 E+2 | 3.3 E+3 | 4.6 E+2 |
| 5 | $K_M$ [$M^{-1}$] | 3.7 E−4 | 1.2 E−4 | 1.2 E−4 | 1.2 E−4 | 6.8 E−5 | 1.2 E−4 | 1.0 E−4 | 9.0 E−5 | 5.6 E−5 | 4.2 E−4 |
| | $K_M$ ci [$M^{-1}$] | 1.2 E−4 | 3.8 E−5 | 3.3 E−5 | 1.8 E−5 | 1.6 E−5 | 2.8 E−5 | 1.6 E−5 | 1.5 E−5 | 2.4 E−5 | 3.1 E−4 |
| | $k_{cat}$ [$s^{-1}$] | 5.8 E−1 | 5.5 E−2 | 1.3 E−4 | 4.7 E−2 | 3.6 E−1 | 2.7 E−2 | 3.1 E−2 | 1.1 E−2 | 1.7 E−1 | 3.0 E−1 |
| | $k_{cat}$ ci [$s^{-1}$] | 1.4 E−1 | 8.6 E−3 | 1.9 E−5 | 3.6 E−3 | 3.5 E−2 | 3.2 E−3 | 2.4 E−3 | 8.6 E−4 | 2.8 E−2 | 1.6 E−1 |
| | $k_{cat}/K_M$ [$M^{-1}s^{-1}$] | 1.6 E+3 | 4.4 E+2 | 1.1 E+0 | 3.9 E+2 | 5.3 E+3 | 2.2 E+2 | 3.1 E+2 | 1.2 E+2 | 3.1 E+3 | 7.2 E+2 |
| 6 | $K_M$ [$M^{-1}$] | 4.8 E−4 | 1.3 E−4 | 1.0 E−4 | 1.2 E−4 | 4.7 E−5 | 1.8 E−4 | 1.2 E−4 | 1.0 E−4 | 5.3 E−5 | 9.0 E−4 |
| | $K_M$ ci [$M^{-1}$] | 1.4 E−4 | 4.4 E−5 | 1.8 E−5 | 2.2 E−5 | 1.8 E−5 | 2.4 E−5 | 3.9 E−5 | 2.2 E−5 | 2.3 E−5 | 4.6 E−4 |
| | $k_{cat}$ [$s^{-1}$] | 1.1 E+0 | 1.3 E−1 | 2.9 E−4 | 5.4 E−2 | 5.1 E−1 | 4.8 E−2 | 5.3 E−2 | 2.3 E−2 | 2.4 E−1 | 1.1 E+0 |
| | $k_{cat}$ ci [$s^{-1}$] | 2.4 E−1 | 2.2 E−2 | 2.4 E−5 | 5.0 E−3 | 7.2 E−2 | 3.8 E−3 | 9.1 E−3 | 2.3 E−3 | 3.9 E−2 | 4.9 E−1 |
| | $k_{cat}/K_M$ [$M^{-1}s^{-1}$] | 2.3 E+3 | 9.8 E+2 | 2.8 E+0 | 4.4 E+2 | 1.1 E+4 | 2.7 E+2 | 4.5 E+2 | 2.2 E+2 | 4.6 E+3 | 1.2 E+3 |

Example 19: Enzymatic Activity of Wild-Type Cp Caspases-2 and P1'Tolerable Cp Caspases-2 with Fusion Proteins (Substrates)

Fusion proteins comprising a tag and the protein of interest (PoI) and hFGF-2 without a tag were cloned as described in Example 11, section 11.1. In table 52 all fusion proteins for cleavage reactions in Examples 11 to 13 are described.

19.1 Fusion Proteins

TABLE 52

19.1 Fusion proteins
fusion proteins for cleavages as described in Examples 20 to 23.

| Fusion Protein (as expressed) | Description of fusion protein | SEQ ID No. XX | N-terminus of the PoI |
|---|---|---|---|
| ompA-T7AC-6H-GSG-VDVAD-rhGH | Recombinant human growth hormone | 257 | Phe (F) |
| T7AC-6H-GSG-VDVAD-PTH | Parathyroid hormone | 259 | Ser (S) |
| T7AC-6H-GSG-VDVAD-GCSF | Granulocyte colony stimulating factor | 261 | Ala (A) |
| T7AC-6H-GSG-VDVAD-TNF-alpha (TNFα, TNFa) | Tumor necrosos factor alpha | 263 | Val (V) |
| hFGF-2 | Human fibroblast growth factor-2 | 265 | Ala (A) |
| 6H-hFGF-2 | Human fibroblast growth factor-2 | 266 | Ala (A) |
| 6H-GSG-VDVAD-hFGF-2 | Human fibroblast growth factor-2 | 32 | Ala (A) |
| T7AC-6H-GSG-VDVAD-hFGF-2 | Human fibroblast growth factor-2 | 267 | Ala (A) |
| T7AC_6H_GSG_VDSAD-hFGF2 | Human fibroblast growth factor-2 | 268 | Ala (A) |
| T7A3-6H-GSG-VDVAD-hFGF-2 | Human fibroblast growth factor-2 | 269 | Ala (A) |
| T7AC-6H-VDVAD-hFGF2 | Human fibroblast growth factor-2 | 270 | Ala (A) |
| T7AC_6H_GSGSGSG_VDVAD-hFGF2 | Human fibroblast growth factor-2 | 271 | Ala (A) |
| ompA-6H-GSG-VDVAD-TNF-alpha(TNFα, TNFa) | Tumor necrosos factor alpha | 273 | Val (V) |
| 6H-GSG-VDVAD-BIWA4** | anti CD44 scFv (LC-HC | 275 | Glu (E) |
| 6H(SEQ ID NO: 315)-GSG-VDVAD (SEQ ID NO: 45)-GFPmut3.1 (GFP) | GFPmut3.1 * | * | Met (M) |

* B.P. Cormack, R.H. Valdivia, S. Falkow, FACS-optimized mutants of the green fluorescent protein (GFP), Gene, 173 (1996) 33-38.
**BIWA4 was also expressed with a T7AC-6H (SEQ ID NO: 315)-GSG-VDVAD (SEQ ID NO: 45) tag resulting in the construct: T7AC-6H (SEQ ID NO: 315)-GSG-VDVAD (SEQ ID NO: 45)-BIWA4

19.2 Fermentation of Fusion Proteins

The *E. coli* strain BL21(DE3) [$F^-$, fhuA2, Ion, ompT, gal, dcm, ΔhsdS λ DE3 [A sBamHlo, ΔEcoRI-B int::(lacI::PlacUV5::T7 gene1) i21 Δnin5], purchased from Novagen, was transformed with a pET30a vector carrying the gene for the respective fusion proteins resp fusion protein construct of table 52, under the T7 promoter/operator system. The expression clones cultivated in lab-scale bioreactors are listed in Table 52. Fermentation of fusion proteins (substrates) was performed analogous to fermentation of cp caspases-2 as described in section 18.1.2 if not stated otherwise. Fermentation media was prepared using the same components and methods listed in section 18.1.2.1 but was calculated according to the CDM and volumes given in Table 53. Fermentations were carried out as described in section 18.1.2.2. In case of TNFα (TNFalpha), the fermentations were carried out in a 15 L computer-controlled bioreactor (MBR, Zurich, Switzerland) using the same standard control units as specified in section 18.1.2.2. For rhGH, PTH and GCSF fermentations the computer-controlled fermentation system DASGIP® Bioblock with a working volume of 2 L (Eppendorf, Hamburg, Germany) was employed. This system was controlled using the DASware® control software and the standard control boxes DASGIP® TC4SC4, DASGIP® PH4PO4L and DASGIP® MX4/4 from Eppendorf. Precultures for fusion protein substrates were carried out according to the methods described in section 18.1.2.2 using semisynthetic medium (SSM), which has the same composition as the batch medium and was prepared for a CDM of 3 g/L. In case of rhGH, PTH and GCSF, inoculation was performed using 25 OD units (at a wavelength of 600 nm) of preculture. Additionally, for the cultivations in the DASGIP® Bioblock, the pH was maintained with 12.5% ammonia solution (w/w). All other fermentation parameters and procedures if not stated otherwise in this chapter or in table 53 were carried out as described in section 18.1.2.2. Fermentation monitoring was performed as described in section 18.1.2.4 with the exception of determination of CDM of rhGH, PTH and GCSF fermentations, which was performed using the same methods as described but with 1 mL of cell suspension.

Determination of specific and volumetric fusion protein titer was performed as described in section 18.1.2.5:

TABLE 53

| Fermentation parameters for production of the fusion proteins | | | | | | | | |
|---|---|---|---|---|---|---|---|---|
| Model substrate fusion proteins | SEQ ID No | Batch CDM [g/L] | Batch V [L] | Fed-batch CDM [g/L] | total V [L] | μ growth | μ production | Induction IPTG |
| ompA-T7AC-6H-GSG-VDVAD-rhGH | 257 | 4.0 | 0.5 | 35.8 | 0.9 | $0.12\ h^{-1}$ 2.6 gen. $0.05\ h^{-1}$ 0.29 gen. | $0.05\ h^{-1}$ 1.08 gen. | 2 μmol/g CDM pulsed |
| T7AC-6H-GSG-VDVAD-PTH | 259 | 4.0 | 0.5 | 35.8 | 0.9 | $0.12\ h^{-1}$ 2.6 gen. $0.05\ h^{-1}$ 0.29 gen. | $0.05\ h^{-1}$ 1.08 gen. | 2 μmol/g CDM pulsed |
| T7AC-6H-GSG-VDVAD-GCSF | 261 | 4.0 | 0.5 | 35.8 | 0.9 | $0.12\ h^{-1}$ 2.6 gen. $0.05\ h^{-1}$ 0.29 gen. | $0.05\ h^{-1}$ 1.08 gen. | 2 μmol/g CDM pulsed |
| T7AC-6H-GSG-VDVAD-TNFa | 263 | 8.0 | 5.0 | 80.1 | 9.1 | | $0.1\ h^{-1}$ 4.18 gen. | 0.5 μmol/g CDM constant |
| hFGF2-all variants | | 8.0 | 10.0 | 78.9 | 18.4 | $0.1\ h^{-1}$ 2.02 gen. | $0.1\ h^{-1}$ 2.16 gen. | 0.9 μmol/g CDM constant |
| 6H-GSG-VDVAD-TNFalpha | 315, 45 | 8.0 | 5.0 | 79.9 | 9.1 | | $0.1\ h^{-1}$ 4.18 gen. | 0.5 μmol/g CDM over feed |
| 6H-GSG-VDVAD-BIWA4 | 275 | 6.3 | 9.0 | 43.8 | 15.6 | $0.1\ h^{-1}$ 2.74 gen. | $0.1\ h^{-1}$ 0.87 gen. | 1 mM over feed |
| 6H-GSG-VDVAD-GFP | 315, 45 | 8.0 | 8.0 | 64.4 | 13.4 | $0.1\ h^{-1}$ 2.74 gen. | $0.1\ h^{-1}$ 1.01 gen. | 20 μmol/g CDM constant |

Figure 35:
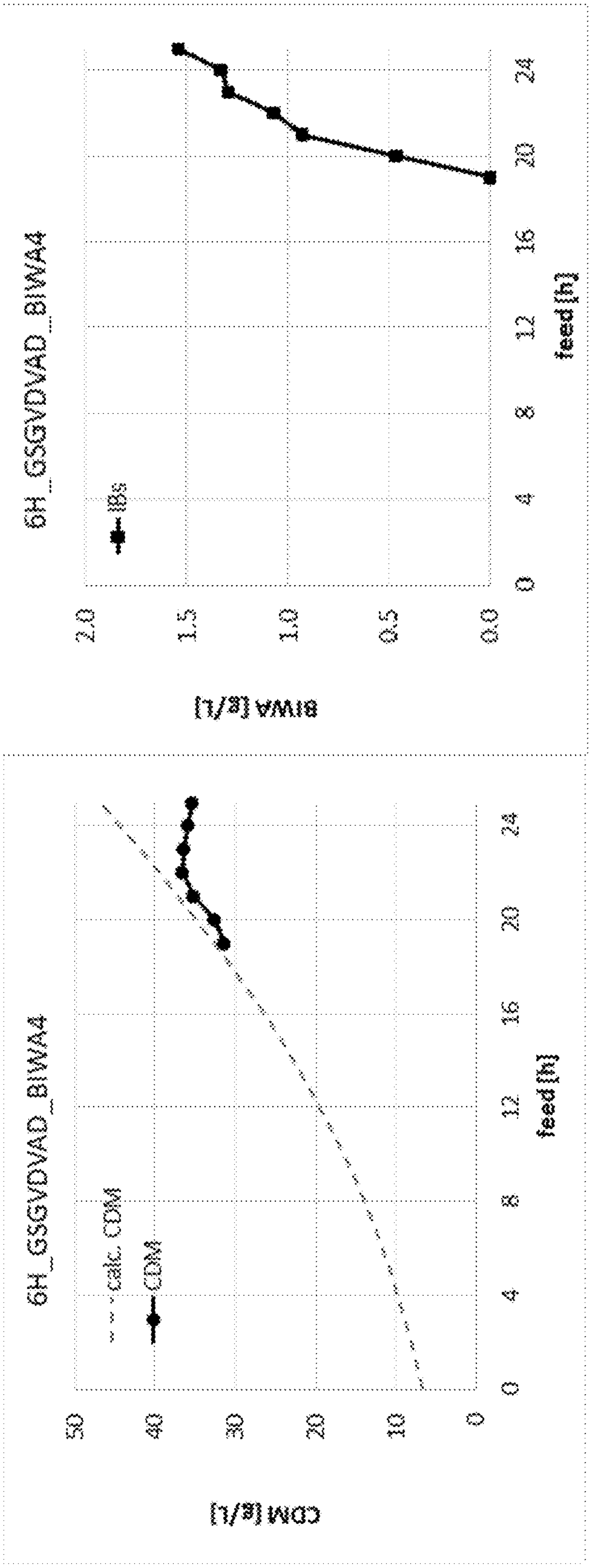
Figure 36:
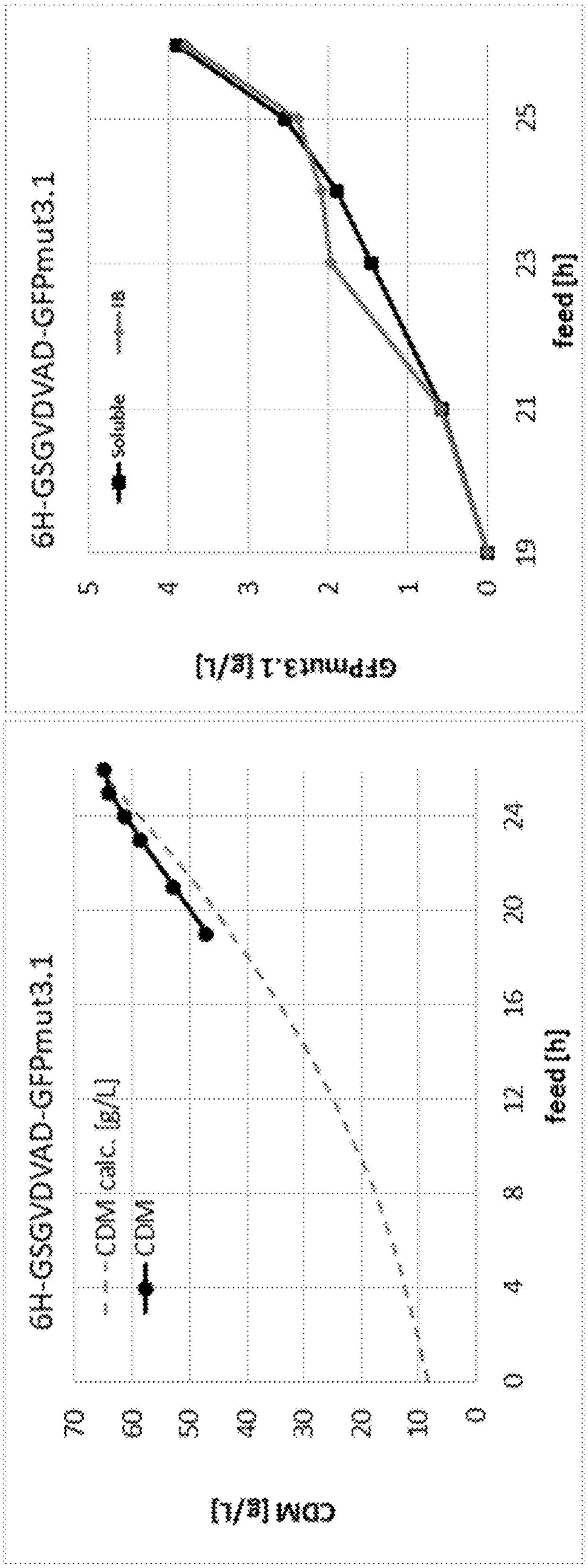
Figure 37:
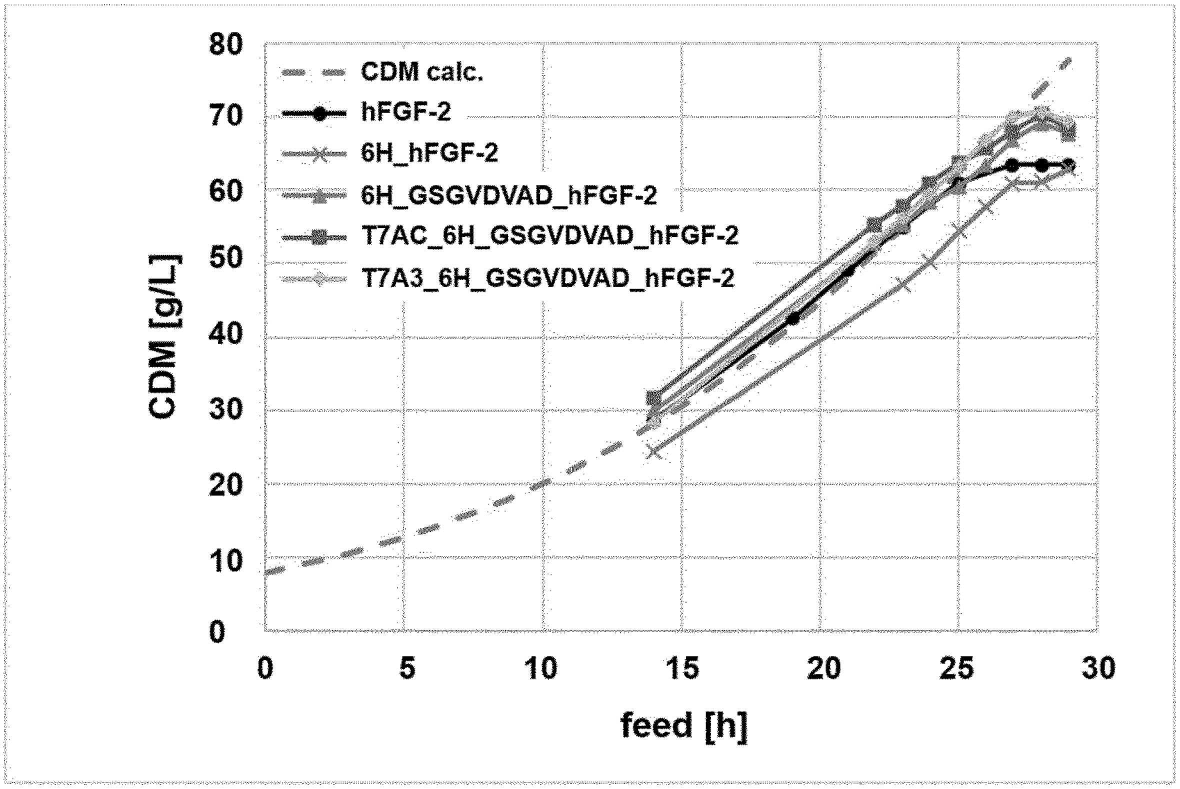
Figure 38:
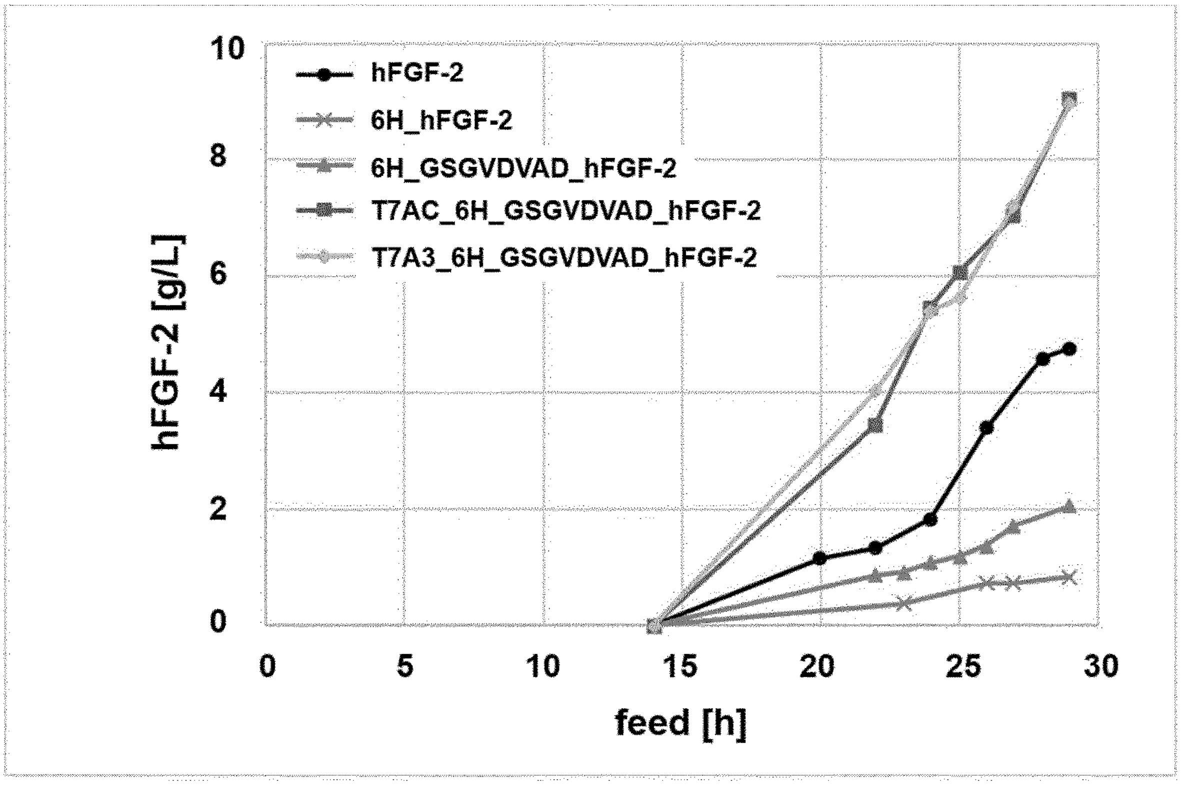
Figure 39:
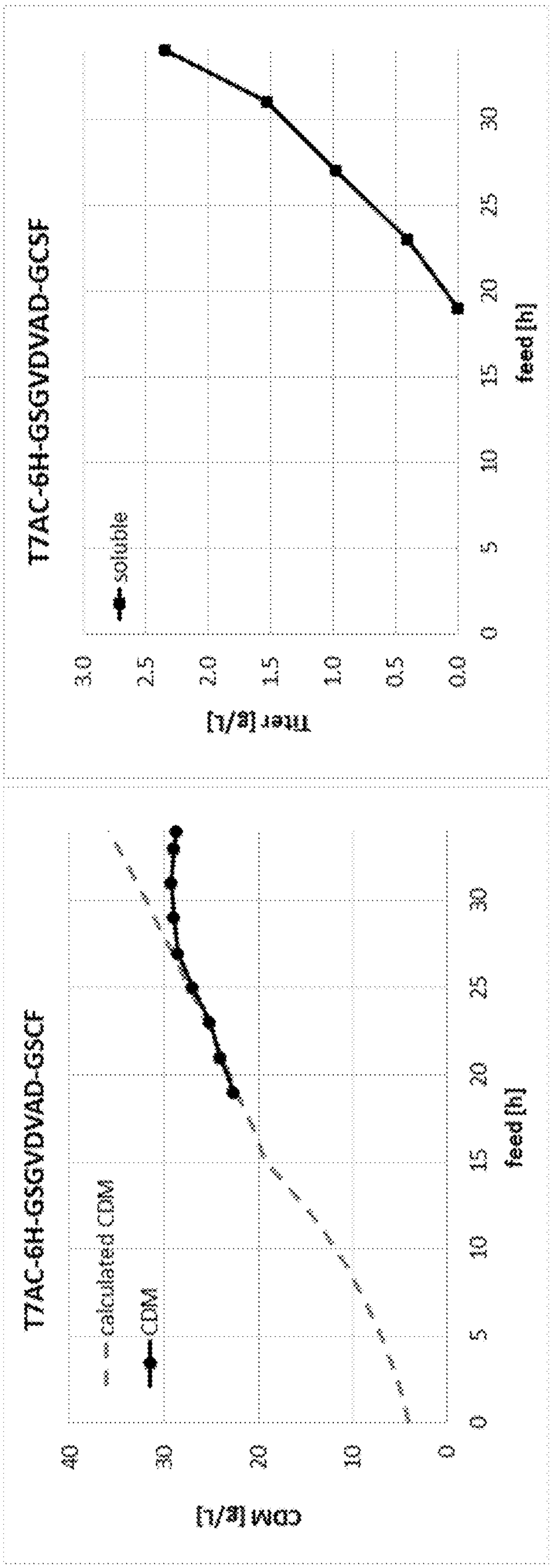
Figure 40:
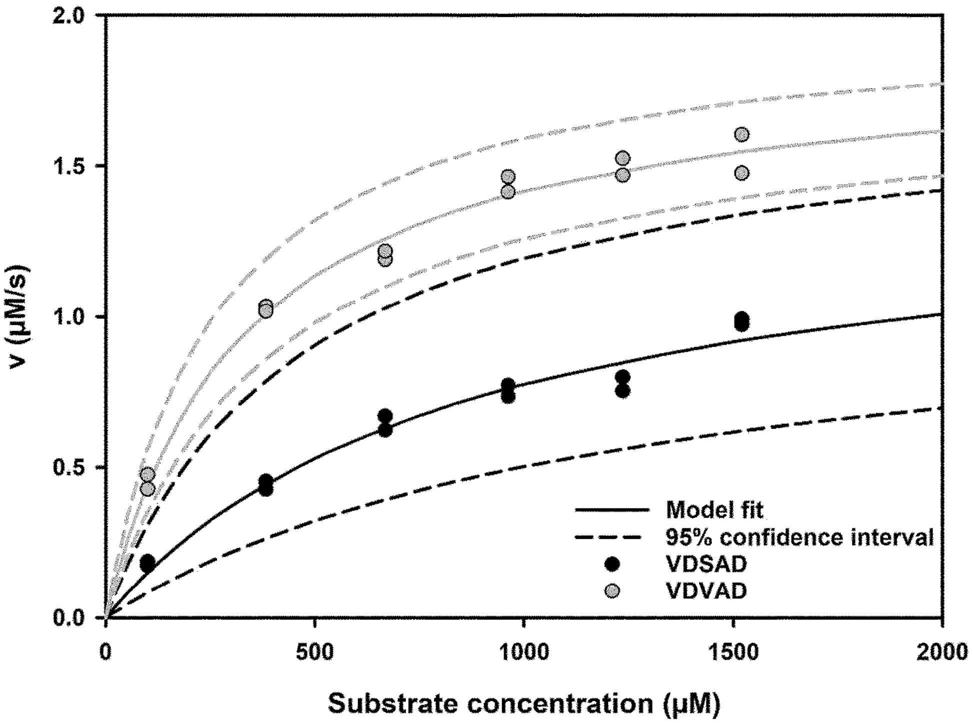
Figure 58:
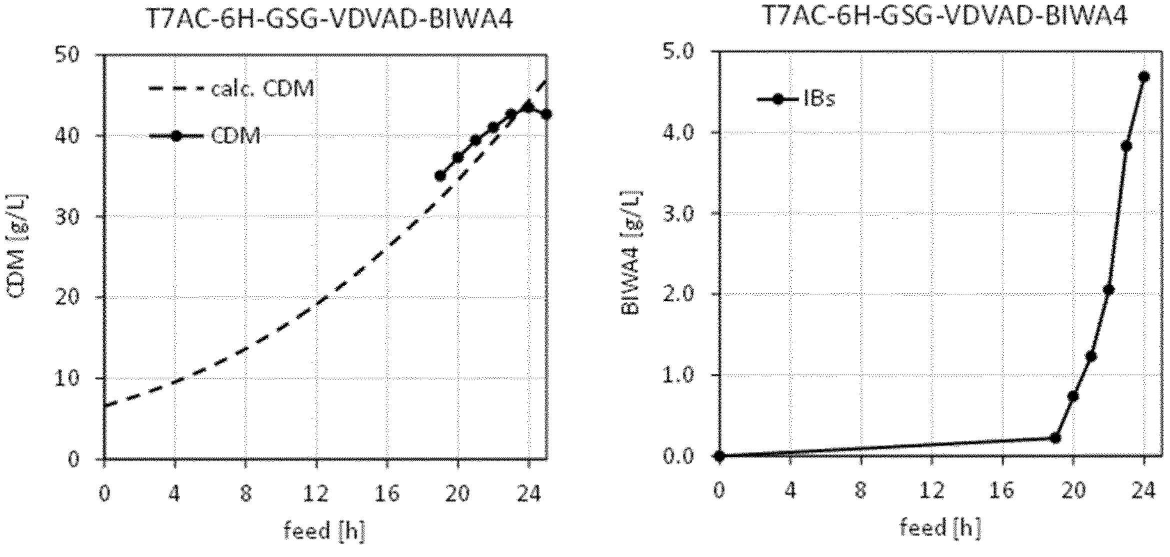
Figure 59:
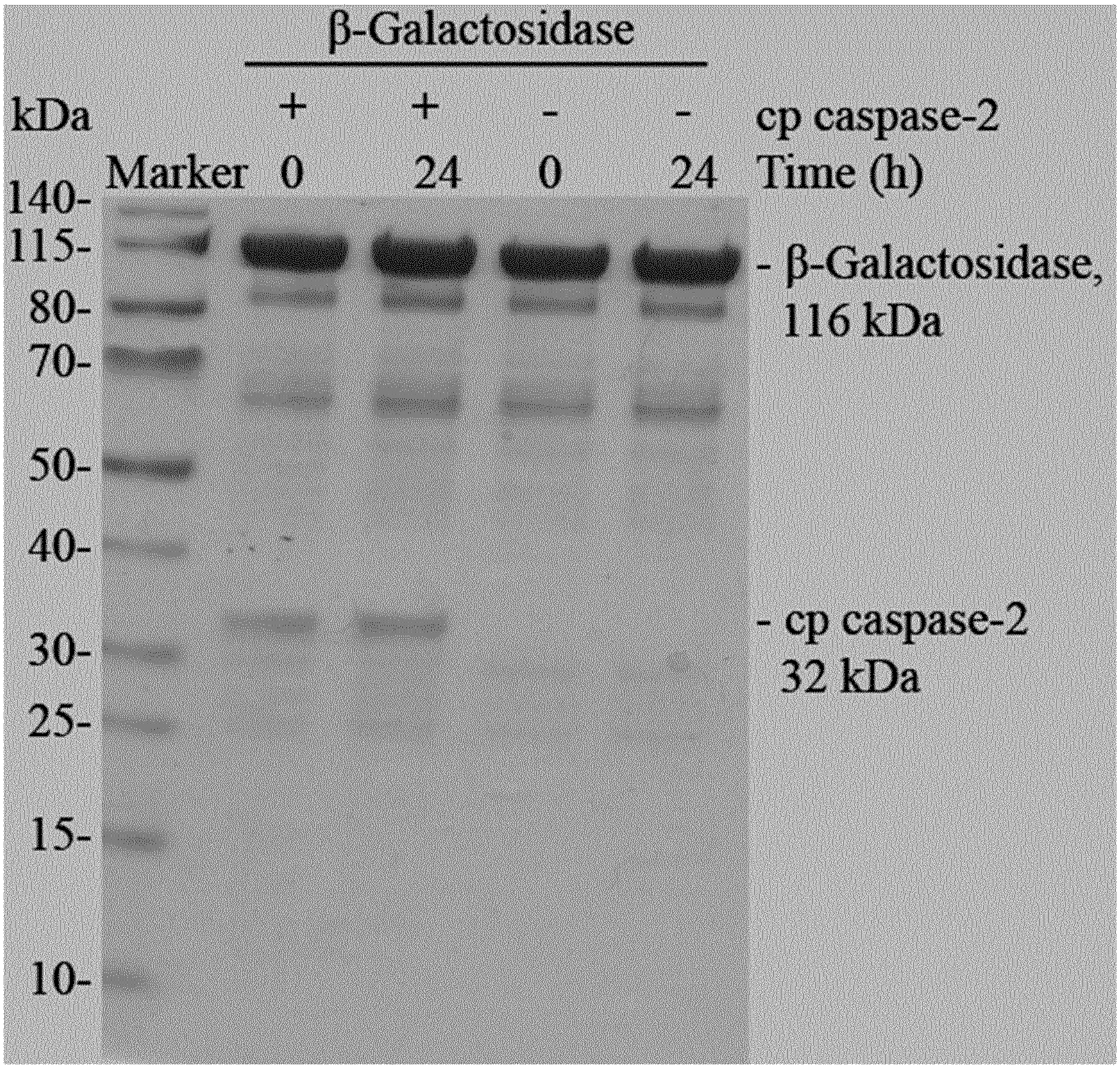
Figure 60:
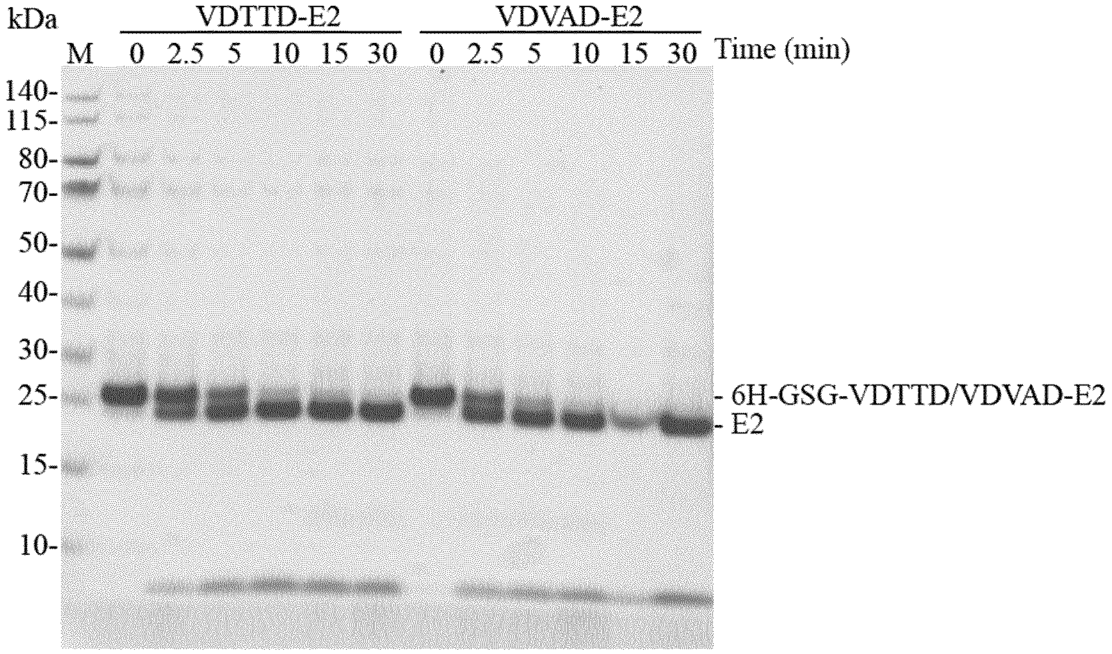

In addition to 6H-GSG-VDVAD-BIWA4 (SEQ ID NO-275) in Table 53 also T7AC-6H-GSG-VDVAD-BIWA4 (T7AC-SEQ ID NO-275) was fermented under the same conditions as 6H-GSG-VDVAD-BIWA4 (SEQ ID NO-275). The T7AC-6H-GSG-VDVAD-BIWA4 (T7AC-SEQ ID NO-275) fusion protein was also expressed as unsoluble Inclusion Bodies (IB), but with a 3-fold titer (Figures. 35 and 58)

hFGF-2—all variants in table 53 means all hFGF-2 variants described in Table 41 except: T7AC-6H-GSG-VDSAD-hFGF2 (SEQ ID NO-268), T7AC-6H-VDVAD-hFGF2 (SEQ ID NO-267) and T7AC-6H-GSGSGSG-VDVAD-hFGF2 (SEQ ID NO-271), which were produced as described Example 10

The course of biomass and fusion protein formation for all fusion protein fermentations of table 53 can be seen in FIGS. 31 to 39.

The titer of the His tagged 6H-hFGF-2 (SEQ ID NO-266) is significantly lower than the untagged hFGF-2. Surprisingly the additional GSG and/or VDVAD (SEQ ID NO-45) sequence in the 6H-GSG-VDVAD-hFGF-2 (SEQ ID NO-32) increases the titer of the His tagged hFGF-2 by a factor of 2,5-fold, since the recognition site is not known to act as an expression enhancer. The further addition of a T7AC or aT7A3 tag further increases the titer for hFGF-2 resp. the fusion protein, which is surprising since the titer for the untagged hFGF-2 could not only be restored, but was increased about 2-fold. All this can be seen in FIG. 38.

19.3 Purification of Fusion Proteins (of Sections 19.1 and 19.2) Before Cleavage with Wild-Type Cp Caspases-2 and P1'Tolerable Cp Caspases-2

The *E. coli* cell harvest was solubilized using homogenization buffer: 50 mM sodium phosphate—buffer and NaCl and pH as indicated in Table 54.

The cells were re-suspended at a concentration of 150 g wet cell mass per L. Cell lysis was performed through high pressure homogenization at 1000 bar/100 bar with two passages with an in line counter current chiller set to 10° C. The homogenate was centrifuged at 18,590 rcf for 2 hours at 4° C. The pellet was discarded and the supernatant used. Before chromatography the supernatant was filtered through a 0.22 μm membrane.

The 6H (SEQ ID NO:315)_GSG_VDVAD (SEQ ID NO:45)- or T7AC_6H(SEQ ID NO:315)_GSG_VDVAD (SEQ ID NO:45)-tagged Pols (fusion proteins) were captured using immobilized metal affinity chromatography (IMAC). The following buffers were used: equilibration buffer A1: 50 mM sodium phosphate, 150 or 500 mM NaCl (see Table 54), 20 mM imidazole, pH 7.0 or pH 7.4 (see Table 54. Wash buffer A2: 50 mM sodium phosphate, 500 mM NaCl, 20 mM imidazole, pH 7.0, 30% isopropanol. Elution buffer: 50 mM sodium phosphate, 150 or 500 mM NaCl (see Table 54), 500 mM imidazole, pH 7.0 or pH 7.4 (see Table 54).

Imidazole was added to the clarified supernatant before IMAC, to a final concentration of 20 mM imidazole. The clarified supernatant was loaded to an equilibrated Ni-Sepharose 6 Fast Flow column. A residence time of 7 minutes was used during loading and 3 minutes for subsequent steps. After loading was completed the column was washed with equilibration buffer for 5, 10 or 15 CV (see Table 54). The bound fusion protein was eluted using a step gradient to 100% elution buffer for 10 CV or a linear gradient from 0-100% B over 5 CV with a 5 CV hold step, see Table 54.

TABLE 54

| Conditions used for IMAC capture of 6H-tagged Pols. | | | | |
|---|---|---|---|---|
| Fusion protein (after expression) | Column dimension | NaCl concentration, pH | Wash | Elution |
| 6H_GSG_VDVAD-hFGF2 (SEQ ID NO: 32) | 26 × 55 mm | 500 mM NaCl, pH 7.0 | 10 CV A1 | Linear gradient 0-100% B 10 CV |
| T7AC_6H_GSG_ | 50 × 15 mm | 500 mM NaCl, | 10 CV A1 | Step 100% B 10 |

TABLE 54-continued

Conditions used for IMAC capture of 6H-tagged Pols.

| Fusion protein (after expression) | Column dimension | NaCl concentration, pH | Wash | Elution |
|---|---|---|---|---|
| VDVAD-hFGF2 (SEQ ID NO: 267) | | pH 7.0 | | CV |
| T7AC_6H_GSG_ VDSAD-hFGF2 (SEQ ID NO: 268) | 10 × 60 mm | 150 mM NaCl, pH 7.4 | 10 CV A1 | Linear gradient 0-100% B 5 CV |
| T7AC_6H_VDVAD-hFGF2 (SEQ ID NO: 270) | 10 × 60 mm | 150 mM NaCl, pH 7.4 | 10 CV A1 | Linear gradient 0-100% B 5 CV |
| T7AC_6H_GSGSGSG_ VDVAD-hFGF2 (SEQ ID NO: 271) | 10 × 60 mm | 150 mM NaCl, pH 7.4 | 10 CV A1 | Linear gradient 0-100% B 5 CV |
| 6H_(SEQ ID NO: 315)_GSG_VD-VAD (SEQ ID NO: 45)-TNFα | 26 × 65 mm | 500 mM NaCl, pH 7.0 | 20 CV A1 | Linear gradient 0-100% B 10 CV |
| T7AC_6H_GSG_ VDVAD-TNFα (SEQ ID NO: 263) | 26 × 59 mm | 500 mM NaCl, pH 7.0 | 15 CV A1 | Linear gradient 0-100% B 10 CV |
| 6H_(SEQ ID NO: 315)GSG_VDVAD (SEQ ID NO: 45)-GFP | 26 × 28 mm | 500 mM NaCl, pH 7.0 | 5 CV A1, 5 CV A2, 1 CV A1 | Linear gradient 0-100% B 10 CV |
| T7AC_6H(SEQ ID NO: 315)_GSG_ VDVAD(SEQ ID NO: 45)-rhGH | 10 × 89 mm | 150 mM NaCl, pH 7.4 | 5 CV A1 | Linear gradient 0-100% B 5 CV |
| T7AC_6H_GSG_ VDVAD-PTH (SEQ ID NO: 259) | 10 × 89 mm | 150 mM NaCl, pH 7.4 | 5 CV A1 | Linear gradient 0-100% B 5 CV |
| T7AC_6H_GSG_ VDVAD-GCSF (SEQ ID NO: 261) | 10 × 89 mm | 150 mM NaCl, pH 7.4 | 5 CV A1 | Linear gradient 0-100% B 5 CV |
| 6H-GSG-VDVAD-BIWA4 (SEQ ID NO: 275) | 50 × 15 mm | 500 mM NaCl, pH 7.0 | 10 CV A1 | Step 100% B 10 CV |

The elution fractions were analyzed using SDS-PAGE and all fractions containing POI were pooled. The product pool was buffer exchanged to phosphate buffered saline (PBS) using UF/DF. UF/DF for was performed in Amicon centrifugal filter vials with a 10 kDa nominal membrane cut off (3 kDa cut-off for T7AC_6H_GSG_VDVAD-PTH (SEQ ID NO:259)). In total 5 volumes were exchanged.

Figure 41:
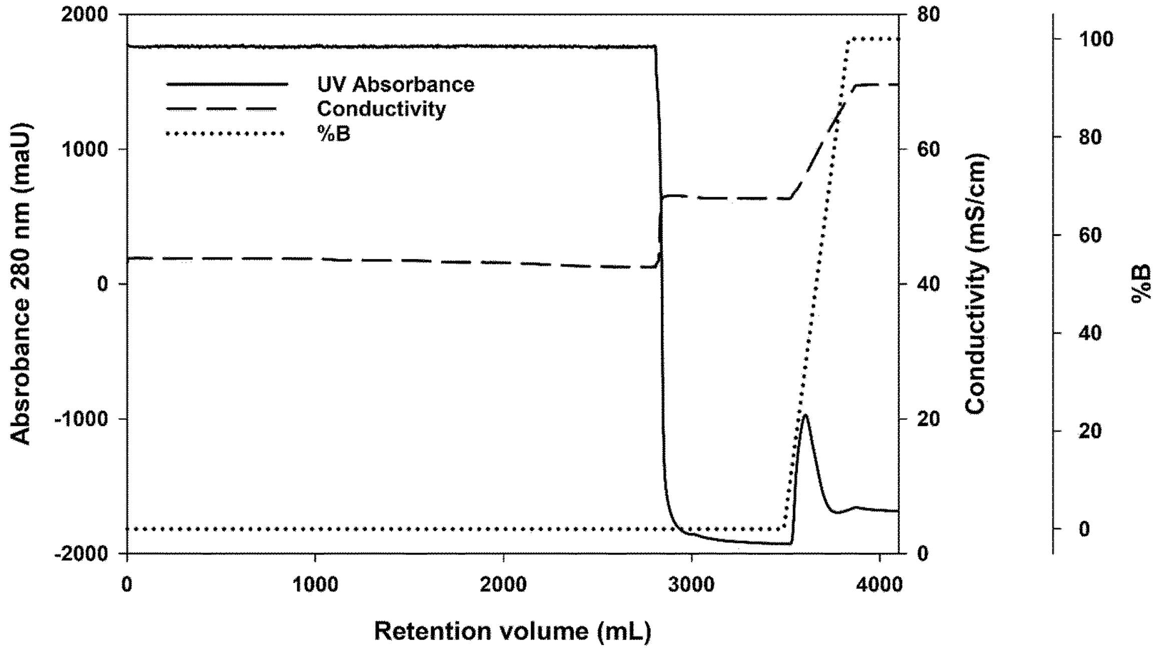
Figure 42:
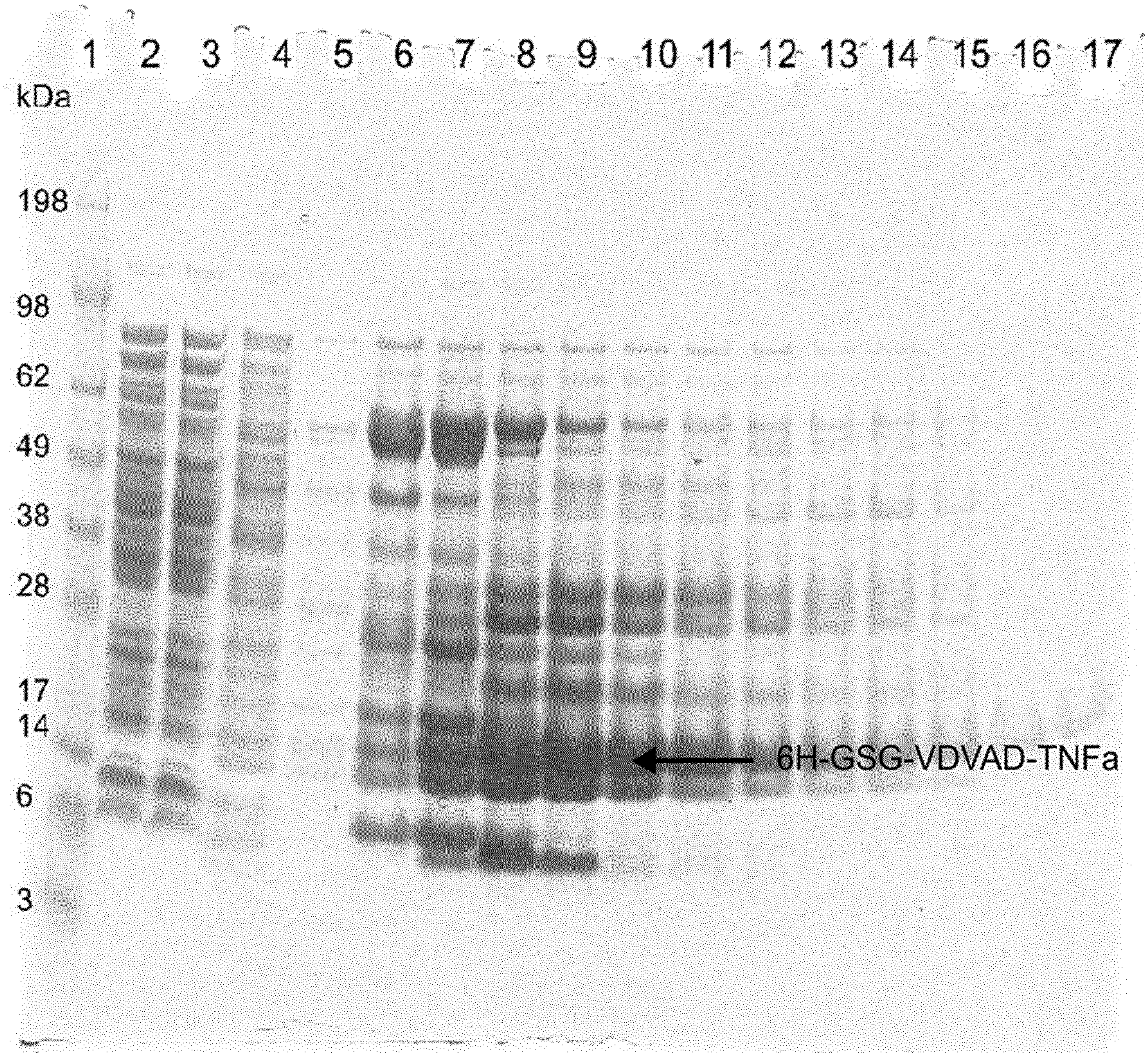
Figure 43:
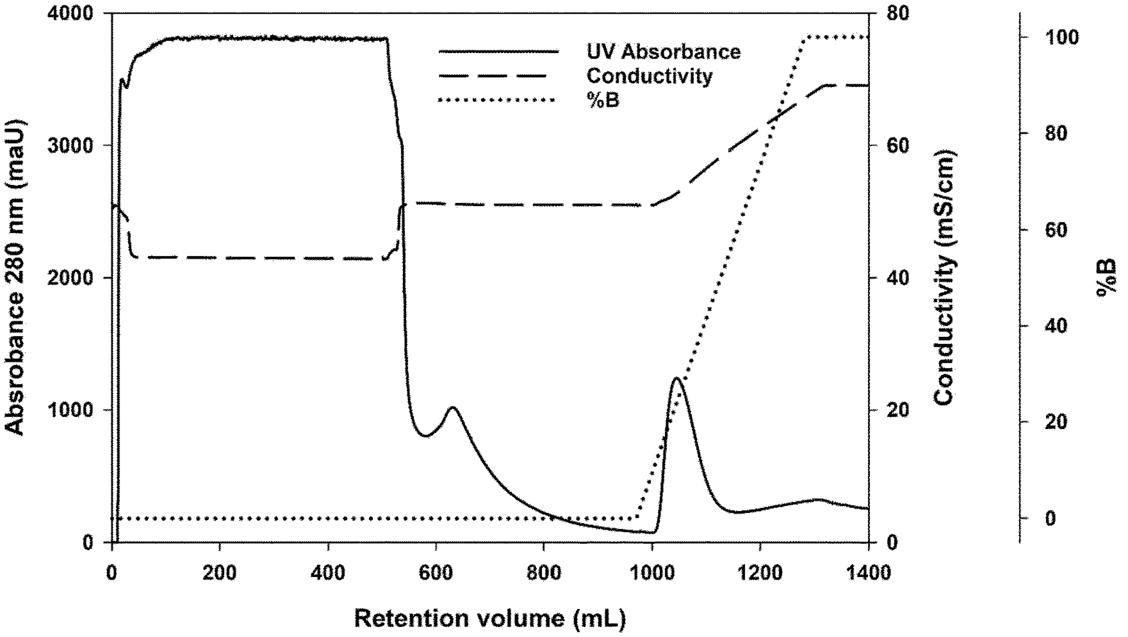
Figure 44:
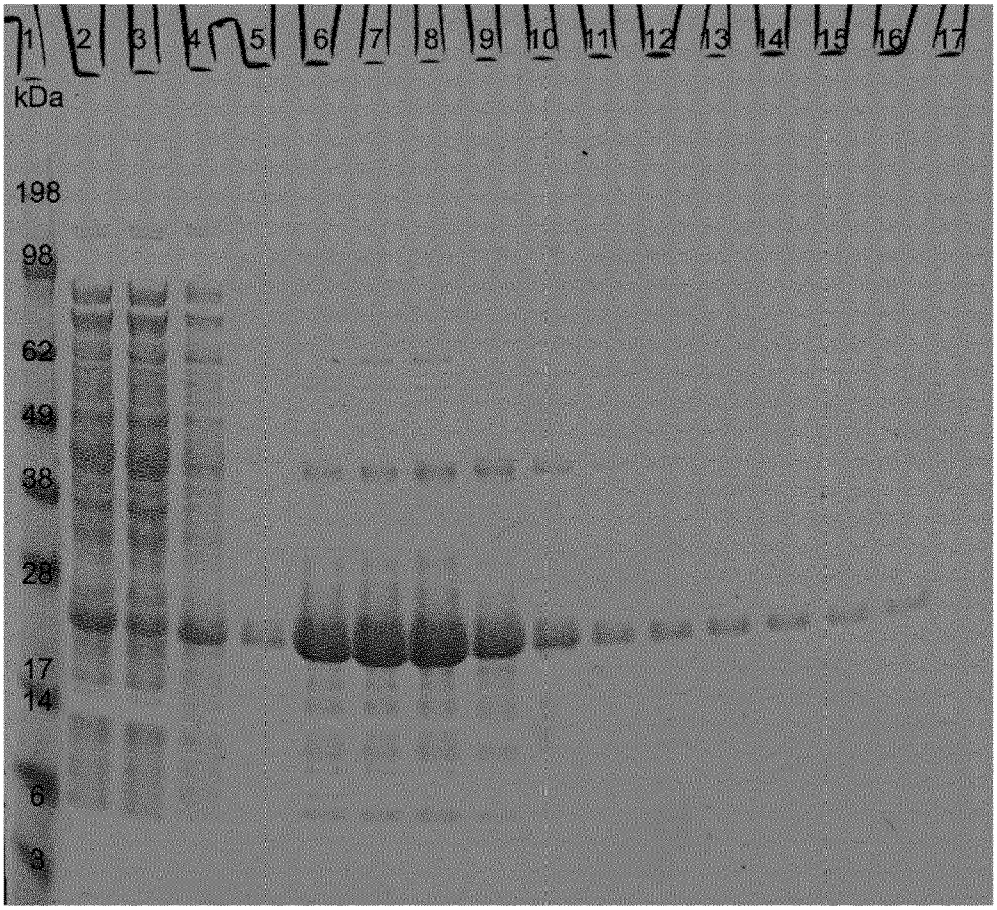

Purification of 6H (SEQ ID NO:315)_GSG_VDVAD (SEQ ID NO:45)-TNFα and T7AC_6H_GSG_VDVAD-TNFα (SEQ ID NO:263) was performed by IMAC capture. Different volumes of cell lysis supernatant were loaded based on the specific protein content. Apart from the differing loading times, the chromatograms of both POIs looked similar (see FIG. 41 and FIG. 43). Due to the higher specific protein content, the elution fractions of T7AC_6H_GSG_VDVAD-TNFα (SEQ ID NO:263) had a higher purity as determined by SDS-PAGE (FIG. 44) compared to 6H (SEQ ID NO:315)_GSG_VDVAD (SEQ ID NO:315)-TNFα (FIG. 42).

Example 20: Michaelis-Menten Kinetics for the Cleavage of Fusion Proteins of Example 10 with Cp Caspase-2 wt and Variants Fusion proteins as produced in Example 19, sections 19.2 and 19.3, were cleaved with several cp caspases-2 at different substrate (fusion protein) concentrations with the same amount of the respective cp caspase-2 variant.

To determine the Michaelis Menten kinetic different concentrations of the fusion protein were incubated with a certain amount of different wild-type cp caspases-2 and P1'tolerable cp-caspase-2 variants. The buffer is PBS (137 mM NaCl, 2.7 mM KCl, 10 mM Na2HPO4, 1.8 mM $KH_2PO4$, pH 7.4) and the digests are incubated at room temperature for a certain time. The reaction was stopped by addition of 20 mM cysteamine to a final concentration of 2 mM. The samples were then analyzed by RP-HPLC as described in section 18.3.2. The initial rate ($v_0$) in μM/s of each concentration was calculated using the cleaved fusion tag peak area from HPLC at the time point of the initial slope. These data were transferred to TableCurve 2D to fit a Michaelis Menten kinetic in order to calculate values for $V_{max}$ and $K_M$.

TABLE 55

Conditions for determining the Michaelis Menten Kinetic for different fusion proteins

| Fusion Protein | Concentrations of the fusion protein | Incubation time | Concentration of the cp caspase-2 variant |
|---|---|---|---|
| 6H-GSG-VDVAD-hFGF-2 (SEQ ID NO:32) | 100, 384, 668, 952, 1236, 1520 μM | 45 s | 1 μM |
| T7AC-6H-GSG-VDVAD-hFGF-2 (SEQ ID NO: 267) | 100, 384, 668, 952, 1236, 1520 μM | 45 s | 1 μM |
| T7AC-6H-VDVAD-hFGF-2 (SEQ ID NO: 270) | 100, 384, 668, 952, 1236, 1520 μM | 215 s | 1 μM |
| T7AC-6H-GSGSGSG-VDVAD-hFGF-2 (SEQ ID NO: 271) | 100, 384, 668, 952, 1236, 1520 μM | 45 s | 1 μM |
| 6H-GSG-VDVAD-TNFalpha (SEQ ID NO: 269) | 100, 299, 498, 697, 896, 1093 μM | 420 s | 10 μM |
| 6H-GSG-VDVAD-BIWA4 (SEQ ID NO: 275) | 50, 140, 230, 320 μM | 420 s | 10 μM |
| 6H(SEQ ID NO: 315)-GSG-VDVAD (SEQ ID NO: 45)-GFPmut3.1 | 100, 503, 905, 1307, 1709, 2111, 3133, 4155, 5060 μM | 420 s | 10 μM |

Figure 45:
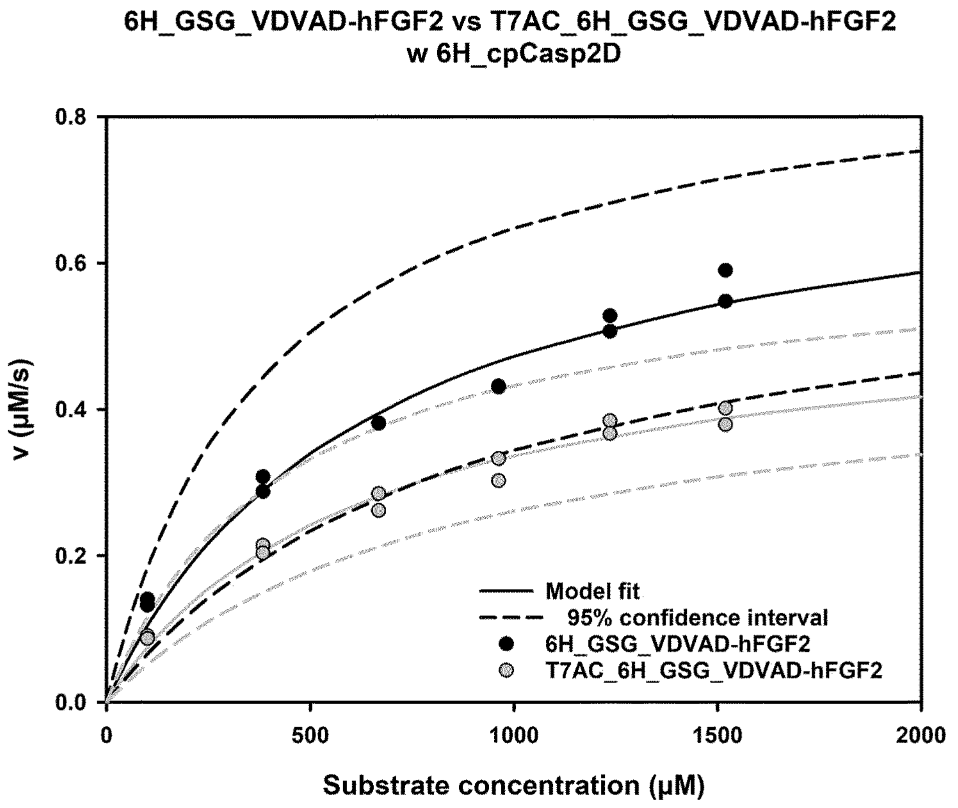

A Michaelis Menten kinetic was measured with 6H_GSG_VDVAD-hFGF2 (SEQ ID NO:32) and T7AC_6H_GSG_VDVAD-hFGF2 (SEQ ID NO:267) with the enzyme 6H_cpCasp2D (SEQ ID NO:6). No significant difference in cleavage kinetics was observed (FIG. 45).

TABLE 56

Michaelis-Menten kinetic parameters of the cleavage of 6H-GSG-VDVAD-hFGF2 (SEQ ID NO: 32)and T7AC-6H-GSG-VDVAD-hFGF2 (SEQ ID NO: 267) with 6H-cpCasp2D (SEQ ID NO: 6).

| | 6H-GSG-VDVAD-hFGF2 (SEQ ID NO: 32) | T7AC-6H-GSG-VDVAD-hFGF2 (SEQ ID NO: 32) |
|---|---|---|
| $K_M$ (μM) | 642 | 639 |
| $k_{cat}$ (1/s) | 0.78 | 0.55 |
| $k_{cat}/K_M$ ($s^{-1}$*$\mu M^{-1}$) | 1208 | 862 |

Figure 46:
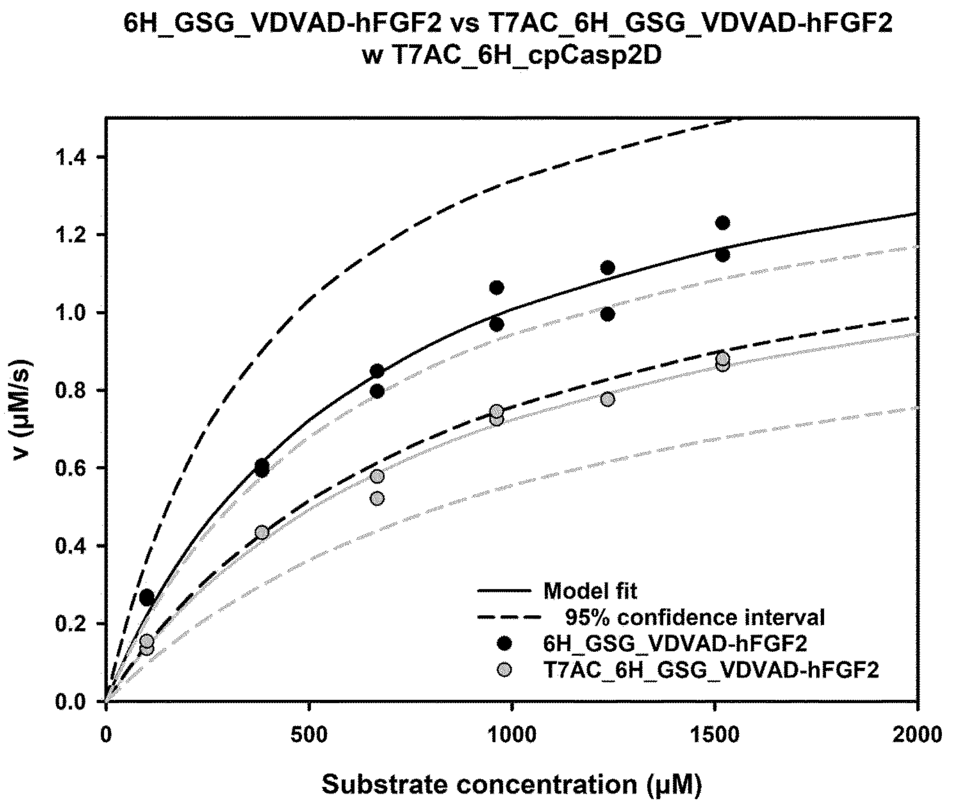

A Michaelis Menten kinetic was measured with 6H_GSG_VDVAD-hFGF2 (SEQ ID NO:32) and T7AC_6H_GSG_VDVAD-hFGF2 (SEQ ID NO:32) with the enzyme T7AC_6H_cpCasp2D(SEQ ID NO:41). No significant difference in cleavage kinetics was observed (FIG. 46).

TABLE 57

Michaelis-Menten kinetic parameters of the cleavage of 6H-GSG-VDVAD-hFGF2 (SEQ ID NO: 32) and T7AC-6H-GSG-VDVAD-hFGF2 (SEQ ID NO: 267) with T7AC-6H-cpCasp2D (SEQ ID NO: 41).

| | 6H-GSG-VDVAD-hFGF2 (SEQ ID NO: 32) | T7AC-6H-GSG-VDVAD-hFGF2 (SEQ ID NO: 267) |
|---|---|---|
| $K_M$ (μM) | 650 | 881 |
| $k_{cat}$ (1/s) | 1.7 | 1.4 |
| $k_{cat}/K_M$ ($s^{-1}$*$\mu M^{-1}$) | 2558 | 1545 |

Figure 47:
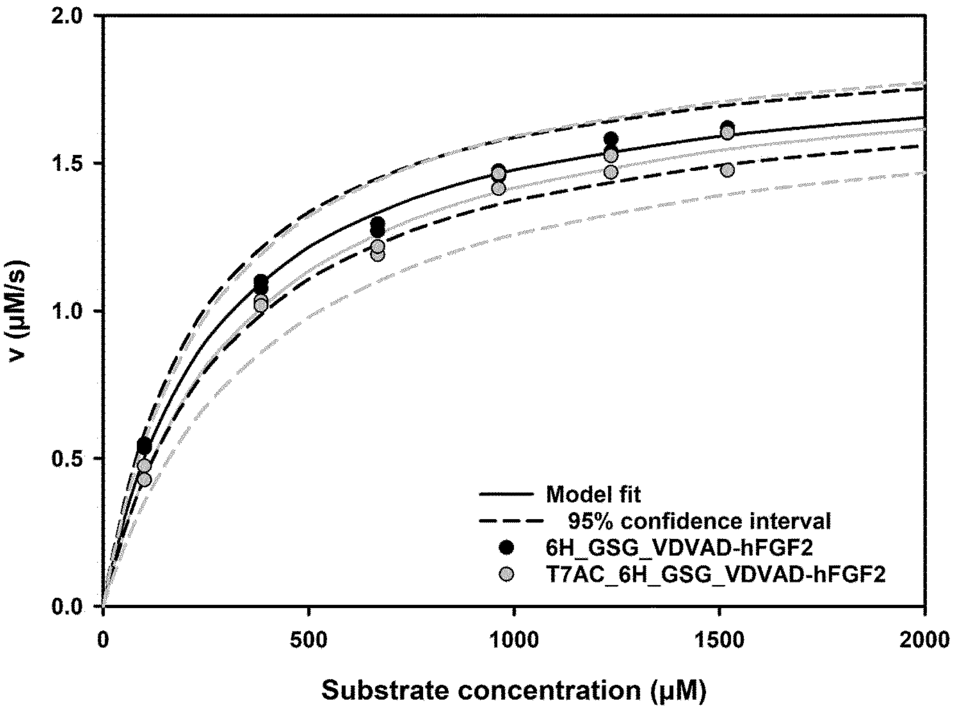

A Michaelis Menten kinetic was measured with 6H_GSG_VDVAD-hFGF2 (SEQ ID NO:32) and T7AC_6H_GSG_VDVAD-hFGF2 (SEQ ID NO:267) with the enzyme T7AC_6H_mS9ProD (SEQ ID NO:72). No significant difference in cleavage kinetics was observed (FIG. 47).

TABLE 58

Michaelis-Menten kinetic parameters of the cleavage of 6H-GSG-VDVAD-hFGF2 (SEQ ID NO: 32) and T7AC-6H-GSG-VDVAD-hFGF2 (SEQ ID NO: 267) with T7AC-6H-mS9ProD (SEQ ID NO: 72).

| | 6H-GSG-VDVAD-hFGF2 (SEQ ID NO: 32) | T7AC-6H-GSG-VDVAD-hFGF2 (SEQ ID NO: 267) |
|---|---|---|
| $K_M$ (μM) | 274 | 329 |
| $k_{cat}$ (1/s) | 1.9 | 1.9 |
| $k_{cat}/K_M$ ($s^{-1}$*$\mu M^{-1}$) | 6876 | 5724 |

Figure 48:
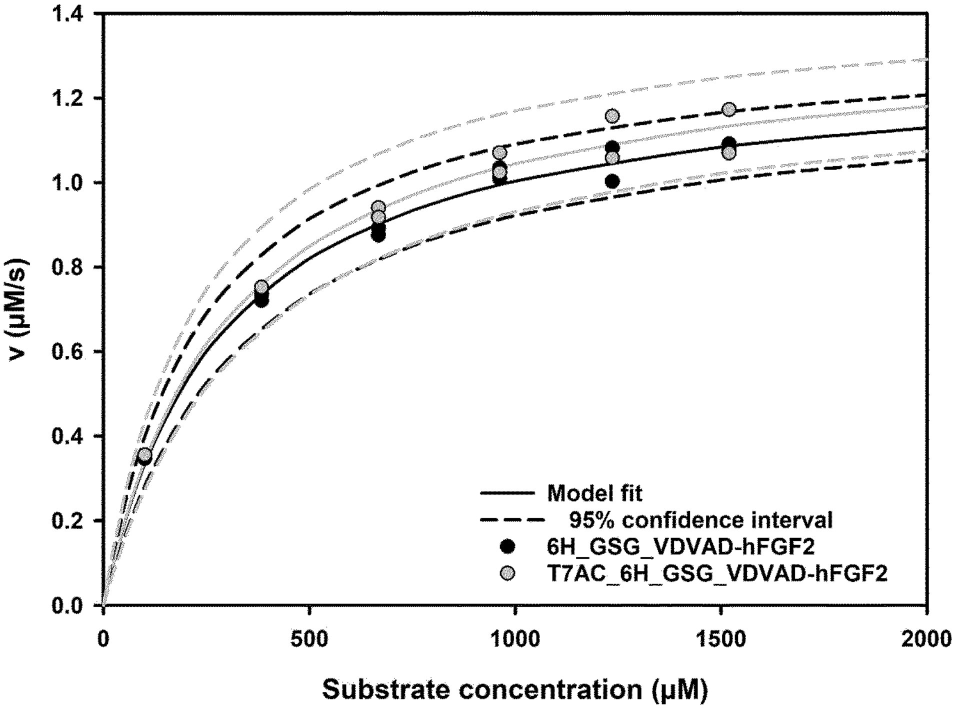

A Michaelis Menten kinetic was measured with 6H_GSG_VDVAD-hFGF2 (SEQ ID NO:32) and T7AC_6H_GSG_VDVAD-hFGF2 (SEQ ID NO:267) with the enzyme T7AC_6H_mS9ProE (SEQ ID NO:71). No significant difference in cleavage kinetics was observed (FIG. 48).

TABLE 59

Michaelis-Menten kinetic parameters of the cleavage of 6H-GSG-VDVAD-hFGF2 (SEQ ID NO: 32) and T7AC-6H-GSG-VDVAD-hFGF2 (SEQ ID NO: 267) with T7AC-6H-mS9ProE (SEQ ID NO: 71).

| | 6H-GSG-VDVAD-hFGF2 (SEQ ID NO: 32) | T7AC-6H-GSG-VDVAD-hFGF2 (SEQ ID NO: 267) |
|---|---|---|
| $K_M$ (μM) | 287 | 298 |
| $k_{cat}$ (1/s) | 1.3 | 1.4 |
| $k_{cat}/K_M$ ($s^{-1}$*$\mu M^{-1}$) | 4498 | 4549 |

Figure 49:
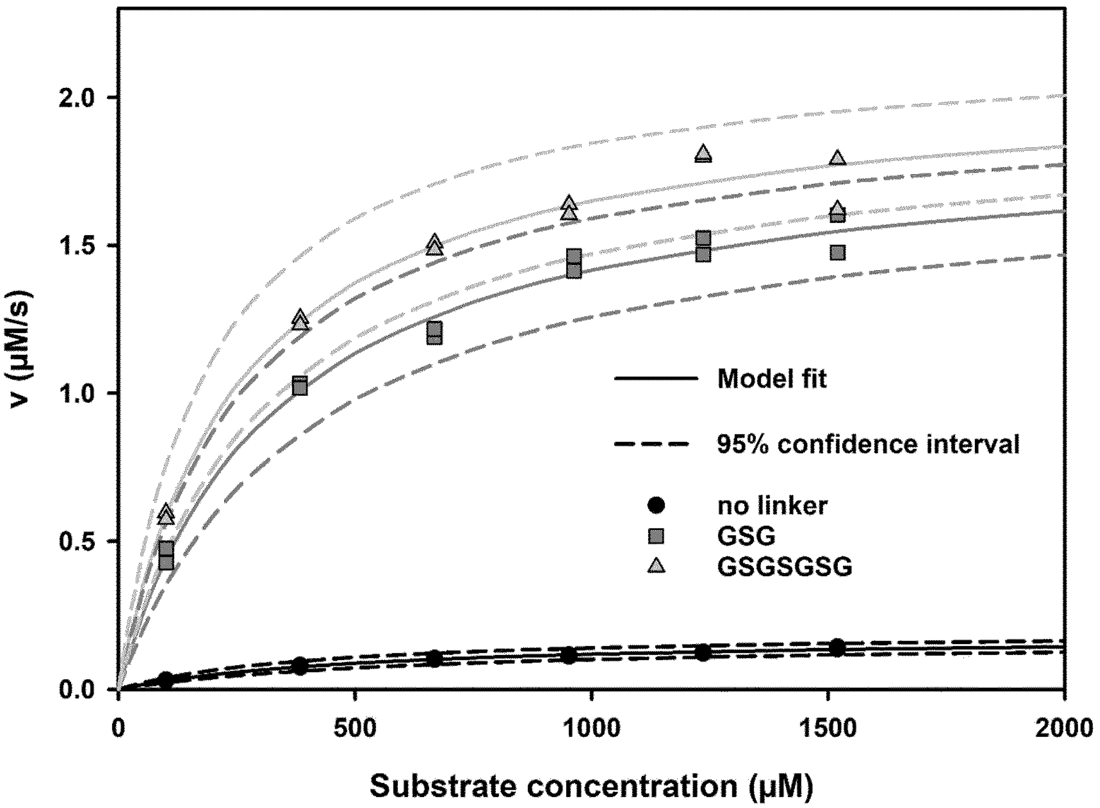

A Michaelis Menten kinetic was measured with T7AC_6H_VDVAD-hFGF2 (SEQ ID NO:270), T7AC_6H_GSG_VDVAD-hFGF2 (SEQ ID NO:267) and T7AC_6H_GSGSGSG_VDVAD-hFGF2 (SEQ ID NO:271) with the enzyme T7AC_6H_mS9ProD (SEQ ID NO:72). Cleavage of hFGF2 without a linker between 6H (SEQ ID NO:315) and VDVAD (SEQ ID NO:45) was significantly less efficient (FIG. 49 and Table 6).

TABLE 60

Michaelis-Menten kinetic parameters of the cleavage of T7AC_6H_VDVAD-hFGF2 (SEQ ID NO: 270), _ T7AC_6H_GSGVDVAD-hFGF2 (SEQ ID NO: 267) and T7AC_6H_GSGSGSG_VDVAD-hFGF2 (SEQ ID NO: 271) with T7AC-6H-mS9ProD (SEQ ID NO: 72).

| | T7AC-6H-VDVAD-hFGF2 (SEQ ID NO: 270) | T7AC-6H-GSG-VDVAD-hFGF2 (SEQ ID NO: 267) | T7AC-6H-GSGSGSG-VDVAD-hFGF2 (SEQ ID NO: 271) |
|---|---|---|---|
| $K_M$ (μM) | 529 | 329 | 252 |
| $k_{cat}$ (1/s) | 0.18 | 1.9 | 2.1 |
| $k_{cat}/K_M$ ($s^{-1}$*$\mu M^{-1}$) | 342 | 5724 | 8197 |

Surprisingly with a linker between the 6H (SEQ ID NO:315)tag and the recognition site, VDVAD (SEQ ID NO:45), the $k_{kat}$ is dramatically increased, which further improves the production technology for a POI, which is expressed as a fusion protein, and wherein the fusion tag is cleaved by a wild-type cp caspase-2 or a P1'tolerable cp caspase-2.

A Michaelis Menten kinetic was measured with the fusion proteins, 6H-GSG-VDVAD-hFGF-2 (SEQ ID NO:32), 6H (SEQ ID NO:315)-GSG-VDVAD(SEQ ID NO:45)-TNFalpha, 6H-GSG-VDVAD-BIWA4 (SEQ ID NO:275). The measured values are shown in Table 61.

TABLE 61

Michaelis Menten Kinetic parameters of the cleavage of 6H-GSG-VDVAD-hFGF-2 (SEQ ID NO: 32), 6H-GSG-VDVAD-TNFalpha (SEQ ID NO: 263), 6H-GSG-VDVAD-BIWA4 (SEQ ID NO: 275), with different wild-type cp caspases-2 and P1' tolerable cp caspases-2.

| Caspase | | hFGF-2 | BIWA4 | TNFa |
|---|---|---|---|---|
| 6H_cpCasp2D (SEQ ID NO: 6) | $K_M$ [$M^{-1}$] | 5.9 E−4 | n.d. | n.d. |
| | KM ci [M − 1] | 1.7 E−4 | n.d. | n.d. |
| | $k_{cat}$ [$s^{-1}$] | 6.2 E−1 | n.d. | n.d. |
| | kcat ci [s − 1] | 6.8 E−2 | n.d. | n.d. |
| | kcat/KM [M − 1s − 1] | 1.1 E+3 | n.d. | n.d. |
| T7AC_6H_ | $K_M$ [$M^{-1}$] | 6.5 E−4 | n.d. | 2.8 E−4 |

TABLE 61-continued

Michaelis Menten Kinetic parameters of the cleavage of 6H-GSG-VDVAD-hFGF-2 (SEQ ID NO: 32), 6H-GSG-VDVAD-TNFalpha (SEQ ID NO: 263), 6H-GSG-VDVAD-BIWA4 (SEQ ID NO: 275), with different wild-type cp caspases-2 and P1' tolerable cp caspases-2.

| Caspase | | hFGF-2 | BIWA4 | TNFa |
|---|---|---|---|---|
| cpCasp2D | KM ci [M − 1] | 2.3 E−4 | n.d. | 6.5 E−5 |
| (SEQ ID | $k_{cat}$ [$S^{-1}$] | 1.7 E+0 | n.d. | 1.3 E−2 |
| NO: 41) | kcat ci [s − 1] | 2.4 E−1 | n.d. | 9.8 E−4 |
| | $k_{cat}/K_M$ [$M^{-1}s^{-1}$] | 2.6 E+3 | n.d. | 4.7 E+1 |
| T7AC_6H_ | $K_M$ [$M^{-1}$] | 2.9 E−4 | 1.6 E−4 | 5.2 E−4 |
| mS9ProE | KM ci [M − 1] | 4.8 E−5 | 1.4 E−4 | 1.7 E−4 |
| (SEQ ID | $k_{cat}$ [$s^{-1}$] | 1.3 E+0 | 5.8 E−3 | 7.9 E−2 |
| NO: 71) | kcat ci [s − 1] | 6.0 E−2 | 1.0 E−2 | 1.1 E−2 |
| | $k_{cat}/K_M$ [$M^{-1}s^{-1}$] | 4.5 E+3 | 3.6 E+1 | 1.5 E+2 |
| T7AC_6H_ | $K_M$ [$M^{-1}$] | 2.7 E−4 | 2.3 E−4 | n.d. |
| mS9ProD | KM ci [M − 1] | 4.1 E−5 | 4.7 E−5 | n.d. |
| (SEQ ID | $k_{cat}$ [$s^{-1}$] | 1.9 E+0 | 3.2 E−3 | n.d. |
| NO: 72) | kcat ci [s − 1] | 7.6 E−2 | 3.6 E−4 | n.d. |
| | $k_{cat}/K_M$ [$M^{-1}s^{-1}$] | 6.9 E+3 | 1.4 E+1 | n.d. |

n.d. = not determined.

conf int = 95% confidence interval.

Example 21: Fusion Protein (Prepared as Described in Example 19, Sections 19.1-19.3) Cleavage in Solution A fusion protein (tagged POI) at 1 g/L was incubated with a cp-caspase-2 variant in a dilution of 50:1 or 100:1 (M/M) fusion protein to cp caspase-2 variant. The digest is incubated at room temperature in PBS for i or 2 hours. The reaction was stopped by addition of 20 mM cysteamine to a final concentration of 2 mM. The samples were then analyzed by SDS-PAGF.

The tag cleavage of five fusion proteins with the T7AC_6H(SFQ ID NO:315)_GSG_VDVAD (SEQ ID NO:45)-tag were tested with the enzymes T7AC_6H-cpCasp2D (SEQ ID No. 4i), T7AC_6H-mS9ProD (SEQ ID NO:72), T7AC_6H-mS9ProE (SEQ ID No. 71).

Figure 50:
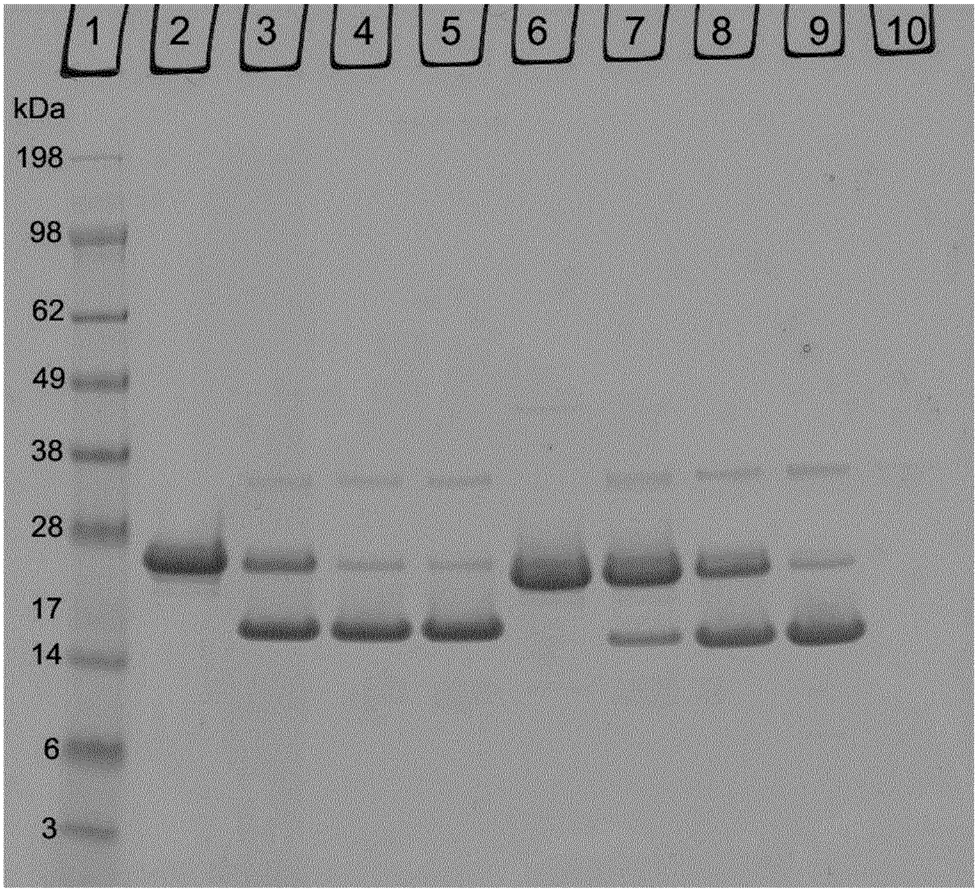

When cleaving T7AC_6H_GSG_VDVAD-hFGF2 (SEQ ID NO:267), T7AC_6H-mS9ProD (SEQ ID NO:72) and T7AC_6H-mS9ProE (SEQ ID No. 71) have a higher yield than T7AC_6H-cpCasp2D (SEQ ID No. 41) (FIG. 50). The reaction was performed in a 1:100 molar ratio for i hours.

When cleaving T7AC_6H_GSG_VDVAD-TNFα (SEQ ID NO:263), T7AC_6H-mS9ProD (SEQ ID NO:72) and T7AC_6H-mS9ProE (SEQ ID No. 71) have a higher yield than T7AC_6H-cpCasp2D (SEQ ID No. 41) (FIG. 50). The reaction was performed in a 1:100 molar ratio for 1 hours. T7AC_6H-mS9ProD (SEQ ID NO:72) had the highest yield overall.

Figure 51:
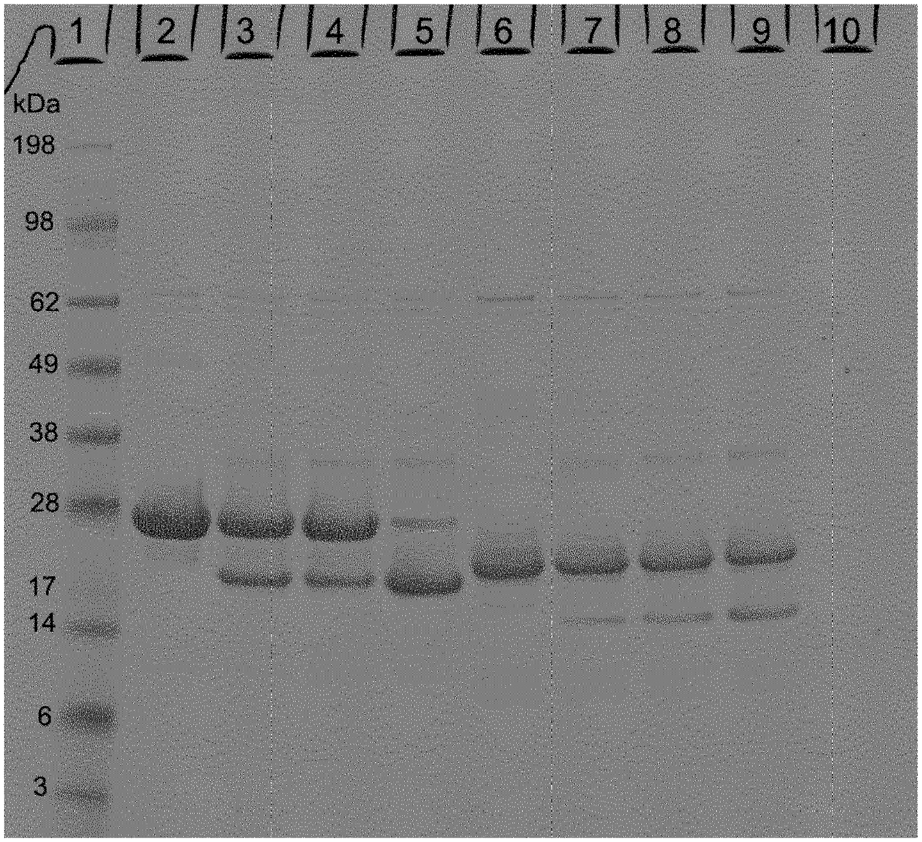

When cleaving T7AC_6H_GSG_VDVAD-rhGH (SEQ ID NO:257), T7AC_6H-mS9ProD (SEQ ID NO:72) has a higher yield than T7AC_6H-cpCasp2D (SEQ ID No. 41) and T7AC_6H-mS9ProE (SEQ ID No. 71) (FIG. 51). The reaction was performed in a 1:100 molar ratio for 2 hours.

When cleaving T7AC_6H_GSG_VDVAD-GCSF (SEQ ID NO:261), T7AC_6H-mS9ProD (SEQ ID NO:72) and T7AC_6H-mS9ProE (SEQ ID No. 71) have a higher yield than T7AC_6H-cpCasp2D (SEQ ID No. 41) (FIG. 51). The reaction was performed in a 1:100 molar ratio for 2 hours. T7AC_6H-mS9ProD (SEQ ID NO:72) had the highest yield overall.

Figure 52:
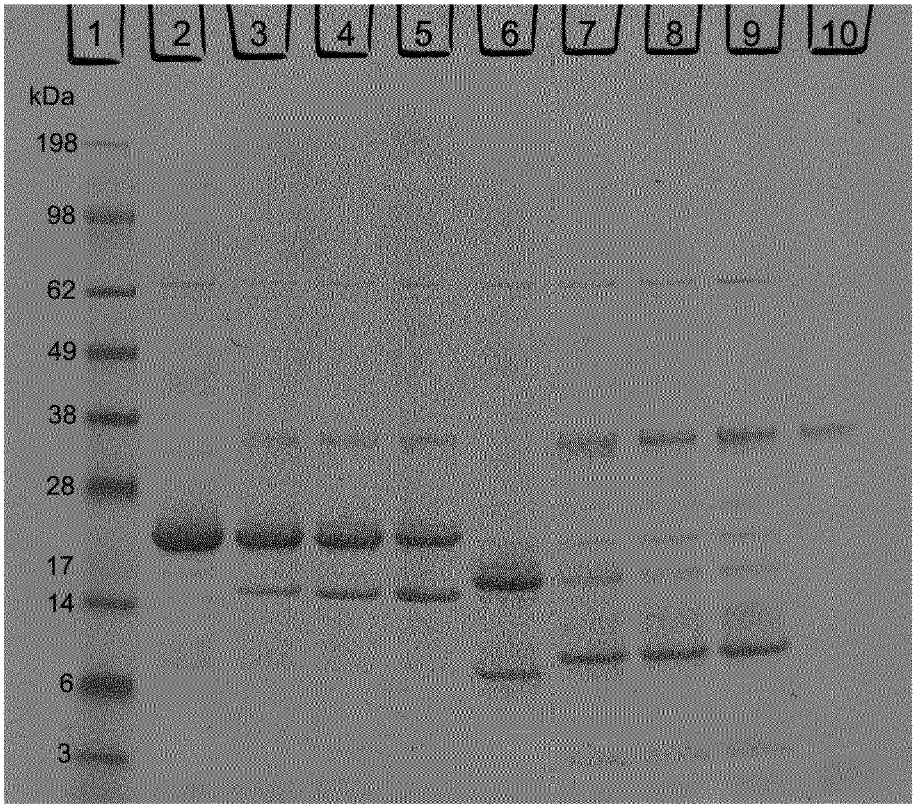

When cleaving T7AC_6H_GSG_VDVAD-GCSF (SEQ ID NO:261), T7AC_6H-mS9ProD (SEQ ID NO:72) and T7AC_6H-mS9ProE (SEQ ID No. 71) have a higher yield than T7AC_6H-cpCasp2D (SEQ ID No. 41) (FIG. 52). The reaction was performed in a 1:50 molar ratio for 2 hours. T7AC_6H-mS9ProD (SEQ ID NO:72) had the highest yield overall.

When cleaving T7AC_6H_GSG_VDVAD-PTH (SEQ ID NO:259), T7AC_6H-mS9ProD (SEQ ID NO:72) and T7AC_6H-mS9ProE (SEQ ID No. 71) have a higher yield than T7AC_6H-cpCasp2D (SEQ ID No. 41) (FIG. 52). The reaction was performed in a 1:50 molar ratio for 2 hours.

Example 22: Protein Cleavage with Immobilized Enzyme

Enzyme immobilization was performed through amine coupling. The primary amino groups of the lysine residues on the enzyme were coupled to activated NHS-groups, placed on spacer arms in the resin. The coupling forms a stable amide bond. Cp caspase-2 was immobilized at the following concentrations 1 μM, 10 μM, 50 μM and 100 μM. The enzyme was diluted in coupling buffer (0.2 M $NaHCO_3$, 0.5 M NaCl, pH 8.3) to reach the desired concentration. For a 500 μl column, around 1.5-2 ml of resin slurry in 100% isopropanol was transferred to a 15 ml centrifuge tube. The first step was to wash the resin for removal of the isopropanol. This was done with 10 to 15 resin volumes of cold 1 mM HCl. Immediately after the washing step, the resin and the coupling buffer with enzyme were mixed using a vortex. The sample was left at 4° C. overnight for the coupling reaction. After the coupling the samples were mixed with blocking buffer (0.1 M Tris-HCl, pH 8.5) and kept in the buffer for 2 to 4 hours to block all non-reacted NHS groups in the resin. The samples were then washed alternating two buffers with high (0.1 M Tris-HCl, pH 8.5) respectively low (0.1 M HAc, 0.5 M NaCl, pH 4.7) pH using 3 medium volumes each time and repeating the procedure for 3 to 6 times. In each step, the buffer was added, the sample vortexed, thereafter centrifuged (1.000×g, 1 min, 4° C.) and the supernatant was discarded. The immobilized resin was then stored at 4° C. in either 20% EtOH or 0.01% $NaN_3$ in 1×PBS to prevent microbial contamination before packed in columns.

To determine the kinetics and activity of the immobilized cp caspase-2, the columns were tested with different concentrations of the model protein, hFGF-2 at varying residence times in the column. The flow through from the sample application and first column wash was collected in fractions in 96 deep well plates containing 1/1000 formic acid to deactivate any leaked enzyme and to stop the reaction. The amount of product was quantified using the RP-HPLC method outlined in section 18.3.2.

Figure 21:
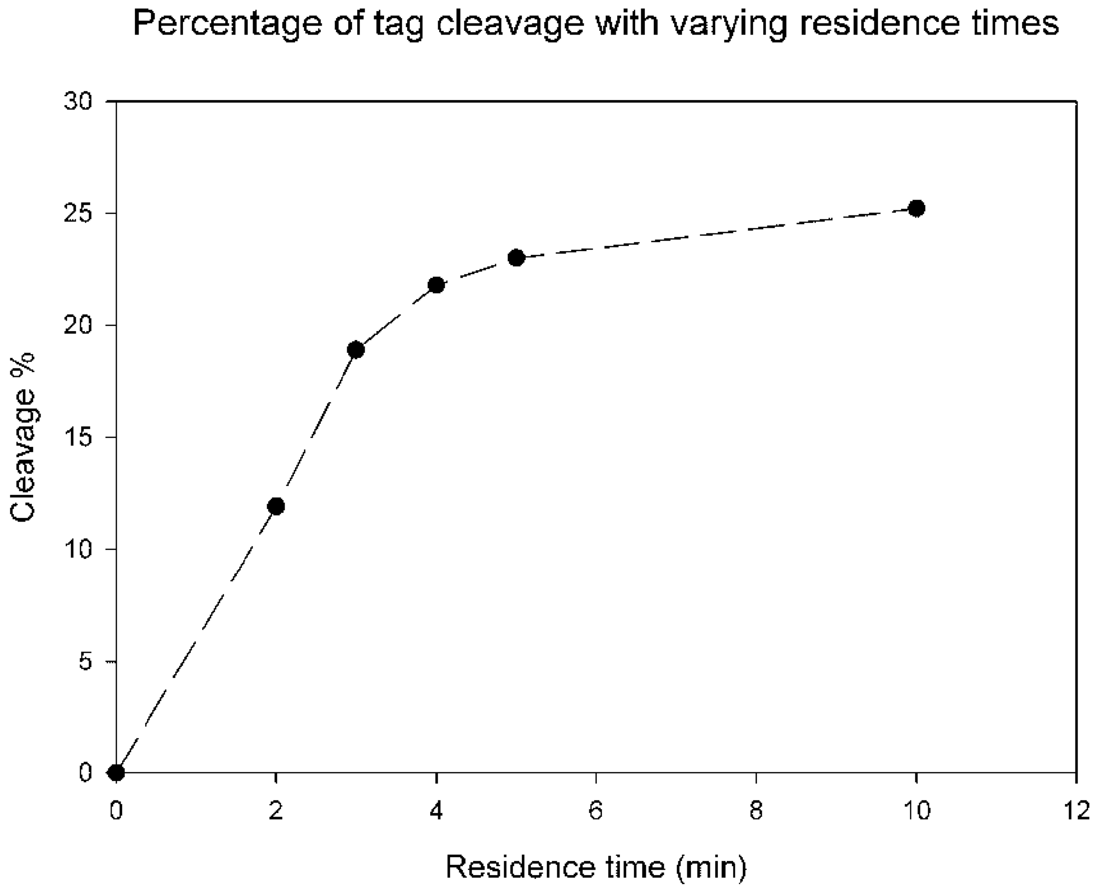
Figure 22:
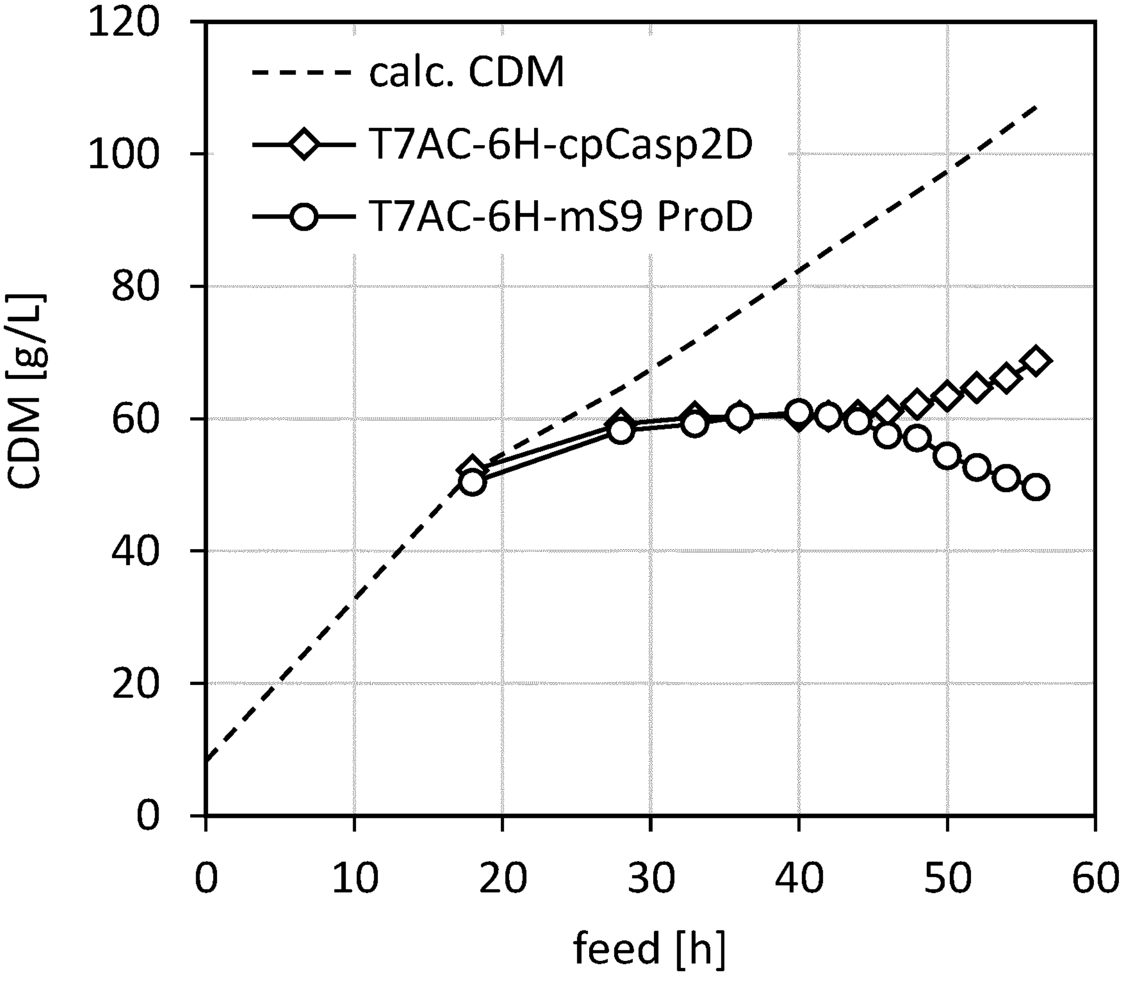
Figure 24:
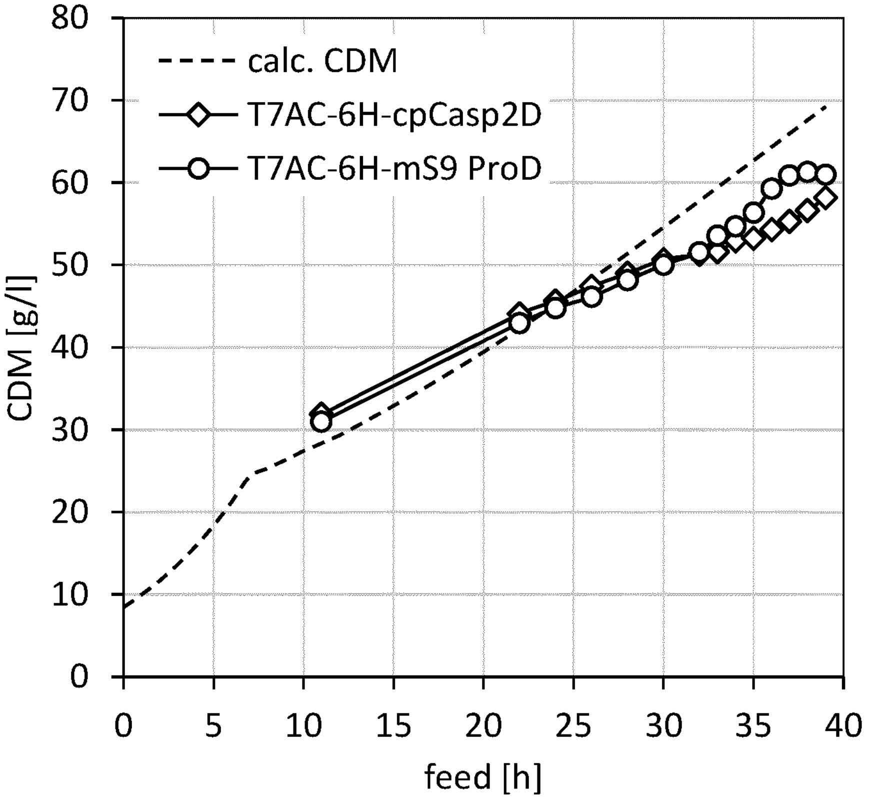
Figure 25:
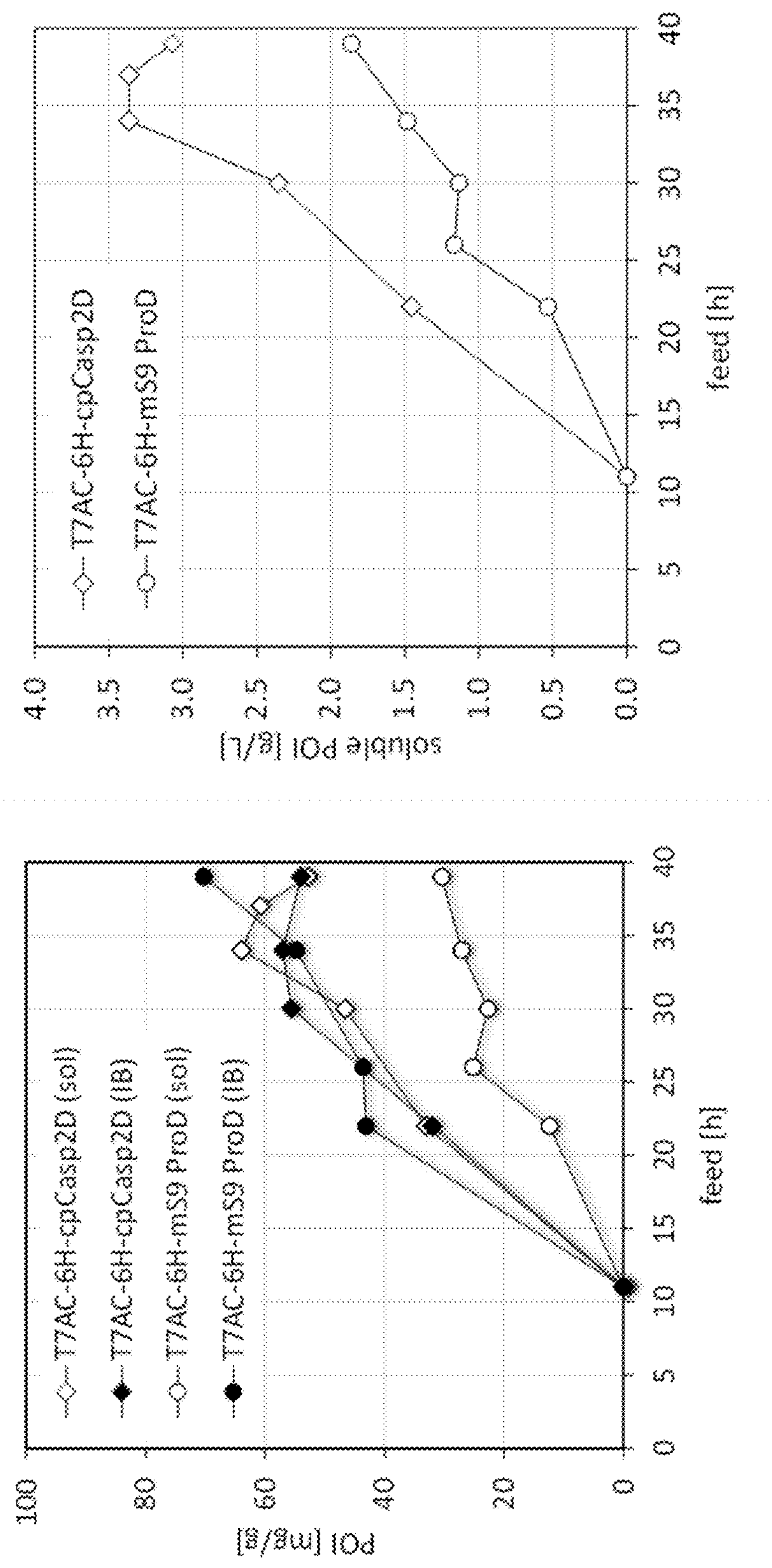
Figure 26:
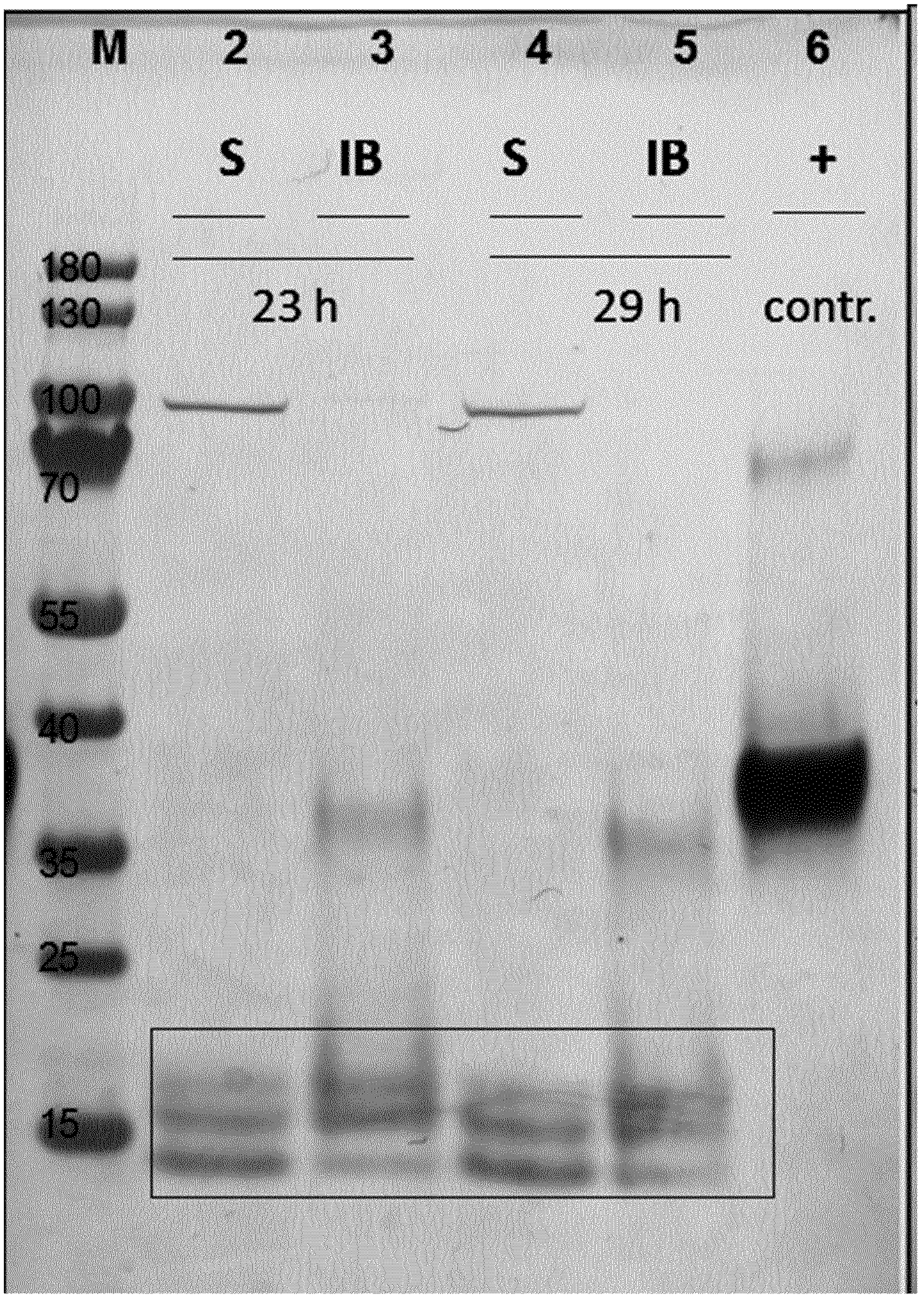
FIG. 26 shows lab-scale fermentations of *E. coli* BL21 (DE3)(pET30a_wt caspase-2-6H(SEQ ID NO:6)): expression of soluble and insoluble caspase-2-6H (SEQ ID NO:6) is shown in the course of time (23 h and 29 h after induction). At beginning of feed, expression was induced with IPTG (0.5 μmol/g CDM).
Figure 27:
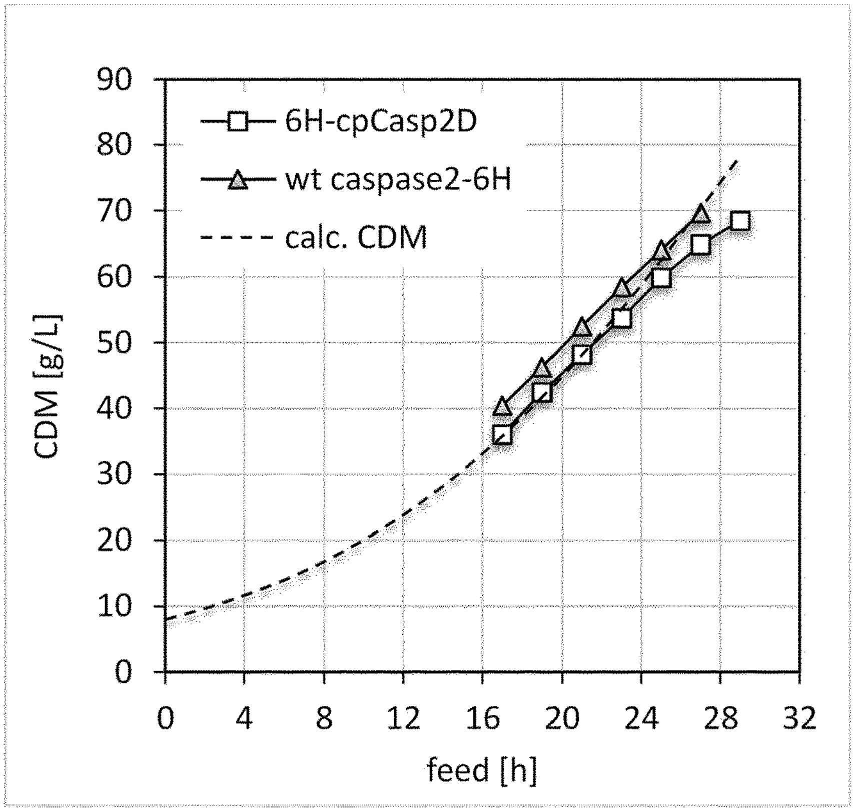
FIG. 27 shows lab-scale fermentations of *E. coli* BL21 (DE3)(pET30a_wt caspase-2-6H) (SEQ ID NO:6) and BL21(DE3) (pET30a_6H-cpCasp2D)(SEQ ID NO:6): biomass course.
Figure 28:
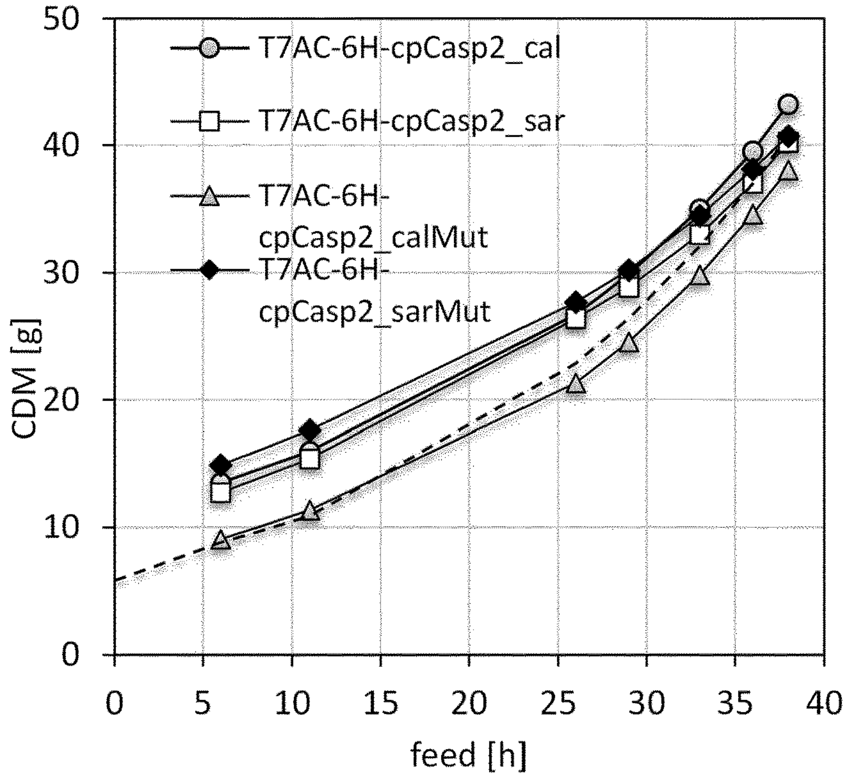
Figure 29:
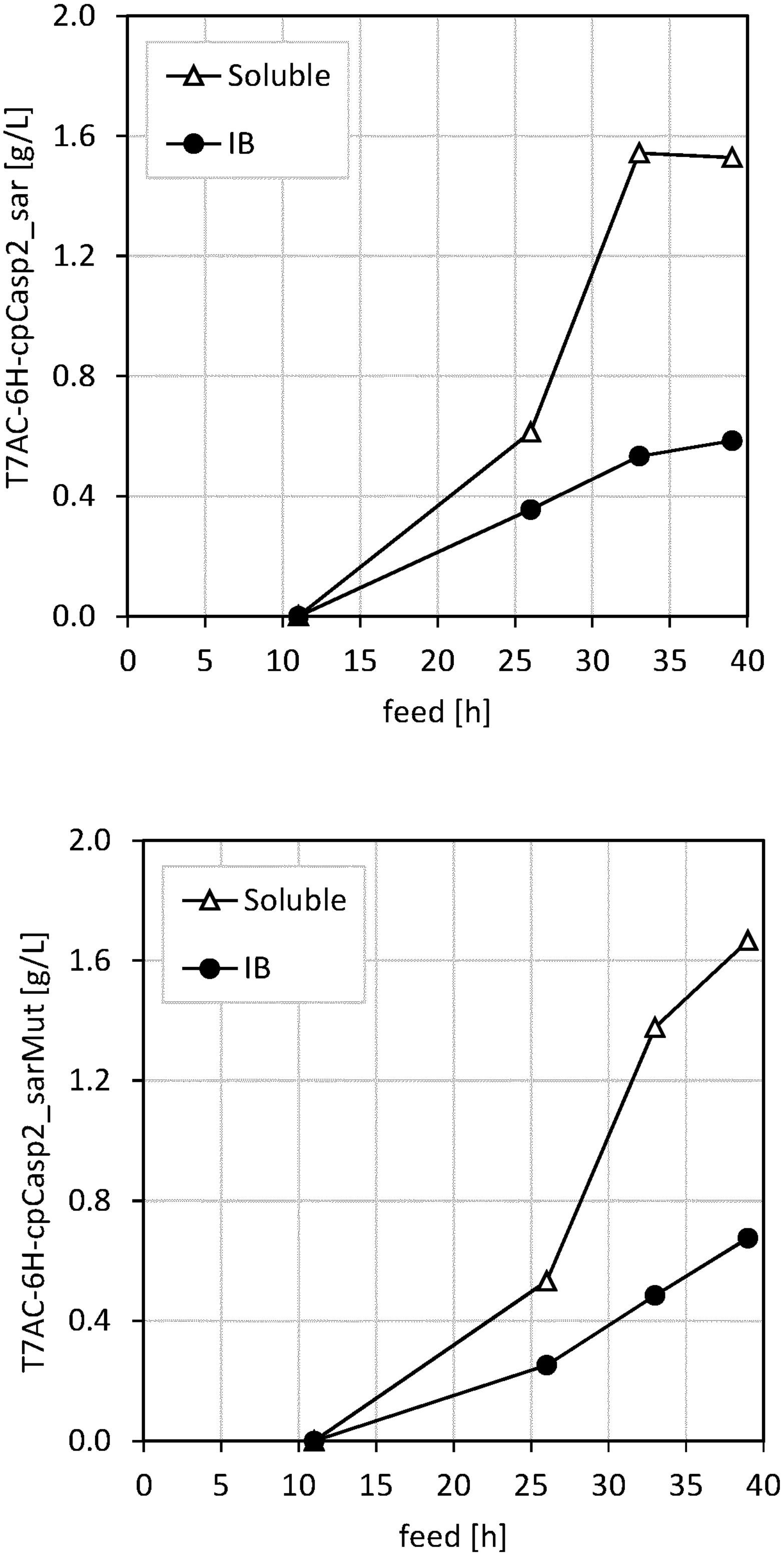

The amount of cleavage varied with residence time (See FIG. 21). At low residence times, less cleavage was observed, due to mass transfer limitation of the stationary phase.

Example 23: Complete Downstream Process for the Purification of Proteins of Interest (PoIs)

Production of the Protein of Interest, hFGF-2

The protein was produced in a fermentation as described in Example 19, section 19.2 as a fusion protein, 6H_GSG_VDVAD_hFGF-2 (SEQ ID NO:32).

Cell Harvest of the Fusion Protein, Cell Disintegration and Clarification

The cell mass was harvested by centrifugation at 18,590 rcf for 15 minutes. The pellet was stored at −80° C. until further use and the supernatant was discarded. The *E. coli* harvest was solubilized using homogenization buffer: 50 mM NaPO4, 500 mM NaCl, pH 7.0. The cells were re suspended at a concentration of 30 g cell dry mass per L. Cell lysis was performed through high pressure homogenization (Panda PLUS 2000, Gea, Dusseldorf, Germany) with two passages at 1000 bar for 6H_GSG_VDVAD_hFGF-2 (SEQ ID NO:32). The homogenate was centrifuged (Beckman Coulter GmbH, Vienna, Austria) at 18,590 rcf for 2 hours. The supernatant was filtered through a 0.2 μm membrane (Kleenpak™ Capsule with Fluorodyne® EX Grade EDF Membrane, Pall, New York, USA).

Chromatographic Purification Steps

Preparative chromatography runs were performed on an Akta Pure 25 system, equipped with a S9 sample pump (GE Healthcare, Uppsala, Sweden).

6H_GSG_VDVAD_hFGF-2 (SEQ ID NO:32) was captured on a Ni-Sepharose 6 Fast Flow column equilibrated with 50 mM NaPO4, 500 mM NaCl, 5 mM imidazole, pH 7.0. The imidazole concentration of the clarified supernatant was adjusted to 5 mM using a solution of 8 M imidazole. The residence time throughout the capture step was 2 minutes. After sample application, the column was washed for 15 CV with equilibration buffer and 6H_GSG_VDVAD_hFGF-2 (SEQ ID NO:32) was eluted using a linear gradient for 5 CV with elution buffer, 50 mM NaPO4, 500 mM NaCl, 500 mM imidazole, pH 7.0, followed by a 5 CV hold step. The tagged POI (fusion protein) eluted in the linear portion of the gradient. A 30-minute CIP cycle using 0.1 M NaOH was used after elution.

The eluate was buffer exchanged using UF/DF using a membrane with a nominal 5 kDa cut-off in Amicon Ultra spin vials (Merck). 5 volumes were exchanged in a discontinuous fashion, until the imidazole concentration was reduced to 5 mM. The buffer exchanged product pool was digested using a 1:100 (w/w/) dilution of T7AC-&H cp caspase-2D (produced as described in Example 18, sections 18.1 and 18.2) per fusion protein at room temperature for 4 hours, to ensure full cleavage of the tag.

This solution (the enzymatic tag removal pool) was loaded on the subtractive IMAC step, using the same column and buffers as before. The hFGF-2 product (which was cleaved by the cp-caspase-2 variant in the step before from the fusion protein) eluted in the flow-through of the chromatographic run. After a wash step with equilibration buffer for 5 CV, the remaining impurities and tagged enzyme were eluted using a 5 CV step gradient with elution buffer. The flow-through was pooled and analyzed:

HCP ELISA, dsDNA Quantification and Endotoxin Assay

The analytical assays for HCP determination via ELISA, dsDNA quantification via PicoGreen assay and Endotoxin quantification via recombinant Factor C assay were performed as previously described by Sauer et al. 2019. A two-step process for capture and purification of human basic fibroblast growth factor from *E. coli* homogenate: Yield versus endotoxin clearance. Protein Expr Purif, 153, 70-82. doi:10.1016/j.pep.2018.08.009.

Mass Spectrometric Analysis

For intact mass analysis, the proteins were directly injected to a LC-ESI-MS system (LC: Dionex Ultimate 3000 LC, Thermo, Sunnyvale, California, USA). A gradient from 10 to 80% acetonitrile in 0.05% trifluoroacetic acid (using a Thermo ProSwift™ RP-4H column (0.2×250 mm)) at a flow rate of 8 μL/min was applied (30-minute gradient time). Detection was performed with a Q-TOF instrument (Bruker maXis 4G, Billerica, Massachusetts, USA) equipped with the standard ESI source in positive ion, MS mode (range: 400-3000 Da). Instrument calibration was performed using ESI calibration mixture (Agilent, Santa Clara, California, USA). Data was processed using Data Analysis 4.0 (Bruker) and the spectrum was deconvoluted by MaxEnt.

Figure 53:
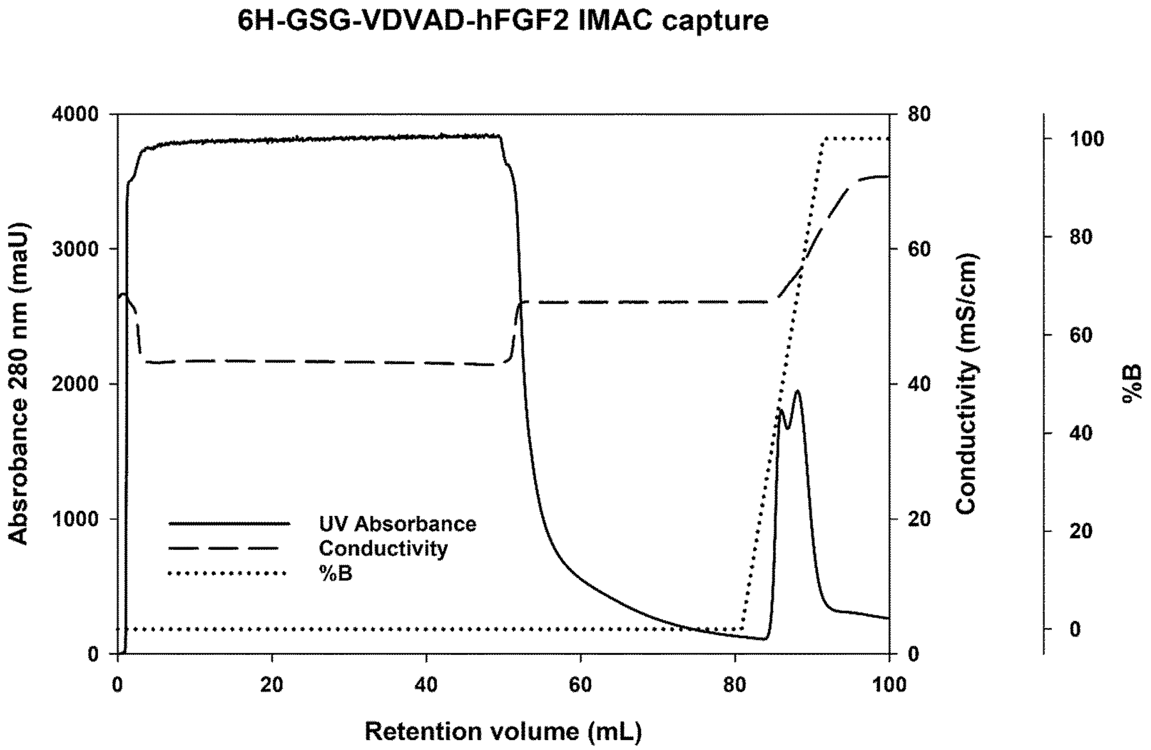

6H_GSG_VDVAD_hFGF-2 (SEQ ID NO:32) was purified using a downstream process consisting of IMAC capture step, buffer exchange, enzymatic tag removal and hFGF-2 was then purified by a subtractive IMAC step. The capture IMAC chromatogram can be seen in FIG. 53.

Figure 55:
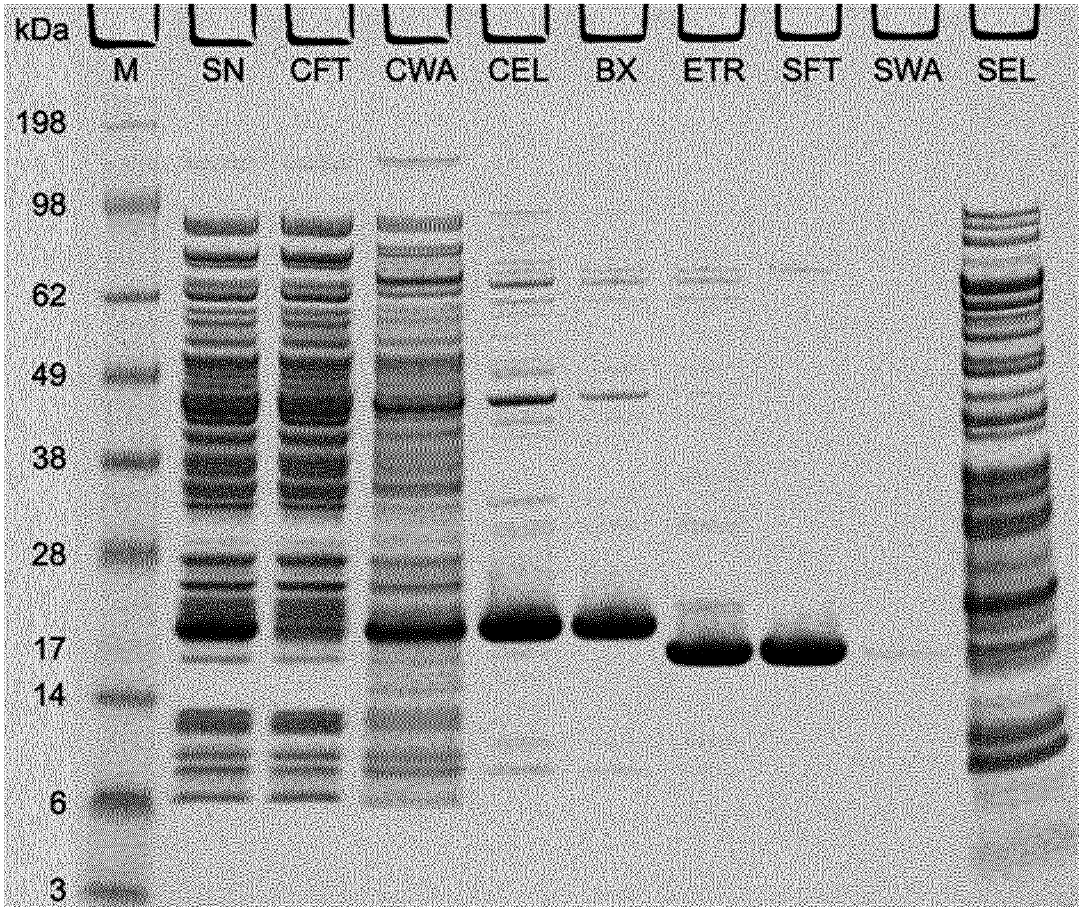

The cleavage of 6H_GSG_VDVAD_FGF2 (SEQ ID NO:32) with 6H-cpCasp2 (SEQ ID NO:6) yielded a 99% stochiometric yield, which equals a 91% mass yield, due to the loss of the tag (Table 62 and lane ETR in FIG. 55).

Figure 54:
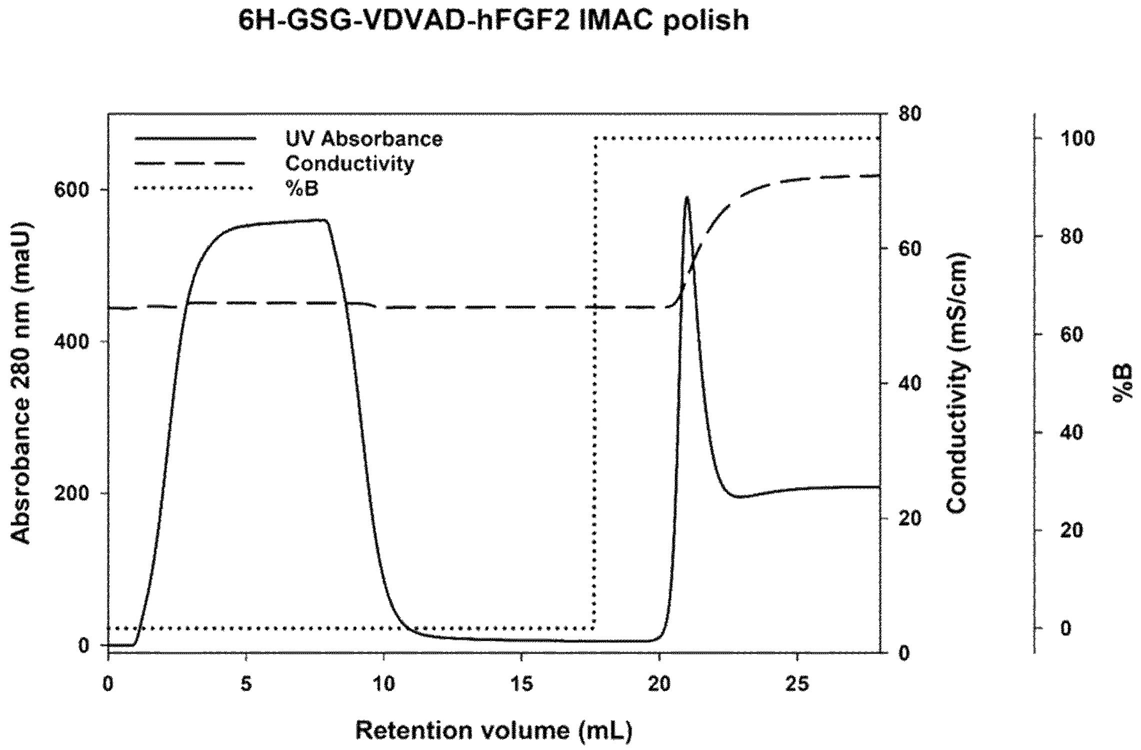

The second, subtractive IMAC step can be used to bind all previously co-purified metal binding host cell proteins, the cleaved tag and eventually residual uncleaved fusion protein as well as the 6H (SEQ ID NO:315) tagged cp-caspase-2, since the Pol, hFGF-2 does not have a his-tag after tag cleavage, shown in FIG. 54.

This process sequence is generic and can be applied to any fusion protein comprising an appropriate tag as described in Example 19, sections 19.1-19.3 (this is a tag comprising 6H (SEQ ID NO:315) and the VDVAD (SEQ ID NO:45) recognition site for a cp caspase-2 variant) and any Pol. FIG. 55 shows the increase in purity from initial cell lysis supernatant (SN), to the eluate fraction of the capture step (CEL), to the final flow-through fraction of the subtractive IMAC step (SFT). In the CEL fraction, a few host cell proteins can still be seen on the SDS-PAGE, and after tag removal and subtractive IMAC step, the POI, hFGF-2, is highly pure. The elution fraction of the subtractive IMAC step (SEL) shows all the host cell proteins that were removed from the CEL fraction after tag removal.

Table 62 shows yield and purity data for FGF2.

TABLE 62

Purity of FGF2 samples throughout platform DSP. Purity as determined by RP HPLC with experimental standard deviation. HCP as determined by ELISA. dsDNA concentration as determined by PicoGreen assay with experimental standard deviation. Endotoxin concentration as determined by recombinant assay with experimental standard deviation.

| Sample | FGF2 (mg/mL) | Yield | Purity (%) | HCP (ppm) | dsDNA (ng/mL) | Endotoxin (EU/mL) |
|---|---|---|---|---|---|---|
| Capture affinity chromatography eluate (CEL) | 2.7 | 69% | 91.7 ± 0.4 | 56 | 14,718 ± 1,125 | 1,103 ± 438 |
| Buffer exchange (BX) | 4.3 | n.d. | 82.4 ± 0.5 | 41 | 8,215 ± 307 | 2,315 ± 352 |
| Enzymatic tag removal (ETR) | 3.4 | 91%/99%† | 76.4 ± 0.3 | 20 | 7,094 ± 183 | 2,663 ± 266 |
| Subtractive affinity chromatography flow-through (SFT) | 1.9 | 85% | 97.7 ± 0.4 | 42 | 3,659 ± 148 | 984 ± 232 |
| Subtractive affinity chromatography eluate (SEL) | 0.1 | n.d. | n.d. | 934 | 402 ± 32 | n.d. |

N.d. = not determined.
CEL = capture IMAC eluate;
BX = UF/DF buffer exchange;
ETR = enzymatic tag removal;
SFT = subtractive IMAC flow-through;
SEL = subtractive IMAC eluate,
† = the stochiometric yield of the cleavage reaction was 99%, but the mass yield was 91 % due to the loss of the tag.

Figure 56:
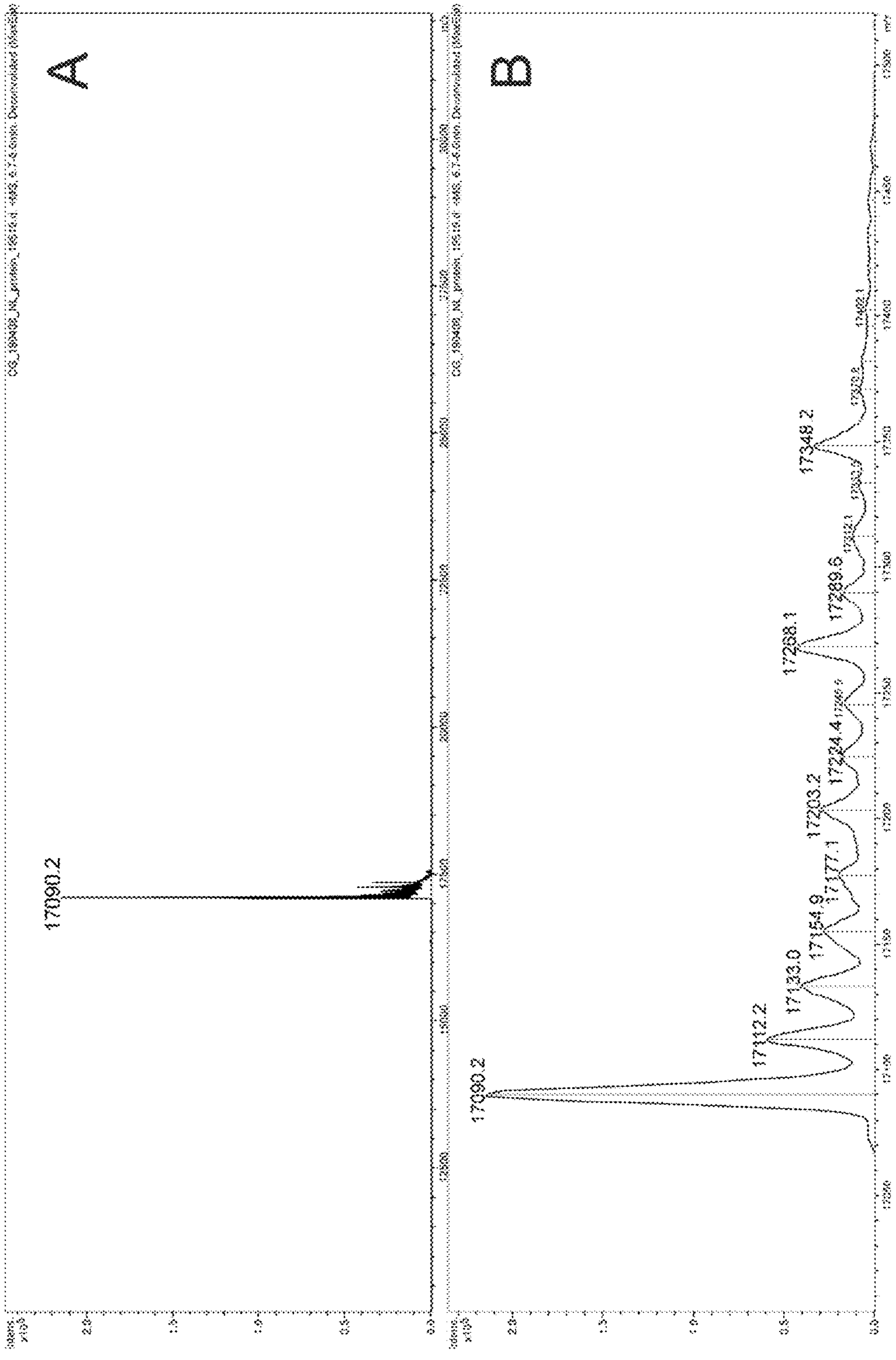
Figure 57:
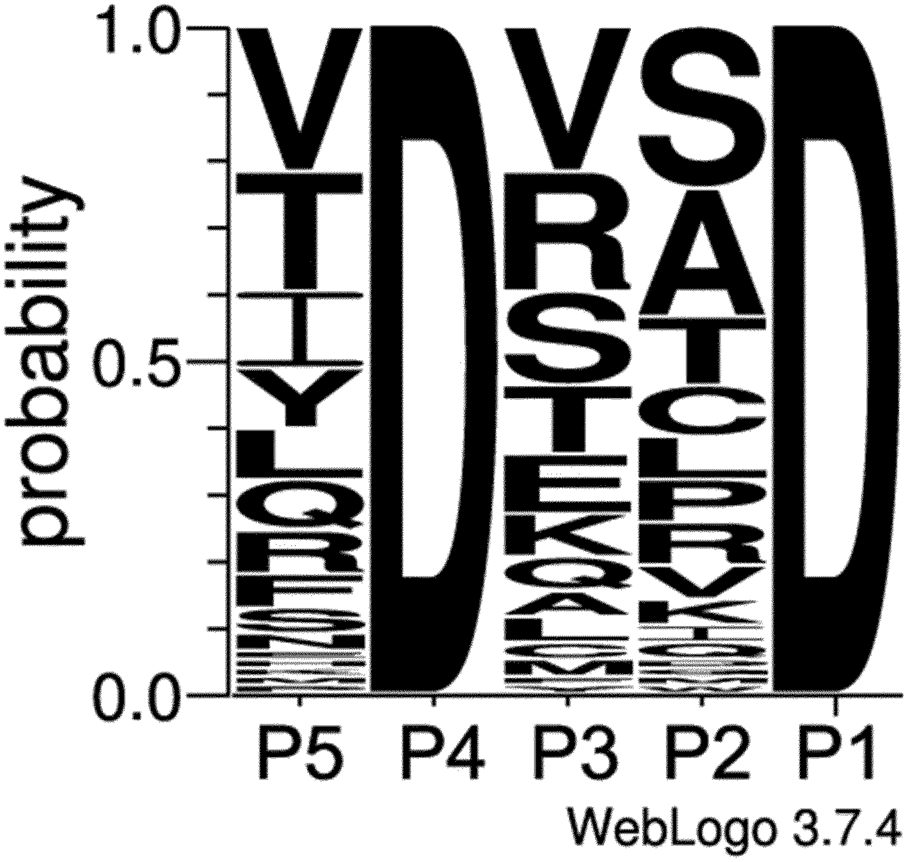

The final fraction was analyzed using LG-MS to confirm the correct mass and N-terminus. The theoretical mass of native hFGF2 is 17,090.5 Da. The major ion detected in MS had a mass of 17,090.2 Da and matches the expected value very well (FIG. 56), with a deviation of only 0.0018%, confirming the native sequence of hFGF-2 and thus the correct cleavage by the cp-caspase-2 variant between P1 of the recognition sequence VDVAD (SEQ ID NO-45) and the P1', which is the N-terminal amino acid of the Pol, hFGF-2.

REFERENCES

1. Itakura, K., Hirose, T., Crea, R., Riggs, A. D., Heyneker, H. L., Bolivar, F., and Boyer, H. W. Expression in *Escherichia coli* of a chemically synthesized gene for the hormone somatostatin. *Science* 198, 4321 (12 1977), 1056 LP-1063.
2. Goeddel, D. V., Kleid, D. G., Bolivar, F., Heyneker, H. L., Yansura, D. G., Crea, R., Hirose, T., Kraszewski, A., Itakura, K., and Riggs, A. D. Expression in *Escherichia coli* of chemically synthesized genes for human insulin. *Proceedings of the National Academy of Sciences of the United States of America* 76, 1 (1979), 106-110.
3. Khan, F., Legler, P. M., Mease, R. M., Duncan, E. H., Bergmann-Leitner, E. S., and Angov, E. Histidine affinity tags affect MSP142 structural stability and immunodominance in mice. *Biotechnology Journal* 7, 1 (2012), 133-147.
4. Cheung, R. C. F., Wong, J. H., and Ng, T. B. Immobilized metal ion affinity chromatography: A review on its applications. *Applied Microbiology and Biotechnology* 96, 6 (2012), 1411-1420.
5. Guan, D., and Chen, Z. Challenges and recent advances in affinity purification of tag-free proteins. *Biotechnology Letters* 36 (2014), 1391-1406.
6. Alnemri, E. S., Livingston, D. J., Nicholson, D. W., Salvesen, G., Thornberry, N. a., Wong, W. W., and Yuan, J. Human ICE/CED-3 protease nomenclature. *Cell* 87, 2 (1996), 171.
7. Shalini, S., Dorstyn, L., Dawar, S., and Kumar, S. Old, new and emerging functions of caspases. *Cell Death and Differentiation* 22, 4 (2015).
8. Xue, D., Shaham, S., and Horvitz, H. R. The *Caenorhabditis elegans* cell-death protein CED-3 is a cysteine protease with substrate specificities similar to those of the human CPP32 protease. *Genes and Development* 10, 9 (1996), 1073-1083.
9. Thornberry, N. A., Rano, T. A., Peterson, P., Rasper, D. M., Timkey, T., Garcia-calvo, M., Houtzager, V. M., Nordstrom, P. A., Roy, S., John, P., Chapman, K. T., Nicholson, W., Thornberry, N. A., Rano, T. A., Peterson, E. P., Rasper, D. M., Timkey, T., Garciacalvo, M., Houtzager, V. M., Nordstrom, P. A., Roy, S., Vaillancourt, J. P., Chapman, K. T., and Nicholson, D. W. A Combinatorial Approach Defines Specificities of Members of the Caspase Family and Granzyme B: Functional relationships established for key mediators of apoptosis. *The Journal of Biological Chemistry* 272, 29 (1997), 17907-17911.
10. Arama, E., Agapite, J., and Steller, H. Caspase activity and a specific cytochrome C are required for sperm differentiation in *Drosophila*. Developmental Cell 4, 5 (2003), 687-697.
11. Salmena, L., Lemmers, B., Hakem, A., Matysiak-Zablocki, E., Murakami, K., Au, P. Y. B., Berry, D. M., Tamblyn, L., Shehabeldin, A., Migon, E., Wakeham, A., Bouchard, D., Yeh, W. C., McGlade, J. C., Ohashi, P. S., and Hakem, R. Essential role for caspase 8 in T-cell homeostasis and T-cell mediated immunity. *Genes and Development* 17 (2003), 883-895.
12. Geisbrecht, E. R., and Montell, D. J. A role for *Drosophila* IAP1-mediated caspase inhibition in Rac-dependent cell migration. *Cell* 118, 1 (2004), 111-125.
13. Feeney, B., Soderblom, E. J., Goshe, M. B., and Clark, A. C. Novel protein purification system utilizing an N-terminal fusion protein and a caspase-3 cleavable linker. *Protein Expression and Purification* (2006).

14. Mertens, N. M. A. C., and Kelly, A. G. Use of caspase enzymes for maturation of engineered recombinant polypeptide fusions EP1597369B1, 2007.

15. Purbey, P. K., Jayakumar, P. C., Deepalakshmi, P. D., Patole, M. S., and Galande, S. GST fusion vector with caspase-6 cleavage site for removal of fusion tag during column purification. *BioTechniques* 38, 3 (2005), 360-366.

16. Allet, B., Hochmann, A., Martinou, I., Berger, A., Missotten, M., Antonsson, B., Sadoul, R., Martinou, J. C., and Bernasconi, L. Dissecting processing and apoptotic activity of a cysteine protease by mutant analysis. *Journal of Cell Biology* 135, 2 (1996), 479-486.

17. Kumar, P., Kumar, D., Parikh, A., Rananaware, D., Gupta, M., Singh, Y., and Nandicoori, V. K. The *Mycobacterium tuberculosis* protein kinase K modulates activation of transcription from the promoter of mycobacterial monooxygenase operon through phosphorylation of the transcriptional regulator VirS. Journal of *Biological Chemistry* 284, 17 (2009), 11090-11099.

18. Srivastava, A., Dwivedi, N., and Sau, A. K. Role of a disulphide bond in *Helicobacter pylori* arginase. *Biochemical and Biophysical Research Communications* 395, 3 (2010), 348-351.

19. Garcia-Calvo, M., Peterson, E. P., Rasper, D. M., Vaillancourt, J. P., Zamboni, R., Nicholson, D. W., and Thornberry, N. A. Purification and catalytic properties of human caspase family members. *Cell Death and Differentiation* 6 (1999), 362-369.

20. Stennicke, H. R., and Salvesen, G. S. Caspases: Preparation and Characterization. *Methods: A Companion to Methods in Enzymology* 17, 4 (1999), 313-319.

21. Boucher, D., Duclos, C., and Denault, J.-B. General In Vitro Caspase Assay Procedures. In *Caspases, Paracaspases, and Metacaspases, Methods and Protocols*, P. V. Bozhkov and G. S. Salvesen, Eds., methods in ed. Springer Science+Business Media, New York, NY, USA, 2014, pp. 3-30.

22. Timmer, J., and Salvesen, G. Caspase substrates. *Cell Death and Differentiation* 14 (2007), 66-72.

23. Walsh, J. G., Cullen, S. P., Sheridan, C., Luthi, A. U., Gerner, C., and Martin, S. J. Executioner caspase-3 and caspase-7 are functionally distinct proteases. *Proceedings of the National Academy of Sciences* 105, 35 (2008), 12815-12819.

24. Talanian, R. V., Quinlan, C., Trautz, S., Hackett, M. C., Mankovich, J. A., Banach, D., Ghayur, T., Brady, K. D., and Wong, W. W. Substrate specificities of caspase family proteases. *Journal of Biological Chemistry* 272, 15 (1997), 9677-9682.

25. Beernink, P. T., Yang, Y. R., Graf, R., King, D. S., Shah, S. S., and Schachman, H. K., Random circular permutation leading to chain disruption within and near alpha helices in the catalytic chains of aspartate transcarbamoylase: effects on assembly, stability, and function. *Protein Science* 10, 3 (2001), 528-537.

26. Schweizer, A., Briand, C., and Grütter, M. G. Crystal Structure of Caspase-2, Apical Initiator of the Intrinsic Apoptotic Pathway. *Journal of Biological Chemistry* 278, 43 (2003), 42441-42447.

The invention claimed is:

1. A single-chain circular permuted caspase-2 (cp caspase-2) comprising the following structure from N- to C-terminus:

i. a small subunit of a caspase-2; and ii. a large subunit of a caspase-2, wherein said cp caspase-2 comprises an amino acid sequence having at least 90% sequence identity to SEQ ID NO: 6, and wherein said cp caspase-2 comprises one or more amino acid substitutions increasing P1' tolerance of said cp caspase-2 compared to a cp caspase-2 without said amino acid substitutions.

2. The cp caspase-2 of claim 1 comprising:

(A)

a) one or more amino acid substitutions at positions 171, 105, 172, 282, 225, 83, 185, 255, or 285 of SEQ ID NO: 6 or any combination thereof;

b) one or more amino acid substitutions, selected from
i. Gly171, substituted with D, or an amino acid selected from the group consisting of R, K, E, Q, N, A, S, T, P, H, and Y,
ii. Glu105, substituted with V, or an amino acid selected from the group consisting of C, L, I, M, F, W, R, K, D, Q, and N,
iii. Glu172, substituted with V, or an amino acid selected from the group consisting of C, L, I, M, F, W, R, K, D, Q, and N,
iv. Asp282, substituted with E, or T, or an amino acid selected from the group consisting of R, K, Q, N, G, A, S, P, H, and Y,
v. Val225, substituted with G, or an amino acid selected from the group consisting of A, S, T, P, H, Y, C, L, I, M, F, and W,
vi. Lys83, substituted with E, or an amino acid selected from the group consisting of R, D, Q, and N,
vii. His185, substituted with A, or an amino acid selected from the group consisting of G, S, T, P, and Y,
viii. Val255, substituted with M, or an amino acid selected from the group consisting of C, L, I, F, and W, and/or
ix. Asp285, substituted with E, or Y, or an amino acid selected from the group consisting of R, K, Q, N, G, A, S, T, P, and H,
with reference to the positions of SEQ ID NO: 6;
c) amino acid substitutions at positions of SEQ ID NO: 6 selected from the group consisting of
i. His185 and Asp282;
ii. Glu105 and Asp285;
iii. Val225 and Asp282;
iv. Val225, Asp282 and Asp285;
v. Lys83, Glu105,Glu172, Val255 and Asp285;
vi. Glu105 and Gly171;
vii. Glu105 and Glu172; and
viii. Gly171 and Glu172,
wherein said cp caspase-2 has increased P1' tolerance compared to a cp caspase-2 without the respective amino acid substitution;
d) amino acid substitutions at positions of SEQ ID NO: 6 selected from the group consisting of
i. H185A and D282T substitutions;
ii. E105V and D285E substitutions;
iii. E105V, G171D, V225G and D282E substitutions;
iv. E105V, G171D, V225G, D282E and D285E substitutions;
v. K83E, E105V, E172V, V255M and D285Y substitutions;
vi. E105V and G171D substitutions;
vii. E105V and E172V substitutions; and
viii. G171 D and E172V substitutions,
wherein said cp caspase-2 has increased P1' tolerance compared to a cp caspase-2 without the respective amino acid substitution; or
e) any one or more of amino acid substitutions at positions of SEQ ID NO: 6 selected from the group consisting of G171D, E105V, E172V, D282E, D282T, V225G, K83E, H185A, V255M, D285Y and D285E; or
(B) an amino acid sequence selected from the group consisting of SEQ ID NO: 1, 13, 17, 18, 23, 24, 51, 52, 54, 70, 71, 72, 179, 180, 181, 182, 183, 184, 185, 186, 187, 188, 189, 190, 191 and 192 or an amino acid sequence having at least 99% sequence identity with any one of SEQ ID NO: 1, 13, 17, 18, 23, 24, 51, 52, 54, 70, 71, 72, 179, 180, 181, 182, 183, 184, 185, 186, 187, 188, 189, 190, 191 and 192; and
wherein said amino acid substitution increases P1' tolerance compared to a caspase-2 comprising the same sequence but not comprising said amino acid substitutions.

3. The cp caspase-2 of claim 1, further comprising:
(A) a C-terminal tag and an amino acid substitution at positions 285 and 292 of SEQ ID NO: 6;
(B) a C-terminal tag and an amino acid substitutions D285E and D292S of SEQ ID NO: 6; and/or
(C) (i) an N-terminal and/or C-terminal truncation; and/or (ii) an N-terminal and/or C-terminal extension.

4. The cp caspase-2 of claim 3, wherein the cp caspase 2 further comprises one or more linker sequences and at least one of the following conditions is met:
(A) the linker sequence:
i. consists of 1, 2, 3, 4, 5, 6, 7, 8, 9, 10, 11 or 12 amino acid residues;
ii. comprises glycine and/or serine residues; and/or
iii. is GS, GGSGG (SEQ ID NO:278), GSAGSAAGSG (SEQ ID NO:279), (GS)n, GSG or G4S;
(B) the linker sequence is a subunit-linker sequence between the small subunit and the large subunit;
(C) the linker sequence is a tag-linker sequence, linking two tags or linking a tag and the small subunit, the large subunit or the small subunit propeptide of the cp caspase-2.

5. The cp caspase-2 of claim 1, wherein the cp caspase 2 further comprises one or more C-terminal or N-terminal tags and at least one of the following conditions is met:
(A) the one or more C-terminal or N-terminal tags are selected from the group consisting of affinity tags, solubility enhancement tags and monitoring tags, wherein:
i. the affinity tag is selected from the group consisting of poly-histidine tag, poly-arginine tag, peptide substrate for antibodies, chitin binding domain, RNAse S peptide, protein A, β-galactosidase, FLAG tag, Strep II tag, streptavidin-binding peptide (SBP) tag, calmodulin-binding peptide (CBP), glutathione S-transferase (GST), maltose-binding protein (MBP), S-tag, HA tag, c-Myc tag, SUMO tag, *E. coli* thioredoxin, NusA, chitin binding domain CBD, chloramphenicol acetyl transferase CAT, LysRS, ubiquitin, calmodulin, and lambda gpV; and/or
ii. the solubility enhancement tag is selected from the group consisting of T7C, T7B, T7B1, T7B2, T7B3, T7B4, T7B5, T7B6, T7B7, T7B8, T7B9, T7B10, T7B11, T7B12, T7B13, T7A, T7A1, T7A2, T7A3, T7A4, T7A5, T3, N1, N2, N3, N4, N5, N6, N7, T7AC, calmodulin-binding peptide (CBP), DsbA, DsbC, poly Arg, poly Lys, G B1 domain, protein D, Z domain of Staphylococcal protein A, and thioredoxin; and/or
iii. the monitoring tag is selected from the group consisting of m-Cherry, GFP and f-Actin;
(B) the cp caspase-2 further comprises more than one tag;
(C) the cp caspase-2 further comprises an affinity tag and a solubility enhancement tag;
(D) the cp caspase-2 further comprises an affinity tag and a solubility enhancement tag, wherein the affinity tag is a hexahistidine tag and the solubility enhancement tag is a T7AC or a T7A3 tag;
(E) the cp caspase 2 further comprises one or more N-terminal tags and optionally one or more tag-linker sequences between the tags or between a tag and the N-terminus of the small subunit or between a tag and a propeptide of a small caspase-2 subunit fused to the N-terminus of the small subunit;

(F) the cp caspase 2 further comprises one or more C-terminal tags and optionally one or more tag-linker sequences between the tags or between a tag and the C-terminus of the large subunit.

6. A functionally active variant of the cp caspase-2 of claim 1, wherein (A) i. the small subunit of the cp caspase-2 comprises a) a first conserved region of the active center with at least 37.5% amino acid sequence identity to SEQ ID No. 177 (1st consensus: AAMRNTKR) or 100% sequence identity to XXXRNTXX (SEQ ID No. 200), wherein X is any amino acid, b) a second conserved region of the active center with at least 61.5% amino acid sequence identity to SEQ ID No. 178 (2nd consensus: EGYAPGTEFHRCK) or 100% sequence identity to EGXXPGXXXHRCK (SEQ ID No. 194), wherein X is any amino acid, and ii. the large subunit of the cp caspase-2 comprises a) a third conserved region of the active center with at least 25.0% amino acid sequence identity to SEQ ID No. 174 (3rd consensus: G-EKDLEFRSGGDVDH) or 100% sequence identity to X-XXXLXXRXGXXXDX (SEQ ID No. 195), wherein X is any amino acid, b) a fourth conserved region of the active center with at least 53.3% amino acid sequence identity to SEQ ID No. 175 (4th consensus: LLSHGVEGGXYGVDG) or 100% sequence identity to XXSHGXXGXX-YGXDG (SEQ ID No. 196), wherein X is any amino acid, and c) a fifth conserved region of the active center with at least 50.0% amino acid sequence identity to SEQ ID No. 176 (5th consensus: QACRGDET) or 100% sequence identity to QACXGXXX (SEQ ID No. 197), wherein X is any amino acid; or (B) the functionally active variant comprises at least 91, 92, 93, 94, 95, 96, 97 or 98% sequence identity to the cp caspase-2 as set forth in SEQ ID NO: 6; or (C) the functionally active variant comprises at least 91, 92, 93, 94, 95, 96, 97 or 98% sequence identity to SEQ ID NO: 9, 6, 14, 15, 16, 80, 88, 25, 26, 27, 28, 29, 30, 35, 39, 41, 73, 74, 75, 76, 77, 81, 82 or 83.

7. The cp caspase-2 of claim 1, wherein:

i. the small subunit is selected from the group consisting of SEQ ID NO: 3, SEQ ID NO: 91, SEQ ID NO: 94, SEQ ID NO: 97, SEQ ID NO: 100, SEQ ID NO: 103, SEQ ID NO: 106, SEQ ID NO: 109, SEQ ID NO: 115 and SEQ ID NO: 118, or ii. the large subunit is selected from the group consisting of SEQ ID NO: 4, SEQ ID NO: 90, SEQ ID NO: 93 and SEQ ID NO: 96.

8. The cp caspase-2 of claim 1, wherein said cp caspase-2 is recruited by a recognition site for proteolytic cleavage, comprising 5 amino acids of the sequence PS P4 P3 P2 P1, wherein P1 can be any amino acid, optionally it is D or E, P2 can be any amino acid, optionally it is A, P3 can be any amino acid, optionally it is V, P4 can be any amino acid, optionally it is D, and P5 can be any amino acid, optionally it is V.

9. An isolated nucleotide sequence encoding the cp caspase-2 of claim 1.

10. A vector comprising the nucleotide sequence of claim 9 or an expression cassette comprising the nucleotide sequence of claim 9 operably linked to regulatory elements.

11. A host cell or a host cell line expressing the cp caspase-2 of claim 1, wherein the host cells are selected from the group consisting of bacterial cells, yeast cells, insect cells, mammalian cells and plant cells.

12. An expression system comprising (i) an expression vector, said vector comprising an isolated nucleotide sequence encoding the cp caspase-2 of claim 1, or an expression cassette, said expression cassette comprising an isolated nucleotide sequence encoding the cp caspase-2 of claim 1 operably linked to regulatory elements, and (ii) a host cell expressing the cp caspase-2 of claim 1, wherein the host cell is selected from the group consisting of bacterial cells, yeast cells, insect cells, mammalian cells and plant cells.

13. A kit comprising the cp caspase-2 of claim 1 and an expression vector, said expression vector comprising a polynucleotide encoding a protein tag for enhanced expression of a protein of interest, wherein the protein tag comprises a solubility enhancement tag and the amino acid sequence VDVAD (SEQ ID NO:45), and wherein the sequence VDVAD is located at the C-terminus of the protein tag.

* * * * *

SEQUENCE LISTING

```
<160> NUMBER OF SEQ ID NOS: 323

<210> SEQ ID NO 1
<211> LENGTH: 292
<212> TYPE: PRT
<213> ORGANISM: Artificial Sequence
<220> FEATURE:
<223> OTHER INFORMATION: caspase 2

<400> SEQUENCE: 1

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
```

-continued

```
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Asp
    290


<210> SEQ ID NO 2
<211> LENGTH: 14
<212> TYPE: PRT
<213> ORGANISM: Artificial Sequence
<220> FEATURE:
<223> OTHER INFORMATION: ss propeptide
<220> FEATURE:
<221> NAME/KEY: MOD_RES
<222> LOCATION: (14)..(14)
<223> OTHER INFORMATION: X can be any amino acid except D or E

<400> SEQUENCE: 2

Gly Lys Asn His Ala Gly Ser Pro Gly Cys Glu Glu Ser Xaa
1               5                   10


<210> SEQ ID NO 3
<211> LENGTH: 105
<212> TYPE: PRT
<213> ORGANISM: Homo sapiens

<400> SEQUENCE: 3

Ala Gly Lys Glu Lys Leu Pro Lys Met Arg Leu Pro Thr Arg Ser Asp
1               5                   10                  15

Met Ile Cys Gly Tyr Ala Cys Leu Lys Gly Thr Ala Ala Met Arg Asn
            20                  25                  30

Thr Lys Arg Gly Ser Trp Tyr Ile Glu Ala Leu Ala Gln Val Phe Ser
        35                  40                  45

Glu Arg Ala Cys Asp Met His Val Ala Asp Met Leu Val Lys Val Asn
    50                  55                  60

Ala Leu Ile Lys Asp Arg Glu Gly Tyr Ala Pro Gly Thr Glu Phe His
65                  70                  75                  80

Arg Cys Lys Glu Met Ser Glu Tyr Cys Ser Thr Leu Cys Arg His Leu
                85                  90                  95

Tyr Leu Phe Pro Gly His Pro Pro Thr
            100                 105


<210> SEQ ID NO 4
<211> LENGTH: 157
<212> TYPE: PRT
```

<213> ORGANISM: Homo sapiens

<400> SEQUENCE: 4

```
Gly Pro Val Cys Leu Gln Val Lys Pro Cys Thr Pro Gly Phe Tyr Gln
1               5                   10                  15

Thr His Phe Gln Leu Ala Tyr Arg Leu Gln Ser Arg Pro Arg Gly Leu
            20                  25                  30

Ala Leu Val Leu Ser Asn Val His Phe Thr Gly Glu Lys Glu Leu Glu
        35                  40                  45

Phe Arg Ser Gly Gly Asp Val Asp His Ser Thr Leu Val Thr Leu Phe
    50                  55                  60

Lys Leu Leu Gly Tyr Asp Val Arg Val Leu Cys Asp Gln Thr Ala Gln
65                  70                  75                  80

Glu Met Gln Glu Lys Leu Gln Asn Phe Ala Gln Leu Pro Ala His Arg
                85                  90                  95

Val Thr Asp Ser Cys Ile Val Ala Leu Leu Ser His Gly Val Glu Gly
            100                 105                 110

Ala Ile Tyr Gly Val Asp Gly Lys Leu Leu Gln Leu Gln Glu Val Phe
        115                 120                 125

Gln Leu Phe Asp Asn Ala Asn Cys Pro Ser Leu Gln Asn Lys Pro Lys
    130                 135                 140

Met Phe Phe Ile Gln Ala Cys Arg Gly Asp Glu Thr Asp
145                 150                 155
```

<210> SEQ ID NO 5
<211> LENGTH: 7
<212> TYPE: PRT
<213> ORGANISM: Homo sapiens

<400> SEQUENCE: 5

```
Arg Gly Val Asp Gln Gln Asp
1               5
```

<210> SEQ ID NO 6
<211> LENGTH: 292
<212> TYPE: PRT
<213> ORGANISM: Artificial Sequence
<220> FEATURE:
<223> OTHER INFORMATION: caspase 2

<400> SEQUENCE: 6

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125
```

-continued

```
Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290
```

```
<210> SEQ ID NO 7
<211> LENGTH: 879
<212> TYPE: DNA
<213> ORGANISM: Artificial Sequence
<220> FEATURE:
<223> OTHER INFORMATION: caspase 2

<400> SEQUENCE: 7

atgcaccatc atcaccatca tggcaaaaat catgcaggta gtccgggttg tgaagaaagc      60

gcagcaggta aagaaaaact gccgaaaatg cgtctgccga cccgtagcga tatgatttgt     120

ggttatgcat gtctgaaagg caccgcagca atgcgtaata ccaaacgtgg tagctggtat     180

attgaagcac tggcacaggt ttttagcgaa cgtgcatgtg atatgcatgt tgcagatatg     240

ctggttaaag tgaacgccct gattaaagat cgtgaaggtt atgcaccggg tacagaattt     300

catcgttgta aagaaatgag cgagtattgt agcaccctgt gtcgtcatct gtacctgttt     360

ccgggtcatc ctccgaccgg atccggtccg gtttgtctgc aggttaaacc gtgtacaccg     420

gaattttatc agacccattt tcagctggca tatcgtctgc agagccgtcc gcgtggtctg     480

gcactggttc tgagcaatgt tcattttacc ggtgaaaaag aactggaatt tcgtagcggt     540

ggtgatgttg atcatagtac cctggttacc ctgtttaaac tgctgggtta tgacgttcat     600

gttctgtgtg atcagaccgc acaagaaatg caagagaaac tgcagaattt tgcacagctg     660

cctgcacatc gtgttaccga tagctgtatt gttgcactgc tgagccatgg tgttgaaggt     720

gcaatttatg gtgtggatgg caaactgctg caactgcaag aagtgtttca gctgtttgat     780

aatgcaaatt gtccgagcct gcagaataaa ccgaaaatgt tttttatcca ggcctgccgt     840

ggtgatgaaa ccgatcgtgg tgttgatcag caggattaa                            879


<210> SEQ ID NO 8
<211> LENGTH: 858
<212> TYPE: DNA
<213> ORGANISM: Artificial Sequence
<220> FEATURE:
```

<223> OTHER INFORMATION: caspase 2

<400> SEQUENCE: 8

```
atgggcaaaa atcatgcagg tagtccgggt tgtgaagaaa gcgcagcagg taaagaaaaa     60
ctgccgaaaa tgcgtctgcc gacccgtagc gatatgattt gtggttatgc atgtctgaaa    120
ggcaccgcag caatgcgtaa taccaaacgt ggtagctggt atattgaagc actggcacag    180
gtttttagcg aacgtgcatg tgatatgcat gttgcagata tgctggttaa agtgaacgcc    240
ctgattaaag atcgtgaagg ttatgcaccg ggtacagaat ttcatcgttg taaagaaatg    300
agcgagtatt gtagcaccct gtgtcgtcat ctgtacctgt ttccgggtca tcctccgacc    360
ggatccggtc cggtttgtct gcaggttaaa ccgtgtacac cggaatttta tcagacccat    420
tttcagctgg catatcgtct gcagagccgt ccgcgtggtc tggcactggt tctgagcaat    480
gttcatttta ccggtgaaaa agaactggaa tttcgtagcg gtggtgatgt tgatcatagt    540
accctggtta ccctgtttaa actgctgggt tatgacgttc atgttctgtg tgatcagacc    600
gcacaagaaa tgcaagagaa actgcagaat tttgcacagc tgcctgcaca tcgtgttacc    660
gatagctgta ttgttgcact gctgagccat ggtgttgaag gtgcaattta tggtgtggat    720
ggcaaactgc tgcaactgca agaagtgttt cagctgtttg ataatgcaaa ttgtccgagc    780
ctgcagaata aaccgaaaat gtttttttatc caggcctgcc gtggtgatga aaccgatcgt    840
ggtgttgatc agcaggat                                                  858
```

<210> SEQ ID NO 9
<211> LENGTH: 286
<212> TYPE: PRT
<213> ORGANISM: Artificial Sequence
<220> FEATURE:
<223> OTHER INFORMATION: caspase 2

<400> SEQUENCE: 9

```
Met Gly Lys Asn His Ala Gly Ser Pro Gly Cys Glu Glu Ser Ala Ala
1               5                   10                  15

Gly Lys Glu Lys Leu Pro Lys Met Arg Leu Pro Thr Arg Ser Asp Met
            20                  25                  30

Ile Cys Gly Tyr Ala Cys Leu Lys Gly Thr Ala Ala Met Arg Asn Thr
        35                  40                  45

Lys Arg Gly Ser Trp Tyr Ile Glu Ala Leu Ala Gln Val Phe Ser Glu
    50                  55                  60

Arg Ala Cys Asp Met His Val Ala Asp Met Leu Val Lys Val Asn Ala
65                  70                  75                  80

Leu Ile Lys Asp Arg Glu Gly Tyr Ala Pro Gly Thr Glu Phe His Arg
                85                  90                  95

Cys Lys Glu Met Ser Glu Tyr Cys Ser Thr Leu Cys Arg His Leu Tyr
            100                 105                 110

Leu Phe Pro Gly His Pro Pro Thr Gly Ser Gly Pro Val Cys Leu Gln
        115                 120                 125

Val Lys Pro Cys Thr Pro Glu Phe Tyr Gln Thr His Phe Gln Leu Ala
    130                 135                 140

Tyr Arg Leu Gln Ser Arg Pro Arg Gly Leu Ala Leu Val Leu Ser Asn
145                 150                 155                 160

Val His Phe Thr Gly Glu Lys Glu Leu Glu Phe Arg Ser Gly Gly Asp
                165                 170                 175

Val Asp His Ser Thr Leu Val Thr Leu Phe Lys Leu Leu Gly Tyr Asp
            180                 185                 190
```

-continued

```
Val His Val Leu Cys Asp Gln Thr Ala Gln Glu Met Gln Glu Lys Leu
        195                 200                 205

Gln Asn Phe Ala Gln Leu Pro Ala His Arg Val Thr Asp Ser Cys Ile
    210                 215                 220

Val Ala Leu Leu Ser His Gly Val Glu Gly Ala Ile Tyr Gly Val Asp
225                 230                 235                 240

Gly Lys Leu Leu Gln Leu Gln Glu Val Phe Gln Leu Phe Asp Asn Ala
                245                 250                 255

Asn Cys Pro Ser Leu Gln Asn Lys Pro Lys Met Phe Phe Ile Gln Ala
            260                 265                 270

Cys Arg Gly Asp Glu Thr Asp Arg Gly Val Asp Gln Gln Asp
        275                 280                 285


<210> SEQ ID NO 10
<211> LENGTH: 1308
<212> TYPE: DNA
<213> ORGANISM: Homo sapiens

<400> SEQUENCE: 10

atggccgctg acaggggacg caggatattg ggagtgtgtg gcatgcatcc tcatcatcag      60

gaaactctaa aaaagaaccg agtggtgcta gccaaacagc tgttgttgag cgaattgtta     120

gaacatcttc tggagaagga catcatcacc ttggaaatga gggagctcat ccaggccaaa     180

gtgggcagtt tcagccagaa tgtggaactc ctcaacttgc tgcctaagag ggggtcccaa     240

gcttttgatg ccttctgtga agcactgagg gagaccaagc aaggccacct ggaggatatg     300

ttgctcacca ccctttctgg gcttcagcat gtactcccac cgttgagctg tgactacgac     360

ttgagtctcc cttttccggt gtgtgagtcc tgtccccttt acaagaagct ccgcctgtcg     420

acagatactg tggaacactc cctagacaat aaagatggtc ctgtctgcct tcaggtgaag     480

ccttgcactc ctgaatttta tcaaacacac ttccagctgg catataggtt gcagtctcgg     540

cctcgtggcc tagcactggt gttgagcaat gtgcacttca ctggagagaa agaactggaa     600

tttcgctctg gaggggatgt ggaccacagt actctagtca ccctcttcaa gcttttgggc     660

tatgacgtcc atgttctatg tgaccagact gcacaggaaa tgcaagagaa actgcagaat     720

tttgcacagt tacctgcaca ccgagtcacg gactcctgca tcgtggcact cctctcgcat     780

ggtgtggagg gcgccatcta tggtgtggat gggaaactgc tccagctcca agaggttttt     840

cagctctttg acaacgccaa ctgcccaagc ctacagaaca aaccaaaaat gttcttcatc     900

caggcctgcc gtggagatga gactgatcgt ggggttgacc aacaagatgg aaagaaccac     960

gcaggatccc ctgggtgcga ggagagtgat gccggtaaag aaaagttgcc gaagatgaga    1020

ctgcccacgc gctcagacat gatatgcggc tatgcctgcc tcaaagggac tgccgccatg    1080

cggaacacca aacgaggttc ctggtacatc gaggctcttg ctcaagtgtt ttctgagcgg    1140

gcttgtgata tgcacgtggc cgacatgctg gttaaggtga acgcacttat caaggatcgg    1200

gaaggttatg ctcctggcac agaattccac cggtgcaagg aaatgtctga atactgcagc    1260

actctgtgcc gccacctcta cctgttccca ggacaccctc ccacatga                 1308


<210> SEQ ID NO 11
<211> LENGTH: 452
<212> TYPE: PRT
<213> ORGANISM: Homo sapiens

<400> SEQUENCE: 11
```

-continued

```
Met Ala Ala Pro Ser Ala Gly Ser Trp Ser Thr Phe Gln His Lys Glu
1               5                   10                  15

Leu Met Ala Ala Asp Arg Gly Arg Arg Ile Leu Gly Val Cys Gly Met
            20                  25                  30

His Pro His His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Val Gly Ser
65                  70                  75                  80

Phe Ser Gln Asn Val Glu Leu Leu Asn Leu Leu Pro Lys Arg Gly Pro
                85                  90                  95

Gln Ala Phe Asp Ala Phe Cys Glu Ala Leu Arg Glu Thr Lys Gln Gly
            100                 105                 110

His Leu Glu Asp Met Leu Leu Thr Thr Leu Ser Gly Leu Gln His Val
        115                 120                 125

Leu Pro Pro Leu Ser Cys Asp Tyr Asp Leu Ser Leu Pro Phe Pro Val
    130                 135                 140

Cys Glu Ser Cys Pro Leu Tyr Lys Lys Leu Arg Leu Ser Thr Asp Thr
145                 150                 155                 160

Val Glu His Ser Leu Asp Asn Lys Asp Gly Pro Val Cys Leu Gln Val
                165                 170                 175

Lys Pro Cys Thr Pro Glu Phe Tyr Gln Thr His Phe Gln Leu Ala Tyr
            180                 185                 190

Arg Leu Gln Ser Arg Pro Arg Gly Leu Ala Leu Val Leu Ser Asn Val
        195                 200                 205

His Phe Thr Gly Glu Lys Glu Leu Glu Phe Arg Ser Gly Gly Asp Val
    210                 215                 220

Asp His Ser Thr Leu Val Thr Leu Phe Lys Leu Leu Gly Tyr Asp Val
225                 230                 235                 240

His Val Leu Cys Asp Gln Thr Ala Gln Glu Met Gln Glu Lys Leu Gln
                245                 250                 255

Asn Phe Ala Gln Leu Pro Ala His Arg Val Thr Asp Ser Cys Ile Val
            260                 265                 270

Ala Leu Leu Ser His Gly Val Glu Gly Ala Ile Tyr Gly Val Asp Gly
        275                 280                 285

Lys Leu Leu Gln Leu Gln Glu Val Phe Gln Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Ala Gly Ser Pro Gly Cys Glu Glu Ser Asp Ala Gly Lys Glu Lys
            340                 345                 350

Leu Pro Lys Met Arg Leu Pro Thr Arg Ser Asp Met Ile Cys Gly Tyr
        355                 360                 365

Ala Cys Leu Lys Gly Thr Ala Ala Met Arg Asn Thr Lys Arg Gly Ser
    370                 375                 380

Trp Tyr Ile Glu Ala Leu Ala Gln Val Phe Ser Glu Arg Ala Cys Asp
385                 390                 395                 400

Met His Val Ala Asp Met Leu Val Lys Val Asn Ala Leu Ile Lys Asp
                405                 410                 415

Arg Glu Gly Tyr Ala Pro Gly Thr Glu Phe His Arg Cys Lys Glu Met
```

-continued

```
                420                425                430
Ser Glu Tyr Cys Ser Thr Leu Cys Arg His Leu Tyr Leu Phe Pro Gly
        435                440                445

His Pro Pro Thr
    450

<210> SEQ ID NO 12
<211> LENGTH: 879
<212> TYPE: DNA
<213> ORGANISM: Artificial Sequence
<220> FEATURE:
<223> OTHER INFORMATION: caspase 2

<400> SEQUENCE: 12

atgcaccatc atcaccatca tggcaaaaat catgcaggta gtccgggttg tgaagaaagc      60

gcagcaggta aagaaaaact gccgaaaatg cgtctgccga cccgtagcga tatgatttgt     120

ggttatgcat gtctgaaagg caccgcagca atgcgtaata ccaaacgtgg tagctggtat     180

attgaagcac tggcacaggt ttttagcgaa cgtgcatgtg atatgcatgt tgcagatatg     240

ctggttaaag tgaacgccct gattaaagat cgtgaaggtt atgcaccggg tacagaattt     300

catcgttgta aagaaatgag cgagtattgt agcaccctgt gtcgtcatct gtacctgttt     360

ccgggtcatc ctccgaccgg atccggtccg gtttgtctgc aggttaaacc gtgtacaccg     420

gaattttatc agacccattt tcagctggca tatcgtctgc agagccgtcc gcgtggtctg     480

gcactggttc tgagcaatgt tcattttacc ggtgaaaaag aactggaatt tcgtagcggt     540

ggtgatgttg atcatagtac cctggttacc ctgtttaaac tgctgggtta tgacgttcat     600

gttctgtgtg atcagaccgc acaagaaatg caagagaaac tgcagaattt tgcacagctg     660

cctgcacatc gtgttaccga tagctgtatt gttgcactgc tgagccatgg tgttgaaggt     720

gcaatttatg gtgtggatgg caaactgctg caactgcaag aagtgtttca gctgtttgat     780

aatgcaaatt gtccgagcct gcagaataaa ccgaaaatgt tttttatcca ggcctgccgt     840

ggtgatgaaa ccgagcgtgg tgttgatcag caggattaa                           879

<210> SEQ ID NO 13
<211> LENGTH: 292
<212> TYPE: PRT
<213> ORGANISM: Artificial Sequence
<220> FEATURE:
<223> OTHER INFORMATION: caspase 2

<400> SEQUENCE: 13

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
                20                  25                  30

Pro Thr Arg Ser Asp Met Ile Cys Gly Tyr Ala Cys Leu Lys Gly Thr
            35                  40                  45

Ala Ala Met Arg Asn Thr Lys Arg Gly Ser Trp Tyr Ile Glu Ala Leu
        50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110
```

```
Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Asp
    290


<210> SEQ ID NO 14
<211> LENGTH: 285
<212> TYPE: PRT
<213> ORGANISM: Artificial Sequence
<220> FEATURE:
<223> OTHER INFORMATION: caspase 2

<400> SEQUENCE: 14

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175
```

```
Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp
        275                 280                 285


<210> SEQ ID NO 15
<211> LENGTH: 303
<212> TYPE: PRT
<213> ORGANISM: Artificial Sequence
<220> FEATURE:
<223> OTHER INFORMATION: caspase 2

<400> SEQUENCE: 15

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255
```

-continued

```
Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Ser Gly Ser Gly Trp Ser His Pro Gln Phe Glu Lys
    290                 295                 300


<210> SEQ ID NO 16
<211> LENGTH: 303
<212> TYPE: PRT
<213> ORGANISM: Artificial Sequence
<220> FEATURE:
<223> OTHER INFORMATION: caspase 2

<400> SEQUENCE: 16

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Ser Gly Ser Gly Trp Ser His Pro Gln Phe Glu Lys
    290                 295                 300


<210> SEQ ID NO 17
<211> LENGTH: 292
```

<212> TYPE: PRT
<213> ORGANISM: Artificial Sequence
<220> FEATURE:
<223> OTHER INFORMATION: caspase

<400> SEQUENCE: 17

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Thr Glu Thr Asp Arg Gly Val
        275                 280                 285

Asp Gln Gln Asp
    290

<210> SEQ ID NO 18
<211> LENGTH: 292
<212> TYPE: PRT
<213> ORGANISM: Artificial Sequence
<220> FEATURE:
<223> OTHER INFORMATION: caspase 2

<400> SEQUENCE: 18

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

```
Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp Ala Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Thr Glu Thr Asp Arg Gly Val
        275                 280                 285

Asp Gln Gln Asp
    290
```

<210> SEQ ID NO 19
<211> LENGTH: 185
<212> TYPE: PRT
<213> ORGANISM: Artificial Sequence
<220> FEATURE:
<223> OTHER INFORMATION: fusion protein

<400> SEQUENCE: 19

```
Met Arg Gly Ser His His His His His His Gly Ser Gly Val Asp Thr
1               5                   10                  15

Thr Asp Gly Ile Arg Met Arg Ala Arg Tyr Pro Ser Val Leu Asp Met
            20                  25                  30

Ala Ala Ser Arg Arg Leu Met Lys Glu Leu Glu Glu Ile Arg Lys Cys
        35                  40                  45

Gly Met Lys Asn Phe Arg Asn Ile Gln Val Asp Glu Ala Asn Leu Leu
    50                  55                  60

Thr Trp Gln Gly Leu Ile Val Pro Asp Asn Pro Pro Tyr Asp Lys Gly
65                  70                  75                  80

Ala Phe Arg Ile Glu Ile Asn Phe Pro Ala Glu Tyr Pro Phe Lys Pro
                85                  90                  95
```

```
Pro Lys Ile Thr Phe Lys Thr Lys Ile Tyr His Pro Asn Ile Asp Glu
            100                 105                 110

Lys Gly Gln Val Cys Leu Pro Val Ile Ser Ala Glu Asn Trp Lys Pro
        115                 120                 125

Ala Thr Lys Thr Asp Gln Val Ile Gln Ser Leu Ile Ala Leu Val Asn
    130                 135                 140

Asp Pro Gln Pro Glu His Pro Leu Arg Ala Asp Leu Ala Glu Glu Tyr
145                 150                 155                 160

Ser Lys Asp Arg Lys Lys Phe Cys Lys Asn Ala Glu Glu Phe Thr Lys
                165                 170                 175

Lys Tyr Gly Glu Lys Arg Pro Val Asp
            180                 185
```

<210> SEQ ID NO 20
<211> LENGTH: 154
<212> TYPE: PRT
<213> ORGANISM: Artificial Sequence
<220> FEATURE:
<223> OTHER INFORMATION: MCSI (pyrI D73E)

<400> SEQUENCE: 20

```
Met Gly Thr His Asp Asn Lys Leu Gln Val Glu Ala Ile Lys Arg Gly
1               5                   10                  15

Thr Val Ile Asp His Ile Pro Ala Gln Ile Gly Phe Lys Leu Leu Ser
            20                  25                  30

Leu Phe Lys Leu Thr Glu Thr Asp Gln Arg Ile Thr Ile Gly Leu Asn
        35                  40                  45

Leu Pro Ser Gly Glu Met Gly Arg Lys Asp Leu Ile Lys Ile Glu Asn
    50                  55                  60

Thr Phe Leu Ser Glu Asp Gln Val Glu Gln Leu Ala Leu Tyr Ala Pro
65                  70                  75                  80

Gln Ala Thr Val Asn Arg Ile Asp Asn Tyr Glu Val Val Gly Lys Ser
                85                  90                  95

Arg Pro Ser Leu Pro Glu Arg Ile Asp Asn Val Leu Val Cys Pro Asn
            100                 105                 110

Ser Asn Cys Ile Ser His Ala Glu Pro Val Ser Ser Ser Phe Ala Val
        115                 120                 125

Arg Lys Arg Ala Asn Asp Ile Ala Leu Lys Cys Lys Tyr Cys Glu Lys
    130                 135                 140

Glu Phe Ser His Asn Val Val Leu Ala Asn
145                 150
```

<210> SEQ ID NO 21
<211> LENGTH: 306
<212> TYPE: PRT
<213> ORGANISM: Artificial Sequence
<220> FEATURE:
<223> OTHER INFORMATION: MCSII (cp pyrB)

<400> SEQUENCE: 21

```
Met Thr Arg Val Gln Lys Glu Arg Leu Asp Pro Ser Glu Tyr Ala Asn
1               5                   10                  15

Val Lys Ala Gln Phe Val Leu Arg Ala Ser Asp Leu His Asn Ala Lys
            20                  25                  30

Ala Asn Met Lys Val Leu His Pro Leu Pro Arg Val Asp Glu Ile Ala
        35                  40                  45

Thr Asp Val Asp Lys Thr Pro His Ala Trp Tyr Phe Gln Gln Ala Gly
```

50 55 60

Asn Gly Ile Phe Ala Arg Gln Ala Leu Leu Ala Leu Val Leu Asn Arg
65 70 75 80

Ala Asn Pro Leu Tyr Gln Lys His Ile Ile Ser Ile Asn Asp Leu Ser
85 90 95

Arg Asp Asp Leu Asn Leu Val Leu Ala Thr Ala Ala Lys Leu Lys Ala
100 105 110

Asn Pro Gln Pro Glu Leu Leu Lys His Lys Val Ile Ala Ser Cys Phe
115 120 125

Phe Glu Ala Ser Thr Arg Thr Arg Leu Ser Phe Glu Thr Ser Met His
130 135 140

Arg Leu Gly Ala Ser Val Val Gly Phe Ser Asp Ser Ala Asn Thr Ser
145 150 155 160

Leu Gly Lys Lys Gly Glu Thr Leu Ala Asp Thr Ile Ser Val Ile Ser
165 170 175

Thr Tyr Val Asp Ala Ile Val Met Arg His Pro Gln Glu Gly Ala Ala
180 185 190

Arg Leu Ala Thr Glu Phe Ser Gly Asn Val Pro Val Leu Asn Ala Gly
195 200 205

Asp Gly Ser Asn Gln His Pro Thr Gln Thr Leu Leu Asp Leu Phe Thr
210 215 220

Ile Gln Glu Thr Gln Gly Arg Leu Asp Asn Leu His Val Ala Met Val
225 230 235 240

Gly Asp Leu Lys Tyr Gly Arg Thr Val His Ser Leu Thr Gln Ala Leu
245 250 255

Ala Lys Phe Asp Gly Asn Arg Phe Tyr Phe Ile Ala Pro Asp Ala Leu
260 265 270

Ala Met Pro Gln Tyr Ile Leu Asp Met Leu Asp Glu Lys Gly Ile Ala
275 280 285

Trp Ser Leu His Ser Ser Ile Glu Glu Val Met Ala Glu Val Asp Ile
290 295 300

Leu Tyr
305

<210> SEQ ID NO 22
<211> LENGTH: 320
<212> TYPE: PRT
<213> ORGANISM: Artificial Sequence
<220> FEATURE:
<223> OTHER INFORMATION: cp ATCase
<220> FEATURE:
<221> NAME/KEY: MOD_RES
<222> LOCATION: (16)..(16)
<223> OTHER INFORMATION: X can be any amino acid

<400> SEQUENCE: 22

Met His His His His His His Gly Ser Gly Val Asp Val Ala Asp Xaa
1 5 10 15

Arg Val Gln Lys Glu Arg Leu Asp Pro Ser Glu Tyr Ala Asn Val Lys
20 25 30

Ala Gln Phe Val Leu Arg Ala Ser Asp Leu His Asn Ala Lys Ala Asn
35 40 45

Met Lys Val Leu His Pro Leu Pro Arg Val Asp Glu Ile Ala Thr Asp
50 55 60

Val Asp Lys Thr Pro His Ala Trp Tyr Phe Gln Gln Ala Gly Asn Gly
65 70 75 80

Ile Phe Ala Arg Gln Ala Leu Leu Ala Leu Val Leu Asn Arg Ala Asn
85 90 95

Pro Leu Tyr Gln Lys His Ile Ile Ser Ile Asn Asp Leu Ser Arg Asp
100 105 110

Asp Leu Asn Leu Val Leu Ala Thr Ala Ala Lys Leu Lys Ala Asn Pro
115 120 125

Gln Pro Glu Leu Leu Lys His Lys Val Ile Ala Ser Cys Phe Phe Glu
130 135 140

Ala Ser Thr Arg Thr Arg Leu Ser Phe Glu Thr Ser Met His Arg Leu
145 150 155 160

Gly Ala Ser Val Val Gly Phe Ser Asp Ser Ala Asn Thr Ser Leu Gly
165 170 175

Lys Lys Gly Glu Thr Leu Ala Asp Thr Ile Ser Val Ile Ser Thr Tyr
180 185 190

Val Asp Ala Ile Val Met Arg His Pro Gln Glu Gly Ala Ala Arg Leu
195 200 205

Ala Thr Glu Phe Ser Gly Asn Val Pro Val Leu Asn Ala Gly Asp Gly
210 215 220

Ser Asn Gln His Pro Thr Gln Thr Leu Leu Asp Leu Phe Thr Ile Gln
225 230 235 240

Glu Thr Gln Gly Arg Leu Asp Asn Leu His Val Ala Met Val Gly Asp
245 250 255

Leu Lys Tyr Gly Arg Thr Val His Ser Leu Thr Gln Ala Leu Ala Lys
260 265 270

Phe Asp Gly Asn Arg Phe Tyr Phe Ile Ala Pro Asp Ala Leu Ala Met
275 280 285

Pro Gln Tyr Ile Leu Asp Met Leu Asp Glu Lys Gly Ile Ala Trp Ser
290 295 300

Leu His Ser Ser Ile Glu Glu Val Met Ala Glu Val Asp Ile Leu Tyr
305 310 315 320

<210> SEQ ID NO 23
<211> LENGTH: 285
<212> TYPE: PRT
<213> ORGANISM: Artificial Sequence
<220> FEATURE:
<223> OTHER INFORMATION: caspase 2

<400> SEQUENCE: 23

Gly Lys Asn His Ala Gly Ser Pro Gly Cys Glu Glu Ser Ala Ala Gly
1 5 10 15

Lys Glu Lys Leu Pro Lys Met Arg Leu Pro Thr Arg Ser Asp Met Ile
20 25 30

Cys Gly Tyr Ala Cys Leu Lys Gly Thr Ala Ala Met Arg Asn Thr Lys
35 40 45

Arg Gly Ser Trp Tyr Ile Glu Ala Leu Ala Gln Val Phe Ser Glu Arg
50 55 60

Ala Cys Asp Met His Val Ala Asp Met Leu Val Lys Val Asn Ala Leu
65 70 75 80

Ile Lys Asp Arg Glu Gly Tyr Ala Pro Gly Thr Glu Phe His Arg Cys
85 90 95

Lys Val Met Ser Glu Tyr Cys Ser Thr Leu Cys Arg His Leu Tyr Leu
100 105 110

Phe Pro Gly His Pro Pro Thr Gly Ser Gly Pro Val Arg Leu Gln Val
115 120 125

-continued

```
Lys Pro Cys Thr Pro Gly Phe Tyr Gln Thr His Phe Gln Leu Ala Tyr
    130                 135                 140

Arg Leu Gln Ser Arg Pro Arg Gly Leu Ala Leu Val Leu Ser Asn Val
145                 150                 155                 160

His Phe Thr Gly Glu Lys Glu Leu Glu Phe Arg Ser Gly Gly Asp Val
                165                 170                 175

Asp His Ser Thr Leu Val Thr Leu Phe Lys Leu Leu Gly Tyr Asp Val
            180                 185                 190

Arg Val Leu Cys Asp Gln Thr Ala Gln Glu Met Gln Glu Lys Leu Gln
        195                 200                 205

Asn Phe Ala Gln Leu Pro Ala His Arg Val Thr Asp Ser Cys Ile Val
    210                 215                 220

Ala Leu Leu Ser His Gly Val Glu Gly Ala Ile Tyr Gly Val Asp Gly
225                 230                 235                 240

Lys Leu Leu Gln Leu Gln Glu Val Phe Gln Leu Phe Asp Asn Ala Asn
                245                 250                 255

Cys Pro Ser Leu Gln Asn Lys Pro Lys Met Phe Phe Ile Gln Ala Cys
            260                 265                 270

Arg Gly Asp Glu Thr Glu Arg Gly Val Asp Gln Gln Asp
        275                 280                 285


<210> SEQ ID NO 24
<211> LENGTH: 292
<212> TYPE: PRT
<213> ORGANISM: Artificial Sequence
<220> FEATURE:
<223> OTHER INFORMATION: caspase 2

<400> SEQUENCE: 24

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Arg Leu Gln Val Lys Pro Cys Thr Pro Gly Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val Arg Val Leu Cys Asp Gln Thr Ala Gln
        195                 200                 205
```

-continued

```
Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Asp
    290


<210> SEQ ID NO 25
<211> LENGTH: 285
<212> TYPE: PRT
<213> ORGANISM: Artificial Sequence
<220> FEATURE:
<223> OTHER INFORMATION: caspase 2

<400> SEQUENCE: 25

Gly Lys Asn His Ala Gly Ser Pro Gly Cys Glu Glu Ser Ala Ala Gly
1               5                   10                  15

Lys Glu Lys Leu Pro Lys Met Arg Leu Pro Thr Arg Ser Asp Met Ile
            20                  25                  30

Cys Gly Tyr Ala Cys Leu Lys Gly Thr Ala Ala Met Arg Asn Thr Lys
        35                  40                  45

Arg Gly Ser Trp Tyr Ile Glu Ala Leu Ala Gln Val Phe Ser Glu Arg
    50                  55                  60

Ala Cys Asp Met His Val Ala Asp Met Leu Val Lys Val Asn Ala Leu
65                  70                  75                  80

Ile Lys Asp Arg Glu Gly Tyr Ala Pro Gly Thr Glu Phe His Arg Cys
                85                  90                  95

Lys Glu Met Ser Glu Tyr Cys Ser Thr Leu Cys Arg His Leu Tyr Leu
            100                 105                 110

Phe Pro Gly His Pro Pro Thr Gly Ser Gly Pro Val Cys Leu Gln Val
        115                 120                 125

Lys Pro Cys Thr Pro Glu Phe Tyr Gln Thr His Phe Gln Leu Ala Tyr
    130                 135                 140

Arg Leu Gln Ser Arg Pro Arg Gly Leu Ala Leu Val Leu Ser Asn Val
145                 150                 155                 160

His Phe Thr Gly Glu Lys Glu Leu Glu Phe Arg Ser Gly Gly Asp Val
                165                 170                 175

Asp His Ser Thr Leu Val Thr Leu Phe Lys Leu Leu Gly Tyr Asp Val
            180                 185                 190

His Val Leu Tyr Asp Gln Thr Ala Gln Glu Met Gln Glu Lys Leu Gln
        195                 200                 205

Asn Phe Ala Gln Leu Pro Ala His Arg Val Thr Asp Ser Cys Ile Val
    210                 215                 220

Ala Leu Leu Ser His Gly Val Glu Gly Ala Ile Tyr Gly Val Asp Gly
225                 230                 235                 240

Lys Leu Leu Gln Leu Gln Glu Val Phe Gln Leu Phe Asp Asn Ala Asn
                245                 250                 255

Cys Pro Ser Leu Gln Asn Lys Pro Lys Met Phe Phe Ile Gln Ala Cys
            260                 265                 270
```

```
Arg Gly Asp Glu Thr Glu Arg Gly Val Asp Gln Gln Asp
        275                 280                 285


<210> SEQ ID NO 26
<211> LENGTH: 292
<212> TYPE: PRT
<213> ORGANISM: Artificial Sequence
<220> FEATURE:
<223> OTHER INFORMATION: caspase 2

<400> SEQUENCE: 26

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Tyr Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Asp
    290


<210> SEQ ID NO 27
<211> LENGTH: 285
<212> TYPE: PRT
<213> ORGANISM: Artificial Sequence
<220> FEATURE:
<223> OTHER INFORMATION: caspase 2

<400> SEQUENCE: 27
```

Gly Lys Asn His Ala Gly Ser Pro Gly Cys Glu Glu Ser Ala Ala Gly
1 5 10 15

Lys Glu Lys Leu Pro Lys Met Arg Leu Pro Thr Arg Ser Asp Met Ile
20 25 30

Cys Gly Tyr Ala Cys Leu Lys Gly Thr Ala Ala Met Arg Asn Thr Lys
35 40 45

Arg Gly Ser Trp Tyr Ile Glu Ala Leu Ala Gln Val Phe Ser Glu Arg
50 55 60

Ala Cys Asp Met His Val Ala Asp Met Leu Val Lys Val Asn Ala Leu
65 70 75 80

Ile Lys Asp Arg Glu Gly Tyr Ala Pro Gly Thr Glu Phe His Arg Cys
85 90 95

Lys Glu Met Ser Glu Tyr Cys Ser Thr Leu Cys Arg His Leu Tyr Leu
100 105 110

Phe Pro Gly His Pro Pro Thr Gly Ser Gly Pro Val Cys Leu Gln Val
115 120 125

Lys Pro Cys Thr Pro Glu Phe Tyr Gln Thr His Phe Gln Leu Ala Tyr
130 135 140

Arg Leu Gln Ser Arg Pro Arg Gly Leu Ala Leu Val Leu Ser Asn Val
145 150 155 160

His Phe Thr Gly Glu Lys Glu Leu Glu Phe Arg Ser Gly Gly Asp Val
165 170 175

Asp His Ser Thr Leu Val Thr Leu Phe Lys Leu Leu Gly Tyr Asp Val
180 185 190

His Ala Leu Cys Asp Gln Thr Ala Gln Glu Met Gln Glu Lys Leu Gln
195 200 205

Asn Phe Ala Gln Leu Pro Ala His Arg Val Thr Asp Ser Cys Ile Val
210 215 220

Ala Leu Leu Ser His Gly Val Glu Gly Ala Ile Tyr Gly Val Asp Gly
225 230 235 240

Lys Leu Leu Gln Leu Gln Glu Val Phe Gln Leu Phe Asp Asn Ala Asn
245 250 255

Cys Pro Ser Leu Gln Asn Lys Pro Lys Met Phe Phe Ile Gln Ala Cys
260 265 270

Arg Gly Asp Glu Thr Glu Arg Gly Val Asp Gln Gln Asp
275 280 285

<210> SEQ ID NO 28
<211> LENGTH: 292
<212> TYPE: PRT
<213> ORGANISM: Artificial Sequence
<220> FEATURE:
<223> OTHER INFORMATION: caspase 2

<400> SEQUENCE: 28

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Glu Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Gly Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Ala Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Glu Arg Gly Val
275 280 285

Asp Gln Gln Asp
290

<210> SEQ ID NO 29
<211> LENGTH: 285
<212> TYPE: PRT
<213> ORGANISM: Artificial Sequence
<220> FEATURE:
<223> OTHER INFORMATION: caspase 2

<400> SEQUENCE: 29

Gly Lys Asn His Ala Gly Ser Pro Gly Cys Glu Glu Ser Ala Ala Gly
1 5 10 15

Lys Glu Lys Leu Pro Lys Met Arg Leu Pro Thr Arg Ser Asp Met Ile
20 25 30

Cys Gly Tyr Ala Cys Leu Lys Gly Thr Ala Ala Met Arg Asn Thr Lys
35 40 45

Arg Gly Ser Trp Tyr Ile Glu Ala Leu Ala Gln Val Phe Ser Glu Arg
50 55 60

Ala Cys Asp Met His Val Ala Asp Met Leu Val Lys Val Asn Ala Leu
65 70 75 80

Ile Lys Asp Arg Glu Gly Tyr Ala Pro Gly Thr Glu Phe His Arg Cys
85 90 95

Lys Glu Met Ser Glu Tyr Cys Ser Thr Leu Cys Arg His Leu Tyr Leu
100 105 110

Phe Pro Gly His Pro Pro Thr Gly Ser Gly Pro Val Cys Leu Gln Val
115 120 125

Lys Pro Cys Thr Pro Glu Phe Tyr Gln Thr His Phe Gln Leu Ala Tyr
130 135 140

Arg Leu Gln Ser Arg Pro Arg Gly Leu Ala Leu Val Leu Ser Asn Val
145 150 155 160

His Phe Thr Gly Glu Lys Gly Leu Glu Phe Arg Ser Gly Gly Asp Val
165 170 175

Asp His Ser Thr Leu Val Thr Leu Phe Lys Leu Leu Gly Tyr Asp Val
180 185 190

His Val Leu Cys Asp Gln Thr Ala Gln Glu Met Gln Glu Lys Leu Gln
195 200 205

Asn Phe Ala Gln Leu Pro Ala His Arg Val Thr Asp Ser Cys Ile Val
210 215 220

Ala Leu Leu Ser His Gly Val Glu Gly Ala Ile Tyr Gly Val Asp Gly
225 230 235 240

Lys Leu Leu Gln Leu Gln Glu Val Phe Gln Leu Phe Asp Asn Ala Asn
245 250 255

Cys Pro Ser Leu Gln Asn Lys Pro Lys Met Phe Phe Ile Gln Ala Cys
260 265 270

Arg Gly Asp Glu Thr Glu Arg Gly Val Asp Gln Gln Asp
275 280 285

<210> SEQ ID NO 30
<211> LENGTH: 292
<212> TYPE: PRT
<213> ORGANISM: Artificial Sequence
<220> FEATURE:
<223> OTHER INFORMATION: caspase 2

<400> SEQUENCE: 30

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Glu Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Gly Glu Lys Gly Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

```
Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Glu Arg Gly Val
        275                 280                 285

Asp Gln Gln Asp
    290


<210> SEQ ID NO 31
<211> LENGTH: 510
<212> TYPE: DNA
<213> ORGANISM: Artificial Sequence
<220> FEATURE:
<223> OTHER INFORMATION: fusion protein

<400> SEQUENCE: 31

atgcaccatc accatcacca tggcagcggc gtggatgtgg cggatgccgc tggttcgatt      60

actaccctgc ctgctttacc tgaagatggt ggttctggtg cgttcccgcc gggtcacttc     120

aaagacccaa aacgtttgta ctgtaaaaac ggtggctttt ttctgcgcat ccatccggac     180

ggccgcgtgg atggtgtccg tgaaaagtcc gacccgcaca ttaagctgca actgcaggcc     240

gaggagcgtg gtgttgttag catcaaaggc gtgagcgcaa atcgttacct ggcgatgaaa     300

gaggatggcc gtctgctggc gagcaagagc gttaccgacg agtgcttctt ctttgaacgc     360

ctggagagca ataattacaa cacctaccgt agccgcaagt atacctcttg gtatgtggcg     420

ctgaagcgta cgggccagta taaattgggt agcaaaacgg gtccgggcca aaaggcaatc     480

ctgttcctgc cgatgagcgc gaaatcctaa                                      510


<210> SEQ ID NO 32
<211> LENGTH: 169
<212> TYPE: PRT
<213> ORGANISM: Artificial Sequence
<220> FEATURE:
<223> OTHER INFORMATION: fusion protein

<400> SEQUENCE: 32

Met His His His His His His Gly Ser Gly Val Asp Val Ala Asp Ala
1               5                   10                  15

Ala Gly Ser Ile Thr Thr Leu Pro Ala Leu Pro Glu Asp Gly Gly Ser
            20                  25                  30

Gly Ala Phe Pro Pro Gly His Phe Lys Asp Pro Lys Arg Leu Tyr Cys
        35                  40                  45

Lys Asn Gly Gly Phe Phe Leu Arg Ile His Pro Asp Gly Arg Val Asp
    50                  55                  60

Gly Val Arg Glu Lys Ser Asp Pro His Ile Lys Leu Gln Leu Gln Ala
65                  70                  75                  80

Glu Glu Arg Gly Val Val Ser Ile Lys Gly Val Ser Ala Asn Arg Tyr
                85                  90                  95

Leu Ala Met Lys Glu Asp Gly Arg Leu Leu Ala Ser Lys Ser Val Thr
            100                 105                 110

Asp Glu Cys Phe Phe Phe Glu Arg Leu Glu Ser Asn Asn Tyr Asn Thr
        115                 120                 125

Tyr Arg Ser Arg Lys Tyr Thr Ser Trp Tyr Val Ala Leu Lys Arg Thr
```

-continued 130 135 140

Gly Gln Tyr Lys Leu Gly Ser Lys Thr Gly Pro Gly Gln Lys Ala Ile
145 150 155 160

Leu Phe Leu Pro Met Ser Ala Lys Ser
165

<210> SEQ ID NO 33
<211> LENGTH: 185
<212> TYPE: PRT
<213> ORGANISM: Artificial Sequence
<220> FEATURE:
<223> OTHER INFORMATION: fusion protein

<400> SEQUENCE: 33

Met Arg Gly Ser His His His His His His Gly Ser Gly Val Asp Val
1 5 10 15

Ala Asp Gly Ile Arg Met Arg Ala Arg Tyr Pro Ser Val Leu Asp Met
20 25 30

Ala Ala Ser Arg Arg Leu Met Lys Glu Leu Glu Glu Ile Arg Lys Cys
35 40 45

Gly Met Lys Asn Phe Arg Asn Ile Gln Val Asp Glu Ala Asn Leu Leu
50 55 60

Thr Trp Gln Gly Leu Ile Val Pro Asp Asn Pro Pro Tyr Asp Lys Gly
65 70 75 80

Ala Phe Arg Ile Glu Ile Asn Phe Pro Ala Glu Tyr Pro Phe Lys Pro
85 90 95

Pro Lys Ile Thr Phe Lys Thr Lys Ile Tyr His Pro Asn Ile Asp Glu
100 105 110

Lys Gly Gln Val Cys Leu Pro Val Ile Ser Ala Glu Asn Trp Lys Pro
115 120 125

Ala Thr Lys Thr Asp Gln Val Ile Gln Ser Leu Ile Ala Leu Val Asn
130 135 140

Asp Pro Gln Pro Glu His Pro Leu Arg Ala Asp Leu Ala Glu Glu Tyr
145 150 155 160

Ser Lys Asp Arg Lys Lys Phe Cys Lys Asn Ala Glu Glu Phe Thr Lys
165 170 175

Lys Tyr Gly Glu Lys Arg Pro Val Asp
180 185

<210> SEQ ID NO 34
<211> LENGTH: 1039
<212> TYPE: PRT
<213> ORGANISM: Artificial Sequence
<220> FEATURE:
<223> OTHER INFORMATION: fusion protein

<400> SEQUENCE: 34

Met His His His His His His Gly Ser Gly Val Asp Val Ala Asp Met
1 5 10 15

Thr Met Ile Thr Asp Ser Leu Ala Val Val Leu Gln Arg Arg Asp Trp
20 25 30

Glu Asn Pro Gly Val Thr Gln Leu Asn Arg Leu Ala Ala His Pro Pro
35 40 45

Phe Ala Ser Trp Arg Asn Ser Glu Glu Ala Arg Thr Asp Arg Pro Ser
50 55 60

Gln Gln Leu Arg Ser Leu Asn Gly Glu Trp Arg Phe Ala Trp Phe Pro
65 70 75 80

-continued

```
Ala Pro Glu Ala Val Pro Glu Ser Trp Leu Glu Cys Asp Leu Pro Glu
                85                  90                  95

Ala Asp Thr Val Val Val Pro Ser Asn Trp Gln Met His Gly Tyr Asp
            100                 105                 110

Ala Pro Ile Tyr Thr Asn Val Thr Tyr Pro Ile Thr Val Asn Pro Pro
        115                 120                 125

Phe Val Pro Thr Glu Asn Pro Thr Gly Cys Tyr Ser Leu Thr Phe Asn
    130                 135                 140

Val Asp Glu Ser Trp Leu Gln Glu Gly Gln Thr Arg Ile Ile Phe Asp
145                 150                 155                 160

Gly Val Asn Ser Ala Phe His Leu Trp Cys Asn Gly Arg Trp Val Gly
                165                 170                 175

Tyr Gly Gln Asp Ser Arg Leu Pro Ser Glu Phe Asp Leu Ser Ala Phe
            180                 185                 190

Leu Arg Ala Gly Glu Asn Arg Leu Ala Val Met Val Leu Arg Trp Ser
        195                 200                 205

Asp Gly Ser Tyr Leu Glu Asp Gln Asp Met Trp Arg Met Ser Gly Ile
    210                 215                 220

Phe Arg Asp Val Ser Leu Leu His Lys Pro Thr Thr Gln Ile Ser Asp
225                 230                 235                 240

Phe His Val Ala Thr Arg Phe Asn Asp Asp Phe Ser Arg Ala Val Leu
                245                 250                 255

Glu Ala Glu Val Gln Met Cys Gly Glu Leu Arg Asp Tyr Leu Arg Val
            260                 265                 270

Thr Val Ser Leu Trp Gln Gly Glu Thr Gln Val Ala Ser Gly Thr Ala
        275                 280                 285

Pro Phe Gly Gly Glu Ile Ile Asp Glu Arg Gly Gly Tyr Ala Asp Arg
    290                 295                 300

Val Thr Leu Arg Leu Asn Val Glu Asn Pro Lys Leu Trp Ser Ala Glu
305                 310                 315                 320

Ile Pro Asn Leu Tyr Arg Ala Val Val Glu Leu His Thr Ala Asp Gly
                325                 330                 335

Thr Leu Ile Glu Ala Glu Ala Cys Asp Val Gly Phe Arg Glu Val Arg
            340                 345                 350

Ile Glu Asn Gly Leu Leu Leu Leu Asn Gly Lys Pro Leu Leu Ile Arg
        355                 360                 365

Gly Val Asn Arg His Glu His His Pro Leu His Gly Gln Val Met Asp
    370                 375                 380

Glu Gln Thr Met Val Gln Asp Ile Leu Leu Met Lys Gln Asn Asn Phe
385                 390                 395                 400

Asn Ala Val Arg Cys Ser His Tyr Pro Asn His Pro Leu Trp Tyr Thr
                405                 410                 415

Leu Cys Asp Arg Tyr Gly Leu Tyr Val Val Asp Glu Ala Asn Ile Glu
            420                 425                 430

Thr His Gly Met Val Pro Met Asn Arg Leu Thr Asp Asp Pro Arg Trp
        435                 440                 445

Leu Pro Ala Met Ser Glu Arg Val Thr Arg Met Val Gln Arg Asp Arg
    450                 455                 460

Asn His Pro Ser Val Ile Ile Trp Ser Leu Gly Asn Glu Ser Gly His
465                 470                 475                 480

Gly Ala Asn His Asp Ala Leu Tyr Arg Trp Ile Lys Ser Val Asp Pro
                485                 490                 495

Ser Arg Pro Val Gln Tyr Glu Gly Gly Gly Ala Asp Thr Thr Ala Thr
```

-continued

```
            500                 505                 510

Asp Ile Ile Cys Pro Met Tyr Ala Arg Val Asp Glu Asp Gln Pro Phe
        515                 520                 525

Pro Ala Val Pro Lys Trp Ser Ile Lys Lys Trp Leu Ser Leu Pro Gly
    530                 535                 540

Glu Thr Arg Pro Leu Ile Leu Cys Glu Tyr Ala His Ala Met Gly Asn
545                 550                 555                 560

Ser Leu Gly Gly Phe Ala Lys Tyr Trp Gln Ala Phe Arg Gln Tyr Pro
                565                 570                 575

Arg Leu Gln Gly Gly Phe Val Trp Asp Trp Val Asp Gln Ser Leu Ile
            580                 585                 590

Lys Tyr Asp Glu Asn Gly Asn Pro Trp Ser Ala Tyr Gly Gly Asp Phe
        595                 600                 605

Gly Asp Thr Pro Asn Asp Arg Gln Phe Cys Met Asn Gly Leu Val Phe
    610                 615                 620

Ala Asp Arg Thr Pro His Pro Ala Leu Thr Glu Ala Lys His Gln Gln
625                 630                 635                 640

Gln Phe Phe Gln Phe Arg Leu Ser Gly Gln Thr Ile Glu Val Thr Ser
                645                 650                 655

Glu Tyr Leu Phe Arg His Ser Asp Asn Glu Leu Leu His Trp Met Val
            660                 665                 670

Ala Leu Asp Gly Lys Pro Leu Ala Ser Gly Glu Val Pro Leu Asp Val
        675                 680                 685

Ala Pro Gln Gly Lys Gln Leu Ile Glu Leu Pro Glu Leu Pro Gln Pro
    690                 695                 700

Glu Ser Ala Gly Gln Leu Trp Leu Thr Val Arg Val Val Gln Pro Asn
705                 710                 715                 720

Ala Thr Ala Trp Ser Glu Ala Gly His Ile Ser Ala Trp Gln Gln Trp
                725                 730                 735

Arg Leu Ala Glu Asn Leu Ser Val Thr Leu Pro Ala Ala Ser His Ala
            740                 745                 750

Ile Pro His Leu Thr Thr Ser Glu Met Asp Phe Cys Ile Glu Leu Gly
        755                 760                 765

Asn Lys Arg Trp Gln Phe Asn Arg Gln Ser Gly Phe Leu Ser Gln Met
    770                 775                 780

Trp Ile Gly Asp Lys Lys Gln Leu Leu Thr Pro Leu Arg Asp Gln Phe
785                 790                 795                 800

Thr Arg Ala Pro Leu Asp Asn Asp Ile Gly Val Ser Glu Ala Thr Arg
                805                 810                 815

Ile Asp Pro Asn Ala Trp Val Glu Arg Trp Lys Ala Ala Gly His Tyr
            820                 825                 830

Gln Ala Glu Ala Ala Leu Leu Gln Cys Thr Ala Asp Thr Leu Ala Asp
        835                 840                 845

Ala Val Leu Ile Thr Thr Ala His Ala Trp Gln His Gln Gly Lys Thr
    850                 855                 860

Leu Phe Ile Ser Arg Lys Thr Tyr Arg Ile Asp Gly Ser Gly Gln Met
865                 870                 875                 880

Ala Ile Thr Val Asp Val Glu Val Ala Ser Asp Thr Pro His Pro Ala
                885                 890                 895

Arg Ile Gly Leu Asn Cys Gln Leu Ala Gln Val Ala Glu Arg Val Asn
            900                 905                 910

Trp Leu Gly Leu Gly Pro Gln Glu Asn Tyr Pro Asp Arg Leu Thr Ala
        915                 920                 925
```

Ala Cys Phe Asp Arg Trp Asp Leu Pro Leu Ser Asp Met Tyr Thr Pro
930 935 940

Tyr Val Phe Pro Ser Glu Asn Gly Leu Arg Cys Gly Thr Arg Glu Leu
945 950 955 960

Asn Tyr Gly Pro His Gln Trp Arg Gly Asp Phe Gln Phe Asn Ile Ser
965 970 975

Arg Tyr Ser Gln Gln Gln Leu Met Glu Thr Ser His Arg His Leu Leu
980 985 990

His Ala Glu Glu Gly Thr Trp Leu Asn Ile Asp Gly Phe His Met Gly
995 1000 1005

Ile Gly Gly Asp Asp Ser Trp Ser Pro Ser Val Ser Ala Glu Phe
1010 1015 1020

Gln Leu Ser Ala Gly Arg Tyr His Tyr Gln Leu Val Trp Cys Gln
1025 1030 1035

Lys

<210> SEQ ID NO 35
<211> LENGTH: 314
<212> TYPE: PRT
<213> ORGANISM: Artificial Sequence
<220> FEATURE:
<223> OTHER INFORMATION: caspase 2

<400> SEQUENCE: 35

Met His His His His His His Leu Glu Asp Pro Glu Arg Asn Lys Glu
1 5 10 15

Arg Lys Glu Ala Glu Leu Glu Ala Glu Thr Ala Glu Gln Gly Lys Asn
20 25 30

His Ala Gly Ser Pro Gly Cys Glu Glu Ser Ala Ala Gly Lys Glu Lys
35 40 45

Leu Pro Lys Met Arg Leu Pro Thr Arg Ser Asp Met Ile Cys Gly Tyr
50 55 60

Ala Cys Leu Lys Gly Thr Ala Ala Met Arg Asn Thr Lys Arg Gly Ser
65 70 75 80

Trp Tyr Ile Glu Ala Leu Ala Gln Val Phe Ser Glu Arg Ala Cys Asp
85 90 95

Met His Val Ala Asp Met Leu Val Lys Val Asn Ala Leu Ile Lys Asp
100 105 110

Arg Glu Gly Tyr Ala Pro Gly Thr Glu Phe His Arg Cys Lys Glu Met
115 120 125

Ser Glu Tyr Cys Ser Thr Leu Cys Arg His Leu Tyr Leu Phe Pro Gly
130 135 140

His Pro Pro Thr Gly Ser Gly Pro Val Cys Leu Gln Val Lys Pro Cys
145 150 155 160

Thr Pro Glu Phe Tyr Gln Thr His Phe Gln Leu Ala Tyr Arg Leu Gln
165 170 175

Ser Arg Pro Arg Gly Leu Ala Leu Val Leu Ser Asn Val His Phe Thr
180 185 190

Gly Glu Lys Glu Leu Glu Phe Arg Ser Gly Gly Asp Val Asp His Ser
195 200 205

Thr Leu Val Thr Leu Phe Lys Leu Leu Gly Tyr Asp Val His Val Leu
210 215 220

Cys Asp Gln Thr Ala Gln Glu Met Gln Glu Lys Leu Gln Asn Phe Ala
225 230 235 240

```
Gln Leu Pro Ala His Arg Val Thr Asp Ser Cys Ile Val Ala Leu Leu
                245                 250                 255

Ser His Gly Val Glu Gly Ala Ile Tyr Gly Val Asp Gly Lys Leu Leu
            260                 265                 270

Gln Leu Gln Glu Val Phe Gln Leu Phe Asp Asn Ala Asn Cys Pro Ser
        275                 280                 285

Leu Gln Asn Lys Pro Lys Met Phe Phe Ile Gln Ala Cys Arg Gly Asp
    290                 295                 300

Glu Thr Asp Arg Gly Val Asp Gln Gln Asp
305                 310
```

<210> SEQ ID NO 36
<211> LENGTH: 945
<212> TYPE: DNA
<213> ORGANISM: Artificial Sequence
<220> FEATURE:
<223> OTHER INFORMATION: caspase 2

<400> SEQUENCE: 36

```
atgcaccatc atcaccatca tctggaggat ccggaacgca acaaagagcg aaaggaagct      60

gagttggaag ctgagaccgc tgagcaaggc aaaaatcatg caggtagtcc gggttgtgaa     120

gaaagcgcag caggtaaaga aaaactgccg aaaatgcgtc tgccgacccg tagcgatatg     180

atttgtggtt atgcatgtct gaaaggcacc gcagcaatgc gtaataccaa acgtggtagc     240

tggtatattg aagcactggc acaggttttt agcgaacgtg catgtgatat gcatgttgca     300

gatatgctgg ttaaagtgaa cgccctgatt aaagatcgtg aaggttatgc accgggtaca     360

gaatttcatc gttgtaaaga aatgagcgag tattgtagca ccctgtgtcg tcatctgtac     420

ctgtttccgg gtcatcctcc gaccggatcc ggtccggttt gtctgcaggt taaaccgtgt     480

acaccggaat tttatcagac ccattttcag ctggcatatc gtctgcagag ccgtccgcgt     540

ggtctggcac tggttctgag caatgttcat tttaccggtg aaaaagaact ggaatttcgt     600

agcggtggtg atgttgatca tagtaccctg gttaccctgt ttaaactgct gggttatgac     660

gttcatgttc tgtgtgatca gaccgcacaa gaaatgcaag agaaactgca gaattttgca     720

cagctgcctg cacatcgtgt taccgatagc tgtattgttg cactgctgag ccatggtgtt     780

gaaggtgcaa tttatggtgt ggatggcaaa ctgctgcaac tgcaagaagt gtttcagctg     840

tttgataatg caaattgtcc gagcctgcag aataaaccga aaatgttttt tatccaggcc     900

tgccgtggtg atgaaaccga tcgtggtgtt gatcagcagg attaa                     945
```

<210> SEQ ID NO 37
<211> LENGTH: 22
<212> TYPE: PRT
<213> ORGANISM: Artificial Sequence
<220> FEATURE:
<223> OTHER INFORMATION: T7A3 tag

<400> SEQUENCE: 37

```
Leu Glu Asp Pro Glu Arg Asn Lys Glu Arg Lys Glu Ala Glu Leu Glu
1               5                   10                  15

Ala Glu Thr Ala Glu Gln
            20
```

<210> SEQ ID NO 38
<211> LENGTH: 66
<212> TYPE: DNA
<213> ORGANISM: Artificial Sequence
<220> FEATURE:

<223> OTHER INFORMATION: T7A3 tag

<400> SEQUENCE: 38
ctggaggatc cggaacgcaa caaagagcga aaggaagctg agttggaagc tgagaccgct 60
gagcaa 66

<210> SEQ ID NO 39
<211> LENGTH: 314
<212> TYPE: PRT
<213> ORGANISM: Artificial Sequence
<220> FEATURE:
<223> OTHER INFORMATION: caspase 2

<400> SEQUENCE: 39

Met Leu Glu Asp Pro Glu Arg Asn Lys Glu Arg Lys Glu Ala Glu Leu
1 5 10 15

Glu Ala Glu Thr Ala Glu Gln His His His His His His Gly Lys Asn
20 25 30

His Ala Gly Ser Pro Gly Cys Glu Glu Ser Ala Ala Gly Lys Glu Lys
35 40 45

Leu Pro Lys Met Arg Leu Pro Thr Arg Ser Asp Met Ile Cys Gly Tyr
50 55 60

Ala Cys Leu Lys Gly Thr Ala Ala Met Arg Asn Thr Lys Arg Gly Ser
65 70 75 80

Trp Tyr Ile Glu Ala Leu Ala Gln Val Phe Ser Glu Arg Ala Cys Asp
85 90 95

Met His Val Ala Asp Met Leu Val Lys Val Asn Ala Leu Ile Lys Asp
100 105 110

Arg Glu Gly Tyr Ala Pro Gly Thr Glu Phe His Arg Cys Lys Glu Met
115 120 125

Ser Glu Tyr Cys Ser Thr Leu Cys Arg His Leu Tyr Leu Phe Pro Gly
130 135 140

His Pro Pro Thr Gly Ser Gly Pro Val Cys Leu Gln Val Lys Pro Cys
145 150 155 160

Thr Pro Glu Phe Tyr Gln Thr His Phe Gln Leu Ala Tyr Arg Leu Gln
165 170 175

Ser Arg Pro Arg Gly Leu Ala Leu Val Leu Ser Asn Val His Phe Thr
180 185 190

Gly Glu Lys Glu Leu Glu Phe Arg Ser Gly Gly Asp Val Asp His Ser
195 200 205

Thr Leu Val Thr Leu Phe Lys Leu Leu Gly Tyr Asp Val His Val Leu
210 215 220

Cys Asp Gln Thr Ala Gln Glu Met Gln Glu Lys Leu Gln Asn Phe Ala
225 230 235 240

Gln Leu Pro Ala His Arg Val Thr Asp Ser Cys Ile Val Ala Leu Leu
245 250 255

Ser His Gly Val Glu Gly Ala Ile Tyr Gly Val Asp Gly Lys Leu Leu
260 265 270

Gln Leu Gln Glu Val Phe Gln Leu Phe Asp Asn Ala Asn Cys Pro Ser
275 280 285

Leu Gln Asn Lys Pro Lys Met Phe Phe Ile Gln Ala Cys Arg Gly Asp
290 295 300

Glu Thr Asp Arg Gly Val Asp Gln Gln Asp
305 310

<210> SEQ ID NO 40
<211> LENGTH: 945
<212> TYPE: DNA
<213> ORGANISM: Artificial Sequence
<220> FEATURE:
<223> OTHER INFORMATION: caspase 2

<400> SEQUENCE: 40
atgctggagg atccggaacg caacaaagag cgaaaggaag ctgagttgga agctgagacc 60
gctgagcaac accatcatca ccatcatggc aaaaatcatg caggtagtcc gggttgtgaa 120
gaaagcgcag caggtaaaga aaaactgccg aaaatgcgtc tgccgacccg tagcgatatg 180
atttgtggtt atgcatgtct gaaaggcacc gcagcaatgc gtaataccaa acgtggtagc 240
tggtatattg aagcactggc acaggttttt agcgaacgtg catgtgatat gcatgttgca 300
gatatgctgg ttaaagtgaa cgccctgatt aaagatcgtg aaggttatgc accgggtaca 360
gaatttcatc gttgtaaaga aatgagcgag tattgtagca ccctgtgtcg tcatctgtac 420
ctgtttccgg gtcatcctcc gaccggatcc ggtccggttt gtctgcaggt taaaccgtgt 480
acaccggaat tttatcagac ccattttcag ctggcatatc gtctgcagag ccgtccgcgt 540
ggtctggcac tggttctgag caatgttcat tttaccggtg aaaaagaact ggaatttcgt 600
agcggtggtg atgttgatca tagtaccctg gttaccctgt ttaaactgct gggttatgac 660
gttcatgttc tgtgtgatca gaccgcacaa gaaatgcaag agaaactgca gaattttgca 720
cagctgcctg cacatcgtgt taccgatagc tgtattgttg cactgctgag ccatggtgtt 780
gaaggtgcaa tttatggtgt ggatggcaaa ctgctgcaac tgcaagaagt gtttcagctg 840
tttgataatg caaattgtcc gagcctgcag aataaaccga aaatgttttt tatccaggcc 900
tgccgtggtg atgaaaccga tcgtggtgtt gatcagcagg attaa 945

<210> SEQ ID NO 41
<211> LENGTH: 314
<212> TYPE: PRT
<213> ORGANISM: Artificial Sequence
<220> FEATURE:
<223> OTHER INFORMATION: caspase 2

<400> SEQUENCE: 41

Met Leu Glu Asp Pro Glu Arg Asn Lys Glu Arg Lys Glu Ala Glu Leu
1 5 10 15

Gln Ala Gln Thr Ala Glu Gln His His His His His His Gly Lys Asn
20 25 30

His Ala Gly Ser Pro Gly Cys Glu Glu Ser Ala Ala Gly Lys Glu Lys
35 40 45

Leu Pro Lys Met Arg Leu Pro Thr Arg Ser Asp Met Ile Cys Gly Tyr
50 55 60

Ala Cys Leu Lys Gly Thr Ala Ala Met Arg Asn Thr Lys Arg Gly Ser
65 70 75 80

Trp Tyr Ile Glu Ala Leu Ala Gln Val Phe Ser Glu Arg Ala Cys Asp
85 90 95

Met His Val Ala Asp Met Leu Val Lys Val Asn Ala Leu Ile Lys Asp
100 105 110

Arg Glu Gly Tyr Ala Pro Gly Thr Glu Phe His Arg Cys Lys Glu Met
115 120 125

Ser Glu Tyr Cys Ser Thr Leu Cys Arg His Leu Tyr Leu Phe Pro Gly
130 135 140

His Pro Pro Thr Gly Ser Gly Pro Val Cys Leu Gln Val Lys Pro Cys

-continued

```
145                 150                 155                 160

Thr Pro Glu Phe Tyr Gln Thr His Phe Gln Leu Ala Tyr Arg Leu Gln
                165                 170                 175

Ser Arg Pro Arg Gly Leu Ala Leu Val Leu Ser Asn Val His Phe Thr
            180                 185                 190

Gly Glu Lys Glu Leu Glu Phe Arg Ser Gly Gly Asp Val Asp His Ser
        195                 200                 205

Thr Leu Val Thr Leu Phe Lys Leu Leu Gly Tyr Asp Val His Val Leu
    210                 215                 220

Cys Asp Gln Thr Ala Gln Glu Met Gln Glu Lys Leu Gln Asn Phe Ala
225                 230                 235                 240

Gln Leu Pro Ala His Arg Val Thr Asp Ser Cys Ile Val Ala Leu Leu
                245                 250                 255

Ser His Gly Val Glu Gly Ala Ile Tyr Gly Val Asp Gly Lys Leu Leu
            260                 265                 270

Gln Leu Gln Glu Val Phe Gln Leu Phe Asp Asn Ala Asn Cys Pro Ser
        275                 280                 285

Leu Gln Asn Lys Pro Lys Met Phe Phe Ile Gln Ala Cys Arg Gly Asp
    290                 295                 300

Glu Thr Asp Arg Gly Val Asp Gln Gln Asp
305                 310
```

<210> SEQ ID NO 42
<211> LENGTH: 945
<212> TYPE: DNA
<213> ORGANISM: Artificial Sequence
<220> FEATURE:
<223> OTHER INFORMATION: caspase 2

<400> SEQUENCE: 42

```
atgctggagg atccggaacg caacaaagag cgaaaggaag ctgagttgca agctcaaacc     60

gctgagcaac accatcatca ccatcatggc aaaaatcatg caggtagtcc gggttgtgaa    120

gaaagcgcag caggtaaaga aaaactgccg aaaatgcgtc tgccgacccg tagcgatatg    180

atttgtggtt atgcatgtct gaaaggcacc gcagcaatgc gtaataccaa acgtggtagc    240

tggtatattg aagcactggc acaggttttt agcgaacgtg catgtgatat gcatgttgca    300

gatatgctgg ttaaagtgaa cgccctgatt aaagatcgtg aaggttatgc accgggtaca    360

gaatttcatc gttgtaaaga aatgagcgag tattgtagca ccctgtgtcg tcatctgtac    420

ctgtttccgg gtcatcctcc gaccggatcc ggtccggttt gtctgcaggt taaaccgtgt    480

acaccggaat tttatcagac ccattttcag ctggcatatc gtctgcagag ccgtccgcgt    540

ggtctggcac tggttctgag caatgttcat tttaccggtg aaaaagaact ggaatttcgt    600

agcggtggtg atgttgatca tagtaccctg gttaccctgt ttaaactgct gggttatgac    660

gttcatgttc tgtgtgatca gaccgcacaa gaaatgcaag agaaactgca gaattttgca    720

cagctgcctg cacatcgtgt taccgatagc tgtattgttg cactgctgag ccatggtgtt    780

gaaggtgcaa tttatggtgt ggatggcaaa ctgctgcaac tgcaagaagt gtttcagctg    840

tttgataatg caaattgtcc gagcctgcag aataaaccga aaatgttttt tatccaggcc    900

tgccgtggtg atgaaaccga tcgtggtgtt gatcagcagg attaa                    945
```

<210> SEQ ID NO 43
<211> LENGTH: 22
<212> TYPE: PRT
<213> ORGANISM: Artificial Sequence
<220> FEATURE:
<223> OTHER INFORMATION: T7AC tag

<400> SEQUENCE: 43

Leu Glu Asp Pro Glu Arg Asn Lys Glu Arg Lys Glu Ala Glu Leu Gln
1               5                   10                  15

Ala Gln Thr Ala Glu Gln
            20

<210> SEQ ID NO 44
<211> LENGTH: 66
<212> TYPE: DNA
<213> ORGANISM: Artificial Sequence
<220> FEATURE:
<223> OTHER INFORMATION: T7AC tag

<400> SEQUENCE: 44
ctggaggatc cggaacgcaa caaagagcga aaggaagctg agttgcaagc tcaaaccgct     60
gagcaa                                                                66

<210> SEQ ID NO 45
<211> LENGTH: 5
<212> TYPE: PRT
<213> ORGANISM: Artificial Sequence
<220> FEATURE:
<223> OTHER INFORMATION: recognition site

<400> SEQUENCE: 45

Val Asp Val Ala Asp
1               5

<210> SEQ ID NO 46
<211> LENGTH: 15
<212> TYPE: PRT
<213> ORGANISM: Artificial Sequence
<220> FEATURE:
<223> OTHER INFORMATION: caspase 2

<400> SEQUENCE: 46

Gly Glu Lys Glu Leu Glu Phe Arg Ser Gly Gly Asp Val Asp His
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: caspase 2

<400> SEQUENCE: 47

Leu Leu Ser His Gly Val Glu Gly Ala Ala Ile Tyr Gly Val Asp Gly
1               5                   10                  15

<210> SEQ ID NO 48
<211> LENGTH: 8
<212> TYPE: PRT
<213> ORGANISM: Artificial Sequence
<220> FEATURE:
<223> OTHER INFORMATION: caspase 2

<400> SEQUENCE: 48

Gln Ala Cys Arg Gly Asp Glu Thr
1               5

<210> SEQ ID NO 49

<211> LENGTH: 8
<212> TYPE: PRT
<213> ORGANISM: Artificial Sequence
<220> FEATURE:
<223> OTHER INFORMATION: caspase 2

<400> SEQUENCE: 49

```
Ala Ala Met Arg Asn Thr Lys Arg
1               5
```

<210> SEQ ID NO 50
<211> LENGTH: 13
<212> TYPE: PRT
<213> ORGANISM: Artificial Sequence
<220> FEATURE:
<223> OTHER INFORMATION: caspase 2

<400> SEQUENCE: 50

```
Glu Gly Tyr Ala Pro Gly Thr Glu Phe His Arg Cys Lys
1               5                   10
```

<210> SEQ ID NO 51
<211> LENGTH: 292
<212> TYPE: PRT
<213> ORGANISM: Artificial Sequence
<220> FEATURE:
<223> OTHER INFORMATION: caspase 2

<400> SEQUENCE: 51

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240
```

```
Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290
```

<210> SEQ ID NO 52
<211> LENGTH: 292
<212> TYPE: PRT
<213> ORGANISM: Artificial Sequence
<220> FEATURE:
<223> OTHER INFORMATION: caspase 2

<400> SEQUENCE: 52

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Asp Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Gly Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Glu Glu Thr Asp Arg Gly Val
        275                 280                 285

Asp Gln Gln Asp
    290
```

<210> SEQ ID NO 53
<211> LENGTH: 882
<212> TYPE: DNA
<213> ORGANISM: Artificial Sequence
<220> FEATURE:
<223> OTHER INFORMATION: caspase 2

<400> SEQUENCE: 53

```
atgcaccatc atcaccatca tggcaaaaat catgcaggta gtccgggttg tgaagaaagc     60

gcagcaggta aagaaaaact gccgaaaatg cgtctgccga cccgtagcga tatgatttgt    120

ggttatgcat gtctgaaagg caccgcagca atgcgtaata ccaaacgtgg tagctggtat    180

attgaagcac tggcacaggt ttttagcgaa cgtgcatgtg atatgcatgt tgcagatatg    240

ctggttgaag tgaacgccct gattaaagat cgtgaaggtt atgcaccggg tacagaattt    300

catcgttgta aagtaatgag cgagtattgt agcaccctgt gtcgacatct atacctgttt    360

ccgggtcatc ctccgaccgg atccggtccg gtttgtctgc aggttaaacc gtgtacaccg    420

gaattttatc agacccattt tcagctggca tatcgtctgc agagccgtcc gcgtggtctg    480

gcactggttc tgagcaatgt tcattttacc ggtgtaaaag aactggaatt tcgtagcggt    540

ggtgatgttg atcatagtac cctggttacc ctgtttaaac tgctgggtta tgacgttcat    600

gttctgtgtg atcagaccgc acaagaaatg caagagaaac tgcagaattt tgcacagctg    660

cctgcacatc gtgttaccga tagctgtatt gttgcactgc tgagccatgg tgttgaaggt    720

gcaatttatg gtgtggatgg caaactgctg caactgcaag aaatgtttca gctgtttgat    780

aatgcaaatt gtccgagcct gcagaataaa ccgaaaatgt tttttatcca ggcctgccgt    840

ggtgatgaaa cctatcgggg tgtggatcag caggattaat aa                        882
```

<210> SEQ ID NO 54
<211> LENGTH: 292
<212> TYPE: PRT
<213> ORGANISM: Artificial Sequence
<220> FEATURE:
<223> OTHER INFORMATION: caspase 2

<400> SEQUENCE: 54

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Glu Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160
```

```
Ala Leu Val Leu Ser Asn Val His Phe Thr Gly Val Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Met Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Tyr Arg Gly Val
        275                 280                 285

Asp Gln Gln Asp
    290
```

<210> SEQ ID NO 55
<211> LENGTH: 558
<212> TYPE: DNA
<213> ORGANISM: Artificial Sequence
<220> FEATURE:
<223> OTHER INFORMATION: fusion protein

<400> SEQUENCE: 55

```
atgagaggat ctcaccatca ccatcaccat ggcagcggcg tggatgtggc ggatgggatc     60

cgcatgcgag ctcggtaccc cagtgtgctg gacatggcgg ccagcaggag gctgatgaag    120

gagcttgaag aaatccgcaa atgtgggatg aaaaacttcc gtaacatcca ggttgatgaa    180

gctaatttat tgacttggca agggcttatt gttcctgaca accctcccta tgataaggga    240

gccttcagaa tcgaaatcaa ctttccagca gagtacccat tcaaaccacc gaagatcaca    300

tttaaaacaa agatctatca cccaaacatc gacgaaaagg ggcaggtctg tctgccagta    360

attagtgccg aaaactggaa gccagcaacc aaaaccgacc aagtaatcca gtccctcata    420

gcactggtga atgaccccca gcctgagcac ccgcttcggg ctgacctagc tgaagaatac    480

tctaaggacc gtaaaaaatt ctgtaagaat gctgaagagt ttacaaagaa atatggggaa    540

aagcgacctg tggactaa                                                  558
```

<210> SEQ ID NO 56
<211> LENGTH: 185
<212> TYPE: PRT
<213> ORGANISM: Artificial Sequence
<220> FEATURE:
<223> OTHER INFORMATION: fusion protein
<220> FEATURE:
<221> NAME/KEY: MOD_RES
<222> LOCATION: (19)..(19)
<223> OTHER INFORMATION: X can be any amino acid

<400> SEQUENCE: 56

```
Met Arg Gly Ser His His His His His His Gly Ser Gly Val Asp Val
1               5                   10                  15

Ala Asp Xaa Ile Arg Met Arg Ala Arg Tyr Pro Ser Val Leu Asp Met
            20                  25                  30

Ala Ala Ser Arg Arg Leu Met Lys Glu Leu Glu Glu Ile Arg Lys Cys
```

```
        35                  40                  45

Gly Met Lys Asn Phe Arg Asn Ile Gln Val Asp Glu Ala Asn Leu Leu
    50                  55                  60

Thr Trp Gln Gly Leu Ile Val Pro Asp Asn Pro Pro Tyr Asp Lys Gly
65                  70                  75                  80

Ala Phe Arg Ile Glu Ile Asn Phe Pro Ala Glu Tyr Pro Phe Lys Pro
                85                  90                  95

Pro Lys Ile Thr Phe Lys Thr Lys Ile Tyr His Pro Asn Ile Asp Glu
            100                 105                 110

Lys Gly Gln Val Cys Leu Pro Val Ile Ser Ala Glu Asn Trp Lys Pro
        115                 120                 125

Ala Thr Lys Thr Asp Gln Val Ile Gln Ser Leu Ile Ala Leu Val Asn
    130                 135                 140

Asp Pro Gln Pro Glu His Pro Leu Arg Ala Asp Leu Ala Glu Glu Tyr
145                 150                 155                 160

Ser Lys Asp Arg Lys Lys Phe Cys Lys Asn Ala Glu Glu Phe Thr Lys
                165                 170                 175

Lys Tyr Gly Glu Lys Arg Pro Val Asp
            180                 185


<210> SEQ ID NO 57
<211> LENGTH: 184
<212> TYPE: PRT
<213> ORGANISM: Artificial Sequence
<220> FEATURE:
<223> OTHER INFORMATION: fusion protein

<400> SEQUENCE: 57

Met Arg Gly Ser His His His His His His Gly Ser Gly Asp Glu Val
1               5                   10                  15

Asp Gly Ile Arg Met Arg Ala Arg Tyr Pro Ser Val Leu Asp Met Ala
            20                  25                  30

Ala Ser Arg Arg Leu Met Lys Glu Leu Glu Glu Ile Arg Lys Cys Gly
        35                  40                  45

Met Lys Asn Phe Arg Asn Ile Gln Val Asp Glu Ala Asn Leu Leu Thr
    50                  55                  60

Trp Gln Gly Leu Ile Val Pro Asp Asn Pro Pro Tyr Asp Lys Gly Ala
65                  70                  75                  80

Phe Arg Ile Glu Ile Asn Phe Pro Ala Glu Tyr Pro Phe Lys Pro Pro
                85                  90                  95

Lys Ile Thr Phe Lys Thr Lys Ile Tyr His Pro Asn Ile Asp Glu Lys
            100                 105                 110

Gly Gln Val Cys Leu Pro Val Ile Ser Ala Glu Asn Trp Lys Pro Ala
        115                 120                 125

Thr Lys Thr Asp Gln Val Ile Gln Ser Leu Ile Ala Leu Val Asn Asp
    130                 135                 140

Pro Gln Pro Glu His Pro Leu Arg Ala Asp Leu Ala Glu Glu Tyr Ser
145                 150                 155                 160

Lys Asp Arg Lys Lys Phe Cys Lys Asn Ala Glu Glu Phe Thr Lys Lys
                165                 170                 175

Tyr Gly Glu Lys Arg Pro Val Asp
            180


<210> SEQ ID NO 58
<211> LENGTH: 184
<212> TYPE: PRT
```

<213> ORGANISM: Artificial Sequence
<220> FEATURE:
<223> OTHER INFORMATION: fusion protein

<400> SEQUENCE: 58

Met Arg Gly Ser His His His His His His Gly Ser Gly Glu Ile Ser
1 5 10 15

Asp Gly Ile Arg Met Arg Ala Arg Tyr Pro Ser Val Leu Asp Met Ala
20 25 30

Ala Ser Arg Arg Leu Met Lys Glu Leu Glu Glu Ile Arg Lys Cys Gly
35 40 45

Met Lys Asn Phe Arg Asn Ile Gln Val Asp Glu Ala Asn Leu Leu Thr
50 55 60

Trp Gln Gly Leu Ile Val Pro Asp Asn Pro Pro Tyr Asp Lys Gly Ala
65 70 75 80

Phe Arg Ile Glu Ile Asn Phe Pro Ala Glu Tyr Pro Phe Lys Pro Pro
85 90 95

Lys Ile Thr Phe Lys Thr Lys Ile Tyr His Pro Asn Ile Asp Glu Lys
100 105 110

Gly Gln Val Cys Leu Pro Val Ile Ser Ala Glu Asn Trp Lys Pro Ala
115 120 125

Thr Lys Thr Asp Gln Val Ile Gln Ser Leu Ile Ala Leu Val Asn Asp
130 135 140

Pro Gln Pro Glu His Pro Leu Arg Ala Asp Leu Ala Glu Glu Tyr Ser
145 150 155 160

Lys Asp Arg Lys Lys Phe Cys Lys Asn Ala Glu Glu Phe Thr Lys Lys
165 170 175

Tyr Gly Glu Lys Arg Pro Val Asp
180

<210> SEQ ID NO 59
<211> LENGTH: 184
<212> TYPE: PRT
<213> ORGANISM: Artificial Sequence
<220> FEATURE:
<223> OTHER INFORMATION: fusion protein

<400> SEQUENCE: 59

Met Arg Gly Ser His His His His His His Gly Ser Gly Glu Phe Lys
1 5 10 15

Asp Gly Ile Arg Met Arg Ala Arg Tyr Pro Ser Val Leu Asp Met Ala
20 25 30

Ala Ser Arg Arg Leu Met Lys Glu Leu Glu Glu Ile Arg Lys Cys Gly
35 40 45

Met Lys Asn Phe Arg Asn Ile Gln Val Asp Glu Ala Asn Leu Leu Thr
50 55 60

Trp Gln Gly Leu Ile Val Pro Asp Asn Pro Pro Tyr Asp Lys Gly Ala
65 70 75 80

Phe Arg Ile Glu Ile Asn Phe Pro Ala Glu Tyr Pro Phe Lys Pro Pro
85 90 95

Lys Ile Thr Phe Lys Thr Lys Ile Tyr His Pro Asn Ile Asp Glu Lys
100 105 110

Gly Gln Val Cys Leu Pro Val Ile Ser Ala Glu Asn Trp Lys Pro Ala
115 120 125

Thr Lys Thr Asp Gln Val Ile Gln Ser Leu Ile Ala Leu Val Asn Asp
130 135 140

```
Pro Gln Pro Glu His Pro Leu Arg Ala Asp Leu Ala Glu Glu Tyr Ser
145                 150                 155                 160

Lys Asp Arg Lys Lys Phe Cys Lys Asn Ala Glu Glu Phe Thr Lys Lys
                165                 170                 175

Tyr Gly Glu Lys Arg Pro Val Asp
            180


<210> SEQ ID NO 60
<211> LENGTH: 185
<212> TYPE: PRT
<213> ORGANISM: Artificial Sequence
<220> FEATURE:
<223> OTHER INFORMATION: fusion protein

<400> SEQUENCE: 60

Met Arg Gly Ser His His His His His His Gly Ser Gly Val Asp Gln
1               5                   10                  15

Gln Glu Gly Ile Arg Met Arg Ala Arg Tyr Pro Ser Val Leu Asp Met
            20                  25                  30

Ala Ala Ser Arg Arg Leu Met Lys Glu Leu Glu Glu Ile Arg Lys Cys
        35                  40                  45

Gly Met Lys Asn Phe Arg Asn Ile Gln Val Asp Glu Ala Asn Leu Leu
    50                  55                  60

Thr Trp Gln Gly Leu Ile Val Pro Asp Asn Pro Pro Tyr Asp Lys Gly
65                  70                  75                  80

Ala Phe Arg Ile Glu Ile Asn Phe Pro Ala Glu Tyr Pro Phe Lys Pro
                85                  90                  95

Pro Lys Ile Thr Phe Lys Thr Lys Ile Tyr His Pro Asn Ile Asp Glu
            100                 105                 110

Lys Gly Gln Val Cys Leu Pro Val Ile Ser Ala Glu Asn Trp Lys Pro
        115                 120                 125

Ala Thr Lys Thr Asp Gln Val Ile Gln Ser Leu Ile Ala Leu Val Asn
    130                 135                 140

Asp Pro Gln Pro Glu His Pro Leu Arg Ala Asp Leu Ala Glu Glu Tyr
145                 150                 155                 160

Ser Lys Asp Arg Lys Lys Phe Cys Lys Asn Ala Glu Glu Phe Thr Lys
                165                 170                 175

Lys Tyr Gly Glu Lys Arg Pro Val Asp
            180                 185


<210> SEQ ID NO 61
<211> LENGTH: 185
<212> TYPE: PRT
<213> ORGANISM: Artificial Sequence
<220> FEATURE:
<223> OTHER INFORMATION: fusion protein

<400> SEQUENCE: 61

Met Arg Gly Ser His His His His His His Gly Ser Gly Val Asp Gln
1               5                   10                  15

Gln Ser Gly Ile Arg Met Arg Ala Arg Tyr Pro Ser Val Leu Asp Met
            20                  25                  30

Ala Ala Ser Arg Arg Leu Met Lys Glu Leu Glu Glu Ile Arg Lys Cys
        35                  40                  45

Gly Met Lys Asn Phe Arg Asn Ile Gln Val Asp Glu Ala Asn Leu Leu
    50                  55                  60

Thr Trp Gln Gly Leu Ile Val Pro Asp Asn Pro Pro Tyr Asp Lys Gly
65                  70                  75                  80
```

Ala Phe Arg Ile Glu Ile Asn Phe Pro Ala Glu Tyr Pro Phe Lys Pro
85 90 95

Pro Lys Ile Thr Phe Lys Thr Lys Ile Tyr His Pro Asn Ile Asp Glu
100 105 110

Lys Gly Gln Val Cys Leu Pro Val Ile Ser Ala Glu Asn Trp Lys Pro
115 120 125

Ala Thr Lys Thr Asp Gln Val Ile Gln Ser Leu Ile Ala Leu Val Asn
130 135 140

Asp Pro Gln Pro Glu His Pro Leu Arg Ala Asp Leu Ala Glu Glu Tyr
145 150 155 160

Ser Lys Asp Arg Lys Lys Phe Cys Lys Asn Ala Glu Glu Phe Thr Lys
165 170 175

Lys Tyr Gly Glu Lys Arg Pro Val Asp
180 185

<210> SEQ ID NO 62
<211> LENGTH: 184
<212> TYPE: PRT
<213> ORGANISM: Artificial Sequence
<220> FEATURE:
<223> OTHER INFORMATION: fusion protein

<400> SEQUENCE: 62

Met Arg Gly Ser His His His His His His Gly Ser Gly Asp Glu Thr
1 5 10 15

Glu Arg Ile Arg Met Arg Ala Arg Tyr Pro Ser Val Leu Asp Met Ala
20 25 30

Ala Ser Arg Arg Leu Met Lys Glu Leu Glu Glu Ile Arg Lys Cys Gly
35 40 45

Met Lys Asn Phe Arg Asn Ile Gln Val Asp Glu Ala Asn Leu Leu Thr
50 55 60

Trp Gln Gly Leu Ile Val Pro Asp Asn Pro Pro Tyr Asp Lys Gly Ala
65 70 75 80

Phe Arg Ile Glu Ile Asn Phe Pro Ala Glu Tyr Pro Phe Lys Pro Pro
85 90 95

Lys Ile Thr Phe Lys Thr Lys Ile Tyr His Pro Asn Ile Asp Glu Lys
100 105 110

Gly Gln Val Cys Leu Pro Val Ile Ser Ala Glu Asn Trp Lys Pro Ala
115 120 125

Thr Lys Thr Asp Gln Val Ile Gln Ser Leu Ile Ala Leu Val Asn Asp
130 135 140

Pro Gln Pro Glu His Pro Leu Arg Ala Asp Leu Ala Glu Glu Tyr Ser
145 150 155 160

Lys Asp Arg Lys Lys Phe Cys Lys Asn Ala Glu Glu Phe Thr Lys Lys
165 170 175

Tyr Gly Glu Lys Arg Pro Val Asp
180

<210> SEQ ID NO 63
<211> LENGTH: 184
<212> TYPE: PRT
<213> ORGANISM: Artificial Sequence
<220> FEATURE:
<223> OTHER INFORMATION: fusion protein

<400> SEQUENCE: 63

Met Arg Gly Ser His His His His His His Gly Ser Gly Asp Glu Thr

```
1               5                   10                  15

Asp Arg Ile Arg Met Arg Ala Arg Tyr Pro Ser Val Leu Asp Met Ala
            20                  25                  30

Ala Ser Arg Arg Leu Met Lys Glu Leu Glu Glu Ile Arg Lys Cys Gly
        35                  40                  45

Met Lys Asn Phe Arg Asn Ile Gln Val Asp Glu Ala Asn Leu Leu Thr
    50                  55                  60

Trp Gln Gly Leu Ile Val Pro Asp Asn Pro Pro Tyr Asp Lys Gly Ala
65                  70                  75                  80

Phe Arg Ile Glu Ile Asn Phe Pro Ala Glu Tyr Pro Phe Lys Pro Pro
                85                  90                  95

Lys Ile Thr Phe Lys Thr Lys Ile Tyr His Pro Asn Ile Asp Glu Lys
            100                 105                 110

Gly Gln Val Cys Leu Pro Val Ile Ser Ala Glu Asn Trp Lys Pro Ala
        115                 120                 125

Thr Lys Thr Asp Gln Val Ile Gln Ser Leu Ile Ala Leu Val Asn Asp
    130                 135                 140

Pro Gln Pro Glu His Pro Leu Arg Ala Asp Leu Ala Glu Glu Tyr Ser
145                 150                 155                 160

Lys Asp Arg Lys Lys Phe Cys Lys Asn Ala Glu Glu Phe Thr Lys Lys
                165                 170                 175

Tyr Gly Glu Lys Arg Pro Val Asp
            180
```

<210> SEQ ID NO 64
<211> LENGTH: 292
<212> TYPE: PRT
<213> ORGANISM: Artificial Sequence
<220> FEATURE:
<223> OTHER INFORMATION: caspase 2

<400> SEQUENCE: 64

```
Met His His His His His His Gly Lys Glu His Met Ala Ser Pro Gly
1               5                   10                  15

Cys Glu Gln Ser Ala Ala Gly Lys Glu Lys Ile Leu Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Thr Gln Val Phe Ser Glu Arg Ala Arg Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Ser Ser Thr
            100                 105                 110

Leu Cys Arg His Leu Tyr Leu Phe Pro Gly His Pro Pro Thr Gly Ser
        115                 120                 125

Gly Pro Pro Ser Leu Gln Val Lys Pro Cys Thr Ser Glu Phe Tyr Arg
    130                 135                 140

Thr His His His Leu Ala Tyr Arg Leu Gln Ser Arg Pro Arg Gly Leu
145                 150                 155                 160

Ala Leu Val Leu Ser Asn Val His Phe Asn Gly Glu Lys Asp Leu Glu
                165                 170                 175

Phe Arg Ser Gly Gly Asp Val Asp His Ser Ser Leu Val Thr Leu Phe
```

```
            180                 185                 190

Lys Leu Leu Asp Tyr Asp Val His Val Leu Arg Asp Gln Thr Ala Gln
        195                 200                 205

Glu Met Tyr Glu Lys Leu Gln Arg Phe Ala Gln Leu Ser Thr His Gln
    210                 215                 220

Asn Thr Asp Ser Cys Val Val Ala Leu Leu Ser His Gly Ile Glu Gly
225                 230                 235                 240

Gly Ile Tyr Gly Val Asp Gly Gln Leu Leu Gln Leu Gln Glu Val Phe
                245                 250                 255

Gln Leu Phe Asp Asn Ala Asn Cys Pro Asn Leu Gln Asn Lys Pro Lys
            260                 265                 270

Met Phe Phe Ile Gln Ala Cys Arg Gly Asp Glu Thr Asp Arg Gly Val
        275                 280                 285

Asp Leu Arg Asp
    290
```

<210> SEQ ID NO 65
<211> LENGTH: 885
<212> TYPE: DNA
<213> ORGANISM: Artificial Sequence
<220> FEATURE:
<223> OTHER INFORMATION: caspase 2

<400> SEQUENCE: 65

```
atgatgcacc atcatcatca ccatggtaaa gaacacatgg caagtccggg ttgtgaacag      60

agcgcagcag gtaaagaaaa aattctgaaa atgcgtctgc cgacacgtag cgatatgatt     120

tgtggttatg catgtctgaa aggcaccgca gcaatgcgta ataccaaacg tggtagctgg     180

tatattgaag cactgaccca ggtttttagc gaacgtgccc gtgatatgca tgttgcagat     240

atgctggtta aagtgaacgc cctgattaaa gatcgtgaag gttatgcacc gggtacagaa     300

tttcatcgtt gtaaagaaat gagcgagtat agcagcaccc tgtgtcgtca tctgtacctg     360

tttccgggtc atcctccgac cggtagcggt ccgcctagcc tgcaggttaa accgtgtacc     420

agcgaatttt atcgtaccca tcaccatctg gcatatcgtc tgcagagccg tccgcgtggt     480

ctggcactgg ttctgagcaa tgttcatttt aatggcgaga aagatctgga atttcgtagc     540

ggtggtgatg ttgatcatag cagcctggtt accctgttta aactgctgga ttatgacgtt     600

catgttctgc gtgatcagac cgcacaagaa atgtatgaaa aactgcagcg ttttgcacag     660

ctgagcaccc atcagaatac cgatagctgt gttgttgccc tgctgagcca tggtattgaa     720

ggtggtattt atggtgttga tggtcagctg ctgcaactgc aagaagtttt tcagctgttt     780

gataatgcga attgtccgaa cctgcagaac aaaccgaaaa tgttttttat ccaggcatgc     840

cgtggtgatg aaaccgatcg tggtgtggat ctgcgcgatt aataa                     885
```

<210> SEQ ID NO 66
<211> LENGTH: 292
<212> TYPE: PRT
<213> ORGANISM: Artificial Sequence
<220> FEATURE:
<223> OTHER INFORMATION: caspase 2

<400> SEQUENCE: 66

```
Met His His His His His His Gly Asn Asp Cys Ala Ser Ser Pro Gly
1               5                   10                  15

Cys Glu Glu Thr Ala Ala Asn Lys Lys Glu Asn Pro Lys Leu Arg Leu
            20                  25                  30
```

```
Pro Thr Cys Ser Asp Met Ile Cys Gly Tyr Ala Cys Leu Lys Gly Thr
        35                  40                  45

Ala Ala Met Arg Asn Thr Lys His Gly Ser Trp Tyr Val Glu Ala Leu
    50                  55                  60

Thr Ser Val Phe Ala Glu Asp Ser Gly His Met His Val Ala Asp Met
65                  70                  75                  80

Leu Val Lys Val Asn Arg Leu Ile Lys Leu Arg Glu Gly His Ala Pro
                85                  90                  95

Gly Thr Glu Phe His Arg Cys Lys Glu Met Ser Glu Tyr Cys Ser Thr
            100                 105                 110

Leu Cys Gln Asp Leu Tyr Leu Phe Pro Gly Tyr Phe Pro Gly Gly Ser
        115                 120                 125

Gly Pro His Tyr Pro Gln Val Met Pro Cys Thr Pro Glu Phe Tyr Arg
    130                 135                 140

Thr His Glu Gln Leu Ala Tyr Lys Leu Lys Ser Gln Pro Arg Gly Leu
145                 150                 155                 160

Ala Leu Ile Leu Ser Asn Ile His Phe Asn Lys Glu Thr Asp Leu Asp
                165                 170                 175

Phe Arg Ser Gly Gly Asp Val Asp Asn Thr Ala Leu His Met Leu Phe
            180                 185                 190

Lys His Leu Gly Tyr Gln Val Val Val Arg Gln Asp Arg Thr Ala Gln
        195                 200                 205

Glu Met Lys Glu Glu Leu Glu Ile Phe Ser Lys His Pro Ala His Arg
    210                 215                 220

Asn Val Asp Ser Cys Ile Val Ser Leu Leu Ser His Gly Ile Glu Gly
225                 230                 235                 240

Gly Ile Tyr Gly Ile Asp Gly Lys Leu Leu Gln Leu Gln Glu Ile Phe
                245                 250                 255

Arg Leu Phe Asp Asn Ala Asn Cys Pro Asn Leu Gln Asn Lys Pro Lys
            260                 265                 270

Met Phe Phe Val Gln Ala Cys Arg Gly Asp Glu Thr Asp His Gly Val
        275                 280                 285

Asp Gln Ile Asp
    290
```

<210> SEQ ID NO 67
<211> LENGTH: 882
<212> TYPE: DNA
<213> ORGANISM: Artificial Sequence
<220> FEATURE:
<223> OTHER INFORMATION: caspase 2

<400> SEQUENCE: 67

```
atgcatcatc accatcatca tggcaatgat tgtgcaagca gtccgggttg tgaagaaacc      60

gcagcaaaca aaaaagaaaa tccgaaactg cgtctgccga cctgtagcga tatgatttgt     120

ggttatgcat gtctgaaagg caccgcagcc atgcgtaata ccaaacatgg tagctggtat     180

gttgaagcac tgaccagcgt ttttgccgaa gatagcggtc acatgcacgt tgcagatatg     240

ctggttaaag ttaaccgtct gattaaactg cgtgaaggtc atgcaccggg tacagaattt     300

catcgttgta aagaaatgag cgagtattgt agcaccctgt gtcaggatct gtacctgttt     360

ccgggttatt ttcctggtgg tagcggtccg cattatccgc aggttatgcc gtgtacaccg     420

gaattttatc gtacccatga acagctggca tacaaactga aagccagcc tcgtggtctg      480

gcactgattc tgagcaatat tcactttaac aaagaaaccg atctggattt tcgtagcggt     540
```

-continued

```
ggtgatgttg ataataccgc actgcacatg ctgttcaaac atctgggtta tcaggttgtt    600

gttcgtcagg atcgcaccgc acaagaaatg aaagaagaac tggaaatctt cagcaaacat    660

ccggcacatc gtaatgttga tagctgtatt gttagcctgc tgagccatgg tattgaaggt    720

ggtatttatg gcattgatgg taaactgctg caactgcaag aaatctttcg cctgtttgat    780

aatgccaatt gtccgaatct gcagaacaaa ccgaaaatgt tttttgttca ggcatgccgt    840

ggtgatgaaa cggatcatgg tgttgatcag atcgattgat aa                       882


<210> SEQ ID NO 68
<211> LENGTH: 295
<212> TYPE: PRT
<213> ORGANISM: Artificial Sequence
<220> FEATURE:
<223> OTHER INFORMATION: caspase 2

<400> SEQUENCE: 68

Met His His His His His His Gly Ala Asp Ala Pro Gly Cys Glu Glu
1               5                   10                  15

Cys Ala Ala Gly Lys Glu Arg Glu Arg Thr Arg Arg Gly Lys Leu Pro
            20                  25                  30

Thr Gln Ser Asp Ile Ile Cys Gly Tyr Ala Cys Leu Arg Gly Thr Ala
        35                  40                  45

Ala Leu Arg Asn Thr Arg Gln Gly Ser Trp Tyr Ile Gln Ala Leu Val
    50                  55                  60

Lys Val Phe Thr Glu Arg Ala His Asn Thr His Val Ala Asp Met Leu
65                  70                  75                  80

Val Gln Val Asn Ala Val Ile Arg Asp Arg Glu Gly Phe Ala Pro Gly
                85                  90                  95

Thr Asp Phe His Arg Cys Lys Glu Met Ala Glu Tyr Ser Ile Phe Glu
            100                 105                 110

Glu Met Glu Gly Glu Thr Gln Arg Lys Gln Arg Arg Arg Lys Thr Ala
        115                 120                 125

Ala Pro Gly Ser Gly Ser Gly Thr Phe Ser Val Arg Pro Thr Thr Ala
    130                 135                 140

Gln Phe Tyr His Glu His His Lys Gln Ser Tyr Arg Met Ala Ser Arg
145                 150                 155                 160

Pro Arg Gly Ala Ala Leu Ile Val Ser Asn Glu Val Phe Val Gly Glu
                165                 170                 175

Gly Leu Gly His Arg Pro Gly Gly Ala Ala Asp Thr Gly Val Leu Arg
            180                 185                 190

Ala Leu Leu Ser Gln Leu Gly Tyr Arg Val Thr Ser Val Cys Asn Ser
        195                 200                 205

Pro Ala Gln Glu Leu Glu Thr Arg Leu Arg Asp Phe Ala Leu Ser Ala
    210                 215                 220

Asp His Arg Arg Thr Asp Ser Cys Val Val Val Leu Leu Ser His Gly
225                 230                 235                 240

Val Glu Gly Ala Ile Tyr Gly Val Asp Gly Lys Leu Val Gln Ile His
                245                 250                 255

Asp Ile Phe Gln Leu Phe Asp Asn Ala Asn Cys Pro Asn Leu Gln Asn
            260                 265                 270

Lys Pro Lys Met Phe Phe Ile Gln Ala Cys Arg Gly Asp Arg Thr Asp
        275                 280                 285

Arg Gly Val Asp Arg Leu Asp
    290                 295
```

<210> SEQ ID NO 69
<211> LENGTH: 891
<212> TYPE: DNA
<213> ORGANISM: Artificial Sequence
<220> FEATURE:
<223> OTHER INFORMATION: caspase 2

<400> SEQUENCE: 69
atgcatcatc accatcatca tggtgcagat gcaccgggtt gtgaagaatg tgcagcaggt 60
aaagaacgtg aacgtacccg tcgtggtaaa ctgccgacac agagcgatat tatctgtggt 120
tatgcatgtc tgcgtggcac cgcagcactg cgtaataccc gtcaaggtag ctggtatatt 180
caggcactgg ttaaagtttt taccgaacgt gcacataata cccatgttgc agatatgctg 240
gttcaggtta atgcagttat tcgtgatcgt gaaggttttg ctccgggtac agattttcat 300
cgttgtaaag aaatggccga gtatagcatc tttgaagaaa tggaaggtga aacccagcgt 360
aaacagcgtc gtcgtaaaac cgcagcgcct ggtagcggta gcggcacctt tagcgttcgt 420
ccgaccaccg cacagtttta tcatgaacat cataaacaga gctatcgtat ggcaagccgt 480
ccgcgtggtg cagcactgat tgttagcaat gaagtttttg ttggtgaagg tctgggtcat 540
cgtcctggtg gtgccgcaga taccggtgtt ctgcgtgcac tgctgagcca gctgggttat 600
cgtgttacca gcgtttgtaa tagtccggca caagaactgg aaacccgtct gcgtgatttt 660
gcactgagcg cagatcatcg tcgtaccgat agctgtgttg ttgttctgct gagtcatggt 720
gttgaaggtg caatttatgg tgtggatggc aaactggttc agatccatga tatttttcag 780
ctgtttgata atgcgaattg cccgaatctg cagaacaaac cgaaaatgtt ttttatccag 840
gcatgtcgtg gtgatcgcac cgatcgtggt gttgatcgtc tggattaata a 891

<210> SEQ ID NO 70
<211> LENGTH: 292
<212> TYPE: PRT
<213> ORGANISM: Artificial Sequence
<220> FEATURE:
<223> OTHER INFORMATION: caspase 2

<400> SEQUENCE: 70

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Val Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Asp Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Gly Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Glu Glu Thr Glu Arg Gly Val
275 280 285

Asp Gln Gln Asp
290

<210> SEQ ID NO 71
<211> LENGTH: 314
<212> TYPE: PRT
<213> ORGANISM: Artificial Sequence
<220> FEATURE:
<223> OTHER INFORMATION: caspase 2

<400> SEQUENCE: 71

Met Leu Glu Asp Pro Glu Arg Asn Lys Glu Arg Lys Glu Ala Glu Leu
1 5 10 15

Gln Ala Gln Thr Ala Glu Gln His His His His His His Gly Lys Asn
20 25 30

His Ala Gly Ser Pro Gly Cys Glu Glu Ser Ala Ala Gly Lys Glu Lys
35 40 45

Leu Pro Lys Met Arg Leu Pro Thr Arg Ser Asp Met Ile Cys Gly Tyr
50 55 60

Ala Cys Leu Lys Gly Thr Ala Ala Met Arg Asn Thr Lys Arg Gly Ser
65 70 75 80

Trp Tyr Ile Glu Ala Leu Ala Gln Val Phe Ser Glu Arg Ala Cys Asp
85 90 95

Met His Val Ala Asp Met Leu Val Lys Val Asn Ala Leu Ile Lys Asp
100 105 110

Arg Glu Gly Tyr Ala Pro Gly Thr Glu Phe His Arg Cys Lys Val Met
115 120 125

Ser Glu Tyr Cys Ser Thr Leu Cys Arg His Leu Tyr Leu Phe Pro Gly
130 135 140

His Pro Pro Thr Gly Ser Gly Pro Val Cys Leu Gln Val Lys Pro Cys
145 150 155 160

Thr Pro Glu Phe Tyr Gln Thr His Phe Gln Leu Ala Tyr Arg Leu Gln
165 170 175

Ser Arg Pro Arg Gly Leu Ala Leu Val Leu Ser Asn Val His Phe Thr
180 185 190

Asp Glu Lys Glu Leu Glu Phe Arg Ser Gly Gly Asp Val Asp His Ser
195 200 205

Thr Leu Val Thr Leu Phe Lys Leu Leu Gly Tyr Asp Val His Val Leu
210 215 220

Cys Asp Gln Thr Ala Gln Glu Met Gln Glu Lys Leu Gln Asn Phe Ala
225 230 235 240

Gln Leu Pro Ala His Arg Gly Thr Asp Ser Cys Ile Val Ala Leu Leu
245 250 255

Ser His Gly Val Glu Gly Ala Ile Tyr Gly Val Asp Gly Lys Leu Leu
260 265 270

Gln Leu Gln Glu Val Phe Gln Leu Phe Asp Asn Ala Asn Cys Pro Ser
275 280 285

Leu Gln Asn Lys Pro Lys Met Phe Phe Ile Gln Ala Cys Arg Gly Glu
290 295 300

Glu Thr Glu Arg Gly Val Asp Gln Gln Asp
305 310

<210> SEQ ID NO 72
<211> LENGTH: 314
<212> TYPE: PRT
<213> ORGANISM: Artificial Sequence
<220> FEATURE:
<223> OTHER INFORMATION: caspase 2

<400> SEQUENCE: 72

Met Leu Glu Asp Pro Glu Arg Asn Lys Glu Arg Lys Glu Ala Glu Leu
1 5 10 15

Gln Ala Gln Thr Ala Glu Gln His His His His His His Gly Lys Asn
20 25 30

His Ala Gly Ser Pro Gly Cys Glu Glu Ser Ala Ala Gly Lys Glu Lys
35 40 45

Leu Pro Lys Met Arg Leu Pro Thr Arg Ser Asp Met Ile Cys Gly Tyr
50 55 60

Ala Cys Leu Lys Gly Thr Ala Ala Met Arg Asn Thr Lys Arg Gly Ser
65 70 75 80

Trp Tyr Ile Glu Ala Leu Ala Gln Val Phe Ser Glu Arg Ala Cys Asp
85 90 95

Met His Val Ala Asp Met Leu Val Lys Val Asn Ala Leu Ile Lys Asp
100 105 110

Arg Glu Gly Tyr Ala Pro Gly Thr Glu Phe His Arg Cys Lys Val Met
115 120 125

Ser Glu Tyr Cys Ser Thr Leu Cys Arg His Leu Tyr Leu Phe Pro Gly
130 135 140

His Pro Pro Thr Gly Ser Gly Pro Val Cys Leu Gln Val Lys Pro Cys
145 150 155 160

Thr Pro Glu Phe Tyr Gln Thr His Phe Gln Leu Ala Tyr Arg Leu Gln
165 170 175

Ser Arg Pro Arg Gly Leu Ala Leu Val Leu Ser Asn Val His Phe Thr
180 185 190

Asp Glu Lys Glu Leu Glu Phe Arg Ser Gly Gly Asp Val Asp His Ser
195 200 205

Thr Leu Val Thr Leu Phe Lys Leu Leu Gly Tyr Asp Val His Val Leu
210 215 220

Cys Asp Gln Thr Ala Gln Glu Met Gln Glu Lys Leu Gln Asn Phe Ala
225 230 235 240

Gln Leu Pro Ala His Arg Gly Thr Asp Ser Cys Ile Val Ala Leu Leu
245 250 255

Ser His Gly Val Glu Gly Ala Ile Tyr Gly Val Asp Gly Lys Leu Leu
260 265 270

```
Gln Leu Gln Glu Val Phe Gln Leu Phe Asp Asn Ala Asn Cys Pro Ser
        275                 280                 285

Leu Gln Asn Lys Pro Lys Met Phe Phe Ile Gln Ala Cys Arg Gly Glu
    290                 295                 300

Glu Thr Asp Arg Gly Val Asp Gln Gln Asp
305                 310
```

<210> SEQ ID NO 73
<211> LENGTH: 290
<212> TYPE: PRT
<213> ORGANISM: Artificial Sequence
<220> FEATURE:
<223> OTHER INFORMATION: caspase 2

<400> SEQUENCE: 73

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Pro
        115                 120                 125

Val Cys Leu Gln Val Lys Pro Cys Thr Pro Glu Phe Tyr Gln Thr His
    130                 135                 140

Phe Gln Leu Ala Tyr Arg Leu Gln Ser Arg Pro Arg Gly Leu Ala Leu
145                 150                 155                 160

Val Leu Ser Asn Val His Phe Thr Gly Glu Lys Glu Leu Glu Phe Arg
                165                 170                 175

Ser Gly Gly Asp Val Asp His Ser Thr Leu Val Thr Leu Phe Lys Leu
            180                 185                 190

Leu Gly Tyr Asp Val His Val Leu Cys Asp Gln Thr Ala Gln Glu Met
        195                 200                 205

Gln Glu Lys Leu Gln Asn Phe Ala Gln Leu Pro Ala His Arg Val Thr
    210                 215                 220

Asp Ser Cys Ile Val Ala Leu Leu Ser His Gly Val Glu Gly Ala Ile
225                 230                 235                 240

Tyr Gly Val Asp Gly Lys Leu Leu Gln Leu Gln Glu Val Phe Gln Leu
                245                 250                 255

Phe Asp Asn Ala Asn Cys Pro Ser Leu Gln Asn Lys Pro Lys Met Phe
            260                 265                 270

Phe Ile Gln Ala Cys Arg Gly Asp Glu Thr Asp Arg Gly Val Asp Gln
        275                 280                 285

Gln Asp
    290
```

<210> SEQ ID NO 74

<211> LENGTH: 295
<212> TYPE: PRT
<213> ORGANISM: Artificial Sequence
<220> FEATURE:
<223> OTHER INFORMATION: caspase 2

<400> SEQUENCE: 74

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Gly
        115                 120                 125

Ser Gly Gly Gly Pro Val Cys Leu Gln Val Lys Pro Cys Thr Pro Glu
    130                 135                 140

Phe Tyr Gln Thr His Phe Gln Leu Ala Tyr Arg Leu Gln Ser Arg Pro
145                 150                 155                 160

Arg Gly Leu Ala Leu Val Leu Ser Asn Val His Phe Thr Gly Glu Lys
                165                 170                 175

Glu Leu Glu Phe Arg Ser Gly Gly Asp Val Asp His Ser Thr Leu Val
            180                 185                 190

Thr Leu Phe Lys Leu Leu Gly Tyr Asp Val His Val Leu Cys Asp Gln
        195                 200                 205

Thr Ala Gln Glu Met Gln Glu Lys Leu Gln Asn Phe Ala Gln Leu Pro
    210                 215                 220

Ala His Arg Val Thr Asp Ser Cys Ile Val Ala Leu Leu Ser His Gly
225                 230                 235                 240

Val Glu Gly Ala Ile Tyr Gly Val Asp Gly Lys Leu Leu Gln Leu Gln
                245                 250                 255

Glu Val Phe Gln Leu Phe Asp Asn Ala Asn Cys Pro Ser Leu Gln Asn
            260                 265                 270

Lys Pro Lys Met Phe Phe Ile Gln Ala Cys Arg Gly Asp Glu Thr Asp
        275                 280                 285

Arg Gly Val Asp Gln Gln Asp
    290                 295
```

<210> SEQ ID NO 75
<211> LENGTH: 300
<212> TYPE: PRT
<213> ORGANISM: Artificial Sequence
<220> FEATURE:
<223> OTHER INFORMATION: caspase 2

<400> SEQUENCE: 75

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
```

```
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Ala Gly Ser Ala Ala Gly Ser Gly Gly Pro Val Cys Leu Gln Val Lys
    130                 135                 140

Pro Cys Thr Pro Glu Phe Tyr Gln Thr His Phe Gln Leu Ala Tyr Arg
145                 150                 155                 160

Leu Gln Ser Arg Pro Arg Gly Leu Ala Leu Val Leu Ser Asn Val His
                165                 170                 175

Phe Thr Gly Glu Lys Glu Leu Glu Phe Arg Ser Gly Gly Asp Val Asp
            180                 185                 190

His Ser Thr Leu Val Thr Leu Phe Lys Leu Leu Gly Tyr Asp Val His
        195                 200                 205

Val Leu Cys Asp Gln Thr Ala Gln Glu Met Gln Glu Lys Leu Gln Asn
    210                 215                 220

Phe Ala Gln Leu Pro Ala His Arg Val Thr Asp Ser Cys Ile Val Ala
225                 230                 235                 240

Leu Leu Ser His Gly Val Glu Gly Ala Ile Tyr Gly Val Asp Gly Lys
                245                 250                 255

Leu Leu Gln Leu Gln Glu Val Phe Gln Leu Phe Asp Asn Ala Asn Cys
            260                 265                 270

Pro Ser Leu Gln Asn Lys Pro Lys Met Phe Phe Ile Gln Ala Cys Arg
        275                 280                 285

Gly Asp Glu Thr Asp Arg Gly Val Asp Gln Gln Asp
    290                 295                 300


<210> SEQ ID NO 76
<211> LENGTH: 277
<212> TYPE: PRT
<213> ORGANISM: Artificial Sequence
<220> FEATURE:
<223> OTHER INFORMATION: caspase 2

<400> SEQUENCE: 76

Met His His His His His His Gly Lys Glu Lys Leu Pro Lys Met Arg
1               5                   10                  15

Leu Pro Thr Arg Ser Asp Met Ile Cys Gly Tyr Ala Cys Leu Lys Gly
            20                  25                  30

Thr Ala Ala Met Arg Asn Thr Lys Arg Gly Ser Trp Tyr Ile Glu Ala
        35                  40                  45

Leu Ala Gln Val Phe Ser Glu Arg Ala Cys Asp Met His Val Ala Asp
    50                  55                  60

Met Leu Val Lys Val Asn Ala Leu Ile Lys Asp Arg Glu Gly Tyr Ala
65                  70                  75                  80

Pro Gly Thr Glu Phe His Arg Cys Lys Glu Met Ser Glu Tyr Cys Ser
```

```
                85                  90                  95

Thr Leu Cys Arg His Leu Tyr Leu Phe Pro Gly His Pro Pro Thr Gly
            100                 105                 110

Ser Gly Pro Val Cys Leu Gln Val Lys Pro Cys Thr Pro Glu Phe Tyr
        115                 120                 125

Gln Thr His Phe Gln Leu Ala Tyr Arg Leu Gln Ser Arg Pro Arg Gly
    130                 135                 140

Leu Ala Leu Val Leu Ser Asn Val His Phe Thr Gly Glu Lys Glu Leu
145                 150                 155                 160

Glu Phe Arg Ser Gly Gly Asp Val Asp His Ser Thr Leu Val Thr Leu
                165                 170                 175

Phe Lys Leu Leu Gly Tyr Asp Val His Val Leu Cys Asp Gln Thr Ala
            180                 185                 190

Gln Glu Met Gln Glu Lys Leu Gln Asn Phe Ala Gln Leu Pro Ala His
        195                 200                 205

Arg Val Thr Asp Ser Cys Ile Val Ala Leu Leu Ser His Gly Val Glu
    210                 215                 220

Gly Ala Ile Tyr Gly Val Asp Gly Lys Leu Leu Gln Leu Gln Glu Val
225                 230                 235                 240

Phe Gln Leu Phe Asp Asn Ala Asn Cys Pro Ser Leu Gln Asn Lys Pro
                245                 250                 255

Lys Met Phe Phe Ile Gln Ala Cys Arg Gly Asp Glu Thr Asp Arg Gly
            260                 265                 270

Val Asp Gln Gln Asp
        275


<210> SEQ ID NO 77
<211> LENGTH: 284
<212> TYPE: PRT
<213> ORGANISM: Artificial Sequence
<220> FEATURE:
<223> OTHER INFORMATION: caspase 2

<400> SEQUENCE: 77

Met His His His His His His Gly Cys Glu Glu Ser Ala Ala Gly Lys
1               5                   10                  15

Glu Lys Leu Pro Lys Met Arg Leu Pro Thr Arg Ser Asp Met Ile Cys
            20                  25                  30

Gly Tyr Ala Cys Leu Lys Gly Thr Ala Ala Met Arg Asn Thr Lys Arg
        35                  40                  45

Gly Ser Trp Tyr Ile Glu Ala Leu Ala Gln Val Phe Ser Glu Arg Ala
    50                  55                  60

Cys Asp Met His Val Ala Asp Met Leu Val Lys Val Asn Ala Leu Ile
65                  70                  75                  80

Lys Asp Arg Glu Gly Tyr Ala Pro Gly Thr Glu Phe His Arg Cys Lys
                85                  90                  95

Glu Met Ser Glu Tyr Cys Ser Thr Leu Cys Arg His Leu Tyr Leu Phe
            100                 105                 110

Pro Gly His Pro Pro Thr Gly Ser Gly Pro Val Cys Leu Gln Val Lys
        115                 120                 125

Pro Cys Thr Pro Glu Phe Tyr Gln Thr His Phe Gln Leu Ala Tyr Arg
    130                 135                 140

Leu Gln Ser Arg Pro Arg Gly Leu Ala Leu Val Leu Ser Asn Val His
145                 150                 155                 160

Phe Thr Gly Glu Lys Glu Leu Glu Phe Arg Ser Gly Gly Asp Val Asp
```

```
                165                 170                 175

His Ser Thr Leu Val Thr Leu Phe Lys Leu Leu Gly Tyr Asp Val His
            180                 185                 190

Val Leu Cys Asp Gln Thr Ala Gln Glu Met Gln Glu Lys Leu Gln Asn
        195                 200                 205

Phe Ala Gln Leu Pro Ala His Arg Val Thr Asp Ser Cys Ile Val Ala
    210                 215                 220

Leu Leu Ser His Gly Val Glu Gly Ala Ile Tyr Gly Val Asp Gly Lys
225                 230                 235                 240

Leu Leu Gln Leu Gln Glu Val Phe Gln Leu Phe Asp Asn Ala Asn Cys
                245                 250                 255

Pro Ser Leu Gln Asn Lys Pro Lys Met Phe Phe Ile Gln Ala Cys Arg
            260                 265                 270

Gly Asp Glu Thr Asp Arg Gly Val Asp Gln Gln Asp
        275                 280


<210> SEQ ID NO 78
<211> LENGTH: 292
<212> TYPE: PRT
<213> ORGANISM: Artificial Sequence
<220> FEATURE:
<223> OTHER INFORMATION: caspase 2

<400> SEQUENCE: 78

Met His His His His His His Gly Lys Glu His Met Ala Ser Pro Gly
1               5                   10                  15

Cys Glu Gln Ser Ala Ala Gly Lys Glu Lys Ile Leu Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Thr Gln Val Phe Ser Glu Arg Ala Arg Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Ser Ser Thr
            100                 105                 110

Leu Cys Arg His Leu Tyr Leu Phe Pro Gly His Pro Pro Thr Gly Ser
        115                 120                 125

Gly Pro Pro Ser Leu Gln Val Lys Pro Cys Thr Ser Glu Phe Tyr Arg
    130                 135                 140

Thr His His His Leu Ala Tyr Arg Leu Gln Ser Arg Pro Arg Gly Leu
145                 150                 155                 160

Ala Leu Val Leu Ser Asn Val His Phe Asn Gly Val Lys Asp Leu Glu
                165                 170                 175

Phe Arg Ser Gly Gly Asp Val Asp His Ser Ser Leu Val Thr Leu Phe
            180                 185                 190

Lys Leu Leu Asp Tyr Asp Val His Val Leu Arg Asp Gln Thr Ala Gln
        195                 200                 205

Glu Met Tyr Glu Lys Leu Gln Arg Phe Ala Gln Leu Ser Thr His Gln
    210                 215                 220

Asn Thr Asp Ser Cys Val Val Ala Leu Leu Ser His Gly Ile Glu Gly
225                 230                 235                 240

Gly Ile Tyr Gly Val Asp Gly Gln Leu Leu Gln Leu Gln Glu Val Phe
```

```
                245                 250                 255

Gln Leu Phe Asp Asn Ala Asn Cys Pro Asn Leu Gln Asn Lys Pro Lys
            260                 265                 270

Met Phe Phe Ile Gln Ala Cys Arg Gly Asp Glu Thr Asp Arg Gly Val
        275                 280                 285

Asp Leu Arg Asp
    290


<210> SEQ ID NO 79
<211> LENGTH: 295
<212> TYPE: PRT
<213> ORGANISM: Artificial Sequence
<220> FEATURE:
<223> OTHER INFORMATION: caspase 2

<400> SEQUENCE: 79

Met His His His His His His Gly Ala Asp Ala Pro Gly Cys Glu Glu
1               5                   10                  15

Cys Ala Ala Gly Lys Glu Arg Glu Arg Thr Arg Arg Gly Lys Leu Pro
            20                  25                  30

Thr Gln Ser Asp Ile Ile Cys Gly Tyr Ala Cys Leu Arg Gly Thr Ala
        35                  40                  45

Ala Leu Arg Asn Thr Arg Gln Gly Ser Trp Tyr Ile Gln Ala Leu Val
    50                  55                  60

Lys Val Phe Thr Glu Arg Ala His Asn Thr His Val Ala Asp Met Leu
65                  70                  75                  80

Val Gln Val Asn Ala Val Ile Arg Asp Arg Glu Gly Phe Ala Pro Gly
                85                  90                  95

Thr Asp Phe His Arg Cys Lys Val Met Ala Glu Tyr Ser Ile Phe Glu
            100                 105                 110

Glu Met Glu Gly Glu Thr Gln Arg Lys Gln Arg Arg Arg Lys Thr Ala
        115                 120                 125

Ala Pro Gly Ser Gly Ser Gly Thr Phe Ser Val Arg Pro Thr Thr Ala
    130                 135                 140

Gln Phe Tyr His Glu His His Lys Gln Ser Tyr Arg Met Ala Ser Arg
145                 150                 155                 160

Pro Arg Gly Ala Ala Leu Ile Val Ser Asn Glu Val Phe Val Asp Glu
                165                 170                 175

Gly Leu Gly His Arg Pro Gly Gly Ala Ala Asp Thr Gly Val Leu Arg
            180                 185                 190

Ala Leu Leu Ser Gln Leu Gly Tyr Arg Val Thr Ser Val Cys Asn Ser
        195                 200                 205

Pro Ala Gln Glu Leu Glu Thr Arg Leu Arg Asp Phe Ala Leu Ser Ala
    210                 215                 220

Asp His Arg Arg Thr Asp Ser Cys Val Val Val Leu Leu Ser His Gly
225                 230                 235                 240

Val Glu Gly Ala Ile Tyr Gly Val Asp Gly Lys Leu Val Gln Ile His
                245                 250                 255

Asp Ile Phe Gln Leu Phe Asp Asn Ala Asn Cys Pro Asn Leu Gln Asn
            260                 265                 270

Lys Pro Lys Met Phe Phe Ile Gln Ala Cys Arg Gly Asp Arg Thr Asp
        275                 280                 285

Arg Gly Val Asp Arg Leu Asp
    290                 295
```

<210> SEQ ID NO 80
<211> LENGTH: 292
<212> TYPE: PRT
<213> ORGANISM: Artificial Sequence
<220> FEATURE:
<223> OTHER INFORMATION: caspase 2

<400> SEQUENCE: 80

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Cys Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290
```

<210> SEQ ID NO 81
<211> LENGTH: 292
<212> TYPE: PRT
<213> ORGANISM: Artificial Sequence
<220> FEATURE:
<223> OTHER INFORMATION: caspase 2

<400> SEQUENCE: 81

```
Met His His His His His His Gly Lys Asn His Ala Gly Ser Pro Gly
1               5                   10                  15
```

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Glu Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Gly Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Asp His Gly Ala
275 280 285

Val Leu Arg Gly
290

<210> SEQ ID NO 82
<211> LENGTH: 277
<212> TYPE: PRT
<213> ORGANISM: Artificial Sequence
<220> FEATURE:
<223> OTHER INFORMATION: caspase 2

<400> SEQUENCE: 82

Met His His His His His His Lys Leu Pro Lys Met Arg Leu Pro Thr
1 5 10 15

Arg Ser Asp Met Ile Cys Gly Tyr Ala Cys Leu Lys Gly Thr Ala Ala
20 25 30

Met Arg Asn Thr Lys Arg Gly Ser Trp Tyr Ile Glu Ala Leu Ala Gln
35 40 45

Val Phe Ser Glu Arg Ala Cys Asp Met His Val Ala Asp Met Leu Val
50 55 60

Lys Val Asn Ala Leu Ile Lys Asp Arg Glu Gly Tyr Ala Pro Gly Thr
65 70 75 80

```
Glu Phe His Arg Cys Lys Glu Met Ser Glu Tyr Cys Ser Thr Leu Cys
                85                  90                  95

Arg His Leu Tyr Leu Phe Pro Gly His Pro Pro Thr Gly Ser Gly Pro
            100                 105                 110

Val Cys Leu Gln Val Lys Pro Cys Thr Pro Glu Phe Tyr Gln Thr His
        115                 120                 125

Phe Gln Leu Ala Tyr Arg Leu Gln Ser Arg Pro Arg Gly Leu Ala Leu
    130                 135                 140

Val Leu Ser Asn Val His Phe Thr Gly Glu Lys Glu Leu Glu Phe Arg
145                 150                 155                 160

Ser Gly Gly Asp Val Asp His Ser Thr Leu Val Thr Leu Phe Lys Leu
                165                 170                 175

Leu Gly Tyr Asp Val His Val Leu Cys Asp Gln Thr Ala Gln Glu Met
            180                 185                 190

Gln Glu Lys Leu Gln Asn Phe Ala Gln Leu Pro Ala His Arg Val Thr
        195                 200                 205

Asp Ser Cys Ile Val Ala Leu Leu Ser His Gly Val Glu Gly Ala Ile
    210                 215                 220

Tyr Gly Val Asp Gly Lys Leu Leu Gln Leu Gln Glu Val Phe Gln Leu
225                 230                 235                 240

Phe Asp Asn Ala Asn Cys Pro Ser Leu Gln Asn Lys Pro Lys Met Phe
                245                 250                 255

Phe Ile Gln Ala Cys Arg Gly Asp Glu Thr Glu Arg Gly Val Asp Gln
            260                 265                 270

Gln Ser Gly Lys Glu
        275


<210> SEQ ID NO 83
<211> LENGTH: 277
<212> TYPE: PRT
<213> ORGANISM: Artificial Sequence
<220> FEATURE:
<223> OTHER INFORMATION: caspase 2

<400> SEQUENCE: 83

Met His His His His His His Gln Gln Asp Gly Lys Glu Lys Leu Pro
1               5                   10                  15

Lys Met Arg Leu Pro Thr Arg Ser Asp Met Ile Cys Gly Tyr Ala Cys
            20                  25                  30

Leu Lys Gly Thr Ala Ala Met Arg Asn Thr Lys Arg Gly Ser Trp Tyr
        35                  40                  45

Ile Glu Ala Leu Ala Gln Val Phe Ser Glu Arg Ala Cys Asp Met His
    50                  55                  60

Val Ala Asp Met Leu Val Lys Val Asn Ala Leu Ile Lys Asp Arg Glu
65                  70                  75                  80

Gly Tyr Ala Pro Gly Thr Glu Phe His Arg Cys Lys Glu Met Ser Glu
                85                  90                  95

Tyr Cys Ser Thr Leu Cys Arg His Leu Tyr Leu Phe Pro Gly His Pro
            100                 105                 110

Pro Thr Gly Ser Gly Pro Val Cys Leu Gln Val Lys Pro Cys Thr Pro
        115                 120                 125

Glu Phe Tyr Gln Thr His Phe Gln Leu Ala Tyr Arg Leu Gln Ser Arg
    130                 135                 140

Pro Arg Gly Leu Ala Leu Val Leu Ser Asn Val His Phe Thr Gly Glu
145                 150                 155                 160
```

```
Lys Glu Leu Glu Phe Arg Ser Gly Gly Asp Val Asp His Ser Thr Leu
                165                 170                 175

Val Thr Leu Phe Lys Leu Leu Gly Tyr Asp Val His Val Leu Cys Asp
            180                 185                 190

Gln Thr Ala Gln Glu Met Gln Glu Lys Leu Gln Asn Phe Ala Gln Leu
        195                 200                 205

Pro Ala His Arg Val Thr Asp Ser Cys Ile Val Ala Leu Leu Ser His
    210                 215                 220

Gly Val Glu Gly Ala Ile Tyr Gly Val Asp Gly Lys Leu Leu Gln Leu
225                 230                 235                 240

Gln Glu Val Phe Gln Leu Phe Asp Asn Ala Asn Cys Pro Ser Leu Gln
                245                 250                 255

Asn Lys Pro Lys Met Phe Phe Ile Gln Ala Cys Arg Gly Asp Glu Thr
            260                 265                 270

Asp Arg Gly Val Asp
        275


<210> SEQ ID NO 84
<211> LENGTH: 314
<212> TYPE: PRT
<213> ORGANISM: Artificial Sequence
<220> FEATURE:
<223> OTHER INFORMATION: caspase 2

<400> SEQUENCE: 84

Met Leu Glu Asp Pro Glu Arg Asn Lys Glu Arg Lys Glu Ala Glu Leu
1               5                   10                  15

Gln Ala Gln Thr Ala Glu Gln His His His His His His Gly Lys Glu
            20                  25                  30

His Met Ala Ser Pro Gly Cys Glu Gln Ser Ala Ala Gly Lys Glu Lys
        35                  40                  45

Ile Leu Lys Met Arg Leu Pro Thr Arg Ser Asp Met Ile Cys Gly Tyr
    50                  55                  60

Ala Cys Leu Lys Gly Thr Ala Ala Met Arg Asn Thr Lys Arg Gly Ser
65                  70                  75                  80

Trp Tyr Ile Glu Ala Leu Thr Gln Val Phe Ser Glu Arg Ala Arg Asp
                85                  90                  95

Met His Val Ala Asp Met Leu Val Lys Val Asn Ala Leu Ile Lys Asp
            100                 105                 110

Arg Glu Gly Tyr Ala Pro Gly Thr Glu Phe His Arg Cys Lys Glu Met
        115                 120                 125

Ser Glu Tyr Ser Ser Thr Leu Cys Arg His Leu Tyr Leu Phe Pro Gly
    130                 135                 140

His Pro Pro Thr Gly Ser Gly Pro Pro Ser Leu Gln Val Lys Pro Cys
145                 150                 155                 160

Thr Ser Glu Phe Tyr Arg Thr His His His Leu Ala Tyr Arg Leu Gln
                165                 170                 175

Ser Arg Pro Arg Gly Leu Ala Leu Val Leu Ser Asn Val His Phe Asn
            180                 185                 190

Gly Glu Lys Asp Leu Glu Phe Arg Ser Gly Gly Asp Val Asp His Ser
        195                 200                 205

Ser Leu Val Thr Leu Phe Lys Leu Leu Asp Tyr Asp Val His Val Leu
    210                 215                 220

Arg Asp Gln Thr Ala Gln Glu Met Tyr Glu Lys Leu Gln Arg Phe Ala
225                 230                 235                 240
```

-continued

```
Gln Leu Ser Thr His Gln Asn Thr Asp Ser Cys Val Val Ala Leu Leu
                245                 250                 255

Ser His Gly Ile Glu Gly Gly Ile Tyr Gly Val Asp Gly Gln Leu Leu
            260                 265                 270

Gln Leu Gln Glu Val Phe Gln Leu Phe Asp Asn Ala Asn Cys Pro Asn
        275                 280                 285

Leu Gln Asn Lys Pro Lys Met Phe Phe Ile Gln Ala Cys Arg Gly Asp
    290                 295                 300

Glu Thr Asp Arg Gly Val Asp Leu Arg Asp
305                 310


<210> SEQ ID NO 85
<211> LENGTH: 317
<212> TYPE: PRT
<213> ORGANISM: Artificial Sequence
<220> FEATURE:
<223> OTHER INFORMATION: caspase 2

<400> SEQUENCE: 85

Met Leu Glu Asp Pro Glu Arg Asn Lys Glu Arg Lys Glu Ala Glu Leu
1               5                   10                  15

Gln Ala Gln Thr Ala Glu Gln His His His His His His Gly Ala Asp
            20                  25                  30

Ala Pro Gly Cys Glu Glu Cys Ala Ala Gly Lys Glu Arg Glu Arg Thr
        35                  40                  45

Arg Arg Gly Lys Leu Pro Thr Gln Ser Asp Ile Ile Cys Gly Tyr Ala
    50                  55                  60

Cys Leu Arg Gly Thr Ala Ala Leu Arg Asn Thr Arg Gln Gly Ser Trp
65                  70                  75                  80

Tyr Ile Gln Ala Leu Val Lys Val Phe Thr Glu Arg Ala His Asn Thr
                85                  90                  95

His Val Ala Asp Met Leu Val Gln Val Asn Ala Val Ile Arg Asp Arg
            100                 105                 110

Glu Gly Phe Ala Pro Gly Thr Asp Phe His Arg Cys Lys Glu Met Ala
        115                 120                 125

Glu Tyr Ser Ile Phe Glu Glu Met Glu Gly Glu Thr Gln Arg Lys Gln
    130                 135                 140

Arg Arg Arg Lys Thr Ala Ala Pro Gly Ser Gly Ser Gly Thr Phe Ser
145                 150                 155                 160

Val Arg Pro Thr Thr Ala Gln Phe Tyr His Glu His His Lys Gln Ser
                165                 170                 175

Tyr Arg Met Ala Ser Arg Pro Arg Gly Ala Ala Leu Ile Val Ser Asn
            180                 185                 190

Glu Val Phe Val Gly Glu Gly Leu Gly His Arg Pro Gly Gly Ala Ala
        195                 200                 205

Asp Thr Gly Val Leu Arg Ala Leu Leu Ser Gln Leu Gly Tyr Arg Val
    210                 215                 220

Thr Ser Val Cys Asn Ser Pro Ala Gln Glu Leu Glu Thr Arg Leu Arg
225                 230                 235                 240

Asp Phe Ala Leu Ser Ala Asp His Arg Arg Thr Asp Ser Cys Val Val
                245                 250                 255

Val Leu Leu Ser His Gly Val Glu Gly Ala Ile Tyr Gly Val Asp Gly
            260                 265                 270

Lys Leu Val Gln Ile His Asp Ile Phe Gln Leu Phe Asp Asn Ala Asn
        275                 280                 285
```

Cys Pro Asn Leu Gln Asn Lys Pro Lys Met Phe Phe Ile Gln Ala Cys
    290                 295                 300

Arg Gly Asp Arg Thr Asp Arg Gly Val Asp Arg Leu Asp
305                 310                 315

<210> SEQ ID NO 86
<211> LENGTH: 314
<212> TYPE: PRT
<213> ORGANISM: Artificial Sequence
<220> FEATURE:
<223> OTHER INFORMATION: caspase 2

<400> SEQUENCE: 86

Met Leu Glu Asp Pro Glu Arg Asn Lys Glu Arg Lys Glu Ala Glu Leu
1               5                   10                  15

Gln Ala Gln Thr Ala Glu Gln His His His His His His Gly Lys Glu
            20                  25                  30

His Met Ala Ser Pro Gly Cys Glu Gln Ser Ala Ala Gly Lys Glu Lys
        35                  40                  45

Ile Leu Lys Met Arg Leu Pro Thr Arg Ser Asp Met Ile Cys Gly Tyr
    50                  55                  60

Ala Cys Leu Lys Gly Thr Ala Ala Met Arg Asn Thr Lys Arg Gly Ser
65                  70                  75                  80

Trp Tyr Ile Glu Ala Leu Thr Gln Val Phe Ser Glu Arg Ala Arg Asp
                85                  90                  95

Met His Val Ala Asp Met Leu Val Lys Val Asn Ala Leu Ile Lys Asp
            100                 105                 110

Arg Glu Gly Tyr Ala Pro Gly Thr Glu Phe His Arg Cys Lys Val Met
        115                 120                 125

Ser Glu Tyr Ser Ser Thr Leu Cys Arg His Leu Tyr Leu Phe Pro Gly
    130                 135                 140

His Pro Pro Thr Gly Ser Gly Pro Pro Ser Leu Gln Val Lys Pro Cys
145                 150                 155                 160

Thr Ser Glu Phe Tyr Arg Thr His His His Leu Ala Tyr Arg Leu Gln
                165                 170                 175

Ser Arg Pro Arg Gly Leu Ala Leu Val Leu Ser Asn Val His Phe Asn
            180                 185                 190

Gly Val Lys Asp Leu Glu Phe Arg Ser Gly Gly Asp Val Asp His Ser
        195                 200                 205

Ser Leu Val Thr Leu Phe Lys Leu Leu Asp Tyr Asp Val His Val Leu
    210                 215                 220

Arg Asp Gln Thr Ala Gln Glu Met Tyr Glu Lys Leu Gln Arg Phe Ala
225                 230                 235                 240

Gln Leu Ser Thr His Gln Asn Thr Asp Ser Cys Val Val Ala Leu Leu
                245                 250                 255

Ser His Gly Ile Glu Gly Gly Ile Tyr Gly Val Asp Gly Gln Leu Leu
            260                 265                 270

Gln Leu Gln Glu Val Phe Gln Leu Phe Asp Asn Ala Asn Cys Pro Asn
        275                 280                 285

Leu Gln Asn Lys Pro Lys Met Phe Phe Ile Gln Ala Cys Arg Gly Asp
    290                 295                 300

Glu Thr Asp Arg Gly Val Asp Leu Arg Asp
305                 310

<210> SEQ ID NO 87
<211> LENGTH: 317

<212> TYPE: PRT
<213> ORGANISM: Artificial Sequence
<220> FEATURE:
<223> OTHER INFORMATION: caspase 2

<400> SEQUENCE: 87

Met Leu Glu Asp Pro Glu Arg Asn Lys Glu Arg Lys Glu Ala Glu Leu
1 5 10 15

Gln Ala Gln Thr Ala Glu Gln His His His His His His Gly Ala Asp
20 25 30

Ala Pro Gly Cys Glu Glu Cys Ala Ala Gly Lys Glu Arg Glu Arg Thr
35 40 45

Arg Arg Gly Lys Leu Pro Thr Gln Ser Asp Ile Ile Cys Gly Tyr Ala
50 55 60

Cys Leu Arg Gly Thr Ala Ala Leu Arg Asn Thr Arg Gln Gly Ser Trp
65 70 75 80

Tyr Ile Gln Ala Leu Val Lys Val Phe Thr Glu Arg Ala His Asn Thr
85 90 95

His Val Ala Asp Met Leu Val Gln Val Asn Ala Val Ile Arg Asp Arg
100 105 110

Glu Gly Phe Ala Pro Gly Thr Asp Phe His Arg Cys Lys Val Met Ala
115 120 125

Glu Tyr Ser Ile Phe Glu Glu Met Glu Gly Glu Thr Gln Arg Lys Gln
130 135 140

Arg Arg Arg Lys Thr Ala Ala Pro Gly Ser Gly Ser Gly Thr Phe Ser
145 150 155 160

Val Arg Pro Thr Thr Ala Gln Phe Tyr His Glu His His Lys Gln Ser
165 170 175

Tyr Arg Met Ala Ser Arg Pro Arg Gly Ala Ala Leu Ile Val Ser Asn
180 185 190

Glu Val Phe Val Asp Glu Gly Leu Gly His Arg Pro Gly Gly Ala Ala
195 200 205

Asp Thr Gly Val Leu Arg Ala Leu Leu Ser Gln Leu Gly Tyr Arg Val
210 215 220

Thr Ser Val Cys Asn Ser Pro Ala Gln Glu Leu Glu Thr Arg Leu Arg
225 230 235 240

Asp Phe Ala Leu Ser Ala Asp His Arg Arg Thr Asp Ser Cys Val Val
245 250 255

Val Leu Leu Ser His Gly Val Glu Gly Ala Ile Tyr Gly Val Asp Gly
260 265 270

Lys Leu Val Gln Ile His Asp Ile Phe Gln Leu Phe Asp Asn Ala Asn
275 280 285

Cys Pro Asn Leu Gln Asn Lys Pro Lys Met Phe Phe Ile Gln Ala Cys
290 295 300

Arg Gly Asp Arg Thr Asp Arg Gly Val Asp Arg Leu Asp
305 310 315

<210> SEQ ID NO 88
<211> LENGTH: 292
<212> TYPE: PRT
<213> ORGANISM: Artificial Sequence
<220> FEATURE:
<223> OTHER INFORMATION: caspase 2

<400> SEQUENCE: 88

Met His His His His His His Gly Lys Asn His Ala Gly Ser Pro Gly
1 5 10 15

```
Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Cys Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290


<210> SEQ ID NO 89
<211> LENGTH: 452
<212> TYPE: PRT
<213> ORGANISM: Mus sp.

<400> SEQUENCE: 89

Met Ala Ala Pro Ser Gly Arg Ser Gln Ser Ser Leu His Arg Lys Gly
1               5                   10                  15

Leu Met Ala Ala Asp Arg Arg Ser Arg Ile Leu Ala Val Cys Gly Met
            20                  25                  30

His Pro Asp His Gln Glu Thr Leu Lys Lys Asn Arg Val Val Leu Ala
        35                  40                  45

Lys Gln Leu Leu Leu Ser Glu Leu Leu Glu His Leu Leu Glu Lys Asp
    50                  55                  60

Ile Ile Thr Leu Glu Met Arg Glu Leu Ile Gln Ala Lys Gly Gly Ser
65                  70                  75                  80

Phe Ser Gln Asn Val Glu Leu Leu Asn Leu Leu Pro Lys Arg Gly Pro
```

```
                85                  90                  95

Gln Ala Phe Asp Ala Phe Cys Glu Ala Leu Arg Glu Thr Arg Gln Gly
            100                 105                 110

His Leu Glu Asp Leu Leu Leu Thr Thr Leu Ser Asp Ile Gln His Val
        115                 120                 125

Leu Pro Pro Leu Ser Cys Asp Tyr Asp Thr Ser Leu Pro Phe Ser Val
    130                 135                 140

Cys Glu Ser Cys Pro Pro His Lys Gln Leu Arg Leu Ser Thr Asp Ala
145                 150                 155                 160

Thr Glu His Ser Leu Asp Asn Gly Asp Gly Pro Pro Cys Leu Leu Val
                165                 170                 175

Lys Pro Cys Thr Pro Glu Phe Tyr Gln Ala His Tyr Gln Leu Ala Tyr
            180                 185                 190

Arg Leu Gln Ser Gln Pro Arg Gly Leu Ala Leu Val Leu Ser Asn Val
        195                 200                 205

His Phe Thr Gly Glu Lys Asp Leu Glu Phe Arg Ser Gly Gly Asp Val
    210                 215                 220

Asp His Thr Thr Leu Val Thr Leu Phe Lys Leu Leu Gly Tyr Asn Val
225                 230                 235                 240

His Val Leu His Asp Gln Thr Ala Gln Glu Met Gln Glu Lys Leu Gln
                245                 250                 255

Asn Phe Ala Gln Leu Pro Ala His Arg Val Thr Asp Ser Cys Val Val
            260                 265                 270

Ala Leu Leu Ser His Gly Val Glu Gly Gly Ile Tyr Gly Val Asp Gly
        275                 280                 285

Lys Leu Leu Gln Leu Gln Glu Val Phe Arg Leu Phe Asp Asn Ala Asn
    290                 295                 300

Cys Pro Ser Leu Gln Asn Lys Pro Lys Met Phe Phe Ile Gln Ala Cys
305                 310                 315                 320

Arg Gly Asp Glu Thr Asp Arg Gly Val Asp Gln Gln Asp Gly Lys Asn
                325                 330                 335

His Thr Gln Ser Pro Gly Cys Glu Glu Ser Asp Ala Gly Lys Glu Glu
            340                 345                 350

Leu Met Lys Met Arg Leu Pro Thr Arg Ser Asp Met Ile Cys Gly Tyr
        355                 360                 365

Ala Cys Leu Lys Gly Asn Ala Ala Met Arg Asn Thr Lys Arg Gly Ser
    370                 375                 380

Trp Tyr Ile Glu Ala Leu Thr Gln Val Phe Ser Glu Arg Ala Cys Asp
385                 390                 395                 400

Met His Val Ala Asp Met Leu Val Lys Val Asn Ala Leu Ile Lys Glu
                405                 410                 415

Arg Glu Gly Tyr Ala Pro Gly Thr Glu Phe His Arg Cys Lys Glu Met
            420                 425                 430

Ser Glu Tyr Cys Ser Thr Leu Cys Gln Gln Leu Tyr Leu Phe Pro Gly
        435                 440                 445

Tyr Pro Pro Thr
    450


<210> SEQ ID NO 90
<211> LENGTH: 164
<212> TYPE: PRT
<213> ORGANISM: Mus sp.

<400> SEQUENCE: 90
```

-continued

```
Gly Pro Pro Cys Leu Leu Val Lys Pro Cys Thr Pro Glu Phe Tyr Gln
1               5                   10                  15

Ala His Tyr Gln Leu Ala Tyr Arg Leu Gln Ser Gln Pro Arg Gly Leu
            20                  25                  30

Ala Leu Val Leu Ser Asn Val His Phe Thr Gly Glu Lys Asp Leu Glu
        35                  40                  45

Phe Arg Ser Gly Gly Asp Val Asp His Thr Thr Leu Val Thr Leu Phe
    50                  55                  60

Lys Leu Leu Gly Tyr Asn Val His Val Leu His Asp Gln Thr Ala Gln
65                  70                  75                  80

Glu Met Gln Glu Lys Leu Gln Asn Phe Ala Gln Leu Pro Ala His Arg
                85                  90                  95

Val Thr Asp Ser Cys Val Val Ala Leu Leu Ser His Gly Val Glu Gly
            100                 105                 110

Gly Ile Tyr Gly Val Asp Gly Lys Leu Leu Gln Leu Gln Glu Val Phe
        115                 120                 125

Arg Leu Phe Asp Asn Ala Asn Cys Pro Ser Leu Gln Asn Lys Pro Lys
    130                 135                 140

Met Phe Phe Ile Gln Ala Cys Arg Gly Asp Glu Thr Asp Arg Gly Val
145                 150                 155                 160

Asp Gln Gln Asp


<210> SEQ ID NO 91
<211> LENGTH: 105
<212> TYPE: PRT
<213> ORGANISM: Mus sp.

<400> SEQUENCE: 91

Ala Gly Lys Glu Glu Leu Met Lys Met Arg Leu Pro Thr Arg Ser Asp
1               5                   10                  15

Met Ile Cys Gly Tyr Ala Cys Leu Lys Gly Asn Ala Ala Met Arg Asn
            20                  25                  30

Thr Lys Arg Gly Ser Trp Tyr Ile Glu Ala Leu Thr Gln Val Phe Ser
        35                  40                  45

Glu Arg Ala Cys Asp Met His Val Ala Asp Met Leu Val Lys Val Asn
    50                  55                  60

Ala Leu Ile Lys Glu Arg Glu Gly Tyr Ala Pro Gly Thr Glu Phe His
65                  70                  75                  80

Arg Cys Lys Glu Met Ser Glu Tyr Cys Ser Thr Leu Cys Gln Gln Leu
                85                  90                  95

Tyr Leu Phe Pro Gly Tyr Pro Pro Thr
            100                 105


<210> SEQ ID NO 92
<211> LENGTH: 461
<212> TYPE: PRT
<213> ORGANISM: Ovis sp.

<400> SEQUENCE: 92

Met Ala Ala Pro Ser Ala Gly Ser Gln Ser Ala Leu Gln Pro Lys Glu
1               5                   10                  15

Gln Met Ala Ala Asp Arg Gly Arg Arg Met Leu Arg Gly Cys Gly Met
            20                  25                  30

His Pro Asp His Gln Glu Ala Leu Lys Lys Asn Arg Val Val Leu Ala
        35                  40                  45

Lys Glu Leu Leu Leu Ser Glu Leu Leu Glu His Leu Leu Glu Arg Asp
```

```
    50                  55                  60

Ile Ile Thr Leu Glu Met Arg Glu His Ile Gln Ala Lys Thr Gly Ser
65                  70                  75                  80

Phe Gly Gln Asn Val Glu Leu Leu Asn Leu Leu Pro Lys Arg Gly Pro
                85                  90                  95

Gln Ala Phe Asp Ala Phe Cys Val Ala Leu Arg Glu Thr Lys Gln Ser
            100                 105                 110

His Leu Glu Glu Leu Leu Leu Arg Thr Leu Ser Gly Leu Gln Pro Val
        115                 120                 125

Val Pro Pro Leu Ser Cys Asp Tyr Asp Leu Ser Leu Pro Phe Pro Val
    130                 135                 140

Cys Glu Ser Cys Ala Pro His Lys Arg Leu Arg Leu Ser Pro Gly Leu
145                 150                 155                 160

Cys Ala Ala Asp Ala Val Glu His Ser Leu Asp His Gly Asp Gly Pro
                165                 170                 175

Pro Cys Leu Gln Val Lys Pro Cys Thr Pro Glu Phe Tyr Gln Thr His
            180                 185                 190

His Gln Leu Ala Tyr Arg Leu Gln Ser Arg Pro Arg Gly Leu Ala Leu
        195                 200                 205

Val Leu Ser Asn Val His Phe Thr Gly Glu Lys Asp Leu Glu Phe Arg
    210                 215                 220

Ser Gly Gly Asp Val Asp His Ser Thr Leu Val Thr Leu Phe Lys Leu
225                 230                 235                 240

Leu Gly Tyr Lys Val His Val Leu Leu Asp Gln Thr Ala Gln Glu Met
                245                 250                 255

Gln Glu Lys Leu Gln Ser Phe Ala Gln Leu Pro Ala Pro Arg Leu Thr
            260                 265                 270

Asp Ser Thr Asp Ser Cys Ile Val Ala Leu Leu Ser His Gly Val Glu
        275                 280                 285

Gly Ser Val Tyr Gly Val Asp Gly Lys Leu Leu Gln Gln Leu Gln Glu
    290                 295                 300

Val Phe Arg Leu Phe Asp Asn Ala Asn Cys Pro Ser Leu Gln Asn Lys
305                 310                 315                 320

Pro Lys Met Phe Phe Ile Gln Ala Cys Arg Gly Asp Glu Thr Asp Arg
                325                 330                 335

Gly Val Asp Gln Gln Asp Gly Lys Asn His Asp Arg Ser Pro Glu Cys
            340                 345                 350

Glu Glu Ser Asp Ala Ser Gly Glu Glu Leu Leu Lys Thr Arg Leu Pro
        355                 360                 365

Thr Arg Ser Asp Met Ile Cys Gly Tyr Ala Cys Leu Arg Gly Thr Ala
    370                 375                 380

Ala Met Arg Asn Thr Lys Arg Gly Ser Trp Tyr Val Glu Ala Leu Thr
385                 390                 395                 400

Gln Val Phe Ser Glu Arg Ala Cys Asp Met His Val Ala Asp Met Leu
                405                 410                 415

Val Lys Val Asn Ala Leu Ile Lys Glu Arg Glu Gly Tyr Ala Pro Gly
            420                 425                 430

Thr Glu Phe His Arg Cys Lys Glu Met Ser Glu Tyr Cys Ser Thr Leu
        435                 440                 445

Cys Arg His Leu Tyr Leu Phe Pro Gly His Pro Pro Thr
    450                 455                 460
```

<210> SEQ ID NO 93

<211> LENGTH: 168
<212> TYPE: PRT
<213> ORGANISM: Ovis sp.

<400> SEQUENCE: 93

```
Gly Pro Pro Cys Leu Gln Val Lys Pro Cys Thr Pro Glu Phe Tyr Gln
1               5                   10                  15

Thr His His Gln Leu Ala Tyr Arg Leu Gln Ser Arg Pro Arg Gly Leu
            20                  25                  30

Ala Leu Val Leu Ser Asn Val His Phe Thr Gly Glu Lys Asp Leu Glu
        35                  40                  45

Phe Arg Ser Gly Gly Asp Val Asp His Ser Thr Leu Val Thr Leu Phe
    50                  55                  60

Lys Leu Leu Gly Tyr Lys Val His Val Leu Leu Asp Gln Thr Ala Gln
65                  70                  75                  80

Glu Met Gln Glu Lys Leu Gln Ser Phe Ala Gln Leu Pro Ala Pro Arg
                85                  90                  95

Leu Thr Asp Ser Thr Asp Ser Cys Ile Val Ala Leu Leu Ser His Gly
            100                 105                 110

Val Glu Gly Ser Val Tyr Gly Val Asp Gly Lys Leu Leu Gln Gln Leu
        115                 120                 125

Gln Glu Val Phe Arg Leu Phe Asp Asn Ala Asn Cys Pro Ser Leu Gln
    130                 135                 140

Asn Lys Pro Lys Met Phe Phe Ile Gln Ala Cys Arg Gly Asp Glu Thr
145                 150                 155                 160

Asp Arg Gly Val Asp Gln Gln Asp
                165
```

<210> SEQ ID NO 94
<211> LENGTH: 105
<212> TYPE: PRT
<213> ORGANISM: Ovis sp.

<400> SEQUENCE: 94

```
Ala Ser Gly Glu Glu Leu Leu Lys Thr Arg Leu Pro Thr Arg Ser Asp
1               5                   10                  15

Met Ile Cys Gly Tyr Ala Cys Leu Arg Gly Thr Ala Ala Met Arg Asn
            20                  25                  30

Thr Lys Arg Gly Ser Trp Tyr Val Glu Ala Leu Thr Gln Val Phe Ser
        35                  40                  45

Glu Arg Ala Cys Asp Met His Val Ala Asp Met Leu Val Lys Val Asn
    50                  55                  60

Ala Leu Ile Lys Glu Arg Glu Gly Tyr Ala Pro Gly Thr Glu Phe His
65                  70                  75                  80

Arg Cys Lys Glu Met Ser Glu Tyr Cys Ser Thr Leu Cys Arg His Leu
                85                  90                  95

Tyr Leu Phe Pro Gly His Pro Pro Thr
            100                 105
```

<210> SEQ ID NO 95
<211> LENGTH: 429
<212> TYPE: PRT
<213> ORGANISM: Sarcophilus harrisii

<400> SEQUENCE: 95

```
Ser Arg Met Leu Gly Val Trp Gly Met Glu Arg Glu His Gln Glu Ala
1               5                   10                  15
```

-continued

Leu Lys Lys Asn Arg Val Val Leu Ala Lys Gln Leu Leu Leu Ser Glu
20 25 30

Leu Leu Glu His Leu Leu Glu Lys Asp Ile Ile Thr Leu Glu Met Arg
35 40 45

Glu Leu Ile Gln Ala Lys Val Gly Ser Phe Ser Gln Asn Val Glu Phe
50 55 60

Leu Asn Leu Leu Pro Lys Arg Gly Pro His Ala Phe Gly Ala Phe Cys
65 70 75 80

Asp Ala Leu Arg Glu Thr Lys Gln Gly His Leu Glu Asp Leu Leu His
85 90 95

Lys Thr Leu Tyr Ser Phe Gln Gln Leu Leu Pro Ser Leu Asn Cys Asp
100 105 110

Asp Asp Ser Asn Leu Pro Leu Pro Val Cys Glu Ser Cys Ser Pro His
115 120 125

Lys Gln Leu Arg Leu Ser Val Glu Thr Met Glu His Ser Leu Asp Asn
130 135 140

Gly Asp Gly Pro Pro Ser Leu Gln Val Lys Pro Cys Thr Ser Glu Phe
145 150 155 160

Tyr Arg Thr His His His Leu Ala Tyr Arg Leu Gln Ser Arg Pro Arg
165 170 175

Gly Leu Ala Leu Val Leu Ser Asn Val His Phe Asn Gly Glu Lys Asp
180 185 190

Leu Glu Phe Arg Ser Gly Gly Asp Val Asp His Ser Ser Leu Val Thr
195 200 205

Leu Phe Lys Leu Leu Asp Tyr Asp Val His Val Leu Arg Asp Gln Thr
210 215 220

Ala Gln Glu Met Tyr Glu Lys Leu Gln Arg Phe Ala Gln Leu Ser Thr
225 230 235 240

His Gln Asn Thr Asp Ser Cys Val Val Ala Leu Leu Ser His Gly Ile
245 250 255

Glu Gly Gly Ile Tyr Gly Val Asp Gly Gln Leu Leu Gln Leu Gln Glu
260 265 270

Val Phe Gln Leu Phe Asp Asn Ala Asn Cys Pro Asn Leu Gln Asn Lys
275 280 285

Pro Lys Met Phe Phe Ile Gln Ala Cys Arg Gly Asp Glu Thr Asp Arg
290 295 300

Gly Val Asp Leu Arg Asp Gly Lys Glu His Met Ala Ser Pro Gly Cys
305 310 315 320

Glu Gln Ser Asp Ala Gly Lys Glu Lys Ile Leu Lys Met Arg Leu Pro
325 330 335

Thr Arg Ser Asp Met Ile Cys Gly Tyr Ala Cys Leu Lys Gly Thr Ala
340 345 350

Ala Met Arg Asn Thr Lys Arg Gly Ser Trp Tyr Ile Glu Ala Leu Thr
355 360 365

Gln Val Phe Ser Glu Arg Ala Arg Asp Met His Val Ala Asp Met Leu
370 375 380

Val Lys Val Asn Ala Leu Ile Lys Asp Arg Glu Gly Tyr Ala Pro Gly
385 390 395 400

Thr Glu Phe His Arg Cys Lys Glu Met Ser Glu Tyr Ser Ser Thr Leu
405 410 415

Cys Arg His Leu Tyr Leu Phe Pro Gly His Pro Pro Thr
420 425

<210> SEQ ID NO 96
<211> LENGTH: 164
<212> TYPE: PRT
<213> ORGANISM: Sarcophilus harrisii

<400> SEQUENCE: 96

```
Gly Pro Pro Ser Leu Gln Val Lys Pro Cys Thr Ser Glu Phe Tyr Arg
1               5                   10                  15

Thr His His His Leu Ala Tyr Arg Leu Gln Ser Arg Pro Arg Gly Leu
            20                  25                  30

Ala Leu Val Leu Ser Asn Val His Phe Asn Gly Glu Lys Asp Leu Glu
        35                  40                  45

Phe Arg Ser Gly Gly Asp Val Asp His Ser Ser Leu Val Thr Leu Phe
    50                  55                  60

Lys Leu Leu Asp Tyr Asp Val His Val Leu Arg Asp Gln Thr Ala Gln
65                  70                  75                  80

Glu Met Tyr Glu Lys Leu Gln Arg Phe Ala Gln Leu Ser Thr His Gln
                85                  90                  95

Asn Thr Asp Ser Cys Val Val Ala Leu Leu Ser His Gly Ile Glu Gly
            100                 105                 110

Gly Ile Tyr Gly Val Asp Gly Gln Leu Leu Gln Leu Gln Glu Val Phe
        115                 120                 125

Gln Leu Phe Asp Asn Ala Asn Cys Pro Asn Leu Gln Asn Lys Pro Lys
    130                 135                 140

Met Phe Phe Ile Gln Ala Cys Arg Gly Asp Glu Thr Asp Arg Gly Val
145                 150                 155                 160

Asp Leu Arg Asp
```

<210> SEQ ID NO 97
<211> LENGTH: 105
<212> TYPE: PRT
<213> ORGANISM: Sarcophilus harrisii

<400> SEQUENCE: 97

```
Ala Gly Lys Glu Lys Ile Leu Lys Met Arg Leu Pro Thr Arg Ser Asp
1               5                   10                  15

Met Ile Cys Gly Tyr Ala Cys Leu Lys Gly Thr Ala Ala Met Arg Asn
            20                  25                  30

Thr Lys Arg Gly Ser Trp Tyr Ile Glu Ala Leu Thr Gln Val Phe Ser
        35                  40                  45

Glu Arg Ala Arg Asp Met His Val Ala Asp Met Leu Val Lys Val Asn
    50                  55                  60

Ala Leu Ile Lys Asp Arg Glu Gly Tyr Ala Pro Gly Thr Glu Phe His
65                  70                  75                  80

Arg Cys Lys Glu Met Ser Glu Tyr Ser Ser Thr Leu Cys Arg His Leu
                85                  90                  95

Tyr Leu Phe Pro Gly His Pro Pro Thr
            100                 105
```

<210> SEQ ID NO 98
<211> LENGTH: 424
<212> TYPE: PRT
<213> ORGANISM: Gallus sp.

<400> SEQUENCE: 98

```
Met Leu Gly Ala Cys Gly Met Gln Arg Tyr His Gln Glu Ala Leu Lys
1               5                   10                  15
```

-continued

```
Lys Asn Arg Val Met Leu Ala Arg Glu Leu Val Leu Lys Glu Leu Met
            20                  25                  30

Glu His Met Ile Glu Lys Asp Ile Ile Thr Ile Glu Met Val Glu Met
        35                  40                  45

Ile Gln Ala Lys Ser Gly Ser Phe Ser Gln Asn Val Glu Phe Leu Asn
    50                  55                  60

Leu Leu Pro Lys Arg Gly Pro Asn Ala Phe Ser Ala Phe Cys Glu Ala
65                  70                  75                  80

Leu Gln Glu Thr Lys Gln Gln His Leu Ala Glu Met Ile Leu Lys Thr
                85                  90                  95

Glu Ser Ser Leu Arg His Gly Ile Ala Thr Leu Glu Gln Arg Tyr Gly
            100                 105                 110

Ser Asn Leu Pro Leu Pro Leu Ser Glu Ser Cys Asn Ser Lys Arg Pro
        115                 120                 125

Arg Leu Ile Val Glu His Ser Leu Asp Ser Gly Asp Gly Pro Pro Ile
    130                 135                 140

Pro Pro Val Lys His Cys Thr Pro Glu Phe Tyr Arg Asp His Gln His
145                 150                 155                 160

Leu Ala Tyr Lys Leu Ile Ser Glu Pro Arg Gly Leu Ala Leu Ile Leu
                165                 170                 175

Ser Asn Ile His Phe Ser Ser Glu Lys Asp Leu Glu Tyr Arg Ser Gly
            180                 185                 190

Gly Asp Val Asp Cys Ala Ser Leu Glu Leu Leu Phe Lys His Leu Gly
        195                 200                 205

Tyr Gln Val Thr Val Phe His Asp Gln Ser Ala Glu Glu Met Glu Ser
    210                 215                 220

Ala Leu Glu Arg Phe Ser Lys Leu Pro Asp His Gln Asp Val Asp Ser
225                 230                 235                 240

Cys Ile Val Ala Leu Leu Ser His Gly Val Glu Gly Gly Val Tyr Gly
                245                 250                 255

Thr Asp Gly Lys Leu Leu Gln Leu Gln Glu Ala Phe Arg Leu Phe Asp
            260                 265                 270

Asn Ala Asn Cys Pro Asn Leu Gln Asn Lys Pro Lys Met Phe Phe Ile
        275                 280                 285

Gln Ala Cys Arg Gly Asp Glu Thr Asp Arg Gly Val Asp Gln Arg Asp
    290                 295                 300

Gly Lys Glu Arg Ser Asp Ser Pro Gly Cys Glu Glu Ser Asp Ala Asn
305                 310                 315                 320

Lys Glu Glu Asn Leu Lys Leu Arg Leu Pro Thr Arg Ser Asp Met Ile
                325                 330                 335

Cys Gly Tyr Ala Cys Leu Lys Gly Thr Ala Ala Met Arg Asn Thr Lys
            340                 345                 350

Arg Gly Ser Trp Tyr Ile Glu Ala Leu Thr Thr Val Phe Ala Glu Asp
        355                 360                 365

Ser Arg Asp Thr His Val Ala Asp Met Leu Val Lys Val Asn Arg Gln
    370                 375                 380

Ile Lys Gln Arg Glu Gly Tyr Ala Pro Gly Thr Glu Phe His Arg Cys
385                 390                 395                 400

Lys Glu Met Ser Glu Tyr Cys Ser Thr Leu Cys Arg Asp Leu Tyr Leu
                405                 410                 415

Phe Pro Gly Tyr Val Pro Gly Lys
            420
```

<210> SEQ ID NO 99
<211> LENGTH: 164
<212> TYPE: PRT
<213> ORGANISM: Gallus sp.

<400> SEQUENCE: 99

```
Gly Pro Pro Ile Pro Pro Val Lys His Cys Thr Pro Glu Phe Tyr Arg
1               5                   10                  15

Asp His Gln His Leu Ala Tyr Lys Leu Ile Ser Glu Pro Arg Gly Leu
            20                  25                  30

Ala Leu Ile Leu Ser Asn Ile His Phe Ser Ser Glu Lys Asp Leu Glu
        35                  40                  45

Tyr Arg Ser Gly Gly Asp Val Asp Cys Ala Ser Leu Glu Leu Leu Phe
    50                  55                  60

Lys His Leu Gly Tyr Gln Val Thr Val Phe His Asp Gln Ser Ala Glu
65                  70                  75                  80

Glu Met Glu Ser Ala Leu Glu Arg Phe Ser Lys Leu Pro Asp His Gln
                85                  90                  95

Asp Val Asp Ser Cys Ile Val Ala Leu Leu Ser His Gly Val Glu Gly
            100                 105                 110

Gly Val Tyr Gly Thr Asp Gly Lys Leu Leu Gln Leu Gln Glu Ala Phe
        115                 120                 125

Arg Leu Phe Asp Asn Ala Asn Cys Pro Asn Leu Gln Asn Lys Pro Lys
    130                 135                 140

Met Phe Phe Ile Gln Ala Cys Arg Gly Asp Glu Thr Asp Arg Gly Val
145                 150                 155                 160

Asp Gln Arg Asp
```

<210> SEQ ID NO 100
<211> LENGTH: 106
<212> TYPE: PRT
<213> ORGANISM: Gallus sp.

<400> SEQUENCE: 100

```
Ala Asn Lys Glu Glu Asn Leu Lys Leu Arg Leu Pro Thr Arg Ser Asp
1               5                   10                  15

Met Ile Cys Gly Tyr Ala Cys Leu Lys Gly Thr Ala Ala Met Arg Asn
            20                  25                  30

Thr Lys Arg Gly Ser Trp Tyr Ile Glu Ala Leu Thr Thr Val Phe Ala
        35                  40                  45

Glu Asp Ser Arg Asp Thr His Val Ala Asp Met Leu Val Lys Val Asn
    50                  55                  60

Arg Gln Ile Lys Gln Arg Glu Gly Tyr Ala Pro Gly Thr Glu Phe His
65                  70                  75                  80

Arg Cys Lys Glu Met Ser Glu Tyr Cys Ser Thr Leu Cys Arg Asp Leu
                85                  90                  95

Tyr Leu Phe Pro Gly Tyr Val Pro Gly Lys
            100                 105
```

<210> SEQ ID NO 101
<211> LENGTH: 446
<212> TYPE: PRT
<213> ORGANISM: Anolis carolinensis

<400> SEQUENCE: 101

```
Met Glu His Val Glu Ser Lys Phe His Leu Cys Ile Val Ile Cys Phe
1               5                   10                  15
```

-continued

```
Ile Ser Arg Met Leu Gly Val Cys Gly Met Gln Lys Cys His Gln Glu
            20                  25                  30

Ala Leu Lys Lys Asn Arg Val Ser Leu Ala Lys Gln Leu Val Leu Lys
        35                  40                  45

Glu Leu Met Glu His Leu Ile Glu Lys Asp Val Ile Thr Glu Glu Met
    50                  55                  60

Met Glu Met Ile Gln Ala Lys Ala Gly Asn Phe Ser Gln Asn Ile Glu
65                  70                  75                  80

Phe Leu Asn Leu Leu Pro Lys Arg Gly Pro Lys Ala Phe Ser Ala Phe
                85                  90                  95

Cys Glu Ala Leu Arg Glu Thr Lys Gln Pro His Leu Glu Glu Met Leu
            100                 105                 110

Leu Arg Ser Val Ser Arg His Cys Asn Gly Ile Ala Lys Leu Ser His
        115                 120                 125

Ser Cys Glu Glu His Leu Ser Phe Pro Val Ser Glu Ser Gly Ile Leu
    130                 135                 140

Gln Lys Trp Pro Arg Arg Asn Pro Glu Pro Met Glu His Ser Leu Asp
145                 150                 155                 160

Asp Gly Asp Gly Pro His Tyr Pro Gln Val Met Pro Cys Thr Pro Glu
                165                 170                 175

Phe Tyr Arg Thr His Glu Gln Leu Ala Tyr Lys Leu Lys Ser Gln Pro
            180                 185                 190

Arg Gly Leu Ala Leu Ile Leu Ser Asn Ile His Phe Asn Lys Glu Thr
        195                 200                 205

Asp Leu Asp Phe Arg Ser Gly Gly Asp Val Asp Asn Thr Ala Leu His
    210                 215                 220

Met Leu Phe Lys His Leu Gly Tyr Gln Val Val Val Arg Gln Asp Arg
225                 230                 235                 240

Thr Ala Gln Glu Met Lys Glu Glu Leu Glu Ile Phe Ser Lys His Pro
                245                 250                 255

Ala His Arg Asn Val Asp Ser Cys Ile Val Ser Leu Leu Ser His Gly
            260                 265                 270

Ile Glu Gly Gly Ile Tyr Gly Ile Asp Gly Lys Leu Leu Gln Leu Gln
        275                 280                 285

Glu Ile Phe Arg Leu Phe Asp Asn Ala Asn Cys Pro Asn Leu Gln Asn
    290                 295                 300

Lys Pro Lys Met Phe Phe Val Gln Ala Cys Arg Gly Asp Glu Thr Asp
305                 310                 315                 320

His Gly Val Asp Gln Ile Asp Gly Asn Asp Cys Ala Ser Ser Pro Gly
                325                 330                 335

Cys Glu Glu Thr Asp Ala Asn Lys Lys Glu Asn Pro Lys Leu Arg Leu
            340                 345                 350

Pro Thr Cys Ser Asp Met Ile Cys Gly Tyr Ala Cys Leu Lys Gly Thr
        355                 360                 365

Ala Ala Met Arg Asn Thr Lys His Gly Ser Trp Tyr Val Glu Ala Leu
    370                 375                 380

Thr Ser Val Phe Ala Glu Asp Ser Gly His Met His Val Ala Asp Met
385                 390                 395                 400

Leu Val Lys Val Asn Arg Leu Ile Lys Leu Arg Glu Gly His Ala Pro
                405                 410                 415

Gly Thr Glu Phe His Arg Cys Lys Glu Met Ser Glu Tyr Cys Ser Thr
            420                 425                 430

Leu Cys Gln Asp Leu Tyr Leu Phe Pro Gly Tyr Phe Pro Gly
```

435 440 445

<210> SEQ ID NO 102
<211> LENGTH: 164
<212> TYPE: PRT
<213> ORGANISM: Anolis carolinensis

<400> SEQUENCE: 102

Gly Pro His Tyr Pro Gln Val Met Pro Cys Thr Pro Glu Phe Tyr Arg
1 5 10 15

Thr His Glu Gln Leu Ala Tyr Lys Leu Lys Ser Gln Pro Arg Gly Leu
20 25 30

Ala Leu Ile Leu Ser Asn Ile His Phe Asn Lys Glu Thr Asp Leu Asp
35 40 45

Phe Arg Ser Gly Gly Asp Val Asp Asn Thr Ala Leu His Met Leu Phe
50 55 60

Lys His Leu Gly Tyr Gln Val Val Val Arg Gln Asp Arg Thr Ala Gln
65 70 75 80

Glu Met Lys Glu Glu Leu Glu Ile Phe Ser Lys His Pro Ala His Arg
85 90 95

Asn Val Asp Ser Cys Ile Val Ser Leu Leu Ser His Gly Ile Glu Gly
100 105 110

Gly Ile Tyr Gly Ile Asp Gly Lys Leu Leu Gln Leu Gln Glu Ile Phe
115 120 125

Arg Leu Phe Asp Asn Ala Asn Cys Pro Asn Leu Gln Asn Lys Pro Lys
130 135 140

Met Phe Phe Val Gln Ala Cys Arg Gly Asp Glu Thr Asp His Gly Val
145 150 155 160

Asp Gln Ile Asp

<210> SEQ ID NO 103
<211> LENGTH: 105
<212> TYPE: PRT
<213> ORGANISM: Anolis carolinensis

<400> SEQUENCE: 103

Ala Asn Lys Lys Glu Asn Pro Lys Leu Arg Leu Pro Thr Cys Ser Asp
1 5 10 15

Met Ile Cys Gly Tyr Ala Cys Leu Lys Gly Thr Ala Ala Met Arg Asn
20 25 30

Thr Lys His Gly Ser Trp Tyr Val Glu Ala Leu Thr Ser Val Phe Ala
35 40 45

Glu Asp Ser Gly His Met His Val Ala Asp Met Leu Val Lys Val Asn
50 55 60

Arg Leu Ile Lys Leu Arg Glu Gly His Ala Pro Gly Thr Glu Phe His
65 70 75 80

Arg Cys Lys Glu Met Ser Glu Tyr Cys Ser Thr Leu Cys Gln Asp Leu
85 90 95

Tyr Leu Phe Pro Gly Tyr Phe Pro Gly
100 105

<210> SEQ ID NO 104
<211> LENGTH: 427
<212> TYPE: PRT
<213> ORGANISM: Alligator sp.

<400> SEQUENCE: 104

-continued

```
Met Ser Gly Ala Cys Gly Met Gln Pro Cys His Gln Glu Ala Leu Arg
1               5                   10                  15

Arg His Arg Val Pro Leu Ala Lys Gln Leu Val Leu Gln Glu Leu Leu
            20                  25                  30

Glu His Leu Leu Ala Arg Ala Val Leu Thr Pro Glu Met Lys Glu Ala
        35                  40                  45

Ile Gln Thr Lys Ala Gly Ser Phe Ser Gln Asn Val Glu Phe Leu Ser
    50                  55                  60

Leu Leu Pro Lys Arg Gly Pro Gln Ala Phe Ser Ala Phe Cys Glu Ala
65                  70                  75                  80

Leu Arg Glu Thr Arg Gln Glu His Leu Glu Glu Met Leu Leu Asn Ala
                85                  90                  95

Ile Gln His Ser Ser Asn Gly Tyr Val Lys Arg Gly His Asp Tyr Asp
            100                 105                 110

Ser Ser Leu Pro Phe Pro Val Cys Glu Ser Tyr His Leu Ser Lys Arg
        115                 120                 125

Pro Arg Cys Ile Glu Pro Phe Glu His Ser Leu Asp Asn Gly Asp Gly
    130                 135                 140

Pro Pro Tyr Pro Gln Val Arg Ala Cys Thr Pro Glu Phe Tyr Arg Thr
145                 150                 155                 160

His Gln Arg Leu Ala Tyr Lys Leu Thr Ser Asp Pro Arg Gly Leu Ala
                165                 170                 175

Leu Val Leu Ser Asn Val His Phe Asn Gly Glu Lys Asp Leu Glu Phe
            180                 185                 190

Arg Ser Gly Gly Asp Val Asp Cys Ala Ala Leu Glu Lys Leu Phe Glu
        195                 200                 205

Cys Leu Gly Tyr Lys Val Thr Val His His Asp Gln Ser Ala Gln Glu
    210                 215                 220

Met Gln Glu Thr Leu Gln Lys Phe Ser Gln Lys Pro Thr His Gln Glu
225                 230                 235                 240

Val Asp Ser Cys Ile Val Ala Leu Leu Ser His Gly Val Glu Gly Gly
                245                 250                 255

Val Tyr Gly Ile Asp Gly Lys Leu Leu Gln Leu Gln Glu Val Phe Arg
            260                 265                 270

Leu Phe Asp Asn Ala Asn Cys Leu Asn Leu Gln Asn Lys Pro Lys Met
        275                 280                 285

Phe Phe Ile Gln Ala Cys Arg Gly Asp Glu Thr Asp Arg Gly Val Asp
    290                 295                 300

Gln Arg Asp Gly Lys Glu Arg Ser Asp Ser Pro Gly Tyr Glu Glu Ser
305                 310                 315                 320

Asp Ala Asn Lys Glu Glu Asn Pro Arg Leu Arg Leu Pro Thr Cys Ser
                325                 330                 335

Asp Met Ile Cys Gly Tyr Ala Cys Leu Lys Gly Thr Ala Ala Met Arg
            340                 345                 350

Asn Thr Lys Arg Gly Ser Trp Tyr Ile Glu Ala Leu Thr Ser Val Phe
        355                 360                 365

Ala Glu Asp Ser His Asn Thr His Val Ala Asp Met Leu Val Lys Val
    370                 375                 380

Asn Arg Met Ile Lys His Arg Glu Gly Tyr Ala Pro Gly Thr Glu Phe
385                 390                 395                 400

His Arg Cys Lys Glu Met Ser Glu Tyr Cys Ser Thr Leu Cys Arg Asp
                405                 410                 415

Leu Tyr Leu Phe Pro Gly Tyr Leu Pro Gly Asn
```

```
            420                 425


<210> SEQ ID NO 105
<211> LENGTH: 164
<212> TYPE: PRT
<213> ORGANISM: Alligator sp.

<400> SEQUENCE: 105

Gly Pro Pro Tyr Pro Gln Val Arg Ala Cys Thr Pro Glu Phe Tyr Arg
1               5                   10                  15

Thr His Gln Arg Leu Ala Tyr Lys Leu Thr Ser Asp Pro Arg Gly Leu
            20                  25                  30

Ala Leu Val Leu Ser Asn Val His Phe Asn Gly Glu Lys Asp Leu Glu
        35                  40                  45

Phe Arg Ser Gly Gly Asp Val Asp Cys Ala Ala Leu Glu Lys Leu Phe
    50                  55                  60

Glu Cys Leu Gly Tyr Lys Val Thr Val His His Asp Gln Ser Ala Gln
65                  70                  75                  80

Glu Met Gln Glu Thr Leu Gln Lys Phe Ser Gln Lys Pro Thr His Gln
                85                  90                  95

Glu Val Asp Ser Cys Ile Val Ala Leu Leu Ser His Gly Val Glu Gly
            100                 105                 110

Gly Val Tyr Gly Ile Asp Gly Lys Leu Leu Gln Leu Gln Glu Val Phe
        115                 120                 125

Arg Leu Phe Asp Asn Ala Asn Cys Leu Asn Leu Gln Asn Lys Pro Lys
    130                 135                 140

Met Phe Phe Ile Gln Ala Cys Arg Gly Asp Glu Thr Asp Arg Gly Val
145                 150                 155                 160

Asp Gln Arg Asp


<210> SEQ ID NO 106
<211> LENGTH: 106
<212> TYPE: PRT
<213> ORGANISM: Alligator sp.

<400> SEQUENCE: 106

Ala Asn Lys Glu Glu Asn Pro Arg Leu Arg Leu Pro Thr Cys Ser Asp
1               5                   10                  15

Met Ile Cys Gly Tyr Ala Cys Leu Lys Gly Thr Ala Ala Met Arg Asn
            20                  25                  30

Thr Lys Arg Gly Ser Trp Tyr Ile Glu Ala Leu Thr Ser Val Phe Ala
        35                  40                  45

Glu Asp Ser His Asn Thr His Val Ala Asp Met Leu Val Lys Val Asn
    50                  55                  60

Arg Met Ile Lys His Arg Glu Gly Tyr Ala Pro Gly Thr Glu Phe His
65                  70                  75                  80

Arg Cys Lys Glu Met Ser Glu Tyr Cys Ser Thr Leu Cys Arg Asp Leu
                85                  90                  95

Tyr Leu Phe Pro Gly Tyr Leu Pro Gly Asn
            100                 105


<210> SEQ ID NO 107
<211> LENGTH: 421
<212> TYPE: PRT
<213> ORGANISM: Xenopus sp.

<400> SEQUENCE: 107
```

-continued

```
Met Leu Gly Gly Met Gln Lys His His Lys Asp Ala Leu Gln Arg Leu
1               5                   10                  15

Arg Val Thr Leu Leu His Asp Met Ile Ile Glu Glu Leu Val Glu His
            20                  25                  30

Leu Val Ser Ser Gly Ile Leu Thr Pro Ile Met His Ser Thr Ile Met
        35                  40                  45

Ala His Arg Ser Glu Tyr Lys Gln Asn Val Thr Leu Leu Thr Gln Leu
    50                  55                  60

Pro Lys Arg Gly Pro Arg Ala Phe Ser Glu Phe Cys Asn Ala Leu His
65                  70                  75                  80

Ala Thr Gly Gln Arg His Leu Ala Glu Gln Leu Glu Glu Glu Ala Gln
                85                  90                  95

Gln Gln Gln Met Glu Ser Val Thr Pro Glu Val His Glu Arg Ser Phe
            100                 105                 110

Pro Leu Pro Val Gln Glu Ser Thr Pro Ser Arg Pro Arg Arg Gln Phe
        115                 120                 125

Cys Arg Glu Tyr Asn Glu Glu Ser Ile Asp Asp Gly Asp Gly Pro Gly
    130                 135                 140

Thr Val Gln Leu Cys Ser Val Asp Phe Tyr Leu Ser His His Gln Gln
145                 150                 155                 160

Ala Tyr Lys Met His Ser Cys Pro Arg Gly Arg Ala Leu Ile Ile Ser
                165                 170                 175

Asn Val Ala Phe Glu Thr Gln Asp Leu Asp His Arg Tyr Gly Gly Glu
            180                 185                 190

Val Asp Val Thr Ser Leu Glu Lys Leu Phe Ser Ser Leu Gly Phe Gln
        195                 200                 205

Val Glu Val Arg Arg Asn Leu Asn Ala Gln Asn Met Met Ser Gln Leu
    210                 215                 220

Gly Ala Phe Ser Ala Leu Pro Ala His Ser Ala Leu Asp Ser Cys Val
225                 230                 235                 240

Val Ala Val Leu Ser His Gly Leu Asp Gly Ala Val Tyr Gly Thr Asp
                245                 250                 255

Gly Lys Leu Val Gln Leu Gln Asp Val Phe Thr Ala Met Asp Asn Ala
            260                 265                 270

His Cys Pro Gln Leu Gln Asn Lys Pro Lys Met Phe Phe Ile Gln Ala
        275                 280                 285

Cys Arg Gly Glu Glu Ala Asp Arg Gly Val Asp Gln Arg Asp Gly Arg
    290                 295                 300

Glu Gln Ser Ala Ser Pro Gly Cys Glu Gln Ser Asp Ala Gly Arg Glu
305                 310                 315                 320

Asp Ile Lys Val Arg Leu Pro Thr Gln Ser Asp Met Ile Cys Ala Tyr
                325                 330                 335

Ala Cys Leu Lys Gly Thr Val Ser Leu Arg Asn Thr Lys Arg Gly Ser
            340                 345                 350

Trp Phe Val Gln Asp Leu Val Ser Val Phe Ser Gln Tyr Ser Lys Asn
        355                 360                 365

Thr His Val Ala Asp Met Leu Val Lys Val Asn Ala Leu Ile Lys Glu
    370                 375                 380

Arg Glu Gly His Ala Pro Gly Thr Glu Phe His Arg Cys Lys Glu Met
385                 390                 395                 400

Ser Glu Tyr Cys Ser Thr Leu Cys Arg Asp Leu Tyr Leu Phe Pro Gly
                405                 410                 415

Ile Gly Pro Pro Lys
```

420

<210> SEQ ID NO 108
<211> LENGTH: 161
<212> TYPE: PRT
<213> ORGANISM: Xenopus sp.

<400> SEQUENCE: 108

Gly Pro Gly Thr Val Gln Leu Cys Ser Val Asp Phe Tyr Leu Ser His
1 5 10 15

His Gln Gln Ala Tyr Lys Met His Ser Cys Pro Arg Gly Arg Ala Leu
20 25 30

Ile Ile Ser Asn Val Ala Phe Glu Thr Gln Asp Leu Asp His Arg Tyr
35 40 45

Gly Gly Glu Val Asp Val Thr Ser Leu Glu Lys Leu Phe Ser Ser Leu
50 55 60

Gly Phe Gln Val Glu Val Arg Arg Asn Leu Asn Ala Gln Asn Met Met
65 70 75 80

Ser Gln Leu Gly Ala Phe Ser Ala Leu Pro Ala His Ser Ala Leu Asp
85 90 95

Ser Cys Val Val Ala Val Leu Ser His Gly Leu Asp Gly Ala Val Tyr
100 105 110

Gly Thr Asp Gly Lys Leu Val Gln Leu Gln Asp Val Phe Thr Ala Met
115 120 125

Asp Asn Ala His Cys Pro Gln Leu Gln Asn Lys Pro Lys Met Phe Phe
130 135 140

Ile Gln Ala Cys Arg Gly Glu Glu Ala Asp Arg Gly Val Asp Gln Arg
145 150 155 160

Asp

<210> SEQ ID NO 109
<211> LENGTH: 105
<212> TYPE: PRT
<213> ORGANISM: Xenopus sp.

<400> SEQUENCE: 109

Ala Gly Arg Glu Asp Ile Lys Val Arg Leu Pro Thr Gln Ser Asp Met
1 5 10 15

Ile Cys Ala Tyr Ala Cys Leu Lys Gly Thr Val Ser Leu Arg Asn Thr
20 25 30

Lys Arg Gly Ser Trp Phe Val Gln Asp Leu Val Ser Val Phe Ser Gln
35 40 45

Tyr Ser Lys Asn Thr His Val Ala Asp Met Leu Val Lys Val Asn Ala
50 55 60

Leu Ile Lys Glu Arg Glu Gly His Ala Pro Gly Thr Glu Phe His Arg
65 70 75 80

Cys Lys Glu Met Ser Glu Tyr Cys Ser Thr Leu Cys Arg Asp Leu Tyr
85 90 95

Leu Phe Pro Gly Ile Gly Pro Pro Lys
100 105

<210> SEQ ID NO 110
<211> LENGTH: 435
<212> TYPE: PRT
<213> ORGANISM: Danio sp.

<400> SEQUENCE: 110

-continued

```
Met Leu Gly Glu Cys Gly Met Thr Lys Trp Glu Arg Leu Ala Leu Arg
1               5                   10                  15

Arg Asn Ser Val Lys Met Leu Gln Asp Leu Val Val Asp Asp Leu Leu
            20                  25                  30

Ile Gln Cys Leu Gln Gln Asp Gly Ile Leu Thr Asp Ser Met Ala Glu
        35                  40                  45

Ser Ile Met Ala Lys Pro Thr Ser Gln Gly Arg Ser His Gln Leu Leu
    50                  55                  60

Phe Leu Leu Pro Lys Arg Gly Pro Arg Ala Phe Ser Thr Phe Cys Ser
65                  70                  75                  80

Ala Leu Lys Glu Thr Glu Gln His His Leu Cys Lys Leu Leu Met Asp
                85                  90                  95

Phe Thr Glu Lys Asp Lys Cys Phe Ser Glu Pro Ser Leu Ser Leu Pro
            100                 105                 110

Thr Gln Glu Cys Val Thr Pro Ala Lys Arg Pro Arg Thr His Glu Ser
        115                 120                 125

Met Glu Met Cys Leu Asp Ala Asp Ser Pro Val Thr Thr Ala Val Leu
    130                 135                 140

Pro Cys Thr Pro Glu Phe Tyr Gln Ser His Arg Pro Gln Ala Tyr Pro
145                 150                 155                 160

Met Arg Ser Cys Pro Arg Gly Leu Ala Leu Val Leu Ser Asn Val Arg
                165                 170                 175

Phe Asp Ser Ala Asn Thr Asp Leu Asp Ile Arg Arg Gly Gly Glu Val
            180                 185                 190

Asp Glu Glu Thr Leu Arg Arg Leu Phe Thr Glu Leu Asp Phe Lys Val
        195                 200                 205

Ser Leu His Arg Asp Leu Thr Ala Glu Ala Met Arg Arg Cys Leu Glu
    210                 215                 220

Gln Phe Ala Gln Gln Gln Glu His Ala Ala Tyr Asp Cys Ala Val Val
225                 230                 235                 240

Cys Leu Leu Ser His Gly Val Glu Gly Ser Val Tyr Gly Thr Asp Gly
                245                 250                 255

Gln Leu Leu Glu Leu Asp Trp Val Phe Glu Val Phe Asp Asn Ala Arg
            260                 265                 270

Cys Pro Leu Leu Gln Asn Lys Pro Lys Met Phe Phe Ile Gln Ala Cys
        275                 280                 285

Arg Gly Glu Glu Met Asp Asn Gly Val Asp Gln Leu Asp Gly Gln Glu
    290                 295                 300

Arg Thr Gln Ser Pro Gly Cys Glu Gln Arg Asp Ala Gly Arg Glu Gly
305                 310                 315                 320

Glu Arg Asp Asn Arg Glu Lys Lys Glu Glu Lys Glu Arg Glu Arg Leu
                325                 330                 335

Arg Val Lys Leu Pro Gln Arg Ser Asp Met Ile Cys Gly Phe Ala Thr
            340                 345                 350

Leu Lys Gly Thr Ala Ala Met Arg Asn Thr Lys Lys Gly Ser Trp Phe
        355                 360                 365

Ile Gln Glu Leu Asn Thr Ala Ile Arg Gln Arg Ala Asn Asn Thr His
    370                 375                 380

Leu Ser Asp Ile Leu Val Gln Val Asn Gly Gln Ile Lys Ser Arg Glu
385                 390                 395                 400

Gly Tyr Ala Pro Gly Ser Ala His His Arg Cys Lys Glu Met Ser Glu
                405                 410                 415

Phe Thr Ser Ser Leu Cys Lys Asp Leu Tyr Leu Phe Pro Lys Tyr Tyr
```

420 425 430

Pro Ser Asn
435

<210> SEQ ID NO 111
<211> LENGTH: 165
<212> TYPE: PRT
<213> ORGANISM: Danio sp.

<400> SEQUENCE: 111

Ser Pro Val Thr Thr Ala Val Leu Pro Cys Thr Pro Glu Phe Tyr Gln
1 5 10 15

Ser His Arg Pro Gln Ala Tyr Pro Met Arg Ser Cys Pro Arg Gly Leu
20 25 30

Ala Leu Val Leu Ser Asn Val Arg Phe Asp Ser Ala Asn Thr Asp Leu
35 40 45

Asp Ile Arg Arg Gly Gly Glu Val Asp Glu Glu Thr Leu Arg Arg Leu
50 55 60

Phe Thr Glu Leu Asp Phe Lys Val Ser Leu His Arg Asp Leu Thr Ala
65 70 75 80

Glu Ala Met Arg Arg Cys Leu Glu Gln Phe Ala Gln Gln Gln Glu His
85 90 95

Ala Ala Tyr Asp Cys Ala Val Val Cys Leu Leu Ser His Gly Val Glu
100 105 110

Gly Ser Val Tyr Gly Thr Asp Gly Gln Leu Leu Glu Leu Asp Trp Val
115 120 125

Phe Glu Val Phe Asp Asn Ala Arg Cys Pro Leu Leu Gln Asn Lys Pro
130 135 140

Lys Met Phe Phe Ile Gln Ala Cys Arg Gly Glu Glu Met Asp Asn Gly
145 150 155 160

Val Asp Gln Leu Asp
165

<210> SEQ ID NO 112
<211> LENGTH: 120
<212> TYPE: PRT
<213> ORGANISM: Danio sp.

<400> SEQUENCE: 112

Ala Gly Arg Glu Gly Glu Arg Asp Asn Arg Glu Lys Lys Glu Glu Lys
1 5 10 15

Glu Arg Glu Arg Leu Arg Val Lys Leu Pro Gln Arg Ser Asp Met Ile
20 25 30

Cys Gly Phe Ala Thr Leu Lys Gly Thr Ala Ala Met Arg Asn Thr Lys
35 40 45

Lys Gly Ser Trp Phe Ile Gln Glu Leu Asn Thr Ala Ile Arg Gln Arg
50 55 60

Ala Asn Asn Thr His Leu Ser Asp Ile Leu Val Gln Val Asn Gly Gln
65 70 75 80

Ile Lys Ser Arg Glu Gly Tyr Ala Pro Gly Ser Ala His His Arg Cys
85 90 95

Lys Glu Met Ser Glu Phe Thr Ser Ser Leu Cys Lys Asp Leu Tyr Leu
100 105 110

Phe Pro Lys Tyr Tyr Pro Ser Asn
115 120

<210> SEQ ID NO 113
<211> LENGTH: 417
<212> TYPE: PRT
<213> ORGANISM: Callorhinchus milii

<400> SEQUENCE: 113

```
Met Lys Gly Lys Trp Glu Met Lys Ser Ala Glu Ser Glu Ala Leu Arg
1               5                   10                  15

Lys Val His Val Thr Leu Ala Lys Gln Leu Val Ser Thr Glu Ile Val
            20                  25                  30

His His Leu Leu Ser Ala Glu Ile Leu Thr Glu Glu Met Val Asp Leu
        35                  40                  45

Leu Glu Thr Cys Arg Gly Thr Phe Gln Lys Asn Thr Glu Leu Leu Arg
    50                  55                  60

Leu Leu Pro Lys Arg Gly Pro Arg Ala Phe Glu Glu Phe Cys Arg Ala
65                  70                  75                  80

Leu Asp Arg Thr Lys Gln Ser His Leu Thr Gly Leu Leu Arg Glu Ser
                85                  90                  95

Val Thr Glu Glu Glu Ala Leu Cys Lys Pro Thr Gln Glu Ser Glu Cys
            100                 105                 110

Val Thr Pro Ala Lys Lys Phe Cys Ser Leu Trp Arg Val Cys Leu Asp
        115                 120                 125

Ala Gly Asp Gly Ser Gly Thr Phe Ser Val Arg Pro Thr Thr Ala Gln
    130                 135                 140

Phe Tyr His Glu His His Lys Gln Ser Tyr Arg Met Ala Ser Arg Pro
145                 150                 155                 160

Arg Gly Ala Ala Leu Ile Val Ser Asn Glu Val Phe Val Gly Glu Gly
                165                 170                 175

Leu Gly His Arg Pro Gly Gly Ala Ala Asp Thr Gly Val Leu Arg Ala
            180                 185                 190

Leu Leu Ser Gln Leu Gly Tyr Arg Val Thr Ser Val Cys Asn Ser Pro
        195                 200                 205

Ala Gln Glu Leu Glu Thr Arg Leu Arg Asp Phe Ala Leu Ser Ala Asp
    210                 215                 220

His Arg Arg Thr Asp Ser Cys Val Val Val Leu Leu Ser His Gly Val
225                 230                 235                 240

Glu Gly Ala Ile Tyr Gly Val Asp Gly Lys Leu Val Gln Ile His Asp
                245                 250                 255

Ile Phe Gln Leu Phe Asp Asn Ala Asn Cys Pro Asn Leu Gln Asn Lys
            260                 265                 270

Pro Lys Met Phe Phe Ile Gln Ala Cys Arg Gly Asp Arg Thr Asp Arg
        275                 280                 285

Gly Val Asp Arg Leu Asp Gly Ala Asp Ala Pro Gly Cys Glu Glu Cys
    290                 295                 300

Asp Ala Gly Lys Glu Arg Glu Arg Thr Arg Arg Gly Lys Leu Pro Thr
305                 310                 315                 320

Gln Ser Asp Ile Ile Cys Gly Tyr Ala Cys Leu Arg Gly Thr Ala Ala
                325                 330                 335

Leu Arg Asn Thr Arg Gln Gly Ser Trp Tyr Ile Gln Ala Leu Val Lys
            340                 345                 350

Val Phe Thr Glu Arg Ala His Asn Thr His Val Ala Asp Met Leu Val
        355                 360                 365

Gln Val Asn Ala Val Ile Arg Asp Arg Glu Gly Phe Ala Pro Gly Thr
    370                 375                 380
```

Asp Phe His Arg Cys Lys Glu Met Ala Glu Tyr Ser Ile Phe Glu Glu
385 390 395 400

Met Glu Gly Glu Thr Gln Arg Lys Gln Arg Arg Arg Lys Thr Ala Ala
405 410 415

Pro

<210> SEQ ID NO 114
<211> LENGTH: 162
<212> TYPE: PRT
<213> ORGANISM: Callorhinchus milii

<400> SEQUENCE: 114

Ser Gly Thr Phe Ser Val Arg Pro Thr Thr Ala Gln Phe Tyr His Glu
1 5 10 15

His His Lys Gln Ser Tyr Arg Met Ala Ser Arg Pro Arg Gly Ala Ala
20 25 30

Leu Ile Val Ser Asn Glu Val Phe Val Gly Glu Gly Leu Gly His Arg
35 40 45

Pro Gly Gly Ala Ala Asp Thr Gly Val Leu Arg Ala Leu Leu Ser Gln
50 55 60

Leu Gly Tyr Arg Val Thr Ser Val Cys Asn Ser Pro Ala Gln Glu Leu
65 70 75 80

Glu Thr Arg Leu Arg Asp Phe Ala Leu Ser Ala Asp His Arg Arg Thr
85 90 95

Asp Ser Cys Val Val Val Leu Leu Ser His Gly Val Glu Gly Ala Ile
100 105 110

Tyr Gly Val Asp Gly Lys Leu Val Gln Ile His Asp Ile Phe Gln Leu
115 120 125

Phe Asp Asn Ala Asn Cys Pro Asn Leu Gln Asn Lys Pro Lys Met Phe
130 135 140

Phe Ile Gln Ala Cys Arg Gly Asp Arg Thr Asp Arg Gly Val Asp Arg
145 150 155 160

Leu Asp

<210> SEQ ID NO 115
<211> LENGTH: 112
<212> TYPE: PRT
<213> ORGANISM: Callorhinchus milii

<400> SEQUENCE: 115

Ala Gly Lys Glu Arg Glu Arg Thr Arg Arg Gly Lys Leu Pro Thr Gln
1 5 10 15

Ser Asp Ile Ile Cys Gly Tyr Ala Cys Leu Arg Gly Thr Ala Ala Leu
20 25 30

Arg Asn Thr Arg Gln Gly Ser Trp Tyr Ile Gln Ala Leu Val Lys Val
35 40 45

Phe Thr Glu Arg Ala His Asn Thr His Val Ala Asp Met Leu Val Gln
50 55 60

Val Asn Ala Val Ile Arg Asp Arg Glu Gly Phe Ala Pro Gly Thr Asp
65 70 75 80

Phe His Arg Cys Lys Glu Met Ala Glu Tyr Ser Ile Phe Glu Glu Met
85 90 95

Glu Gly Glu Thr Gln Arg Lys Gln Arg Arg Arg Lys Thr Ala Ala Pro
100 105 110

<210> SEQ ID NO 116

<211> LENGTH: 351
<212> TYPE: PRT
<213> ORGANISM: Unknown
<220> FEATURE:
<223> OTHER INFORMATION: Description of Unknown:
Ascidiacea sequence

<400> SEQUENCE: 116

```
Met Asp Asp Ala Pro Ser Pro Thr Asp Ser Leu Ser Asn Ile Arg Ser
1               5                   10                  15

Thr Ala Ser Val His Ser Leu Phe Ser Arg Ser Asp Val Arg Thr Gln
            20                  25                  30

Ser Asn Thr Ala Ile Asn His Ile Asn Thr Val Gln Ser Pro Thr Ser
        35                  40                  45

Thr Lys Ala Ala Thr Ser Tyr Gln Ile Asn Leu His Gln Gly Met Asp
    50                  55                  60

Leu Phe Asp Gly Pro Thr Val Ser Asp Leu Thr Val Arg Lys Ser Thr
65                  70                  75                  80

His Gln His Leu Met Gln His Thr Asp Cys Tyr Gln Met Thr Met Arg
                85                  90                  95

Gly Arg Pro Lys Gly Ala Ala Leu Ile Ile Ser Val Glu Lys Phe His
            100                 105                 110

Pro Glu Ser Asp Leu Leu Asn Arg Glu Gly Ser Glu Lys Asp Arg Val
        115                 120                 125

Arg Leu Glu Leu Val Leu Gln Gln Ile Gly Phe Gln Cys Tyr Val Leu
    130                 135                 140

Ile Asn Gly Thr Ala Glu Gln Ile Val Ser Thr Leu Gln Thr Phe Ala
145                 150                 155                 160

Glu Leu Glu Glu His Tyr Tyr Asn Ser Cys Ser Leu Val Ala Ala Met
                165                 170                 175

Ser His Gly Asp Ala Gly Cys Phe Tyr Gly Ser Asp Gly Val Ser Val
            180                 185                 190

Ala Ile Asp Thr Val Val Asn Phe Phe Ser Asn Gln Asn Cys His Ser
        195                 200                 205

Leu Gln Lys Lys Pro Lys Ile Phe Leu Phe Gln Ala Cys Gln Gly Asp
    210                 215                 220

Glu Tyr Asp Met Gly Val Asp Glu Val Asp Gly Pro Val Gln Ala Pro
225                 230                 235                 240

Val Gly Asp Val Asp Asn Thr Ser Thr Ser Ser Ser Asn Asp His Ile
                245                 250                 255

Arg Asn Lys Leu Pro Gln Lys Ser Asp Met Leu Ile Gly Gln Ala Thr
            260                 265                 270

Met Lys Gly Phe Ala Ala Met Arg Asn Thr Lys His Gly Ser Trp Tyr
        275                 280                 285

Ile Gln Ala Phe Val Arg Val Leu Ala Arg His Ala Cys Asp Thr Asp
    290                 295                 300

Leu Leu Asp Met Met Thr Lys Val Asn Asn Ile Leu Lys His Lys Glu
305                 310                 315                 320

Gly Trp Cys Pro Gly Ser Val Tyr His Arg Cys Lys Val Met Pro Glu
                325                 330                 335

Phe Lys Ser Ser Leu Ser Lys Lys Leu Tyr Phe Phe Pro Gly Ile
            340                 345                 350
```

<210> SEQ ID NO 117
<211> LENGTH: 167
<212> TYPE: PRT

<213> ORGANISM: Unknown
<220> FEATURE:
<223> OTHER INFORMATION: Description of Unknown:
Ascidiacea sequence

<400> SEQUENCE: 117

Gly Pro Thr Val Ser Asp Leu Thr Val Arg Lys Ser Thr His Gln His
1 5 10 15

Leu Met Gln His Thr Asp Cys Tyr Gln Met Thr Met Arg Gly Arg Pro
20 25 30

Lys Gly Ala Ala Leu Ile Ile Ser Val Glu Lys Phe His Pro Glu Ser
35 40 45

Asp Leu Leu Asn Arg Glu Gly Ser Glu Lys Asp Arg Val Arg Leu Glu
50 55 60

Leu Val Leu Gln Gln Ile Gly Phe Gln Cys Tyr Val Leu Ile Asn Gly
65 70 75 80

Thr Ala Glu Gln Ile Val Ser Thr Leu Gln Thr Phe Ala Glu Leu Glu
85 90 95

Glu His Tyr Tyr Asn Ser Cys Ser Leu Val Ala Ala Met Ser His Gly
100 105 110

Asp Ala Gly Cys Phe Tyr Gly Ser Asp Gly Val Ser Val Ala Ile Asp
115 120 125

Thr Val Val Asn Phe Phe Ser Asn Gln Asn Cys His Ser Leu Gln Lys
130 135 140

Lys Pro Lys Ile Phe Leu Phe Gln Ala Cys Gln Gly Asp Glu Tyr Asp
145 150 155 160

Met Gly Val Asp Glu Val Asp
165

<210> SEQ ID NO 118
<211> LENGTH: 106
<212> TYPE: PRT
<213> ORGANISM: Unknown
<220> FEATURE:
<223> OTHER INFORMATION: Description of Unknown:
Ascidiacea sequence

<400> SEQUENCE: 118

Asn Thr Ser Thr Ser Ser Ser Asn Asp His Ile Arg Asn Lys Leu Pro
1 5 10 15

Gln Lys Ser Asp Met Leu Ile Gly Gln Ala Thr Met Lys Gly Phe Ala
20 25 30

Ala Met Arg Asn Thr Lys His Gly Ser Trp Tyr Ile Gln Ala Phe Val
35 40 45

Arg Val Leu Ala Arg His Ala Cys Asp Thr Asp Leu Leu Asp Met Met
50 55 60

Thr Lys Val Asn Asn Ile Leu Lys His Lys Glu Gly Trp Cys Pro Gly
65 70 75 80

Ser Val Tyr His Arg Cys Lys Val Met Pro Glu Phe Lys Ser Ser Leu
85 90 95

Ser Lys Lys Leu Tyr Phe Phe Pro Gly Ile
100 105

<210> SEQ ID NO 119
<211> LENGTH: 15
<212> TYPE: PRT
<213> ORGANISM: Homo sapiens

<400> SEQUENCE: 119

Gly Glu Lys Glu Leu Glu Phe Arg Ser Gly Gly Asp Val Asp His
1 5 10 15

<210> SEQ ID NO 120
<211> LENGTH: 15
<212> TYPE: PRT
<213> ORGANISM: Mus sp.

<400> SEQUENCE: 120

Gly Glu Lys Asp Leu Glu Phe Arg Ser Gly Gly Asp Val Asp His
1 5 10 15

<210> SEQ ID NO 121
<211> LENGTH: 15
<212> TYPE: PRT
<213> ORGANISM: Ovis sp.

<400> SEQUENCE: 121

Gly Glu Lys Asp Leu Glu Phe Arg Ser Gly Gly Asp Val Asp His
1 5 10 15

<210> SEQ ID NO 122
<211> LENGTH: 15
<212> TYPE: PRT
<213> ORGANISM: Sarcophilus harrisii

<400> SEQUENCE: 122

Gly Glu Lys Asp Leu Glu Phe Arg Ser Gly Gly Asp Val Asp His
1 5 10 15

<210> SEQ ID NO 123
<211> LENGTH: 15
<212> TYPE: PRT
<213> ORGANISM: Gallus sp.

<400> SEQUENCE: 123

Ser Glu Lys Asp Leu Glu Tyr Arg Ser Gly Gly Asp Val Asp Cys
1 5 10 15

<210> SEQ ID NO 124
<211> LENGTH: 15
<212> TYPE: PRT
<213> ORGANISM: Anolis carolinensis

<400> SEQUENCE: 124

Lys Glu Thr Asp Leu Asp Phe Arg Ser Gly Gly Asp Val Asp Asn
1 5 10 15

<210> SEQ ID NO 125
<211> LENGTH: 15
<212> TYPE: PRT
<213> ORGANISM: Alligator sp.

<400> SEQUENCE: 125

Gly Glu Lys Asp Leu Glu Phe Arg Ser Gly Gly Asp Val Asp Cys
1 5 10 15

<210> SEQ ID NO 126
<211> LENGTH: 14
<212> TYPE: PRT
<213> ORGANISM: Xenopus sp.

<400> SEQUENCE: 126

Thr Gln Asp Leu Asp His Arg Tyr Gly Gly Glu Val Asp Val 1 5 10

<210> SEQ ID NO 127
<211> LENGTH: 16
<212> TYPE: PRT
<213> ORGANISM: Danio sp.

<400> SEQUENCE: 127

Ser Ala Asn Thr Asp Leu Asp Ile Arg Arg Gly Gly Glu Val Asp Glu
1 5 10 15

<210> SEQ ID NO 128
<211> LENGTH: 14
<212> TYPE: PRT
<213> ORGANISM: Callorhinchus milii

<400> SEQUENCE: 128

Gly Glu Gly Leu Gly His Arg Pro Gly Gly Ala Ala Asp Thr
1 5 10

<210> SEQ ID NO 129
<211> LENGTH: 15
<212> TYPE: PRT
<213> ORGANISM: Unknown
<220> FEATURE:
<223> OTHER INFORMATION: Description of Unknown:
Ascidiacea sequence

<400> SEQUENCE: 129

Pro Glu Ser Asp Leu Leu Asn Arg Glu Gly Ser Glu Lys Asp Arg
1 5 10 15

<210> SEQ ID NO 130
<211> LENGTH: 15
<212> TYPE: PRT
<213> ORGANISM: Homo sapiens

<400> SEQUENCE: 130

Leu Leu Ser His Gly Val Glu Gly Ala Ile Tyr Gly Val Asp Gly
1 5 10 15

<210> SEQ ID NO 131
<211> LENGTH: 15
<212> TYPE: PRT
<213> ORGANISM: Mus sp.

<400> SEQUENCE: 131

Leu Leu Ser His Gly Val Glu Gly Gly Ile Tyr Gly Val Asp Gly
1 5 10 15

<210> SEQ ID NO 132
<211> LENGTH: 15
<212> TYPE: PRT
<213> ORGANISM: Ovis sp.

<400> SEQUENCE: 132

Leu Leu Ser His Gly Val Glu Gly Ser Val Tyr Gly Val Asp Gly
1 5 10 15

<210> SEQ ID NO 133
<211> LENGTH: 15
<212> TYPE: PRT
<213> ORGANISM: Sarcophilus harrisii

<400> SEQUENCE: 133

```
Leu Leu Ser His Gly Ile Glu Gly Gly Ile Tyr Gly Val Asp Gly
1               5                   10                  15


<210> SEQ ID NO 134
<211> LENGTH: 15
<212> TYPE: PRT
<213> ORGANISM: Ovis sp.

<400> SEQUENCE: 134

Leu Leu Ser His Gly Val Glu Gly Gly Val Tyr Gly Thr Asp Gly
1               5                   10                  15


<210> SEQ ID NO 135
<211> LENGTH: 15
<212> TYPE: PRT
<213> ORGANISM: Anolis sp.

<400> SEQUENCE: 135

Leu Leu Ser His Gly Ile Glu Gly Gly Ile Tyr Gly Ile Asp Gly
1               5                   10                  15


<210> SEQ ID NO 136
<211> LENGTH: 15
<212> TYPE: PRT
<213> ORGANISM: Alligator sp.

<400> SEQUENCE: 136

Leu Leu Ser His Gly Val Glu Gly Gly Val Tyr Gly Ile Asp Gly
1               5                   10                  15


<210> SEQ ID NO 137
<211> LENGTH: 15
<212> TYPE: PRT
<213> ORGANISM: Xenopus sp.

<400> SEQUENCE: 137

Val Leu Ser His Gly Leu Asp Gly Ala Val Tyr Gly Thr Asp Gly
1               5                   10                  15


<210> SEQ ID NO 138
<211> LENGTH: 15
<212> TYPE: PRT
<213> ORGANISM: Danio sp.

<400> SEQUENCE: 138

Leu Leu Ser His Gly Val Glu Gly Ser Val Tyr Gly Thr Asp Gly
1               5                   10                  15


<210> SEQ ID NO 139
<211> LENGTH: 15
<212> TYPE: PRT
<213> ORGANISM: Callorhinchus milii

<400> SEQUENCE: 139

Leu Leu Ser His Gly Val Glu Gly Ala Ile Tyr Gly Val Asp Gly
1               5                   10                  15


<210> SEQ ID NO 140
<211> LENGTH: 15
<212> TYPE: PRT
<213> ORGANISM: Unknown
<220> FEATURE:
<223> OTHER INFORMATION: Description of Unknown:
      Ascidiacea sequence

<400> SEQUENCE: 140
```

Ala Met Ser His Gly Asp Ala Gly Cys Phe Tyr Gly Ser Asp Gly
1 5 10 15

<210> SEQ ID NO 141
<211> LENGTH: 8
<212> TYPE: PRT
<213> ORGANISM: Homo sapiens

<400> SEQUENCE: 141

Gln Ala Cys Arg Gly Asp Glu Thr
1 5

<210> SEQ ID NO 142
<211> LENGTH: 8
<212> TYPE: PRT
<213> ORGANISM: Mus sp.

<400> SEQUENCE: 142

Gln Ala Cys Arg Gly Asp Glu Thr
1 5

<210> SEQ ID NO 143
<211> LENGTH: 8
<212> TYPE: PRT
<213> ORGANISM: Ovis sp.

<400> SEQUENCE: 143

Gln Ala Cys Arg Gly Asp Glu Thr
1 5

<210> SEQ ID NO 144
<211> LENGTH: 8
<212> TYPE: PRT
<213> ORGANISM: Sarcophilus harrisii

<400> SEQUENCE: 144

Gln Ala Cys Arg Gly Asp Glu Thr
1 5

<210> SEQ ID NO 145
<211> LENGTH: 8
<212> TYPE: PRT
<213> ORGANISM: Gallus sp.

<400> SEQUENCE: 145

Gln Ala Cys Arg Gly Asp Glu Thr
1 5

<210> SEQ ID NO 146
<211> LENGTH: 8
<212> TYPE: PRT
<213> ORGANISM: Anolis sp.

<400> SEQUENCE: 146

Gln Ala Cys Arg Gly Asp Glu Thr
1 5

<210> SEQ ID NO 147
<211> LENGTH: 8
<212> TYPE: PRT
<213> ORGANISM: Alligator sp.

<400> SEQUENCE: 147

Gln Ala Cys Arg Gly Asp Glu Thr 1 5

<210> SEQ ID NO 148
<211> LENGTH: 8
<212> TYPE: PRT
<213> ORGANISM: Xenopus sp.

<400> SEQUENCE: 148

Gln Ala Cys Arg Gly Glu Glu Ala
1 5

<210> SEQ ID NO 149
<211> LENGTH: 8
<212> TYPE: PRT
<213> ORGANISM: Danio sp.

<400> SEQUENCE: 149

Gln Ala Cys Arg Gly Glu Glu Met
1 5

<210> SEQ ID NO 150
<211> LENGTH: 8
<212> TYPE: PRT
<213> ORGANISM: Callorhinchus milii

<400> SEQUENCE: 150

Gln Ala Cys Arg Gly Asp Arg Thr
1 5

<210> SEQ ID NO 151
<211> LENGTH: 8
<212> TYPE: PRT
<213> ORGANISM: Unknown
<220> FEATURE:
<223> OTHER INFORMATION: Description of Unknown:
Ascidiacea sequence

<400> SEQUENCE: 151

Gln Ala Cys Gln Gly Asp Glu Tyr
1 5

<210> SEQ ID NO 152
<211> LENGTH: 8
<212> TYPE: PRT
<213> ORGANISM: Homo sapiens

<400> SEQUENCE: 152

Ala Ala Met Arg Asn Thr Lys Arg
1 5

<210> SEQ ID NO 153
<211> LENGTH: 8
<212> TYPE: PRT
<213> ORGANISM: Mus sp.

<400> SEQUENCE: 153

Ala Ala Met Arg Asn Thr Lys Arg
1 5

<210> SEQ ID NO 154
<211> LENGTH: 8
<212> TYPE: PRT
<213> ORGANISM: Ovis sp.

<400> SEQUENCE: 154

Ala Ala Met Arg Asn Thr Lys Arg
1 5

<210> SEQ ID NO 155
<211> LENGTH: 8
<212> TYPE: PRT
<213> ORGANISM: Sarcophilus harrisii

<400> SEQUENCE: 155

Ala Ala Met Arg Asn Thr Lys Arg
1 5

<210> SEQ ID NO 156
<211> LENGTH: 8
<212> TYPE: PRT
<213> ORGANISM: Gallus sp.

<400> SEQUENCE: 156

Ala Ala Met Arg Asn Thr Lys Arg
1 5

<210> SEQ ID NO 157
<211> LENGTH: 8
<212> TYPE: PRT
<213> ORGANISM: Anolis sp.

<400> SEQUENCE: 157

Ala Ala Met Arg Asn Thr Lys His
1 5

<210> SEQ ID NO 158
<211> LENGTH: 8
<212> TYPE: PRT
<213> ORGANISM: Alligator sp.

<400> SEQUENCE: 158

Ala Ala Met Arg Asn Thr Lys Arg
1 5

<210> SEQ ID NO 159
<211> LENGTH: 8
<212> TYPE: PRT
<213> ORGANISM: Xenopus sp.

<400> SEQUENCE: 159

Val Ser Leu Arg Asn Thr Lys Arg
1 5

<210> SEQ ID NO 160
<211> LENGTH: 8
<212> TYPE: PRT
<213> ORGANISM: Danio sp.

<400> SEQUENCE: 160

Ala Ala Met Arg Asn Thr Lys Lys
1 5

<210> SEQ ID NO 161
<211> LENGTH: 8
<212> TYPE: PRT
<213> ORGANISM: Callorhinchus milii

<400> SEQUENCE: 161

Ala Ala Leu Arg Asn Thr Arg Gln
1 5

<210> SEQ ID NO 162
<211> LENGTH: 8
<212> TYPE: PRT
<213> ORGANISM: Unknown
<220> FEATURE:
<223> OTHER INFORMATION: Description of Unknown:
      Ascidiacea sequence

<400> SEQUENCE: 162

Ala Ala Met Arg Asn Thr Lys His
1               5

<210> SEQ ID NO 163
<211> LENGTH: 13
<212> TYPE: PRT
<213> ORGANISM: Homo sapiens

<400> SEQUENCE: 163

Glu Gly Tyr Ala Pro Gly Thr Glu Phe His Arg Cys Lys
1               5                   10

<210> SEQ ID NO 164
<211> LENGTH: 13
<212> TYPE: PRT
<213> ORGANISM: Mus sp.

<400> SEQUENCE: 164

Glu Gly Tyr Ala Pro Gly Thr Glu Phe His Arg Cys Lys
1               5                   10

<210> SEQ ID NO 165
<211> LENGTH: 13
<212> TYPE: PRT
<213> ORGANISM: Ovis sp.

<400> SEQUENCE: 165

Glu Gly Tyr Ala Pro Gly Thr Glu Phe His Arg Cys Lys
1               5                   10

<210> SEQ ID NO 166
<211> LENGTH: 13
<212> TYPE: PRT
<213> ORGANISM: Sarcophilus harrisii

<400> SEQUENCE: 166

Glu Gly Tyr Ala Pro Gly Thr Glu Phe His Arg Cys Lys
1               5                   10

<210> SEQ ID NO 167
<211> LENGTH: 13
<212> TYPE: PRT
<213> ORGANISM: Gallus sp.

<400> SEQUENCE: 167

Glu Gly Tyr Ala Pro Gly Thr Glu Phe His Arg Cys Lys
1               5                   10

<210> SEQ ID NO 168
<211> LENGTH: 13
<212> TYPE: PRT
<213> ORGANISM: Anolis sp.

<400> SEQUENCE: 168

Glu Gly His Ala Pro Gly Thr Glu Phe His Arg Cys Lys 1 5 10

<210> SEQ ID NO 169
<211> LENGTH: 13
<212> TYPE: PRT
<213> ORGANISM: Alligator sp.

<400> SEQUENCE: 169

Glu Gly Tyr Ala Pro Gly Thr Glu Phe His Arg Cys Lys
1 5 10

<210> SEQ ID NO 170
<211> LENGTH: 13
<212> TYPE: PRT
<213> ORGANISM: Xenopus sp.

<400> SEQUENCE: 170

Glu Gly His Ala Pro Gly Thr Glu Phe His Arg Cys Lys
1 5 10

<210> SEQ ID NO 171
<211> LENGTH: 13
<212> TYPE: PRT
<213> ORGANISM: Danio sp.

<400> SEQUENCE: 171

Glu Gly Tyr Ala Pro Gly Ser Ala His His Arg Cys Lys
1 5 10

<210> SEQ ID NO 172
<211> LENGTH: 13
<212> TYPE: PRT
<213> ORGANISM: Callorhinchus milii

<400> SEQUENCE: 172

Glu Gly Phe Ala Pro Gly Thr Asp Phe His Arg Cys Lys
1 5 10

<210> SEQ ID NO 173
<211> LENGTH: 13
<212> TYPE: PRT
<213> ORGANISM: Unknown
<220> FEATURE:
<223> OTHER INFORMATION: Description of Unknown:
Ascidiacea sequence

<400> SEQUENCE: 173

Glu Gly Trp Cys Pro Gly Ser Val Tyr His Arg Cys Lys
1 5 10

<210> SEQ ID NO 174
<211> LENGTH: 15
<212> TYPE: PRT
<213> ORGANISM: Artificial Sequence
<220> FEATURE:
<223> OTHER INFORMATION: caspase 2

<400> SEQUENCE: 174

Gly Glu Lys Asp Leu Glu Phe Arg Ser Gly Gly Asp Val Asp His
1 5 10 15

<210> SEQ ID NO 175
<211> LENGTH: 15
<212> TYPE: PRT
<213> ORGANISM: Artificial Sequence
<220> FEATURE:

<223> OTHER INFORMATION: consensus sequence
<220> FEATURE:
<221> NAME/KEY: MOD_RES
<222> LOCATION: (10)..(10)
<223> OTHER INFORMATION: X can be any amino acid

<400> SEQUENCE: 175

Leu Leu Ser His Gly Val Glu Gly Gly Xaa Tyr Gly Val Asp Gly
1               5                   10                  15

<210> SEQ ID NO 176
<211> LENGTH: 8
<212> TYPE: PRT
<213> ORGANISM: Artificial Sequence
<220> FEATURE:
<223> OTHER INFORMATION: caspase 2

<400> SEQUENCE: 176

Gln Ala Cys Arg Gly Asp Glu Thr
1               5

<210> SEQ ID NO 177
<211> LENGTH: 8
<212> TYPE: PRT
<213> ORGANISM: Artificial Sequence
<220> FEATURE:
<223> OTHER INFORMATION: caspase 2

<400> SEQUENCE: 177

Ala Ala Met Arg Asn Thr Lys Arg
1               5

<210> SEQ ID NO 178
<211> LENGTH: 13
<212> TYPE: PRT
<213> ORGANISM: Artificial Sequence
<220> FEATURE:
<223> OTHER INFORMATION: caspase 2

<400> SEQUENCE: 178

Glu Gly Tyr Ala Pro Gly Thr Glu Phe His Arg Cys Lys
1               5                   10

<210> SEQ ID NO 179
<211> LENGTH: 272
<212> TYPE: PRT
<213> ORGANISM: Artificial Sequence
<220> FEATURE:
<223> OTHER INFORMATION: caspase 2

<400> SEQUENCE: 179

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys

```
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Asp Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Asp Glu Thr Asp Arg Gly Val Asp Gln Gln Asp
            260                 265                 270


<210> SEQ ID NO 180
<211> LENGTH: 272
<212> TYPE: PRT
<213> ORGANISM: Artificial Sequence
<220> FEATURE:
<223> OTHER INFORMATION: caspase 2

<400> SEQUENCE: 180

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Val Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
```

```
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Asp Glu Thr Asp Arg Gly Val Asp Gln Gln Asp
            260                 265                 270


<210> SEQ ID NO 181
<211> LENGTH: 272
<212> TYPE: PRT
<213> ORGANISM: Artificial Sequence
<220> FEATURE:
<223> OTHER INFORMATION: caspase 2

<400> SEQUENCE: 181

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Val Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Asp Glu Thr Asp Arg Gly Val Asp Gln Gln Asp
            260                 265                 270


<210> SEQ ID NO 182
<211> LENGTH: 272
<212> TYPE: PRT
```

```
<213> ORGANISM: Artificial Sequence
<220> FEATURE:
<223> OTHER INFORMATION: caspase 2

<400> SEQUENCE: 182

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Glu Glu Thr Asp Arg Gly Val Asp Gln Gln Asp
            260                 265                 270


<210> SEQ ID NO 183
<211> LENGTH: 272
<212> TYPE: PRT
<213> ORGANISM: Artificial Sequence
<220> FEATURE:
<223> OTHER INFORMATION: caspase 2

<400> SEQUENCE: 183

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60
```

```
Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Thr Glu Thr Asp Arg Gly Val Asp Gln Gln Asp
            260                 265                 270


<210> SEQ ID NO 184
<211> LENGTH: 272
<212> TYPE: PRT
<213> ORGANISM: Artificial Sequence
<220> FEATURE:
<223> OTHER INFORMATION: caspase 2

<400> SEQUENCE: 184

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160
```

```
Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Gly Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Asp Glu Thr Asp Arg Gly Val Asp Gln Gln Asp
            260                 265                 270


<210> SEQ ID NO 185
<211> LENGTH: 272
<212> TYPE: PRT
<213> ORGANISM: Artificial Sequence
<220> FEATURE:
<223> OTHER INFORMATION: caspase 2

<400> SEQUENCE: 185

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Glu Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255
```

Gln Ala Cys Arg Gly Asp Glu Thr Asp Arg Gly Val Asp Gln Gln Asp
260 265 270

<210> SEQ ID NO 186
<211> LENGTH: 272
<212> TYPE: PRT
<213> ORGANISM: Artificial Sequence
<220> FEATURE:
<223> OTHER INFORMATION: caspase 2

<400> SEQUENCE: 186

Met Ala Gly Lys Glu Lys Leu Pro Lys Met Arg Leu Pro Thr Arg Ser
1 5 10 15

Asp Met Ile Cys Gly Tyr Ala Cys Leu Lys Gly Thr Ala Ala Met Arg
20 25 30

Asn Thr Lys Arg Gly Ser Trp Tyr Ile Glu Ala Leu Ala Gln Val Phe
35 40 45

Ser Glu Arg Ala Cys Asp Met His Val Ala Asp Met Leu Val Lys Val
50 55 60

Asn Ala Leu Ile Lys Asp Arg Glu Gly Tyr Ala Pro Gly Thr Glu Phe
65 70 75 80

His Arg Cys Lys Glu Met Ser Glu Tyr Cys Ser Thr Leu Cys Arg His
85 90 95

Leu Tyr Leu Phe Pro Gly His Pro Pro Thr Gly Ser Gly Pro Val Cys
100 105 110

Leu Gln Val Lys Pro Cys Thr Pro Glu Phe Tyr Gln Thr His Phe Gln
115 120 125

Leu Ala Tyr Arg Leu Gln Ser Arg Pro Arg Gly Leu Ala Leu Val Leu
130 135 140

Ser Asn Val His Phe Thr Gly Glu Lys Glu Leu Glu Phe Arg Ser Gly
145 150 155 160

Gly Asp Val Asp Ala Ser Thr Leu Val Thr Leu Phe Lys Leu Leu Gly
165 170 175

Tyr Asp Val His Val Leu Cys Asp Gln Thr Ala Gln Glu Met Gln Glu
180 185 190

Lys Leu Gln Asn Phe Ala Gln Leu Pro Ala His Arg Val Thr Asp Ser
195 200 205

Cys Ile Val Ala Leu Leu Ser His Gly Val Glu Gly Ala Ile Tyr Gly
210 215 220

Val Asp Gly Lys Leu Leu Gln Leu Gln Glu Val Phe Gln Leu Phe Asp
225 230 235 240

Asn Ala Asn Cys Pro Ser Leu Gln Asn Lys Pro Lys Met Phe Phe Ile
245 250 255

Gln Ala Cys Arg Gly Asp Glu Thr Asp Arg Gly Val Asp Gln Gln Asp
260 265 270

<210> SEQ ID NO 187
<211> LENGTH: 272
<212> TYPE: PRT
<213> ORGANISM: Artificial Sequence
<220> FEATURE:
<223> OTHER INFORMATION: caspase 2

<400> SEQUENCE: 187

Met Ala Gly Lys Glu Lys Leu Pro Lys Met Arg Leu Pro Thr Arg Ser
1 5 10 15

Asp Met Ile Cys Gly Tyr Ala Cys Leu Lys Gly Thr Ala Ala Met Arg
20 25 30

Asn Thr Lys Arg Gly Ser Trp Tyr Ile Glu Ala Leu Ala Gln Val Phe
35 40 45

Ser Glu Arg Ala Cys Asp Met His Val Ala Asp Met Leu Val Lys Val
50 55 60

Asn Ala Leu Ile Lys Asp Arg Glu Gly Tyr Ala Pro Gly Thr Glu Phe
65 70 75 80

His Arg Cys Lys Glu Met Ser Glu Tyr Cys Ser Thr Leu Cys Arg His
85 90 95

Leu Tyr Leu Phe Pro Gly His Pro Pro Thr Gly Ser Gly Pro Val Cys
100 105 110

Leu Gln Val Lys Pro Cys Thr Pro Glu Phe Tyr Gln Thr His Phe Gln
115 120 125

Leu Ala Tyr Arg Leu Gln Ser Arg Pro Arg Gly Leu Ala Leu Val Leu
130 135 140

Ser Asn Val His Phe Thr Gly Glu Lys Glu Leu Glu Phe Arg Ser Gly
145 150 155 160

Gly Asp Val Asp His Ser Thr Leu Val Thr Leu Phe Lys Leu Leu Gly
165 170 175

Tyr Asp Val His Val Leu Cys Asp Gln Thr Ala Gln Glu Met Gln Glu
180 185 190

Lys Leu Gln Asn Phe Ala Gln Leu Pro Ala His Arg Val Thr Asp Ser
195 200 205

Cys Ile Val Ala Leu Leu Ser His Gly Val Glu Gly Ala Ile Tyr Gly
210 215 220

Val Asp Gly Lys Leu Leu Gln Leu Gln Glu Met Phe Gln Leu Phe Asp
225 230 235 240

Asn Ala Asn Cys Pro Ser Leu Gln Asn Lys Pro Lys Met Phe Phe Ile
245 250 255

Gln Ala Cys Arg Gly Asp Glu Thr Asp Arg Gly Val Asp Gln Gln Asp
260 265 270

<210> SEQ ID NO 188
<211> LENGTH: 272
<212> TYPE: PRT
<213> ORGANISM: Artificial Sequence
<220> FEATURE:
<223> OTHER INFORMATION: caspase 2

<400> SEQUENCE: 188

Met Ala Gly Lys Glu Lys Leu Pro Lys Met Arg Leu Pro Thr Arg Ser
1 5 10 15

Asp Met Ile Cys Gly Tyr Ala Cys Leu Lys Gly Thr Ala Ala Met Arg
20 25 30

Asn Thr Lys Arg Gly Ser Trp Tyr Ile Glu Ala Leu Ala Gln Val Phe
35 40 45

Ser Glu Arg Ala Cys Asp Met His Val Ala Asp Met Leu Val Lys Val
50 55 60

Asn Ala Leu Ile Lys Asp Arg Glu Gly Tyr Ala Pro Gly Thr Glu Phe
65 70 75 80

His Arg Cys Lys Glu Met Ser Glu Tyr Cys Ser Thr Leu Cys Arg His
85 90 95

Leu Tyr Leu Phe Pro Gly His Pro Pro Thr Gly Ser Gly Pro Val Cys
100 105 110

Leu Gln Val Lys Pro Cys Thr Pro Glu Phe Tyr Gln Thr His Phe Gln
115 120 125

```
Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220

Val Asp Gly Lys Leu Leu Gln Leu Gln Glu Val Phe Gln Leu Phe Asp
225                 230                 235                 240

Asn Ala Asn Cys Pro Ser Leu Gln Asn Lys Pro Lys Met Phe Phe Ile
                245                 250                 255

Gln Ala Cys Arg Gly Asp Glu Thr Glu Arg Gly Val Asp Gln Gln Asp
            260                 265                 270


<210> SEQ ID NO 189
<211> LENGTH: 272
<212> TYPE: PRT
<213> ORGANISM: Artificial Sequence
<220> FEATURE:
<223> OTHER INFORMATION: caspase 2

<400> SEQUENCE: 189

Met Ala Gly Lys Glu Lys Leu Pro Lys Met Arg Leu Pro Thr Arg Ser
1               5                   10                  15

Asp Met Ile Cys Gly Tyr Ala Cys Leu Lys Gly Thr Ala Ala Met Arg
            20                  25                  30

Asn Thr Lys Arg Gly Ser Trp Tyr Ile Glu Ala Leu Ala Gln Val Phe
        35                  40                  45

Ser Glu Arg Ala Cys Asp Met His Val Ala Asp Met Leu Val Lys Val
    50                  55                  60

Asn Ala Leu Ile Lys Asp Arg Glu Gly Tyr Ala Pro Gly Thr Glu Phe
65                  70                  75                  80

His Arg Cys Lys Glu Met Ser Glu Tyr Cys Ser Thr Leu Cys Arg His
                85                  90                  95

Leu Tyr Leu Phe Pro Gly His Pro Pro Thr Gly Ser Gly Pro Val Cys
            100                 105                 110

Leu Gln Val Lys Pro Cys Thr Pro Glu Phe Tyr Gln Thr His Phe Gln
        115                 120                 125

Leu Ala Tyr Arg Leu Gln Ser Arg Pro Arg Gly Leu Ala Leu Val Leu
    130                 135                 140

Ser Asn Val His Phe Thr Gly Glu Lys Glu Leu Glu Phe Arg Ser Gly
145                 150                 155                 160

Gly Asp Val Asp His Ser Thr Leu Val Thr Leu Phe Lys Leu Leu Gly
                165                 170                 175

Tyr Asp Val His Val Leu Cys Asp Gln Thr Ala Gln Glu Met Gln Glu
            180                 185                 190

Lys Leu Gln Asn Phe Ala Gln Leu Pro Ala His Arg Val Thr Asp Ser
        195                 200                 205

Cys Ile Val Ala Leu Leu Ser His Gly Val Glu Gly Ala Ile Tyr Gly
    210                 215                 220
```

Val Asp Gly Lys Leu Leu Gln Leu Gln Glu Val Phe Gln Leu Phe Asp
225 230 235 240

Asn Ala Asn Cys Pro Ser Leu Gln Asn Lys Pro Lys Met Phe Phe Ile
245 250 255

Gln Ala Cys Arg Gly Asp Glu Thr Tyr Arg Gly Val Asp Gln Gln Asp
260 265 270

<210> SEQ ID NO 190
<211> LENGTH: 292
<212> TYPE: PRT
<213> ORGANISM: Artificial Sequence
<220> FEATURE:
<223> OTHER INFORMATION: caspase 2

<400> SEQUENCE: 190

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Glu Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Asp Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Asp Arg Gly Val
275 280 285

Asp Gln Gln Asp
290

<210> SEQ ID NO 191

<211> LENGTH: 292
<212> TYPE: PRT
<213> ORGANISM: Artificial Sequence
<220> FEATURE:
<223> OTHER INFORMATION: caspase 2

<400> SEQUENCE: 191

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Glu Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Gly Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Glu Glu Thr Asp Arg Gly Val
275 280 285

Asp Gln Gln Asp
290

<210> SEQ ID NO 192
<211> LENGTH: 292
<212> TYPE: PRT
<213> ORGANISM: Artificial Sequence
<220> FEATURE:
<223> OTHER INFORMATION: caspase 2

<400> SEQUENCE: 192

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu

```
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Gly Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290


<210> SEQ ID NO 193
<211> LENGTH: 197
<212> TYPE: PRT
<213> ORGANISM: Artificial Sequence
<220> FEATURE:
<223> OTHER INFORMATION: fusion protein

<400> SEQUENCE: 193

Met His His His His His His Gly Ser Gly Val Asp Val Ala Asp Gly
1               5                   10                  15

Ala Thr Lys Ala Val Cys Val Leu Lys Gly Asp Gly Pro Val Gln Gly
            20                  25                  30

Ile Ile Asn Phe Glu Gln Lys Glu Ser Asn Gly Pro Val Lys Val Trp
        35                  40                  45

Gly Ser Ile Lys Gly Leu Thr Glu Gly Leu His Gly Phe His Val His
    50                  55                  60

Glu Phe Gly Asp Asn Thr Ala Gly Cys Thr Ser Ala Gly Pro His Phe
65                  70                  75                  80

Asn Pro Leu Ser Arg Lys His Gly Gly Pro Lys Asp Glu Glu Arg His
```

```
                85                  90                  95

Val Gly Asp Leu Gly Asn Val Thr Ala Asp Lys Asp Gly Val Ala Asp
            100                 105                 110

Val Ser Ile Glu Asp Ser Val Ile Ser Leu Ser Gly Asp His Cys Ile
        115                 120                 125

Ile Gly Arg Thr Leu Val Val His Glu Lys Ala Asp Asp Leu Gly Lys
    130                 135                 140

Gly Gly Asn Glu Glu Ser Thr Lys Thr Gly Asn Ala Gly Ser Arg Leu
145                 150                 155                 160

Ala Cys Gly Val Ile Gly Thr Ala Gln Val Asp Asp Tyr Lys Asp Asp
                165                 170                 175

Asp Asp Lys Gly Gly Gly Gly Ser Gly Gly Gly Gly Ser Trp Ser His
            180                 185                 190

Pro Gln Phe Glu Lys
        195


<210> SEQ ID NO 194
<211> LENGTH: 13
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (3)..(4)
<223> OTHER INFORMATION: X can be any amino acid
<220> FEATURE:
<221> NAME/KEY: MOD_RES
<222> LOCATION: (7)..(9)
<223> OTHER INFORMATION: X can be any amino acid

<400> SEQUENCE: 194

Glu Gly Xaa Xaa Pro Gly Xaa Xaa Xaa His Arg Cys Lys
1               5                   10


<210> SEQ ID NO 195
<211> LENGTH: 14
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (1)..(3)
<223> OTHER INFORMATION: X can be any amino acid
<220> FEATURE:
<221> NAME/KEY: MOD_RES
<222> LOCATION: (5)..(6)
<223> OTHER INFORMATION: X can be any amino acid
<220> FEATURE:
<221> NAME/KEY: MOD_RES
<222> LOCATION: (8)..(8)
<223> OTHER INFORMATION: X can be any amino acid
<220> FEATURE:
<221> NAME/KEY: MOD_RES
<222> LOCATION: (10)..(12)
<223> OTHER INFORMATION: X can be any amino acid
<220> FEATURE:
<221> NAME/KEY: MOD_RES
<222> LOCATION: (14)..(14)
<223> OTHER INFORMATION: X can be any amino acid

<400> SEQUENCE: 195

Xaa Xaa Xaa Leu Xaa Xaa Arg Xaa Gly Xaa Xaa Xaa Asp Xaa
1               5                   10


<210> SEQ ID NO 196
```

<211> LENGTH: 15
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (1)..(2)
<223> OTHER INFORMATION: X can be any amino acid
<220> FEATURE:
<221> NAME/KEY: MOD_RES
<222> LOCATION: (6)..(7)
<223> OTHER INFORMATION: X can be any amino acid
<220> FEATURE:
<221> NAME/KEY: MOD_RES
<222> LOCATION: (9)..(10)
<223> OTHER INFORMATION: X can be any amino acid
<220> FEATURE:
<221> NAME/KEY: MOD_RES
<222> LOCATION: (13)..(13)
<223> OTHER INFORMATION: X can be any amino acid

<400> SEQUENCE: 196

```
Xaa Xaa Ser His Gly Xaa Xaa Gly Xaa Xaa Tyr Gly Xaa Asp Gly
1               5                   10                  15
```

<210> SEQ ID NO 197
<211> LENGTH: 8
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (4)..(4)
<223> OTHER INFORMATION: X can be any amino acid
<220> FEATURE:
<221> NAME/KEY: MOD_RES
<222> LOCATION: (6)..(8)
<223> OTHER INFORMATION: X can be any amino acid

<400> SEQUENCE: 197

```
Gln Ala Cys Xaa Gly Xaa Xaa Xaa
1               5
```

<210> SEQ ID NO 198
<211> LENGTH: 292
<212> TYPE: PRT
<213> ORGANISM: Artificial Sequence
<220> FEATURE:
<223> OTHER INFORMATION: caspase 2

<400> SEQUENCE: 198

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Glu Met Ser Glu Tyr Cys Ser Thr
            100                 105                 110
```

```
Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Ser Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290


<210> SEQ ID NO 199
<211> LENGTH: 292
<212> TYPE: PRT
<213> ORGANISM: Artificial Sequence
<220> FEATURE:
<223> OTHER INFORMATION: caspase 2

<400> SEQUENCE: 199

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Gly Glu Lys Glu Leu Glu
                165                 170                 175
```

```
Phe Arg Ser Gly Gly Asp Val Asp His Ser Thr Leu Val Thr Leu Phe
            180                 185                 190

Lys Leu Leu Gly Tyr Asp Val His Val Leu Ser Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290


<210> SEQ ID NO 200
<211> LENGTH: 8
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (1)..(3)
<223> OTHER INFORMATION: X can be any amino acid
<220> FEATURE:
<221> NAME/KEY: MOD_RES
<222> LOCATION: (7)..(8)
<223> OTHER INFORMATION: X can be any amino acid

<400> SEQUENCE: 200

Xaa Xaa Xaa Arg Asn Thr Xaa Xaa
1               5


<210> SEQ ID NO 201
<211> LENGTH: 5
<212> TYPE: PRT
<213> ORGANISM: Artificial Sequence
<220> FEATURE:
<223> OTHER INFORMATION: recognition site
<220> FEATURE:
<221> NAME/KEY: MOD_RES
<222> LOCATION: (1)..(1)
<223> OTHER INFORMATION: X can be any amino acid
<220> FEATURE:
<221> NAME/KEY: MOD_RES
<222> LOCATION: (3)..(4)
<223> OTHER INFORMATION: X can be any amino acid

<400> SEQUENCE: 201

Xaa Asp Xaa Xaa Asp
1               5


<210> SEQ ID NO 202
<211> LENGTH: 4
<212> TYPE: PRT
<213> ORGANISM: Artificial Sequence
<220> FEATURE:
<223> OTHER INFORMATION: recognition site
<220> FEATURE:
<221> NAME/KEY: MOD_RES
<222> LOCATION: (3)..(3)
<223> OTHER INFORMATION: X can be any amino acid

<400> SEQUENCE: 202
```

Asp Glu Xaa Asp
1

<210> SEQ ID NO 203
<211> LENGTH: 4
<212> TYPE: PRT
<213> ORGANISM: Artificial Sequence
<220> FEATURE:
<223> OTHER INFORMATION: recognition site
<220> FEATURE:
<221> NAME/KEY: MOD_RES
<222> LOCATION: (3)..(3)
<223> OTHER INFORMATION: X can be any amino acid

<400> SEQUENCE: 203

Asp Val Xaa Asp
1

<210> SEQ ID NO 204
<211> LENGTH: 5
<212> TYPE: PRT
<213> ORGANISM: Artificial Sequence
<220> FEATURE:
<223> OTHER INFORMATION: recognition site

<400> SEQUENCE: 204

Leu Asp Glu Ser Asp
1               5

<210> SEQ ID NO 205
<211> LENGTH: 4
<212> TYPE: PRT
<213> ORGANISM: Artificial Sequence
<220> FEATURE:
<223> OTHER INFORMATION: recognition site

<400> SEQUENCE: 205

Asp Val Ala Asp
1

<210> SEQ ID NO 206
<211> LENGTH: 4
<212> TYPE: PRT
<213> ORGANISM: Artificial Sequence
<220> FEATURE:
<223> OTHER INFORMATION: recognition site

<400> SEQUENCE: 206

Asp Glu Val Asp
1

<210> SEQ ID NO 207
<211> LENGTH: 4
<212> TYPE: PRT
<213> ORGANISM: Artificial Sequence
<220> FEATURE:
<223> OTHER INFORMATION: recognition site

<400> SEQUENCE: 207

Asp Glu Val Glu
1

<210> SEQ ID NO 208
<211> LENGTH: 5
<212> TYPE: PRT
<213> ORGANISM: Artificial Sequence
<220> FEATURE:

<223> OTHER INFORMATION: recognition site

<400> SEQUENCE: 208

Ala Asp Val Ala Asp
1 5

<210> SEQ ID NO 209
<211> LENGTH: 5
<212> TYPE: PRT
<213> ORGANISM: Artificial Sequence
<220> FEATURE:
<223> OTHER INFORMATION: recognition site

<400> SEQUENCE: 209

Val Asp Thr Thr Asp
1 5

<210> SEQ ID NO 210
<211> LENGTH: 4
<212> TYPE: PRT
<213> ORGANISM: Artificial Sequence
<220> FEATURE:
<223> OTHER INFORMATION: recognition site

<400> SEQUENCE: 210

Asp Thr Thr Asp
1

<210> SEQ ID NO 211
<211> LENGTH: 4
<212> TYPE: PRT
<213> ORGANISM: Artificial Sequence
<220> FEATURE:
<223> OTHER INFORMATION: recognition site

<400> SEQUENCE: 211

Asp Val Pro Asp
1

<210> SEQ ID NO 212
<211> LENGTH: 5
<212> TYPE: PRT
<213> ORGANISM: Artificial Sequence
<220> FEATURE:
<223> OTHER INFORMATION: recognition site

<400> SEQUENCE: 212

Val Asp Val Pro Asp
1 5

<210> SEQ ID NO 213
<211> LENGTH: 5
<212> TYPE: PRT
<213> ORGANISM: Artificial Sequence
<220> FEATURE:
<223> OTHER INFORMATION: recognition site

<400> SEQUENCE: 213

Val Asp Gln Gln Asp
1 5

<210> SEQ ID NO 214
<211> LENGTH: 5
<212> TYPE: PRT
<213> ORGANISM: Artificial Sequence
<220> FEATURE:
<223> OTHER INFORMATION: recognition site

<400> SEQUENCE: 214

Thr Asp Thr Ser Asp
1 5

<210> SEQ ID NO 215
<211> LENGTH: 4
<212> TYPE: PRT
<213> ORGANISM: Artificial Sequence
<220> FEATURE:
<223> OTHER INFORMATION: recognition site

<400> SEQUENCE: 215

Asp Arg Lys Asp
1

<210> SEQ ID NO 216
<211> LENGTH: 4
<212> TYPE: PRT
<213> ORGANISM: Artificial Sequence
<220> FEATURE:
<223> OTHER INFORMATION: recognition site

<400> SEQUENCE: 216

Asp Ala Val Asp
1

<210> SEQ ID NO 217
<211> LENGTH: 4
<212> TYPE: PRT
<213> ORGANISM: Artificial Sequence
<220> FEATURE:
<223> OTHER INFORMATION: recognition site

<400> SEQUENCE: 217

Val Lys Val Asp
1

<210> SEQ ID NO 218
<211> LENGTH: 4
<212> TYPE: PRT
<213> ORGANISM: Artificial Sequence
<220> FEATURE:
<223> OTHER INFORMATION: recognition site

<400> SEQUENCE: 218

Asp Thr Leu Asp
1

<210> SEQ ID NO 219
<211> LENGTH: 4
<212> TYPE: PRT
<213> ORGANISM: Artificial Sequence
<220> FEATURE:
<223> OTHER INFORMATION: recognition site

<400> SEQUENCE: 219

Glu Glu Pro Asp
1

<210> SEQ ID NO 220
<211> LENGTH: 4
<212> TYPE: PRT
<213> ORGANISM: Artificial Sequence
<220> FEATURE:
<223> OTHER INFORMATION: recognition site

<400> SEQUENCE: 220

Asp Glu Thr Asp
1

<210> SEQ ID NO 221
<211> LENGTH: 4
<212> TYPE: PRT
<213> ORGANISM: Artificial Sequence
<220> FEATURE:
<223> OTHER INFORMATION: recognition site

<400> SEQUENCE: 221

Asp Ala Thr Asp
1

<210> SEQ ID NO 222
<211> LENGTH: 4
<212> TYPE: PRT
<213> ORGANISM: Artificial Sequence
<220> FEATURE:
<223> OTHER INFORMATION: recognition site

<400> SEQUENCE: 222

Asn Lys Val Asp
1

<210> SEQ ID NO 223
<211> LENGTH: 4
<212> TYPE: PRT
<213> ORGANISM: Artificial Sequence
<220> FEATURE:
<223> OTHER INFORMATION: recognition site

<400> SEQUENCE: 223

Asp Ala Leu Asp
1

<210> SEQ ID NO 224
<211> LENGTH: 4
<212> TYPE: PRT
<213> ORGANISM: Artificial Sequence
<220> FEATURE:
<223> OTHER INFORMATION: recognition site

<400> SEQUENCE: 224

Asp Ser Val Asp
1

<210> SEQ ID NO 225
<211> LENGTH: 4
<212> TYPE: PRT
<213> ORGANISM: Artificial Sequence
<220> FEATURE:
<223> OTHER INFORMATION: recognition site

<400> SEQUENCE: 225

Asn Ala Ile Asp
1

<210> SEQ ID NO 226
<211> LENGTH: 4
<212> TYPE: PRT
<213> ORGANISM: Artificial Sequence
<220> FEATURE:
<223> OTHER INFORMATION: recognition site

<400> SEQUENCE: 226

Asp Lys Pro Asp
1

<210> SEQ ID NO 227
<211> LENGTH: 4
<212> TYPE: PRT
<213> ORGANISM: Artificial Sequence
<220> FEATURE:
<223> OTHER INFORMATION: recognition site

<400> SEQUENCE: 227

Ile Gln Leu Asp
1

<210> SEQ ID NO 228
<211> LENGTH: 4
<212> TYPE: PRT
<213> ORGANISM: Artificial Sequence
<220> FEATURE:
<223> OTHER INFORMATION: recognition site

<400> SEQUENCE: 228

Asp Asn Ala Asp
1

<210> SEQ ID NO 229
<211> LENGTH: 4
<212> TYPE: PRT
<213> ORGANISM: Artificial Sequence
<220> FEATURE:
<223> OTHER INFORMATION: recognition site

<400> SEQUENCE: 229

Asp Val Val Asp
1

<210> SEQ ID NO 230
<211> LENGTH: 4
<212> TYPE: PRT
<213> ORGANISM: Artificial Sequence
<220> FEATURE:
<223> OTHER INFORMATION: recognition site

<400> SEQUENCE: 230

Glu Asn Pro Asp
1

<210> SEQ ID NO 231
<211> LENGTH: 4
<212> TYPE: PRT
<213> ORGANISM: Artificial Sequence
<220> FEATURE:
<223> OTHER INFORMATION: recognition site

<400> SEQUENCE: 231

Asp Met Ala Asp
1

<210> SEQ ID NO 232
<211> LENGTH: 4
<212> TYPE: PRT
<213> ORGANISM: Artificial Sequence
<220> FEATURE:
<223> OTHER INFORMATION: recognition site

<400> SEQUENCE: 232

Asp Leu Ile Asp
1

<210> SEQ ID NO 233
<211> LENGTH: 4
<212> TYPE: PRT
<213> ORGANISM: Artificial Sequence
<220> FEATURE:
<223> OTHER INFORMATION: recognition site

<400> SEQUENCE: 233

Asp Gly Ala Asp
1

<210> SEQ ID NO 234
<211> LENGTH: 4
<212> TYPE: PRT
<213> ORGANISM: Artificial Sequence
<220> FEATURE:
<223> OTHER INFORMATION: recognition site

<400> SEQUENCE: 234

Asp Val Lys Asp
1

<210> SEQ ID NO 235
<211> LENGTH: 4
<212> TYPE: PRT
<213> ORGANISM: Artificial Sequence
<220> FEATURE:
<223> OTHER INFORMATION: recognition site

<400> SEQUENCE: 235

Gly Tyr Asn Asp
1

<210> SEQ ID NO 236
<211> LENGTH: 4
<212> TYPE: PRT
<213> ORGANISM: Artificial Sequence
<220> FEATURE:
<223> OTHER INFORMATION: recognition site

<400> SEQUENCE: 236

Glu Leu Pro Asp
1

<210> SEQ ID NO 237
<211> LENGTH: 4
<212> TYPE: PRT
<213> ORGANISM: Artificial Sequence
<220> FEATURE:
<223> OTHER INFORMATION: recognition site

<400> SEQUENCE: 237

Asp Ser Thr Asp
1

<210> SEQ ID NO 238
<211> LENGTH: 4
<212> TYPE: PRT
<213> ORGANISM: Artificial Sequence
<220> FEATURE:
<223> OTHER INFORMATION: recognition site

<400> SEQUENCE: 238

Asp Arg Gln Asp

1

<210> SEQ ID NO 239
<211> LENGTH: 4
<212> TYPE: PRT
<213> ORGANISM: Artificial Sequence
<220> FEATURE:
<223> OTHER INFORMATION: recognition site

<400> SEQUENCE: 239

His Ala Val Asp
1

<210> SEQ ID NO 240
<211> LENGTH: 5
<212> TYPE: PRT
<213> ORGANISM: Artificial Sequence
<220> FEATURE:
<223> OTHER INFORMATION: recognition site

<400> SEQUENCE: 240

Gln Glu Arg Leu Asp
1               5

<210> SEQ ID NO 241
<211> LENGTH: 4
<212> TYPE: PRT
<213> ORGANISM: Artificial Sequence
<220> FEATURE:
<223> OTHER INFORMATION: recognition site

<400> SEQUENCE: 241

Leu Glu Arg Asp
1

<210> SEQ ID NO 242
<211> LENGTH: 4
<212> TYPE: PRT
<213> ORGANISM: Artificial Sequence
<220> FEATURE:
<223> OTHER INFORMATION: recognition site

<400> SEQUENCE: 242

Met Met Pro Asp
1

<210> SEQ ID NO 243
<211> LENGTH: 4
<212> TYPE: PRT
<213> ORGANISM: Artificial Sequence
<220> FEATURE:
<223> OTHER INFORMATION: recognition site

<400> SEQUENCE: 243

Glu Glu Pro Asp
1

<210> SEQ ID NO 244
<211> LENGTH: 5
<212> TYPE: PRT
<213> ORGANISM: Artificial Sequence
<220> FEATURE:
<223> OTHER INFORMATION: recognition site

<400> SEQUENCE: 244

Val Glu Ser Ile Asp
1               5

<210> SEQ ID NO 245
<211> LENGTH: 4
<212> TYPE: PRT
<213> ORGANISM: Artificial Sequence
<220> FEATURE:
<223> OTHER INFORMATION: recognition site

<400> SEQUENCE: 245

Glu Ala Met Asp
1

<210> SEQ ID NO 246
<211> LENGTH: 4
<212> TYPE: PRT
<213> ORGANISM: Artificial Sequence
<220> FEATURE:
<223> OTHER INFORMATION: recognition site

<400> SEQUENCE: 246

Glu Asp Ala Asp
1

<210> SEQ ID NO 247
<211> LENGTH: 4
<212> TYPE: PRT
<213> ORGANISM: Artificial Sequence
<220> FEATURE:
<223> OTHER INFORMATION: recognition site

<400> SEQUENCE: 247

Glu Glu Glu Asp
1

<210> SEQ ID NO 248
<211> LENGTH: 4
<212> TYPE: PRT
<213> ORGANISM: Artificial Sequence
<220> FEATURE:
<223> OTHER INFORMATION: recognition site

<400> SEQUENCE: 248

Ala Val Leu Asp
1

<210> SEQ ID NO 249
<211> LENGTH: 4
<212> TYPE: PRT
<213> ORGANISM: Artificial Sequence
<220> FEATURE:
<223> OTHER INFORMATION: recognition site

<400> SEQUENCE: 249

Glu Glu Gly Asp
1

<210> SEQ ID NO 250
<211> LENGTH: 5
<212> TYPE: PRT
<213> ORGANISM: Artificial Sequence
<220> FEATURE:
<223> OTHER INFORMATION: recognition site

<400> SEQUENCE: 250

Leu Asp Glu Pro Asp
1               5

<210> SEQ ID NO 251
<211> LENGTH: 5
<212> TYPE: PRT
<213> ORGANISM: Artificial Sequence
<220> FEATURE:
<223> OTHER INFORMATION: recognition site

<400> SEQUENCE: 251

Lys Asp Glu Val Asp
1               5

<210> SEQ ID NO 252
<211> LENGTH: 15
<212> TYPE: PRT
<213> ORGANISM: Artificial Sequence
<220> FEATURE:
<223> OTHER INFORMATION: fusion tag

<400> SEQUENCE: 252

Met His His His His His His Gly Ser Gly Val Asp Val Ala Asp
1               5                   10                  15

<210> SEQ ID NO 253
<211> LENGTH: 292
<212> TYPE: PRT
<213> ORGANISM: Artificial Sequence
<220> FEATURE:
<223> OTHER INFORMATION: cp caspase-2

<400> SEQUENCE: 253

Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys Val Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Asp Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly 225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Asp Arg Gly Val
275 280 285

Asp Gln Gln Asp
290

<210> SEQ ID NO 254
<211> LENGTH: 292
<212> TYPE: PRT
<213> ORGANISM: Artificial Sequence
<220> FEATURE:
<223> OTHER INFORMATION: cp caspase-2

<400> SEQUENCE: 254

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Val Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Val Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Asp Arg Gly Val
275 280 285

Asp Gln Gln Asp

290

<210> SEQ ID NO 255
<211> LENGTH: 292
<212> TYPE: PRT
<213> ORGANISM: Artificial Sequence
<220> FEATURE:
<223> OTHER INFORMATION: cp caspase-2

<400> SEQUENCE: 255

Met His His His His His His Gly Lys Asn His Ala Gly Ser Pro Gly
1 5 10 15

Cys Glu Glu Ser Ala Ala Gly Lys Glu Lys Leu Pro Lys Met Arg Leu
20 25 30

Pro Thr Arg Ser Asp Met Ile Cys Gly Tyr Ala Cys Leu Lys Gly Thr
35 40 45

Ala Ala Met Arg Asn Thr Lys Arg Gly Ser Trp Tyr Ile Glu Ala Leu
50 55 60

Ala Gln Val Phe Ser Glu Arg Ala Cys Asp Met His Val Ala Asp Met
65 70 75 80

Leu Val Lys Val Asn Ala Leu Ile Lys Asp Arg Glu Gly Tyr Ala Pro
85 90 95

Gly Thr Glu Phe His Arg Cys Lys Asn Met Ser Glu Tyr Cys Ser Thr
100 105 110

Leu Cys Arg His Leu Tyr Leu Phe Pro Gly His Pro Pro Thr Gly Ser
115 120 125

Gly Pro Val Cys Leu Gln Val Lys Pro Cys Thr Pro Glu Phe Tyr Gln
130 135 140

Thr His Phe Gln Leu Ala Tyr Arg Leu Gln Ser Arg Pro Arg Gly Leu
145 150 155 160

Ala Leu Val Leu Ser Asn Val His Phe Thr Val Glu Lys Glu Leu Glu
165 170 175

Phe Arg Ser Gly Gly Asp Val Asp His Ser Thr Leu Val Thr Leu Phe
180 185 190

Lys Leu Leu Gly Tyr Asp Val His Val Leu Cys Asp Gln Thr Ala Gln
195 200 205

Glu Met Gln Glu Lys Leu Gln Asn Phe Ala Gln Leu Pro Ala His Arg
210 215 220

Val Thr Asp Ser Cys Ile Val Ala Leu Leu Ser His Gly Val Glu Gly
225 230 235 240

Ala Ile Tyr Gly Val Asp Gly Lys Leu Leu Gln Leu Gln Glu Val Phe
245 250 255

Gln Leu Phe Asp Asn Ala Asn Cys Pro Ser Leu Gln Asn Lys Pro Lys
260 265 270

Met Phe Phe Ile Gln Ala Cys Arg Gly Asp Glu Thr Asp Arg Gly Val
275 280 285

Asp Gln Gln Asp
290

<210> SEQ ID NO 256
<211> LENGTH: 292
<212> TYPE: PRT
<213> ORGANISM: Artificial Sequence
<220> FEATURE:
<223> OTHER INFORMATION: cp caspase-2

<400> SEQUENCE: 256

```
Met His His His His His His Gly Lys Asn His Ala Gly Ser Pro Gly
1               5                   10                  15

Cys Glu Glu Ser Ala Ala Gly Lys Glu Lys Leu Pro Lys Met Arg Leu
            20                  25                  30

Pro Thr Arg Ser Asp Met Ile Cys Gly Tyr Ala Cys Leu Lys Gly Thr
        35                  40                  45

Ala Ala Met Arg Asn Thr Lys Arg Gly Ser Trp Tyr Ile Glu Ala Leu
    50                  55                  60

Ala Gln Val Phe Ser Glu Arg Ala Cys Asp Met His Val Ala Asp Met
65                  70                  75                  80

Leu Val Lys Val Asn Ala Leu Ile Lys Asp Arg Glu Gly Tyr Ala Pro
                85                  90                  95

Gly Thr Glu Phe His Arg Cys Lys His Met Ser Glu Tyr Cys Ser Thr
            100                 105                 110

Leu Cys Arg His Leu Tyr Leu Phe Pro Gly His Pro Pro Thr Gly Ser
        115                 120                 125

Gly Pro Val Cys Leu Gln Val Lys Pro Cys Thr Pro Glu Phe Tyr Gln
    130                 135                 140

Thr His Phe Gln Leu Ala Tyr Arg Leu Gln Ser Arg Pro Arg Gly Leu
145                 150                 155                 160

Ala Leu Val Leu Ser Asn Val His Phe Thr Val Glu Lys Glu Leu Glu
                165                 170                 175

Phe Arg Ser Gly Gly Asp Val Asp His Ser Thr Leu Val Thr Leu Phe
            180                 185                 190

Lys Leu Leu Gly Tyr Asp Val His Val Leu Cys Asp Gln Thr Ala Gln
        195                 200                 205

Glu Met Gln Glu Lys Leu Gln Asn Phe Ala Gln Leu Pro Ala His Arg
    210                 215                 220

Val Thr Asp Ser Cys Ile Val Ala Leu Leu Ser His Gly Val Glu Gly
225                 230                 235                 240

Ala Ile Tyr Gly Val Asp Gly Lys Leu Leu Gln Leu Gln Glu Val Phe
                245                 250                 255

Gln Leu Phe Asp Asn Ala Asn Cys Pro Ser Leu Gln Asn Lys Pro Lys
            260                 265                 270

Met Phe Phe Ile Gln Ala Cys Arg Gly Asp Glu Thr Asp Arg Gly Val
        275                 280                 285

Asp Gln Gln Asp
    290
```

<210> SEQ ID NO 257
<211> LENGTH: 248
<212> TYPE: PRT
<213> ORGANISM: Artificial Sequence
<220> FEATURE:
<223> OTHER INFORMATION: fusion protein

<400> SEQUENCE: 257

```
Met Lys Lys Thr Ala Ile Ala Ile Ala Val Ala Leu Ala Gly Phe Ala
1               5                   10                  15

Thr Val Ala Gln Ala Leu Glu Asp Pro Glu Arg Asn Lys Glu Arg Lys
            20                  25                  30

Glu Ala Glu Leu Gln Ala Gln Thr Ala Glu Gln His His His His His
        35                  40                  45

His Gly Ser Gly Val Asp Val Ala Asp Phe Pro Thr Ile Pro Leu Ser
    50                  55                  60
```

-continued

```
Arg Leu Phe Asp Asn Ala Met Leu Arg Ala His Arg Leu His Gln Leu
65                  70                  75                  80

Ala Phe Asp Thr Tyr Gln Glu Phe Glu Glu Ala Tyr Ile Pro Lys Glu
                85                  90                  95

Gln Lys Tyr Ser Phe Leu Gln Asn Pro Gln Thr Ser Leu Cys Phe Ser
            100                 105                 110

Glu Ser Ile Pro Thr Pro Ser Asn Arg Glu Glu Thr Gln Gln Lys Ser
        115                 120                 125

Asn Leu Glu Leu Leu Arg Ile Ser Leu Leu Leu Ile Gln Ser Trp Leu
    130                 135                 140

Glu Pro Val Gln Phe Leu Arg Ser Val Phe Ala Asn Ser Leu Val Tyr
145                 150                 155                 160

Gly Ala Ser Asp Ser Asn Val Tyr Asp Leu Leu Lys Asp Leu Glu Glu
                165                 170                 175

Gly Ile Gln Thr Leu Met Gly Arg Leu Glu Asp Gly Ser Pro Arg Thr
            180                 185                 190

Gly Gln Ile Phe Lys Gln Thr Tyr Ser Lys Phe Asp Thr Asn Ser His
        195                 200                 205

Asn Asp Asp Ala Leu Leu Lys Asn Tyr Gly Leu Leu Tyr Cys Phe Arg
    210                 215                 220

Lys Asp Met Asp Lys Val Glu Thr Phe Leu Arg Ile Val Gln Cys Arg
225                 230                 235                 240

Ser Val Glu Gly Ser Cys Gly Phe
                245
```

<210> SEQ ID NO 258
<211> LENGTH: 747
<212> TYPE: DNA
<213> ORGANISM: Artificial Sequence
<220> FEATURE:
<223> OTHER INFORMATION: fusion protein

<400> SEQUENCE: 258

```
atgaaaaaga cagctatcgc gattgcagtg gcactggctg gtttcgctac cgtagcgcag      60

gccctggagg atccggaacg caacaaagag cgaaaggaag ctgagttgca agctcaaacc     120

gctgagcaac accatcacca tcaccatggc agcggcgtgg atgtggcgga ttttccgacc     180

attccgctga gccgtctgtt tgataatgca atgctgcgtg cacatcgtct gcatcagctg     240

gcatttgata cctatcaaga atttgaagaa gcgtatatcc cgaaagagca gaaatatagc     300

ttcctgcaga atccgcagac cagcctgtgt tttagcgaaa gcattccgac accgagcaat     360

cgtgaagaaa cccagcagaa aagcaatctg gaactgctgc gtattagcct gctgctgatt     420

cagagctggc tggaaccggt gcagtttctg cgtagcgttt ttgcaaatag cctggtttat     480

ggtgcaagcg atagcaatgt ttatgatctg ctgaaagatc tggaagaagg tattcagacc     540

ctgatgggtc gtctggaaga tggttcaccg cgtaccggtc agatctttaa acagacctat     600

agcaaattcg ataccaacag ccataatgat gatgccctgc tgaaaaacta tggtctgctg     660

tattgtttcc gcaaagatat ggataaagtg gaaacctttc tgcgcattgt tcagtgtcgt     720

agcgttgaag gtagctgtgg tttctaa                                         747
```

<210> SEQ ID NO 259
<211> LENGTH: 121
<212> TYPE: PRT
<213> ORGANISM: Artificial Sequence
<220> FEATURE:
<223> OTHER INFORMATION: fusion protein

<400> SEQUENCE: 259

Met Leu Glu Asp Pro Glu Arg Asn Lys Glu Arg Lys Glu Ala Glu Leu
1 5 10 15

Gln Ala Gln Thr Ala Glu Gln His His His His His His Gly Ser Gly
20 25 30

Val Asp Val Ala Asp Ser Val Ser Glu Ile Gln Leu Met His Asn Leu
35 40 45

Gly Lys His Leu Asn Ser Met Glu Arg Val Glu Trp Leu Arg Lys Lys
50 55 60

Leu Gln Asp Val His Asn Phe Val Ala Leu Gly Ala Pro Leu Ala Pro
65 70 75 80

Arg Asp Ala Gly Ser Gln Arg Pro Arg Lys Lys Glu Asp Asn Val Leu
85 90 95

Val Glu Ser His Glu Lys Ser Leu Gly Glu Ala Asp Lys Ala Asp Val
100 105 110

Asn Val Leu Thr Lys Ala Lys Ser Gln
115 120

<210> SEQ ID NO 260
<211> LENGTH: 366
<212> TYPE: DNA
<213> ORGANISM: Artificial Sequence
<220> FEATURE:
<223> OTHER INFORMATION: fusion protein

<400> SEQUENCE: 260
atgctggagg atccggaacg caacaaagag cgaaaggaag ctgagttgca agctcaaacc 60
gctgagcaac accatcacca tcaccatggc agcggcgtgg atgtggcgga tagcgttagc 120
gaaattcagc tgatgcataa tctgggcaaa catctgaata gcatggaacg tgttgaatgg 180
ctgcgtaaaa aactgcagga tgtgcataat tttgttgcac tgggtgcacc gctggcaccg 240
cgtgatgcag gtagtcagcg tcctcgtaaa aaagaagata acgttctggt tgaaagccac 300
gaaaaaagcc tgggtgaagc agataaagca gatgttaatg ttctgaccaa agccaaaagc 360
cagtaa 366

<210> SEQ ID NO 261
<211> LENGTH: 215
<212> TYPE: PRT
<213> ORGANISM: Artificial Sequence
<220> FEATURE:
<223> OTHER INFORMATION: fusion protein

<400> SEQUENCE: 261

Met Leu Glu Asp Pro Glu Arg Asn Lys Glu Arg Lys Glu Ala Glu Leu
1 5 10 15

Gln Ala Gln Thr Ala Glu Gln His His His His His His Gly Ser Gly
20 25 30

Val Asp Val Ala Asp Ala Thr Pro Leu Gly Pro Ala Ser Ser Leu Pro
35 40 45

Gln Ser Phe Leu Leu Lys Cys Leu Glu Gln Val Arg Lys Ile Gln Gly
50 55 60

Asp Gly Ala Ala Leu Gln Glu Lys Leu Val Ser Glu Cys Ala Thr Tyr
65 70 75 80

Lys Leu Cys His Pro Glu Glu Leu Val Leu Leu Gly His Ser Leu Gly
85 90 95

```
Ile Pro Trp Ala Pro Leu Ser Ser Cys Pro Ser Gln Ala Leu Gln Leu
            100                 105                 110

Ala Gly Cys Leu Ser Gln Leu His Ser Gly Leu Phe Leu Tyr Gln Gly
        115                 120                 125

Leu Leu Gln Ala Leu Glu Gly Ile Ser Pro Glu Leu Gly Pro Thr Leu
    130                 135                 140

Asp Thr Leu Gln Leu Asp Val Ala Asp Phe Ala Thr Thr Ile Trp Gln
145                 150                 155                 160

Gln Met Glu Glu Leu Gly Met Ala Pro Ala Leu Gln Pro Thr Gln Gly
                165                 170                 175

Ala Met Pro Ala Phe Ala Ser Ala Phe Gln Arg Arg Ala Gly Gly Val
            180                 185                 190

Leu Val Ala Ser His Leu Gln Ser Phe Leu Glu Val Ser Tyr Arg Val
        195                 200                 205

Leu Arg His Leu Ala Gln Pro
    210                 215


<210> SEQ ID NO 262
<211> LENGTH: 648
<212> TYPE: DNA
<213> ORGANISM: Artificial Sequence
<220> FEATURE:
<223> OTHER INFORMATION: fusion protein

<400> SEQUENCE: 262

atgctggagg atccggaacg caacaaagag cgaaaggaag ctgagttgca agctcaaacc      60

gctgagcaac accatcacca tcaccatggc agcggcgtgg atgtggcgga tgcaacaccg     120

ctgggtcctg caagcagcct gccgcagagc tttctgctga aatgtctgga acaggttcgt     180

aaaattcaag gtgatggcgc agcactgcaa gaaaaactgg ttagcgaatg tgcaacctat     240

aaactgtgtc atccggaaga actggttctg ctgggtcata gcctgggtat tccgtgggca     300

ccgctgagta gctgtccgag ccaggcactg cagctggcag gttgtctgag tcagctgcat     360

agcggtctgt ttctgtatca gggtctgctg caggcactgg aaggtattag tccggaactg     420

ggtccgacac tggataccct gcaactggat gttgcagatt ttgcaaccac catttggcag     480

cagatggaag aattaggtat ggcaccagcg ctgcagccga cacagggtgc aatgcctgca     540

tttgcaagcg catttcagcg tcgtgccggt ggtgttctgg ttgcaagcca tctgcagagt     600

tttctggaag ttagctatcg tgttctgcgt catctggcac agccgtaa                  648


<210> SEQ ID NO 263
<211> LENGTH: 194
<212> TYPE: PRT
<213> ORGANISM: Artificial Sequence
<220> FEATURE:
<223> OTHER INFORMATION: fusion protein

<400> SEQUENCE: 263

Met Leu Glu Asp Pro Glu Arg Asn Lys Glu Arg Lys Glu Ala Glu Leu
1               5                   10                  15

Gln Ala Gln Thr Ala Glu Gln His His His His His His Gly Ser Gly
            20                  25                  30

Val Asp Val Ala Asp Val Arg Ser Ser Ser Arg Thr Pro Ser Asp Lys
        35                  40                  45

Pro Val Ala His Val Val Ala Asn Pro Gln Ala Glu Gly Gln Leu Gln
    50                  55                  60

Trp Leu Asn Arg Arg Ala Asn Ala Leu Leu Ala Asn Gly Val Glu Leu
```

-continued

```
65                  70                  75                  80

Arg Asp Asn Gln Leu Val Val Pro Ser Glu Gly Leu Tyr Leu Ile Tyr
                85                  90                  95

Ser Gln Val Leu Phe Lys Gly Gln Gly Cys Pro Ser Thr His Val Leu
            100                 105                 110

Leu Thr His Thr Ile Ser Arg Ile Ala Val Ser Tyr Gln Thr Lys Val
        115                 120                 125

Asn Leu Leu Ser Ala Ile Lys Ser Pro Cys Gln Arg Glu Thr Pro Glu
    130                 135                 140

Gly Ala Glu Ala Lys Pro Trp Tyr Glu Pro Ile Tyr Leu Gly Gly Val
145                 150                 155                 160

Phe Gln Leu Glu Lys Gly Asp Arg Leu Ser Ala Glu Ile Asn Arg Pro
                165                 170                 175

Asp Tyr Leu Asp Phe Ala Glu Ser Gly Gln Val Tyr Phe Gly Ile Ile
            180                 185                 190

Ala Leu


<210> SEQ ID NO 264
<211> LENGTH: 585
<212> TYPE: DNA
<213> ORGANISM: Artificial Sequence
<220> FEATURE:
<223> OTHER INFORMATION: fusion protein

<400> SEQUENCE: 264

atgctggagg atccggaacg caacaaagag cgaaaggaag ctgagttgca agctcaaacc      60

gctgagcaac accatcacca tcaccatggc agcggcgtgg atgtggcgga tgtccgttcc     120

agcagccgta cgccgagcga taaacctgtc gcgcacgtag tggcgaatcc gcaagccgag     180

ggtcagctgc agtggctgaa tcgtcgcgcg aacgcgctgc tggccaatgg tgttgagctg     240

cgtgacaacc aactggttgt tccatccgaa ggcctgtacc tgatttattc tcaagtgctg     300

ttcaaaggtc agggttgccc gagcacgcac gtgttgctga cccataccat tagccgcatc     360

gcagtcagct accagaccaa ggtcaacctg ttgagcgcga tcaagtcccc gtgtcaacgt     420

gaaacgcctg agggcgctga ggccaagccg tggtatgagc cgatctacct gggtggcgtg     480

tttcagctgg agaaaggtga ccgtctgagc gcggaaatca accgcccgga ttatttagat     540

tttgccgagt ctggtcaggt gtacttcggc attattgcac tgtga                     585


<210> SEQ ID NO 265
<211> LENGTH: 155
<212> TYPE: PRT
<213> ORGANISM: Artificial Sequence
<220> FEATURE:
<223> OTHER INFORMATION: fusion protein

<400> SEQUENCE: 265

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Ser Ala Asn
65                  70                  75                  80
```

Arg Tyr Leu Ala Met Lys Glu Asp Gly Arg Leu Leu Ala Ser Lys Ser
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

Arg Thr Gly Gln Tyr Lys Leu Gly Ser Lys Thr Gly Pro Gly Gln Lys
130 135 140

Ala Ile Leu Phe Leu Pro Met Ser Ala Lys Ser
145 150 155

<210> SEQ ID NO 266
<211> LENGTH: 161
<212> TYPE: PRT
<213> ORGANISM: Artificial Sequence
<220> FEATURE:
<223> OTHER INFORMATION: fusion protein

<400> SEQUENCE: 266

Met His His His His His His Ala Ala Gly Ser Ile Thr Thr Leu Pro
1 5 10 15

Ala Leu Pro Glu Asp Gly Gly Ser Gly Ala Phe Pro Pro Gly His Phe
20 25 30

Lys Asp Pro Lys Arg Leu Tyr Cys Lys Asn Gly Gly Phe Phe Leu Arg
35 40 45

Ile His Pro Asp Gly Arg Val Asp Gly Val Arg Glu Lys Ser Asp Pro
50 55 60

His Ile Lys Leu Gln Leu Gln Ala Glu Glu Arg Gly Val Val Ser Ile
65 70 75 80

Lys Gly Val Ser Ala Asn Arg Tyr Leu Ala Met Lys Glu Asp Gly Arg
85 90 95

Leu Leu Ala Ser Lys Ser Val Thr Asp Glu Cys Phe Phe Phe Glu Arg
100 105 110

Leu Glu Ser Asn Asn Tyr Asn Thr Tyr Arg Ser Arg Lys Tyr Thr Ser
115 120 125

Trp Tyr Val Ala Leu Lys Arg Thr Gly Gln Tyr Lys Leu Gly Ser Lys
130 135 140

Thr Gly Pro Gly Gln Lys Ala Ile Leu Phe Leu Pro Met Ser Ala Lys
145 150 155 160

Ser

<210> SEQ ID NO 267
<211> LENGTH: 191
<212> TYPE: PRT
<213> ORGANISM: Artificial Sequence
<220> FEATURE:
<223> OTHER INFORMATION: fusion protein

<400> SEQUENCE: 267

Met Leu Glu Asp Pro Glu Arg Asn Lys Glu Arg Lys Glu Ala Glu Leu
1 5 10 15

Gln Ala Gln Thr Ala Glu Gln His His His His His His Gly Ser Gly
20 25 30

Val Asp Val Ala Asp Ala Ala Gly Ser Ile Thr Thr Leu Pro Ala Leu
35 40 45

Pro Glu Asp Gly Gly Ser Gly Ala Phe Pro Pro Gly His Phe Lys Asp
50 55 60

Pro Lys Arg Leu Tyr Cys Lys Asn Gly Gly Phe Phe Leu Arg Ile His
65 70 75 80

Pro Asp Gly Arg Val Asp Gly Val Arg Glu Lys Ser Asp Pro His Ile
85 90 95

Lys Leu Gln Leu Gln Ala Glu Glu Arg Gly Val Val Ser Ile Lys Gly
100 105 110

Val Ser Ala Asn Arg Tyr Leu Ala Met Lys Glu Asp Gly Arg Leu Leu
115 120 125

Ala Ser Lys Ser Val Thr Asp Glu Cys Phe Phe Phe Glu Arg Leu Glu
130 135 140

Ser Asn Asn Tyr Asn Thr Tyr Arg Ser Arg Lys Tyr Thr Ser Trp Tyr
145 150 155 160

Val Ala Leu Lys Arg Thr Gly Gln Tyr Lys Leu Gly Ser Lys Thr Gly
165 170 175

Pro Gly Gln Lys Ala Ile Leu Phe Leu Pro Met Ser Ala Lys Ser
180 185 190

<210> SEQ ID NO 268
<211> LENGTH: 191
<212> TYPE: PRT
<213> ORGANISM: Artificial Sequence
<220> FEATURE:
<223> OTHER INFORMATION: fusion protein

<400> SEQUENCE: 268

Met Leu Glu Asp Pro Glu Arg Asn Lys Glu Arg Lys Glu Ala Glu Leu
1 5 10 15

Gln Ala Gln Thr Ala Glu Gln His His His His His His Gly Ser Gly
20 25 30

Val Asp Ser Ala Asp Ala Ala Gly Ser Ile Thr Thr Leu Pro Ala Leu
35 40 45

Pro Glu Asp Gly Gly Ser Gly Ala Phe Pro Pro Gly His Phe Lys Asp
50 55 60

Pro Lys Arg Leu Tyr Cys Lys Asn Gly Gly Phe Phe Leu Arg Ile His
65 70 75 80

Pro Asp Gly Arg Val Asp Gly Val Arg Glu Lys Ser Asp Pro His Ile
85 90 95

Lys Leu Gln Leu Gln Ala Glu Glu Arg Gly Val Val Ser Ile Lys Gly
100 105 110

Val Ser Ala Asn Arg Tyr Leu Ala Met Lys Glu Asp Gly Arg Leu Leu
115 120 125

Ala Ser Lys Ser Val Thr Asp Glu Cys Phe Phe Phe Glu Arg Leu Glu
130 135 140

Ser Asn Asn Tyr Asn Thr Tyr Arg Ser Arg Lys Tyr Thr Ser Trp Tyr
145 150 155 160

Val Ala Leu Lys Arg Thr Gly Gln Tyr Lys Leu Gly Ser Lys Thr Gly
165 170 175

Pro Gly Gln Lys Ala Ile Leu Phe Leu Pro Met Ser Ala Lys Ser
180 185 190

<210> SEQ ID NO 269
<211> LENGTH: 191
<212> TYPE: PRT
<213> ORGANISM: Artificial Sequence
<220> FEATURE:
<223> OTHER INFORMATION: fusion protein

<400> SEQUENCE: 269

Met Leu Glu Asp Pro Glu Arg Asn Lys Glu Arg Lys Glu Ala Glu Leu
1 5 10 15

Glu Ala Glu Thr Ala Glu Gln His His His His His His Gly Ser Gly
20 25 30

Val Asp Val Ala Asp Ala Ala Gly Ser Ile Thr Thr Leu Pro Ala Leu
35 40 45

Pro Glu Asp Gly Gly Ser Gly Ala Phe Pro Pro Gly His Phe Lys Asp
50 55 60

Pro Lys Arg Leu Tyr Cys Lys Asn Gly Gly Phe Phe Leu Arg Ile His
65 70 75 80

Pro Asp Gly Arg Val Asp Gly Val Arg Glu Lys Ser Asp Pro His Ile
85 90 95

Lys Leu Gln Leu Gln Ala Glu Glu Arg Gly Val Val Ser Ile Lys Gly
100 105 110

Val Ser Ala Asn Arg Tyr Leu Ala Met Lys Glu Asp Gly Arg Leu Leu
115 120 125

Ala Ser Lys Ser Val Thr Asp Glu Cys Phe Phe Phe Glu Arg Leu Glu
130 135 140

Ser Asn Asn Tyr Asn Thr Tyr Arg Ser Arg Lys Tyr Thr Ser Trp Tyr
145 150 155 160

Val Ala Leu Lys Arg Thr Gly Gln Tyr Lys Leu Gly Ser Lys Thr Gly
165 170 175

Pro Gly Gln Lys Ala Ile Leu Phe Leu Pro Met Ser Ala Lys Ser
180 185 190

<210> SEQ ID NO 270
<211> LENGTH: 188
<212> TYPE: PRT
<213> ORGANISM: Artificial Sequence
<220> FEATURE:
<223> OTHER INFORMATION: fusion protein

<400> SEQUENCE: 270

Met Leu Glu Asp Pro Glu Arg Asn Lys Glu Arg Lys Glu Ala Glu Leu
1 5 10 15

Gln Ala Gln Thr Ala Glu Gln His His His His His His Val Asp Val
20 25 30

Ala Asp Ala Ala Gly Ser Ile Thr Thr Leu Pro Ala Leu Pro Glu Asp
35 40 45

Gly Gly Ser Gly Ala Phe Pro Pro Gly His Phe Lys Asp Pro Lys Arg
50 55 60

Leu Tyr Cys Lys Asn Gly Gly Phe Phe Leu Arg Ile His Pro Asp Gly
65 70 75 80

Arg Val Asp Gly Val Arg Glu Lys Ser Asp Pro His Ile Lys Leu Gln
85 90 95

Leu Gln Ala Glu Glu Arg Gly Val Val Ser Ile Lys Gly Val Ser Ala
100 105 110

Asn Arg Tyr Leu Ala Met Lys Glu Asp Gly Arg Leu Leu Ala Ser Lys
115 120 125

Ser Val Thr Asp Glu Cys Phe Phe Phe Glu Arg Leu Glu Ser Asn Asn
130 135 140

Tyr Asn Thr Tyr Arg Ser Arg Lys Tyr Thr Ser Trp Tyr Val Ala Leu
145 150 155 160

Lys Arg Thr Gly Gln Tyr Lys Leu Gly Ser Lys Thr Gly Pro Gly Gln

```
                165                 170                 175

Lys Ala Ile Leu Phe Leu Pro Met Ser Ala Lys Ser
            180                 185


<210> SEQ ID NO 271
<211> LENGTH: 195
<212> TYPE: PRT
<213> ORGANISM: Artificial Sequence
<220> FEATURE:
<223> OTHER INFORMATION: fusion protein

<400> SEQUENCE: 271

Met Leu Glu Asp Pro Glu Arg Asn Lys Glu Arg Lys Glu Ala Glu Leu
1               5                   10                  15

Gln Ala Gln Thr Ala Glu Gln His His His His His His Gly Ser Gly
            20                  25                  30

Ser Gly Ser Gly Val Asp Val Ala Asp Ala Ala Gly Ser Ile Thr Thr
        35                  40                  45

Leu Pro Ala Leu Pro Glu Asp Gly Gly Ser Gly Ala Phe Pro Pro Gly
    50                  55                  60

His Phe Lys Asp Pro Lys Arg Leu Tyr Cys Lys Asn Gly Gly Phe Phe
65                  70                  75                  80

Leu Arg Ile His Pro Asp Gly Arg Val Asp Gly Val Arg Glu Lys Ser
                85                  90                  95

Asp Pro His Ile Lys Leu Gln Leu Gln Ala Glu Glu Arg Gly Val Val
            100                 105                 110

Ser Ile Lys Gly Val Ser Ala Asn Arg Tyr Leu Ala Met Lys Glu Asp
        115                 120                 125

Gly Arg Leu Leu Ala Ser Lys Ser Val Thr Asp Glu Cys Phe Phe Phe
    130                 135                 140

Glu Arg Leu Glu Ser Asn Asn Tyr Asn Thr Tyr Arg Ser Arg Lys Tyr
145                 150                 155                 160

Thr Ser Trp Tyr Val Ala Leu Lys Arg Thr Gly Gln Tyr Lys Leu Gly
                165                 170                 175

Ser Lys Thr Gly Pro Gly Gln Lys Ala Ile Leu Phe Leu Pro Met Ser
            180                 185                 190

Ala Lys Ser
        195


<210> SEQ ID NO 272
<211> LENGTH: 588
<212> TYPE: DNA
<213> ORGANISM: Artificial Sequence
<220> FEATURE:
<223> OTHER INFORMATION: fusion protein

<400> SEQUENCE: 272

atgctggagg atccggaacg caacaaagag cgaaaggaag ctgagttgca agctcaaacc      60

gctgagcaac accatcacca tcaccatggt agcggctctg gcagcggcgt ggatgtggcg     120

gatgccgctg gttcgattac taccctgcct gctttacctg aagatggtgg ttctggtgcg     180

ttcccgccgg gtcacttcaa agacccaaaa cgtttgtact gtaaaaacgg tggctttttt     240

ctgcgcatcc atccggacgg ccgcgtggat ggtgtccgtg aaaagtccga cccgcacatt     300

aagctgcaac tgcaggccga ggagcgtggt gttgttagca tcaaaggcgt gagcgcaaat     360

cgttacctgg cgatgaaaga ggatggccgt ctgctggcga gcaagagcgt taccgacgag     420

tgcttcttct ttgaacgcct ggagagcaat aattacaaca cctaccgtag ccgcaagtat     480
```

acctcttggt atgtggcgct gaagcgtacg ggccagtata aattgggtag caaaacgggt 540
ccgggccaaa aggcaatcct gttcctgccg atgagcgcga aatcctaa 588

<210> SEQ ID NO 273
<211> LENGTH: 192
<212> TYPE: PRT
<213> ORGANISM: Artificial Sequence
<220> FEATURE:
<223> OTHER INFORMATION: fusion protein

<400> SEQUENCE: 273

Met Lys Lys Thr Ala Ile Ala Ile Ala Val Ala Leu Ala Gly Phe Ala
1 5 10 15

Thr Val Ala Gln Ala His His His His His His Gly Ser Gly Val Asp
20 25 30

Val Ala Asp Val Arg Ser Ser Ser Arg Thr Pro Ser Asp Lys Pro Val
35 40 45

Ala His Val Val Ala Asn Pro Gln Ala Glu Gly Gln Leu Gln Trp Leu
50 55 60

Asn Arg Arg Ala Asn Ala Leu Leu Ala Asn Gly Val Glu Leu Arg Asp
65 70 75 80

Asn Gln Leu Val Val Pro Ser Glu Gly Leu Tyr Leu Ile Tyr Ser Gln
85 90 95

Val Leu Phe Lys Gly Gln Gly Cys Pro Ser Thr His Val Leu Leu Thr
100 105 110

His Thr Ile Ser Arg Ile Ala Val Ser Tyr Gln Thr Lys Val Asn Leu
115 120 125

Leu Ser Ala Ile Lys Ser Pro Cys Gln Arg Glu Thr Pro Glu Gly Ala
130 135 140

Glu Ala Lys Pro Trp Tyr Glu Pro Ile Tyr Leu Gly Gly Val Phe Gln
145 150 155 160

Leu Glu Lys Gly Asp Arg Leu Ser Ala Glu Ile Asn Arg Pro Asp Tyr
165 170 175

Leu Asp Phe Ala Glu Ser Gly Gln Val Tyr Phe Gly Ile Ile Ala Leu
180 185 190

<210> SEQ ID NO 274
<211> LENGTH: 579
<212> TYPE: DNA
<213> ORGANISM: Artificial Sequence
<220> FEATURE:
<223> OTHER INFORMATION: fusion protein

<400> SEQUENCE: 274
atgaaaaaga cagctatcgc gattgcagtg gcactggctg gtttcgctac cgtagcgcag 60
gcccaccatc accatcacca tggcagcggc gtggatgtgg cggatgtccg ttccagcagc 120
cgtacgccga gcgataaacc tgtcgcgcac gtagtggcga atccgcaagc cgagggtcag 180
ctgcagtggc tgaatcgtcg cgcgaacgcg ctgctggcca atggtgttga gctgcgtgac 240
aaccaactgg ttgttccatc cgaaggcctg tacctgattt attctcaagt gctgttcaaa 300
ggtcagggtt gcccgagcac gcacgtgttg ctgacccata ccattagccg catcgcagtc 360
agctaccaga ccaaggtcaa cctgttgagc gcgatcaagt ccccgtgtca acgtgaaacg 420
cctgagggcg ctgaggccaa gccgtggtat gagccgatct acctgggtgg cgtgtttcag 480
ctggagaaag gtgaccgtct gagcgcggaa atcaaccgcc cggattattt agattttgcc 540

-continued gagtctggtc aggtgtactt cggcattatt gcactgtga 579

<210> SEQ ID NO 275
<211> LENGTH: 251
<212> TYPE: PRT
<213> ORGANISM: Artificial Sequence
<220> FEATURE:
<223> OTHER INFORMATION: fusion protein

<400> SEQUENCE: 275

Met His His His His His His Gly Ser Gly Val Asp Val Ala Asp Glu
1 5 10 15

Ile Val Leu Thr Gln Ser Pro Ala Thr Leu Ser Leu Ser Pro Gly Glu
20 25 30

Arg Ala Thr Leu Ser Cys Ser Ala Ser Ser Ser Ile Asn Tyr Ile Tyr
35 40 45

Trp Tyr Gln Gln Lys Pro Gly Gln Ala Pro Arg Leu Leu Ile Tyr Leu
50 55 60

Thr Ser Asn Leu Ala Ser Gly Val Pro Ala Arg Phe Ser Gly Ser Gly
65 70 75 80

Ser Gly Thr Asp Phe Thr Leu Thr Ile Ser Ser Leu Glu Pro Glu Asp
85 90 95

Phe Ala Val Tyr Tyr Cys Leu Gln Trp Ser Ser Asn Pro Leu Thr Phe
100 105 110

Gly Gly Gly Thr Lys Val Glu Ile Lys Arg Gly Gly Gly Gly Ser Gly
115 120 125

Gly Gly Gly Ser Gly Gly Gly Gly Ser Glu Val Gln Leu Val Glu Ser
130 135 140

Gly Gly Gly Leu Val Lys Pro Gly Gly Ser Leu Arg Leu Ser Cys Ala
145 150 155 160

Ala Ser Gly Phe Thr Phe Ser Ser Tyr Asp Met Ser Trp Val Arg Gln
165 170 175

Ala Pro Gly Lys Gly Leu Glu Trp Val Ser Thr Ile Ser Ser Gly Gly
180 185 190

Ser Tyr Thr Tyr Tyr Leu Asp Ser Ile Lys Gly Arg Phe Thr Ile Ser
195 200 205

Arg Asp Asn Ala Lys Asn Ser Leu Tyr Leu Gln Met Asn Ser Leu Arg
210 215 220

Ala Glu Asp Thr Ala Val Tyr Tyr Cys Ala Arg Gln Gly Leu Asp Tyr
225 230 235 240

Trp Gly Arg Gly Thr Leu Val Thr Val Ser Ser
245 250

<210> SEQ ID NO 276
<211> LENGTH: 756
<212> TYPE: DNA
<213> ORGANISM: Artificial Sequence
<220> FEATURE:
<223> OTHER INFORMATION: fusion protein

<400> SEQUENCE: 276
atgcaccatc accatcacca tggcagcggc gtggatgtgg cggatgaaat tgtgctgacc 60
cagagcccgg cgaccctgag cctgagcccg ggtgaacgtg ccaccctgag ctgtagcgcg 120
agcagcagca ttaactatat ctattggtat cagcagaaac cgggccaggc gccgcgtctg 180
ctgatttatc tgaccagcaa cctggccagc ggtgttccgg cgcgttttag cggcagcggt 240
agcggcaccg attttaccct gaccattagc agcctggaac cggaagattt tgcggtgtat 300

```
tattgcctgc agtggagcag caatccgctg acctttggcg gtggcaccaa agtggaaatt    360

aaacgtggcg gcggtggcag cggtggtggt ggtagcggcg gtggcggcag cgaagtgcag    420

ctggttgaaa gcggtggcgg cctggtgaaa ccgggtggca gcctgcgtct gagctgtgcg    480

gcgagcggct ttacctttag cagctatgat atgagctggg tgcgtcaggc gccgggcaaa    540

ggcctggaat gggtgagcac catcagcagc ggcggcagct atacctatta tctggatagc    600

atcaaaggcc gttttaccat tagccgtgat aacgcgaaaa acagcctgta tctgcagatg    660

aacagcctgc gtgcggaaga taccgcggtt tattattgcg cgcgtcaggg cctggattat    720

tggggccgtg gcaccctggt taccgtgagc agctaa                               756


<210> SEQ ID NO 277
<211> LENGTH: 276
<212> TYPE: PRT
<213> ORGANISM: Artificial Sequence
<220> FEATURE:
<223> OTHER INFORMATION: consensus sequence
<220> FEATURE:
<221> NAME/KEY: MOD_RES
<222> LOCATION: (2)..(3)
<223> OTHER INFORMATION: X can be any amino acid
<220> FEATURE:
<221> NAME/KEY: MOD_RES
<222> LOCATION: (5)..(5)
<223> OTHER INFORMATION: X can be any amino acid
<220> FEATURE:
<221> NAME/KEY: MOD_RES
<222> LOCATION: (11)..(11)
<223> OTHER INFORMATION: X can be any amino acid
<220> FEATURE:
<221> NAME/KEY: MOD_RES
<222> LOCATION: (16)..(16)
<223> OTHER INFORMATION: X can be any amino acid
<220> FEATURE:
<221> NAME/KEY: MOD_RES
<222> LOCATION: (18)..(18)
<223> OTHER INFORMATION: X can be any amino acid
<220> FEATURE:
<221> NAME/KEY: MOD_RES
<222> LOCATION: (21)..(21)
<223> OTHER INFORMATION: X can be any amino acid
<220> FEATURE:
<221> NAME/KEY: MOD_RES
<222> LOCATION: (24)..(25)
<223> OTHER INFORMATION: X can be any amino acid
<220> FEATURE:
<221> NAME/KEY: MOD_RES
<222> LOCATION: (32)..(32)
<223> OTHER INFORMATION: X can be any amino acid
<220> FEATURE:
<221> NAME/KEY: MOD_RES
<222> LOCATION: (34)..(34)
<223> OTHER INFORMATION: X can be any amino acid
<220> FEATURE:
<221> NAME/KEY: MOD_RES
<222> LOCATION: (37)..(38)
<223> OTHER INFORMATION: X can be any amino acid
<220> FEATURE:
<221> NAME/KEY: MOD_RES
<222> LOCATION: (42)..(43)
<223> OTHER INFORMATION: X can be any amino acid
<220> FEATURE:
<221> NAME/KEY: MOD_RES
<222> LOCATION: (46)..(46)
<223> OTHER INFORMATION: X can be any amino acid
<220> FEATURE:
<221> NAME/KEY: MOD_RES
<222> LOCATION: (49)..(49)
<223> OTHER INFORMATION: X can be any amino acid
<220> FEATURE:
<221> NAME/KEY: MOD_RES
<222> LOCATION: (53)..(53)
```

<223> OTHER INFORMATION: X can be any amino acid
<220> FEATURE:
<221> NAME/KEY: MOD_RES
<222> LOCATION: (58)..(60)
<223> OTHER INFORMATION: X can be any amino acid
<220> FEATURE:
<221> NAME/KEY: MOD_RES
<222> LOCATION: (66)..(66)
<223> OTHER INFORMATION: X can be any amino acid
<220> FEATURE:
<221> NAME/KEY: MOD_RES
<222> LOCATION: (76)..(76)
<223> OTHER INFORMATION: X can be any amino acid
<220> FEATURE:
<221> NAME/KEY: MOD_RES
<222> LOCATION: (83)..(83)
<223> OTHER INFORMATION: X can be any amino acid
<220> FEATURE:
<221> NAME/KEY: MOD_RES
<222> LOCATION: (85)..(91)
<223> OTHER INFORMATION: X can be any amino acid
<220> FEATURE:
<221> NAME/KEY: MOD_RES
<222> LOCATION: (94)..(94)
<223> OTHER INFORMATION: X can be any amino acid
<220> FEATURE:
<221> NAME/KEY: MOD_RES
<222> LOCATION: (99)..(99)
<223> OTHER INFORMATION: X can be any amino acid
<220> FEATURE:
<221> NAME/KEY: MOD_RES
<222> LOCATION: (101)..(101)
<223> OTHER INFORMATION: X can be any amino acid
<220> FEATURE:
<221> NAME/KEY: MOD_RES
<222> LOCATION: (106)..(106)
<223> OTHER INFORMATION: X can be any amino acid
<220> FEATURE:
<221> NAME/KEY: MOD_RES
<222> LOCATION: (113)..(113)
<223> OTHER INFORMATION: X can be any amino acid
<220> FEATURE:
<221> NAME/KEY: MOD_RES
<222> LOCATION: (118)..(118)
<223> OTHER INFORMATION: X can be any amino acid
<220> FEATURE:
<221> NAME/KEY: MOD_RES
<222> LOCATION: (121)..(121)
<223> OTHER INFORMATION: X can be any amino acid
<220> FEATURE:
<221> NAME/KEY: MOD_RES
<222> LOCATION: (124)..(128)
<223> OTHER INFORMATION: X can be any amino acid
<220> FEATURE:
<221> NAME/KEY: MOD_RES
<222> LOCATION: (131)..(135)
<223> OTHER INFORMATION: X can be any amino acid
<220> FEATURE:
<221> NAME/KEY: MOD_RES
<222> LOCATION: (137)..(137)
<223> OTHER INFORMATION: X can be any amino acid
<220> FEATURE:
<221> NAME/KEY: MOD_RES
<222> LOCATION: (139)..(141)
<223> OTHER INFORMATION: X can be any amino acid
<220> FEATURE:
<221> NAME/KEY: MOD_RES
<222> LOCATION: (147)..(147)
<223> OTHER INFORMATION: X can be any amino acid
<220> FEATURE:
<221> NAME/KEY: MOD_RES
<222> LOCATION: (156)..(156)
<223> OTHER INFORMATION: X can be any amino acid
<220> FEATURE:
<221> NAME/KEY: MOD_RES
<222> LOCATION: (183)..(183)
<223> OTHER INFORMATION: X can be any amino acid
<220> FEATURE:
<221> NAME/KEY: MOD_RES
<222> LOCATION: (185)..(185)
<223> OTHER INFORMATION: X can be any amino acid
<220> FEATURE:
<221> NAME/KEY: MOD_RES
<222> LOCATION: (189)..(189)
<223> OTHER INFORMATION: X can be any amino acid
<220> FEATURE:
<221> NAME/KEY: MOD_RES
<222> LOCATION: (199)..(199)
<223> OTHER INFORMATION: X can be any amino acid
<220> FEATURE:
<221> NAME/KEY: MOD_RES
<222> LOCATION: (208)..(209)
<223> OTHER INFORMATION: X can be any amino acid
<220> FEATURE:
<221> NAME/KEY: MOD_RES
<222> LOCATION: (211)..(211)
<223> OTHER INFORMATION: X can be any amino acid
<220> FEATURE:
<221> NAME/KEY: MOD_RES
<222> LOCATION: (213)..(216)
<223> OTHER INFORMATION: X can be any amino acid
<220> FEATURE:
<221> NAME/KEY: MOD_RES
<222> LOCATION: (218)..(218)
<223> OTHER INFORMATION: X can be any amino acid
<220> FEATURE:
<221> NAME/KEY: MOD_RES
<222> LOCATION: (220)..(220)
<223> OTHER INFORMATION: X can be any amino acid
<220> FEATURE:
<221> NAME/KEY: MOD_RES
<222> LOCATION: (224)..(224)
<223> OTHER INFORMATION: X can be any amino acid
<220> FEATURE:
<221> NAME/KEY: MOD_RES
<222> LOCATION: (236)..(237)
<223> OTHER INFORMATION: X can be any amino acid
<220> FEATURE:
<221> NAME/KEY: MOD_RES
<222> LOCATION: (240)..(241)
<223> OTHER INFORMATION: X can be any amino acid
<220> FEATURE:
<221> NAME/KEY: MOD_RES
<222> LOCATION: (246)..(246)
<223> OTHER INFORMATION: X can be any amino acid
<220> FEATURE:
<221> NAME/KEY: MOD_RES
<222> LOCATION: (248)..(248)
<223> OTHER INFORMATION: X can be any amino acid
<220> FEATURE:
<221> NAME/KEY: MOD_RES
<222> LOCATION: (250)..(250)
<223> OTHER INFORMATION: X can be any amino acid
<220> FEATURE:
<221> NAME/KEY: MOD_RES
<222> LOCATION: (257)..(257)
<223> OTHER INFORMATION: X can be any amino acid
<220> FEATURE:
<221> NAME/KEY: MOD_RES
<222> LOCATION: (260)..(260)
<223> OTHER INFORMATION: X can be any amino acid
<220> FEATURE:
<221> NAME/KEY: MOD_RES
<222> LOCATION: (267)..(267)
<223> OTHER INFORMATION: X can be any amino acid
<220> FEATURE:
<221> NAME/KEY: MOD_RES
<222> LOCATION: (269)..(269)
<223> OTHER INFORMATION: X can be any amino acid
<220> FEATURE:
<221> NAME/KEY: MOD_RES
<222> LOCATION: (273)..(273)
<223> OTHER INFORMATION: X can be any amino acid

<400> SEQUENCE: 277

Gln Xaa Xaa Arg Xaa Cys Ser Ser Pro Arg Xaa Cys Ala Leu Val Xaa
1 5 10 15

```
Ser Xaa Val Thr Xaa Asp Pro Xaa Xaa Ala Asp Pro Leu Asp His Xaa
            20                  25                  30

Lys Xaa Gly Glu Xaa Xaa Glu Glu Val Xaa Xaa Lys Val Xaa Thr Glu
        35                  40                  45

Xaa Asp Phe Val Xaa Ser Val His Arg Xaa Xaa Xaa Ala Gln Ala Met
    50                  55                  60

Arg Xaa Cys Ile Glu Gln Phe Cys Gln Leu Pro Xaa His Arg Thr Ala
65                  70                  75                  80

Asp Gly Xaa Val Xaa Xaa Xaa Xaa Xaa Xaa Xaa Val Asp Xaa Ala Val
                85                  90                  95

Tyr Ser Xaa Asp Xaa Glu Leu Leu Gln Xaa Asp Trp Val Phe Glu Ala
            100                 105                 110

Xaa Asp Asn Ser His Xaa Pro Leu Xaa Gln Asn Xaa Xaa Xaa Xaa Xaa
        115                 120                 125

Phe Val Xaa Xaa Xaa Xaa Xaa Glu Xaa Met Xaa Xaa Xaa Val Val Gln
    130                 135                 140

Asp Thr Xaa Pro Glu Arg Thr Gly Ser Pro Ser Xaa Glu Gln Arg Asp
145                 150                 155                 160

Ala Gly Arg Glu Gly Glu Gly Asp Pro Gly Ser Arg Arg Pro Val Ser
                165                 170                 175

Leu Gly Arg Pro Arg Ile Xaa Leu Xaa Gln Arg Ser Xaa Met Ile Cys
            180                 185                 190

Gly Phe Ala Ser Leu Lys Xaa Gln Arg Leu Ser Thr Ala Ala Met Xaa
        195                 200                 205

Xaa Thr Xaa Arg Xaa Xaa Xaa Xaa Val Xaa Glu Xaa Asn Glu Ala Xaa
    210                 215                 220

Arg Leu Arg Ser Arg Asp Thr His Leu Ala Asp Xaa Xaa Val Gln Xaa
225                 230                 235                 240

Xaa Ala Arg Ile Lys Xaa Arg Xaa Gly Xaa Ala Pro Gly Thr Pro His
                245                 250                 255

Xaa Arg Cys Xaa Glu Met Ser Glu Phe Thr Xaa Ser Xaa Cys Asn Asp
            260                 265                 270

Xaa Phe Leu Phe
        275


<210> SEQ ID NO 278
<211> LENGTH: 5
<212> TYPE: PRT
<213> ORGANISM: Artificial Sequence
<220> FEATURE:
<223> OTHER INFORMATION: linker

<400> SEQUENCE: 278

Gly Gly Ser Gly Gly
1               5


<210> SEQ ID NO 279
<211> LENGTH: 10
<212> TYPE: PRT
<213> ORGANISM: Artificial Sequence
<220> FEATURE:
<223> OTHER INFORMATION: linker

<400> SEQUENCE: 279

Gly Ser Ala Gly Ser Ala Ala Gly Ser Gly
1               5                   10
```

<210> SEQ ID NO 280
<211> LENGTH: 7
<212> TYPE: PRT
<213> ORGANISM: Artificial Sequence
<220> FEATURE:
<223> OTHER INFORMATION: linker

<400> SEQUENCE: 280

Gly Ser Gly Ser Gly Ser Gly
1 5

<210> SEQ ID NO 281
<211> LENGTH: 5
<212> TYPE: PRT
<213> ORGANISM: Artificial Sequence
<220> FEATURE:
<223> OTHER INFORMATION: linker

<400> SEQUENCE: 281

Gly Gly Gly Gly Ser
1 5

<210> SEQ ID NO 282
<211> LENGTH: 19
<212> TYPE: PRT
<213> ORGANISM: Artificial Sequence
<220> FEATURE:
<223> OTHER INFORMATION: Polypeptide

<400> SEQUENCE: 282

Met Lys Lys Ile Trp Leu Ala Leu Ala Gly Leu Val Leu Ala Phe Ser
1 5 10 15

Ala Ser Ala

<210> SEQ ID NO 283
<211> LENGTH: 28
<212> TYPE: PRT
<213> ORGANISM: Artificial Sequence
<220> FEATURE:
<223> OTHER INFORMATION: Polypeptide

<400> SEQUENCE: 283

Met Phe Lys Phe Lys Lys Lys Phe Leu Val Gly Leu Thr Ala Ala Phe
1 5 10 15

Met Ser Ile Ser Met Phe Ser Ala Thr Ala Ser Ala
20 25

<210> SEQ ID NO 284
<211> LENGTH: 25
<212> TYPE: PRT
<213> ORGANISM: Artificial Sequence
<220> FEATURE:
<223> OTHER INFORMATION: Polypeptide

<400> SEQUENCE: 284

Met Met Ile Thr Leu Arg Lys Leu Pro Leu Ala Val Ala Val Ala Ala
1 5 10 15

Gly Val Met Ser Ala Gln Ala Met Ala
20 25

<210> SEQ ID NO 285
<211> LENGTH: 20
<212> TYPE: PRT
<213> ORGANISM: Artificial Sequence
<220> FEATURE:
<223> OTHER INFORMATION: Polypeptide

<400> SEQUENCE: 285

Met Lys Ala Thr Lys Leu Val Leu Gly Ala Val Ile Leu Gly Ser Thr
1 5 10 15

Leu Leu Ala Gly
20

<210> SEQ ID NO 286
<211> LENGTH: 21
<212> TYPE: PRT
<213> ORGANISM: Artificial Sequence
<220> FEATURE:
<223> OTHER INFORMATION: Polypeptide

<400> SEQUENCE: 286

Met Asn Lys Val Lys Cys Tyr Val Leu Phe Thr Ala Leu Leu Ser Ser
1 5 10 15

Leu Tyr Ala His Gly
20

<210> SEQ ID NO 287
<211> LENGTH: 26
<212> TYPE: PRT
<213> ORGANISM: Artificial Sequence
<220> FEATURE:
<223> OTHER INFORMATION: Polypeptide

<400> SEQUENCE: 287

Met Lys Ile Lys Thr Gly Ala Arg Ile Leu Ala Leu Ser Ala Leu Thr
1 5 10 15

Thr Met Met Phe Ser Ala Ser Ala Leu Ala
20 25

<210> SEQ ID NO 288
<211> LENGTH: 21
<212> TYPE: PRT
<213> ORGANISM: Artificial Sequence
<220> FEATURE:
<223> OTHER INFORMATION: Polypeptide

<400> SEQUENCE: 288

Met Lys Lys Thr Ala Ile Ala Ile Ala Val Ala Leu Ala Gly Phe Ala
1 5 10 15

Thr Val Ala Gln Ala
20

<210> SEQ ID NO 289
<211> LENGTH: 21
<212> TYPE: PRT
<213> ORGANISM: Artificial Sequence
<220> FEATURE:
<223> OTHER INFORMATION: Polypeptide

<400> SEQUENCE: 289

Met Lys Val Lys Val Leu Ser Leu Leu Val Pro Ala Leu Leu Val Ala
1 5 10 15

Gly Ala Ala Asn Ala
20

<210> SEQ ID NO 290
<211> LENGTH: 22
<212> TYPE: PRT
<213> ORGANISM: Artificial Sequence
<220> FEATURE:

<223> OTHER INFORMATION: Polypeptide

<400> SEQUENCE: 290

Met Met Lys Arg Asn Ile Leu Ala Val Ile Val Pro Ala Leu Leu Val
1 5 10 15

Ala Gly Thr Ala Asn Ala
20

<210> SEQ ID NO 291
<211> LENGTH: 20
<212> TYPE: PRT
<213> ORGANISM: Artificial Sequence
<220> FEATURE:
<223> OTHER INFORMATION: Polypeptide

<400> SEQUENCE: 291

Met Arg Ala Lys Leu Leu Gly Ile Val Leu Thr Thr Pro Ile Ala Ile
1 5 10 15

Ser Ser Phe Ala
20

<210> SEQ ID NO 292
<211> LENGTH: 22
<212> TYPE: PRT
<213> ORGANISM: Artificial Sequence
<220> FEATURE:
<223> OTHER INFORMATION: Polypeptide

<400> SEQUENCE: 292

Met Lys Tyr Leu Leu Pro Thr Ala Ala Ala Gly Leu Leu Leu Leu Ala
1 5 10 15

Ala Gln Pro Ala Met Ala
20

<210> SEQ ID NO 293
<211> LENGTH: 21
<212> TYPE: PRT
<213> ORGANISM: Artificial Sequence
<220> FEATURE:
<223> OTHER INFORMATION: Polypeptide

<400> SEQUENCE: 293

Met Lys Gln Ser Thr Ile Ala Leu Ala Leu Leu Pro Leu Leu Phe Thr
1 5 10 15

Pro Val Thr Lys Ala
20

<210> SEQ ID NO 294
<211> LENGTH: 21
<212> TYPE: PRT
<213> ORGANISM: Artificial Sequence
<220> FEATURE:
<223> OTHER INFORMATION: Polypeptide

<400> SEQUENCE: 294

Met Lys Lys Ser Thr Leu Ala Leu Val Val Met Gly Ile Val Ala Ser
1 5 10 15

Ala Ser Val Gln Ala
20

<210> SEQ ID NO 295
<211> LENGTH: 23
<212> TYPE: PRT
<213> ORGANISM: Artificial Sequence
<220> FEATURE:
<223> OTHER INFORMATION: Polypeptide

<400> SEQUENCE: 295

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 296
<211> LENGTH: 7
<212> TYPE: PRT
<213> ORGANISM: Artificial Sequence
<220> FEATURE:
<223> OTHER INFORMATION: RECOGNITION SITE

<400> SEQUENCE: 296

Val Asp Val Ala Asp Phe Ala
1               5

<210> SEQ ID NO 297
<211> LENGTH: 7
<212> TYPE: PRT
<213> ORGANISM: Artificial Sequence
<220> FEATURE:
<223> OTHER INFORMATION: RECOGNITION SITE

<400> SEQUENCE: 297

Val Asp Val Ala Asp Gly Ala
1               5

<210> SEQ ID NO 298
<211> LENGTH: 7
<212> TYPE: PRT
<213> ORGANISM: Artificial Sequence
<220> FEATURE:
<223> OTHER INFORMATION: RECOGNITION SITE

<400> SEQUENCE: 298

Val Asp Val Ala Asp Gln Ala
1               5

<210> SEQ ID NO 299
<211> LENGTH: 7
<212> TYPE: PRT
<213> ORGANISM: Artificial Sequence
<220> FEATURE:
<223> OTHER INFORMATION: RECOGNITION SITE

<400> SEQUENCE: 299

Val Asp Val Ala Asp Val Ala
1               5

<210> SEQ ID NO 300
<211> LENGTH: 7
<212> TYPE: PRT
<213> ORGANISM: Artificial Sequence
<220> FEATURE:
<223> OTHER INFORMATION: RECOGNITION SITE

<400> SEQUENCE: 300

Val Asp Val Ala Asp His Ala
1               5

<210> SEQ ID NO 301
<211> LENGTH: 20

<212> TYPE: PRT
<213> ORGANISM: Artificial Sequence
<220> FEATURE:
<223> OTHER INFORMATION: Polypeptide

<400> SEQUENCE: 301

His His His His His His His His His His His His His His His His
1               5                   10                  15

His His His His
            20

<210> SEQ ID NO 302
<211> LENGTH: 19
<212> TYPE: PRT
<213> ORGANISM: Artificial Sequence
<220> FEATURE:
<223> OTHER INFORMATION: Polypeptide

<400> SEQUENCE: 302

His His His His His His His His His His His His His His His His
1               5                   10                  15

His His His

<210> SEQ ID NO 303
<211> LENGTH: 18
<212> TYPE: PRT
<213> ORGANISM: Artificial Sequence
<220> FEATURE:
<223> OTHER INFORMATION: Polypeptide

<400> SEQUENCE: 303

His His His His His His His His His His His His His His His His
1               5                   10                  15

His His

<210> SEQ ID NO 304
<211> LENGTH: 17
<212> TYPE: PRT
<213> ORGANISM: Artificial Sequence
<220> FEATURE:
<223> OTHER INFORMATION: Polypeptide

<400> SEQUENCE: 304

His His His His His His His His His His His His His His His His
1               5                   10                  15

His

<210> SEQ ID NO 305
<211> LENGTH: 16
<212> TYPE: PRT
<213> ORGANISM: Artificial Sequence
<220> FEATURE:
<223> OTHER INFORMATION: Polypeptide

<400> SEQUENCE: 305

His His His His His His His His His His His His His His His His
1               5                   10                  15

<210> SEQ ID NO 306
<211> LENGTH: 15
<212> TYPE: PRT
<213> ORGANISM: Artificial Sequence
<220> FEATURE:
<223> OTHER INFORMATION: Polypeptide -continued

<400> SEQUENCE: 306

His His His His His His His His His His His His His His His
1 5 10 15

<210> SEQ ID NO 307
<211> LENGTH: 14
<212> TYPE: PRT
<213> ORGANISM: Artificial Sequence
<220> FEATURE:
<223> OTHER INFORMATION: Polypeptide

<400> SEQUENCE: 307

His His His His His His His His His His His His His His
1 5 10

<210> SEQ ID NO 308
<211> LENGTH: 13
<212> TYPE: PRT
<213> ORGANISM: Artificial Sequence
<220> FEATURE:
<223> OTHER INFORMATION: Polypeptide

<400> SEQUENCE: 308

His His His His His His His His His His His His His
1 5 10

<210> SEQ ID NO 309
<211> LENGTH: 12
<212> TYPE: PRT
<213> ORGANISM: Artificial Sequence
<220> FEATURE:
<223> OTHER INFORMATION: Polypeptide

<400> SEQUENCE: 309

His His His His His His His His His His His His
1 5 10

<210> SEQ ID NO 310
<211> LENGTH: 11
<212> TYPE: PRT
<213> ORGANISM: Artificial Sequence
<220> FEATURE:
<223> OTHER INFORMATION: Polypeptide

<400> SEQUENCE: 310

His His His His His His His His His His His
1 5 10

<210> SEQ ID NO 311
<211> LENGTH: 10
<212> TYPE: PRT
<213> ORGANISM: Artificial Sequence
<220> FEATURE:
<223> OTHER INFORMATION: Polypeptide

<400> SEQUENCE: 311

His His His His His His His His His His
1 5 10

<210> SEQ ID NO 312
<211> LENGTH: 9
<212> TYPE: PRT
<213> ORGANISM: Artificial Sequence
<220> FEATURE:
<223> OTHER INFORMATION: Polypeptide

<400> SEQUENCE: 312

His His His His His His His His His
1 5

<210> SEQ ID NO 313
<211> LENGTH: 8
<212> TYPE: PRT
<213> ORGANISM: Artificial Sequence
<220> FEATURE:
<223> OTHER INFORMATION: Polypeptide

<400> SEQUENCE: 313

His His His His His His His His
1 5

<210> SEQ ID NO 314
<211> LENGTH: 7
<212> TYPE: PRT
<213> ORGANISM: Artificial Sequence
<220> FEATURE:
<223> OTHER INFORMATION: Polypeptide

<400> SEQUENCE: 314

His His His His His His His
1 5

<210> SEQ ID NO 315
<211> LENGTH: 6
<212> TYPE: PRT
<213> ORGANISM: Artificial Sequence
<220> FEATURE:
<223> OTHER INFORMATION: Polypeptide

<400> SEQUENCE: 315

His His His His His His
1 5

<210> SEQ ID NO 316
<211> LENGTH: 5
<212> TYPE: PRT
<213> ORGANISM: Artificial Sequence
<220> FEATURE:
<223> OTHER INFORMATION: Polypeptide

<400> SEQUENCE: 316

His His His His His
1 5

<210> SEQ ID NO 317
<211> LENGTH: 4
<212> TYPE: PRT
<213> ORGANISM: Artificial Sequence
<220> FEATURE:
<223> OTHER INFORMATION: Polypeptide

<400> SEQUENCE: 317

His His His His
1

<210> SEQ ID NO 318
<211> LENGTH: 7
<212> TYPE: PRT
<213> ORGANISM: Artificial Sequence
<220> FEATURE:
<223> OTHER INFORMATION: Polypeptide

<400> SEQUENCE: 318

-continued

```
Val Asp Val Ala Asp Phe Ala
1               5


<210> SEQ ID NO 319
<211> LENGTH: 7
<212> TYPE: PRT
<213> ORGANISM: Artificial Sequence
<220> FEATURE:
<223> OTHER INFORMATION: Polypeptide

<400> SEQUENCE: 319

Val Asp Val Ala Asp Gly Ala
1               5


<210> SEQ ID NO 320
<211> LENGTH: 7
<212> TYPE: PRT
<213> ORGANISM: Artificial Sequence
<220> FEATURE:
<223> OTHER INFORMATION: Polypeptide

<400> SEQUENCE: 320

Val Asp Val Ala Asp Gln Ala
1               5


<210> SEQ ID NO 321
<211> LENGTH: 7
<212> TYPE: PRT
<213> ORGANISM: Artificial Sequence
<220> FEATURE:
<223> OTHER INFORMATION: Polypeptide

<400> SEQUENCE: 321

Val Asp Val Ala Asp Val Ala
1               5


<210> SEQ ID NO 322
<211> LENGTH: 19
<212> TYPE: DNA
<213> ORGANISM: Artificial Sequence
<220> FEATURE:
<223> OTHER INFORMATION: probe

<400> SEQUENCE: 322

gatacccgcg tgcaaaaag                                               19


<210> SEQ ID NO 323
<211> LENGTH: 18
<212> TYPE: DNA
<213> ORGANISM: Artificial Sequence
<220> FEATURE:
<223> OTHER INFORMATION: probe

<400> SEQUENCE: 323

gccgctgcca tgatgatg                                                18
```